(12) United States Patent
Saavedra et al.

(10) Patent No.: US 7,790,729 B2
(45) Date of Patent: Sep. 7, 2010

(54) INHIBITORS OF VEGF RECEPTOR AND HGF RECEPTOR SIGNALING

(75) Inventors: Oscar Mario Saavedra, Montreal (CA); Stephen William Claridge, Montreal (CA); Lijie Zhan, Montreal (CA); Franck Raeppel, Montreal (CA); Arkadii Vaisburg, Kirkland (CA); Stephane Raeppel, St. Lazare (CA); Robert Deziel, Mount-Royal (CA); Michael Mannion, Cuthbert (CA); Nancy Z. Zhou, Kirkland (CA); Ljubomir Isakovic, Montreal (CA)

(73) Assignee: Methylgene Inc., St. Laurent, Quebec (CA)

( * ) Notice: Subject to any disclaimer, the term of this patent is extended or adjusted under 35 U.S.C. 154(b) by 151 days.

(21) Appl. No.: 11/419,353

(22) Filed: May 19, 2006

(65) Prior Publication Data

US 2006/0287343 A1 Dec. 21, 2006

Related U.S. Application Data

(60) Provisional application No. 60/683,038, filed on May 20, 2005.

(51) Int. Cl.
*A01N 43/90* (2006.01)
*A61K 31/517* (2006.01)
*A61K 31/519* (2006.01)
*C07D 471/02* (2006.01)
*C07D 491/02* (2006.01)
*C07D 513/02* (2006.01)
*C07D 239/70* (2006.01)

(52) U.S. Cl. .............. 514/258.1; 514/262.1; 514/301; 514/303; 514/300; 546/113; 546/114; 546/115; 546/117; 546/118; 544/253; 544/255

(58) Field of Classification Search .......... 546/113, 546/114, 115, 117, 118; 544/253, 255; 514/300, 514/301, 302, 303, 258.1, 262.1
See application file for complete search history.

(56) References Cited

U.S. PATENT DOCUMENTS

| | | | |
|---|---|---|---|
| 6,232,320 B1 | 5/2001 | Stewart | |
| 6,448,261 B1 | 9/2002 | Bakthavatchalam | |
| 6,492,383 B1 | 12/2002 | Munchhof | |
| 6,833,456 B2 | 12/2004 | Romines | |
| 6,995,171 B2 | 2/2006 | Autry | |
| 2002/0004511 A1 | 1/2002 | Figley | |
| 2005/0116028 A1 | 6/2005 | Cohen | |
| 2005/0239820 A1 | 10/2005 | Borzilleri | |
| 2005/0245547 A1 | 11/2005 | Kim | |
| 2005/0288290 A1 | 12/2005 | Borzilleri et al. | |
| 2006/0004006 A1 | 1/2006 | Borzilleri | |
| 2006/0074056 A1* | 4/2006 | Vaisburg et al. | 514/151 |
| 2006/0211695 A1 | 9/2006 | Borzilleri et al. | |
| 2007/0004675 A1 | 1/2007 | Saavedra | |

FOREIGN PATENT DOCUMENTS

| | | |
|---|---|---|
| CA | 2309690 A1 | 5/1999 |
| CA | 2451678 A1 | 1/2003 |
| CA | 2477651 A1 | 10/2003 |
| CA | 2502614 A1 | 6/2004 |
| WO | WO99/24440 | 5/1999 |
| WO | WO99/62908 | 12/1999 |
| WO | WO00/75145 | 12/2000 |
| WO | WO01/94353 | 12/2001 |
| WO | WO03/000194 | 1/2003 |
| WO | WO03/000688 | 1/2003 |
| WO | WO03/074529 | 9/2003 |
| WO | WO2004/048386 | 6/2004 |
| WO | WO2005/021554 | 3/2005 |
| WO | WO2006/014325 | 7/2005 |
| WO | WO2005/073224 | 8/2005 |
| WO | 2005/121125 | * 12/2005 |
| WO | WO2005/117867 | 12/2005 |
| WO | WO2005/121125 | 12/2005 |
| WO | WO2006/004636 | 1/2006 |
| WO | WO2006/004833 | 1/2006 |
| WO | WO2006/116713 | 2/2006 |
| WO | WO/2006010264 A1 | 2/2006 |
| WO | WO2006/036266 | 4/2006 |
| WO | WO2006/104161 | 10/2006 |
| WO | WO/2006104161 A1 | 10/2006 |
| WO | WO2008/063202 | 5/2008 |

OTHER PUBLICATIONS

McMeel et al., American Journal of Pathology, 2000, 156(4), pp. 1337-1344.*
Iruela-Arispe et al., The American journal of pathology, (Dec. 1995) vol. 147, No. 6, pp. 1715-1727.*

(Continued)

*Primary Examiner*—D. Margaret Seaman
*Assistant Examiner*—Niloofar Rahmani
(74) *Attorney, Agent, or Firm*—Wood, Phillips, Katz, Clark & Mortimer

(57) ABSTRACT

The invention relates to the inhibition of VEGF receptor signaling and HGF receptor signaling. The invention provides compounds and methods for inhibiting VEGF receptor signaling and HGF receptor signaling. The invention also provides compositions and methods for treating cell proliferative diseases and conditions.

55 Claims, No Drawings

OTHER PUBLICATIONS

Fan et al., "Controlling the Vasculature: Angiogenesis . . . ", Trends Pharmacol. Sci. 16:57-66 (1995).

Folkman, J., Angiogenesis in Cancer, Vascular, Rheumatoid and Other . . . , Nat. Med. 1:27-31 (1995).

Jakeman et al., "Developmental Expression of Binding Sites . . . ", Endocrinology, 133:848-859 (1993).

Connolly et al., "Human Vascular Permeability Factor . . . ", J. Biol. Chem. 264:20017-20024 (1989).

Plowman et al., "Receptor Tyrosine Kinases as Targets for . . . ", Drug News Perspect. 7:334-339 (1994).

Strawn et al., "Tyrosine Kinases in Disease: Overview . . . ", Exp. Opin. Invest. Drugs 7:553-573 (1998).

Shawver et al., "Receptor Tyrosine Kinases as Targets for . . . ", Drug Discov. Today 2:50-63 (1997).

De Vries et al., "The FMS-Like Tyrosine Kinases, a Receptor . . . " Science 255:989-991 (1992).

Terman et al., "identification of the KDR . . . ", Biochem. Biophys. Res. Commun. 187:1579-1586 (1992).

Plate et al. "Vascular Endothelial Growth Factor and Glioma . . . ", Int. J. Cancer 59:520-529 (1994).

Fuh et al., "Requirements for Binding and Signaling of the . . . ", J. Biol. Chem. 273:11197-11204 (1998).

Wheeler-Jones et al., "Vascular Endothelial Growth . . . ", FEBS Lett. 420:28-32 (1997).

Kim et al., "Inhibition of Vascular Endothelial Growth . . . ", Nature (Lond.) 362:841-844 (1993).

Kanai et al., "Anti-Tumor and Anti-Metastatic Effects . . . ", Int. J. Cancer 77:933-936 (1998).

Zhu et al., "Inhibition of Vascular Endothelial Growth Factor . . . ", Cancer Res. 58:3209-3214 (1998).

Siemeister et al., "An Antagonistic Vascular Endo . . . ", Proc. Natl. Acad. Sci. USA 95:4625-4629 (1998).

Lin, P. et al. "Inhibition of Tumor Growth by Targeting . . . ", Cell Growth Differ. 9:49-58 (1998).

Cheng et al., "Suppression of Glioblastoma Angiogenicity . . . ", Proc. Natl. Acad. Sci. USA 93:8502-8507 (1996).

Millauer et al. "Dominant-Negative Inhibition of Flk-1 Suppresses . . . ", Cancer Res. 56:1615-1620 (1996).

Pennacchietti et al., "Hypoxia Promotes Invasive Growth by Transcriptional Activation of the Met Protooncogene", Cancer Cell. 3(4):347-361 (2003).

Camps et al., "Fibroblast-Mediate Acceleration of Human Epithelial Tumor Growth in Vivo", Proc. Natl. Acad. Sci. USA 87:75-9 (1990).

Nakamura et al., "Induction of Hepatocyte Growth Factor in Fibroblasts by Tumor-Derived Factors Affects Invasive Growth of Tumor Cells: In Vitro Analysis of Tumor-Stromal Interactions", Cancer Res. 57:3305-3313 (1997).

Nishimura et al., "Regulation of Invasive Potential of Human . . . ", Int. J. Urol. 5:276-281 (1998).

Bae-Jump et al., "Hepatocyte Growth Factor (HGF) Induces . . . ", Gynecol. Oncol. 73:265-272 (1999).

Nakamura et al., "A Partial Purification and Characterization . . . ", Bioch. Bio. Res. Com. 122:1450-9 (1984).

Nakamura et al., "Molecular Cloning and Expression of Human . . . ", Nature 342:440-443 (1989).

Ebert et al., "Coexpression of the C-Met Proto-oncogene and . . . ", Cancer Res. 54:5775-5778 (1994).

DiRenzo et al., "Expression of the Met-HGF Receptor in normal . . . ", Oncogene 6:1997-2003 (1991).

DiRenzo et al., "Expression of the Met/Hepatocyte Growth Factor . . . " Cancer Res. 11:1129-1138 (1995).

Delehedde et al., "Hepatocyte Growth Factor/Scatter Factor . . . " Eur. J. Biochem. 269:4423-4429 (2001).

Bardelli et al., "Concomitant Activation of Pathways Downstream . . . ", Oncogene 18:1139-1146 (1999).

Saucier et al., "The SHC Adaptor Protein is Critical for . . . " Nat. Acad. Sci. USA 101(8):2345-2350 (2004).

Evans et al., "Addition of Lithiated 9-Deazapurine Derivatives", J. Org. Chem. 66(17):5723-5730 (2001).

Tsou et al., "6-Substituted-4-(3-bromophenylamino) Quinazolines . . . ", J. Med. Chem. 44:2719-2734 (2001).

Cliff et al., "Synthesis of 4,4'-Biimidazoles", Synthesis pp. 681-682 (1994).

He et al., "A Convenient Synthesis of 1,4-Disubstituted . . . ", Tetrahedron Lett. 45(28):5529-5532 (2004).

O'Connell et al., "Convenient Synthesis of Methyl 1-Methyl-2,4-Dibromo . . . ", Synthesis pp. 767-771 (1988).

Gutschow et al., "2-(Diethylamino)Thieno[1,3]Oxazin-4 . . . ", J. Med. Chem. 42(26):5437-5447 (1999).

Robba et al., "Thienopyrimidines", Bull Soc. Chem. Fr. 587-591 (1975).

Hodgson et al., "The Nitrosation of Phenols. Part VII . . . ", J. Chem. Soc. pp. 2775-2778 (1929).

Smith et al., "Cyclization of Isothiocyanates as a Route to . . . ", J. Org. Chem. pp. 2261-2265 (1964).

Evans et al., "Addition of Lithiated 9-Deazapurine . . . ", J. Org. Chem. 66(17):5723-5730 (2001).

Antilla et al., "The Copper-Catalyzed N-Arylation of Indoles", JACS 124:11684-11688 (2002).

Zhang et al., "A General Method for the Preparation of . . . ", J. Org. Chem. 67:2345-2347 (2002).

Almansa et al., "Synthesis and SAR of a New Series of COX-2 . . . ", J. med. Chem. 44:350-361 (2001).

Hill et al., "Dialkylacetyl Biurets", JACS 62:1595-1596 (1940).

* cited by examiner

INHIBITORS OF VEGF RECEPTOR AND HGF RECEPTOR SIGNALING

RELATED APPLICATIONS

This application claims the benefit of U.S. Provisional Patent Application Ser. No. 60/683,038, filed on May 20, 2005, the contents of which are incorporated herein by reference in its entirety.

BACKGROUND OF THE INVENTION

1. Field of the Invention

This invention relates to the inhibition of VEGF receptor signaling and HGF receptor signaling. More particularly, the invention relates to compounds and methods for the inhibition of VEGF receptor signaling and HGF receptor signaling.

2. Summary of the Related Art

Angiogenesis is an important component of certain normal physiological processes such as embryogenesis and wound healing, but aberrant angiogenesis contributes to some pathological disorders and in particular to tumor growth.[1,2] VEGF-A (vascular endothelial growth factor A) is a key factor promoting neovascularization (angiogenesis) of tumors.[3-7] VEGF induces endothelial cell proliferation and migration by signaling through two high affinity receptors, the fins-like tyrosine kinase receptor, Flt-1, and the kinase insert domain-containing receptor, KDR.[8,9,10] These signaling responses are critically dependent upon receptor dimerization and activation of intrinsic receptor tyrosine kinase (RTK) activity. The binding of VEGF as a disulfide-linked homodimer stimulates receptor dimerization and activation of the RTK domain[11]. The kinase activity autophosphorylates cytoplasmic receptor tyrosine residues, which then serve as binding sites for molecules involved in the propagation of a signaling cascade. Although multiple pathways are likely to be elucidated for both receptors, KDR signaling is most extensively studied, with a mitogenic response suggested to involve ERK-1 and ERK-2 mitogen-activated protein kinases[12].

Disruption of VEGF receptor signaling is a highly attractive therapeutic target in cancer, as angiogenesis is a prerequisite for all solid tumor growth, and that the mature endothelium remains relatively quiescent (with the exception of the female reproductive system and wound healing). A number of experimental approaches to inhibiting VEGF signaling have been examined, including use of neutralizing antibodies[13,14,15], receptor antagonists[16], soluble receptors[17], antisense constructs[18] and dominant-negative strategies[19].

Despite the attractiveness of anti-angiogenic therapy by VEGF inhibition alone, several issues may limit this approach. VEGF expression levels can themselves be elevated by numerous diverse stimuli and perhaps most importantly, the hypoxic state of tumors resulting from VEGFr inhibition, can lead to the induction of factors that themselves promote tumor invasion and metastasis thus, potentially undermining the impact of VEGF inhibitors as cancer therapeutics[20].

The HGF (hepatocyte growth factor) and the HGF receptor, c-met, are implicated in the ability of tumor cells to undermine the activity of VEGF inhibition[20]. HGF derived from either stromal fibroblasts surrounding tumor cells or expressed from the tumor itself has been suggested to play a critical role in tumor angiogenesis, invasion and metastasis[21,22]. For example, invasive growth of certain cancer cells is drastically enhanced by tumor-stromal interactions involving the HGF/c-Met (HGF receptor) pathway[23,24,25] HGF, which was originally identified as a potent mitogen for hepatocytes[26,27] is primarily secreted from stromal cells, and the secreted HGF can promote motility and invasion of various cancer cells that express c-Met in a paracrine manner[28,29,30]. Binding of HGF to c-Met leads to receptor phosphorylation and activation of Ras/mitogen-activated protein kinase (MAPK) signaling pathway, thereby enhancing malignant behaviors of cancer cells[30,31]. Moreover, stimulation of the HGF/c-met pathway itself can lead to the induction of VEGF expression, itself contributing directly to angiogenic activity[32].

Thus, anti-tumor anti-angiogenic strategies or approaches that target both VEGF/VEGFr signaling and HGF/c-met signaling may circumvent the ability of tumor cells to overcome VEGF inhibition alone and may represent improved cancer therapeutics.

Here we describe small molecules that are potent inhibitors of both the VEGF receptor KDR and the HGF receptor c-met.

BRIEF SUMMARY OF THE INVENTION

The present invention provides new compounds and methods for treating cell proliferative diseases. The compounds of the invention are inhibitors of protein tyrosine kinase activity. Preferably, the compounds of the invention are dual function inhibitors, capable of inhibiting both VEGF and HGF receptor signaling. Accordingly, the invention provides new inhibitors of protein tyrosine kinase receptor signaling, such as for example, VEGF receptor signaling and HGF receptor signaling, including the VEGF receptor KDR and the HGF receptor c-met.

In a first aspect, the invention provides compounds of formula A that are useful as kinase inhibitors and, therefore, are useful research tools for the study of the role of kinases in both normal and disease states. Preferably, the invention provides compounds of Formula I that are useful as inhibitors of VEGF receptor signaling and HGF receptor signaling and, therefore, are useful research tools for the study of the role of VEGF and HGF in both normal and disease states.

In a first aspect, the invention provides compounds of formula A-0 that are useful as kinase inhibitors and, therefore, are useful research tools for the study of the role of kinases in both normal and disease states. Preferably, the invention provides compounds of Formula I that are useful as inhibitors of VEGF receptor signaling and HGF receptor signaling and, therefore, are useful research tools for the study of the role of VEGF and HGF in both normal and disease states.

In a third aspect, the invention provides compositions comprising a compound that is an inhibitor of kinase, or an N-oxide, hydrate, solvate, pharmaceutically acceptable salt, prodrug or complexe thereof, and a pharmaceutically acceptable carrier, excipient or diluent. Preferably, the invention provides compositions comprising a compound that is an inhibitor of VEGF receptor signaling and HGF receptor signaling, or an N-oxide, hydrate, solvate, pharmaceutically acceptable salt, prodrug or complexe thereof, and a pharmaceutically acceptable carrier, excipient, or diluent. In a preferred embodiment, the composition further comprises an additional therapeutic agent.

In a fourth aspect, the invention provides a method of inhibiting kinase, the method comprising contacting the kinase with a compound according to the present invention, or with a composition according to the present invention. Preferably the invention provides a method of inhibiting VEGF receptor signaling and HGF receptor signaling, the method comprising contacting the receptor with a compound according to the present invention, or with a composition according to the present invention. Inhibition of receptor protein kinase activity, preferably VEGF and HGF receptor signaling, can be in a cell or a multicellular organism. If in a multicellular organism, the method according to this aspect of the invention comprises administering to the organism a compound according to the present invention, or a composition according to the present invention. Preferably the organism is a mammal, more preferably a human. In a preferred embodiment, the method further comprises contacting the kinase with an additional therapeutic agent.

In a fifth aspect, the invention provides a method of inhibiting proliferative activity of a cell, the method comprising contacting the cell with an effective proliferative inhibiting amount of a compound according to the present invention or a composition thereof. In a preferred embodiment, the method further comprises contacting the cell with an additional therapeutic agent.

In a sixth aspect, the invention provides a method of treating a cell proliferative disease in a patient, the method comprising administering to the patient in need of such treatment an effective therapeutical amount of a compound according to the present invention or a composition thereof. In a preferred embodiment, the method further comprises administering an additional therapeutic agent.

In a seventh aspect, the invention provides a method of inhibiting tumor growth in a patient, the method comprising administering to the patient in need thereof an effective therapeutical amount of a compound according to the present invention or a composition thereof. In a preferred embodiment, the method further comprises administering an additional therapeutic agent.

The foregoing merely summarizes certain aspects of the invention and is not intended to be limiting in nature. These aspects and other aspects and embodiments are described more fully below.

DETAILED DESCRIPTION OF THE PREFERRED EMBODIMENTS

The invention provides compounds and methods for inhibiting the VEGF receptor KDR and the HGF receptor c-met. The invention also provides compositions and methods for treating cell proliferative diseases and conditions. The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

For purposes of the present invention, the following definitions will be used (unless expressly stated otherwise):

The terms "inhibitor of VEGF receptor signaling" and "inhibitor of HGF receptor signaling" are used to identify a compound having a structure as defined herein, which is capable of interacting with a HGF receptor and a VEGF receptor and inhibiting the activity of HGF and VEGF. In some preferred embodiments, such reduction of activity is at least about 50%, more preferably at least about 75%, and still more preferably at least about 90%.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as $(A)_a$-B—, wherein a is 0 or 1. In such instances, when a is 0 the moiety is B— and when a is 1 the moiety is A-B—. Also, a number of moieties disclosed herein exist in multiple tautomeric forms, all of which are intended to be encompassed by any given tautomeric structure.

The term "hydrocarbyl" refers to a straight, branched, or cyclic alkyl, alkenyl, or alkynyl, each as defined herein. A "$C_0$" hydrocarbyl is used to refer to a covalent bond. Thus, "$C_0$-$C_3$-hydrocarbyl" includes a covalent bond, methyl, ethyl, ethenyl, ethynyl, propyl, propenyl, propynyl, and cyclopropyl.

The term "alkyl" as employed herein refers to straight and branched chain aliphatic groups having from 1 to 12 carbon atoms, preferably 1-8 carbon atoms, and more preferably 1-6 carbon atoms, which is optionally substituted with one, two or three substituents. Preferred alkyl groups include, without limitation, methyl, ethyl, propyl, isopropyl, butyl, isobutyl, sec-butyl, tert-butyl, pentyl, and hexyl. A "$C_0$" alkyl (as in "$C_0$-$C_3$-alkyl") is a covalent bond (like "$C_0$" hydrocarbyl).

The term "alkenyl" as used herein means an unsaturated straight or branched chain aliphatic group with one or more carbon-carbon double bonds, having from 2 to 12 carbon atoms, preferably 2-8 carbon atoms, and more preferably 2-6 carbon atoms, which is optionally substituted with one, two or three substituents. Preferred alkenyl groups include, without limitation, ethenyl, propenyl, butenyl, pentenyl, and hexenyl.

The term "alkynyl" as used herein means an unsaturated straight or branched chain aliphatic group with one or more carbon-carbon triple bonds, having from 2 to 12 carbon atoms, preferably 2-8 carbon atoms, and more preferably 2-6 carbon atoms, which is optionally substituted with one, two or three substituents. Preferred alkynyl groups include, without limitation, ethynyl, propynyl, butynyl, pentynyl, and hexynyl.

An "alkylene," "alkenylene," or "alkynylene" group is an alkyl, alkenyl, or alkynyl group, as defined hereinabove, that is positioned between and serves to connect two other chemical groups. Preferred alkylene groups include, without limitation, methylene, ethylene, propylene, and butylene. Preferred alkenylene groups include, without limitation, ethenylene, propenylene, and butenylene. Preferred alkynylene groups include, without limitation, ethynylene, propynylene, and butynylene.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally is optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroalkyl" refers to an alkyl group, as defined hereinabove, wherein one or more carbon atoms in the chain are replaced by a heteroatom selected from the group consisting of O, S, NH, N-alkyl, SO, $SO_2$, $SO_2NH$, or $NHSO_2$.

An "aryl" group is a $C_6$-$C_{14}$ aromatic moiety comprising one to three aromatic rings, which is optionally substituted.

Preferably, the aryl group is a $C_6$-$C_{10}$ aryl group. Preferred aryl groups include, without limitation, phenyl, naphthyl, anthracenyl, and fluorenyl. An "aralkyl" or "arylalkyl" group comprises an aryl group covalently linked to an alkyl group, either of which may independently be optionally substituted or unsubstituted. Preferably, the aralkyl group is $(C_1$-$C_6)$alk $(C_6$-$C_{10})$aryl, including, without limitation, benzyl, phenethyl, and naphthylmethyl.

A "heterocyclyl" or "heterocyclic" group is a ring structure having from about 3 to about 12 atoms, wherein one or more atoms are selected from the group consisting of N, O, S, SO, and $SO_2$. The heterocyclic group is optionally substituted on carbon at one or more positions. The heterocyclic group is also independently optionally substituted on nitrogen with alkyl, aryl, aralkyl, alkylcarbonyl, alkylsulfonyl, arylcarbonyl, arylsulfonyl, alkoxycarbonyl, or aralkoxycarbonyl. Preferred heterocyclic groups include, without limitation, epoxy, aziridinyl, tetrahydro furanyl, pyrrolidinyl, piperidinyl, piperazinyl, thiazolidinyl, oxazolidinyl, oxazolidinonyl, and morpholino. In certain preferred embodiments, the heterocyclic group is fused to an aryl, heteroaryl, or cycloalkyl group. Examples of such fused heterocycles include, without limitation, tetrahydroquinoline and dihydrobenzofuran. Specifically excluded from the scope of this term are compounds where an annular O or S atom is adjacent to another O or S atom.

As used herein, the term "heteroaryl" refers to groups having 5 to 14 ring atoms, preferably 5, 6, 9, or 10 ring atoms; having 6, 10, or 14 π-electrons shared in a cyclic array; and having, in addition to carbon atoms, from one to three heteroatoms per ring selected from the group consisting of N, O, and S. The term "heteroaryl" is also meant to encompass monocyclic and bicyclic groups. For example, a heteroaryl group may be pyrimidinyl, pyridinyl, benzimidazolyl, thienyl, benzothiazolyl, benzofuranyl and indolinyl. A "heteroaralkyl" or "heteroarylalkyl" group comprises a heteroaryl group covalently linked to an alkyl group, either of which is independently optionally substituted or unsubstituted. Preferred heteroalkyl groups comprise a $C_1$-$C_6$ alkyl group and a heteroaryl group having 5, 6, 9, or 10 ring atoms. Specifically excluded from the scope of this term are compounds having adjacent annular O and/or S atoms. Examples of preferred heteroaralkyl groups include pyridylmethyl, pyridylethyl, pyrrolylmethyl, pyrrolylethyl, imidazolylmethyl, imidazolylethyl, thiazolylmethyl, and thiazolylethyl. Specifically excluded from the scope of this term are compounds having adjacent annular O and/or S atoms.

For simplicity, reference to a "$C_n$-$C_m$" heterocyclyl or heteroaryl means a heterocyclyl or heteroaryl having from "n" to "m" annular atoms, where "n" and "m" are integers. Thus, for example, a $C_5$-$C_6$-heterocyclyl is a 5- or 6-membered ring having at least one heteroatom, and includes pyrrolidinyl ($C_5$) and piperidinyl ($C_6$); $C_6$-hetoaryl includes, for example, pyridyl and pyrimidyl.

An "arylene," "heteroarylene," or "heterocyclylene" group is an aryl, heteroaryl, or heterocyclyl group, as defined hereinabove, that is positioned between and serves to connect two other chemical groups.

Preferred heterocyclyls and heteroaryls include, but are not limited to, acridinyl, azocinyl, benzimidazolyl, benzofuranyl, benzothiophenyl, benzoxazolyl, benzthiazolyl, benztriazolyl, pyridotriazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,3,4-triazolyl, and xanthenyl.

As employed herein, when a moiety (e.g., cycloalkyl, hydrocarbyl, aryl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—) nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, hydroxy, cyano, oxo, carboxy, formyl, nitro, amino, amidino, guanidino, (b) $C_1$-$C_5$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$ alkylsulfinyl, arylalkylsulfinyl, arylsulfinyl, $C_1$-$C_8$ alkylsulfonyl, arylalkylsulfonyl, arylsulfonyl, $C_0$-$C_6$ N-alkyl carbamoyl, $C_2$-$C_{15}$ N,N-dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, $C_5$-$C_{14}$ heteroaryl, or any of these rings fused or spiro-fused to a cycloalkyl, heterocyclyl, or aryl, wherein each of the foregoing is further optionally substituted with one more moieties listed in (a), above; and (c) —$(CH_2)_s$—$NR^{30}R^{31}$, wherein s is from 0 (in which case the nitrogen is directly bonded to the moiety that is substituted) to 6, and $R^{30}$ and $R^{31}$ are each independently hydrogen, cyano, oxo, carboxamido, amidino, $C_1$-$C_8$ hydroxyalkyl, $C_1$-$C_3$ alkylaryl, aryl-$C_1$-$C_3$ alkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, aryl-$C_1$-$C_3$ alkoxycarbonyl, $C_2$-$C_8$ acyl, $C_1$-$C_8$ alkylsulfonyl, arylalkylsulfonyl, arylsulfonyl, aroyl, aryl, cycloalkyl, heterocyclyl, or heteroaryl, wherein each of the foregoing is further optionally substituted with one more moieties listed in (a), above; or $R^{30}$ and $R^{31}$ taken together with the N to which they are attached form a heterocyclyl or heteroaryl, each of which is optionally substituted with from 1 to 3 substituents from (a), above.

Especially preferred substituents on alkyl groups include halogen, hydroxy, alkoxy and alkylamine.

Especially preferred substituents or ring groups, such as aryl, heteroaryl, cycloalkyl and heterocyclyl, include halogen, alkoxy and alkyl.

A "halohydrocarbyl" is a hydrocarbyl moiety in which from one to all hydrogens have been replaced with one or more halo.

The term "halogen" or "halo" as employed herein refers to chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., $NH_2$—CO—). The nitrogen atom of an acylamino or carbamoyl substituent is additionally substituted. The term "sulfonamido" refers to a sulfonamide substituent attached by either the sulfur or the nitrogen atom. The term "amino" is meant to include $NH_2$, alkylamino, arylamino, and cyclic amino groups. The term "ureido" as employed herein refers to a substituted or unsubstituted urea moiety.

The term "radical" as used herein means a chemical moiety comprising one or more unpaired electrons.

A moiety that is substituted is one in which one or more hydrogens have been independently replaced with another chemical substituent. As a non-limiting example, substituted phenyls include 2-fluorophenyl, 3,4-dichlorophenyl, 3-chloro-4-fluoro-phenyl, 2-fluoro-3-propylphenyl. As another non-limiting example, substituted n-octyls include 2,4-dimethyl-5-ethyl-octyl and 3-cyclopentyl-octyl. Included within this definition are methylenes (—$CH_2$—) substituted with oxygen to form carbonyl —CO—).

An "unsubstituted" moiety as defined above (e.g., unsubstituted cycloalkyl, unsubstituted heteroaryl, etc.) means that moiety as defined above that does not have any of the optional substituents for which the definition of the moiety (above) otherwise provides. Thus, for example, while an "aryl" includes phenyl and phenyl substituted with a halo, "unsubstituted aryl" does not include phenyl substituted with a halo.

Examples of kinases that are inhibited by the compounds and compositions described herein and against which the methods described herein are useful include, but are not limited to, c-Met and KDR.

Depending on the particular condition, or disease, to be treated, additional therapeutic agents, which could be normally administered to treat that condition, may also be present in the compositions of this invention. In other words, compounds of this invention can be administered as the sole pharmaceutical agent or in combination with one or more other additional therapeutic (pharmaceutical) agents where the combination causes no unacceptable adverse effects. This may be of particular relevance for the treatment of hyperproliferative diseases such as cancer. In this instance, the compound of this invention can be combined with known cytotoxic agents, signal transduction inhibitors, or with other anti-cancer agents, as well as with admixtures and combinations thereof. As used herein, additional therapeutic agents that are normally administered to treat a particular disease, or condition, are known as "appropriate for the disease, or condition, being treated". As used herein, "additional therapeutic agents" is meant to include chemotherapeutic agents and other anti-proliferative agents.

For example, chemotherapeutic agents or other anti-proliferative agents may be combined with the compounds of this invention to treat proliferative disease or cancer. Examples of chemotherapeutic agents or other anti-proliferative agents include HDAC inhibitors including, but are not limited to, SAHA, MS-275, MG0103, and those described in WO 2006/010264, WO 03/024448, WO 2004/069823, US 2006/0058298, US 2005/0288282, WO 00/71703, WO 01/38322, WO 01/70675, WO 03/006652, WO 2004/035525, WO 2005/030705, WO 2005/092899, and demethylating agents including, but not limited to, 5-aza-dC, Vidaza and Decitabine and those described in U.S. Pat. No. 6,268,137, U.S. Pat. No. 5,578,716, U.S. Pat. No. 5,919,772, U.S. Pat. No. 6,054,439, U.S. Pat. No. 6,184,211, U.S. Pat. No. 6,020,318, U.S. Pat. No. 6,066,625, U.S. Pat. No. 6,506,735, U.S. Pat. No. 6,221,849, U.S. Pat. No. 6,953,783, U.S. Ser. No. 11/393,380 and PCT/US2006/001791.

In another embodiment of the present invention, for example, chemotherapeutic agents or other anti-proliferative agents may be combined with the compounds of this invention to treat proliferative diseases and cancer. Examples of known chemotherapeutic agents include, but are not limited to, for example, other therapies or anticancer agents that may be used in combination with the inventive anticancer agents of the present invention and include surgery, radiotherapy (in but a few examples, gamma-radiation, neutron beam radiotherapy, electron beam radiotherapy, proton therapy, brachytherapy, and systemic radioactive isotopes, to name a few), endocrine therapy, taxanes (taxol, taxotere etc), platinum derivatives, biologic response modifiers (interferons, interleukins, and tumor necrosis factor (TNF), TRAIL receptor targeting agents, to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate, Pemetrexed etc), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), Cell cycle inhibitors (KSP mitotic kinesin inhibitors, CENP-E and CDK inhibitors), enzymes (Asparaginase), and hormones (Tamoxifen, Leuprolide, Flutamide, and Megestrol), Gleevec™, adriamycin, dexamethasone, and cyclophosphamide. Antiangiogenic agents (Avastin and others). Kinase inhibitors (Imatinib (Gleevec), Sutent, Nexavar, Erbitux, Herceptin, Tarceva, Iressa and others). Agents inhibiting or activating cancer pathways such as the mTOR, HIF (hypoxia induced factor) pathways and others. For a more comprehensive discussion of updated cancer therapies see, http://www.nci.nih.gov/, a list of the FDA approved oncology drugs at http://www.fda.gov/cder/cancer/druglistframe.htm, and The Merck Manual, Eighteenth Ed. 2006, the entire contents of which are hereby incorporated by reference.

In another embodiment, the compounds of the present invention can be combined with cytotoxic anti-cancer agents. Examples of such agents can be found in the 13th Edition of the Merck Index (2001) These agents include, by no way of limitation, asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other cytotoxic drugs suitable for use with the compounds of the invention include, but are not limited to, those compounds acknowledged to be used in the treatment of neoplastic diseases, such as those for example in Goodman and Gilman's The Pharmacological Basis of Therapeutics (Ninth Edition, 1996, McGraw-Hill). These agents include, by no way of limitation, aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other cytotoxic anti-cancer agents suitable for use in combination with the compounds of the invention also include newly discovered cytotoxic principles such as oxaliplatin, gemcitabine, capecitabine, epothilone and its natural or synthetic derivatives, temozolomide (Quinn et al., J. Clin. Oncology 2003, 21(4), 646-651), tositumomab (Bexxar), trabedectin (Vidal et al., Proceedings of the American Society for Clinical Oncology 2004, 23, abstract 3181), and the inhibitors of the kinesin spindle protein Eg5 (Wood et al., Curr. Opin. Pharmacol. 2001, 1, 370-377).

In another embodiment, the compounds of the present invention can be combined with other signal transduction inhibitors. Of particular interest are signal transduction inhibitors which target the EGFR family, such as EGFR, HER-2, and HER-4 (Raymond et al., Drugs 2000, 60 (Suppl.1), 15-23; Harari et al., Oncogene 2000, 19 (53), 6102-6114), and their respective ligands. Examples of such agents include, by no way of limitation, antibody therapies such as Herceptin (trastuzumab), Erbitux (cetuximab), and pertuzumab. Examples of such therapies also include, by no way of limitation, small-molecule kinase inhibitors such as ZD-1839/Iressa (Baselga et al., Drugs 2000, 60 (Suppl. 1), 33-40), OSI-774/Tarceva (Pollack et al. J. Pharm. Exp. Ther. 1999, 291(2), 739-748), CI-1033 (Bridges, Curr. Med. Chem. 1999, 6, 825-843), GW-2016 (Lackey et al., 92nd AACR Meeting, New Orleans, Mar. 24-28, 2001, abstract 4582), CP-724,714 (Jani et al., Proceedings of the American Society for Clinical Oncology 2004, 23, abstract 3122), HKI-272 (Rabindran et al., Cancer Res. 2004, 64, 3958-3965), and EKB-569 (Greenberger et al., 11th NCI-EORTC-AACR Symposium on New Drugs in Cancer Therapy, Amsterdam, Nov. 7-10, 2000, abstract 388).

In another embodiment, the compounds of the present invention can be combined with other signal transduction inhibitors targeting receptor kinases of the split-kinase domain families (VEGFR, FGFR, PDGFR, flt-3, c-kit, c-fms, and the like), and their respective ligands. These agents include, by no way of limitation, antibodies such as Avastin (bevacizumab). These agents also include, by no way of limitation, small-molecule inhibitors such as STI-571/Gleevec (Zvelebil, Curr. Opin. Oncol., Endocr. Metab. Invest. Drugs 2000, 2(1), 74-82), PTK-787 (Wood et al., Cancer Res. 2000, 60(8), 2178-2189), SU-11248 (Demetri et al., Proceedings of the American Society for Clinical Oncology 2004, 23, abstract 3001), ZD-6474 (Hennequin et al., 92nd AACR Meeting, New Orleans, Mar. 24-28, 2001, abstract 3152), AG-13736 (Herbst et al., Clin. Cancer Res. 2003, 9, 16 (suppl 1), abstract C253), KRN-951 (Taguchi et al., 95<th> AACR Meeting, Orlando, Fla., 2004, abstract 2575), CP-547,632 (Beebe et al., Cancer Res. 2003, 63, 7301-7309), CP-673,451 (Roberts et al., Proceedings of the American Association of Cancer Research 2004, 45, abstract 3989), CHIR-258 (Lee et al., Proceedings of the American Association of Cancer Research 2004, 45, abstract 2130), MLN-518 (Shen et al., Blood 2003, 102, 11, abstract 476), and AZD-2171 (Hennequin et al., Proceedings of the American Association of Cancer Research 2004, 45, abstract 4539).

In another embodiment, the compounds of the present invention can be combined with inhibitors of the Raf/MEK/ERK transduction pathway (Avruch et al., Recent Prog. Horm. Res. 2001, 56, 127-155), or the PKB (akt) pathway (Lawlor et al., J. Cell Sci. 2001, 114, 2903-2910). These include, by no way of limitation, PD-325901 (Sebolt-Leopold et al., Proceedings of the American Association of Cancer Research 2004, 45, abstract 4003), and ARRY-142886 (Wallace et al., Proceedings of the American Association of Cancer Research 2004, 45, abstract 3891).

In another embodiment, the compounds of the present invention can be combined with inhibitors of histone deacetylase. Examples of such agents include, by no way of limitation, suberoylanilide hydroxamic acid (SAHA), LAQ-824 (Ottmann et al., Proceedings of the American Society for Clinical Oncology 2004, 23, abstract 3024), LBH-589 (Beck et al., Proceedings of the American Society for Clinical Oncology 2004, 23, abstract 3025), MS-275 (Ryan et al., Proceedings of the American Association of Cancer Research 2004, 45, abstract 2452), FR-901228 (Piekarz et al., Proceedings of the American Society for Clinical Oncology 2004, 23, abstract 3028) and MGCD0103 (U.S. Pat. No. 6,897,220).

In another embodiment, the compounds of the present invention can be combined with other anti-cancer agents such as proteasome inhibitors, and m-TOR inhibitors. These include, by no way of limitation, bortezomib (Mackay et al., Proceedings of the American Society for Clinical Oncology 2004, 23, Abstract 3109), and CCI-779 (Wu et al., Proceedings of the American Association of Cancer Research 2004, 45, abstract 3849). The compounds of the present invention can be combined with other anti-cancer agents such as topoisomerase inhibitors, including but not limited to camptothecin.

Those additional agents may be administered separately from the compound-containing composition, as part of a multiple dosage regimen. Alternatively, those agents may be part of a single dosage form, mixed together with the compound of this invention in a single composition. If administered as part of a multiple dosage regimen, the two active agents may be submitted simultaneously, sequentially or within a period of time from one another which would result in the desired activity of the agents.

The amount of both the compound and the additional therapeutic agent (in those compositions which comprise an additional therapeutic agent as described above) that may be combined with the carrier materials to produce a single dosage form will vary depending upon the host treated and the particular mode of administration.

In those compositions which comprise an additional therapeutic agent, that additional therapeutic agent and the compound of this invention may act synergistically.

Throughout the specification, preferred embodiments of one or more chemical substituents are identified. Also preferred are combinations of preferred embodiments, for example, preferred embodiments of E and preferred embodiments of T. Furthermore, compounds excluded from any one particular genus of compounds (e.g., through a proviso clause) are intended to be excluded from the scope of the invention entirely, including from other disclosed genera, unless expressly stated to the contrary.

Compounds

In the first aspect, the invention comprises compounds of formula (A), that are inhibitors of VEGF receptor signaling and HGF receptor signaling:

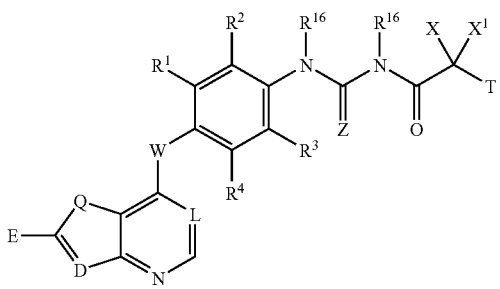

and N-oxides, hydrates, solvates, pharmaceutically acceptable salts, prodrugs and complexes thereof, wherein T is selected from the group consisting of arylalkyl, cycloalkyl, heterocyclyl, aryl and heteroaryl, wherein each of said arylalkyl, cycloalkyl, heterocyclyl, aryl and heteroaryl is optionally substituted with 1 to 3 independently selected $R^{20}$;

each $R^{20}$ is independently selected from the group consisting of —H, halogen, trihalomethyl, —CN, —$NO_2$, —$NH_2$, —$OR^{17}$, —$OCF_3$, —$NR^{17}R^{18}$, —$S(O)_{0-2}R^{17}$, —$S(O)_2NR^{17}R^{17}$, —$C(O)OR^{17}$, —$C(O)NR^{17}R^{17}$, —$N(R^{17})SO_2R^{17}$, —$N(R^{17})C(O)R^{17}$, —$N(R^{17})C(O)OR^{17}$, —$C(O)R^{17}$, —$C(O)SR^{17}$, $C_1$-$C_4$ alkoxy, $C_1$-$C_4$ alkylthio, —$O(CH_2)_n$aryl, —$O(CH_2)_n$heteroaryl, —$(CH_2)_{0-5}$(aryl), —$(CH_2)_{0-5}$(heteroaryl), $C_1$-$C_6$ alkyl, $C_2$-$C_6$ alkenyl, $C_2$-$C_6$ alkynyl, —$CH_2(CH_2)_{0-4}$-$T^2$, an optionally substituted $C_{1-4}$ alkylcarbonyl, $C_{1-4}$ alkoxy, an amino optionally substituted by $C_{1-4}$ alkyl optionally substituted by $C_{1-4}$ alkoxy and a saturated or unsaturated three- to seven-membered carboxylic or heterocyclic group, wherein $T^2$ is selected from the group consisting of —OH, —OMe, —OEt, —$NH_2$, —NHMe, —$NMe_2$, —NHEt and —$NEt_2$, and wherein the aryl, heteroaryl, $C_1$-$C_6$ alkyl, $C_2$-$C_6$ alkenyl, and $C_2$-$C_6$ alkynyl are optionally substituted;

W is selected from the group consisting of O, S, NH and NMe;

Z is selected from the group consisting of O, or S and NH;

X and $X^1$ are independently selected from the group consisting of H, $C_1$-$C_6$ alkyl, halo, cyano, or nitro, wherein $C_1$-$C_6$ alkyl is optionally substituted, or X and $X^1$ taken together with the atom to which they are attached, form a $C_3$-$C_7$ cycloalkyl;

$R^1$, $R^2$, $R^3$ and $R^4$ independently represent hydrogen, halo, trihalomethyl, —CN, —$NO_2$, —$NH_2$, —$OR^{17}$, —$NR^{17}R^{18}$, —$C(O)OR^{17}$, —$C(O)R^{17}$, $C_1$-$C_4$ alkoxy, $C_1$-$C_4$ alkylthio, $C_1$-$C_6$ alkyl, $C_2$-$C_6$ alkenyl or $C_2$-$C_6$ alkynyl, wherein $C_1$-$C_6$ alkyl, $C_2$-$C_6$ alkenyl and $C_2$-$C_6$ alkynyl are optionally substituted;

$R^{17}$ is selected from the group consisting of H and $R^{18}$;

$R^{18}$ is selected from the group consisting of a ($C_1$-$C_6$)alkyl, an aryl, a aryl($C_1$-$C_6$)alkyl, a heterocyclyl and a heterocyclyl ($C_1$-$C_6$)alkyl, each of which is optionally substituted, or $R^{17}$ and $R^{18}$, taken together with a common nitrogen to which they are attached, form an optionally substituted five- to seven-membered heterocyclyl, the optionally substituted five- to seven-membered heterocyclyl optionally containing at least one additional annular heteroatom selected from the group consisting of N, O, S and P;

$R^{16}$ is selected from the group consisting of —H, —CN, —$(CH_2)_{0-5}$(aryl), —$(CH_2)_{0-5}$(heteroaryl), $C_1$-$C_6$ alkyl, $C_2$-$C_6$ alkenyl, $C_2$-$C_6$ alkynyl, —$CH_2(CH_2)_{0-4}$-$T^2$, an optionally substituted $C_{1-4}$ alkylcarbonyl, and a saturated or unsaturated three- to seven-membered carboxylic or heterocyclic group, wherein $T^2$ is selected from the group consisting of —OH, —OMe, —OEt, —$NH_2$, —NHMe, —$NMe_2$, —NHEt and —$NEt_2$, and wherein the aryl, heteroaryl, $C_1$-$C_6$ alkyl, $C_2$-$C_6$ alkenyl, and $C_2$-$C_6$ alkynyl are optionally substituted;

Q is selected from the group consisting of $CH_2$, O, S, N(H), N($C_1$-$C_6$ alkyl), N—Y-(aryl), —N—OMe, —$NCH_2OMe$ and —N-Bn;

D is selected from the group consisting of C-E and N;

L is N, or CR, wherein R is selected from the group consisting of —H, halo, —CN, $C_1$-$C_6$ alkyl, $C_2$-$C_6$ alkenyl, and $C_2$-$C_6$ alkynyl, wherein $C_1$-$C_6$ alkyl, $C_2$-$C_6$ alkenyl, and $C_2$-$C_6$ alkynyl are optionally substituted; and E is selected from the group consisting of $E^1$, $E^2$ and $E^3$, wherein $E^1$ is selected from the group consisting of —H, halogen, nitro, azido, $C_1$-$C_6$ alkyl, $C_3$-$C_{10}$ cycloalkyl, —C(O) $NR^{42}R^{43}$, —Y—$NR^{42}R^{43}$, —$NR^{42}C(=O)R^{43}$, —$SO_2R^{42}$, —$SO_2NR^{42}R^{43}$, —$NR^{37}SO_2R^{42}$, —$NR^{37}SO_2NR^{42}R^{43}$, —C(=N—$OR^{42}$)$R^{43}$, —C(=$NR^{42}$)$R^{43}$, —$NR^{37}C(=NR^{42})R^{43}$, —C(=$NR^{42}$) $NR^{37}R^{43}$, —$NR^{37}C(=NR^{42})NR^{37}R^{43}$, —$C(O)R^{42}$, —$CO_2R^{42}$, —C(O)(heterocyclyl), —C(O)($C_6$-$C_{10}$ aryl), —C(O)(heteroaryl), —Y—($C_6$-$C_{10}$ aryl), —Y-(heteroaryl), —Y-(5-10 membered heterocyclic), —$NR^{6a}R^{6b}$, —$NR^{6a}SO_2R^{6b}$, —$NR^{6a}C(O)R^{6b}$, —$OC(O)R^{6b}$, —$NR^{6a}C(O)OR^{6b}$, —$OC(O)NR^{6a}R^{6b}$, —$OR^{6a}$, $SR^{6a}$, —$S(O)R^{6a}$, —$SO_2R^{6a}$, —$SO_3R^{6a}$, —$SO_2NR^{6a}R^{6b}$, —$SO_2NR^{42}R^{43}$, —$COR^{6a}$, —$CO_2R^{6a}$, —$CONR^{6a}R^{6b}$, —($C_1$-$C_4$)fluoroalkyl, —($C_1$-$C_4$)fluoroalkoxy, —($CZ^3Z^4$)$_a$CN, wherein n is an integer ranging from 0 to 6, and the aforementioned $E^1$ groups other than —H and halogen are optionally substituted by 1 to 5 independently selected $R^{38}$, or $E^1$ is selected from a moiety selected from the group consisting of —($CZ^3Z_4$)$_a$-aryl, —($CZ^3Z^4$)$_a$-heterocycle, ($C_2$-$C_6$)alkynyl, —($CZ^3Z^4$)$_a$—($C_3$-$C_6$)cycloalkyl, —($CZ^3Z^4$)$_a$-($C_5$-$C_6$)cycloalkenyl, ($C_2$-$C_6$) alkenyl and ($C_1$-$C_6$)alkyl, which is optionally substituted with 1 to 3 independently selected $Y^2$ groups, where a is 0, 1, 2, or 3, and wherein when a is 2 or 3, the $CZ^3Z^4$ units may be the same or different; wherein each $R^{38}$ is independently selected from halo, cyano, nitro, trifluoromethoxy, trifluoromethyl, azido, —$C(O)R^{40}$, —$C(O)OR^{40}$, —$OC(O)R^{40}$, —$OC(O)OR^{40}$, —$NR^{36}C(O)$ $R^{39}$, —$C(O)NR^{36}R^{39}$, —$NR^{36}R^{39}$, —$OR^{37}$, —$SO_2NR^{36}R^{39}$, $C_1$-$C_6$ alkyl, —$(CH_2)_jO(CH_2)_iNR^{36}R^{39}$, —$(CH_2)_nO(CH_2)_iOR^{37}$, —$(CH_2)_nOR^{37}$, —$S(O)_j(C_1$-$C_6$ alkyl), —$(CH_2)_n(C_6$-$C_{10}$ aryl), —$(CH_2)_n(C_5$-$C_{10}$ heteroaryl), —$(CH_2)_n$(5-10 membered heterocyclyl); —C(O) $(CH_2)_n(C_6$-$C_{10}$ aryl), —$(CH_2)_nO(CH_2)_j(C_6$-$C_{10}$ aryl), —$(CH_2)_nO(CH_2)_i$(5-10 membered heterocyclyl), —C(O) $(CH_2)_n$(5-10 membered heterocyclyl), —$(CH_2)_jNR^{39}$ $-(CH_2)_iNR^{36}R^{39}$, $-(CH_2)_jNR^{39}CH_2C(O)NR^{36}R^{39}$, $-(CH_2)_jNR^{39}(CH_2)_iNR^{37}C(O)R^{40}$, $-(CH_2)_jNR^{39}(CH_2)_nO(CH_2)_iOR^{37}$, $-(CH_2)_jNR^{39}(CH_2)_iS(O)_j(C_1-C_6$ alkyl), $-(CH_2)_jNR^{39}(CH_2)_nR^{36}$, $-SO_2(CH_2)_n(C_6-C_{10}$ aryl), $-SO_2(CH_2)_n$(5-10 membered heterocyclyl), $-(CH_2)_nNR^{36}R^{39}$, $-NR^{37}SO_2NR^{36}R^{39}$, $SO_2R^{36}$, $C_2-C_6$ alkenyl, $C_3-C_{10}$ cycloalkyl and $C_1-C_6$ alkylamino, wherein j is an integer ranging from 0 to 2, n is an integer ranging from 0 to 6, i is an integer ranging from 0 to 6, the $-(CH_2)_i-$ and $-(CH_2)_n-$ moieties of the foregoing $R^{38}$ groups optionally include a carbon-carbon double or triple bond where n is an integer between 2 and 6, and the alkyl, aryl, heteroaryl and heterocyclyl moieties of the foregoing $R^{38}$ groups are optionally substituted by one or more substituents independently selected from the group consisting of halo, cyano, nitro, trifluoromethyl, azido, $-OH$, $-C(O)R^{40}$, $-C(O)OR^{40}$, $-OC(O)R^{40}$, $-OC(O)OR^{40}$, $-NR^{36}C(O)R^{39}$, $-C(O)NR^{36}R^{39}$, $-(CH_2)_nNR^{36}R^{39}$, $C_1-C_6$ alkyl, $C_3-C_{10}$cycloalkyl, $-(CH_2)_n(C_6-C_{10}$ aryl), $-(CH_2)_n$(5-10 membered heterocyclyl), $-(CH_2)_nO(CH_2)_iOR^{37}$, and $-(CH_2)_nOR^{37}$, wherein n is an integer ranging from 0 to 6 and i is an integer ranging from 2 to 6;

each $R^{42}$ and $R^{43}$ is independently selected from the group consisting of H, $C_1-C_6$ alkyl, $C_1-C_6$ heteroalkyl, $-Y-(C_3-C_{10}$ cycloalkyl), $-Y-(C_6-C_{10}$ aryl), $-Y-(C_6-C_{10}$ heteroaryl), $-Y$-(5-10 membered heterocyclic), $-Y-O-Y^1-OR^{37}$, $-Y^1-CO_2-R^{37}$, and $-Y-OR^{37}$, wherein the alkyl, heteroalkyl, cycloalkyl, aryl, heteroaryl and heterocyclic moieties of the foregoing $R^{42}$ and $R^{43}$ groups are optionally substituted by 1 or more substituents independently selected from $R^{44}$, wherein Y is a bond or is $-(C(R^{37})(H))_n$, n is an integer ranging from 1 to 6, and $Y^1$ is $-(C(R^{37})(H))_n$, or $R^{42}$ and $R^{43}$ taken together with the nitrogen to which they are attached form a $C_5-C_9$ heterocyclyl ring or a heteroaryl ring, wherein said ring is optionally substituted by 1 to 5 independently selected $R^{44}$ substituents, with the proviso that $R^{42}$ and $R^{43}$ are not both bonded to the nitrogen directly through an oxygen;

each $R^{44}$ is independently selected from the group consisting of halo, cyano, nitro, trifluoromethoxy, trifluoromethyl, azido, $-C(O)R^{40}$, $-C(O)OR^{40}$, $-OC(O)R^{40}$, $-OC(O)OR^{40}$, $-NR^{36}C(O)R^{39}$, $-C(O)NR^{36}R^{39}$, $-NR^{36}R^{39}$, $-OR^{37}$, $-SO_2NR^{36}R^{39}$, $-SO_2R^{36}$, $-NR^{36}SO_2R^{39}$, $-NR^{36}SO_2NR^{37}R^{41}$, $C_1-C_6$ alkyl, $C_2-C_6$ alkenyl, $C_2-C_6$ alkynyl, $C_3-C_{10}$ cycloalkyl, $-C_1-C_6$ alkylamino, $-(CH_2)_jO(CH_2)_iNR^{36}R^{39}$, $-(CH_2)_nO(CH_2)_iOR^{37}$, $-(CH_2)_nOR^{37}$, $-S(O)_j(C_1-C_6$ alkyl), $-(CH_2)_n(C_6-C_{10}$ aryl), $-(CH_2)_n$(5-10 membered heterocyclic), $-C(O)(CH_2)_n(C_6-C_{10}$ aryl), $-(CH_2)_nO(CH_2)_j(C_6-C_{10}$ aryl), $-(CH_2)_nO(CH_2)_i$(5 to 10 membered heterocyclic), $-C(O)(CH_2)_n$(5 to 10 membered heterocyclic), $-(CH_2)_jNR^{39}(CH_2)_iNR^{36}R^{39}$, $-(CH_2)_jNR^{39}CH_2C(O)NR^{36}R^{39}$, $-(CH_2)_jNR^{39}(CH_2)_iNR^{37}C(O)R^{40}$, $-(CH_2)_jNR^{39}(CH_2)_iO(CH_2)_iOR^{37}$, $-(CH_2)_jNR^{39}(CH_2)_iS(O)_j(C_1-C_6$ alkyl), $-(CH_2)_jNR^{39}(CH_2)_nR^{36}$, $-SO_2(CH_2)_n(C_6-C_{10}$ aryl), and $-SO_2(CH_2)_n$(5 to 10 membered heterocyclic) wherein, j is an integer from 0 to 2, n is an integer from 0 to 6 and i is an integer ranging from 2 to 6, the $-(CH_2)_i-$ and $-(CH_2)_{n1}-$ moieties of the foregoing $R^{44}$ groups optionally include a carbon-carbon double or triple bond wherein n is an integer from 2 to 6, and the alkyl, aryl and heterocyclic moieties of the foregoing $R^{44}$ groups are optionally substituted by 1 or more substituents independently selected from the group consisting of halo, cyano, nitro, trifluoromethyl, azido, $-OH$, $-C(O)R^{40}$, $-C(O)OR^{40}$, $-OC(O)R^{40}$, $-OC(O)OR^{40}$, $-NR^{36}C(O)R^{39}$, $-C(O)NR^{36}R^{39}$, $-(CH_2)_nNR^{36}R^{39}$, $-SO_2R^{36}$, $-SO_2NR^{36}R^{39}$, $C_1-C_6$ alkyl, $C_3-C_{10}$ cycloalkyl, $-(CH_2)_n(C_6-C_{10}$ aryl), $-(CH_2)_n$(5 to 10 membered heterocyclic), $-(CH_2)_nO(CH_2)_iOR^{37}$ and $-(CH_2)_nOR^{37}$, wherein n is an integer from 0 to 6 and i is an integer from 2 to 6; and each $R^{40}$ is independently selected from H, $C_1-C_{10}$ alkyl, $-(CH_2)_n(C_6-C_{10}$ aryl), $C_3-C_{10}$ cycloalkyl, and $-(CH_2)_n$(5-10 membered heterocyclic), wherein n is an integer ranging from 0 to 6;

each $R^{36}$ and $R^{39}$ is independently selected from the group consisting of H, $-OH$, $C_1-C_6$ alkyl, $C_3-C_{10}$ cycloalkyl, $-(CH_2)_n(C_6-C_{10}$ aryl), $-(CH_2)_n$(5-10 membered heterocyclic), $-(CH_2)_nO(CH_2)_iOR^{37}$, $-(CH_2)_nCN$ $(CH_2)_nOR^{37}$, $-(CH_2)_nCN(CH_2)_nR^{37}$, and $-(CH_2)_nOR^{37}$, wherein n is an integer ranging from 0 to 6 and i is an integer ranging from 2 to 6, and the alkyl, aryl and heterocyclic moieties of the foregoing $R^{36}$ and $R^{39}$ groups are optionally substituted by one or more substituents independently selected from $-OH$, halo, cyano, nitro, trifluoromethyl, azido, $-C(O)R^{40}$, $-C(O)OR^{40}$, $-CO(O)R^{40}$, $-OC(O)OR^{40}$, $-NR^{37}C(O)R^{41}$, $-C(O)NR^{37}R^{41}$, $-NR^{37}R^{41}$, $-C_1-C_6$ alkyl, $-(CH_2)_n(C_6-C_{10}$ aryl), $-(CH_2)_n$(5 to 10 membered heterocyclic), $-(CH_2)_nO(CH_2)_iOR^{37}$, and $-(CH_2)_nOR^{37}$, wherein n is an integer ranging from 0 to 6 and i is an integer ranging from 2 to 6, with the proviso that when $R^{36}$ and $R^{39}$ are both attached to the same nitrogen, then $R^{36}$ and $R^{39}$ are not both bonded to the nitrogen directly through an oxygen;

each $R^{37}$ and $R^{41}$ is independently selected from the group consisting of H, $OR^{36}$, $C_1-C_6$ alkyl and $C_3-C_{10}$ cycloalkyl;

each $R^{6a}$ and $R^{6b}$ is independently selected from the group consisting of hydrogen, $-(CZ^5Z^6)_u-(C_3-C_6)$cycloalkyl, $-(CZ^5Z^6)_u-(C_5-C_6)$cycloalkenyl, $-(CZ^5Z^6)_u$-aryl, $-(CZ^5Z^6)_u$-heteroaryl, $-(CZ^5Z^6)_u$-heterocycle, $(C_2-C_6)$ alkenyl, and $(C_1-C_6)$alkyl, each of which is optionally substituted with 1 to 3 independently selected $Y^3$ groups, where u is 0, 1, 2, or 3, and wherein when u is 2 or 3, the $CZ^5Z^6$ units may be the same or different, or $R^{6a}$ and $R^{6b}$ taken together with adjacent atoms can form a heterocycle;

each $Z^3$, $Z^4$, $Z^5$ and $Z^6$ is independently selected from the group consisting of H, F and $(C_1-C_6)$alkyl, or each $Z^3$ and $Z^4$, or $Z^5$ and $Z^6$ are selected together to form a carbocycle, or two $Z^3$ groups on adjacent carbon atoms are selected together to optionally form a carbocycle;

each $Y^2$ and $Y^3$ is independently selected from the group consisting of halogen, cyano, nitro, tetrazolyl, guanidino, amidino, methylguanidino, azido, $-C(O)Z^7$, $-OC(O)NH_2$, $-OC(O)NHZ^7$, $-OC(O)NZ^7Z^8$, $-NHC(O)Z^7$, $-NHC(O)NH_2$, $-NHC(O)NHZ^7$, $-NHC(O)NZ^7Z^8$, $-C(O)OH$, $-C(O)OZ^7$, $-C(O)NH_2$, $-C(O)NHZ^7$, $-C(O)NZ^7Z^8$, $-P(O)_3H_2$, $-P(O)_3(Z^7)_2$, $-S(O)_3H$, $-S(O)Z^7$, $-S(O)_2Z^7$, $-S(O)_3Z^7$, $-Z^7$, $-OZ^7$, $-OH$, $-NH_2$, $-NHZ^7$, $-NZ^7Z^8$, $-C(=NH)NH_2$, $-C(=NOH)NH_2$, $-N$-morpholino, $(C_1-C_6)$alkyl, $(C_2-C_6)$alkenyl, $(C_2-C_6)$alkynyl, $(C_1-C_6)$haloalkyl, $(C_2-C_6)$haloalkenyl, $(C_2-C_6)$haloalkynyl, $(C_1-C_6)$haloalkoxy, $-(CZ^9Z^{10})_rNH_2$, $-(CZ^9Z^{10})_rNHZ^3$, $-(CZ^9Z^{10})_rNZ^7Z^8$, $-X^6(CZ^9Z^{10})_r-(C_3-C_8)$cycloalkyl, $-X^6(CZ^9Z^{10})_r-(C_5-C_8)$cycloalkenyl, $-X^6(CZ^9Z^{10})_r$-aryl and $-X^6(CZ^9Z^{10})_r$-heterocycle, wherein r is 1, 2, 3 or 4;

$X^6$ is selected from the group consisting of O, S, NH, —C(O)—, —C(O)NH—, —C(O)O—, —S(O)—, —S(O)$_2$— and —S(O)$_3$—;

$Z^7$ and $Z^8$ are independently selected from the group consisting of an alkyl of 1 to 12 carbon atoms, an alkenyl of 2 to 12 carbon atoms, an alkynyl of 2 to 12 carbon atoms, a cycloalkyl of 3 to 8 carbon atoms, a cycloalkenyl of 5 to 8 carbon atoms, an aryl of 6 to 14 carbon atoms, a heterocycle of 5 to 14 ring atoms, an aralkyl of 7 to 15 carbon atoms, and a heteroaralkyl of 5 to 14 ring atoms, or $Z^7$ and $Z^8$ together may optionally form a heterocycle;

$Z^9$ and $Z^{10}$ are independently selected from the group consisting of H, F, a $(C_1-C_{12})$alkyl, a $(C_6-C_{14})$aryl, a $(C_5-C_{14})$heteroaryl, a $(C_7-C_{15})$aralkyl and a $(C_5-C_{14})$heteroaralkyl, or $Z^9$ and $Z^{10}$ are taken together form a carbocycle, or two $Z^9$ groups on adjacent carbon atoms are taken together to form a carbocycle; or any two $Y^2$ or $Y^3$ groups attached to adjacent carbon atoms may be taken together to be —O[C($Z^9$)($Z^{10}$)]$_r$O or —O[C($Z^9$)($Z^{10}$)]$_{r+1}$, or any two $Y^2$ or $Y^3$ groups attached to the same or adjacent carbon atoms may be selected together to form a carbocycle or heterocycle; and wherein any of the above-mentioned substituents comprising a $CH_3$ (methyl), $CH_2$ (methylene), or CH (methine) group which is not attached to a halogen, SO or $SO_2$ group or to a N, O or S atom optionally bears on said group a substituent selected from hydroxy, halogen, $(C_1-C_4)$alkyl, $(C_1-C_4)$alkoxy and an —N[$(C_1-C_4)$alkyl][$(C_1-C_4)$alkyl];

$E_2$ is —C≡CH or —C≡C—(CR$^{45}$R$^{45}$)$_n$R$^{46}$;

$R^{45}$ is independently selected from the group consisting of H, a $(C_1-C_6)$alkyl and a $(C_3-C_8)$cycloalkyl;

$R^{46}$ is selected from the group consisting of heterocyclyl, —N($R^{47}$)—C(O)—N($R^{47}$)($R^{48}$), —N($R^{47}$)—C(S)—N($R^{47}$)($R^{48}$), —N($R^{47}$)—C(O)—OR$^{48}$, —N($R^{47}$)—C(O)—(CH$_2$)$_n$—R$^{48}$, —N($R^{47}$)—SO$_2$R$^{47}$, —(CH$_2$)$_n$NR$^{47}$R$^{48}$, —(CH$_2$)$_n$OR$^{48}$, —(CH$_2$)$_n$SR$^{49}$, —(CH$_2$)$_n$S(O)R$^{49}$, —(CH$_2$)$_n$S(O)$_2$R$^{49}$, —OC(O)R$^{49}$, —OC(O)OR$^{49}$, —C(O)NR$^{47}$R$^{48}$, heteroaryl optionally substituted with one or more substituents selected from the group consisting of halo, —CF$_3$, $(C_1-C_6)$alkoxy, —NO$_2$, $(C_1-C_6)$alkyl, —CN, —SO$_2$R$^{50}$ and —(CH$_2$)$_n$NR$^{50}$R$^{51}$, and aryl optionally substituted with one or more substituents selected from the group consisting of halo, —CF$_3$, $(C_1-C_6)$alkoxy, —NO$_2$, $(C_1-C_6)$alkyl, —CN, —SO$_2$R$^{50}$ and —(CH$_2$)$_n$NR$^{50}$R$^{51}$;

$R^{47}$ and $R^{48}$ are independently selected from the group consisting of H, $(C_1-C_6)$alkyl, $(C_3-C_8)$cycloalkyl, heterocyclyl, —(CH$_2$)$_n$NR$^{50}$R$^{51}$, —(CH$_2$)$_n$OR$^{50}$, (CH$_2$)$_n$C(O)R$^{49}$, —C(O)R$^{49}$, —(CH$_2$)$_n$SR$^{49}$, —(CH$_2$)$_n$S(O)R$^{49}$, —(CH$_2$)$_n$S(O)$_2$R$^{49}$, —(CH$_2$)$_n$R$^{49}$, —(CH$_2$)$_n$CN, aryl optionally substituted with one or more substituents selected from the group consisting of halo, —CF$_3$, $(C_1-C_6)$alkoxy, —NO$_2$, $(C_1-C_6)$alkyl, —CN, —(CH$_2$)$_n$OR$^{49}$, —(CH$_2$)$_n$heterocyclyl, —(CH$_2$)$_n$heteroaryl, —SO$_2$R$^{50}$ and —(CH$_2$)$_n$NR$^{50}$R$^{51}$, and heteroaryl optionally substituted with one or more substituents selected from the group consisting of halo, —CF$_3$, $(C_1-C_6)$alkoxy, —NO$_2$, $(C_1-C_6)$alkyl, —CN, —(CH$_2$)$_n$OR$^{49}$, —(CH$_2$)$_n$heterocyclyl, —(CH$_2$)$_n$heteroaryl, —SO$_2$R$^{50}$ and —(CH$_2$)$_n$NR$^{50}$OR$^{51}$, or $R^{47}$ and $R^{48}$, together with the atom to which they are attached, form a 3-8 membered ring;

$R^{49}$ is selected from the group consisting of $(C_1-C_6)$alkyl, $(C_3-C_8)$cycloalkyl, heterocyclyl$(C_1-C_6)$alkylene, aryl$(C_1-C_6)$alkylene wherein the aryl is optionally substituted with one or more substituents selected from the group consisting of halo, —CF$_3$, $(C_1-C_6)$alkoxy, —NO$_2$, $(C_1-C_6)$alkyl, —CN, —SO$_2$R$^{50}$ and —(CH$_2$)$_n$NR$^{50}$R$^{51}$, heteroaryl$(C_1-C_6)$alkylene wherein the heteroaryl is optionally substituted with one or more substituents selected from the group consisting of halo, —CF$_3$, $(C_1-C_6)$alkoxy, —NO$_2$, $(C_1-C_6)$alkyl, —CN, —SO$_2$R$^{50}$ and —(CH$_2$)$_n$NR$^{50}$R$^{51}$, aryl optionally substituted with one or more substituents selected from the group consisting of halo, —CF$_3$, $(C_1-C_6)$alkoxy, —NO$_2$, $(C_1-C_6)$alkyl, —CN, —SO$_2$R$^{50}$ and —(CH$_2$)$_n$NR$^{50}$R$^{51}$, and heteroaryl optionally substituted with one or more substituents selected from the group consisting of halo, —CF$_3$, $(C_1-C_6)$alkoxy, —NO$_2$, $(C_1-C_6)$alkyl, —CN, —SO$_2$R$^{50}$ and —(CH$_2$)$_n$NR$^{50}$R$^{51}$;

$R^{50}$ and $R^{51}$ are independently selected from the group consisting of H, $(C_1-C_6)$alkyl, $(C_3-C_8)$cycloalkyl and —C(O)R$^{45}$, or $R^{50}$ and $R^{51}$, together with the atom to which they are attached, form a 3-8 membered ring; and $E^3$ is the group defined by —($Z^{11}$)—($Z^{12}$)$_m$—($Z^{13}$)$_{m1}$, wherein $Z^{11}$ is heterocyclyl or heterocyclylene;

$Z^{12}$ is selected from the group consisting of OC(O), OC(S) and C(O);

$Z^{13}$ is selected from the group consisting of heterocyclyl, aralkyl, N(H)R$^{52}$, $(C_1-C_3)$alkyl, —OR$^{52}$, halo, S(O)$_2$R$^{56}$, $(C_1-C_3)$hydroxyalkyl and $(C_1-C_3)$haloalkyl;

m is 0 or 1;

m1 is 0 or 1;

$R^{52}$ is selected from the group consisting of H, —(CH$_2$)$_q$S(O)$_2$R$^{54}$, R$^{55}$ NR$^{53}$R$^{53}$, $(C_1-C_3$alkyl), —(CH$_2$)$_q$OR$^{53}$, —C(O)R$^{54}$ and —C(O)OR$^{53}$;

q is 0, 1, 2, 3 or 4;

$R^{53}$ is $(C_1-C_3)$alkyl;

$R^{54}$ is $(C_1-C_3)$alkyl or N(H)R$^{53}$;

$R^{55}$ is $(C_1-C_6)$ alkyl; and $R^{56}$ is selected from the group consisting of NH$_2$, $(C_1-C_3)$alkyl and OR$^{52}$.

In a preferred embodiment of the compounds according to the present invention, T is aryl or heteroaryl, wherein each of said aryl and heteroaryl is optionally substituted with 1 to 3 independently selected $R^{20}$.

In a preferred embodiment of the compounds according to the present invention, T is selected from the group consisting of arylalkyl, cycloalkyl and heterocyclyl, wherein each of said arylalkyl, cycloalkyl and heterocyclyl is optionally substituted with 1 to 3 independently selected $R^{20}$.

In a preferred embodiment of the compounds according to the present invention, $R^{20}$ is selected from the group consisting of H, halogen, —OR$^{17}$ and —C(O)OR$^{17}$.

In a preferred embodiment of the compounds according to the present invention, $R^{20}$ is fluorine or chloride.

In a preferred embodiment of the compounds according to the present invention, W is O.

In a preferred embodiment of the compounds according to the present invention, Z is S or O.

In a preferred embodiment of the compounds according to the present invention, Z is S.

In a preferred embodiment of the compounds according to the present invention, X and $X^1$ are independently selected from the group consisting of H and $C_1-C_6$alkyl, wherein the $C_1-C_6$alkyl is optionally substituted.

In a preferred embodiment of the compounds according to the present invention, X and $X^1$ are both H.

In a preferred embodiment of the compounds according to the present invention, X and $X^1$ taken together with the atom to which they are attached, form a $C_3$-$C_7$cycloalkyl.

In a preferred embodiment of the compounds according to the present invention, $R^1$, $R^2$, $R^3$ and $R^4$ are independently selected from the group consisting of H, halogen, trihalomethyl, $OR^{17}$, —$NR^{17}R^{18}$ and $C_1$-$C_6$alkyl.

In a preferred embodiment of the compounds according to the present invention, $R^1$, $R^2$ and $R^4$ are independently selected from the group consisting of H, halo and —$OR^{17}$.

In a preferred embodiment of the compounds according to the present invention, $R^1$ is H or halogen.

In a preferred embodiment of the compounds according to the present invention, $R^1$ is halogen.

In a preferred embodiment of the compounds according to the present invention, $R^2$, $R^3$ and $R^4$ are each H.

In a preferred embodiment of the compounds according to the present invention, $R^{17}$ is a $C_1$-$C_6$alkyl.

In a preferred embodiment of the compounds according to the present invention, $R^{16}$ is H or $C_1$-$C_6$alkyl.

In a preferred embodiment of the compounds according to the present invention, Q is selected from the group consisting of $CH_2$, S, —N—($C_1$-$C_6$alkyl), N—Y-(aryl) and —N—OMe.

In a preferred embodiment of the compounds according to the present invention, Q is S.

In a preferred embodiment of the compounds according to the present invention, Q is $CH_2$.

In a preferred embodiment of the compounds according to the present invention, Q is —N—($C_1$-$C_6$alkyl).

In a preferred embodiment of the compounds according to the present invention, Q is —N—Y-(aryl).

In a preferred embodiment of the compounds according to the present invention, Q is —N—OMe.

In a preferred embodiment of the compounds according to the present invention, D is C-E.

In a preferred embodiment of the compounds according to the present invention, D is CH.

In a preferred embodiment of the compounds according to the present invention, L is C—R.

In a preferred embodiment of the compounds according to the present invention, R is H or halogen.

In a preferred embodiment of the compounds according to the present invention, L is N.

In a preferred embodiment of the compounds according to the present invention, E is selected from the group consisting of $E^1$ and $E^2$.

In a preferred embodiment of the compounds according to the present invention, E is $E^1$.

In a preferred embodiment of the compounds according to the present invention, E is $E^1$, wherein $E^1$ is selected from the group consisting of H, halogen, —C(=N—$OR^{42}$)$R^{43}$, —C(O)$NR^{42}R^{43}$, —$SO_2NR^{42}R^{43}$, C(=$NR^{42}$)$NR^{37}R^{43}$, —$CO_2R^{42}$, —C(O)(heterocyclyl), —C(O)(heteroaryl), —Y—($C_6$-$C_{10}$ aryl), —Y-(heteroaryl), —Y-(5 to 10 membered heterocyclic), —$SR^{6a}$, —S(O)$R^{6a}$, —$SO_2R^{6a}$, wherein each of said $E^1$ other than H and halogen are optionally substituted with 1 to 5 independently selected $R^{38}$, or E1 is (C1-C6)alkyl, which is optionally substituted with 1 to 3 independently selected Y2 groups.

In a preferred embodiment of the compounds according to the present invention, $R^{38}$ is selected from the group consisting of halogen, —C(O)$OR^{40}$, —$NR^{36}C(O)R^{39}$, —C(O)$NR^{36}R^{39}$, —$NR^{36}R^{39}$, —$OR^{37}$, $C_1$-$C_6$alkyl, —C(CH$_2$)$_i$O(CH$_2$)$_j$$NR^{36}R^{39}$, —(CH$_2$)$_n$$OR^{37}$, —S(O)$_i$($C_1$-$C_6$alkyl), —(CH$_2$)$_n$-(5 to 10 membered heterocyclic), —(CH$_2$)$_n$O(CH$_2$)$_i$(5 to 10 membered heterocyclic), —(CH$_2$)$_n$(5 to 10 membered heteroaryl), —(CH$_2$)$_j$$NR^{39}$(CH$_2$)$_i$$NR^{36}R^{39}$, —(CH$_2$)$_j$$NR^{39}$(CH$_2$)$_n$$R^{36}$, —(CH$_2$)$_n$$NR^{36}R^{39}$, wherein j is an integer ranging from 0 to 2, n is an integer ranging from 0 to 6, i is an integer ranging from 1 to 6, the —(CH$_2$)$_i$— and —(CH$_2$)$_n$— moieties of the foregoing $R^{38}$ groups optionally include a carbon-carbon double or triple bond where n is an integer between 2 and 6, and the alkyl, aryl, heteroaryl, and heterocyclic moieties of the foregoing $R^{38}$ groups are optionally substituted by one or more substituents independently selected from the group consisting of halo, cyano, nitro, trifluoromethyl, azido, —OH, —C(O)$R^{40}$, —C(O)$OR^{40}$, —OC(O)$R^{40}$, —OC(O)$OR^{40}$, —$NR^{36}C(O)R^{39}$, —C(O)$NR^{36}R^{39}$, —(CH$_2$)$_n$$NR^{36}R^{39}$, $C_1$-$C_6$ alkyl, $C_3$-$C_{10}$ cycloalkyl, —(CH$_2$)$_n$($C_6$-$C_{10}$ aryl), —(CH$_2$)$_n$(5-10 membered heterocyclyl), —(CH$_2$)$_n$O(CH$_2$)$_i$$OR^{37}$, and —(CH$_2$)$_n$$OR^{37}$, wherein n is an integer ranging from 0 to 6 and i is an integer ranging from 2 to 6.

In a preferred embodiment of the compounds according to the present invention, the alkyl, aryl, heteroaryl, and heterocyclic moieties of the foregoing $R^{38}$ groups are optionally substituted by one or more substituents independently selected from the group consisting of —OH and —C(O)$OR^{40}$.

In a preferred embodiment of the compounds according to the present invention, each $R^{42}$ and $R^{43}$ is independently selected from the group consisting of H, —Y—($C_3$-$C_{10}$ cycloalkyl), —Y—($C_6$-$C_{10}$ aryl), —Y—($C_6$-$C_{10}$ heteroaryl) and —Y-(5 to 10 membered heterocyclic), wherein the cycloalkyl, aryl, heteroaryl and heterocyclic moieties of the foregoing $R^{42}$ and $R^{43}$ groups are optionally substituted by 1 or more substituents independently selected from $R^{44}$.

In a preferred embodiment of the compounds according to the present invention, each $R^{42}$ and $R^{43}$ is independently selected from the group consisting of H, $C_1$-$C_6$ alkyl, $C_1$-$C_6$ heteroalkyl, —$Y^1$—$CO_2$—$R^{37}$ and —Y—$OR^{37}$.

In a preferred embodiment of the compounds according to the present invention, one of $R^{42}$ and $R^{43}$ is H.

In a preferred embodiment of the compounds according to the present invention, one of $R^{42}$ and $R^{43}$ is —($C_6$-$C_{10}$ heteroaryl) or —Y-(5 to 10 membered heterocyclic).

In a preferred embodiment of the compounds according to the present invention, Y is a bond.

In a preferred embodiment of the compounds according to the present invention, Y is —(C($R^{37}$)(H))$_n$.

In a preferred embodiment of the compounds according to the present invention, $R^{42}$ and $R^{43}$ taken together with the nitrogen to which they are attached form a $C_5$-$C_9$ heterocyclyl ring or a heteroaryl ring, wherein said ring is optionally substituted by 1 to 5 independently selected $R^{44}$ substituents, with the proviso that $R^{42}$ and $R^{43}$ are not both bonded to the nitrogen directly through an oxygen.

In a preferred embodiment of the compounds according to the present invention, $R^{44}$ is independently selected from the group consisting of —C(O)$N^{36}R^{39}$, —$OR^{37}$ and $C_1$-$C_6$alkyl.

In a preferred embodiment of the compounds according to the present invention, each $R^{40}$ is independently selected from the group consisting of H and $C_1$-$C_{10}$ alkyl.

In a preferred embodiment of the compounds according to the present invention, each $R^{36}$ and $R^{39}$ is independently selected from the group consisting of H, $C_1$-$C_6$alkyl, —(CH$_2$)$_n$(5 to 10 membered heterocyclic), —(CH$_2$)$_n$$OR^{37}$ and —C(O)$OR^{40}$, wherein n is an integer ranging from 0 to 6 and i is an integer ranging from 2 to 6, with the proviso that when $R^{36}$ and $R^{39}$ are both attached to the same nitrogen, then $R^{36}$ and $R^{39}$ are not both bonded to the nitrogen directly through an oxygen.

In a preferred embodiment of the compounds according to the present invention, each $R^{37}$ and $R^{41}$ is independently selected from the group consisting of H and $C_1$-$C_6$ alkyl.

In a preferred embodiment of the compounds according to the present invention, $R^{6a}$ is selected from the group consisting of —$(CZ^5Z^6)_u$-aryl, —$(CZ^5Z^6)_u$-heteroaryl and $C_1$-$C_6$alkyl, each of which is optionally substituted with 1 to 3 independently selected $Y^3$ groups, wherein u is 0, 1, 2 or 3, and wherein when u is 2 or 3, the $CZ^5Z^6$ units may be the same or different.

In a preferred embodiment of the compounds according to the present invention, $R^{6a}$ is selected from the group consisting of —$(CZ^5Z^6)_u$-aryl and —$(CZ^5Z^6)_u$-heteroaryl, each of which is optionally substituted with 1 to 3 independently selected $Y^3$ groups, wherein u is 0.

In a preferred embodiment of the compounds according to the present invention, $Y^2$ is —OH.

In a preferred embodiment of the compounds according to the present invention, $Y^3$ is —OH.

In a preferred embodiment of the compounds according to the present invention, $E^2$ is —C≡C—$(CR^{45}R^{45})_n$—$R^{46}$ wherein n is an integer ranging from 1 to 6.

In a preferred embodiment of the compounds according to the present invention, $R^{45}$ is H.

In a preferred embodiment of the compounds according to the present invention, $R^{46}$ is a heterocyclyl.

In a preferred embodiment of the compounds according to the present invention, the compounds are represented by the formula A-0:

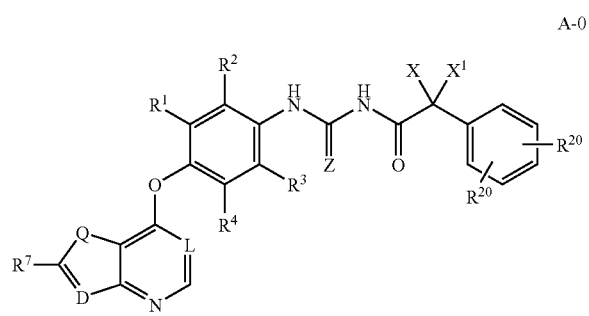

A-0 and N-oxides, hydrates, solvates, pharmaceutically acceptable salts, prodrugs and complexes thereof, wherein Z is O or S;

X and $X^1$ are independently selected from the group consisting of H, $C_1$-$C_6$ alkyl, halo, cyano and nitro, wherein $C_1$-$C_6$ alkyl is optionally substituted;

$R^1$, $R^2$, $R^3$ and $R^4$ are independently selected from the group consisting of hydrogen, halo, trihalomethyl, —$OR^{17}$, $C_1$-$C_6$ alkyl, $C_2$-$C_6$ alkenyl or $C_2$-$C_6$ alkynyl, wherein $C_1$-$C_6$ alkyl, $C_2$-$C_6$ alkenyl and $C_2$-$C_6$ alkynyl are optionally substituted;

Q is O, S, NH, N($C_1$-$C_6$ alkyl), or N—Y-(aryl);

D is $CR^{11}$, or N;

L is N, or CR, wherein R is H, halo, —CN, $C_1$-$C_6$ alkyl, $C_2$-$C_6$ alkenyl, or $C_2$-$C_6$ alkynyl, wherein $C_1$-$C_6$ alkyl, $C_2$-$C_6$ alkenyl, and $C_2$-$C_6$ alkynyl are optionally substituted; and $R^7$ is H, halogen, $C_1$-$C_6$ alkyl, —C(=O)$NR^9R^{10}$, —C(=O)(aryl), —C(=O)(heterocyclyl), —C(=O)(heteroaryl), —Y-(aryl), —Y-(heterocyclyl), —Y-(heteroaryl), —S-aryl, —S—$C_1$-$C_6$ alkyl, —SO—$C_1$-$C_6$ alkyl, —$SO_2$—$C_1$-$C_6$ alkyl, —Y—$NR^9R^{10}$, —$SO_2NR^9R^{10}$ or —$CO_2R^9$, wherein $C_1$-$C_6$ alkyl, aryl, heterocycle and heteroaryl are each independently optionally substituted;

$R^9$ and $R^{10}$ are independently selected from H, $C_1$-$C_6$ alkyl, —Y-(cycloalkyl), —Y-(aryl), —Y-(heterocyclyl), —Y-(heteroaryl), —Y—O—$Y^1$—O—$R^{11}$, —$Y^1$—$CO_2$—$R^{11}$, and —Y—O—$R^{11}$, wherein $C_1$-$C_6$ alkyl, cycloalkyl, aryl, heterocycle, and heteroaryl are each optionally substituted, or $R^9$ and $R^{10}$ taken together with the nitrogen to which they are attached form a $C_5$-$C_9$ heterocyclyl ring or a heteroaryl ring, wherein said ring is optionally substituted;

Y is a bond or is —$(C(R^{11})(H))_t$—, wherein t is an integer from 1 to 6;

$Y^1$ is —$(C(R^{11})(H))_t$—, $R^{11}$ at each occurrence is independently H or $C_1$-$C_6$ alkyl, wherein $C_1$-$C_6$ alkyl is optionally substituted, each $R^{20}$ is independently selected from the group consisting of hydrogen, halo, trihalomethyl, $OR^{17}$, $C_1$-$C_6$ alkyl, $C_2$-$C_6$ alkenyl or $C_2$-$C_6$ alkynyl, wherein $C_1$-$C_6$ alkyl, $C_2$-$C_6$ alkenyl and $C_2$-$C_6$ alkynyl are optionally substituted, and each $R^{17}$ is an independently selected $C_1$-$C_6$alkyl, wherein said $C_1$-$C_6$alkyl is optionally substituted.

In a preferred embodiment of the compounds according to the present invention, X and $X^1$ are both hydrogen.

In a preferred embodiment of the compounds according to the present invention, $R^1$ is hydrogen or halogen.

In a preferred embodiment of the compounds according to the present invention, $R^1$ is fluorine.

In a preferred embodiment of the compounds according to the present invention, $R^4$ is hydrogen or halogen.

In a preferred embodiment of the compounds according to the present invention, $R^4$ is fluorine.

In a preferred embodiment of the compounds according to the present invention, $R^2$ is selected from the group consisting of H, halogen, trihalomethyl and —$OR^{17}$.

In a preferred embodiment of the compounds according to the present invention, $R^3$, and $R^{20}$ are each hydrogen.

In a preferred embodiment of the compounds according to the present invention, $R^{20}$ is —$OR^{17}$.

In a preferred embodiment of the compounds according to the present invention, Q is S, N($C_1$-$C_6$ alkyl), or N—Y-(aryl), more preferably S.

In a preferred embodiment of the compounds according to the present invention, Q is NH.

In a preferred embodiment of the compounds according to the present invention, D is $CR^{11}$, more preferably CH.

In a preferred embodiment of the compounds according to the present invention, L is CH or N, more preferably CH.

In a preferred embodiment of the compounds according to the present invention, $R^7$ is H, halogen, $C_1$-$C_6$ alkyl, —C(=N—$OR^{42}$)$R^{43}$, —C(O)-heterocyclyl, Y-aryl, —$CONR^9R^{10}$, —$SO_2NH_2$, —$SO_2NR^9R^{10}$, —Y-heterocyclyl, —Y-heteroaryl, —S-aryl, —S—$C_1$-$C_6$ alkyl, —SO—$C_1$-$C_6$ alkyl, or —$SO_2$—$C_1$-$C_6$ alkyl, wherein $C_1$-$C_6$ alkyl, is unsubstituted or is substituted with one or two of hydroxy or halogen, and heterocyclyl, and heteroaryl are unsubstituted or substituted with one or two of alkoxy, alkyl, or haloalkyl.

In a preferred embodiment of the compounds according to the present invention, $R^7$ is —$CONR^9R^{10}$.

In a preferred embodiment of the compound according to the present invention, $R^7$ is Y-heteroaryl.

In a preferred embodiment of the compounds according to the present invention, $R^9$ and $R^{10}$ are independently H, $C_1$-$C_6$ alkyl, —Y—O—$R^{11}$, —Y-(heterocycle), —$Y^1$—$CO_2$—$R^{11}$, or —Y-(aryl), wherein $C_1$-$C_6$ alkyl is unsubstituted or is substituted with one or two of hydroxy or halogen, and heterocyclyl, and aryl are unsubstituted or are substituted with one or two of alkoxy, alkyl, or haloalkyl.

In a preferred embodiment of the compounds according to the present invention, $R^9$ and $R^{10}$ are taken together with the nitrogen to which they are attached to form a pyrrolidinyl, piperidinyl, piperazinyl, morpholinyl, or thiomorpholinyl ring, wherein said ring is unsubstituted or is substituted with one or two of alkoxy, alkyl, or haloalkyl.

In a preferred embodiment of the compounds according to the present invention, $R^7$ is H, halogen, $C_1$-$C_6$ alkyl, —$SO_2NR^9R^{10}$, —C(=O)(heterocyclyl), —Y-(heterocyclyl), or —Y-(heteroaryl), wherein $C_1$-$C_6$ alkyl is unsubstituted or is substituted with one or two of hydroxy or halogen, and heterocyclyl, and heteroaryl are unsubstituted or are substituted with one or two of alkoxy, alkyl, or haloalkyl.

In a preferred embodiment of the compounds according to the present invention, Z is sulfur.

In a preferred embodiment of the compounds according to the present invention, $R^7$ is optionally substituted Y-heteroaryl.

In a preferred embodiment of the compounds according to the present invention, $R^7$ is Y-heteroaryl optionally substituted on carbon with a substituent selected from the group consisting of alkyl, -alkyl-C(O)—$NR^{36}R^{39}$, —$(CH_2)_{0-6}$heterocyclyl and —$(CH_2)_{0-2}NR^{39}(CH_2)_{0-6}R^{36}$, and on nitrogen with oxygen.

In a preferred embodiment of the compounds according to the present invention, $R^7$ is selected from the group consisting of —C(=N—$OR^{42}$)$R^{43}$ and —$NR^{6a}R^{6b}$, each of which is optionally substituted.

In a preferred embodiment of the compounds according to the present invention, $R^7$ is optionally substituted —C(O)-heterocyclyl.

In a preferred embodiment of the compounds according to the present invention, $R^7$ is —C(O)-heterocyclyl, optionally substituted with —$NR^{36}R^{39}$.

In a preferred embodiment of the compounds according to the present invention, $R^7$ is optionally substituted heterocyclyl.

In a preferred embodiment of the compounds according to the present invention, $R^7$ is heterocyclyl optionally substituted with a substituent selected from the group consisting of alkyl and —C(O)$R^{40}$.

In a preferred embodiment of the compounds according to the present invention, $R^7$ is optionally substituted aryl.

In a preferred embodiment of the compounds according to the present invention, $R^7$ is aryl optionally substituted with a substituent selected from the group consisting of —$(CH_2)_{0-2}NR^{39}(CH_2)_{0-6}R^{36}$, heterocyclyl, halogen, —$S(O)_2$alkyl, —C(O)$NR^{36}R^{39}$, —$(CH_2)_{0-6}$heterocyclyl, each of which with the exception of halogen can be optionally substituted. Preferrably the heterocyclyl moiety is optionally substituted with alkyl or —C(O)$NR^{36}R^{39}$.

In a preferred embodiment of the compounds according to the present invention, $R^{20}$ is selected from the group consisting of H, halogen, alkyl, alkenyl, alkynyl and —$OR^{17}$, wherein the alkyl, alkenyl, alkynyl and —$OR^{17}$ are optionally substituted.

In a preferred embodiment of the compounds according to the present invention, the compounds are represented by the formula A-1:

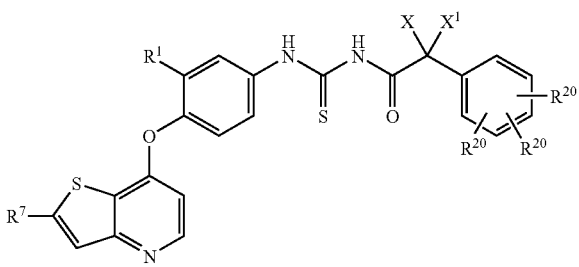

and N-oxides, hydrates, solvates, pharmaceutically acceptable salts, prodrugs and complexes thereof, wherein $R^1$ is selected from the group consisting of hydrogen, halo, $C_1$-$C_6$ alkyl, $C_2$-$C_6$ alkenyl or $C_2$-$C_6$ alkynyl, wherein $C_1$-$C_6$ alkyl, $C_2$-$C_6$ alkenyl and $C_2$-$C_6$ alkynyl are optionally substituted;

X and $X^1$ are independently selected from the group consisting of H and $C_1$-$C_6$ alkyl, wherein $C_1$-$C_6$ alkyl is optionally substituted, or X and $X^1$ taken together with the atom to which they are attached, form a $C_3$-$C_7$ cycloalkyl;

$R^7$ is H, halogen, $C_1$-$C_6$ alkyl, —C(=O)$NR^9R^{10}$, —C(=O)(aryl), —C(=O)(heterocyclyl), —C(=O)(heteroaryl), —Y-(aryl), —Y-(heterocyclyl), —Y-(heteroaryl), —$SR^{6a}$, —S-aryl, —S-(heteroaryl), —S—$C_1$-$C_6$ alkyl, —SO—$C_1$-$C_6$ alkyl, —$SO_2$—$C_1$-$C_6$ alkyl, —Y—$NR^9R^{10}$, —$SO_2NR^9R^{10}$, $CO_2R^9$, —C≡C—(CR$^{45}$R$^{45}$)$_n$—$R^{46}$ and —C(=$NR^{42}$)$NR^{37}R^{43}$, wherein n is an integer ranging from 0 to 6 and wherein $C_1$-$C_6$ alkyl, aryl, heterocycle and heteroaryl are each independently optionally substituted with 1 to 5 independently selected $R^{38}$;

$R^9$ and $R^{10}$ are independently selected from H, $C_1$-$C_6$ alkyl, —Y-(cycloalkyl), —Y—($C_1$-$C_6$ heteroalkyl), —Y-(aryl), —Y-(heterocyclyl), —Y-(heteroaryl), —Y—O—$Y^1$—O—$R^{11}$, —$Y^1$—$CO_2$—$R^{11}$, Y—C(O)$OR^{37}$ and —Y—O—$R^{11}$, wherein said $C_1$-$C_6$ alkyl, heteroalkyl, cycloalkyl, aryl, heterocycle, and heteroaryl are each optionally substituted with one or more independently selected $R^{44}$, or $R^9$ and $R^{10}$ taken together with the nitrogen to which they are attached form a $C_5$-$C_9$ heterocyclyl ring or a heteroaryl ring, wherein said ring is optionally substituted with 1 to 5 independently selected $R^{44}$;

each $R^{20}$ is independently selected from the group consisting of H, halo, —$OR^{17}$ and —C(O)$OR^{17}$;

Y is a bond or is —$(C(R^{11})(H))_t$—, wherein t is an integer from 1 to 6;

$Y^1$ is —$(C(R^{11})(H))_t$—, and $R^{11}$ at each occurrence is independently H or $C_1$-$C_6$ alkyl, wherein $C_1$-$C_6$ alkyl is optionally substituted.

In a preferred embodiment of the compounds according to the present invention, $R^1$ is hydrogen or halogen.

In a preferred embodiment of the compounds according to the present invention, $R^1$ is fluorine.

In a preferred embodiment of the compounds according to the present invention, $R^7$ is selected from the group consisting of H, —C(=O)$NR^9R^{10}$, —Y-(aryl), —Y-(heteroaryl) and —S—$C_1$-$C_6$ alkyl, wherein said —Y-(aryl), —Y-(heteroaryl) and —S—$C_1$-$C_6$ alkyl are optionally substituted with 1 to 5 independently selected $R^{38}$.

In a preferred embodiment of the compounds according to the present invention, $R^7$ is —C(=O)NR$^9$R$^{10}$, optionally substituted with one or more independently selected $R^{44}$.

In a preferred embodiment of the compounds according to the present invention, $R^7$ is —Y-(aryl), optionally substituted with 1 to 5 independently selected $R^{38}$.

In a preferred embodiment of the compounds according to the present invention, $R^7$ is —Y-(heteroaryl), optionally substituted with 1 to 5 independently selected $R^{38}$.

In a preferred embodiment of the compounds according to the present invention, $R^{38}$ is selected from the group consisting of halogen, —OR$^{37}$, C$_1$-C$_6$alkyl, —(CH$_2$)$_n$-(5 to 10 membered heterocyclyl), —(CH$_2$)$_j$NR$^{39}$(CH$_2$)$_n$R$^{36}$, —(CH$_2$)$_j$NR$^{39}$(CH$_2$)$_j$NR$^{36}$R$^{39}$, —(CH$_2$)$_n$-heteroaryl, —C(O)NR$^{36}$R$^{39}$, —(CH$_2$)$_n$O(CH$_2$)$_i$(5 to 10 membered heterocyclyl) and —(CH$_2$)$_j$O(CH$_2$)$_i$NR$^{36}$R$^{39}$, wherein n is an integer ranging from 0 to 6, j is an integer ranging from 0 to 2, j is an integer ranging from 1 to 6 and wherein the alkyl, heteroaryl and heterocyclyl moieties of the foregoing $R^{38}$ groups are optionally substituted by one or more substituents independently selected from the group consisting of halo, cyano, nitro, trifluoromethyl, azido, —OH, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —(CH$_2$)$_n$NR$^{36}$R$^{39}$, C$_1$-C$_6$ alkyl, C$_3$-C$_{10}$ cycloalkyl, —(CH$_2$)$_n$(C$_6$-C$_{10}$ aryl), —(CH$_2$)$_n$(5-10 membered heterocyclyl), —(CH$_2$)$_n$O(CH$_2$)$_i$R$^{37}$, and —(CH$_2$)$_n$OR$^{37}$, wherein n is an integer ranging from 0 to 6 and i is an integer ranging from 2 to 6.

In a preferred embodiment of the compounds according to the present invention, $R^{38}$ is selected from the group consisting of —OR$^{37}$, C$_1$-C$_6$alkyl, —(CH$_2$)$_n$(5 to 10 membered heterocyclyl) and —(CH$_2$)$_n$O(CH$_2$)$_i$(5 to 10 membered heterocyclyl).

In a preferred embodiment of the compounds according to the present invention, $R^9$ and $R^{10}$ are independently selected from the group consisting of H, C$_1$-C$_6$ alkyl, —C$_1$-C$_6$ heteroalkyl, —Y-(aryl), —Y-(heterocyclyl), —Y-(heteroaryl), —Y—O—R$^{11}$ and Y—C(O)OR$^{37}$, wherein a C$_1$-C$_6$ alkyl, C$_1$-C$_6$ heteroalkyl, aryl, heterocyclcyl and heteroaryl are each optionally substituted with 1 or more independently selected $R^{44}$.

In a preferred embodiment of the compounds according to the present invention, $R^{44}$ is selected from the group consisting of C$_1$-C$_6$ alkyl, —OR$^{37}$, —C(O)NR$^{36}$R$^{39}$ and —C(O)OR$^{46}$.

In a preferred embodiment of the compounds according to the present invention, $R^{36}$ is selected from the group consisting of H, C$_1$-C$_6$ alkyl, —(CH$_2$)$_n$OR$^{37}$ and —(CH$_2$)$_n$(heterocyclyl).

In a preferred embodiment of the compounds according to the present invention, $R^{39}$ is H or C$_1$-C$_6$ alkyl.

In a preferred embodiment of the compounds according to the present invention, $R^{37}$ is H or C$_1$-C$_6$ alkyl.

In a preferred embodiment of the compounds according to the present invention, $R^{20}$ is selected from the group consisting of H, halogen, —OR$^{17}$ and —C(O)OR$^{17}$.

In a preferred embodiment of the compounds according to the present invention, $R^{17}$ is H or C$_1$-C$_6$ alkyl.

In a preferred embodiment of the compounds according to the present invention, $R^{20}$ is halogen.

In a preferred embodiment of the compounds according to the present invention, $R^{20}$ is Cl or F.

In a preferred embodiment of the compounds according to the present invention, $R^{6a}$ is —(CZ$^5$Z$^6$)$_u$-aryl.

In a preferred embodiment of the compounds according to the present invention, $R^7$ is selected from the group consisting of H, halogen, C$_1$-C$_6$ alkyl, —CONR$^9$R$^{10}$, —SO$_2$NH$_2$, —SO$_2$NR$^9$R$^{10}$, —Y-heterocyclyl, —Y-heteroaryl, —S-aryl, —S—C$_1$-C$_6$ alkyl, —SO—C$_1$-C$_6$ alkyl, or —SO$_2$—C$_1$-C$_6$ alkyl, wherein C$_1$-C$_6$ alkyl is unsubstituted or is substituted with one or two of hydroxy or halogen, and the heterocyclyl, and heteroaryl are unsubstituted or are substituted with one or two of alkoxy, alkyl, or haloalkyl.

In a preferred embodiment of the compounds according to the present invention, $R^7$ is selected from the group consisting of H, halogen, C$_1$-C$_6$ alkyl, —SO$_2$NR$^9$R$^{10}$, —C(=O)(heterocyclyl), —Y-(heterocyclyl), —Y-(heteroaryl), —S-aryl, —S—C$_1$-C$_6$ alkyl, —SO—C$_1$-C$_6$ alkyl, or —SO$_2$—C$_1$-C$_6$ alkyl, wherein C$_1$-C$_6$ alkyl is unsubstituted or is substituted with one or two of hydroxy or halogen, and the heterocyclyl, and heteroaryl are unsubstituted or are substituted with one or two of alkoxy, alkyl, or haloalkyl.

In a preferred embodiment of the compounds according to the present invention, $R^9$ and $R^{10}$ are independently selected from the group consisting of H, C$_1$-C$_6$ alkyl, C$_1$-C$_6$ heteroalkyl, —Y—O—R$^{11}$, —Y-(heterocycle), —Y—CO$_2$—R$^{11}$, —Y-(aryl) and —Y-(heteroaryl), wherein C$_1$-C$_6$ alkyl is unsubstituted or is substituted with one or two of hydroxy or halogen, and the heterocyclyl, aryl and heteroaryl are unsubstituted or are substituted with one or two of alkoxy, alkyl, or haloalkyl.

In a preferred embodiment of the compounds according to the present invention, $R^9$ and $R^{10}$ are taken together with the nitrogen to which they are attached to form a pyrrolidinyl, piperidinyl, piperazinyl, morpholinyl, or thiomorpholinyl ring, wherein said ring is unsubstituted or is substituted with one or two of alkoxy, alkyl, or haloalkyl.

In a preferred embodiment of the compounds according to the present invention, NR$^9$R$^{10}$ is selected from:

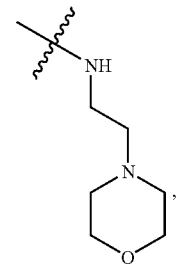

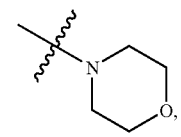

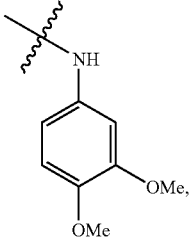

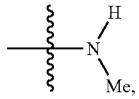

-continued
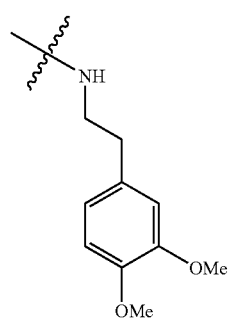
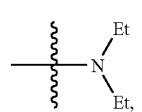
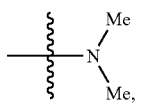
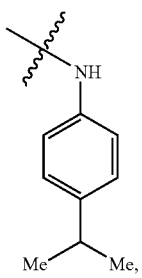
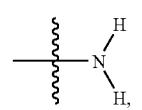
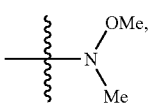
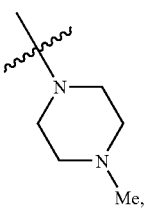
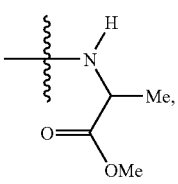
-continued
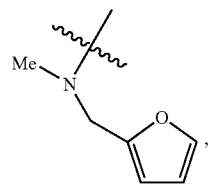
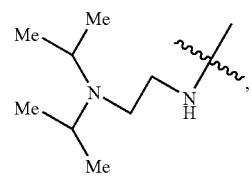
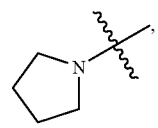
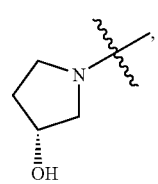
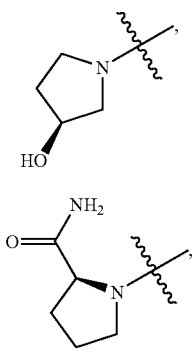
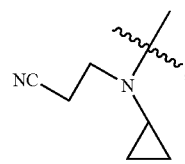
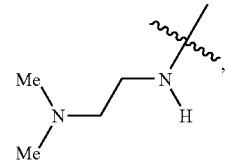
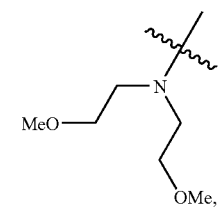

-continued

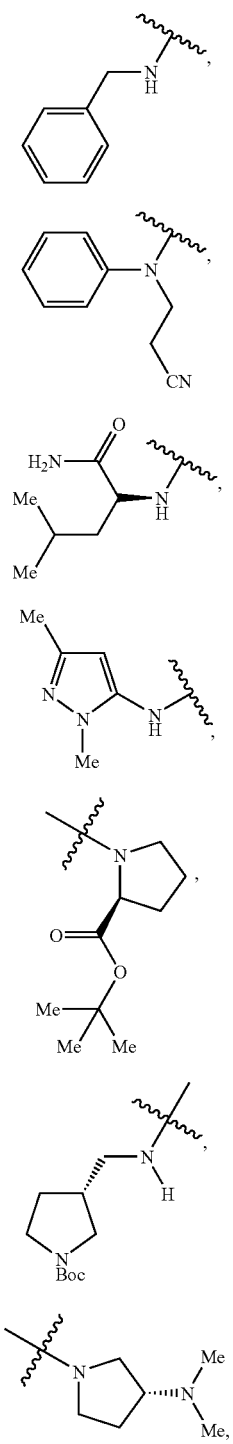

-continued

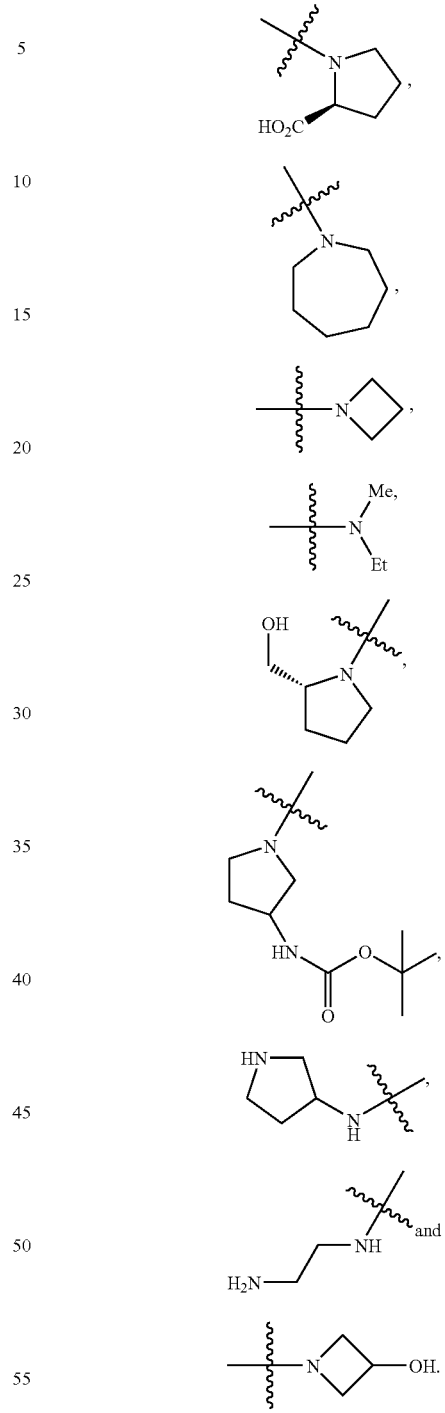

In a preferred embodiment of the compounds according to the present invention, $R^7$ is unsubstituted heteroaryl.

In a preferred embodiment of the compounds according to the present invention, $R^7$ is thiazolyl, pyridinyl, pyrimidinyl, and imidazolyl, each of which is preferably unsubstituted or is substituted with one or two of alkoxy, or alkyl.

In a preferred embodiment of the compounds according to the present invention, $R^7$ is $C_1$-$C_6$ alkyl, unsubstituted or substituted with hydroxy.

In a preferred embodiment of the compounds according to the present invention, X and $X^1$ are both H.

In a preferred embodiment of the compounds according to the present invention, $R^{17}$ is selected from the group consisting of H and $C_1$-$C_6$ alkyl.

In a preferred embodiment of the compounds according to the present invention, $R^{38}$ is selected from the group consisting of —$OR^{37}$, $C_1$-$C_6$ alkyl and —$(CH_2)_n$(5 to 10 membered heterocylic), wherein n is an integer ranging from 0 to 6.

In a preferred embodiment of the compounds according to the present invention, $R^{37}$ is selected from the group consisting of H and $C_1$-$C_6$ alkyl.

In a preferred embodiment of the compounds according to the present invention, the compounds are represented by the formula A-2:

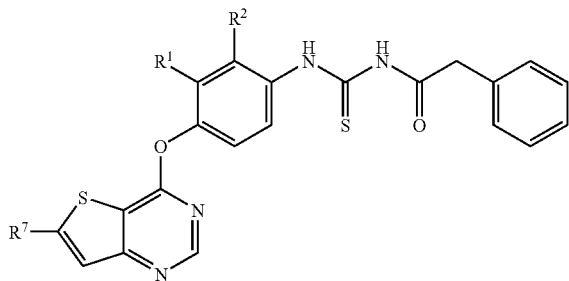

A-2 and N-oxides, hydrates, solvates, pharmaceutically acceptable salts, prodrugs and complexes thereof, wherein $R^1$ is selected from the group consisting of hydrogen, halo, $C_1$-$C_6$ alkyl, $C_2$-$C_6$ alkenyl or $C_2$-$C_6$ alkynyl, wherein $C_1$-$C_6$ alkyl, $C_2$-$C_6$ alkenyl and $C_2$-$C_6$ alkynyl are optionally substituted;

$R^4$ is selected from the group consisting of H and halogen;

$R^7$ is selected from the group consisting of H, halogen, $C_1$-$C_6$ alkyl, —C(═O)$NR^9R^{10}$, —C(═O)(aryl), —C(═O)(heterocyclyl), —C(═O)(heteroaryl), —Y-(aryl), —Y-(heterocyclyl), —Y-(heteroaryl), —S-aryl, —S—$C_1$-$C_6$ alkyl, —SO—$C_1$-$C_6$ alkyl, —$SO_2$—$C_1$-$C_6$ alkyl, —Y—$NR^9R^{10}$, —$SO_2NR^9R^{10}$ and $CO_2R^9$, wherein $C_1$-$C_6$ alkyl, aryl, heterocycle and heteroaryl are each independently optionally substituted with 1 to 5 independently selected $R^{38}$;

$R^9$ and $R^{10}$ are independently selected from the group consisting of H, $C_1$-$C_6$ alkyl, —Y-(cycloalkyl), —Y-(aryl), —Y-(heterocyclyl), —Y-(heteroaryl), —Y—O—$Y^1$—O—$R^{11}$, —$Y^1$—$CO_2$—$R^{11}$ and —Y—O—$R^{11}$, wherein $C_1$-$C_6$ alkyl, cycloalkyl, aryl, heterocycle, and heteroaryl are each optionally substituted with one or more independently selected $R^{44}$, or $R^9$ and $R^{10}$ taken together with the nitrogen to which they are attached form a $C_5$-$C_9$ heterocyclyl ring or a heteroaryl ring, wherein said ring is optionally substituted;

Y is a bond or is —$(C(R^{11})(H))_t$—, wherein t is an integer from 1 to 6;

$Y_1$ is —$(C(R^{11})(H))_t$—, and $R^{11}$ at each occurrence is independently H or $C_1$-$C_6$ alkyl, wherein $C_1$-$C_6$ alkyl is optionally substituted.

In a preferred embodiment of the compounds according to the present invention, R1 is hydrogen or halogen.

In a preferred embodiment of the compounds according to the present invention, R1 is fluorine.

In a preferred embodiment of the compounds according to the present invention, R4 is selected from the group consisting of H and halogen.

In a preferred embodiment of the compounds according to the present invention, R4 is fluorine.

In a preferred embodiment of the compounds according to the present invention, R7 is selected from the group consisting of H, halogen, C1-C6 alkyl, —C(═O)NR9R10, —SO2NH2, —SO2NR9R10, —Y-heterocyclyl —Y-heteroaryl, —S-aryl, —S—C1-C6 alkyl, —SO—C1-C6 alkyl and —SO2-C1-C6 alkyl, wherein C1-C6 alkyl, heterocyclyl, heteroaryl and aryl are each optionally substituted with 1 to 5 independently selected R38.

In a preferred embodiment of the compounds according to the present invention, R7 is selected from the group consisting of H, halogen, C1-C6 alkyl, —C(═O)NR9R10, —SO2NH2, —SO2NR9R10, —Y-heterocyclyl —Y-heteroaryl, —S-aryl, —S—C1-C6 alkyl, —SO—C1-C6 alkyl and —SO2-C1-C6 alkyl, wherein C1-C6 alkyl is unsubstituted or is substituted with one or two of hydroxy or halogen, and the heterocyclyl, and heteroaryl are unsubstituted or are substituted with one or two of alkoxy, alkyl, haloalkyl or (CH2)jNR39(CH2)nO(CH2)iOR37.

In a preferred embodiment of the compounds according to the present invention, R7 is selected from the group consisting of H, halogen, C1-C6 alkyl, —SO2NR9R10, —C(═O)(heterocyclyl), —Y-(heterocyclyl), —Y-(heteroaryl), —S-aryl, —S—C1-C6 alkyl, —SO—C1-C6 alkyl, or —SO2-C1-C6 alkyl, wherein C1-C6 alkyl is unsubstituted or is substituted with one or two of hydroxy or halogen, and the heterocyclyl, and heteroaryl are unsubstituted or are substituted with one or two of alkoxy, alkyl, haloalkyl or (CH2)jNR39(CH2)nO(CH2)iOR37.

In a preferred embodiment of the compounds according to the present invention, R7 is selected from the group consisting of C1-C6 alkyl, —C(═O)NR9R10, —Y-(heterocyclyl), —Y-(heteroaryl), —S—C1-C6 alkyl and —SO—C1-C6 alkyl, wherein C1-C6 alkyl is unsubstituted or is substituted with one or two of hydroxy or halogen, and the heterocyclyl, and heteroaryl are unsubstituted or are substituted with one or two of alkoxy, alkyl, haloalkyl or (CH2)jNR39(CH2)nO(CH2)iOR37.

In a preferred embodiment of the compounds according to the present invention, R7 is CONR9R10.

In a preferred embodiment of the compounds according to the present invention, R9 and R10 are independently selected from the group consisting of H, C1-C6 alkyl, —Y—O—R11, —Y-(heterocycle), —Y1-CO2-R11 and —Y-(aryl), wherein the alkyl, heterocyclyl and aryl moieties of the foregoing R9 and R10 groups are optionally substituted with 1 or more substituents independently selected from R44.

In a preferred embodiment of the compounds according to the present invention, R9 and R10 are independently selected from the group consisting of H, C1-C6 alkyl, —Y—O—R11, —Y-(heterocycle), —Y1-CO2-R11 and —Y-(aryl), wherein C1-C6 alkyl is unsubstituted or is substituted with one or two of hydroxy or halogen, and the heterocyclyl, and aryl are unsubstituted or are substituted with one or two of alkoxy, alkyl, haloalkyl or (CH2)jNR39(CH2)nO(CH2)iOR37.

In a preferred embodiment of the compounds according to the present invention, R9 and R10 taken together with the nitrogen to which they are attached form a C5-C9 heterocyclyl ring or a heteroaryl ring, wherein said ring is optionally substituted.

In a preferred embodiment of the compounds according to the present invention, R9 and R10 are taken together with the nitrogen to which they are attached to form a pyrrolidinyl, piperidinyl, piperazinyl, morpholinyl, or thiomorpholinyl ring, wherein said ring is unsubstituted or is substituted with one or two of alkoxy, alkyl, or haloalkyl.

In a preferred embodiment of the compounds according to the present invention, NR9R10 is selected from the group consisting of:

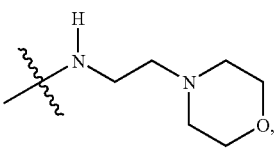
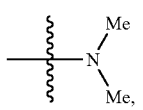
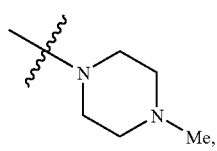
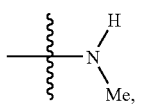
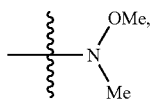
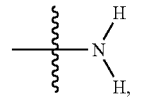
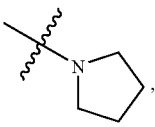
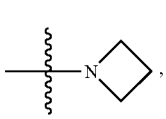
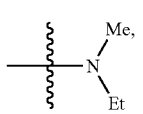
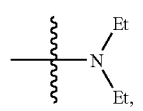
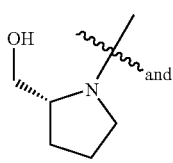

-continued

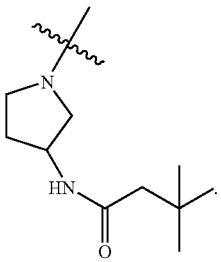

In a preferred embodiment of the compounds according to the present invention, the compounds are represented by the formula A-3:

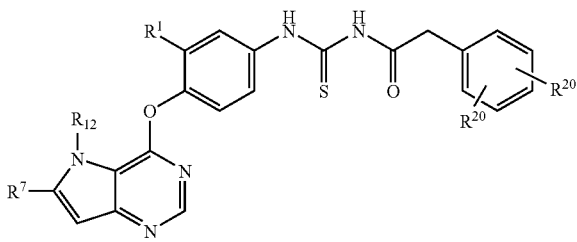

A-3 and N-oxides, hydrates, solvates, pharmaceutically acceptable salts, prodrugs and complexes thereof wherein $R^7$ is selected from the group consisting of H, —Y-(aryl) and —Y-(heteroaryl), wherein —Y-(aryl) and —Y-(heteroaryl) are optionally substituted with 1 to 5 independently selected $R^{38}$;

$R^1$ is selected from the group consisting of hydrogen, halo, $C_1$-$C_6$ alkyl, $C_2$-$C_6$ alkenyl and $C_2$-$C_6$ alkynyl, wherein $C_1$-$C_6$ alkyl, $C_2$-$C_6$ alkenyl and $C_2$-$C_6$ alkynyl are optionally substituted;

$R^{12}$ is selected from the group consisting of H, $C_1$-$C_6$ alkyl, —O($C_1$-$C_6$ alkyl) and —Y-(aryl), wherein $C_1$-$C_6$ alkyl and aryl are optionally substituted;

Y is a bond or is —$(C(R^{11})(H))_t$—, wherein t is an integer from 1 to 6;

$R^{11}$ is H or $C_1$-$C_6$ alkyl, wherein $C_1$-$C_6$ alkyl is optionally substituted; and each $R_{20}$ is independently selected from the group consisting of H and halogen.

In a preferred embodiment of the compounds according to the present invention, $R^1$ is hydrogen or halogen.

In a preferred embodiment of the compounds according to the present invention, $R^1$ is fluorine.

In a preferred embodiment of the compounds according to the present invention, $R^{12}$ is unsubstituted $C_1$-$C_3$ alkyl or unsubstituted —Y-phenyl.

In a preferred embodiment of the compounds according to the present invention, $R^{20}$ is Cl.

In a preferred embodiment of the compounds according to the present invention, the compounds are represented by the formula A-4:

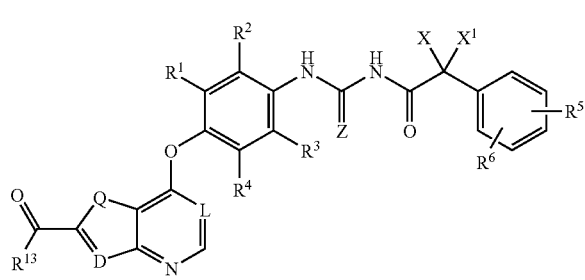

A-4 and N-oxides, hydrates, solvates, pharmaceutically acceptable salts, prodrugs and complexes thereof, wherein
Z is O or S;
X and $X^1$ are independently selected from the group consisting of H, $C_1$-$C_6$ alkyl, halo, cyano and nitro, wherein $C_1$-$C_6$ alkyl is optionally substituted;
$R^1$, $R^2$, $R^3$, $R^4$, $R^5$ and $R^6$ are independently selected from the group consisting of hydrogen halo, $C_1$-$C_6$ alkyl, $C_2$-$C_6$ alkenyl, $C_2$-$C_6$ alkynyl and $NR^{17}R^{18}$, wherein $C_1$-$C_6$ alkyl, $C_2$-$C_6$ alkenyl and $C_2$-$C_6$ alkynyl are optionally substituted;
$R^{17}$ and $R^{18}$ are independently $C_1$-$C_6$alkyl;
Q is O, S, NH, N($C_1$-$C_6$ alkyl), or N—Y-(aryl);
D is $CR^{11}$, or N;
L is N, or CR, wherein R is selected from the group consisting of H, halo, —CN, $C_1$-$C_6$ alkyl, $C_2$-$C_6$ alkenyl and $C_2$-$C_6$ alkynyl, wherein $C_1$-$C_6$ alkyl, $C_2$-$C_6$ alkenyl, and $C_2$-$C_6$ alkynyl are optionally substituted; and
$R^{13}$ is heterocyclyl or heteroaryl, wherein heterocyclyl and heteroaryl are optionally substituted with 1 to 5 independently selected $R^{38}$;
Y is a bond or is —$(C(R^{11})(H))_t$—, wherein t is an integer from 1 to 6; and
$R^{11}$ at each occurrence is independently H or $C_1$-$C_6$ alkyl, wherein $C_1$-$C_6$ alkyl is optionally substituted.

In a preferred embodiment of the compounds according to the present invention, X and $X^1$ are both hydrogen.

In a preferred embodiment of the compounds according to the present invention, $R^1$, $R^2$, $R^3$ and $R^4$ are independently H or halogen.

In a preferred embodiment of the compounds according to the present invention, $R^1$ is hydrogen or halogen.

In a preferred embodiment of the compounds according to the present invention, $R^1$ is fluorine or chlorine.

In a preferred embodiment of the compounds according to the present invention, $R^4$ is hydrogen or halogen.

In a preferred embodiment of the compounds according to the present invention, $R^4$ is fluorine or chlorine.

In a preferred embodiment of the compounds according to the present invention, $R^2$, $R^3$, $R^5$, and $R^6$ are each hydrogen.

In a preferred embodiment of the compounds according to the present invention, Q is selected from the group consisting of S, N($C_1$-$C_6$ alkyl) and N—Y-(aryl).

In a preferred embodiment of the compounds according to the present invention, Q is S.

In a preferred embodiment of the compounds according to the present invention, D is $CR^{11}$.

In a preferred embodiment of the compounds according to the present invention, R11 is H.

In a preferred embodiment of the compounds according to the present invention, L is CH or N.

In a preferred embodiment of the compounds according to the present invention, L is CH.

In a preferred embodiment of the compounds according to the present invention, Z is sulfur.

In a preferred embodiment of the compounds according to the present invention, $R^{38}$ is selected from $C(O)OR^{40}$ and $NR^{36}R^{39}$.

In a preferred embodiment of the compounds according to the present invention, $R^{40}$ is H or $C_1$-$C_{10}$ alkyl.

In a preferred embodiment of the compounds according to the present invention, $R^{36}$ and $R^{39}$ are independently $C_1$-$C_6$ alkyl.

In a preferred embodiment of the compounds according to the present invention, the compounds are represented by the formula A-5:

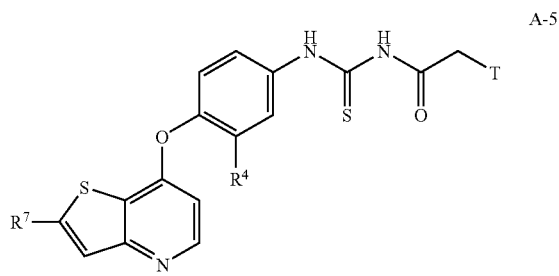

A-5 and N-oxides, hydrates, solvates, pharmaceutically acceptable salts, prodrugs and complexes thereof, wherein
$R^7$ is selected from the group consisting of H, —C(O)$NR^{42}R^{43}$, —Y-(aryl), —Y-(heteroaryl), —C(O)—($C_3$-$C_{10}$ cycloalkyl), —C(O)-(heterocyclyl), —C(O)—($C_6$-$C_{10}$ aryl) and —C(O)-(heteroaryl), wherein the aforementioned $R^7$ groups other than H are optionally substituted with 1 to 5 independently selected $R^{38}$;
$R^4$ is selected from the group consisting of H and halogen; and
T is selected from the group consisting of cycloalkyl, heterocyclyl, aryl, heteroaryl and arylalkyl, each of which is optionally substituted with 1 to 3 independently selected $R^{20}$;

In a preferred embodiment of the compounds according to the present invention, $R^7$ is selected from the group consisting of H, C(O)$NR^{42}R^{43}$ and —Y-(heteroaryl), wherein —Y-(heteroaryl) is optionally substituted with 1 to 5 independently selected $R^{38}$;

In a preferred embodiment of the compounds according to the present invention, $R^7$ is C(O)$NR^{42}R^{43}$;

In a preferred embodiment of the compounds according to the present invention, $R^{42}$ and $R^{43}$ taken together with the nitrogen to which they are attached form a $C_5$-$C_9$ heterocyclyl ring, wherein said ring is optionally substituted with 1 to 5 independently selected $R^{44}$ substituents, with the proviso that $R^{42}$ and $R^{43}$ are not both bonded to the nitrogen directly through and oxygen.

In a preferred embodiment of the compounds according to the present invention, $R^4$ is halogen.

In a preferred embodiment of the compounds according to the present invention, $R^4$ is fluorine.

In a preferred embodiment of the compounds according to the present invention, the compounds are represented by the formula A-6:

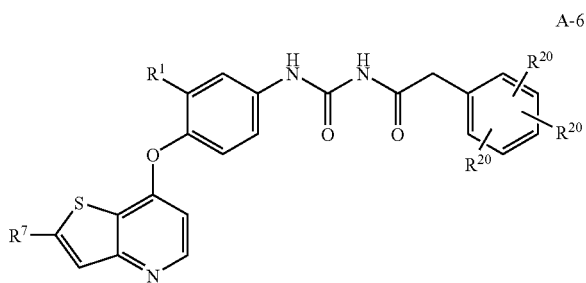

A-6 and N-oxides, hydrates, solvates, pharmaceutically acceptable salts, prodrugs and complexes thereof, wherein $R^1$ is selected from the group consisting of hydrogen, halo, $C_1$-$C_6$ alkyl, $C_2$-$C_6$ alkenyl or $C_2$-$C_6$ alkynyl, wherein $C_1$-$C_6$ alkyl, $C_2$-$C_6$ alkenyl and $C_2$-$C_6$ alkynyl are optionally substituted;

$R^7$ is selected from the group consisting of H, halogen, $C_1$-$C_6$ alkyl, —C(=O)$NR^9R^{10}$, —C(=O)(aryl), —C(=O)(heterocyclyl), —C(=O)(heteroaryl), —Y-(aryl), —Y-(heterocyclyl), —Y-(heteroaryl), —$SR^{6a}$, —S-aryl, —S-(heteroaryl), —S—$C_1$-$C_6$ alkyl, —SO—$C_1$-$C_6$ alkyl, —$SO_2$—$C_1$-$C_6$ alkyl, —Y—$NR^9R^{10}$, —$SO_2NR^9R^{10}$, $CO_2R^9$, —C≡C—($CR^{45}R^{45}$)$_n$—$R^{46}$ and —C(=$NR^{42}$)$NR^{37}R^{43}$, wherein n is an integer ranging from 0 to 6 and wherein $C_1$-$C_6$ alkyl, aryl, heterocycle and heteroaryl are each independently optionally substituted with 1 to 5 independently selected $R^{38}$;

$R^9$ and $R^{10}$ are independently selected from the group consisting of H, $C_1$-$C_6$ alkyl, —Y-(cycloalkyl), —Y—($C_1$-$C_6$ heteroalkyl), —Y-(aryl), —Y-(heterocyclyl), —Y-(heteroaryl), —Y—O—$Y^1$—O—$R^{11}$, —$Y^1$—$CO_2$—$R^{11}$, Y—C(O)$OR^{37}$ and —Y—O—$R^{11}$, wherein said $C_1$-$C_6$ alkyl, heteroalkyl, cycloalkyl, aryl, heterocycle, and heteroaryl are each optionally substituted with one or more independently selected $R^{44}$, or $R^9$ and $R^{10}$ taken together with the nitrogen to which they are attached form a $C_5$-$C_9$ heterocyclyl ring or a heteroaryl ring, wherein said ring is optionally substituted with 1 to 5 independently selected $R^{44}$;

each $R^{20}$ is independently selected from the group consisting of H, halo, —$OR^{17}$ and —C(O)$OR^{17}$;

Y is a bond or is —(C($R^{11}$)(H))$_t$—, wherein t is an integer from 1 to 6;

$Y^1$ is —(C($R^{11}$)(H))$_t$—; and $R^{11}$ at each occurrence is independently H or $C_1$-$C_6$ alkyl, wherein $C_1$-$C_6$ alkyl is optionally substituted.

In a preferred embodiment of the compounds according to the present invention, $R^7$ is selected from the group consisting of H, C(O)$NR^9R^{10}$ and —Y-(heteroaryl), wherein —Y-(heteroaryl) is optionally substituted with 1 to 5 independently selected $R^{38}$;

In a preferred embodiment of the compounds according to the present invention, $R^7$ is C(O)$NR^9R^{10}$;

In a preferred embodiment of the compounds according to the present invention, $R^9$ and $R^{10}$ taken together with the nitrogen to which they are attached form a $C_5$-$C_9$ heterocyclyl ring, wherein said ring is optionally substituted with 1 to 5 independently selected $R^{44}$ substituents.

In a preferred embodiment of the compounds according to the present invention, $R^7$ is —Y-(heteroaryl), wherein said —Y-(heteroaryl) is optionally substituted with 1 to 5 independently selected $R^{38}$.

In a preferred embodiment of the compounds according to the present invention, $R^7$ is —Y-(heteroaryl), wherein said —Y-(heteroaryl) is optionally substituted with one $C_1$-$C_6$ alkyl.

In a preferred embodiment of the compounds according to the present invention, $R^1$ is halogen.

In a preferred embodiment of the compounds according to the present invention, $R^1$ is fluorine.

In a preferred embodiment of the compounds according to the present invention, $R^{17}$ is selected from the group consisting of H and $C_1$-$C_6$ alkyl.

In a preferred embodiment of the compounds according to the present invention, $R^{38}$ is selected from the group consisting of —$OR^{37}$, $C_1$-$C_6$ alkyl and —($CH_2$)$_n$(5 to 10 membered heterocylic), wherein n is an integer ranging from 0 to 6.

In a preferred embodiment of the compounds according to the present invention, $R^{37}$ is selected from the group consisting of H and $C_1$-$C_6$ alkyl.

In a preferred embodiment of the compounds according to the present invention, each $R^{20}$ is independently selected from the group consisting of H, halogen and —O—($C_1$-$C_6$) alkyl.

In a preferred embodiment of the compounds according to the present invention, two $R^{20}$ are H and the third $R^{20}$ is selected from the group consisting of H, halogen and —O—($C_1$-$C_6$ alkyl).

In a second aspect, the invention comprises compounds of formula (B), which are inhibitors of VEGF receptor signaling and HGF receptor signaling:

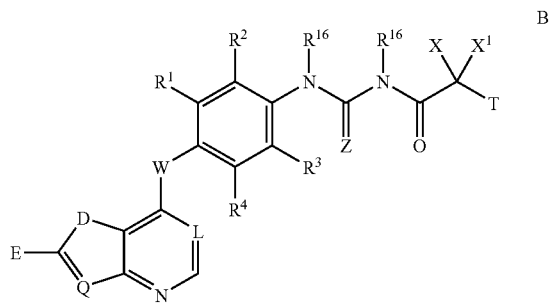

B and N-oxides, hydrates, solvates, pharmaceutically acceptable salts, prodrugs and complexes thereof, wherein T is selected from the group consisting of cycloalkyl, heterocyclyl, aryl and heteroaryl, wherein each of said cycloalkyl, heterocyclyl, aryl and heteroaryl is optionally substituted with 1 to 3 $R^{20}$;

each $R^{20}$ is independently selected from the group consisting of —H, halogen, trihalomethyl, —CN, —$NO_2$, —$NH_2$, —$OR^{17}$, —$OCF_3$, —$NR^{17}R^{18}$, —S(O)$_{0-2}R^{17}$, —S(O)$_2NR^{17}R^{17}$, —C(O)$OR^{17}$, —C(O)$NR^{17}R^{17}$, —N($R^{17}$)$SO_2R^{17}$, —N($R^{17}$)C(O)$R^{17}$, —N($R^{17}$)C(O)$R^{17}$, —C(O)$R^{17}$, —C(O)$SR^{17}$, $C_1$-$C_4$ alkoxy, $C_1$-$C_4$ alkylthio, —O($CH_2$)$_n$aryl, —O($CH_2$)$_n$heteroaryl, —($CH_2$)$_{0-5}$(aryl), —($CH_2$)$_{0-5}$(heteroaryl), $C_1$-$C_6$ alkyl, $C_2$-$C_6$ alkenyl, $C_2$-$C_6$ alkynyl, —$CH_2$($CH_2$)$_{0-4}$-$T^2$, an optionally substituted $C_{1-4}$ alkylcarbonyl, $C_{1-4}$ alkoxy, an amino optionally substituted by $C_{1-4}$ alkyl optionally substituted by $C_{1-4}$ alkoxy and a saturated or unsaturated three- to seven-membered carboxyclic or heterocyclic group, wherein $T^2$ is selected from the group consisting of —OH, —OMe, —OEt, —$NH_2$, —NHMe, —$NMe_2$, —NHEt and —$NEt_2$, and wherein the aryl, heteroaryl, $C_1$-$C_6$ alkyl, $C_2$-$C_6$ alkenyl, and $C_2$-$C_6$ alkynyl are optionally substituted;

W is selected from the group consisting of O, S and NH;

Z is selected from the group consisting of O, or S and NH;

X and $X^1$ are independently selected from the group consisting of H, $C_1$-$C_6$ alkyl, halo, cyano, or nitro, wherein $C_1$-$C_6$ alkyl is optionally substituted, or X and $X^1$ taken together with the atom to which they are attached, form a $C_3$-$C_7$ cycloalkyl;

$R^1$, $R^2$, $R^3$ and $R^4$ are independently selected from the group consisting of hydrogen, halo, trihalomethyl, —CN, —NO$_2$, —NH$_2$, —OR$^{17}$, —NR$^{17}$R$^{18}$, —C(O)OR$^{17}$, —C(O)R$^{17}$, $C_1$-$C_4$ alkoxy, $C_1$-$C_4$ alkylthio, $C_1$-$C_6$ alkyl, $C_2$-$C_6$ alkenyl or $C_2$-$C_6$ alkynyl, wherein $C_1$-$C_6$ alkyl, $C_2$-$C_6$ alkenyl and $C_2$-$C_6$ alkynyl are optionally substituted;

$R^{17}$ is selected from the group consisting of H and $R^{18}$;

$R^{18}$ is selected from the group consisting of a $C_1$-$C_6$ alkyl, an aryl, an aryl($C_1$-$C_6$ alkyl), a heterocyclyl and a heterocyclyl ($C_1$-$C_6$ alkyl), each of which is optionally substituted, or $R^{17}$ and $R^{18}$, taken together with a common nitrogen to which they are attached, form an optionally substituted five- to seven-membered heterocyclyl, the optionally substituted five- to seven-membered heterocyclyl optionally containing at least one additional annular heteroatom selected from the group consisting of N, O, S and P;

$R^{16}$ is selected from the group consisting of —H, —CN, —(CH$_2$)$_{0-5}$(aryl), —(CH$_2$)$_{0-5}$(heteroaryl), $C_1$-$C_6$ alkyl, $C_2$-$C_6$ alkenyl, $C_2$-$C_6$ alkynyl, —CH$_2$(CH$_2$)$_{0-4}$-T$^2$, an optionally substituted $C_{1-4}$ alkylcarbonyl, and a saturated or unsaturated three- to seven-membered carboxylic or heterocyclic group, wherein T$^2$ is selected from the group consisting of —OH, —OMe, —OEt, —NH$_2$, —NHMe, —NMe$_2$, —NHEt and —NEt$_2$, and wherein the aryl, heteroaryl, $C_1$-$C_6$ alkyl, $C_2$-$C_6$ alkenyl, and $C_2$-$C_6$ alkynyl are optionally substituted;

D is selected from the group consisting of CH$_2$, O, S, NH, N—($C_1$-$C_6$ alkyl), or N—Y-(aryl), —N—OMe, —NCH$_2$OMe and —N-Bn;

Q is selected from the group consisting of C-E and N;

L is N, or CR, wherein R is selected from the group consisting of —H, halo, —CN, $C_1$-$C_6$ alkyl, $C_2$-$C_6$ alkenyl, and $C_2$-$C_6$ alkynyl, wherein $C_1$-$C_6$ alkyl, $C_2$-$C_6$ alkenyl, and $C_2$-$C_6$ alkynyl are optionally substituted; and E is selected from the group consisting of $E^1$, $E^2$ and $E^3$, wherein $E^1$ is selected from the group consisting of —H, halogen, nitro, azido, $C_1$-$C_6$ alkyl, $C_3$-$C_{10}$ cycloalkyl, —C(O)NR$^{42}$R$^{43}$, —Y—NR$^{42}$R$^{43}$, —NR$^{42}$C(=O)R$^{43}$, —SO$_2$R$^{42}$, —SO$_2$NR$^{42}$R$^{43}$, —NR$^{37}$SO$_2$R$^{42}$, —NR$^{37}$SO$_2$NR$^{42}$R$^{43}$, —C(=N—OR$^{42}$)R$^{43}$, —C(=NR$^{42}$)R$^{43}$, —NR$^{37}$C(=NR$^{42}$)R$^{43}$, —C(=NR$^{42}$)NR$^{37}$R$^{43}$, —NR$^{37}$C(=NR$^{42}$)NR$^{37}$R$^{43}$, —C(O)R$^{42}$, —CO$_2$R$^{42}$, —C(O)(heterocyclyl), —C(O)(C$_6$-C$_{10}$ aryl), —C(O)(heteroaryl), —Y—(C$_6$-C$_{10}$ aryl), —Y-(heteroaryl), —Y-(5-10 membered heterocyclic), —NR$^{6a}$R$^{6b}$, —NR$^{6a}$SO$_2$R$^{6b}$, —NR$^{6a}$C(O)R$^{6b}$, —OC(O)R$^{6b}$, —NR$^{6a}$C(O)OR$^{6b}$, —OC(O)NR$^{6a}$R$^{6a}$, —OR$^{6a}$, —SR$^{6a}$, —S(O)R$^{6a}$, —SO$_2$R$^{6a}$, —SO$_3$R$^{6a}$, —SO$_2$NR$^{6a}$R$^{6b}$, —SO$_2$NR$^{42}$R$^{43}$, —COR$^{6a}$, —CO$_2$R$^{6a}$, —CONR$^{6a}$R$^{6b}$, —(C$_1$-C$_4$)fluoroalkyl, —(C$_1$-C$_4$)fluoroalkoxy, —(CZ$^3$Z$^4$)$_a$CN, wherein n is an integer ranging from 0 to 6, and the aforementioned $E^1$ groups other than —H and halogen are optionally substituted by 1 to 5 independently selected $R^{38}$, or $E^1$ is selected from a moiety selected from the group consisting of —(CZ$^3$Z$_4$)$_a$-aryl, —(CZ$^3$Z$^4$)$_3$-heterocycle, (C$_2$-C$_6$)alkynyl, —(CZ$^3$Z$^4$)$_n$—(C$_3$-C$_6$)cycloalkyl, —(CZ$^3$Z$^4$)$_a$-(C$_5$-C$_6$)cycloalkenyl, (C$_2$-C$_6$) alkenyl and (C$_1$-C$_6$)alkyl, which is optionally substituted with 1 to 3 independently selected $Y^2$ groups, where a is 0, 1, 2, or 3, and wherein when a is 2 or 3, the CZ$^3$Z$^4$ units may be the same or different; wherein each $R^{38}$ is independently selected from halo, cyano, nitro, trifluoromethoxy, trifluoromethyl, azido, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —NR$^{36}$R$^{39}$, —OR$^{37}$, —SO$_2$NR$^{36}$R$^{39}$, $C_1$-$C_6$ alkyl, —(CH$_2$)$_j$O(CH$_2$)$_i$NR$^{36}$R$^{39}$, —(CH$_2$)$_n$O(CH$_2$)$_i$OR$^{37}$, —(CH$_2$)$_n$OR$^{37}$, —S(O)$_j$(C$_1$-C$_6$ alkyl), —(CH$_2$)$_n$(C$_6$-C$_{10}$ aryl), —(CH$_2$)$_n$(C$_5$-C$_{10}$ heteroaryl), —(CH$_2$)$_n$(5-10 membered heterocyclyl); —C(O)(CH$_2$)$_n$(C$_6$-C$_{10}$ aryl), —(CH$_2$)$_n$O(CH$_2$)$_j$(C$_6$-C$_{10}$ aryl), —(CH$_2$)$_n$O(CH$_2$)$_i$(5-10 membered heterocyclyl), —C(O)(CH$_2$)$_n$(5-10 membered heterocyclyl), —(CH$_2$)$_j$NR$^{39}$(CH$_2$)$_i$NR$^{36}$R$^{39}$, —(CH$_2$)$_j$NR$^{39}$CH$_2$C(O)NR$^{36}$R$^{39}$, —(CH$_2$)$_j$NR$^{39}$(CH$_2$)$_i$NR$^{37}$C(O)R$^{40}$, —(CH$_2$)$_j$NR$^{39}$(CH$_2$)$_n$O(CH$_2$)$_i$OR$^{37}$, —(CH$_2$)$_j$NR$^{39}$(CH$_2$)$_i$S(O)$_j$(C$_1$-C$_6$ alkyl), —(CH$_2$)$_j$NR$^{39}$(CH$_2$)$_n$R$^{36}$, —SO$_2$(CH$_2$)$_n$(C$_6$-C$_{10}$ aryl), —SO$_2$(CH$_2$)$_n$(5-10 membered heterocyclyl), —(CH$_2$)$_n$NR$^{36}$R$^{39}$, —NR$^{37}$SO$_2$NR$^{36}$R$^{39}$, SO$_2$R$^{36}$, $C_2$-$C_6$ alkenyl, $C_3$-$C_{10}$ cycloalkyl and $C_1$-$C_6$ alkylamino, wherein j is an integer ranging from 0 to 2, n is an integer ranging from 0 to 6, i is an integer ranging from 0 to 6, the —(CH$_2$)$_i$— and —(CH$_2$)$_n$— moieties of the foregoing $R^{38}$ groups optionally include a carbon-carbon double or triple bond where n is an integer between 2 and 6, and the alkyl, aryl, heteroaryl and heterocyclyl moieties of the foregoing $R^{38}$ groups are optionally substituted by one or more substituents independently selected from halo, cyano, nitro, trifluoromethyl, azido, —OH, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —(CH$_2$)$_n$NR$^{36}$R$^{39}$, $C_1$-$C_6$ alkyl, $C_3$-$C_{10}$ cycloalkyl, —(CH$_2$)$_n$(C$_6$-C$_{10}$ aryl), —(CH$_2$)$_n$(5-10 membered heterocyclyl), —(CH$_2$)$_n$O(CH$_2$)$_i$OR$^{37}$, and —(CH$_2$)$_n$OR$^{37}$, wherein n is an integer ranging from 0 to 6 and i is an integer ranging from 2 to 6;

each $R^{42}$ and $R^{43}$ is independently selected from the group consisting of H, $C_1$-$C_6$ alkyl, $C_1$-$C_6$ heteroalkyl, —Y—(C$_3$-C$_{10}$ cycloalkyl), —Y—(C$_6$-C$_{10}$ aryl), —Y—(C$_6$-C$_{10}$ heteroaryl), —Y-(5-10 membered heterocyclic), —Y—O—Y$^1$—OR$^{37}$, —Y$^1$—CO$_2$—R$^{37}$, and —Y—OR$^{37}$, wherein the alkyl, heteroalkyl, cycloalkyl, aryl, heteroaryl and heterocyclic moieties of the foregoing $R^{42}$ and $R^{43}$ groups are optionally substituted by 1 or more substituents independently selected from $R^{44}$, wherein Y is a bond or is —(C(R$^{37}$)(H))$_n$, n is an integer ranging from 1 to 6, and $Y^1$ is —(C(R$^{37}$)(H))$_n$, or $R^{42}$ and $R^{43}$ taken together with the nitrogen to which they are attached form a $C_5$-$C_9$ heterocyclyl ring or a heteroaryl ring, wherein said ring is optionally substituted by 1 to 5 $R^{44}$ substituents, with the proviso that $R^{42}$ and $R^{43}$ are not both bonded to the nitrogen directly through an oxygen;

each $R^{44}$ is independently selected from the group consisting of halo, cyano, nitro, trifluoromethoxy, trifluoromethyl, azido, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —NR$^{36}$R$^{39}$, —OR$^{37}$, —SO$_2$NR$^{36}$R$^{39}$, —SO$_2$R$^{36}$, —NR$^{36}$SO$_2$R$^{39}$, —NR$^{36}$SO$_2$NR$^{37}$R$^{41}$, $C_1$-$C_6$ alkyl, $C_2$-$C_6$ alkenyl, $C_2$-$C_6$ alkynyl, $C_3$-$C_{10}$ cycloalkyl, —$C_1$-$C_6$ alkylamino, —(CH$_2$)$_j$O(CH$_2$)$_i$NR$^{36}$R$^{39}$, —(CH$_2$)$_n$O(CH$_2$)$_i$OR$^{37}$, —(CH$_2$)$_n$OR$^{37}$, —S(O)$_j$(C$_1$-C$_6$ alkyl), —(CH$_2$)$_n$(C$_6$-C$_{10}$ aryl), —(CH$_2$)$_n$(5-10 membered heterocyclic), —C(O)(CH$_2$)$_n$(C$_6$-C$_{10}$ aryl), —(CH$_2$)$_n$O(CH$_2$)$_j$(C$_6$-C$_{10}$ aryl), —(CH$_2$)$_n$O(CH$_2$)$_i$(5 to 10 membered heterocyclic), —C(O)(CH$_2$)$_n$(5 to 10 membered heterocyclic), —(CH$_2$)$_j$NR$^{39}$(CH$_2$)$_i$NR$^{36}$R$^{39}$, —(CH$_2$)$_j$NR$^{39}$CH$_2$C(O)NR$^{36}$R$^{39}$, —(CH$_2$)$_j$NR$^{39}$(CH$_2$)$_i$NR$^{37}$C(O)R$^{40}$, —(CH$_2$)$_j$NR$^{39}$(CH$_2$)$_n$O(CH$_2$)$_i$OR$^{37}$, —(CH$_2$)$_j$NR$^{39}$(CH$_2$)$_j$S(O)$_j$(C$_1$-C$_6$ alkyl), —(CH$_2$)$_j$NR$^{39}$(CH$_2$)$_j$R$^{36}$, —SO$_2$(CH$_2$)$_n$(C$_6$-C$_{10}$ aryl), and —SO$_2$(CH$_2$)$_n$(5 to 10 membered heterocyclic) wherein, j is an integer from 0 to 2, n is an integer from 0 to 6 and i is an integer ranging from 2 to 6, the —(CH$_2$)$_i$— and —(CH$_2$)$_{n1}$— moieties of the foregoing R$^{44}$ groups optionally include a carbon-carbon double or triple bond wherein n is an integer from 2 to 6, and the alkyl, aryl and heterocyclic moieties of the foregoing R$^{44}$ groups are optionally substituted by 1 or more substituents independently selected from the group consisting of halo, cyano, nitro, trifluoromethyl, azido, —OH, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —(CH$_2$)$_n$NR$^{36}$R$^{39}$, —SO$_2$R$^{36}$, —SO$_2$NR$^{36}$R$^{39}$, C$_1$-C$_6$ alkyl, C$_3$-C$_{10}$ cycloalkyl, —(CH$_2$)$_n$(C$_6$-C$_{10}$ aryl), —(CH$_2$)$_n$(5 to 10 membered heterocyclic), —(CH$_2$)$_n$O(CH$_2$)$_i$OR$^{37}$ and —(CH$_2$)$_n$OR$^{37}$, wherein n is an integer from 0 to 6 and i is an integer from 2 to 6; and each R$^{40}$ is independently selected from H, C$_1$-C$_{10}$ alkyl, —(CH$_2$)$_n$(C$_6$-C$_{10}$ aryl), C$_3$-C$_{10}$ cycloalkyl, and —(CH$_2$)$_n$(5-10 membered heterocyclic), wherein n is an integer ranging from 0 to 6;

each R$^{36}$ and R$^{39}$ is independently selected from the group consisting of H, —OH, C$_1$-C$_6$ alkyl, C$_3$-C$_{10}$ cycloalkyl, —(CH$_2$)$_n$(C$_6$-C$_{10}$ aryl), —(CH$_2$)$_n$(5-10 membered heterocyclic), —(CH$_2$)$_n$O(CH$_2$)$_i$OR$^{37}$, —(CH$_2$)$_n$CN(CH$_2$)$_n$OR$^{37}$, —(CH$_2$)$_n$CN(CH$_2$)$_i$R$^{37}$, and —(CH$_2$)$_n$OR$^{37}$, wherein n is an integer ranging from 0 to 6 and i is an integer ranging from 2 to 6, and the alkyl, aryl and heterocyclic moieties of the foregoing R$^{36}$ and R$^{39}$ groups are optionally substituted by one or more substituents independently selected from —OH, halo, cyano, nitro, trifluoromethyl, azido, —C(O)R$^{40}$, —C(O)OR$^{40}$, —CO(O)R$^{40}$, —OC(O)OR$^{40}$, —NR$^{37}$C(O)R$^{41}$, —C(O)NR$^{37}$R$^{41}$, —NR$^{37}$R$^{41}$, —C$_1$-C$_6$ alkyl, —(CH$_2$)$_n$(C$_6$-C$_{10}$ aryl), —(CH$_2$)$_n$(5 to 10 membered heterocyclic), —(CH$_2$)$_n$O(CH$_2$)$_i$OR$^{37}$, and —(CH$_2$)$_n$OR$^{37}$, wherein n is an integer ranging from 0 to 6 and i is an integer ranging from 2 to 6, with the proviso that when R$^{36}$ and R$^{39}$ are both attached to the same nitrogen, then R$^{36}$ and R$^{39}$ are not both bonded to the nitrogen directly through an oxygen;

each R$^{37}$ and R$^{41}$ is independently selected from the group consisting of H, OR$^{36}$, C$_1$-C$_6$ alkyl and C$_3$-C$_{10}$ cycloalkyl;

each R$^{6a}$ and R$^{6b}$ is independently selected from the group consisting of hydrogen, —(CZ$^5$Z$^6$)$_u$-(C$_3$-C$_6$)cycloalkyl, —(CZ$^5$Z$^6$)$_u$-(C$_5$-C$_6$)cycloalkenyl, —(CZ$^5$Z$^6$)$_u$-aryl, —(CZ$^5$Z$^6$)$_u$-heterocycle, (C$_2$-C$_6$)alkenyl, and (C$_1$-C$_6$) alkyl, which is optionally substituted with 1 to 3 independently selected Y$^3$ groups, where u is 0, 1, 2, or 3, and wherein when u is 2 or 3, the CZ$^5$Z$^6$ units may be the same or different, or R$^{6a}$ and R$^{6b}$ taken together with adjacent atoms can form a heterocycle;

each Z$^3$, Z$^4$, Z$^5$ and Z$^6$ is independently selected from the group consisting of H, F and (C$_1$-C$_6$)alkyl, or each Z$^3$ and Z$^4$, or Z$^5$ and Z$^6$ are selected together to form a carbocycle, or two Z$^3$ groups on adjacent carbon atoms are selected together to optionally form a carbocycle;

each Y$^2$ and Y$^3$ is independently selected from the group consisting of halogen, cyano, nitro, tetrazolyl, guanidino, amidino, methylguanidino, azido, —C(O)Z$^7$, —OC(O)NH$_2$, —OC(O)NHZ$^7$, —OC(O)NZ$^7$Z$^8$, —NHC(O)Z$^7$, —NHC(O)NH$_2$, —NHC(O)NHZ$^7$, —NHC(O)NZ$^7$Z$^8$, —C(O)OH, —C(O)OZ$^7$, —C(O)NH$_2$, —C(O)NHZ$^7$, —C(O)NZ$^7$Z$^8$, —P(O)$_3$H$_2$, —P(O)$_3$(Z$^7$)$_2$, —S(O)$_3$H, —S(O)Z$^7$, —S(O)$_2$Z$^7$, —S(O)$_3$Z$^7$, —Z$^7$, —OZ$^7$, —OH, —NH$_2$, —NHZ$^7$, —NZ$^7$Z$^8$, —C(═NH)NH$_2$, —C(═NOH)NH$_2$, —N-morpholino, (C$_2$-C$_6$)alkenyl, (C$_2$-C$_6$)alkynyl, (C$_1$-C$_6$)haloalkyl, (C$_2$-C$_6$)haloalkenyl, (C$_2$-C$_6$)haloalkynyl, (C$_1$-C$_6$)haloalkoxy, —(CZ$^9$Z$^{10}$)$_r$NH$_2$, —(CZ$^9$Z$^{10}$)$_r$NHZ$^3$, —(CZ$^9$Z$^{10}$)$_r$NZ$^7$Z$^8$, —X$^6$(CZ$^9$Z$^{10}$)$_r$-(C$_3$-C$_8$)cycloalkyl, —X$^6$(CZ$^9$Z$^{10}$)$_r$-(C$_5$-C$_8$)cycloalkenyl, —X$^6$(CZ$^9$Z$^{10}$)$_r$-aryl and —X$^6$(CZ$^9$Z$^{10}$)$_r$-heterocycle, wherein r is 1, 2, 3 or 4;

X$^6$ is selected from the group consisting of O, S, NH, —C(O)—, —C(O)NH—, —C(O)O—, —S(O)—, —S(O)$_2$— and —S(O)$_3$—;

Z$^7$ and Z$^8$ are independently selected from the group consisting of an alkyl of 1 to 12 carbon atoms, an alkenyl of 2 to 12 carbon atoms, an alkynyl of 2 to 12 carbon atoms, a cycloalkyl of 3 to 8 carbon atoms, a cycloalkenyl of 5 to 8 carbon atoms, an aryl of 6 to 14 carbon atoms, a heterocycle of 5 to 14 ring atoms, an aralkyl of 7 to 15 carbon atoms, and a heteroaralkyl of 5 to 14 ring atoms, or Z$^7$ and Z$^8$ together may optionally form a heterocycle;

Z$^9$ and Z$^{10}$ are independently selected from the group consisting of H, F, a (C$_1$-C$_{12}$)alkyl, a (C$_6$-C$_{14}$)aryl, a (C$_5$-C$_{14}$) heteroaryl, a (C$_7$-C$_{15}$)aralkyl and a (C$_5$-C$_{14}$)heteroaralkyl, or Z$^9$ and Z$^{10}$ are taken together form a carbocycle, or two Z$^9$ groups on adjacent carbon atoms are taken together to form a carbocycle; or any two Y$^2$ or Y$^3$ groups attached to adjacent carbon atoms may be taken together to be —O[C(Z$^9$)(Z$^{10}$)]$_r$O or —O[C(Z$^9$)(Z$^{10}$)]$_{r+1}$, or any two Y$^2$ or Y$^3$ groups attached to the same or adjacent carbon atoms may be selected together to form a carbocycle or heterocycle; and wherein any of the above-mentioned substituents comprising a CH$_3$ (methyl), CH$_2$ (methylene), or CH (methine) group which is not attached to a halogen, SO or SO$_2$ group or to a N, O or S atom optionally bears on said group a substituent selected from hydroxy, halogen, (C$_1$-C$_4$)alkyl, (C$_1$-C$_4$)alkoxy and an —N[(C$_1$-C$_4$)alkyl][(C$_1$-C$_4$)alkyl];

E$^2$ is —C≡CH or —C≡C—(CR$^{45}$R$^{45}$)$_n$—R$^{46}$;

R$^{45}$ is independently selected from the group consisting of H, a (C$_1$-C$_6$)alkyl and a (C$_3$-C$_8$)cycloalkyl;

R$^{46}$ is selected from the group consisting of heterocyclyl, —N(R$^{47}$)—C(O)—N(R$^{47}$)(R$^{48}$), —N(R$^{47}$)—C(S)—N (R$^{47}$)(R$^{48}$), —N(R$^{47}$)—C(O)—OR$^{48}$, —N(R$^{47}$)—C(O)—(CH$_2$)$_n$—R$^{48}$, —N(R$^{47}$)—SO$_2$R$^{47}$, —(CH$_2$)$_n$NR$^{47}$R$^{48}$, —(CH$_2$)$_n$OR$^{48}$, —(CH$_2$)$_n$SR$^{49}$, —(CH$_2$)$_n$S(O)R$^{49}$, —(CH$_2$)$_n$S(O)$_2$R$^{49}$, —OC(O)R$^{49}$, —OC(O)OR$^{49}$, —C(O)NR$^{47}$R$^{48}$, heteroaryl optionally substituted with one or more substituents selected from the group consisting of halo, —CF$_3$, (C$_1$-C$_6$)alkoxy, —NO$_2$, (C$_1$-C$_6$)alkyl, —CN, —SO$_2$R$^{50}$ and —(CH$_2$)$_n$NR$^{50}$R$^{51}$, and aryl optionally substituted with one or more substituents selected from the group consisting of halo, —CF$_3$, (C$_1$-C$_6$)alkoxy, —NO$_2$, (C$_1$-C$_6$)alkyl, —CN, —SO$_2$R$^{50}$ and —(CH$_2$)$_n$NR$^{50}$R$^{51}$;

R$^{47}$ and R$^{48}$ are independently selected from the group consisting of H, (C$_1$-C$_6$)alkyl, (C$_3$-C$_8$)cycloalkyl, heterocyclyl, —(CH$_2$)$_n$NR$^{50}$R$^{51}$, —(CH$_2$)$_n$OR$^{50}$, —(CH$_2$)$_n$C(O)

$R^{49}$, —$C(O)_2R^{49}$, —$(CH_2)_nSR^{49}$, —$(CH_2)_nS(O)R^{49}$, —$(CH_2)_nS(O)_2R^{49}$, —$(CH_2)_nR^{49}$, —$(CH_2)_nCN$, aryl optionally substituted with one or more substituents selected from the group consisting of halo, —$CF_3$, $(C_1-C_6)$ alkoxy, —$NO_2$, $(C_1-C_6)$alkyl, —CN, —$(CH_2)_nOR^{49}$, —$(CH_2)_n$heterocyclyl, —$(CH_2)_n$heteroaryl, —$SO_2R^{50}$ and —$(CH_2)_nNR^{50}R^{51}$, and heteroaryl optionally substituted with one or more substituents selected from the group consisting of halo, —$CF_3$, $(C_1-C_6)$alkoxy, —$NO_2$, $(C_1-C_6)$ alkyl, —CN, —$(CH_2)_nOR^{49}$, —$(CH_2)_n$heterocyclyl, —$(CH_2)_n$heteroaryl, —$SO_2R^{50}$ and —$(CH_2)_nNR^{50}R^{51}$, or $R^{47}$ and $R^{48}$, together with the atom to which they are attached, form a 3-8 membered ring;

$R^{49}$ is selected from the group consisting of $(C_1-C_6)$alkyl, $(C_3-C_8)$cycloalkyl, heterocyclyl($C_1-C_6$)alkylene, aryl($C_1-C_6$)alkylene wherein the aryl is optionally substituted with one or more substituents selected from the group consisting of halo, —$CF_3$, $(C_1-C_6)$alkoxy, —$NO_2$, $(C_1-C_6)$alkyl, —CN, —$SO_2R^{50}$ and —$(CH_2)_nNR^{50}R^{51}$, heteroaryl($C_1-C_6$)alkylene wherein the heteroaryl is optionally substituted with one or more substituents selected from the group consisting of halo, —$CF_3$, $(C_1-C_6)$alkoxy, —$NO_2$, $(C_1-C_6)$ alkyl, —CN, —$SO_2R^{50}$ and —$(CH_2)_nNR^{50}R^{51}$, aryl optionally substituted with one or more substituents selected from the group consisting of halo, —$CF_3$, $(C_1-C_6)$ alkoxy, —$NO_2$, $(C_1-C_6)$alkyl, —CN, —$SO_2R^{50}$ and —$(CH_2)_nNR^{50}R^{51}$, and heteroaryl optionally substituted with one or more substituents selected from the group consisting of halo, —$CF_3$, $(C_1-C_6)$alkoxy, —$NO_2$, $(C_1-C_6)$ alkyl, —CN, —$SO_2R^{50}$ and —$(CH_2)_nNR^{50}R^{51}$;

$R^{50}$ and $R^{51}$ are independently selected from the group consisting of H, $(C_1-C_6)$alkyl, $(C_3-C_8)$cycloalkyl and —$C(O)R^{45}$, or $R^{50}$ and $R^{51}$, together with the atom to which they are attached, form a 3-8 membered ring; and E is the group defined by —$(Z^{11})$-$(Z^{12})_m$-$(Z^{13})_{m1}$, wherein $Z^{11}$ is heterocyclyl or heterocyclylene;

$Z^{12}$ is selected from the group consisting of OC(O), OC(S) and C(O);

$Z^{13}$ is selected from the group consisting of heterocyclyl, aralkyl, N(H)$R^{52}$, $(C_1-C_3)$alkyl, —$OR^{52}$, halo, $S(O)_2R^{56}$, $(C_1-C_3)$hydroxyalkyl and $(C_1-C_3)$haloalkyl;

m is 0 or 1;

m1 is 0 or 1;

$R^{52}$ is selected from the group consisting of H, —$(CH_2)_qS(O)_2R^{54}$, $R^{55}NR^{53}R^{53}$, $(C_1-C_3)$alkyl, —$(CH_2)_qOR^{53}$, —$C(O)R^{54}$ and —$C(O)OR^{53}$;

q is 0, 1, 2, 3 or 4;

$R^{53}$ is $(C_1-C_3)$alkyl;

$R^{54}$ is $(C_1-C_3)$alkyl or $N(H)R^{53}$;

$R^{55}$ is $(C_1-C_6)$ alkyl; and $R^{56}$ is selected from the group consisting of $NH_2$, $(C_1-C_3)$ alkyl and $OR^{52}$.

In a preferred embodiment of the compounds according to the present invention, the compounds are represented by the formula B-0:

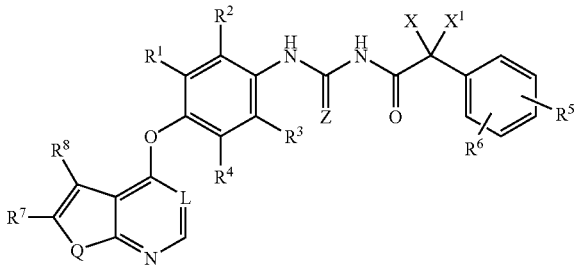

and N-oxides, hydrates, solvates, pharmaceutically acceptable salts, prodrugs and complexes thereof, wherein Z is O or S;

X and $X^1$ are independently selected from the group consisting of H, $C_1-C_6$ alkyl, halo, cyano, or nitro, wherein $C_1-C_6$ alkyl is optionally substituted;

$R^1$, $R^2$, $R^3$, $R^4$, $R^5$ and $R^6$ are independently selected from the group consisting of hydrogen, halo, $C_1-C_6$ alkyl, $C_2-C_6$ alkenyl and $C_2-C_6$ alkynyl, wherein $C_1-C_6$ alkyl, $C_2-C_6$ alkenyl and $C_2-C_6$ alkynyl are optionally substituted;

Q is O, S, NH, N($C_1-C_6$ alkyl), or N—Y-(aryl);

L is N, or CR, wherein R is halo, —CN, $C_1-C_6$ alkyl, $C_2-C_6$ alkenyl, or $C_2-C_6$ alkynyl, wherein $C_1-C_6$ alkyl, $C_2-C_6$ alkenyl, and $C_2-C_6$ alkynyl are optionally substituted; and $R^7$ is selected from the group consisting of H, halogen, $C_1-C_6$ alkyl, —C(=O)$NR^9R^{10}$, —C(=O)(aryl), —C(=O)(heterocyclyl), —C(=O)(heteroaryl), —Y-(aryl), —Y-(heterocyclyl), —Y-(heteroaryl), —Y—$NR^9R^{10}$, —$SO_2NR^9R^{10}$ and $CO_2R^9$, wherein $C_1-C_6$ alkyl, aryl, heterocyclyl and heteroaryl are each optionally substituted;

$R^9$ and $R^{10}$ are independently selected from the group consisting of H, $C_1-C_6$ alkyl, —Y-(cycloalkyl), —Y-(aryl), —Y-(heterocyclyl), —Y-(heteroaryl), —Y—O—$Y^1$—O—$R^{11}$, —$Y^1$—$CO_2$—$R^{11}$, and —Y—O—$R^{11}$, wherein $C_1-C_6$ alkyl, cycloalkyl, aryl, heterocyclyl, and heteroaryl are each optionally substituted, or $R^9$ and $R^{10}$ are taken together with the nitrogen to which they are attached to form a $C_5-C_9$ heterocyclyl ring or a heteroaryl ring, wherein said ring is optionally substituted;

$R^8$ is selected from the group consisting of H, halo and $C_1-C_6$ alkyl, wherein $C_1-C_6$ alkyl is optionally substituted;

Y is a bond or is —$(C(R^{11})(H))_t$—, wherein t is an integer from 1 to 6;

$Y^1$ is —$(C(R^{11})(H))_t$—, and $R^{11}$ at each occurrence is independently H or $C_1-C_6$ alkyl, wherein $C_1-C_6$ alkyl is optionally substituted.

In a preferred embodiment of the compounds according to the present invention, X and $X^1$ are both hydrogen.

In a preferred embodiment of the compounds according to the present invention, $R^1$ is hydrogen or halogen.

In a preferred embodiment of the compounds according to the present invention, $R^1$ is fluorine.

In a preferred embodiment of the compounds according to the present invention, $R^4$ is hydrogen or halogen.

In a preferred embodiment of the compounds according to the present invention, $R^4$ is fluorine.

In a preferred embodiment of the compounds according to the present invention, $R^2$, $R^3$, $R^5$, and $R^6$ are each hydrogen.

In a preferred embodiment of the compounds according to the present invention, Q is S, N($C_1-C_6$ alkyl), or N—Y-(aryl).

In a preferred embodiment of the compounds according to the present invention, L is CH or N.

In a preferred embodiment of the compounds according to the present invention, $R^8$ is selected from the group consisting of H, halo and $C_1$-$C_6$ alkyl, wherein $C_1$-$C_6$ alkyl is optionally substituted with OH or $NR^{14}R^{15}$, where $R^{14}$ and $R^{15}$ are independently H or $C_1$-$C_6$ alkyl, or $R^{14}$ and $R^{15}$ are taken together with the nitrogen to which they are attached to form a $C_5$-$C_9$ heterocyclyl ring or a heteroaryl ring, wherein said ring is optionally substituted.

In a preferred embodiment of the compounds according to the present invention, $R^7$ is selected from the group consisting of H, halogen, $C_1$-$C_6$ alkyl, —$CONR^9R^{10}$, —$SO_2NH_2$, —$SO_2NR^9R^{10}$, —Y-heterocycle —Y-heteroaryl, —S-aryl, —S—$C_1$-$C_6$ alkyl, —SO—$C_1$-$C_6$ alkyl and —$SO_2$—$C_1$-$C_6$ alkyl, wherein $C_1$-$C_6$ alkyl is unsubstituted or is substituted with one or two of hydroxy or halogen, and the heterocycle, and heteroaryl are unsubstituted or are substituted with one or two of alkoxy, alkyl, or haloalkyl.

In a preferred embodiment of the compounds according to the present invention, $R^7$ is —$CONR^9R^{10}$.

In a preferred embodiment of the compounds according to the present invention, $R^9$ and $R^{10}$ are independently selected from the group consisting of H, $C_1$-$C_6$ alkyl, —Y—O—$R^{11}$, —Y-(heterocycle), —$Y^1$—$CO_2$—$R^{11}$ and —Y-(aryl), wherein $C_1$-$C_6$ alkyl is unsubstituted or is substituted with one or two of hydroxy or halogen, and the heterocycle, and aryl are unsubstituted or are substituted with one or two of alkoxy, alkyl, or haloalkyl.

In a preferred embodiment of the compounds according to the present invention, $R^9$ and $R^{10}$ are taken together with the nitrogen to which they are attached to form a pyrrolidinyl, piperidinyl, piperazinyl, morpholinyl, or thiomorpholinyl ring, wherein said ring is unsubstituted or is substituted with one or two of alkoxy, alkyl, or haloalkyl.

In a preferred embodiment of the compounds according to the present invention, $R^7$ is selected from the group consisting of H, halogen, $C_1$-$C_6$ alkyl, —$SO_2NR^9R^{10}$, —C(=O)(heterocyclyl), —Y-(heterocyclyl), —Y-(heteroaryl), —S-aryl, —S—$C_1$-$C_6$ alkyl, —SO—$C_1$-$C_6$ alkyl and —$SO_2$—$C_1$-$C_6$ alkyl, wherein $C_1$-$C_6$ alkyl is unsubstituted or is substituted with one or two of hydroxy or halogen, and the heterocyclyl, and heteroaryl are unsubstituted or are substituted with one or two of alkoxy, alkyl, or haloalkyl.

In a preferred embodiment of the compounds according to the present invention, Z is sulfur.

In a preferred embodiment of the compounds according to the present invention, the compounds are represented by the formula B-1:

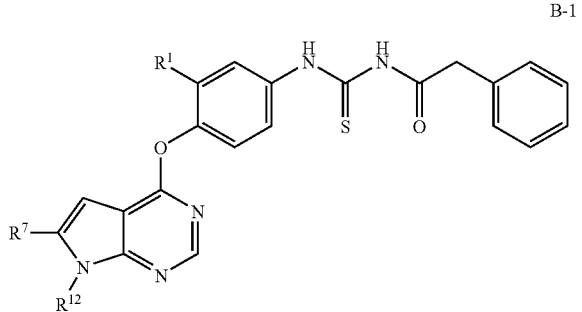

B-1 and N-oxides, hydrates, solvates, pharmaceutically acceptable salts, prodrugs and complexes thereof, wherein $R^1$ is selected from the group consisting of hydrogen, halo, $C_1$-$C_6$ alkyl, $C_2$-$C_6$ alkenyl and $C_2$-$C_6$ alkynyl, wherein $C_1$-$C_6$ alkyl, $C_2$-$C_6$ alkenyl and $C_2$-$C_6$ alkynyl are optionally substituted;

$R^7$ is selected from the group consisting of H, halogen, $C_1$-$C_6$ alkyl, —C(=O)$NR_9R_{10}$, —C(=O)(aryl), —C(=O)(heterocyclyl), —C(=O)(heteroaryl), —Y-(aryl), —Y-(heterocyclyl), —Y-(heteroaryl), —Y—$NR^9R^{10}$, —$SO_2NR^9R^{10}$ and $CO_2R^9$, wherein $C_1$-$C_6$ alkyl, aryl, heterocycle and heteroaryl are each independently optionally substituted;

$R^9$ and $R^{10}$ are independently selected from the group consisting of H, $C_1$-$C_6$ alkyl, —Y-(cycloalkyl), —Y-(aryl), —Y-(heterocyclyl), —Y-(heteroaryl), —Y—O—$Y^1$—O—$R^{11}$, —$Y^1$—$CO_2$—$R^{11}$, and —Y—O—$R^{11}$, wherein $C_1$-$C_6$ alkyl, cycloalkyl, aryl, heterocycle, and heteroaryl are each optionally substituted, or $R^9$ and $R^{10}$ taken together with the nitrogen to which they are attached form a $C_5$-$C_9$ heterocyclyl ring or a heteroaryl ring, wherein said ring is optionally substituted;

Y is a bond or is —$(C(R^{11})(H))_t$—, wherein t is an integer from 1 to 6;

$Y_1$ is —$(C(R^{11})(H))_t$—;

$R^{11}$ at each occurrence is independently H or $C_1$-$C_6$ alkyl, wherein $C_1$-$C_6$ alkyl is optionally substituted; and $R^{12}$ is selected from the group consisting of H, $C_1$-$C_6$ alkyl and —Y-(aryl), wherein $C_1$-$C_6$ alkyl and aryl are optionally substituted.

In a preferred embodiment of the compounds according to the present invention, $R^1$ is hydrogen or halogen.

In a preferred embodiment of the compounds according to the present invention, $R^1$ is fluorine.

In a preferred embodiment of the compounds according to the present invention, $R^{12}$ is unsubstituted $C_1$-$C_3$ alkyl or unsubstituted benzyl.

In a preferred embodiment of the compounds according to the present invention, $R^7$ is —C(O)$NR^9R^{10}$.

In a preferred embodiment of the compounds according to the present invention, $R^7$ is selected from the group consisting of

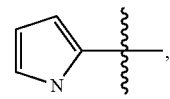,

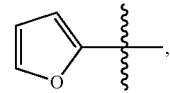,

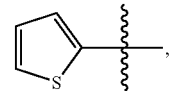,

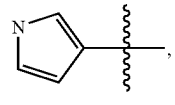,

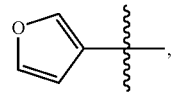,

-continued
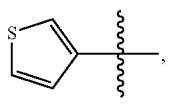,
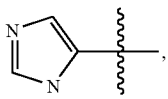,
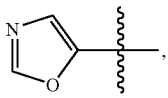,
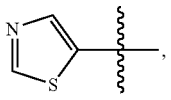,
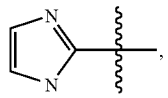,
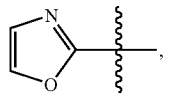,
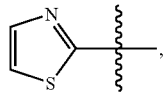,
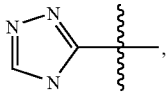,
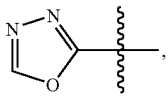,
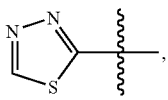,
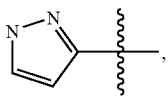,
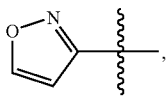,
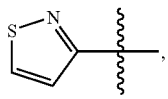,
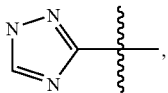,
-continued
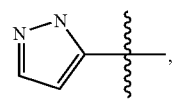,
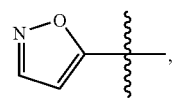,
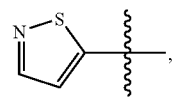,
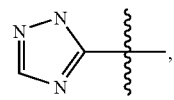,
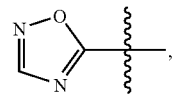,
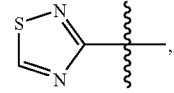,
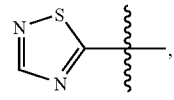,
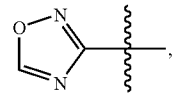,
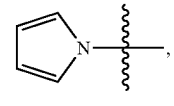,
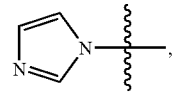,
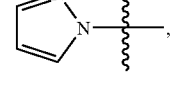,
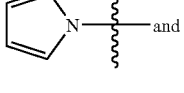 and
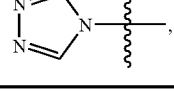,
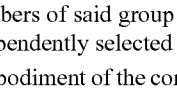,
wherein the members of said group are optionally substituted by 1 to 3 independently selected $R^{38}$.
In a preferred embodiment of the compounds according to the present invention, $R^7$ is selected from the group consisting of

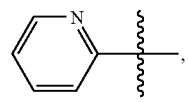,
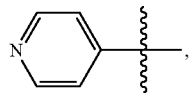,
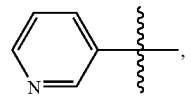,
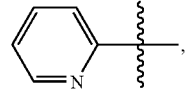,
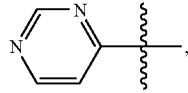,
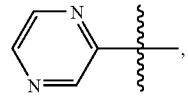,
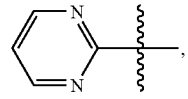,
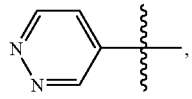,
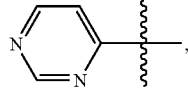,
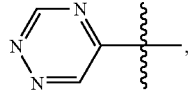,
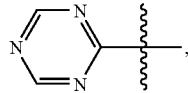,
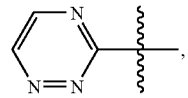,
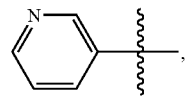,
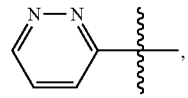,

,
,
,
,
,
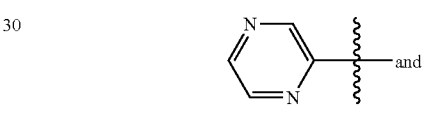 and
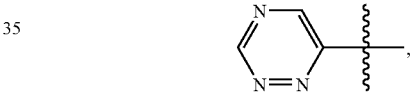, wherein the members of said group are optionally substituted with 1 to 3 independently selected $R^{38}$.

In a third aspect, the invention provides compositions comprising a compound that is an inhibitor of kinase, or an N-oxide, hydrate, solvate, pharmaceutically acceptable salt, prodrug or complex thereof, and a pharmaceutically acceptable carrier, excipient or diluent. Preferably, the invention provides compositions comprising a compound that is an inhibitor of VEGF receptor signaling and HGF receptor signaling, or an N-oxide, hydrate, solvate, pharmaceutically acceptable salt, prodrug or complex thereof, and a pharmaceutically acceptable carrier, excipient, or diluent. In a preferred embodiment, the composition further comprises an additional therapeutic agent.

In a fourth aspect, the invention provides a method of inhibiting kinase, the method comprising contacting the kinase with a compound according to the present invention, or with a composition according to the present invention. Preferably the invention provides a method of inhibiting VEGF receptor signaling and HGF receptor signaling, the method comprising contacting the receptor with a compound according to the present invention, or with a composition according to the present invention. Inhibition of receptor protein kinase activity, preferably VEGF and HGF receptor signaling, can be in a cell or a multicellular organism. If in a multicellular organism, the method according to this aspect of the invention comprises administering to the organism a compound according to the present invention, or a composition according to the present invention. Preferably the organism is a mammal, more preferably a human. In a preferred embodiment, the method further comprises contacting the kinase with an additional therapeutic agent.

The data presented herein demonstrate the inhibitory effects of the VEGF and HGF inhibitors of the invention. These data lead one to reasonably expect that the compounds of the invention are useful not only for inhibition of VEGF receptor signaling and HGF receptor signaling, but also as therapeutic agents for the treatment of proliferative diseases, including cancer and tumor growth.

Preferred compounds according to the invention include those described in the examples below. Compounds were named using Chemdraw Ultra version 6.0.2 or version 8.0.3, which are available through Cambridgesoft.com, 100 Cambridge Park Drive, Cambridge, Mass. 02140, Namepro version 5.09, which is available from ACD labs, 90 Adelaide Street West, Toronto, Ontario, M5H, 3V9, Canada, or were derived therefrom.

Synthetic Schemes and Experimental Procedures

The compounds of the invention can be prepared according to the reaction schemes or the examples illustrated below utilizing methods known to one of ordinary skill in the art. These schemes serve to exemplify some procedures that can be used to make the compounds of the invention. One skilled in the art will recognize that other general synthetic procedures may be used. The compounds of the invention can be prepared from starting components that are commercially available. Any kind of substitutions can be made to the starting components to obtain the compounds of the invention according to procedures that are well known to those skilled in the art.

I. Synthesis (General Schemes)

Thieno[3,2-b]pyridine based compounds of formula A-0 may be prepared according to the procedures illustrated in the scheme A. Thus, thieno[3,2-b]pyridine-7-ol (I) upon treatment with $POCl_3$ is converted to the chloride II. Treatment of this material with a strong base such as n-BuLi followed by an addition of carbon dioxide affords the carboxylate III which is used without purification in the next step, providing the acyl chloride IV (presumably as a hydrochloride salt) upon its reaction with oxalyl chloride. The acyl chloride IV is used for the next step without further purification as well: upon its reaction with different primary and secondary amines the compound IV is converted to a variety of primary and secondary amides V which can further be derivatized via a substitution of the chlorine atom in the pyridine ring.

Thus, V reacting with substituted 4-nitrophenols in a high boiling point solvent, such as diphenyl ether in the presence of a base such as potassium carbonate, produced the nitro derivatives VI which then are reduced to the amines VII upon treatment with a mixture $NiCl_2/NaBH_4$ (or other conventional reagents). The amines VII also may be used for the next step without further purification, and upon treatment with 2-phenylacetyl isothiocyanates afford phenylacetylthioureas VIII bearing the amido-substituents such as the ones shown in the scheme A.

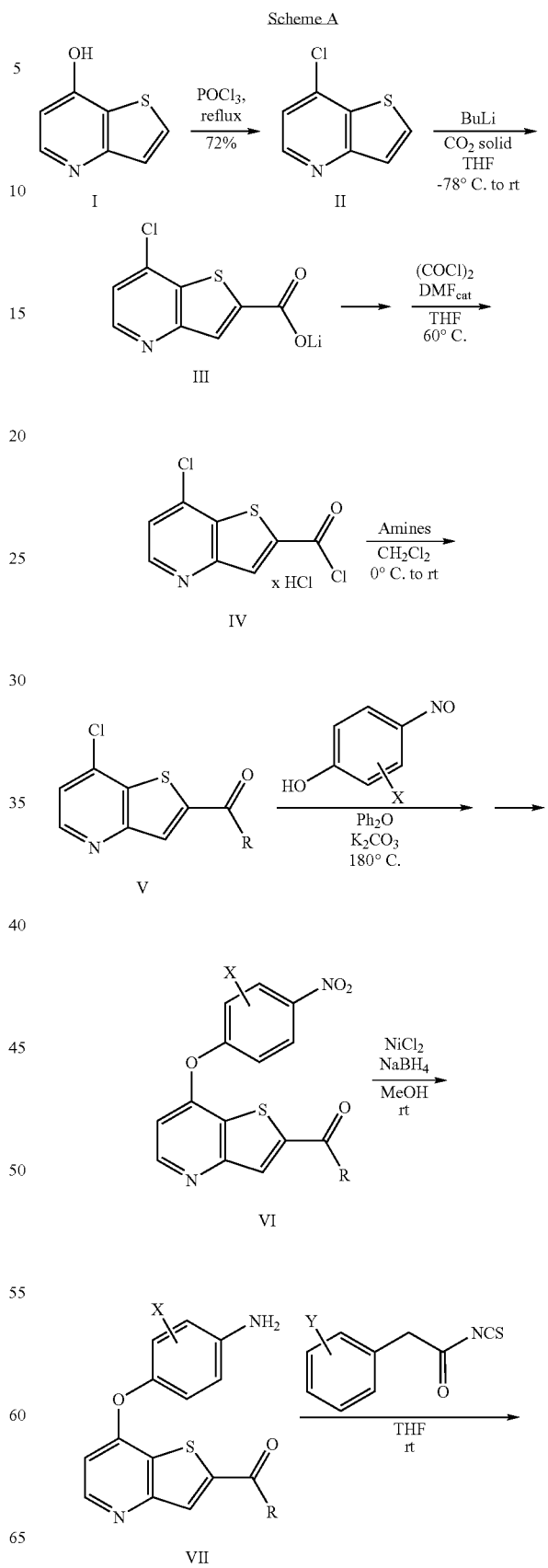

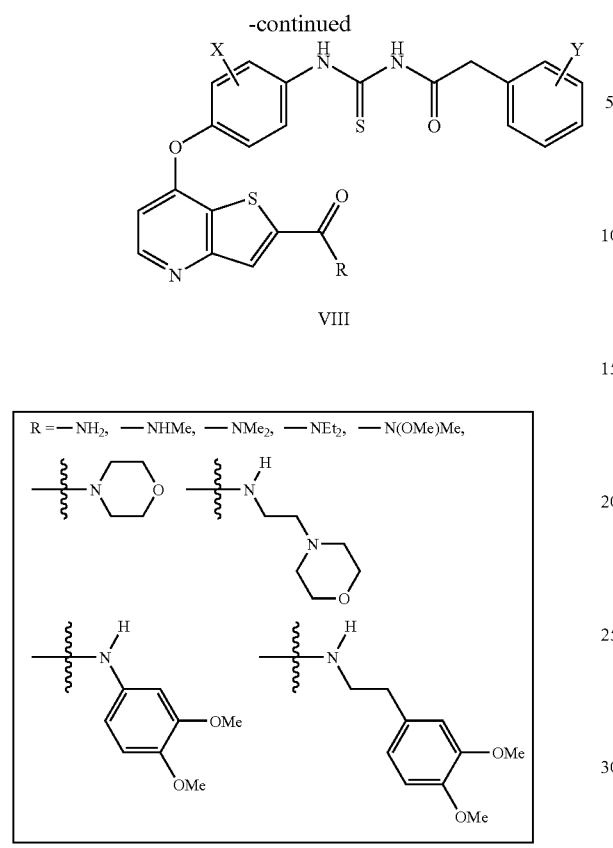

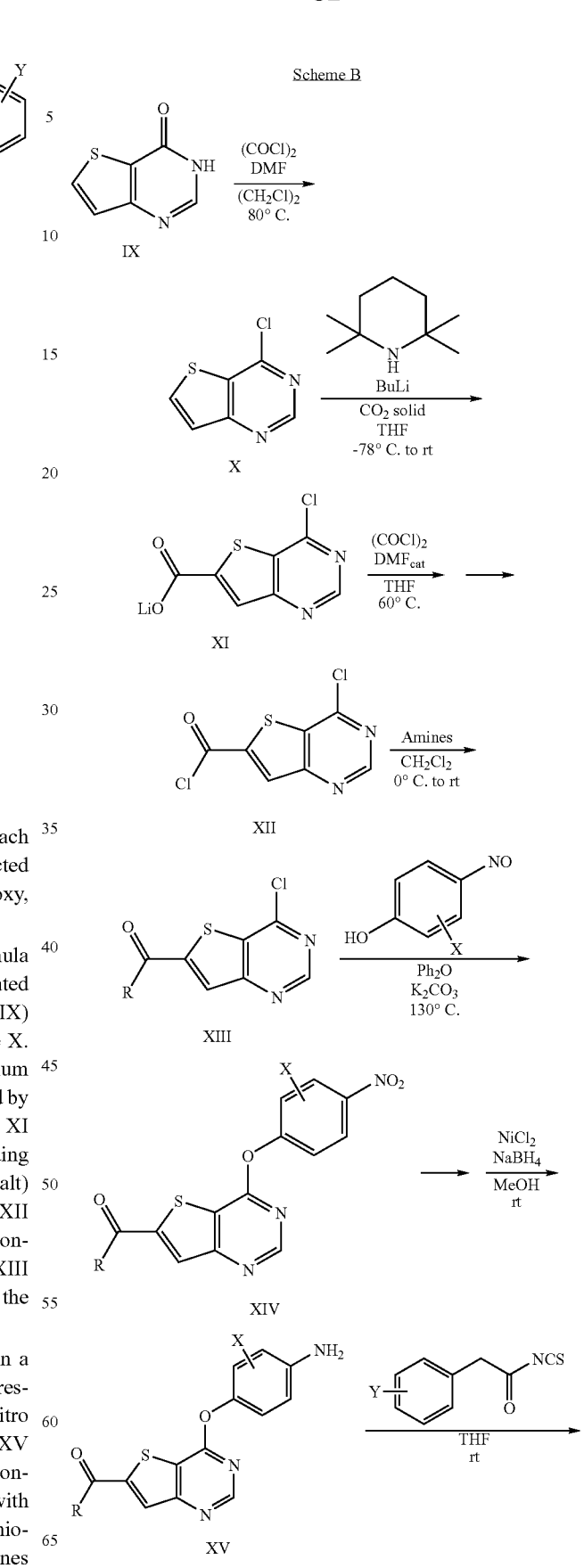

Scheme B

Substituents X and Y (up to three, same or different in each of the indicated benzene rings) are independently selected from halo, $C_1$-$C_6$ alkyl, $C_1$-$C_6$ alkoxy, cyano, nitro, hydroxy, amino, $C_1$-$C_6$ alkylamino Thieno[3,2-d]pyrimidine based compounds of formula A-0 may be prepared according to the procedures illustrated in the scheme B. Thus, thieno[3,2-d]pyrimidine-7-ol (IX) upon treatment with $POCl_3$ is converted to the chloride X. Treatment of this material with a strong base such as lithium tetramethylpiperidide (LiTMP) generated in situ followed by an addition of carbon dioxide affords the carboxylate XI which is used without purification in the next step, providing the acyl chloride XII (presumably as a hydrochloride salt) upon its reaction with oxalyl chloride. The acyl chloride XII reacting with different primary and secondary amines is converted to a variety of primary and secondary amides XIII which can further be derivatized via a substitution of the chlorine atom in the pyrimidine ring.

Thus, XIII reacting with substituted 4-nitrophenols in a high boiling point solvent, such as diphenyl ether in the presence of a base such as potassium carbonate, produce the nitro derivatives XIV which are then reduced to the amines XV upon treatment with a mixture $NiCl_2$/$NaBH_4$ (or other conventional reagents). The amines XV upon treatment with 2-phenylacetyl isothiocyanates afford the phenylacetylthioureas XVI bearing the amido-substituents such as the ones shown in the scheme B.

-continued

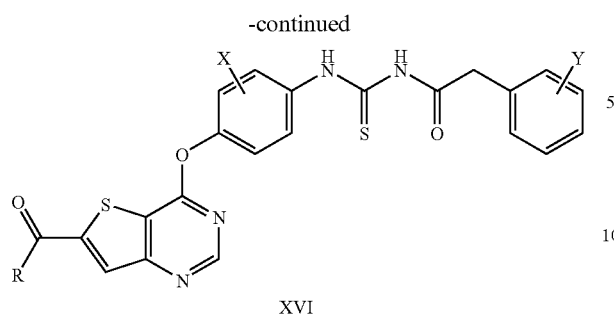

XVI

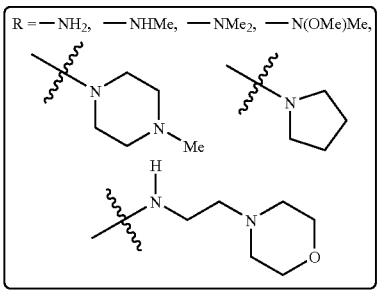

Substituents X and Y (up to three, same or different in each of the indicated benzene rings) are independently selected from halo, $C_1$-$C_6$ alkyl, $C_1$-$C_6$ alkoxy, cyano, nitro, hydroxy, amino, $C_1$-$C_6$ alkylamino Thieno[3,2-b]pyridine based phenylacetylureas of formula A-0 bearing heteroaryl substituents instead of the amido moieties may be prepared according to the procedures illustrated in the scheme C. Thus, treatment of the chloride II with a strong base such as n-BuLi followed by an addition of trimethyltin (or tributyltin) chloride affords the trimethylstannyl (or tributylstannyl) derivative XVII. This material reacting with different heteroaryl bromides in the presence of a Pd-catalyst (Stille coupling reaction or similar type reactions) produces heteroaryl-substituted thienopyridines XVIII which can further be derivatized via a substitution of the chlorine atom in the pyridine ring.

Scheme C

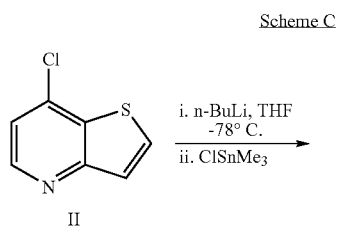

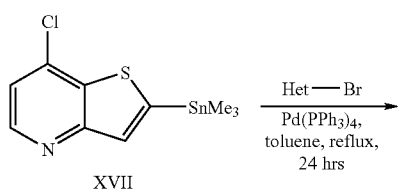

-continued

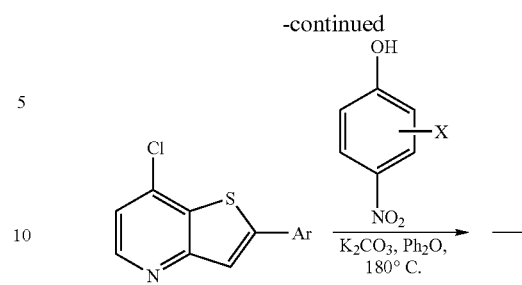

XVIII

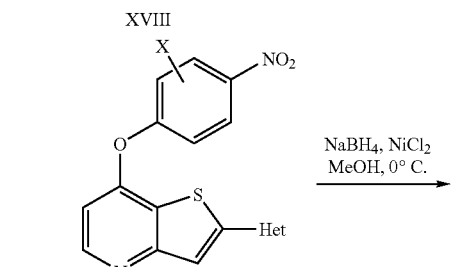

XIX

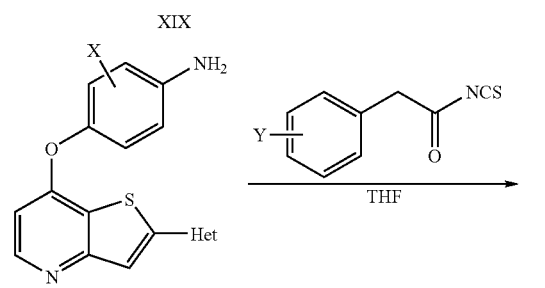

XX

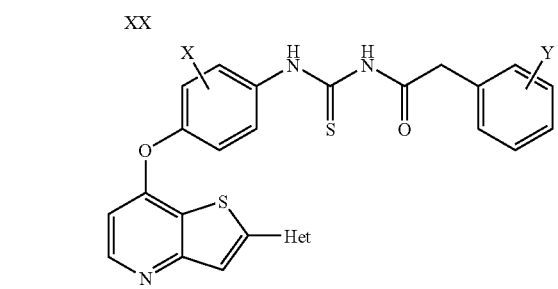

XXI

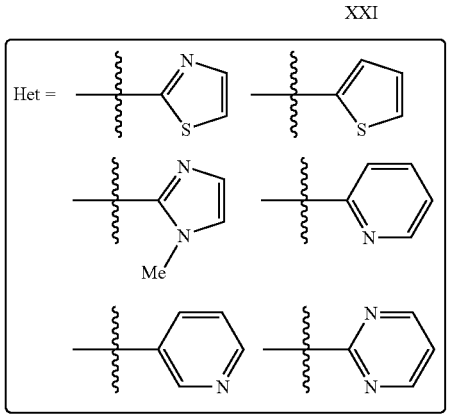

Substituents X and Y (up to three, same or different in each of the indicated benzene rings) are independently selected from halo, $C_1$-$C_6$ alkyl, $C_1$-$C_6$ alkoxy, cyano, nitro, hydroxy, amino, $C_1$-$C_6$ alkylamino Thus, XVIII reacting with substituted 4-nitrophenols in a high boiling point solvent, such as diphenyl ether in the presence of a base such as potassium carbonate, produced the nitro derivatives XIX which are then reduced to the amines XX upon treatment with a mixture $NiCl_2/NaBH_4$ (or other conventional reagents). The amines XX could be used for the next step without further purification, and upon treatment with 2-phenylacetyl isothiocyanates afford the phenylacetylthioureas XXI bearing the heteroaryl substituents such as the ones shown in the scheme C. Heteroaryls shown in the scheme B, in turn may bear additional substituents exemplified (but not limited to) alkyls, amines, alkylamino, aminoalkyls, alkoxyalkyls, hydroxyalkyls, alkylsulfonylalkyls, etc.—known in the art as solubilizing functionalities.

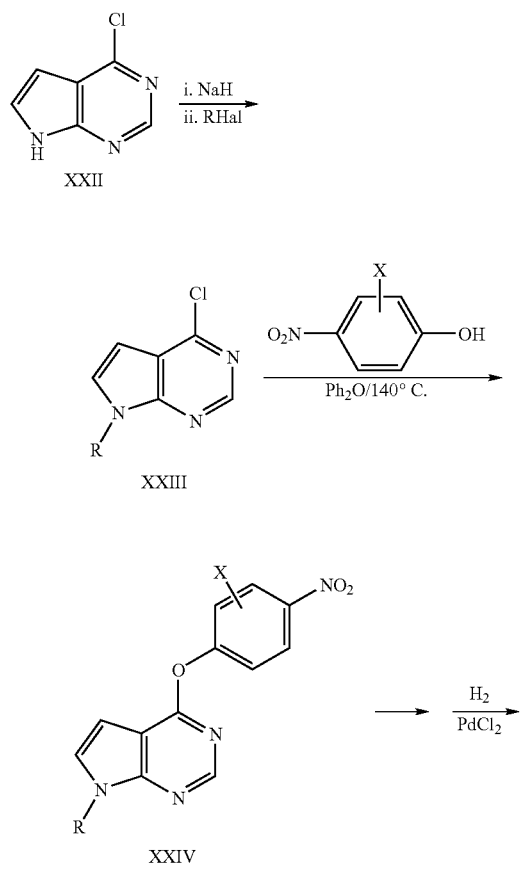

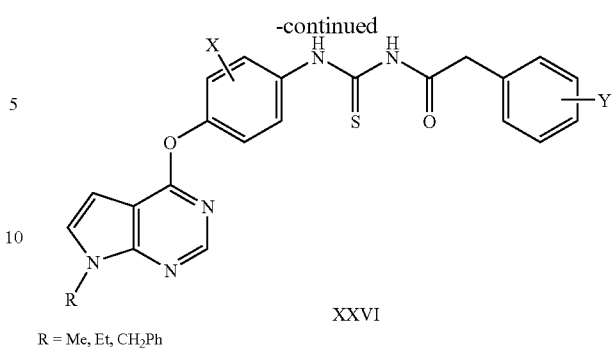

XXVI

R = Me, Et, $CH_2Ph$

Substituents X and Y (up to three, same or different in each of the indicated benzene rings) are independently selected from halo, $C_1$-$C_6$ alkyl, $C_1$-$C_6$ alkoxy, cyano, nitro, hydroxy, amino, $C_1$-$C_6$ alkylamino Pyrrolo[2,3-d]pyrimidine based compounds of formula B-0 may be prepared according to the procedures illustrated in the scheme D. Treatment of the 4-chloro-7H-pyrrolo[2,3-d]pyrimidine (XXII) with an alkyl halide in the presence of a base such as sodium hydride affords the alkylated chlorides XXIII, which reacting with substituted 4-nitrophenols in a high boiling point solvent, such as diphenyl ether in the presence of a base such as cesium carbonate, produced the nitro derivatives XXIV reduced to the amines XXV upon hydrogenation (or treatment with conventional reducing agents). The amines XXV reacting with 2-phenylacetyl isothiocyanates afford the phenylacetylthioureas XXVI bearing the alkyl substituents such as the ones shown in the scheme D.

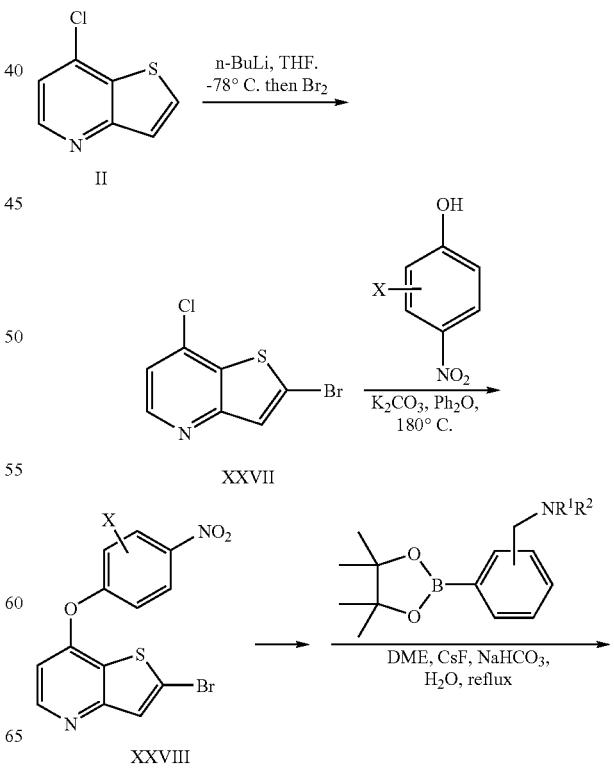

-continued

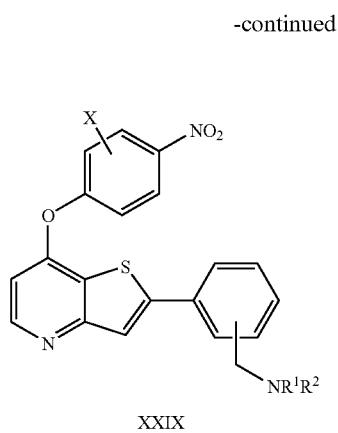

XXIX

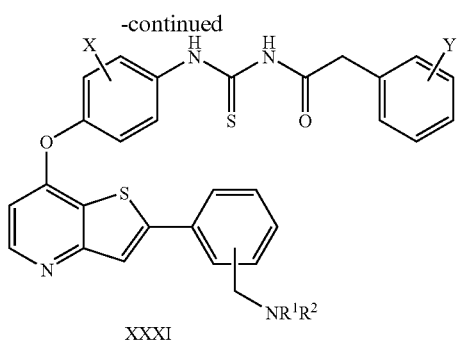

XXXI

R[1] and R[2] are independently selected from alkyl, alkoxy, aminoalkyl, etc., R[1] and R[2] may be attached together to form a carbocyclic or a heterocyclic ring

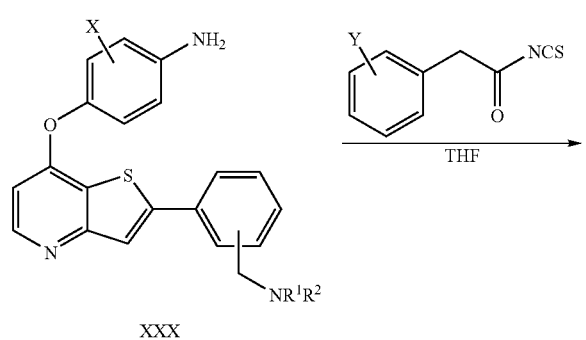

XXX

Substituents X and Y (up to three, same or different in each of the indicated benzene rings) are independently selected from halo, $C_1$-$C_6$alkyl, $C_1$-$C_6$alkoxy, cyano, nitro, hydroxy, amino, $C_1$-$C_6$alkylamino Thieno[3,2-b]pyridine based phenylacetylureas of formula A-0 bearing aryl substituents may be prepared according to the procedures illustrated in the scheme E. Thus chloride II upon lithiation and subsequent bromination is converted to the bromide XXVII that reacting with substituted 4-nitrophenols produces more elaborated compound XXVIII. This material can be used for Suzuki type (and like) reactions with a variety of aryl boronic acids (or boronates), in particular with the ones functionalized with basic groups, thus providing compounds XXIX. Reduction of XXIX with a mixture NiCl$_2$/NaBH$_4$ (or other conventional reagents) affords amines XXX. The latter upon treatment with 2-phenylacetyl isothiocyanates afford the phenylacetylthioureas XXXI bearing aryl substituents such as the ones shown in the scheme E.

Scheme F

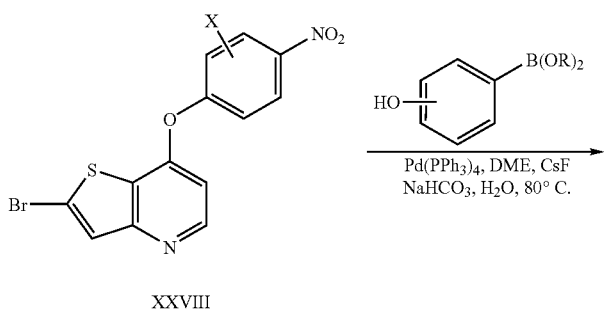

XXVIII

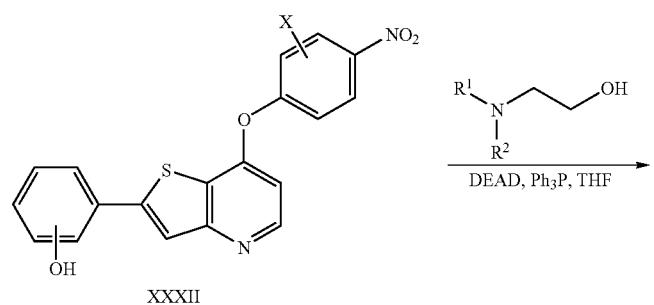

XXXII

-continued
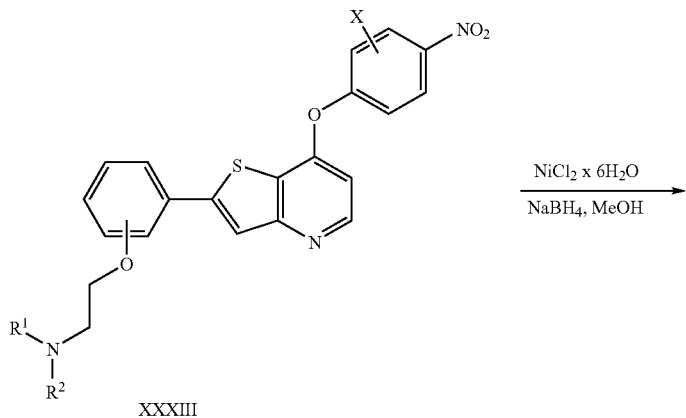
XXXIII
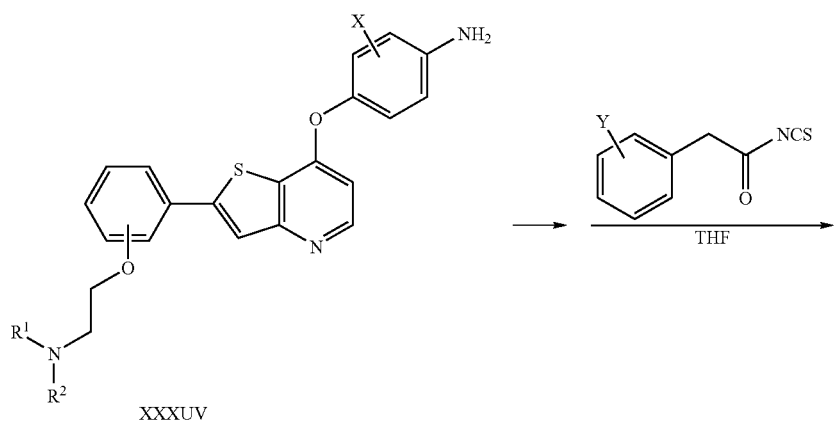
XXXUV
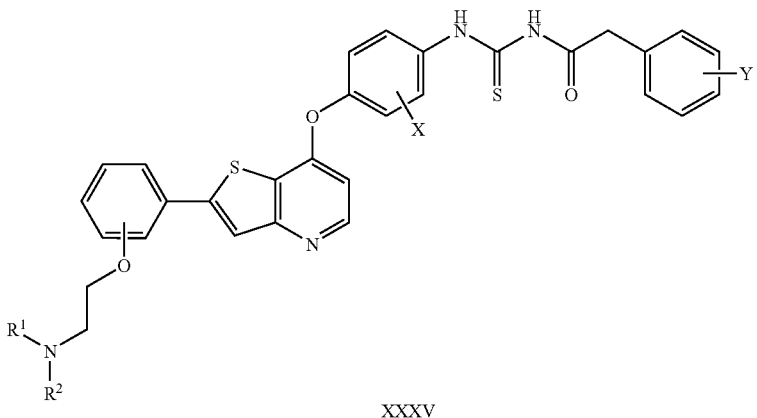
XXXV
R¹ and R² are independently selected from alkyl, alkoxy, aminoalkyl, etc.,
R¹ and R² may be attached together to form a carbocyclic or a heterocyclic ring Substituents X and Y (up to three, same or different in each of the indicated benzene rings) are independently selected from halo, $C_1$-$C_6$alkyl, $C_1$-$C_6$alkoxy, cyano, nitro, hydroxy, amino, $C_1$-$C_6$alkylamino Bromides XXVIII also can be used for Suzuki type (and like) reactions with a variety of hydroxyphenyl boronic acids (boronates), to form phenolic compounds XXXII. These phenols reacting with different alcohols (Mitsunobu reaction), in particular functionalized with basic groups, provide compounds XXXIII. Reduction of XXXIII with a mixture $NiCl_2$/$NaBH_4$ (or other conventional reagents) affords amines XXXIV which upon treatment with 2-phenylacetyl isothiocyanates afford the phenylacetylthioureas XXXV bearing the aryl substituents such as the ones shown in the scheme F.

II. Specific Examples

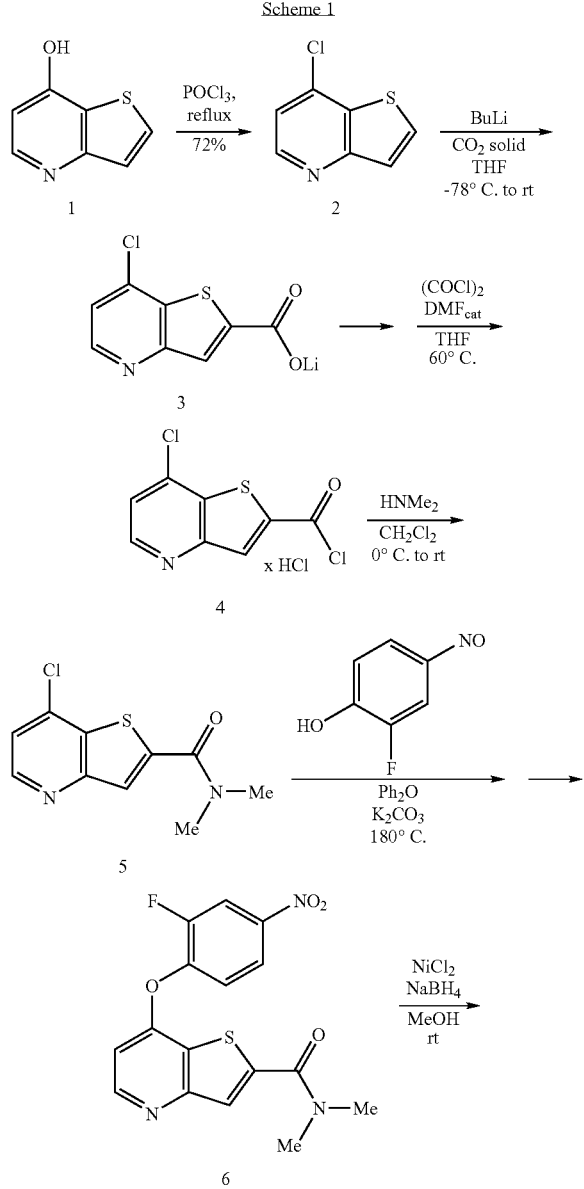

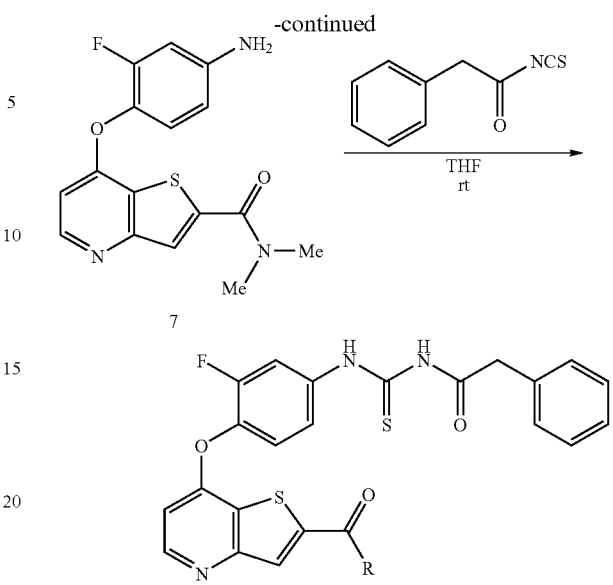

8a: Example 1

Example 1

1-(4-(2-(Dimethylcarbamoyl)thieno[3,2-b]pyridin-7-yloxy)-3-fluorophenyl)-3-(2-phenylacetyl)thiourea (8a)

Step 1: 7-Chlorothieno[3,2-b]pyridine (2)

A stirred suspension of thieno[3,2-b]pyridin-7-ol (1, 5.0 g, 33.1 mmol) in $POCl_3$ (15 mL) was heated to 105° C. in an oil bath for 4 hrs. The resultant solution was cooled to room temperature and the $POCl_3$ was removed under reduced pressure. The residue was cooled in an ice/water bath and cold water was added. The water was made basic with concentrated $NH_4OH$ solution and extracted with EtOAc. The organic extract was dried over anhydrous sodium sulfate and concentrated to produce an oil which was purified by column chromatography (eluent EtOAc-hexane, 1:4) to afford the title compound as a brown solid (4.5 g, 72% yield). $^1$H NMR (400 MHz, $CDCl_3$) δ (ppm): 8.60 (d, J=4.9 Hz, 1H), 7.80 (d, J=5.5 Hz, 1H), 7.60 (d, J=5.5 Hz, 1H), 7.30 (d, J=4.9 Hz, 1H).

Steps 2-4: 7-Chloro-N,N-dimethylthieno[3,2-b]pyridine-2-carboxamide (5)

To a stirred solution of 2 (3.0 g, 17.8 mmol) in dry THF (60 mL) at −78° C. was added n-BuLi (7.8 mL, 19.6 mmol, 2.5 M solution in hexanes) and the resultant suspension was stirred for 15 minutes. Solid carbon dioxide (excess) was added and the mixture was allowed to warm to room temperature over a period of 1 hour. The solvent was removed under reduced pressure and the resultant lithium carboxylate 3 was used without further purification (3.88 g, quantitative).

To a stirred suspension of 3 (3.5 g, 15.9 mmol) in dry DCM (50 mL) was added $(COCl)_2$ (3.96 g, 31.2 mmol) and dry DMF (1 drop). The reaction mixture was heated to reflux for 2 hrs. The solvents were evaporated to produce 4 (presumably as an HCl salt) which was used directly in the next step.

Acyl chloride 4 (2.42 g, 10.5 mmol) was suspended in dry DCM (105 mL) at 0° C. and $Me_2NH$ (15.7 mL, 2M solution in THF, 31.4 mmol) was added and the reaction mixture was stirred overnight. The solvent was removed and the residue was dissolved in EtOAc and washed with water. The organic phase was collected and dried over anhydrous sodium sulfate then filtered and concentrated under reduced pressure to produce a residue, which was purified by column chromatography (eluent EtOAc-hexane, 9:1) to afford 5 as a yellow solid (1.65 g, 45% yield). $^1$H NMR (400 MHz, $CDCl_3$) δ (ppm): 8.62 (d, J=4.8 Hz, 1H), 7.76 (s, 1H), 7.37 (d, J=4.8 Hz, 1H), 3.35-3.25 (m, 3H), 3.25-3.20 (m, 3H).

Step 5: 7-(2-Fluoro-4-nitrophenoxy)-N,N-dimethylthieno[3,2-b]pyridine-2-carboxamide (6)

A mixture of 5 (1.65 g, 6.85 mmol), potassium carbonate (5.68 g, 41.1 mmol) and 2-fluoro-4-nitrophenol (1.65 g, 10.3 mmol) were heated to 170° C. in diphenyl ether (20 mL) for 5 hrs. The mixture was cooled to room temperature, diluted with EtOAc and washed with water. The organic phase was collected, dried over anhydrous sodium sulfate and the solvents were removed under reduced pressure. The residue was purified by column chromatography (eluents EtOAc-hexane 9:1, then MeOH-EtOAc 1:4) to afford 6 as a yellow solid (1.02 g, 41% yield). $^1$H NMR (400 MHz, DMSO-$d_6$) δ (ppm): 8.64 (d, J=5.3 Hz, 1H), 8.46 (dd, J=2.8 and 10.3 Hz, 1H), 8.20 (ddd, J=1.3 and 2.6 and 9.0 Hz, 1H), 7.98 (s, 1H), 7.73 (dd, J=8.3 Hz, 1H), 6.99 (dd, J=0.9 and 4.8 Hz, 1H), 3.25-3.30 (m, 3H), 3.02-3.11 (m, 3H).

Steps 6-7: 1-(4-(2-(Dimethylcarbamoyl)thieno[3,2-b]pyridin-7-yloxy)-3-fluorophenyl)-3-(2-phenylacetyl)thiourea (8a)

To a solution of 6 (190 mg, 0.55 mmol) in MeOH (10 mL) at 0° C. was added $NiCl_2 \times 6H_2O$ (241 mg, 1.02 mmol) and $NaBH_4$ (81.4 mg, 2.2 mmol). The reaction mixture was stirred for 1 hr, concentrated to dryness and the resultant solid was dissolved in 1 M HCl. The aqueous solution was then made basic with concentrated $NH_4OH$ solution and extracted with EtOAc. The organic phase was collected, dried over anhydrous sodium sulfate and filtered. The solvent was evaporated under reduced pressure and the resultant solid was triturated with diethyl ether to afford 7 as a white solid that was used immediately in the next step.

To a suspension of 7 (465.8 mg, 1.41 mmol) in THF (20 mL) was added benzyl isothiocyanate (374 mg, 2.12 mmol) and the reaction mixture was stirred for 1 hr, concentrated under reduced pressure and the resultant residue was purified by column chromatography (eluent EtOAc-MeOH 19:1) to afford a yellow solid which was triturated with $Et_2O$ to afford 8a as an off-white solid (534 mg, 75% yield). $^1$H NMR (400 MHz, DMSO-$d_6$) δ (ppm): 12.47 (s, 1H), 11.78 (s, 1H), 8.57 (d, J=4.2 Hz, 1H), 8.05-7.95 (m, 1H), 7.93 (s, 1H), 7.52 (s, 2H), 7.33 (d, J=3.9 Hz, 1H), 7.28-7.23 (m, 1H), 6.72 (d, J=5.3 Hz, 1H), 3.83 (s, 2H), 3.26 (s broad, 3H), 3.05 (s broad, 3H).

Examples 2-11

Examples 2-11 (compounds 8b-k) were prepared using the same procedures as described for the compound 8a, example 1 (scheme 1). Characterization of 8b-k is provided in table 1.

TABLE 1

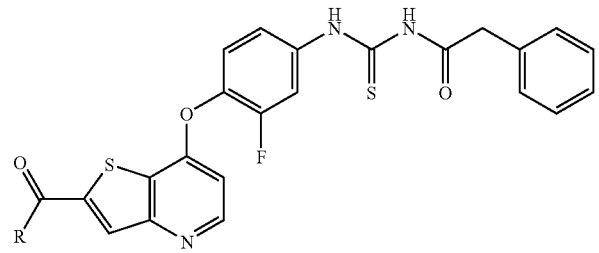

8b–k: Examples 2–11
Characterization of compounds 8b–k (examples 2–11)

| Cpd | Ex | R | Name | Characterization |
|---|---|---|---|---|
| 8b | 2 | (structure: -NH-CH2CH2-morpholine) | 1-(4-(2-(2-morpholinoethylcarbamoyl)thieno[3,2-b]pyridin-7-yloxy)-3-fluorophenyl)-3-(2-phenylacetyl)thiourea | $^1$H NMR (400 MHz, DMSO-$d_6$) δ ppm: 12.52(s, 1H), 11.85(s, 1H), 8.96(t, J=5.3 Hz, 1H), 8.62(d, J=5.5 Hz, 1H), 8.28(s, 1H), 8.06(d, J=10.9 Hz, 1H), 7.57(d, J=6.5 Hz, 2H), 7.38–7.30(m, 5H), 6.77(d, J=5.2 Hz, 1H), 3.86(s, 2H), 3.61(t, J=4.4 Hz, 4H), 3.46(q, J=6.6 Hz, 2H), 3.39–3.36(m, 6H). |
| 8c | 3 | (structure: -N-morpholine) | 1-(4-(2-(morpholinylcarbamoyl)thieno[3,2-b]pyridin-7-yloxy)-3-fluorophenyl)-3-(2-phenylacetyl)thiourea | $^1$H NMR (400 MHz, DMSO-$d_6$). δ ppm: 12.52(s, 1H), 8.72(s, 1), 8.54 (d, J=6.1 Hz, 1H), 8.0–7.98(m, 2H), 7.38–7.26(m, 7H), 6.73(d, J=5.7 Hz, 1H), 3.72(s, 8H), 2.02(s, 2H). |

TABLE 1-continued

8b–k: Examples 2–11
Characterization of compounds 8b–k (examples 2–11)

| Cpd | Ex | R | Name | Characterization |
|---|---|---|---|---|
| 8d | 4 | 3,4-dimethoxyphenyl-NH- | 1-(4-(2-(3,4-dimethoxyphenylcarbamoyl)thieno[3,2-b]pyridin-7-yloxy)-3-fluorophenyl)-3-(2-phenylacetyl)thiourea | ¹H NMR (400 MHz, DMSO-d₆). δ ppm: 10.64(s, 1H), 8.61(d, J=5.4 Hz, 1H), 8.51(s, 1H), 8.03(d, J=12.7 Hz, 1H), 7.92(s, 1H), 7.54(m, 2H), 7.44(d, J=2.4 Hz, 1H), 7.29(m, 7H), 6.96(d, J=8.8 Hz, 1H), 6.76(d, J=6.1 Hz, 1H), 3.82(s, 2H), 3.76(d, J=8.3 Hz, 6H). |
| 8e | 5 | -N(H)Me | 1-(4-(2-(methylcarbamoyl)thieno[3,2-b]pyridin-7-yloxy)-3-fluorophenyl)-3-(2-phenylacetyl)thiourea | ¹H NMR (400 MHz, DMSO-d₆). δ ppm: 12.47(s, 1H), 11.80(s, 1H), 8.92(s, 1H), 8.55(d, J=3.7 Hz, 1H), 8.18(s, 1H), 8.01(d, J=11.9 Hz, 1H), 7.52(s, 2H), 7.32(s, 4H), 7.25(s, 1H), 6.71(d, J=4.9 Hz, 1H), 3.81(s, 2H), 2.83(d, J=3.3 Hz, 3H). |
| 8f | 6 | 3,4-dimethoxyphenethyl-NH- | 1-(4-(2-(3,4-dimethoxyphenethylcarbamoyl)thieno[3,2-b]pyridin-7-yloxy)-3-fluorophenyl)-3-(2-phenylacetyl)thiourea | ¹H NMR (400 MHz, DMSO-d₆). δ ppm: 12.47(s, 1H), 11.81(s, 1H), 9.03(t, J=5.7 Hz, 1H), 8.56(d, J=5.5 Hz, 1H), 8.22(s, 1H), 8.02(d, J=11.4 Hz, 1H), 7.53(s, 2H), 7.33(m, 4H), 7.27(m, 1H), 6.84(m, 2H), 6.73(m, 2H), 3.82(s, 2H), 3.70(d, J=4.5 Hz, 6H), 3.50(q, J=6.6 Hz, 2H), 2.80(t, J=7.0 Hz, 2H). |
| 8g | 7 | -NEt₂ | 1-(4-(2-(diethylcarbamoyl)thieno[3,2-b]pyridin-7-yloxy)-3-fluorophenyl)-3-(2-phenylacetyl)thiourea | ¹H NMR (400 MHz, DMSO-d₆). δ ppm: 12.58(s, 1H), 8.71(s, 1H), 8.59 (s, 1H), 8.05–7.92(m, 2H), 7.40(m, 4H), 7.33(m, 3H), 6.71(s, 1H), 3.80 (s, 2H), 3.59(q, J=7.2 Hz, 4H), 1.29 (m, 6H). |
| 8h | 8 | 4-isopropylphenyl-NH- | 1-(4-(2-(4-isopropylphenylcarbamoyl)thieno[3,2-b]pyridin-7-yloxy)-3-fluorophenyl)-3-(2-pheenylacetyl)thiourea | ¹H NMR (400 MHz, DMSO-d₆). δ ppm: 12.48(s, 1H), 11.81(s, 1H), 10.56(s, 1H), 8.61(d, J=5.4 Hz, 1H), 8.53(s, 1H), 8.03(d, J=12.3 Hz, 2), 7.66(d, J=8.4 Hz, 2H), 7.54(m, 2H), 7.33(m, 4H), 7.23(m, 3H), 6.75(d, J=5.3 Hz,, 1H), 3.82(s, 2H), 2.87(m, 1H), 1.20(d, J=6.8 Hz, 6H). |

TABLE 1-continued

Characterization of compounds 8b–k (examples 2–11)

8b–k: Examples 2–11

| Cpd | Ex | R | Name | Characterization |
|---|---|---|---|---|
| 8i | 9 | –NH₂ | 1-(4-(2-carbamoylthieno[3,2-b]pyridin-7-yloxy)-3-fluorophenyl)-3-(2-phenylacetyl)thiourea | ¹H NMR (400 MHz, DMSO-d₆). δ ppm: 112.48(s, 1H), 11.81(s, 1H), 8.56(dd, J=0.6 Hz and 5.5 Hz, 1H), 8.40(s, 1H), 8.25(d, J=0.8 Hz, 1H), 8.01(d, J=13.3 Hz, 1H), 7.86(s, 1H), 7.33(m, 4H), 7.25(m, 1H), 6.72 (d, J=5.3 Hz, 1H), 3.82(s, 2H). |
| 8j | 10 | –N(OMe)Me | 1-(4-(2-(N-methoxy-N-meethylcarbamoyl)thieno[3,2-b]pyridin-7-yloxy)-3-fluorophenyl)-3-(2-phenylacetyl)thiourea | ¹H NMR (400 MHz, DMSO-d₆). δ ppm: 12.51(s, 1H), 11.85(s, 1H), 8.63(d, J=5.3 Hz, 1H), 8.22(s, 1H), 8.04(d, J=13.1 Hz, 1H), 7.57(m, 2H), 7.36(m, 4H), 7.30(m, 1H), 6.77 (d, J=5.3 Hz, 1H), 3.87(s, 3H), 3.85 (s, 3H), 3.39(s, 3H). |
| 8k | 11 | –NH–CH(Me)–C(O)OMe | Methyl-2-(1-(4-(2-(carbamoyl)thieno[3,2-b]pyridin-7-yloxy)-3-fluorophenyl)-3-(2-phenylacetyl)thioureido)propanoate | ¹H NMR (400 MHz, DMSO-d₆). δ ppm: 12.48(s, 1H), 11.80(s, 1H), 9.28(d, J=6.9 Hz, 1H), 8.59(d, J=5.3 Hz, 1H), 8.38(s, 1H), 8.02(d, J=12.9 Hz, 1H), 7.53(m, 2H), 7.33(m, 4H), 7.28(m, 1H), 6.75(d, J=5.3 Hz, 1H), 4.49(m, 1H), 3.82(s, 2H), 3.66 (s, 3H), 1.44(d, J=7.4 Hz, 3H). |

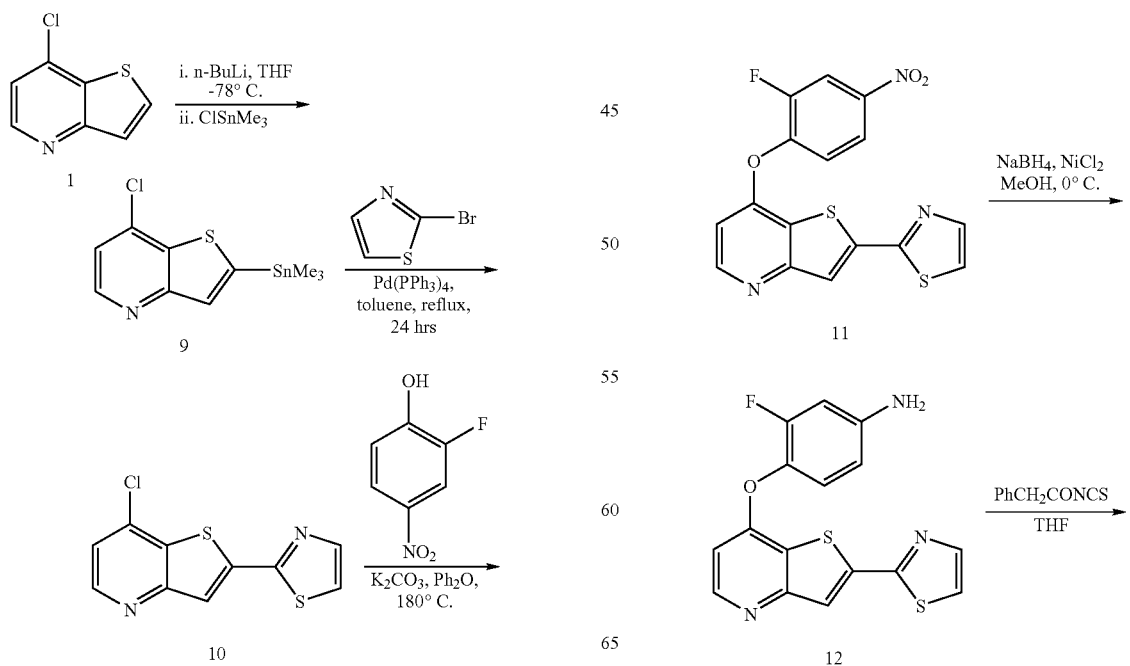

Scheme 2

-continued

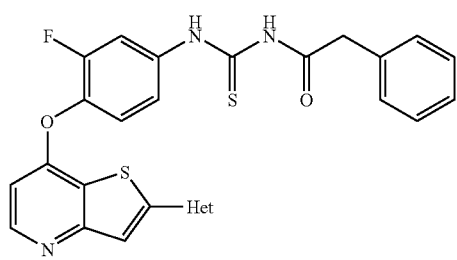

13a: Example 12

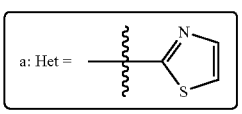

Example 12

1-(4-(2-(Thiazol-2-yl)thieno[3,2-b]pyridin-7-yloxy)-3-fluorophenyl)-3-(2-phenylacetyl)thiourea (13a)

Step 1:
7-Chloro-2-(trimethylstannyl)thieno[3,2-b]pyridine

To a solution of 2 (1.0 g, 5.9 mmol) in dry THF (60 mL) at −78° C. was added n-BuLi (2.36 mL, 5.9 mmol, 2.5 M solution in hexanes) and the resultant brown precipitate was stirred for 10 min. Trimethytin chloride (1.18 g, 5.9 mmol) in dry THF (10 mL) was added slowly and the mixture was allowed to stir at −78° C. for 2 hrs, quenched with methanol at −78° C. and the solvents were removed under reduced pressure. The residue was dissolved in EtOAc and washed with water; the organic phase was collected, dried over anhydrous sodium sulfate and filtered. The EtOAc was evaporated under reduced pressure and the resultant oil was purified by column chromatography (eluent EtOAc-hexane 1:4) to afford 9 (1.2 g, 63% yield) as a brown solid. $^1$H NMR (400 MHz, CDCl$_3$) δ ppm: 8.21 (d, J=5.1 Hz, 1H), 7.36 (s, 1H), 6.91 (m, 1H), 0.16 (s, 9H).

Step 2:
7-Chloro-2-(thiazol-2-yl)thieno[3,2-b]pyridine (10)

To a solution of 9 (175 mg, 0.53 mmol) and 2-bromothiazole (94 mg, 0.58 mmol) in dry toluene (6 mL) was added Pd(PPh$_3$)$_4$ (62 mg, 0.053 mmol) and the reaction mixture was refluxed overnight, cooled to room temperature and the solvents were removed under reduced pressure. The resultant solid was triturated with hexane/Et$_2$O and then purified by column chromatography (eluent EtOAc-hexane 1:1) to give 10 as a white solid (75 mg, 56% yield). $^1$H NMR (400 MHz, DMSO-d$_6$) δ ppm: 8.65 (d, J=5.1 Hz), 8.2 (s, 1H), 7.97 (s, 2H), 7.61 (d, J=5.1 Hz).

Step 3: 7-(2-Fluoro-4-nitrophenoxy)-2-(thiazol-2-yl)thieno[3,2-b]pyridine (11)

To a suspension of 10 (194 mg, 0.77 mmol) in Ph$_2$O (10 mL) was added 2-fluoro-4-nitrophenol (240 mg, 1.53 mmol) and potassium carbonate (425 mg, 3.08 mmol) and the reaction mixture was heated at 180° C. for 4 hrs. The reaction mixture was cooled to room temperature and diluted with EtOAc. The resultant solution was washed with water and the organic layer was collected, dried over anhydrous sodium sulfate and filtered. The solvents were removed under reduced pressure; the residue was dissolved in DCM, and purified by column chromatography (eluent EtOAc-hexane 4:1) to afford 11 (190 mg, 66% yield) as a yellow solid. $^1$H NMR (400 MHz, DMSO-d$_6$) δ ppm: 8.61 (d, J=5.5 Hz, 1H), 8.46 (dd, J=2.74 and 10.37 Hz), 8.24 (s, 1H), 8.20-8.10 (m, 1H), 7.95 (s, 2H), 7.73 (t, J=8 Hz, 1H), 6.98 (d, J=5.3 Hz, 1H).

Steps 4-5. 1-(4-(2-(Thiazol-2-yl)thieno[3,2-b]pyridin-7-yloxy)-3-fluorophenyl)-3-(2-phenylacetyl)thiourea (13a)

To a suspension of 11 (190 mg, 0.55 mmol) in MeOH (10 mL) at 0° C. was added NiCl$_2$.6H$_2$O (241 mg, 1.02 mmol) and NaBH$_4$ (81.4 mg, 2.2 mmol). The reaction mixture was allowed to stir for 1 hr, concentrated to dryness and the resultant solid was dissolved in 1 M HCl. The aqueous solution was then made basic with concentrated ammonium hydroxide solution whereupon 12 precipitated as a grey solid, which was collected by filtration and used crude in the next step.

To a suspension of the amine 12 (152 mg, 0.44 mmol) in THF (10 mL) was added benzyl isothiocyanate (118 mg, 0.66 mmol) and the reaction mixture was stirred for 1 hr, concentrated under reduced pressure and purified by column chromatography (eluents EtOAc-hexane 3:1, then EtOAc) to afford a yellow solid. Trituration of this material with Et$_2$O/hexane gave 13a (100 mg, 43% yield) as a white solid. $^1$H NMR (400 MHz, DMSO-d$_6$) δ ppm: 12.48 (s, 1H), 11.81 (s, 1H), 8.55 (d, J=5.5 Hz, 1H), 8.19 (s, 1H), 8.00 (d, J=13.3 Hz, 1H), 7.95 (d, J=3.1 Hz, 1H), 7.94 (d, J=3.1 Hz, 1H), 7.53 (m, 2H), 7.33 (m, 3H), 7.25 (m, 2H), 6.72 (d, J=5.5 Hz, 1H), 3.82 (s, 2H).

Example 13

Examples 13-19 (compounds 13b-h) were prepared using the same procedures as described for the compound 13a (example 12, scheme 2). Characterization of compounds 13b-h (examples 13-19) is provided in table 2.

TABLE 2

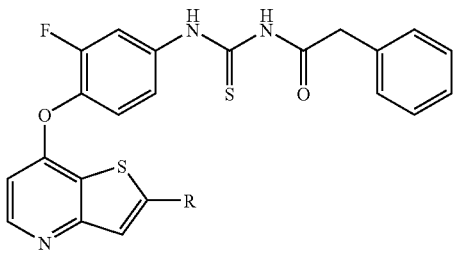

13 b–h: examples 13–19
Characterization of compounds 13b–h (examples 13–19)

| Cpd | Ex | R | Name | Characterization |
|---|---|---|---|---|
| 13b | 13 | 2-pyridinyl | 1-(4-(2-(Pyridin-2-yl)thieno[3,2-b]pyridin-7-yloxy)-3-fluorophenyl)-3-(2-phenylacetyl)thiourea | $^1$H NMR (400 MHz, DMSO-d$_6$). δ ppm: 12.47(s, 1H), 11.81(s, 1H), 8.61(d, J=2.9 Hz, 1H), 8.51 (d, J=5.5 Hz, 1H), 8.36(s, 1H), 8.26(d, J=8.0 Hz, 1H), 8.0(d, J= 17 Hz, 1H), 7.93(dt, J=1.76 and 7.82 Hz, 1H), 7.51(m, 2H), 7.32(m, 4H), 7.26(m, 1H), 6.65 (d, J=5.5 Hz, 1H), 3.82(s, 2H). MS (m/z) 515.2 (M+H) |
| 13c | 14 | pyrimidin-2-yl | N-(3-Fluoro-4-(2-(pyrimidin-2-yl)thieno[3,2-b]pyridin-7-yloxy)phenylcarbamothio-yl)-2-phenylacetamide | $^1$H NMR (400 MHz, DMSO-d$_6$) δ ppm: 12.51(s, 1H), 11.82 (s, 1H), 8.95(m, 2H), 8.59(m, 1H), 8.34(s, 1H), 8.04(m, 1H), 7.55(m, 3H), 7.34(m, 4H), 7.28(m, 1H), 6.75(m, 1H), 3.82(s, 2H). MS (m/z) 516.2 (M+H) |
| 13d | 15 | 1-methyl-1H-imidazol-2-yl | N-(3-Fluoro-4-(2-(1-methyl-1H-imidazol-2-yl)thieno[3,2-b]pyridin-7-yloxy)phenylcarbamothio-yl)-2-phenylacetamide | $^1$H NMR (400 MHz, DMSO-d$_6$). δ ppm: 12.48(s, 1H), 11.84 (s, 1H), 8.50(m, 1H), 8.1(s, 1H), 8.04(d, J=12.1 Hz, 1H), 7.63(s, 1H), 7.56(m, 2H), 7.39 (s, 1H), 7.33(m, 4H), 7.27(m, 1H), 7.19(m, 1H), 6.77(d, J= 5.7 Hz, 1H). MS (m/z) 518.2 (M+H) |
| 13e | 16 | thiophen-2-yl | N-(3-Fluoro-4-(2-(thiophen-2-yl)thieno[3,2-b]pyridin-7-yloxy)phenylcarbamothio-yl)-2-phenylacetamide | $^1$H NMR (400 MHz, DMSO-d$_6$). δ ppm: 12.48(s, 1H), 11.84 (s, 1H), 8.50(m, 1H), 8.04(m, 1H), 7.79(s, 1H), 7.73(s, 1H), 7.63(m, 2H), 7.39(s, 4H), 7.27 (m, 1H), 7.19(m, 1H), 6.65(m, 1H), 5.74(m, 1H), 3.81(s, 2H). MS (m/z) 520.0 (M+H) |
| 13f | 17 | 1,3,4-thiadiazol-2-yl | N-(4-(2-(1,3,4-Thiadiazol-2-yl)thieno[3,2-b]pyridin-7-yloxy)-3-fluorophenylcarbamothio-yl)-2-phenylacetamide | $^1$H NMR (400 MHz, DMSO-d$_6$). δ ppm: 12.47(s, 1H), 11.82 (s, 1H), 8.57(d, J=5.5 Hz, 1H), 8.16(s, 1H), 8.0(d, J=13 Hz, 1H), 7.56(m, 1H), 7.36(m, 4H), 7.26(m, 2H), 6.71(d, J= 5.3 Hz, 1H), 3.82(s, 2H). MS (m/z) 522 (M+H) |
| 13g | 18 | pyridin-3-yl | N-(3-fluoro-4-(2-(pyridin-3-yl)thieno[3,2-b]pyridin-7-yloxy)phenylcarbamoythio-yl)-2-phenylacetamide | $^1$H NMR (400 MHz, DMSO-d$_6$). δ ppm: 12.49(s, 1H), 11.85(s, 1H), 9.12(dd, J=0.8 and 2.3 Hz), 8.63 (dd, H=1.6 and 4,7 Hz, 1H), 8.55 (d, J=5.5 Hz, 1H), 8.27(m, 1H), 8.23(s, 1H), 8.0(d, J=13.1 Hz, 1H), 7.54(m, 3H), 7.32(m, 4H), 7.26(m, 2H), 6.69(dd, J=0.9 and 5.5 Hz, 1H), 3.81(s, 2H). MS (m/z) 515.2 (M+H) |

TABLE 2-continued
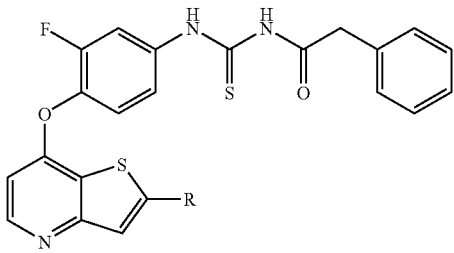
13 b–h: examples 13–19
Characterization of compounds 13b–h (examples 13–19)
| Cpd | Ex | R | Name | Characterization |
|---|---|---|---|---|
| 13h | 19 | (morpholinothiazol group) | N-(3-fluoro-4-(2-(2-morpholinothiazol-5-yl)thieno[3,2-b]pyridin-7-yloxy)phenylcarbamothioyl)-2-phenylacetamide | $^1$H NMR (400 MHz, DMSO-d$_6$). δ ppm: 12.45(s, 1H), 11.81(s, 1H), 8.44(dd, J=1.2, 5.48 Hz, 1H), 7.98(d, J=12 Hz, 1H), 7.74(s, 1H), 7.50(s, 3H), 7.33 (m, 4H), 7.27(m, 2H), 6.59(d, J=5.5 Hz,, 1H), 3.82(s, 2H), 3.72(t, J=4.7 Hz, 4H), 3.47(t, J=4.9 Hz, 4H). MS (m/z) 606.2 (M+H) |
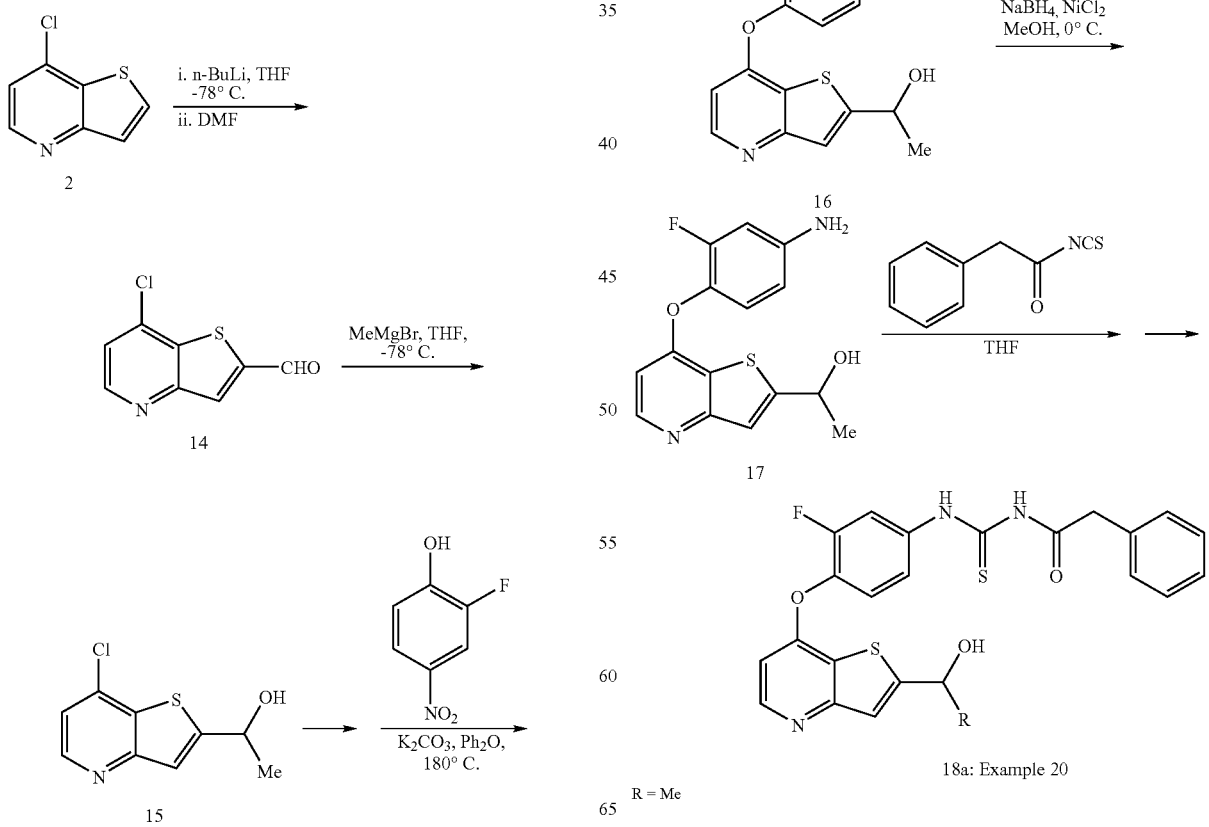
Scheme 3

Example 20

1-(4-(2-(1-Hydroxyethyl)thieno[3,2-b]pyridin-7-yloxy)-3-fluorophenyl)-3-(2-phenylacetyl)thiourea (18a)

Step 1.
7-Chlorothieno[3,2-b]pyridine-2-carbaldehyde (14)

To a solution of 2 (200 mg, 1.18 mmol) in dry THF (10 mL) at −78° C. was added n-BuLi (0.57 mL, 1.42 mmol, 2.5 M solution in hexanes) and the resultant suspension was stirred for 20 min. Dry DMF (0.5 mL, excess) was added and the reaction mixture was stirred for an additional 2 hrs. The reaction mixture was quenched with methanol at −78° C. and water was added. The mixture was extracted with EtOAc and the organic extracts were combined, dried over anhydrous sodium sulfate and filtered. The solvent was removed under reduced pressure and the resultant yellow solid was triturated with hexane to afford 14 (250 mg, 100% yield) as a pale yellow solid. $^1$H NMR (400 MHz, DMSO-d$_6$) δ ppm: 10.2 (s, 1H), 8.78 (d, J=5.1 Hz, 1H), 8.61 (s, 1H), 7.78 (d, J=5.1 Hz, 1H).

Steps 2-3. 1-(7-(2-Fluoro-4-nitrophenoxy)thieno[3,2-b]pyridin-2-yl)ethanol (16)

To a solution of 14 (200 mg, 1 mmol) in dry THF (5 mL) at −78° C. was added methylmagnesium bromide (0.51 mL, 1 mmol, 2 M solution in dibutyl ether) and the reaction mixture was stirred at −78° C. for 1 hr. The reaction was quenched with water and extracted with EtOAc. The organic phase was dried over anhydrous sodium sulfate and evaporated. The resultant solid was washed with hexane to give 15 as a white solid (177 mg, 83% yield), which was used crude in the next step.

To a suspension of 15 (170 mg, 0.79 mmol) in Ph$_2$O (10 mL) was added 2-fluoro-4-nitrophenol (250 mg, 1.58 mmol) and potassium carbonate (436 mg, 3.16 mmol) and the reaction mixture was heated at 180° C. for 4 hrs, cooled to room temperature and diluted with EtOAc. The solution was washed with water and the organic layer was collected, dried over anhydrous sodium sulfate and filtered. The solvents were removed under reduced pressure. The residue was dissolved in DCM, and purified by column chromatography (eluent EtOAc-hexane, 4:1) to afford 16 (125 mg, 47% yield) as a yellow solid. $^1$H NMR (400 MHz, DMSO-d6) δ ppm: 8.52 (dd, J=0.8 and 5.5 Hz, 1H), 8.44 (dd, J=2.5 and 10.2 Hz, 1H), 8.15 (d, J=10.2 Hz, 1H), 7.63 (t, J=8.2 Hz, 1H), 7.41 (s, 1H), 6.86 (d, J=5.3 Hz, 1H), 5.96 (dd, J=0.4 Hz and 4.9 Hz), 5.09 (m, 1H), 1.49 (d, J=6.5 Hz, 3H).

Steps 4-5. 1-(4-(2-(1-Hydroxyethyl)thieno[3,2-b]pyridin-7-yloxy)-3-fluorophenyl)-3-(2-phenylacetyl)thiourea (18a)

To a suspension of 16 (129 mg, 0.39 mmol) in MeOH (5 mL) at 0° C. was added NiCl$_2$.6H$_2$O (183 mg, 0.77 mmol) and sodium borohydride (57 mg, 1.5 mmol). The reaction mixture was allowed to stir for 1 hr, concentrated to dryness and the resultant solid was dissolved in 1 M HCl. The aqueous solution was then made basic with concentrated ammonium hydroxide solution, extracted with EtOAc and the organic extract was dried over anhydrous sodium sulfate then filtered. The solvent was removed under reduced pressure to give 17 (110 mg, 94% yield) as brown oil, which was used immediately in the next step.

To an emulsion of 17 (110 mg, 0.36 mmol) in THF (10 mL) was added 2-phenylacetyl isothiocyanate (76 mg, 0.43 mmol) and the reaction mixture was stirred for 1 hr, concentrated and the residue was purified by column chromatography (eluents EtOAc-hexane 3:1, then EtOAc) to afford a yellow solid which upon trituration with diethyl ether/hexane gave 18a as an off-white solid (90 mg, 52% yield). $^1$H NMR (400 MHz, DMSO-d$_6$) δ ppm: 12.47 (s, 1H), 11.81 (s, 1H), 8.43 (d, J=5.5 Hz, 1H), 8.2 (s, 1H), 7.9 (d, J=12.3 Hz, 1H), 7.51-7.44 (m, 2H), 7.30 (d, J=0.9 Hz, 1H), 7.33-7.31 (m, 3H), 7.30-7.24 (m, 1H), 6.57 (d, J=5.3 Hz, 1H), 5.91 (d, J=4.9 Hz, 1H), 5.09 (m, 1H), 3.9 (s, 2H), 1.49 (d, J=6.3 Hz, 3H).

Example 21

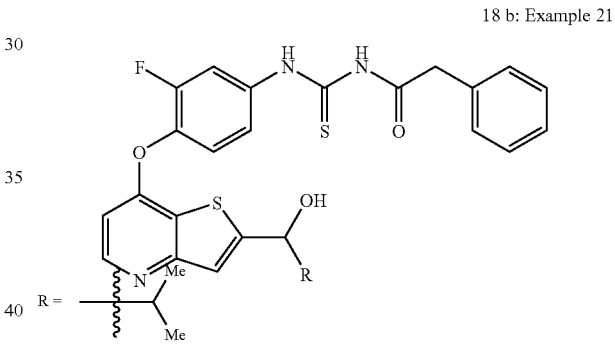

18 b: Example 21

1-(4-(2-(1-Hydroxy-2-methylpropyl)thieno[3,2-b]pyridin-7-yloxy)-3-fluorophenyl)-3-(2-phenylacetyl)thiourea (18b)

Title compound was prepared using the same procedures as described for the compound 18a (example 20, scheme 3). $^1$H NMR (400 MHz, DMSO-d$_6$) δ ppm: 12.46 (s, 1H), 11.80 (s, 1H), 8.43 (d, J=5.9 Hz, 1H), 7.98 (d, J=2.2 Hz, 1H), 7.52-7.45 (m, 2H), 7.35 (s, 1H), 7.32 (m, 3H), 7.28 (m, 1H), 6.55 (d, J=5.5 Hz, 1H), 5.91 (d, J=4.7 Hz, 1H), 4.70 (t, J=5.1 Hz, 1H), 3.8 (s, 2H), 1.95 (m, 1H), 0.9 (dd, J=0.7 and 10.2 Hz, 6H).

Scheme 4

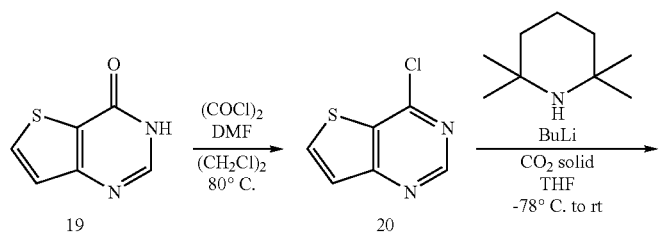

-continued
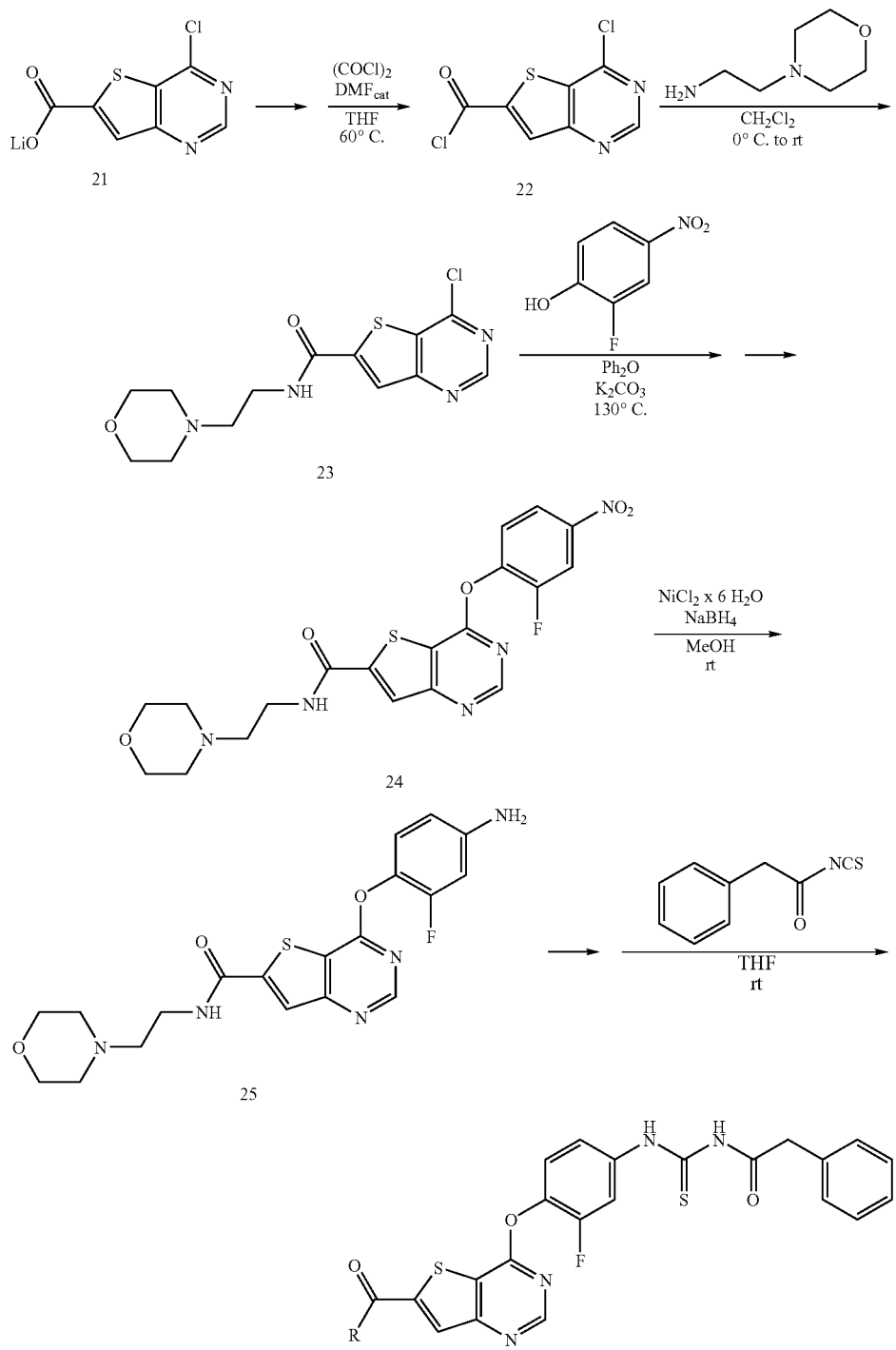
26a: Example 22
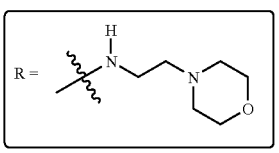

Example 22

1-(4-(6-(2-Morpholinoethylcarbamoyl)thieno[3,2-d]pyrimidin-4-yloxy)-3-fluorophenyl)-3-(2-phenylacetyl)thiourea (26a)

Step 1: 4-Chlorothieno[3,2-d]pyrimidine (20)

To a stirred solution of $(COCl)_2$ (7.33 mL, 84.11 mmol) in anhydrous $(CH_2Cl)_2$ (20 mL) at 0° C. under nitrogen was added DMF (4.47 mL, 57.18 mmol). After 20 min a solution of thieno[3,2-d]pyrimidin-4(3H)-one (19) (4 g, 26.28 mmol) in anhydrous $(CH_2Cl)_2$ (5 mL) was added drop wise to the reaction mixture which was stirred for 20 min at 0° C., warmed to room temperature over another 20 min, heated at 80° C. for 1.5 hours, and cooled to room temperature. Finally, the reaction mixture was poured into water and extracted with DCM. The extract was washed sequentially with water, brine, dried over $Na_2SO_4$, filtered and evaporated to afford the title compound 20 (4.36 g, 97% yield) as a yellow solid. $^1$H NMR (400 MHz, DMSO-$d_6$) δ(ppm): 9.02 (s, 1H), 8.59 (d, J=5.2 Hz, 1H), 7.75 (d, J=5.2 Hz, 1H).

Step 2: 4-Chlorothieno[3,2-d]pyrimidine-6-carbonyl chloride (22)

To a stirred solution of 2,2,6,6-tetramethylpiperidine (4.45 mL, 26.37 mmol) in anhydrous THF (50 mL) at 0° C. under nitrogen was added n-BuLi (10.55 mL, 26.37 mmol, 2.5 M in hexanes). The reaction mixture was stirred for 30 min, then a solution of 20 (3 g, 17.58 mmol) in anhydrous THF (10 mL) was added drop wise at −78° C. over 30 min followed by dry ice (10 g). The resultant suspension was warmed to the room temperature over 2 hours and filtered to afford the lithium carboxylate 21 as a yellow solid (4.5 g), which was used for the next step without further purification.

To a stirred solution of $(COCl)_2$ (2.95 mL, 33.82 mmol) in anhydrous DCM (30 mL) at 0° C. under nitrogen was added DMF (0.5 mL, 6.45 mmol). The reaction mixture was stirred for 20 min and treated with a solution of the carboxylate 21 (3.71 g, 16.89 mmol) in anhydrous DCM (5 mL) (drop wise addition at 0° C.), stirred for additional 10 min and heated at 60° C. for 3 hours, cooled to room temperature and concentrated under reduced pressure to afford the title compound 22 (3.90 g, 99% yield) as a yellow solid. $^1$H NMR (400 MHz, DMSO-$d_6$) δ(ppm): 9.02 (s, 1H), 8.59 (d, J=5.2 Hz, 1H), 7.75 (d, J=5.2 Hz, 1 Hz, 1H).

Step 3: 4-Chloro-N-(2-morpholinoethyl)thieno[3,2-d]pyrimidine-6-carboxamide (23)

To a stirred solution of 22 (500 mg, 2.15 mmol) in anhydrous DCM (20 mL) at 0° C. under nitrogen was added 4-(2-aminoethyl)-morpholine (307 mg, 2.36 mmol). The reaction mixture was allowed to warm to the room temperature over 3 hours and was stirred for additional 14 hours, treated with saturated aqueous solution of $NHCO_3$ and extracted with DCM. The organic layer was dried over $Na_2SO_4$, filtered, and concentrated. The residues was purified by flash chromatography on silica gel (eluents MeOH-DCM, 5:95, then 1:9) to afford the title compound 23 (458 mg, 65% yield) as a white solid. $^1$H NMR (400 MHz, CDCl$_3$) δ(ppm): 9.13 (t, J=5.6 Hz, 1H), 9.08 (s, 1H), 8.32 (s, 1H), 3.60-3.54 (m, 4H), 3.44 (q, J=6.8 Hz, 2H), 2.54-2.48 (m, 2H), 2.46-2.40 (m, 4H).

Step 4: 4-(2-Fluoro-4-nitrophenoxy)-N-(2-morpholinoethyl)thieno[3,2-d]pyrimidine-6-carboxamide (24)

To a stirred solution of compound 23 (458 mg, 1.40 mmol) in $Ph_2O$ (6 mL) was added 2-fluoro-4-nitrophenol (242 mg, 1.54 mmol). The reaction mixture was heated at 120° C. for 2.5 hours, treated with $K_2CO_3$ (80 mg, 0.56 mmol) and heated at the same temperature for additional 18 hours. After cooling, the reaction mixture was purified by flash chromatography on a silica gel column (eluents EtOAc-hexane 5:95, 1:1, then MeOH-DCM, 5:95 and 1:9), to afford the title compound 24 (570 mg, 91% yield) as a yellow solid. $^1$H NMR (400 MHz, CDCl$_3$) δ(ppm): 9.09 (t, J=5.6 Hz, 1H), 8.77 (s, 1H), 8.41 (dd, J=2.4 and 10.4 Hz, 1H), 8.30 (s, 1H), 8.22 (dd, J=2.4 and 8.8 Hz, 1H), 7.88 (t, J=8.8 Hz, 1H), 3.60-3.52 (m, 4H), 3.45 (q, J=6.8 Hz, 2H), 2.50 (q, J=6.8 Hz, 2H), 2.46-2.40 (m, 4H).

Step 5: 4-(4-Amino-2-fluorophenoxy)-N-(2-morpholinoethyl)thieno[3,2-d]pyrimidine-6-carboxamide (25)

To a stirred solution of 24 (1.30 g, 2.72 mmol) in anhydrous MeOH (15 mL) at room temperature under nitrogen were added $NiCl_2 \times 6H_2O$ (605 mg, 2.54 mmol) and $NaBH_4$ (192 mg, 5.08 mmol), respectively. The reaction mixture was stirred for 50 min, concentrated, cooled to 0° C., treated with HCl (10 mL, 1M) followed by addition of $NH_4OH$ (29%) (pH 9-10), and finally extracted with AcOEt. The organic extract was successively washed with water and brine, dried over $Na_2SO_4$, filtered, and concentrated to afford the title compound 25 (450 mg, 85% yield) as a yellow solid. $^1$H NMR (400 MHz, CDCl$_3$) δ(ppm): 9.04 (t, J=5.6 Hz, 1H) 8.73 (s, 1H), 8.23 (s, 1H), 7.07 (t, J=8.8 Hz, 1H), 6.48 (dd, J=2.4 and 13.2 Hz, 1H), 6.40 (dd, J=2.4 and 8.8 Hz, 1H), 5.47 (s, 2H), 3.62-3.52 (m, 4H), 3.44 (q, J=6.8 Hz, 2H), 2.56-2.48 (m, 2H), 2.46-2.40 (m, 4H).

Step 6: 1-(4-(6-(2-Morpholinoethylcarbamoyl)thieno[3,2-d]pyrimidin-4-yloxy)-3-fluorophenyl)-3-(2-phenylacetyl)thiourea (26a)

To a stirred solution of 25 (450 mg, 1.07 mmol) in anhydrous THF (10 mL) under nitrogen was slowly added benzyl isothiocyanate (0.5 mL). The reaction mixture was stirred for 18 hours and concentrated under reduced pressure. The residue was purified by flash chromatography on a silica gel column (eluent MeOH-DCM, 5:95→10:90) followed by reversed phase chromatography purification (column Phenomene X, C18, eluent $H_2O$-MeOH, 50:50→5:95, 10 mL/min) to afford the title compound 26a (104 mg, 16% yield) as a white solid. $^1$H NMR (400 MHz, DMSO-$d_6$) δ((ppm): 12.43 (s, 1H), 11.80 (s, 1H), 9.07(t, J=5.6 Hz, 1H), 8.76 (s, 1H), 8.28 (s, 1H), 7.93(dd, J=2.4 and 12.0 Hz, 1H), 7.54(t, J=8.8 Hz, 1H), 7.48(dd, J=1.2 and 8.8 Hz, 1H), 7.39-7.30 (m, 4H), 7.30-7.20 (m, 1H), 3.82 (s, 2H), 3.60-3.54 (m, 4H), 3.45(q, J=6.4 Hz, 2H), 2.50 (m, 2H), 2.48-2.40 (m, 4H).

Examples 23-27

Examples 23-27 (compounds 26b-e) were prepared using the same procedures as described for the compound 26a, example 22 (scheme 4). Characterization of compounds 26b-e (examples 23-27) is provided in table 3.

TABLE 3

26 b–e: Examples 23–27
Characterization of compounds 26b–e (examples 23–27)

| Cpd | Ex | R | Name | Characterization |
|---|---|---|---|---|
| 26b | 23 | –N(Me)Me | 1-(4-(6-(Dimethylcarbamoyl)thieno[3,2-d]pyrimidin-4-yloxy)-3-fluorophenyl)-3-(2-phenylacetyl)thiourea | $^1$H NMR (400 MHz,, DMSO-$d_6$) δ (ppm): 8.77(s, 1H), 8.01(s, 1H), 7.93(dd, J=2.4 znd 12.4 Hz, 1H), 7.54(t, J=8.4 Hz, 1H), 7.50–7.44 (m, 1H), 7.38–7.30(m, 4H), 7.30–7.23(m, 1H), 3.82(s, 2H), 3.24(s, 3H), 3.07(s, 3H). |
| 26c | 24 | –N(4-methylpiperazinyl) | 1-(4-(6-(4-N-Methylpiperazylcarbamoyl)thieno[3,2-d]pyrimidin-4-yloxy)-3-fluorophenyl)-3-(2-phenylacetyl)thiourea | $^1$H NMR (400 Hz, DMSO-$d_6$) δ (ppm): 12.43(s, 1H), 11.80(s, 1H), 8.77(s, 1H), 7.93(s, 1H), 7.93(dd, J=2.0 and 12.0 Hz, 1H), 7.53(t, J=8.4 Hz, 1H), 7.48(dd, J= 2.0 and 8.4 Hz, 1H), 7.38–7.30 (m, 4H), 7.30–7.224(m, 1H), 3.82 (s, 2H), 3.74–3.62(m, 4H), 2.48–2.36(m, 4H), 2.25(bs, 3H). |
| 26d | 25 | –N(H)Me | 1-(4-(6-(Methylcarbamoyl)thieno[3,2-d]pyrimidin-4-yloxy)-3-fluorophenyl)-3-(2-phenylacetyl)thiourea | $^1$H NMR (400 MHz, DMSO-$d_6$) δ (ppm): 12.42(s, 1H), 11.80(s, 1H), 9.10(q, J=4.4 Hz, 1H), 8.76 (s, 1H), 8.23(s, 1H), 7.92(dd, J= 2.0 and 12.0 Hz, 1H), 7.54(t, J= 8.8 Hz, 1H), 7.48(dd, 2.0 and 8.8 Hz, 1H), 7.36–7.30(m, 4H), 7.30–7.24(m, 1H), 3.82(s, 2H), 2.87(d, J=4.4 Hz, 1H). |
| 26e | 26 | –N(OMe)Me | 1-(4-(6-(N-Methoxy-N-methylcarbamoyl)thieno[3,2-d]pyrimidin-4-yloxy)-3-fluorophenyl)-3-(2-phenylacetyl)thiourea | $^1$H NMR (400 MHz, DMSO-$d_6$) δ (ppm): 8.79(s, 1H), 8.23(s, 1H), 7.93(dd, J=2.0 and 11.6 Hz, 1H), 7.55(t, J=8.8 Hz, 1H), 7.48(dd, J= 2.0 and 8.8 Hz, 1H), 7.36–7.30 (m, 4H), 7.30–7.24(m, 1H), 3.87 (s, 3H), 3.82(s, 2H), 3.39(s, 3H). |
| 26f | 27 | –NH$_2$ | 1-(4-(6-Carbamoylthieno[3,2-d]pyrimidin-4-yloxy)-3-fluorophenyl)-3-(2-phenylacetyl)thiourea | $^1$H NMR (400 MHz, DMSO-$d_6$) δ (ppm): 12.43(s, 1H), 11.80(s, 1H), 8.76(s, 1H), 8.55(bs, 1H), 8.29(s, 1H), 8.07(bs, 1H), 7.93 (dd, J=2.0 and 12 Hz, 1H), 7.54 (t, J=8.8 Hz, 1H), 7.48(dd, J= 2.0 and 8.8 Hz, 1H), 7.36–7.30(m, 4H), 7.30–7.23(m, 1H), 3.82(s, 2H). |

Scheme 5

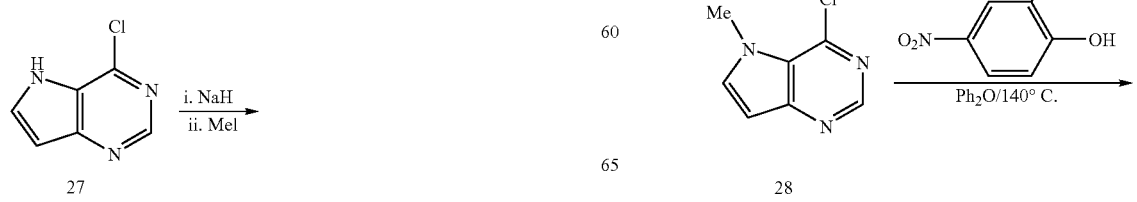

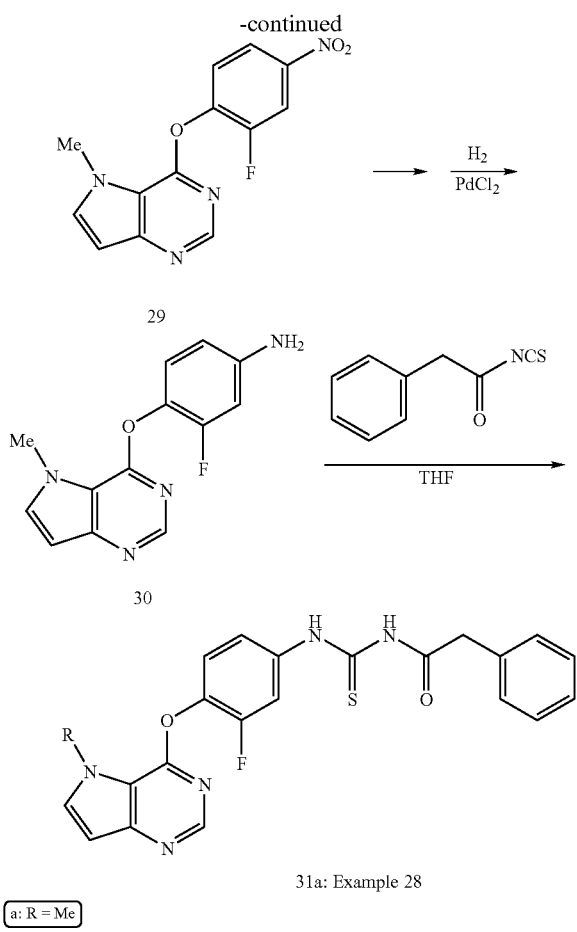

29

30

31a: Example 28 a: R = Me

Example 28

1-(4-(5-Methyl-5H-pyrrolo[3,2-d]pyrimidin-4-yloxy)-3-fluorophenyl)-3-(2-phenylacetyl)thiourea (31a)

Step 1:
4-Chloro-5-methyl-5H-pyrrolo[3,2-d]pyrimidine (28)

To a stirred solution of 4-chloro-5H-pyrrolo[3,2-d]pyrimidine (27) (*J. Org. Chem.*, 2001, 66, 17, 5723-5730) (643 mg, 4.15 mmol) in DMF (41 mL) was added NaH (60% in mineral oil, 330 mg, 8.3 mmol) in one portion at 0° C. and the mixture was stirred for 1 h followed by addition of methyl iodide (0.28 mL, 4.5 mmol). The reaction mixture was allowed to warm up to the room temperature, stirred for an additional hour and quenched with AcOH (1 mL) to form a suspension which was stirred for 10 min and concentrated under reduced pressure to give a solid. This material was dissolved in AcOEt, the solution was washed with cold saturated NaHCO$_3$ solution and water, dried over Na$_2$SO$_4$, and concentrated to produce the title compound 28 as a pale yellow solid (640 mg, 93% yield). $^1$H NMR (400 MHz, CD$_3$OD) δ(ppm): 8.51 (s, 1H), 7.75 (d, J=3.3 Hz, 1H), 6.62 (d, J=3.3 Hz, 2H), 4.15 (s, 1H). LRMS (M+1) 168.1 (100%), 170.1 (34%).

Step 2: 4-(2-Fluoro-4-nitrophenoxy)-5-methyl-5H-pyrrolo[3,2-d]pyrimidine (29)

A suspension of 4-chloro-5-methyl-5H-pyrrolo[3,2-d]pyrimidine (28) (300 mg, 1.79 mmol), 4-nitro-2-fluorophenol (422 mg, 2.69 mmol) and cesium carbonate (1.2 g, 3.58 mmol) in diphenyl ether (18 mL) was stirred overnight at 140° C. The reaction mixture was cooled to room temperature, concentrated under reduced pressure and the residue was triturated with Et$_2$O, filtered, and dried to afford the title compound 29 as a grey solid (258 mg, 49% yield). LRMS (M+1) 289.1 (100%).

Step 3: 4-(5-Methyl-5H-pyrrolo[3,2-d]pyrimidin-4-yloxy)-3-fluorobenzenamine (30)

To a solution of 4-(2-fluoro-4-nitrophenoxy)-5-methyl-5H-pyrrolo[3,2-d]pyrimidine (29) (253.6 mg, 0.879 mmol) in AcOH (3 mL) at 90° C. was added iron powder (245 mg, 4.4 mmol). The mixture was stirred vigorously for 10 min and filtered. The filtrate was concentrated under reduced pressure to produce a solid, which was dissolved in DCM. The resultant solution was washed with cold NaHCO$_3$ solution and water, dried over Na$_2$SO$_4$ and concentrated to provide a residue which was purified by column chromatography (eluent MeOH—CH$_2$Cl$_2$ 1:20) to afford the title compound 30 as a brown solid (120.6 mg, 53% yield). LRMS (M+1) 240.1 (100%).

Step 4: 1-(4-(5-Methyl-5H-pyrrolo[3,2-d]pyrimidin-4-yloxy)-3-fluorophenyl)-3-(2-phenylacetyl)thiourea (31a)

To a solution of 4-(5-methyl-5H-pyrrolo[3,2-d]pyrimidin-4-yloxy)-3-fluorobenzenamine (30) (120.8 mg, 0.5 mmol) and benzyl isothiocyanate (0.1 mL, 0.55 mmol) in THF (5 mL) was stirred 2 h at room temperature, concentrated under reduced pressure and the residue was subjected to a column chromatography on silica gel, (eluent EtOAc-hexane 1:1) to afford the title compound 31a as a white solid (97.6 mg, 45%). $^1$H NMR (400 MHz, DMSO-d$_6$) δ (ppm): 12.42 (s, 1H), 11.79 (s, 1H), 8.28 (d, J=0.6 Hz, 1H), 7.88 (dd, J=2.3 Hz, J=12.1 Hz, 1H), 7.81 (d, J=3.1 Hz, 1H), 7.50 (t, J=8.4 Hz, 1H), 7.44 (dd, J=2.1 Hz, J=8.8 Hz, 1H), 7.33 (m, 4H), 7.28 (m, 1H), 6.65 (dd, J=0.6 Hz, J=2.9 Hz, 1H), 4.10 (s, 3H), 3.83 (s, 2H). LRMS (M+1) 436.1 (100%).

Example 29

1-(4-(5-Ethyl-5H-pyrrolo[3,2-d]pyrimidin-4-yloxy)-3-fluorophenyl)-3-(2-phenylacetyl)thiourea (31b)

Title compound 31b was obtained according to the scheme 5 using procedures similar to the ones described for example 28 but using ethyl iodide (instead of methyl iodide) in the step 1. Characterization of 31b is provided in table 4.

Example 30

1-(4-(5-Benzyl-5H-pyrrolo[3,2-d]pyrimidin-4-yloxy)-3-fluorophenyl)-3-(2-phenylacetyl)thiourea (31c)

Title compound 31c was obtained according to the scheme 5 using procedures similar to the ones described for the example 28 but using benzyl bromide (instead of methyl iodide) in the step 1. Characterization of 31c is provided in table 4.

TABLE 4

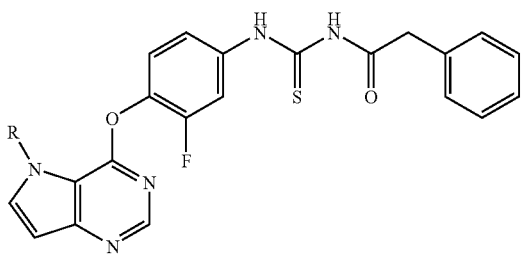

31b–c: Examples 29–30
Characterization of 31b–c (examples 29–30)

| Cpd | Ex | R | Name | Characterization |
|---|---|---|---|---|
| 31b | 29 | Et | 1-(4-(5-Ethyl-5H-pyrrolo[3,2-d]pyrimidin-4-yloxy)-3-fluorophenyl)-3-(2-phenylacetyl)thiourea | $^1$H NMR (400 MHz, DMSO-$d_6$) δ (ppm): 12.4(br, 1H), 11.8(br, 1H), 8.3(s, 1H), 7.90–7.85(m, 2H), 7.54–7.41(m, 2H), 7.40(m, 4H), 7.29(m, 1H), 6.63(d, J=3.1 Hz, 1H), 4.46(q, J=7.0 Hz, J=14.3 Hz, 2H), 3.83(s, 1H), 1.46(t, J=7.0 Hz, 3H). LRMS (M+1) 450.2 (100%). |
| 31c | 30 | —CH$_2$Ph | 1-(4-(5-Benzyl-5H-pyrrolo[3,2-d]pyrimidin-4-yloxy)-3-fluorophenyl)-3-(2-phenylacetyl)thiourea | $^1$H NMR (400 MHz, DMSO-$d_6$) δ (ppm): 12.34(s, 1H), 11.79(s, 1H), 8.3(s, 1H), 8.04(d, J=3.1 Hz, 1H), 7.8(dd, J=2.3 Hz, J=7.8 Hz, 1H), 7.4(m, 1H), 7.35–7.76 (m, 11H), 6.7(d, 3.1 Hz, 1H), 5.66(s, 2H), 3.82(s, 2H). LRMS (M+1) 512.3 (100%). |

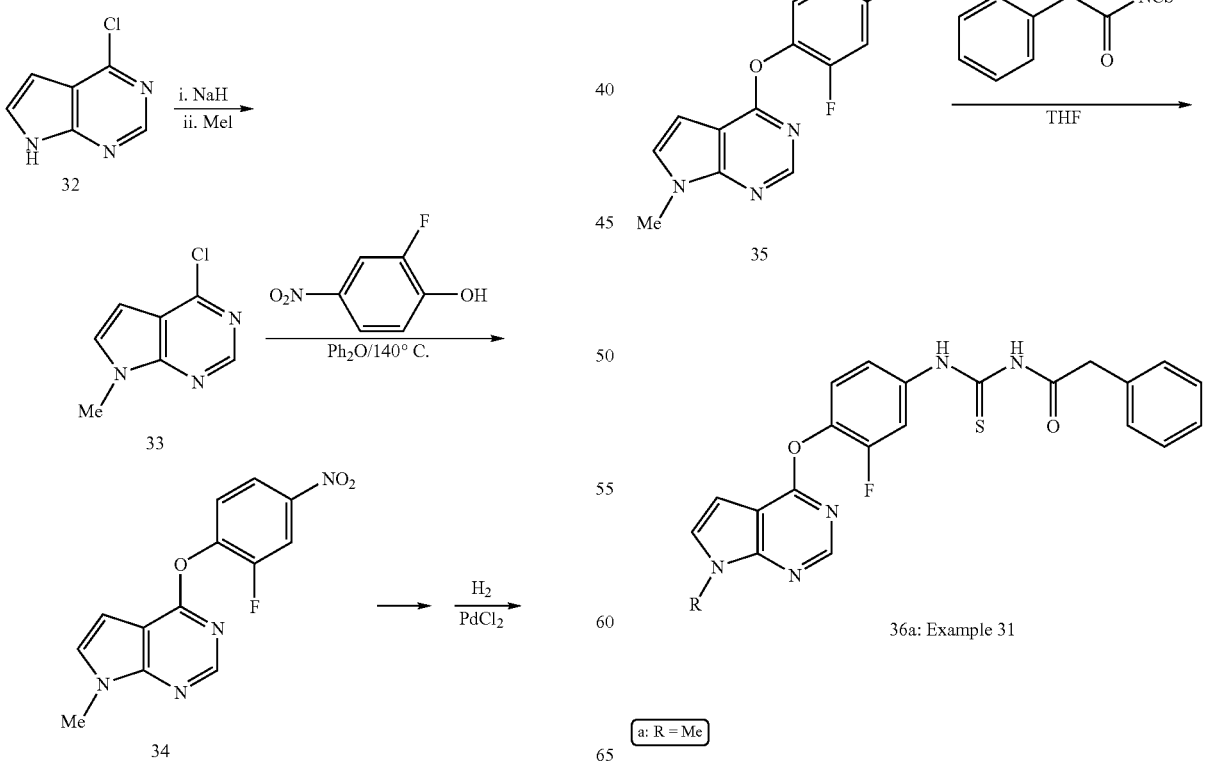

Example 31

1-(4-(7-Methyl-7H-pyrrolo[2,3-d]pyrimidin-4-yloxy)-3-fluorophenyl)-3-(2-phenylacetyl)thiourea (36a)

Title compound 36a (scheme 6) was obtained according to the procedures similar to the ones described for the example 28 (scheme 5) but using as a starting material 4-chloro-7H-pyrrolo[2,3-d]pyrimidine 32 (instead of chloride 27). Characterization of 36a is provided in table 5.

Example 32

1-(4-(7-Ethyl-7H-pyrrolo[2,3-d]pyrimidin-4-yloxy)-3-fluorophenyl)-3-(2-phenylacetyl)thiourea (36b)

Title compound 36b was obtained according to the scheme 6 using the procedures similar to the ones described for the example 31 but using ethyl iodide (instead of methyl iodide) in the step 1. Characterization of 36b is provided in table 5.

Example 33

1-(4-(7-Benzyl-7H-pyrrolo[2,3-d]pyrimidin-4-yloxy)-3-fluorophenyl)-3-(2-phenylacetyl)thiourea (36c)

Title compound 36c was obtained according to the scheme 6 using the procedures similar to the ones described for the example 31 but using benzyl bromide (instead of methyl iodide) in the step 1. Characterization of 36c is provided in table 5.

TABLE 5

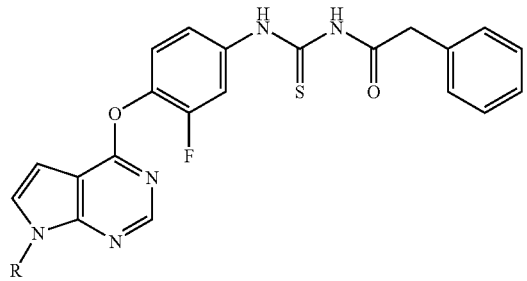

36a–c: Examples 31–33
Characterization of 36a–c (examples 31–33)

| Cpd | Ex | R | Name | Characterization |
|---|---|---|---|---|
| 36a | 31 | Me | 1-(4-(7-Methyl-7H-pyrrolo[2,3-d]pyrimidin-4-yloxy)-3-fluorophenyl)-3-(2-phenyl acetyl)thiourea | $^1$H NMR (400 MHz, DMSO-$d_6$) δ (ppm): 12.43(s, 1H), 11.79(s, 1H), 8.34(s, 1H), 7.87(dd, J=1.8 Hz, J=13.1 Hz, 1H), 7.55(d, J=3.5 Hz, 1H), 7.44(m, 2H), 7.33(m, 4H), 7.27(m, 1H), 6.62(d, J=3.5 Hz, 1H), 3.83(m, 5H). LRMS (M+1) 436.1 (100%). |
| 36b | 32 | Et | 1-(4-(7-Ethyl-7H-pyrrolo[2,3-d]pyrimidin-4-yloxy)-3-fluorophenyl)-3-(2-phenyl acetyl)thiourea | $^1$H NMR (400 MHz, DMSO-$d_6$) δ (ppm): 12.41(br, 1H), 11.78(br, 1H), 8.32(s, 1H), 7.87(m, 1H), 7.63 (d, J=3.5, Hz, 1H), 7.43 (m, 2H), 7.33(m, 4H), 7.27(m, 1H), 6.63(d, J=3.5 Hz, 1H), 4.29(q, J=7.2 Hz, J=14.5 Hz, 2H), 3.82(s, 2H), 1.40(t, J=7.2 Hz, 3H). LRMS (M+1) 450.2 (100%). |
| 36c | 33 | —CH$_2$Ph | 1-(4-(7-Benzyl-7H-pyrrolo[2,3-d]pyrimidin-4-yloxy)-3-fluorophenyl)-3-(2-phenyl acetyl)thiourea | $^1$H NMR (400 MHz, DMSO-$d_6$) δ (ppm): 12.41(s, 1H), 11.79(s, 1H), 8.35(s, 1H), 7.87(m, 1H), 7.68(d, J=3.5 Hz, 1H), 7.44(m, 2H), 7.35–7.23(m, 10H), 6.68(d, 3.5 Hz, 1H), 5.48(s, 2H), 3.82(s, 2H). LRMS (M+1) 512.3 (100%). |

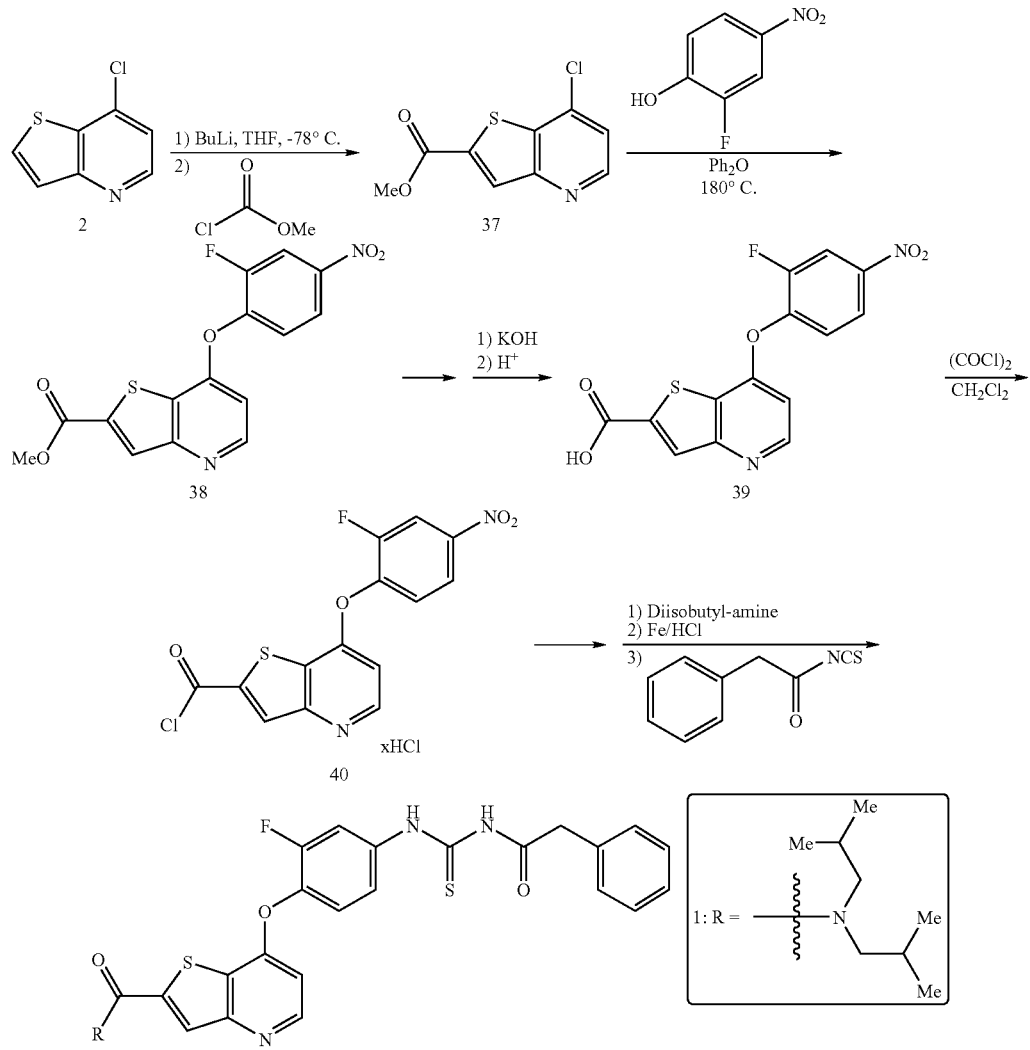

Scheme 7

81: Example 34

Example 34

7-(2-Fluoro-4-(3-(2-phenylacetyl)thioureido)phenoxy)-N,N-diisobutylthieno[3,2-b]pyridine-2-carboxamide (81)

Step 1: Methyl 7-chlorothieno[3,2-b]pyridine-2-carboxylate (37)

To a stirred solution of 2 (7.0 g, 41.3 mmol) in anhydrous THF (100 mL) at −78° C. under a nitrogen atmosphere was added n-BuLi (24.7 mL, 2.5 M in hexanes, 61.8 mmol). After 1 hour, methyl chloroformate (9.6 ml, 124 mmol) was added and the reaction mixture was stirred for an extra hour at the same temperature, quenched with excess methanol and allowed to warm to room temperature. The solvent was then evaporated and the residue was purified by flash chromatography using hexane—AcOEt (70:30) as an eluent. The product from the column was re-crystallized from ethyl acetate to afford title compound 37 (4.3 g, 46% yield) as a white solid.

$^1$H NMR (400 MHz, DMSO-$d_6$) δ(ppm): 8.75 (dd, J=0.8 and 4.8 Hz, 1H), 8.26 (d, J=0.8 Hz, 1H), 7.74 (dd, J=0.8 and 5.2 Hz, 1H), 3.93 (s, 3H).

Step 2: Methyl 7-(2-fluoro-4-nitrophenoxy)thieno[3,2-b]pyridine-2-carboxylate (38)

A mixture of 37 (4.0 g, 17.6 mmol), 2-fluoro-4-nitrophenol (5.5 g, 35.0 mmol) and K$_2$CO$_3$ (12.1 g, 87.5 mmol) in Ph$_2$O was heated at 180° C. for 5 hours. The mixture was cooled to room temperature, diluted with EtOAc and washed with water. The organic phase was collected, dried over anhydrous sodium sulfate and the solvents were removed under reduced pressure. The residue was purified by flash chromatography using hexane—AcOEt (70:30) as an eluent. The product from the column was re-crystallized from a mixture of ethyl acetate-hexanes to afford 38 (3.6 g, 59% yield) as a white solid. $^1$H NMR (400 MHz, DMSO-$d_6$) δ(ppm): 8.69 (d, J=5.2 Hz, 1H), 8.47 (dd, J=2.4 and 10.0 Hz, 1H), 8.27 (s, 1H), 8.21 (m, 1H), 7.77 (dd, J=8.0 and 9.2 Hz, H), 7.06 (dd, J=0.8 and 5.2 Hz, 1H), 3.93 (s, 3H).

Step 3: 7-(2-Fluoro-4-nitrophenoxy)thieno[3,2-b]pyridine-2-carboxylic acid (39)

To a stirred solution of 38 (2.5 g, 7.18 mmol) in THF (50 ml) was added KOH (14.3 ml, 1.0 N in H$_2$O, 14.3 mmol). After 4 hours the reaction mixture was concentrated and the resultant residue was dissolved in H$_2$O (50 ml). The aqueous layer was then washed with ethyl acetate and acidified with 1N HCl (pH=1). The precipitate that formed upon acidification was collected by filtration, washed with water and dried under high vacuum to afford title compound 39 (2.3 g, 96% yield) as a white solid. $^1$H NMR (400 MHz, DMSO-d$_6$) δ(ppm): 8.6 (d, J=5.2 Hz, 1H), 8.47 (dd, J=2.8 and 10.4 Hz, 1H), 8.20 (m, 1H), 8.17 (s, 1), 7.76 (dd, J=8.0 and 8.8 Hz, 1H), 7.04 (d, J=5.2 Hz, 1H).

Step 4: 7-(2-Fluoro-4-nitrophenoxy)thieno[3,2-b]pyridine-2-carbonyl chloride (40)

To a solution of 39 (2.0 g, 5.98 mmol) in anhydrous CH$_2$Cl$_2$ (30 ml) under an atmosphere of nitrogen, was added oxalyl chloride (2.6 ml, 29.8 mmol). After stirring for 2 hours the solvent was evaporated, anhydrous toluene (10 mL) was added and the resultant mixture was evaporated (procedure of addition of toluene followed by evaporation was performed twice) to afford title compound 40 (2.2 g, 94% yield) as a white solid. The product was used without further purification and characterization and was assumed to be the mono-HCl salt.

Step 5: 7-(2-Fluoro-4-(3-(2-phenylacetyl)thioureido)phenoxy)-N,N-diisobutylthieno[3,2-b]pyridine-2-carboxamide (81)

To a solution of 40 (150 mg, 0.385 mmol) and TEA (107 μl, 0.771 mmol) in anhydrous CH$_2$Cl$_2$ under an atmosphere of nitrogen was added diisobutylamine (67 μL, 0.385 mmol). After stirring for 1 hour, methanol (2 mL) was added followed by iron powder (150 mg) and HCl (conc., 0.4 mL). The reaction mixture was stirred for additional 2 hours and then partitioned between ethyl acetate (20 mL) and a mixture of H$_2$O (20 mL) and NH$_4$OH (2 mL). Organic phase was collected, washed with brine, dried over anhydrous MgSO$_4$, filtered and evaporated. The residue was treated with 2-phenylacetyl isothiocyanate (102 mg, 0.58 mmol) in THF (2 mL), the resultant mixture was allowed to stand for 2 hours at ambient temperature, quenched with methanol (5.0 mL), loaded onto 5 ml of silica gel and purified by flash chromatography using hexane—AcOEt (70:30) as an eluent, to afford title compound 81 (41 mg, 18%) as a white solid. $^1$H NMR (400 MHz, CD$_3$OD) δ (ppm): 8.54 (d, J=5.6 Hz, 1H), 8.08 (dd, J=2.0 and 12.0 Hz, 1H), 7.69 (s, 1H), 7.38-7.49 (m, 2H), 7.28-7.35 (m, 5H), 6.77 (dd, J=1.2 and 5.6 Hz, 1H), 3.77 (s, 2H), 3.46 (bs, 4H), 2.18 (bs, 1H), 2.02 (bs, 1H), 1.02 (bs, 6H), 0.87 (bs, 6H). LRMS (M+1):592.7 (calcd), 593.3 (found).

TABLE 6

Characterization of compounds 8m-y (examples 35-47)

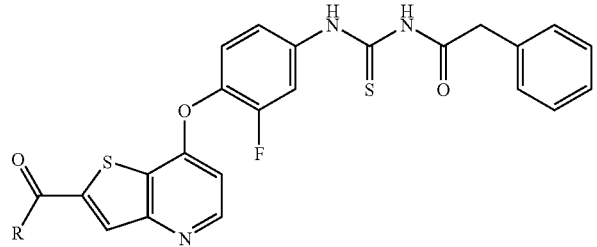

8m-y: Examples 35-47

| Cpd | Ex | R | Name | Characterization |
|---|---|---|---|---|
| 8m | 35 | Me—N, furan-2-yl | 7-[2-Fluoro-4-(3-phenylacetyl-thioureido)-phenoxy]-thieno[3,2-b]pyridine-2-carboxylic acid furan-2-ylmethyl-methyl-amide | $^1$H NMR(400 MHz, DMSO-d$_6$) δ(ppm): 12.49(s, 1H), 11.82(s, 8.59(d, J=5.6 Hz, 1H), 7.92-8.05(m, 2H), 7.67(bs, 1H), 7.54(m, 2H), 7.25-7.37 (m, 5H), 6.75(d, J=0.8, 5.2 Hz, 1H), 6.46(s, 2H), 4.74(bs, 2H), 3.83(s, 2H), 3.27(bs, 1.5H), 2.99(bs, 1.5H). LRMS(M + 1):574.6(cald), 575.2(found). |
| 8n | 36 | Me, Me, Me, Me diisopropylaminoethyl | 7-[2-Fluoro-4-(3-phenylacetyl-thioureido)-phenoxy]-thieno[3,2-b]pyridine-2-carboxylic acid(2-diisopropylamino-ethyl)-amide, formate salt | 12.45(s, 1H), 11.78(s, 1H), 8.92(t, J=5.6 Hz, 1H), 8.53(d, J=5.6 Hz, 1H), 8.16(s, 1H), 8.12(s, 1H), 7.99(m, 1H), 7.50 (m, 2H), 7.21-7.30(m, 5H), 6.69(d, J=5.2 Hz, 1H), 3.79(s, 2H), 3.22(m, 2H), 2.97(m, 2H), 2.55(t, J7.6Hz, 2H), 0.964(d, J=6.4 Hz, 12H). LRMS(M + 1) .607.8(calcd.), 608.3(found). |

TABLE 6-continued

Characterization of compounds 8m-y (examples 35-47)

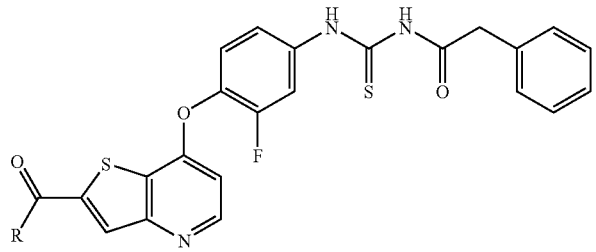

8m-y: Examples 35-47

| Cpd | Ex | R | Name | Characterization |
|-----|----|---|------|------------------|
| 8o | 37 | (pyrrolidinyl) | 1-{3-Fluoro-4-[2-(pyrrolidine-1-carbonyl)-thieno[3,2-b]pyridin-7-yloxy]-phenyl}-3-phenylacetyl-thiourea | $^1$H NMR(400 MHz, DMSO-d$_6$) δ(ppm): 12.48(s, 1H), 11.82(s, 1H), 8.58(d, J=5.3 Hz, 1H), 8.03(m, 2H), 8.00(s, 1H), 7.53 (m, 2H), 7.33(m, 4H), 7.28(m, 1H), 6.73(d, J=5.3 Hz, 1H), 3.86(t, J=6.4 Hz, 2H), 3.83(s, 2H), 3.53(t, J=6.84 Hz, 2H), 1.95-1.86(m, 4H). LRMS(M + 1) .534.6(calcd.), 535.2(found). |
| 8p | 38 | (3-hydroxypyrrolidinyl) OH | (R)-N-(3-Fluoro-4-(2-(3-hydroxypyrrolidine-1-carbonyl)thieno[3,2-b]pyridin-7-yloxy)phenylcarbamothioyl)-2-phenylacetamide | $^1$H NMR(400 MHz, DMSO-d$_6$) δ(ppm): 12.48(s, 1H), 11.81(s, 1H), 8.59(d, J=5.6 Hz, 1H), 8.04(m, 2H), 7.54(m, 2H), 7.22-7.34(m, 5H), 6.74(d, J=5.2 Hz, 1H), 5.07(bs, 1H), 4.36(bd, J=19.6 Hz, 1H), 3.99 (m, 1H), 3.82(s, 2H), 3.38-3.68 (m, 3H), 1.80-2.06(m, 2H). MS(m/z): 551.1 (M + H)(found). |
| 8q | 39 | (3-hydroxypyrrolidinyl) HO | (S)-N-(3-Fluoro-4-(2-(3-hydroxypyrrolidine-1-carbonyl)thieno[3,2-b]pyridin-7-yloxy)phenylcarbamothioyl)-2-phenylacetamide | $^1$H NMR(DMSO-d$_6$) δ(ppm): 12.51(s, 1H), 11.84(s, 1H), 8.62(d. 1H, J=5.3 Hz), 8.08-8.01(m, 2H), 7.56-7.52(m, 2H), 7.36-7.31(m, 4H), 7.28-7.24(m, 1H), 6.77(d, 1H, J=5.7 Hz), 4.38-4.32(m, 1H), 4.00-3.92(m, 1H), 3.81(s, 2H), 3.67-3.55(m, 4H), 2.06-1.83(m, 2H). MS (m/z): 551.1(M + H)(found). |
| 8r | 40 | prolinamide (NH$_2$, C=O) | (S)-1-(7-(2-Fluoro-4-(3-(2-phenylacetyl)thioureido)phenoxy)thieno[3,2-b]pyridine-2-carbonyl)pyrrolidine-2-carboxamide | LRMS(M + 1) 577.6(calcd.), 578.3(found). |
| 8s | 41 | N(cyclopropyl)(CH$_2$CH$_2$CN) | 7-[2-Fluoro-4-(3-phenylacetyl-thioureido)-phenoxy]-thieno[3,2-b]pyridine-2-carboxylic acid(2-cyano-ethyl)-cyclopropyl-amide | LRMS(M + 1): 573.7(calcd.), 574.2(found). |

TABLE 6-continued

Characterization of compounds 8m-y (examples 35-47)

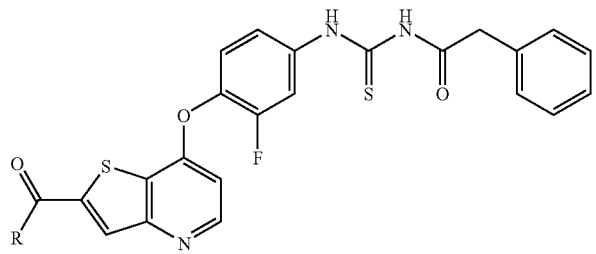

8m-y: Examples 35-47

| Cpd | Ex | R | Name | Characterization |
|---|---|---|---|---|
| 8t | 42 | (Me₂N-CH₂CH₂-N(Me)-) | 7-[2-Fluoro-4-(3-phenylacetyl-thioureido)-phenoxy]-thieno[3,2-b]pyridine-2-carboxylic acid(2-dimethylamino-ethyl)-amide, formate salt | LRMS(M + 1): 551.7(cald), 552.2(found) |
| 8u | 43 | bis(2-methoxyethyl)amino | 7-[2-Fluoro-4-(3-phenylacetyl-thioureido)-phenoxy]-thieno[3,2-b]pyridine-2-carboxylic acid bis-(2-methoxy-ethyl)-amide | LRMS(M + 1): 596.7(cald), 597.3(found). |
| 8v | 44 | benzylamino | 7-[2-Fluoro-4-(3-phenylacetyl-thioureido)-phenoxy]-thieno[3,2-b]pyridine-2-carboxylic acid benzylamide | LRMS(M + 1): 570.7(calcd), 571.3(found). |
| 8w | 45 | N-phenyl-N-(2-cyanoethyl)amino | 7-[2-Fluoro-4-(3-phenylacetyl-thioureido)-phenoxy]-thieno [3,2-b]pyridine-2-carboxylic acid(2-cyano-ethyl)-phenyl-amide | LRMS(M + 1): 609.7(caled.), 610.2 found. |
| 8x | 46 | (R)-leucinamide | (R)-N-(1-amino-4-methyl-1-oxopentan-2-yl)-7-(2-fluoro-4-(3-(2-phenylacetyl)thioureido)phenoxy)thieno[3,2-b]pyridine-2-carboxamide | LRMS(M + 1): 593.6(caled), 594.2(found). |
| 8y | 47 | (1,5-dimethyl-1H-pyrazol-3-yl)amino | 7-[2-Fluoro-4-(3-phenylacetyl-thioureido)-phenoxy]-thieno[3,2-b]pyridine-2-carboxylic acid(2,5-dimethyl-2H-pyrazol-3-yl)-amide | LRMS(M + 1): 574.6(caled), 575.2(found) |

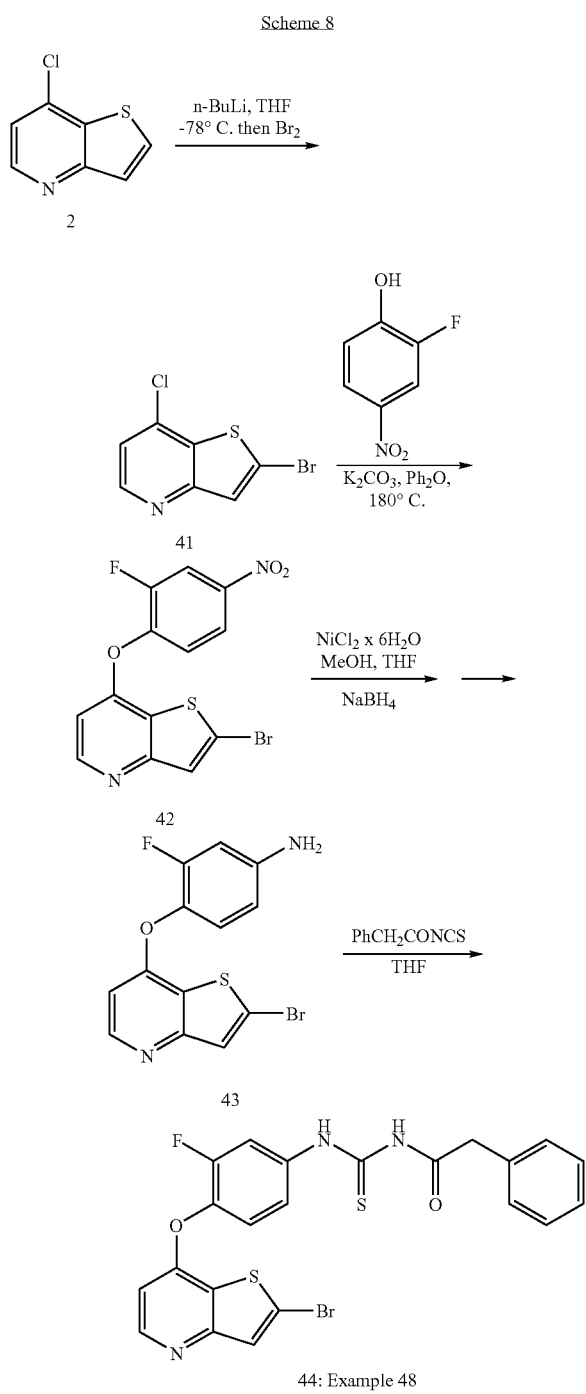

Example 48

N-(4-(2-Bromothieno[3,2-b]pyridin-7-yloxy)-3-fluorophenylcarbamothioyl)-2-phenylacetamide (44)

Step 1. 2-Bromo-7-chlorothieno[3,2-b]pyridine (41)

To a stirred solution of the chloride 2 (10.12 g, 5.59 mmol) in dry THF (200 ml) at −78° C. was added n-BuLi (24 ml, 76.7 mmol, 2.5 M solution in hexanes) and the resultant suspension was stirred for 15 minutes. Bromine (18.9 g, 120 mmol) was added slowly and the reaction mixture was stirred for additional 30 min, quenched with water and diluted with EtOAc. The organic phase was collected, dried over anhydrous sodium sulfate, filtered and concentrated under reduced pressure. Purification by column chromatography (9:1 EtOAc/hexane) afforded title compound 41 (10.5 g, 71% yield) as a yellow solid. $^1$H NMR (400 MHz, CDCl$_3$) δ (ppm): 8.62 (d, J=5.09 Hz, 1H), 7.92 (s, 1H), 7.59 (d, J=5.09 Hz, 1H).

Step 2. 2-Bromo-7-(2-fluoro-4-nitrophenoxy)thieno[3,2-b]pyridine (42)

A mixture of the bromide 41 (5.1 g, 20.5 mmol), potassium carbonate (5.65 g, 4 mmol) and 2-fluoro-4-nitrophenol (4.82 g, 30.7 mmol) was heated at 190° C. in diphenyl ether (25 ml) for 3 hrs. After cooling to room temperature it was diluted with DCM and filtered. The filtrate was concentrated under reduced pressure and the residue was purified by column chromatography (eluent EtOAc:hexane, 3:1) to afford title compound 42 as a yellow solid (5.4 g, 71% yield). $^1$H NMR (400 MHz, DMSO-d$_6$) δ (ppm): 8.55 (d, J=5.28 Hz, 1H), 8.46 (dd, J=2.5 and 10.4 Hz, 1H), 8.19 (d, J=8.8 Hz, 1H), 7.87 (s, 1H), 7.72 (t, J=8.4 Hz), 6.99 (d, J=5.47 Hz, 1H).

Steps 3-4. 1-(4-(2-Bromothieno[3,2-b]pyridin-7-yloxy)-3-fluorophenyl)-3-(2-phenylacetyl)thiourea (44)

To a solution of the nitro compound 42 (100 mg, 0.27 mmol) in THF (2 ml) and water (0.5 ml) was added SnCl$_2$× 2H$_2$O (76.99 mg, 1.5 eq, 0.41 mmol) and the reaction mixture was refluxed for 3 hrs, cooled to room temperature, diluted with EtOAc and washed with conc. ammonium hydroxide solution. EtOAc-extract was collected and the aqueous fractions were combined and washed with DCM. DCM extract was combined with the AcOEt-extract, the mixture was dried over sodium sulfate, filtered and evaporated to form the amine 43 (92 mg, 100%), which was used without any further purification.

To a solution of the amine 43 (92 mg, 0.27 mmol) in THF (10 ml) was added benzyl isothiocyanate (72 mg, 1.5 eq, 0.407 mmol). The reaction mixture was stirred for 1 hr at room temperature, concentrated under reduced pressure and the residue was purified by column chromatography (7:3 hexane:EtOAc to 1:1 MeOH:EtOAc) to afford the title compound 44 as a white solid (28 mg, 20% yield). $^1$H NMR (400 MHz, DMSO-d$_6$) δ (ppm): 12.48 (s, 1H), 11.81 (s, 1H), 8.55-8.52 (m, 1H), 8.01 (d, J=11.9 Hz, 1H), 7.85 (s, 1H), 7.55-7.49 (m, 2H), 7.45-7.19 (m, 5H), 6.73 (d, J=5.7 Hz, 1H), 3.82 (s, 2H). MS (m/z): 518.2/520.2 (M+H).

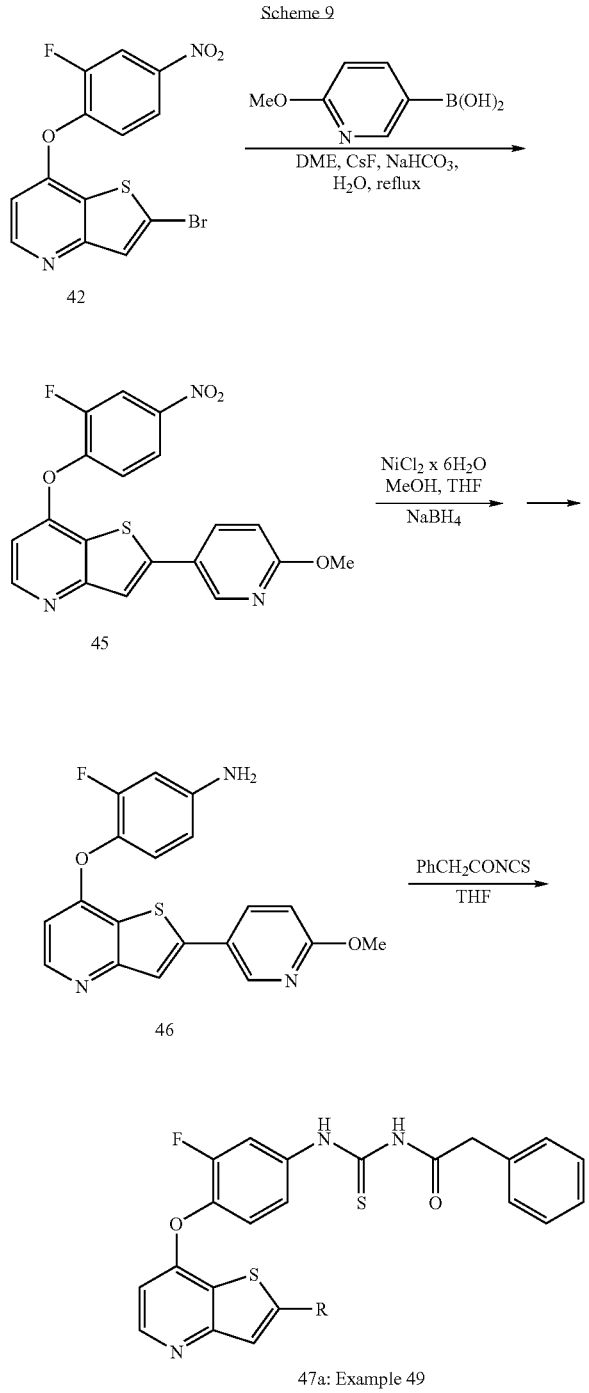

Example 49

N-(3-Fluoro-4-(2-(6-methoxypyridin-3-yl)thieno[3,2-b]pyridin-7-yloxy)phenylcarbamothioyl)-2-phenylacetamide (47a)

Step 1. 7-(2-Fluoro-4-nitrophenoxy)-2-(6-methoxypyridin-3-yl)thieno[3,2-b]pyridine (45)

A mixture of the nitro compound 42 (500 mg, 1.36 mmol), 6-methoxypyridin-3-ylboronic acid (312 mg, 2.04 mmol) and CsF (620 mg, 4.08 mmol) were suspended in DME (12 ml) and NaHCO$_3$ (342 mg, 4.08 mmol), dissolved in the minimum amount of water, was added. The mixture was de-aerated by bubbling N$_2$ through the solution for 10 min, heated at 80° C. for 3 hrs and concentrated to dryness. The formed residue was dissolved in DCM and washed with water. The DCM was collected, dried over sodium sulfate, filtered and the DCM was removed by evaporation. The resultant solid was triturated with Et$_2$O to afford the title compound 45 (176 mg, 32% yield), which was used without further purification. $^1$H NMR (400 MHz, DMSO-d$_6$) δ (ppm): 8.71 (m, 1H), 8.56 (m 1H), 8.46 (m, 1H), 8.22 (m, 2H), 8.01 (s, 1H), 7.72 (t, J=8.6 Hz, 1H), 6.99 (d, J=5.47 Hz, 1H), 6.90 (m, 1H), 3.97 (s, 3H).

Step 2. N-(3-Fluoro-4-(2-(6-methoxypyridin-3-yl)thieno[3,2-b]pyridin-7-yloxy)phenylcarbamothioyl)-2-phenylacetamide (47a)

To a solution of 45 (176 mg, 0.44 mmol) in MeOH (10 ml) and THF (10 ml) at 0° C. was added NiCl$_2$×6H$_2$O (210 mg, 0.89 mmol) and NaBH$_4$ (65 mg, 1.76 mmol). The reaction mixture was stirred for 1 hr, concentrated to dryness and the resultant solid was dissolved in 1 M HCl. The acidic solution was then made basic with aqueous ammonium hydroxide and extracted with EtOAc. The organic phase was collected, dried over anhydrous sodium sulfate and filtered. The filtrate was evaporated under reduced pressure and the residue was triturated with Et$_2$O to afford the amine 46 as a white solid which was used immediately in the next step.

To a suspension of the amine 46 (162 mg, 0.44 mmol) in THF (7 ml) was added 2-phenylacetyl isothiocyanate (117 mg, 0.66 mmol). The reaction mixture was stirred for 1 hr, concentrated under reduced pressure and the residue was purified by column chromatography (eluent EtOAc-MeOH, 95:5); a solid was obtained which was triturated with Et$_2$O to afford title compound 47a (80 mg, 33% yield). $^1$H NMR (400 MHz, DMSO-d$_6$) δ (ppm): 12.50 (s, 1H), 11.85 (s, 1H), 8.70 (s, 1H), 8.68 (d, J=6.07 Hz, 1H), 8.28 (m, 1H), 8.10 (s, 2H), 7.59 (s, 2H), 7.34-7.27 (m, 5H), 7.01 (d, J=8.61 Hz, 1H), 6.93 (d, J=5.7 Hz, 1H), 3.93 (s, 3H), 3.83 (s, 2H).

Examples 50-54

Examples 50-54 (compounds 47b-f) were prepared similarly to the compound 47a (example 49) according to the scheme 9.

TABLE 7

Characterization of compounds 47b-f (examples 50-54)

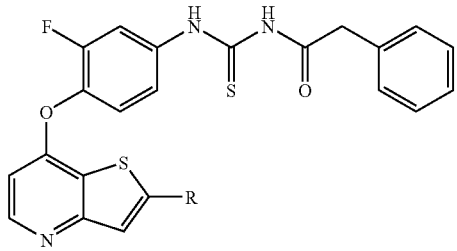

47b-f: Examples 50-54

| Cpd | Ex | R | Name | Characterization |
|---|---|---|---|---|
| 47b | 50 | (6-fluoropyridin-3-yl) | N-(3-Fluoro-4-(2-(6-fluoropyridin-3-yl)thieno[3,2-b]pyridin-7-yloxy)phenylcarbamothioyl)-2-phenylacetamide | $^1$H NMR(400 MHz, DMSO-$d_6$) δ ppm): 12.46(s, 1H), 11.82(s, 1H), 8.79(m, 1H), 8.55(d, J=5.48 Hz, 1H), 8.50(m, 1H), 8.19(s, 1H), 8.02(d, J=13 Hz, 1H), 7.53(m, 1H), 7.37-7.26(m, 6H), 6.68(m, 1H), 6.68(m, 1H), 3.82(s, 2H). |
| 47c | 51 | (pyrimidin-5-yl) | N-(3-Fluoro-4-(2-(pyrimidin-5-yl)thieno[3,2-b]pyridin-7-yloxy)phenylcarbamothioyl)-2-phenylacetamide dihydo chloride. | $^1$H NMR(400 MHz, DMSO-$d_6$) δ ppm): 12.48(s, 1H), 11.83(s, 1H), 9.2(bs, 3H) 8.63(m, 1H), 8.34(s, 1H), 8.03(d, J=11 Hz, 1H), 7.55 (m, 2H), 7.30(m, 6H), 6.68(m, 1H), 3.82(s, 2H). |
| 47d | 52 | (1-methyl-1H-pyrrole-2-yl) | N-(3-Fluoro-4-(2-(1-methyl-1H-pyrrole-2-yl)thieno[3,2-b]pyridin-7-yloxy)phenylcarbamothioyl)-2-phenylacetamide | $^1$H NMR(400 MHz, DMSO-$d_6$) δ (ppm): 8.46(d, J=5.9 Hz, 1H), 8.04 (m, 1H), 7.59(s, 1H), 7.51(m, 2H), 7.3-7.2(m, 6H), 7.01(s, 1H) 6.58 (d, J=5.9 Hz, 1H), 6.53(m, 1H), 6.10(m, 1H), 3.87(s, 3H), 3.81(s, 2H). |
| 47e | 53 | (furan-3-yl) | N-(3-Fluoro-4-(2-(furan-3-yl)thieno[3,2-b]pyridin-7-yloxy)phenylcarbamothioyl)-2-phenylacetamide | $^1$H NMR(DMSO) δ(ppm): 12.49(s, 1H), 11.84(s, 1H), 8.49(d, J=5.5 Hz, 1H), 8.36(s, 1H), 8.00(d, J= 11.3 Hz, 1H), 7.85-7.83(m, 1H), 7.82(s, 1H), 7.52-7.51(m, 2H), 7.34-7.33(m, 4H), 7.28-7.26(m, 1H), 7.09 (brs, 1H), 6.62(d, J=5.3 Hz, 1H), 3.82(s, 2H), MS(m/z) 504.0(M + H) |
| 47f | 54 | (4-methylthiophen-3-yl) | 1-(3-Fluoro-4-(2-(4-methylthiophen-3-yl)thieno[3,2-b]pyridin-7-yloxy)phenyl)-3-(2-phenylacetyl)thiourea | $^1$H NMR(DMSO) δ(ppm): 12.49(s, 1H), 11.84(s, 1H), 8.52(d, J=5.5 Hz, 1H), 8.01(d, J=5.6 Hz, 1H), 7.94(d, J=2.7 Hz, 1H), 7.70(s, 1H), 7.54-7.52(m, 2H), 7.41-7.40(m, 1H), 7.35-7.34(m, 3H), 7.33(s, 1H), 7.27(m, 1H), 6.64(dd, J=4.7 Hz, 1H), 3.82(s, 2H), 2.43(s, 3H), MS (m/z) 534.0(M + H). |

Scheme 10

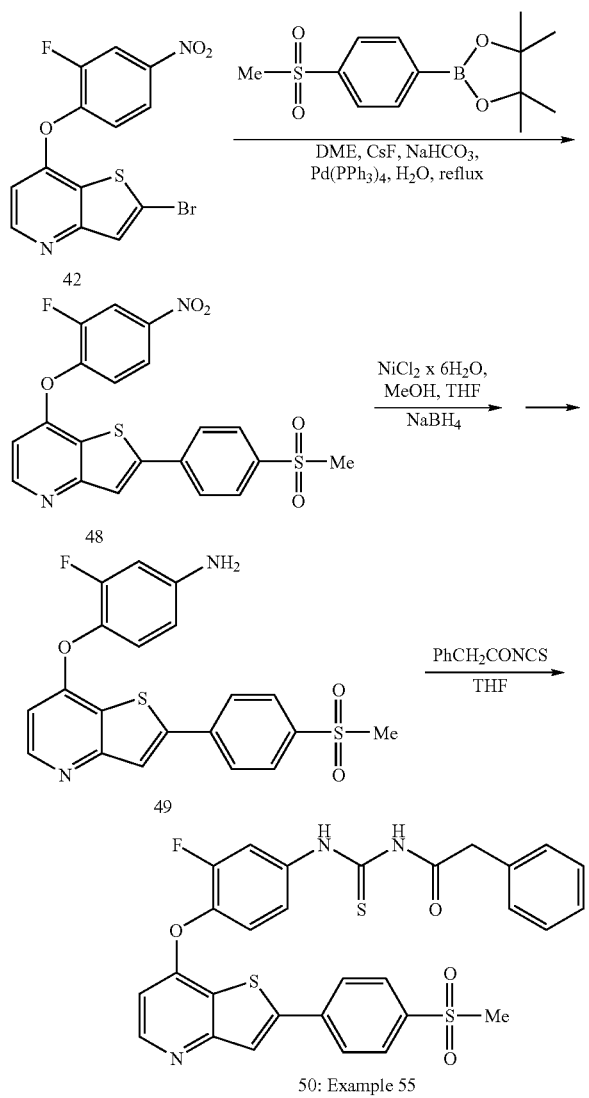

50: Example 55

Example 55

N-(3-Fluoro-4-(2-(4-(methylsulfonyl)phenyl)thieno[3,2-b]pyridin-7-yloxy)phenylcarbamothioyl)-2-phenylacetamide (50)

Step 1. 7-(2-Fluoro-4-nitrophenoxy)-2-(4-(methylsulfonyl)phenyl)thieno[3,2-b]pyridine (48)

To a solution of 42 (461 mg, 1.3 mmol, scheme 8) in DME (4 mL) was added 4,4,5,5-tetramethyl-2-(4-(methylsulfonyl)phenyl)-1,3,2-dioxaborolane (500 mg, 2.5 mmol), CsF (391 mg, 3.8 mmol), Pd(PPh$_3$)$_4$ (72 mg, 63 µmol) and NaHCO$_3$ (315 mg, 3.8 mmol) pre-dissolved in H$_2$O (1 ml). The reaction mixture was purged with nitrogen and refluxed for 2 hours. The DME was removed under reduced pressure and the aqueous layer was extracted with EtOAc. The extract was dried over sodium sulphate, filtered and evaporated to form a residue which was purified by column chromatography (eluent EtOAc/hexane, 1:1) to afford the title compound 48 (97 mg, 18% yield) as a white solid. $^1$HNMR (DMSO) δ (ppm): 8.63 (d, J=1.2 Hz, 1H), 8.49 (d-d, J=2.7 Hz, 1H), 8.33 (s, 1H), 8.22-8.19 (m, 2H), 8.16 (s, 2H), 8.02 (d, J=8.6 Hz, 2H), 7.75 (t, J=8.0 Hz, 1H), 7.77-7.58 (m, 2H), 7.58-7.50 (m, 2H), 6.97 (d, J=5.5 Hz, 1H), 3.33 (s, 3H), MS (m/z): 444.8 (M+H).

Step 2. 3-Fluoro-4-(2-(4-(methylsulfonyl)phenyl)thieno[3,2-b]pyridin-7-yloxy)benzenamine (49)

Nitro compound 48 (97 mg, 2 mmol) was dissolved in a mixture of THF (7 mL) and MeOH (15 mL); NiCl$_2$×6H$_2$O (130 mg, 0.5 mmol) was added and the solution was cooled to 0° C. To the cooled mixture NaBH$_4$ (42 mg, 1.1 mmol) was added portion wise. The reaction was stirred for 20 min and quenched with 2 M HCl. The solvents were removed under reduced pressure and the residue was treated with concentrated ammonium hydroxide solution (pH 10) and extracted with EtOAc. The organic extract was dried over anhydrous sodium sulfate, filtered and evaporated. The residue was purified by column chromatography (eluent EtOAc) to afford the title compound 49 (46.7 mg, 51% yield) as a white solid. $^1$H NMR (DMSO) δ (ppm): 8.52 (d, J=5.5 Hz, 1H), 8.25 (s, 1H), 8.15 (d, J=8.4 Hz, 2H), 8.03 (d, J=8.4 Hz, 2H), 7.63-7.58 (m, 2H), 7.56-7.52 (m, 2H), 7.13 (t, J=8.6 Hz, 1H), 6.61 (d, J=2.2 Hz, 1H), 6.56 (dd, J=10 Hz, 1H), 6.46 (dd, J=5.7 Hz, 1H), 5.57 (s, 2H), 3.29 (s, 3H), MS (m/z): 414.8 (M+H).

Step 3. N-(3-Fluoro-4-(2-(4-(methylsulfonyl)phenyl)thieno[3,2-b]pyridin-7-yloxy)phenylcarbamothioyl)-2-phenylacetamide (50)

To a solution of 49 (46.7 mg, 0.1 mmol) in dry THF (5 mL), 2-phenylacetyl isothiocyanate (40 mg, 0.2 mmol) was added and the reaction was allowed to stir for 30 minutes. The THF was removed under reduced pressure and the resultant product was purified by column chromatography on silica gel, eluent hexane/EtOAc (1:1), to afford the title compound 50 (35.4 mg, 53% yield). $^1$HNMR (DMSO) δ (ppm): 12.49 (s, 1H), 11.85 (s, 1H), 8.57 (d, J=5.5 Hz, 1H), 8.30 (s, 1H), 8.17 (d, J=8.4 Hz, 2H), 8.02 (d, J=8.4 Hz, 2H), 7.63-7.52 (m, 5H), 7.34 (d, J=4.1 Hz, 2H), 6.71 (d, J=5.3 Hz, 1H), 3.82 (brs, 2H), 3.27 (s, 3H) MS (m/z) 592.0 (M$^+$).

Scheme 11

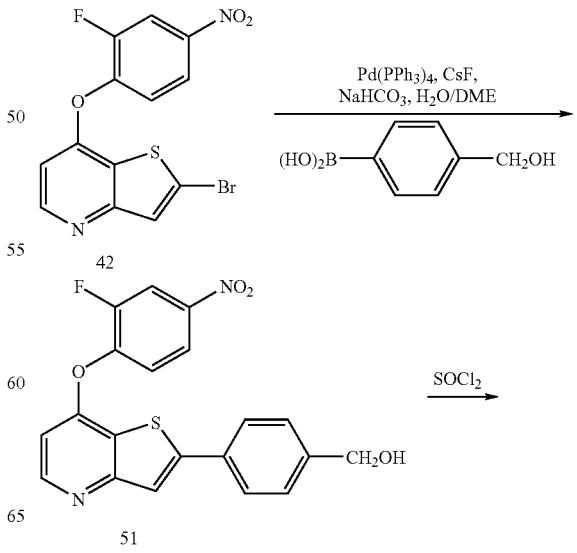

-continued

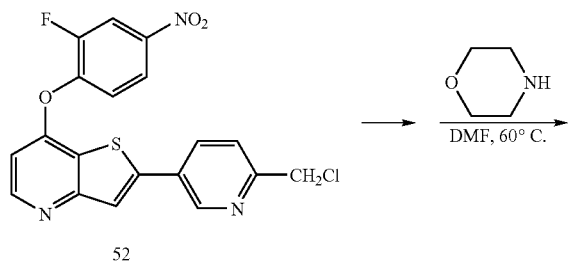

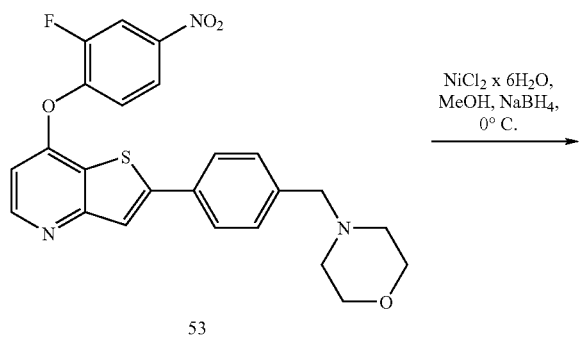

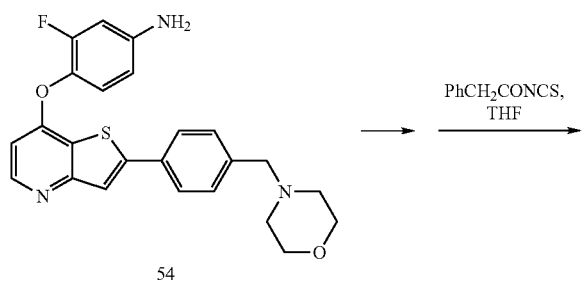

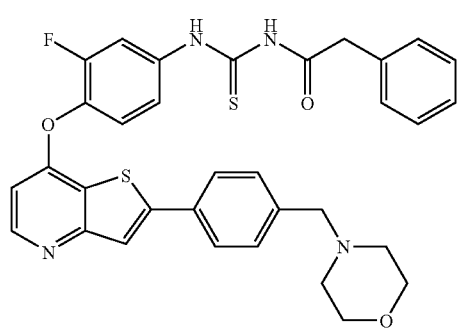

55: Example 56

Example 56

1-(3-Fluoro-4-(2-(4-(morpholinomethyl)phenyl) thieno[3,2-b]pyridin-7-yloxy)phenyl)-3-(2-phenylacetyl)thiourea (55)

Step 1. (4-(7-(2-Fluoro-4-nitrophenoxy)thieno[3,2-b]pyridin-2-yl)phenyl)methanol (51)

To a solution of 42 (1.0 g, 2.71 mmol) in dry DME (20 ml) was added 4-(hydroxymethyl)phenylboronic acid (823 mg, 5.4 mmol), NaHCO$_3$ (682 mg, 8.13 mmol), CsF (820 mg, 5.4 mmol) and water (10 mL) and the reaction mixture was refluxed under nitrogen for 2 hrs. After cooling to room temperature the DME was removed under reduced pressure, the residue was dissolved in EtOAc and the organic solution was washed with water, dried over anhydrous sodium sulfate, filtered and evaporated. The resultant solid residue was triturated with Et$_2$O to afford the title compound 51 as a white solid (880 mg, 82% yield). MS (m/z): 397.1 (M+H).

Step 2. 2-(4-(Chloromethyl)phenyl)-7-(2-fluoro-4-nitrophenoxy)thieno[3,2-b]pyridine (52)

The alcohol 51 (880 mg, 2.22 mmol) was suspended in SOCl$_2$ (10 ml) and the reaction mixture was refluxed for 1 hour, cooled and carefully poured onto ice/water. A precipitate was formed which was collected by filtration, washed with additional cold water and dried under vacuum to afford the title compound 52 (919 mg, 100% yield), which was used without additional purification. MS (m/z): 415.1(100%) (M+H), 417.1 (36%) (M+H).

Step 3. 7-(2-Fluoro-4-nitrophenoxy)-2-(4-(morpholinomethyl)phenyl)thieno[3,2-b]pyridine (53)

To a suspension of 52 (823 mg, 1.82 mmol) in DMF (10 ml) was added morpholine (317 mg, 3.65 mmol) and the reaction mixture was heated for 4 hours at 60° C., the solvent was removed under reduced pressure and the residual solid was triturated with EtOAc and collected by filtration. It was further washed with EtOAc until no color was observed in the filtrate, to form the title compound 53 (800 mg, 94% yield), which was used without additional purification. $^1$HNMR (DMSO) δ (ppm): 8.57 (d, J=4.7 Hz, 1H), 8.46 (dd, J=2.7 and 10.4 Hz, 1H), 8.18 (m, 1H), 8.07 (s, 1H), 7.83 (d, J=12.2 Hz, 1H), 7.71 (t, J=8.02 Hz, 1H), 7.42 (d, J=8.2 Hz, 1H), 6.91 (d, J=5.3 Hz, 1H), 3.56 (m, 4H), 3.51 (m, 2H), 3.33 (m, 3.33 (m, 2H), 2.50 (m, 2H).

Step 4. 1-(3-Fluoro-4-(2-(4-(morpholinomethyl)phenyl)thieno[3,2-b]pyridin-7-yloxy)phenyl)-3-(2-phenylacetyl)thiourea (55)

To a solution of 53 (1.1 g, 2.37 mmol) in MeOH (20 mL) and THF (20 mL) at 0° C. was added NiCl$_2$×6H$_2$O (1.12 g, 4.73 mmol) and NaBH$_4$ (350 mg, 9.48 mmol). The reaction mixture was allowed to stir for 1 hr, solvents were removed under reduced pressure and the resultant solid residue was dissolved in 1 M HCl. This solution was made basic with concentrated aqueous ammonium hydroxide and extracted with EtOAc. The organic phase was collected, dried over anhydrous sodium sulfate and filtered. The filtrate was evaporated under reduced pressure and the resultant solid was triturated with Et$_2$O to afford the amine 54 as a white solid (1.02 g, 100% yield), which was used in the next step without further purification.

To a suspension of the amine 54 (1.02 g, 2.34 mmol) in THF (10 mL) was added 2-phenylacetyl isothiocyanate (622 mg, 3.52 mmol) and the reaction mixture was stirred for 1 hr at room temperature, concentrated under reduced pressure and purified by column chromatography (eluent EtOAc: MeOH, 95:5) to afford title compound 55 as a yellow powder (288 mg, 12% yield). $^1$H NMR (400 MHz, DMSO-$d_6$) δ (ppm): 12.48 (s, 1H), 11.84 (s, 1H), 8.63 (m, 1H), 8.18 (s, 1H), 8.01 (d, J=7.8 Hz, 2H), 7.75 (m, 2H), 7.57 (s, 2H), 7.33 (m, 4H), 6.80 (d, J=11.7 Hz, 2H), 3.83 (s, 5H), 3.37 (d, J=11.7 Hz, 2H), 3.12 (m, 2H). MS (m/z) 613.3 (M+H).

Scheme 12

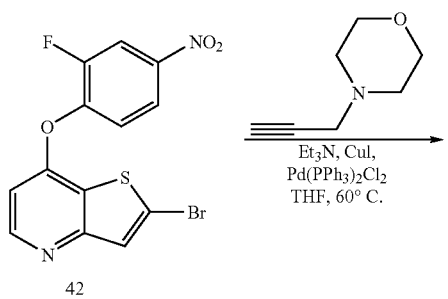

42

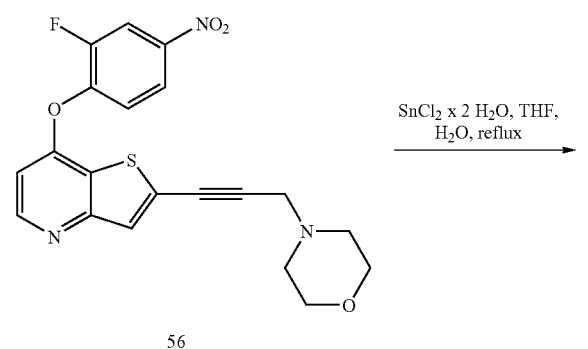

56

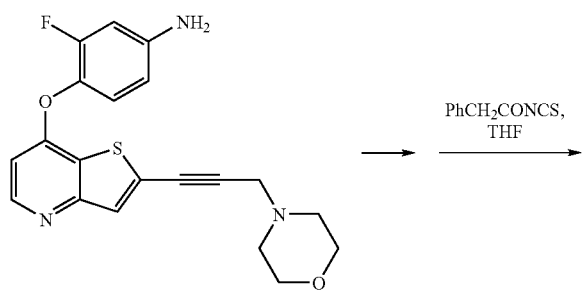

57

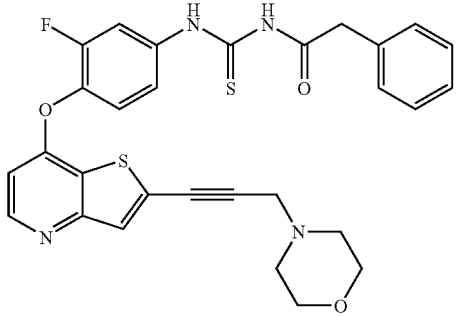

58: Example 57

Example 57

1-(3-Fluoro-4-(2-(3-morpholinoprop-1-ynyl)thieno[3,2-b]pyridin-7-yloxy)phenyl)-3-(2-phenylacetyl)thiourea (58)

Step 1. 7-(2-Fluoro-4-nitrophenoxy)-2-(3-morpholinoprop-1-ynyl)thieno[3,2-b]pyridine (56)

To a solution of bromide 42 (100 mg, 0.27 mmol) in THF (5 ml) was added 4-(prop-2-ynyl)morpholine (68 mg, 0.54 mmol) [H-W. Tsou, et. al. *J. Med. Chem.*, 2001, 44, 2719-2734], triethylamine (68 mg, 0.67 mmol), CuI (5 mg, 0.03 mmol) and Pd(PPh$_3$)$_2$Cl$_2$ (5.3 mg, 7.56 μmol). The reaction mixture was degassed with nitrogen and refluxed for 2 hrs, cooled to room temperature and adsorbed onto silica. Purification by column chromatography (eluent EtOAc) afforded the title compound 56 as a beige solid (88 mg, 79%). MS (m/z): 397.1 (M+H).

Steps 2-3. 1-(3-Fluoro-4-(2-(3-morpholinoprop-1-ynyl)thieno[3,2-b]pyridin-7-yloxy)phenyl)-3-(2-phenylacetyl)thiourea (58)

To a solution of the nitro compound 56 (300 mg, 0.724 mmol) in THF (10 mL) and NH$_4$Cl (6 mL) was added SnCl$_2$×2H$_2$O (489 mg, 2.17 mmol) and the reaction mixture was refluxed for 3 hrs. After cooling the mixture was diluted with EtOAc and washed with concentrated aqueous ammonium hydroxide. EtOAc phase was separated and the aqueous phase was extracted with DCM. Both EtOAc phase and DCM extract were combined, dried over anhydrous sodium sulfate and filtered. The filtrate was evaporated to dryness to afford the amine 57 (277 mg, 100% yield), which was used without further purification.

To a solution of the amine 57 (270 mg, 0.74 mmol) in THF (10 mL) was added 2-phenylacetyl isothiocyanate (188 mg, 1.06 mmol) and the reaction mixture was stirred for 1 hr, concentrated under reduced pressure and purified by column chromatography (eluent EtOAc) to afford title compound 58 (37 mg, 10% yield) as a white solid. $^1$H NMR (400 MHz, DMSO-$d_6$) δ (ppm): 12.47 (s, 1H), 11.82 (s, 1H), 8.55 (d, J=5.3 Hz, 1H), 8.01 (d, J=13.2 Hz, 1H), 7.79 (s, 1H), 7.52 (s, 1H), 7.33 (m, 4H), 7.28 (m, 1H), 6.72 (d, J=5.3 Hz, 1H), 3.82 (s, 2H), 3.64 (s, 2H), 3.61 (m, 5H), 2.51 (m, 4H). MS (m/z): 561.3 (M+H).

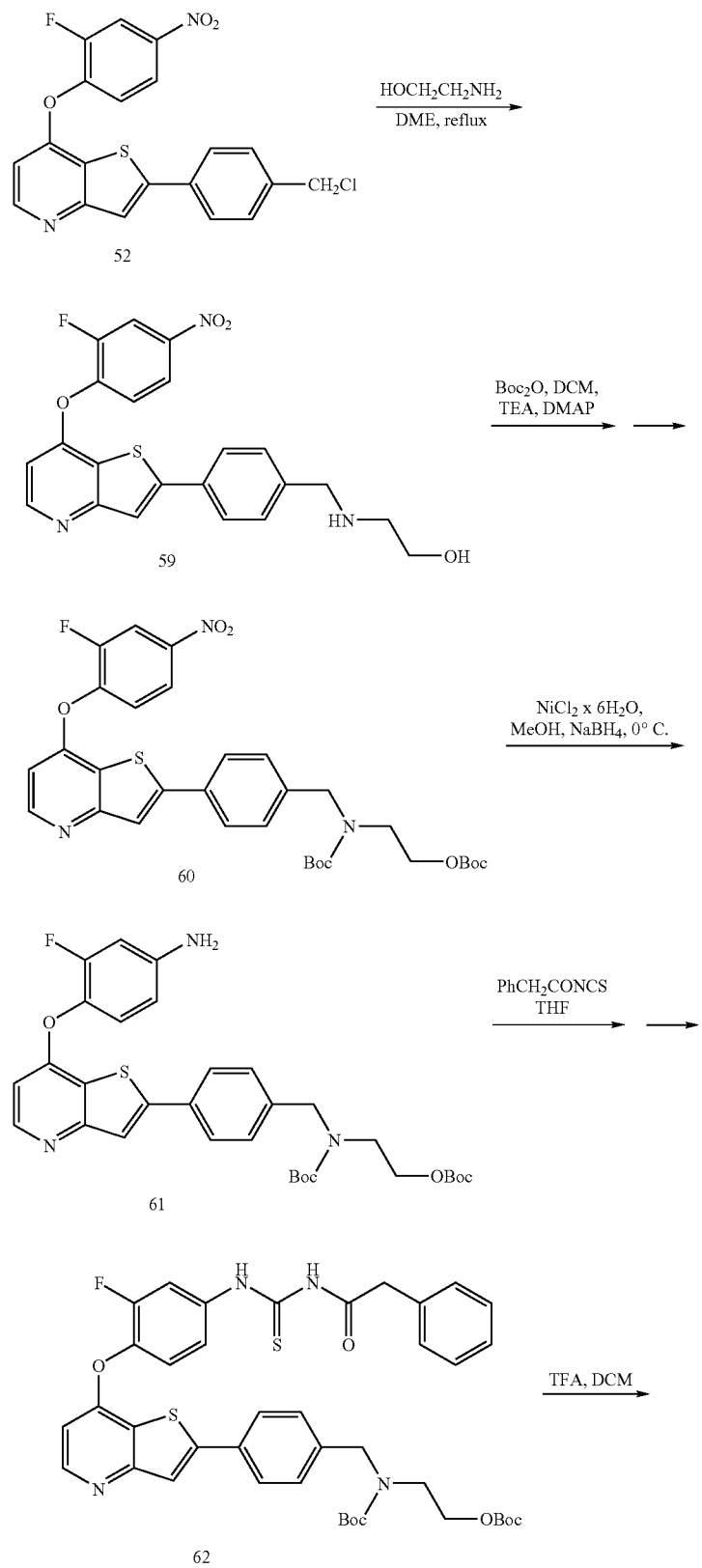

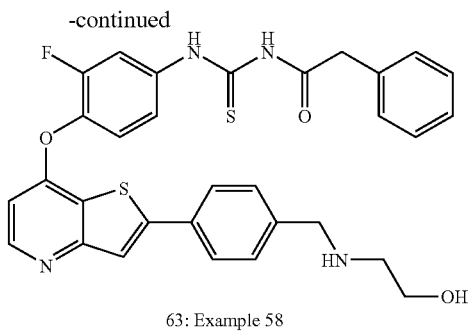

63: Example 58

Example 58

2-((4-(7-(2-Fluoro-4-nitrophenoxy)thieno[3,2-b]pyridin-2-yl)phenyl)methylamino)ethanol (63)

Step 1. 2-{4-[7-(2-Fluoro-4-nitro-phenoxy)-thieno[3,2-b]pyridin-2-yl]-benzylamino}-ethanol (59)

To a suspension of the chloride 52 (500 mg, 1.1 mmol) in DME (10 mL) was added ethanolamine (336 mg, 5.5 mmol). The reaction mixture refluxed for 2 hrs, the solvent was removed under reduced pressure; the residue was dissolved in EtOAc and washed with water. The organic phase was collected, dried over sodium sulfate, filtered and evaporated. The remaining solid was triturated with $Et_2O$ to afford the title compound 59 as a yellow solid (200 mg, 41% yield). $^1H$ NMR (DMSO) δ (ppm): 8.57 (d, J=5.5 Hz, 1H), 8.47 (dd, J=2.7 and 10.4 Hz, 1H), 8.21 (m, 1H), 8.17 (s, 1H), 7.83 (d, J=8.0 Hz, 1H), 7.71 (t, J=8.6 Hz, 1H), 7.44 (d, J=8.0 Hz, 1H), 6.91 (d, J=5.5 Hz, 1H), 4.48 (t, J=5.5 Hz, 1H), 3.75 (s, 2H), 3.45 (q, J=5.6 Hz, 2H), 3.33 (m, 1H), 3.15 (d, J=5.1 Hz, 2H), 2.56 (t, J=5.7 Hz, 2H).

Step 2. Carbonic acid 2-(tert-butoxycarbonyl-{4-[7-(2-fluoro-4-nitro-phenoxy)-thieno[3,2-b]pyridin-2-yl]-benzyl}-amino)-ethyl ester tert-butyl ester (60)

To a solution of 59 (200 mg, 0.45 mmol) in DCM (7 mL) at room temperature was added triethylamine (188 mg, 1.82 mmol), DMAP (cat) and $Boc_2O$ (355 mg, 1.82 mmol). The reaction mixture was stirred at room temperature overnight, the DCM was removed under reduced pressure and the residue was dissolved in EtOAc, washed sequentially with dilute HCl solution, saturated $NaHCO_3$ and brine, dried over anhydrous sodium sulfate and filtered. The filtrate was evaporated and the residue was purified by column chromatography (eluent EtOAc:hexane, 3:7) to afford title compound 60 (200 mg, 69% yield) as a yellow oil. $^1H$ NMR (DMSO) δ (ppm): 8.58 (d, J=5.3 Hz, 1H), 8.47 (dd, J=2.7 and 10.3 Hz, 1H), 8.21 (m, 1H), 8.09 (s, 1H), 7.87 (m, 2H), 7.72 (t, J=8.4 Hz, 1H), 7.33 (d, J=8.2 Hz, 2H), 6.91 (d, J=5.3 Hz, 1H), 4.44 (s, 2H), 4.07 (t, J=5.5 Hz, 2H), 3.40 (m, 2H), 1.36 (m, 18H).

Steps 3-4. Carbonic acid 2-[tert-butoxycarbonyl-(4-{7-[2-fluoro-4-(3-phenylacetyl-thioureido)-phenoxy]-thieno[3,2-b]pyridin-2-yl}-benzyl)-amino]-ethyl ester tert-butyl ester (62)

To a solution of 60 (500 mg, 1.1 mmol) in MeOH (10 mL) at 0° C. was added $NiCl_2 \times 6H_2O$ (148 mg, 0.63 mmol) and $NaBH_4$ (46 mg, 1.24 mmol). The reaction mixture was allowed to stir for 1 hr, concentrated to dryness and the resultant solid was dissolved in 1 M HCl. The acidic solution was then made basic with concentrated ammonium hydroxide solution and extracted with EtOAc. The organic phase was collected, dried over anhydrous sodium sulfate and filtered. The filtrate was evaporated under reduced pressure and the resultant solid was triturated with $Et_2O$ to afford the crude amine 61 as a white solid (190 mg, 100% yield), which was used for the next step without characterization and additional purification.

To a suspension of the amine 61 (190 g, 0.31 mmol) in THF (7 mL) was added 2-phenylacetyl isothiocyanate (118 mg, 0.62 mmol) and the reaction mixture was stirred for 1 hr at room temperature, concentrated under reduced pressure and purified by column chromatography (eluent EtOAc-MeOH, 6:4) to afford title compound 62 as a yellow powder (190 mg, 77% yield). $^1H$ NMR (400 MHz, DMSO-$d_6$) δ (ppm): 12.48 (s, 1H), 11.83 (s, 1H), 8.51 (s, 1H), 8.04 (s, 1H), 8.01 (d, J=11.7 Hz, 1H), 7.86 (d, J=7.7 Hz, 2H), 7.52 (m, 2H), 7.34 (m, 6H), 7.32 (m, 1H), 6.64 (d, J=5.5 Hz, 1H), 4.43 (s, 2H), 4.07 (t, J=5.3 Hz, 2H), 3.81 (s, 2H), 3.44 (m, 2H), 1.37 (m, 18H).

Step 5. 1-(3-Fluoro-4-(2-(4-((2-hydroxyethylamino)methyl)phenyl)thieno[3,2-b]pyridin-7-yloxy)phenyl)-3-(2-phenylacetyl)thiourea (63)

To a solution of 62 in DCM (190 mg, 0.24 mmol) was added TFA (excess) at room temperature and the reaction mixture was stirred for 3 hrs, evaporated under reduced pressure and the residual solid was triturated with $Et_2O$ to afford the title compound 63 as the di-TFA salt (100 mg, 51% yield). $^1H$ NMR (400 MHz, DMSO-$d_6$) δ (ppm): 12.49 (s, 1H), 11.84 (s, 1H), 8.89 (s, 1H), 8.53 (d, J=5.1 Hz, 1H), 8.14 (s, 1H), 8.01 (m, 1H), 7.62 (dd, J=2.5 and 7.7 Hz, 2H), 7.54 (d, J=2.7 Hz, 2H), 7.33 (m, 4H), 7.28 (m, 1H), 6.67 (d, J=5.5 Hz, 1H), 4.64 (m, 1H), 4.30 (m, 1H), 4.22 (t, J=5.3 Hz, 2H), 3.82 (s, 2H), 3.63 (t, J=5.3 Hz, 2H), 2.98 (m, 1H). MS (m/z) 587.0 (M+H).

Scheme 14

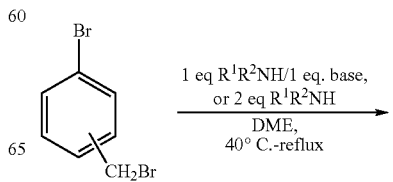

-continued

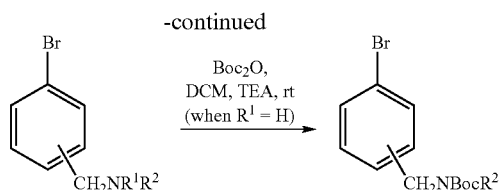

Substituted aryl bromides (compounds 64-71)

N-(3-Bromobenzyl)-2-methoxyethanamine (64)

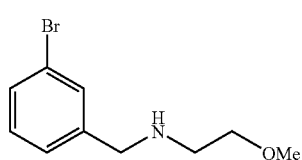

64

To a solution of 2-methoxyethanamine (900 mg, 12 mmol) in DME (15 mL) was added 3-bromobenzylbromide (2.5 g, 10 mmol) and the reaction mixture was stirred at 40° C. (scheme 14). After 30 minutes, Et$_3$N (1.01 g, 10 mmol) was added and the reaction was allowed to stir for another 10 minutes, filtered and the filtrate was concentrated to afford bromide 64 as a colorless oil (2.0 g, 80% yield). MS (m/z): 244.1/246.1 (M+H).

tert-Butyl 3-bromobenzyl(2-methoxyethyl)carbamate (65)

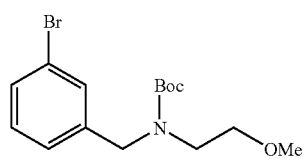

65

To a solution of compound 64 (997 mg, 4 mmol) in CH$_2$Cl$_2$ (12 mL), di-tert-butylcarbonate (1.8 g, 8 mmol) was added and the reaction mixture was stirred for 3 hrs (scheme 14). DMAP (cat.) was added to the solution and the reaction mixture was allowed to stir for additional 76 hours. Solvent was removed under reduced pressure and the crude product was purified by column chromatography, eluent EtOAc/hexane (1:10) to afford the title compound 65 (778 mg, 56% yield) as a colorless oil. MS (m/z): 368.1/370.1 (M+Na).

TABLE 8

Aryl bromides 66-70 prepared according to the scheme 14

| Cpd | Aryl bromide | Chemical name | Characterization MS(m/z) | Amine reagent used to obtain the aryl bromides |
|---|---|---|---|---|
| 66 | ![structure] | tert-Butyl 3-bromobenzyl(2-morpholinoethyl)carbamate | 399.1/401.1 (M + H) | ![structure] |
| 67 | ![structure] | tert-Butyl 4-bromobenzyl(2-methoxyethyl)carbamate | 344.1/346.1 (M + H) | H$_2$N-CH$_2$CH$_2$-OMe |
| 68 | ![structure] | tert-Butyl 2-bromobenzyl(2-methoxyethyl)carbamate | 365.9/367.9 (M + Na) | H$_2$N-CH$_2$CH$_2$-OMe |
| 69 | ![structure] | 1-(4-Bromobenzyl)-1H-tetrazole | 238.9/240.9 (M + H) | ![structure] |

TABLE 8-continued

Aryl bromides 66-70 prepared according to the scheme 14

| Cpd | Aryl bromide | Chemical name | Characterization MS(m/z) | Amine reagent used to obtain the aryl bromides |
|---|---|---|---|---|
| 70 | 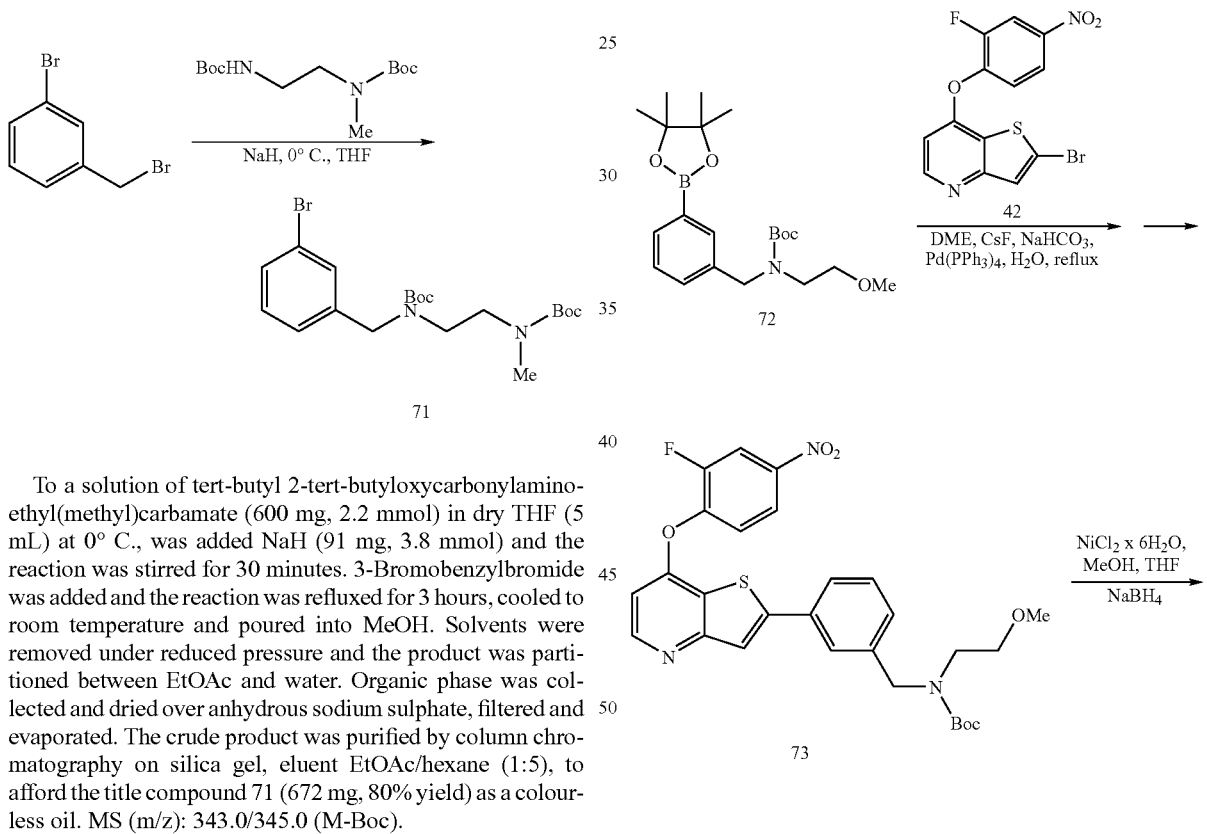 | tert-Butyl 4-bromobenzyl((tetrahydrofuran-2-yl)methyl)carbamate | 370.1/372.1 (M + H) | | bis-tert-Butyl 2-(3-bromobenzylamino)ethyl(methyl)carbamate (71)

To a solution of tert-butyl 2-tert-butyloxycarbonylaminoethyl(methyl)carbamate (600 mg, 2.2 mmol) in dry THF (5 mL) at 0° C., was added NaH (91 mg, 3.8 mmol) and the reaction was stirred for 30 minutes. 3-Bromobenzylbromide was added and the reaction was refluxed for 3 hours, cooled to room temperature and poured into MeOH. Solvents were removed under reduced pressure and the product was partitioned between EtOAc and water. Organic phase was collected and dried over anhydrous sodium sulphate, filtered and evaporated. The crude product was purified by column chromatography on silica gel, eluent EtOAc/hexane (1:5), to afford the title compound 71 (672 mg, 80% yield) as a colourless oil. MS (m/z): 343.0/345.0 (M-Boc).

Scheme 15

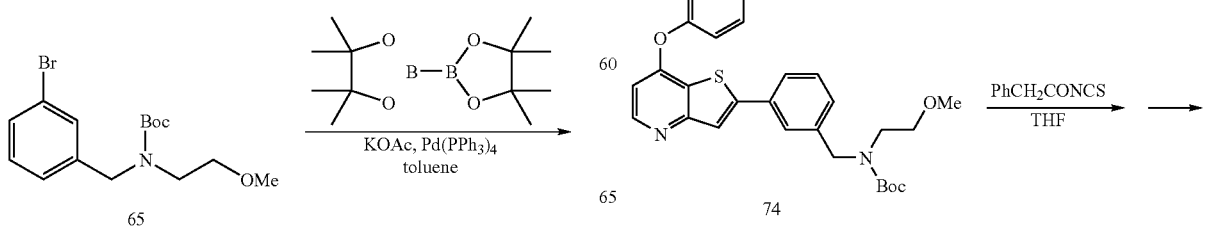

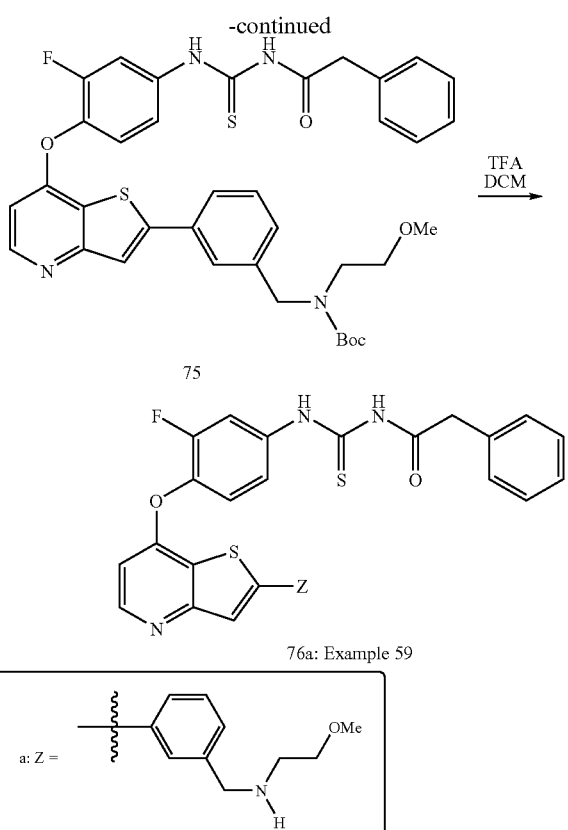

Example 59

N-(3-Fluoro-4-(2-(3-((2-methoxyethylamino)methyl)phenyl)thieno[3,2-b]pyridin-7-yloxy)phenylcarbamothioyl)-2-phenylacetamide (76a)

Step 1. tert-Butyl 2-methoxyethyl(3-(pinacolatoborolan-2-yl)benzyl)carbamate (72)

To a solution of bromide 65 (778 mg, 2.3 mmol), in dry toluene (12 mL), was added the bis(pinacolato)diboron (872 mg, 3.4 mmol), KOAc (677 mg, 6.9 mmol) and Pd(PPh$_3$)$_4$ (80 mg, 69 μmol). The reaction mixture was purged with nitrogen, refluxed for 2 hours and was allowed to cool to room temperature. The solvent was removed under reduced pressure and the residue was partitioned between DCM and water (30 mL/30 mL). The organic phase was collected and dried over anhydrous sodium sulphate, filtered and evaporated. The remained solid was purified by column chromatography, eluent EtOAc/hexane (1:10) to afford title compound 72 (577 mg, 64% yield) as a colorless oil. $^1$H NMR (DMSO) δ (ppm): 7.54-7.52 (m, 2H), 7.33-7.31 (m, 2H), 4.39 (s, 2H), 3.40-3.35 (m, 2H), 3.33-3.25 (m, 2H), 3.20 (s, 3H), 1.43-1.32 (m, 9H), 1.28 (s, 12H).

Step 2. tert-Butyl 3-(7-(2-fluoro-4-nitrophenoxy)thieno{3,2-b}pyridine-2-yl)benzyl(2-methoxyethyl)carbamate (73)

To a solution of the bromo-nitro compound 42 (272 mg, 0.7 mmol) in DME (4 mL), was added pinacolate 72 (578 mg, 1.5 mmol), CsF (226 mg, 2.2 mmol), Pd(PPh$_3$)$_4$ (43 mg, 37 μmol) and NaHCO$_3$ (186 mg, 2.2 mmol) pre-dissolved in water (2 mL). The reaction mixture was purged with nitrogen, refluxed for 1 hour, cooled to room temperature and the solvent was removed under reduced pressure. The residue was extracted with EtOAc, the extract was dried over anhydrous sodium sulfate, filtered and concentrated to produce a brown oil which was purified by chromatography on silica gel, eluent EtOAc, to afford the title compound 73 (347 mg, 85% yield) as a white solid. $^1$H NMR (DMSO) δ (ppm): 8.60 (d, J=5.3 Hz, 1H), 8.47 (d-d, J=7.6 Hz, 1H), 8.19 (d, J=6.5 Hz, 1H), 8.07 (s, 1H), 7.80 (d, J=7.8 Hz, 1H), 7.73-7.69 (m, 2H), 7.48 (t, J=7.8 Hz, 1H), 7.30 (d, J=7.4 Hz, 1H), 6.95 (d, J=5.5 Hz, 1H), 4.48 (s, 2H), 3.21 (s, 3H), 2.50 (q, J=2.2 Hz, 4H), 1.44-1.33 (m, 9H), MS (m/z): 554.0 (M+H).

Step 3. tert-Butyl 3-(7-(4-amino-2-fluorophenoxy)thieno[3,2-b]pyridin-2-yl)benzyl(2-methoxyethyl)carbamate (74)

To a solution of 73 (347 mg, 0.6 mmol) in THF (4 mL) and MeOH (2 mL), NiCl$_2$ (372 mg, 1.6 mmol) was added and the solution was cooled to 0° C. NaBH$_4$ (95 mg, 2.5 mmol) was added portion wise. After 20 minutes, the reaction was treated with 2 M HCl and solvents were removed under reduced pressure. The concentrated mixture was basified to pH 10 with ammonium hydroxide solution and the mixture was extracted with EtOAc, the extract was dried over anhydrous sodium sulfate, filtered and evaporated. The residue was purified by silica gel column chromatography, eluent EtOAc, to afford the title compound 74 (235 mg, 72% yield) as a white solid. $^1$H NMR (DMSO) δ (ppm): 8.47 (d, J=5.6 Hz, 1H), 7.97 (s, 1H), 7.77 (d, J=7.2 Hz, 1H), 7.70 (s, 1H), 7.48 (t, J=7.6 Hz, 1H), 6.56-6.51 (m, 2H), 6.44 (dd, J=6.3 Hz, 1H), 5.54 (s, 2H), 4.84 (s, 2H), 3.43 (s, 2H), 3.23 (s, 3H), 2.50 (q, J=2.2 Hz, 4H), 1.46-1.35 (m, 9H).

Step 4. tert-Butyl 3-(7-(2-fluoro-4-(3-(2-phenylacetyl)thioureido)phenoxy)thieno[3,2-b]pyridin-2-yl)benzyl(2-methoxyethyl)carbamate (75)

To a solution of 74 (235 mg, 0.5 mmol) in dry THF (5 mL), 2-phenylacetyl isothiocyanate (159 mg, 0.9 mmol) was added and the reaction was allowed to stir for 30 min. The solvent was removed under reduced pressure and the resulting product was purified by chromatography on silica gel using EtOAc/hexane (1:1) as eluting system to give the desired product (440 mg, 90%) as a white solid. $^1$H NMR (DMSO) δ (ppm): 8.52 (d, J=5.3 Hz, 1H), 8.01 (t, J=6.5 Hz, 2H), 7.79 (d, J=7.4 Hz, 1H), 7.70 (s, 1H), 7.53-7.52 (m, 2H), 7.47 (t, J=7.6 Hz, 1H), 7.34 (d, J=4.5 Hz, 4H), 7.30-7.24 (m, 2H), 6.67 (d, J=5.3 Hz, 1H), 4.49 (s, 2H), 3.83 (s, 2H), 3.42 (s, 2H), 3.22 (s, 3H), 2.50 (q, J=2.2 Hz, 4H), 1.45-1.33 (m, 9H).

Step 5. N-(3-Fluoro-4-(2-(3-((2-methoxyethylamino)methyl)phenyl)thieno[3,2-b]pyridin-7-yloxy)phenylcarbamothioyl)-2-phenylacetamide (76a)

To a solution of 75 (440 mg, 0.6 mmol) in DCM (10 mL), TFA (145 μL, 1.9 mmol) was added and the reaction was stirred for 12 hours, concentrated under reduced pressure, and the residue was purified by silica gel column chromatography, eluent MeOH/EtOAc (1:10), to afford the title compound 76a (227 mg, 63% yield) as a light yellow solid. $^1$H NMR (DMSO) δ (ppm): 8.54 (d, J=5.5 Hz, 1H), 8.07 (s, 1H), 8.02-8.0 (m, 2H), 7.93 (d-t, J=2.0 Hz, 1H), 7.55-7.53 (m, 4H), 7.34-7.32 (m, 4H), 7.29-7.26 (m, 1H), 6.68 (d, J=5.3 Hz, 1H), 4.19 (s, 2H), 3.81 (s, 1H), 3.57 (t, J=4.9 Hz, 2H), 3.33 (s, 2H), 3.29 (s, 3H), 3.08 (t, J=4.9 Hz, 2H), 2.84 (q, J=2.2 Hz, 4H).

Examples 60-65

Compounds 76b-g (examples 60-65) were synthesized similarly to the compound 76a (example 59) according to the schemes 14-15, starting from bromides 66-69 and 71. Characterization of 76b-g is provided in Table 8a.

TABLE 8a

Characterization of compounds 76b-g(examples 60-65)

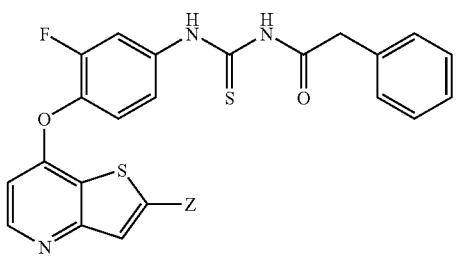

76b-g: Examples 60-65

| Cpd | Ex | Z | Chemical name | Characterization |
|---|---|---|---|---|
| 76b | 60 | 2-((2-methoxyethylamino)methyl)phenyl with NH-CH2CH2-OMe chain | 1-(3-Fluoro-4-(2-(2-((2-methoxyethylamino)methyl)phenyl)thieno[3,2-b]pyridin-7-yloxy)phenyl)-3-(2-phenylacetyl)thiourea | $^1$H NMR(400 MHz, DMSO-$d_6$) δ ppm): 12.50(s, 1H), 11.83(s, 1H), 8.57(d, J=5.5 Hz, 1H), 8.03-8.00 (m, 1H), 7.76-7.74(m, 2H), 7.61-7.50(m, 5H), 7.36-7.25(m, 5H), 6.70(d, J=5.3 Hz, 1H), 4.32(s, 2H), 3.81(s, 2H), 3.52(t, J=5.1 Hz, 2H), 3.16(s, 3H), 3.08(t, J=4.7 Hz, 2H), MS(m/z): 601.0 (M + H). |
| 76c | 61 | 3-((2-morpholinoethylamino)methyl)phenyl | 1-(3-Fluoro-4-(2-(3-((2-morpholinoethylamino)methyl)phenyl)thieno[3,2-b]pyridin-7-yloxy)phenyl)-3-(2-phenylacetyl)thiourea | $^1$H NMR(400 MHz, DMSO-$d_6$) δ (ppm): 12.49(s, 1H), 11.85(s, 1H), 8.56(d, J=5.1 Hz, 1H), 8.09-7.98 (m, 5H), 7.61-7.55(m, 5H), 7.33(s, 1H), 7.27(brs, 2H), 6.70(d, J=5.1 Hz, 1H), 4.30(brs, 2H), 3.82(brs, 2H), 3.73(brs, 4H), MS(m/z) 656.2(M + H). |
| 76d | 62 | 4-((2-(methylamino)ethylamino)methyl)phenyl | N-(3-Fluoro-4-(2-(4-((2-(methylamino)ethylamino)methyl)phenyl)thieno[3,2-b]pyridin-7-yloxy)phenylcarbamothioyl)-2-phenylacetamide | $^1$H NMR(DMSO): 12.49(s, 1H), 11.84(s, 1H), 8.51(d, J=5.5 Hz), 8.04-7.99(m, 2H), 7.87(d, J=7.6 Hz, 2H), 7.54-7.53(m, 2H), 7.34-7.33(m, 5H), 7.29-7.22(m, 2H), 6.64(d, J=5.5 Hz, 1H), 4.42-4.39 (m, 2H), 3.82(s, 2H), 3.29(brs, 2H), 3.23(brs, 3H), 2.78-2.76(m, 2H), MS: calcd 599.74, found 800.1 (M + H). |
| 76e | 63 | 4-((2-methoxyethylamino)methyl)phenyl | 1-(3-Fluoro-4-(2-(4-((2-methoxyethylamino)methyl)phenyl)thieno[3,2-b]pyridin-7-yloxy)phenyl)-3-(2-phenylacetyl)thiourea | $^1$H NMR(400 MHz, DMSO-$d_6$) δ ppm): 12.48(s, 1H), 11.83(s, 1H), 9.02(s, 2H), 8.54(d, J=5.5 Hz, 1H), 8.13(s, 1H), 8.02(d, J=13.3 Hz, 1H), 7.97(d, J=8.2 Hz, 2H), 7.53(m, 2H), 7.33(m, 4H), 7.28 (m, 2H), 6.67(d, J=5.5 Hz, 1H), 4.22(m, 2H), 3.83(s, 2H), 3.59(t, J= 4.9 Hz, 2H), 3.31(s, 3H), 3.12 (m, 2H), MS(m/z): 601.2(M + H). |

TABLE 8a-continued

Characterization of compounds 76b-g(examples 60-65)

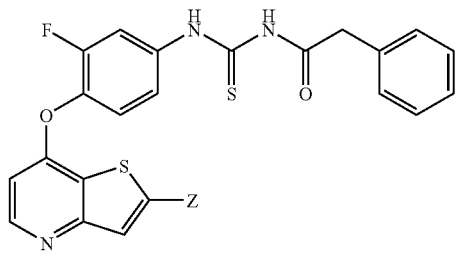

76b-g: Examples 60-65

| Cpd | Ex | Z | Chemical name | Characterization |
|---|---|---|---|---|
| 76f | 64 | | 1-(3-Fluoro-4-(2-(3-((2-(methylamino)ethyl amino)methyl)phenyl) thieno[3,2-b]pyridin-7-yloxy)phenyl)-3-(2-phenylacetyl)thiourea | $^1$H NMR(DMSO) δ(ppm): 12.49 (s, 1H), 11.85(s, 1H), 8.55(d, J=5.09 Hz, 1H), 8.08(s, 1H), 8.04 (brs, 1H), 8.00-7.97(m, 2H), 7.62-7.53(m, 4H), 7.36-7.32(m, 4H), 7.29-7.26(m, 1H), 6.69(d, J=5.5 Hz, 1H), 4.31(brs, 2H), 3.82(s, 2H), 3.31-3.27(m, 4H), 2.63(s, 3H), MS(m/z) 600.2(M + H). |
| 76g | 65 | | 1-(4-(2-(4-((1H-Tetrazol-1-yl)methyl)phenyl) thieno[3,2-b]pyridin-7-yloxy)-3-fluorophenyl)-3-(2-phenylacetyl)thiourea | $^1$H NMR(DMSO) δ(ppm): 12.46 (s, 1H), 11.82(s, 1H), 9.54(s, 1H), 8.51(dd, J=1.1 and 5.09 Hz, 1H), 8.1(s, 1H), 7.96(d, J=23.3 Hz, 1H), 7.90(d, J=6.7 Hz, 2H), 7.53 (m, 2H), 7.43(d, J=8.6 Hz, 2H), 7.32(m, 4H), 7.26(m, 1H), 6.65(d, J=5.5 Hz, 1H), 5.78(s, 2H), 3.82 (s, 2H). MS(m/z) 596.1 (M + H). |

Scheme 16

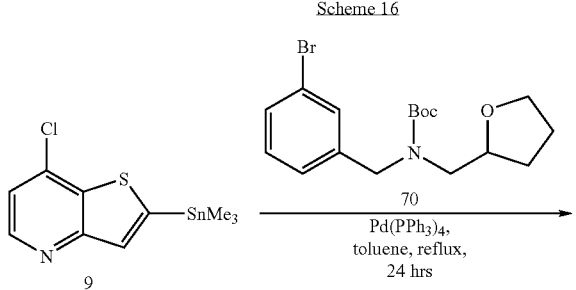

-continued
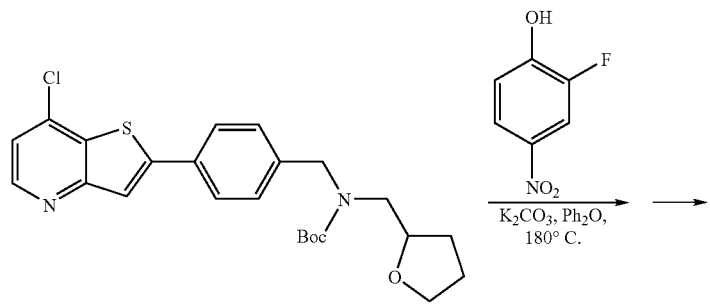
77
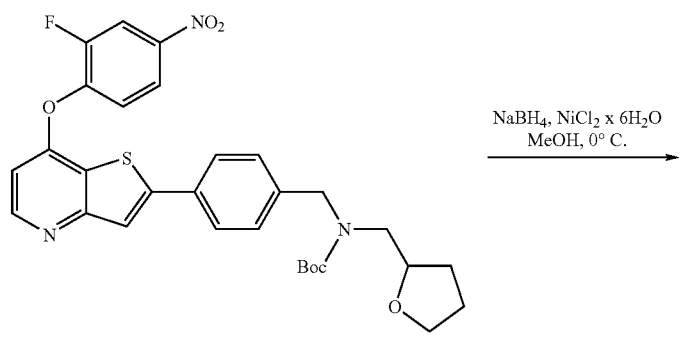
78
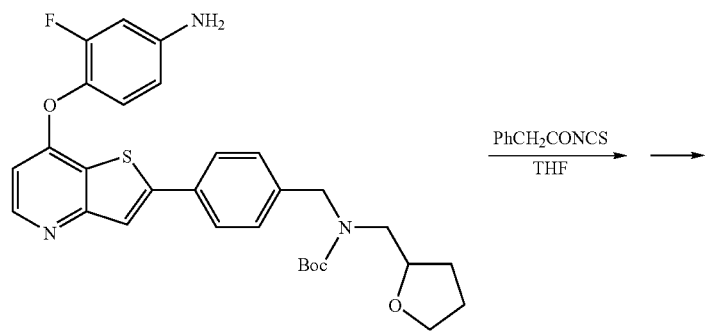
79
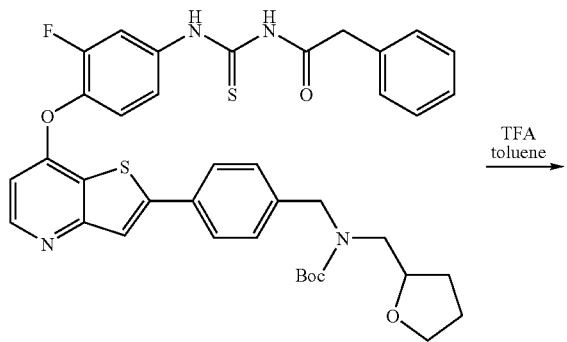
80

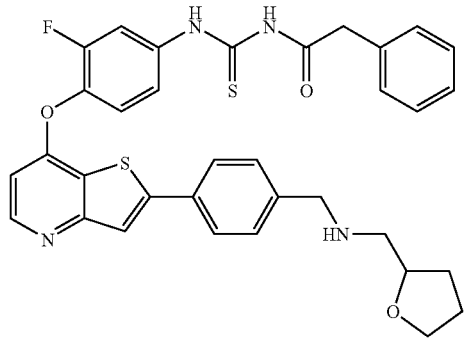

81: Example 66

Example 66

1-(3-Fluoro-4-(2-(4-(((tetrahydrofuran-2-yl)methylamino)methyl)phenyl)thieno[3,2-b]pyridin-7-yloxy)phenyl)-3-(2-phenylacetyl)thiourea (81)

Step 1. tert-Butyl(4-(7-chlorothieno[3,2-b]pyridin-2-yl)phenyl)methyl((tetrahydrofuran-2-yl)methyl)carbamate (77)

To a solution of the trimethyltin compound 9 (1.4 g, 3.06 mmol) (scheme 2) and bromide 70 (2.25 g, 6.11 mmol) (scheme 14, Table 8) in dry toluene (50 ml) was added Pd(PPh$_3$)$_4$ (176 mg, 0.153 mmol). The reaction mixture was refluxed overnight, cooled to room temperature and the solvents were removed under reduced pressure. The resultant solid was triturated with hexane/ether and then purified by column chromatography, eluents EtOAc/Hexane 1:9, then EtOAc:hexane 4:6, to afford title compound 77 as a white solid (1.2 g, 86% yield). MS (m/z): 459.2/461.2 (M+H).

Step 2. tert-Butyl (4-(7-(2-fluoro-4-nitrophenoxy)thieno[3,2-b]pyridin-2-yl)phenyl)methyl((tetrahydrofuran-2-yl)methyl)carbamate (78)

To a solution of 77 (1.0 g, 2.18 mmol) in Ph$_2$O (10 ml) was added 2-fluoro-4-nitrophenol (856 mg, 5.45 mmol) and potassium carbonate (904 mg, 6.55 mmol). The reaction mixture was heated at 180° C. for 4 hrs, cooled to room temperature, diluted with DCM, filtered and concentrated. The residue was purified by column chromatography, eluent EtOAc:hexane 8:2, to afford title compound 78 (250 mg, 20% yield). MS (m/z): 580.3 (M+H).

Steps 3-4. tert-Butyl (4-(7-(2-Fluoro-4-(3-(2-phenylacetyl)thioureido)phenoxy)thieno[3,2-b]pyridin-2-yl)phenyl)methyl((tetrahydrofuran-2-yl)methyl)carbamate (80)

To a solution of 78 (250 mg, 0.431 mmol) in MeOH (10 mL) at 0° C. was added NiCl$_2$×6H$_2$O (205 mg, 0.86 mmol) and NaBH$_4$ (64 mg, 1.72 mmol). The reaction mixture was allowed to stir for 1 hr, concentrated to dryness and the resultant solid was dissolved in 2 M HCl. This solution was then made basic with concentrated aqueous ammonium hydroxide and extracted with DCM. The DCM extract was dried over anhydrous sodium sulfate, filtered and evaporated to form the amine 79 (236 mg, 100% yield), which was used without characterization and further purification.

To a solution of the amine 79 (236 mg, 0.43 mmol) in THF (10 mL) was added 2-phenylacetyl isothiocyanate (114 mg, 6.44 mmol). The reaction mixture was stirred for 1 hr, concentrated and the residue was purified by column chromatography, eluent—gradient from EtOAc:hexane 1:1 to EtOAc, to afford title compound 80 (200 mg, 64% yield) as a white solid. MS (m/z): 725.5 (M+H).

Step 5. 1-(3-Fluoro-4-(2-(4-(((tetrahydrofuran-2-yl)methylamino)methyl)phenyl)thieno[3,2-b]pyridin-7-yloxy)phenyl)-3-(2-phenylacetyl)thiourea (81)

To a solution of 80 (200 mg, 0.28 mmol) in toluene (5 mL), TFA (excess) was added. The reaction mixture was allowed to stir overnight, the solvent was removed under reduced pressure and the remained solid was triturated with diethyl ether to afford title compound 81 as the di-TFA salt (130 mg, 57% yield). $^1$H NMR (DMSO) δ (ppm): 12.47 (s, 1H), 11.83 (s, 1H), 9.06 (s, 2H), 8.53 (dd, J=2.0 and 5.5 Hz, 1H), 8.13 (s, 1H), 8.0 (d, J=12.1 Hz, 1H), 7.97 (d, J=8.7 Hz, 2H), 7.63 (d, J=8.2 Hz, 2H), 7.53 (m, 2H), 7.32 (m, 4H), 7.27 (m, 1H), 6.68 (d, J=5.8 Hz, 1H), 4.23 (m, 1H), 3.82 (s, 2H), 3.78 (m, 1H), 3.71 (m, 1H), 3.11 (m, 1H), 2.95 (m, 1H), 2.0 (m, 1H), 1.98 (m, 2H), 1.56 (m, 1H). MS (m/z) 627.3 (M+H).

Scheme 16a

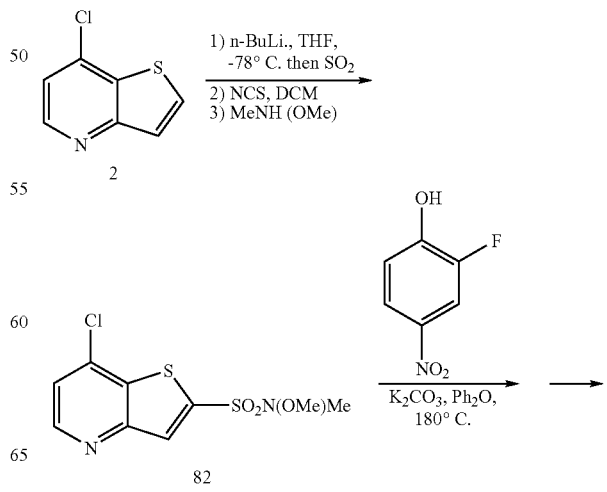

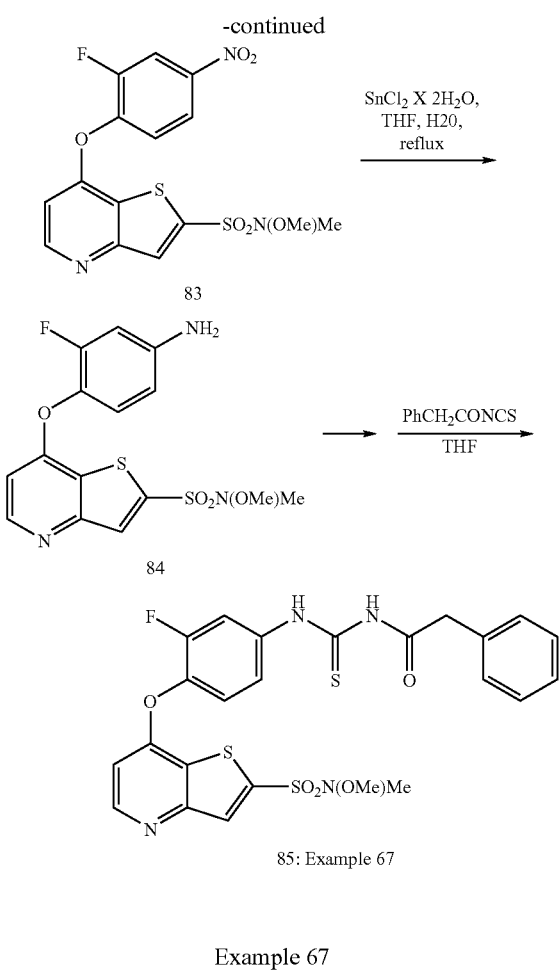

Example 67

7-[2-Fluoro-4-(3-phenylacetyl-thioureido)-phenoxy]-thieno[3,2-b]pyridine-2-sulfonic acid methoxy-methyl-amide (85)

Step 1. 7-Chloro-N-methoxy-N-methylthieno[3,2-b]pyridine-2-sulfonamide (82)

To a solution of chloride 2 (scheme 1) (700 mg, 4.14 mmol) in THF (20 ml) was added n-BuLi (2 ml, 4.97 mmol, 2.5 M solution in hexanes) at −78° C. and the reaction mixture was stirred for 20 mins. $SO_2$-gas was passed over the surface of the solution for 3 hrs at the same temperature, then for an additional hr at 0° C. The reaction mixture was evaporated. DCM (20 ml) and NCS (605 mg, 4.55 mmol) were added and the reaction mixture was stirred at room temperature for 1.5 hrs, filtered through a celite pad and concentrated to produce a pink solid. The solid was dissolved in acetone (20 ml); MeNH(OMe) hydrochloride (608 mg, 6.21 mmol) and triethylamine (627 mg, 6.21 mmol) were added and the reaction mixture was stirred at room temperature overnight. The solvent was removed under reduced pressure and the residue was dissolved in EtOAc. The EtOAc solution was washed with water, dried over anhydrous sodium sulfate, filtered and evaporated. The residue was purified by column chromatography (eluent EtOAc:hexane, 1:1) to afford the title compound 82 (485 mg, 40% yield) as a pink solid. MS (m/z) 561.1 (M+H).

Step 2. 7-(2-Fluoro-4-nitrophenoxy)-N-methoxy-N-methylthieno[3,2-b]pyridine-2-sulfonamide (83)

A mixture of 82 (400 mg, 1.37 mmol), 2-fluoro-4-nitrophenol (321 mg, 2.05 mmol) and $K_2CO_3$ (756 mg, 5.48 mmol) were heated to 190° C. in diphenyl ether (55 ml) for 3 hrs. The mixture was cooled to room temperature, diluted with DCM and filtered. The filtrate was concentrated and purified by column chromatography (eluent EtOAc:hexane, 1:1) to afford title compound 83 (225 mg, 40% yield). MS (m/z) 414.0 (M+H).

Steps 3-4. 7-[2-Fluoro-4-(3-phenylacetyl-thioureido)-phenoxy]-thieno[3,2-b]pyridine-2-sulfonic acid methoxy-methyl-amide (85)

To a solution of the nitro compound 83 (225 mg, 0.54 mmol) in THF (5 ml) and water (2 ml) was added $SnCl_2 \times 2H_2O$ (742 mg, 3.3 mmol). The reaction mixture was refluxed for 3 hrs, diluted with EtOAc and washed with aqueous ammonium hydroxide. The washings were combined and extracted with DCM. Both EtOAc- and DCM-phases were combined, dried over anhydrous sodium sulfate, filtered and evaporated to produce the amine 84 (168 mg, 81% yield), which was used without characterization and further purification.

To a solution of the amine 84 (225 mg, 0.59 mmol) in THF (8 ml) was added phenyl-acetyl isothiocyanate (208 mg, 1.18 mmol). The reaction mixture was stirred for 1 hr, concentrated under reduced pressure and purified by column chromatography (eluent EtOAc) to afford 85 (323 mg, 98% yield) as a white solid. $^1$H NMR (400 MHz, DMSO-$d_6$) δ (ppm): 12.52 (s, 1H), 11.86 (s, 1H), 8.74 (d, J=5.3 Hz, 1H), 8.33 (s, 1H), 8.07 (d, J=13.5 Hz, 1H), 7.61 (m, 2H), 7.36 (m, 4H), 7.29 (m, 1H), 3.86 (s, 3H), 3.84 (s, 2H), 2.96 (s, 3H). MS (m/z): 561.3 (M+H).

Example 68

7-[2-Fluoro-4-(3-phenylacetyl-thioureido)-phenoxy]-thieno[3,2-b]pyridine-2-sulfonic acid amide (86)

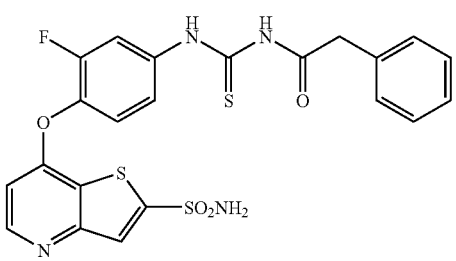

86: Example 68

Title compound 86 was obtained following the procedures described for the compound 85 (example 67, scheme 16) but substituting in the first step O-methyl hydroxylamine for ammonia. $^1$H NMR (400 MHz, DMSO-$d_6$) δ (ppm): 13.82 (s, 1H), 13.15 (s, 1H), 9.98 (m, 1H), 9.4-9.2 (m, 4H), 8.87 (s, 2H), 8.64 (m, 5H), 8.15 (s, 1H), 3.82 (s, 2H). MS (m/z): 517.3 (M+H).

Scheme 17

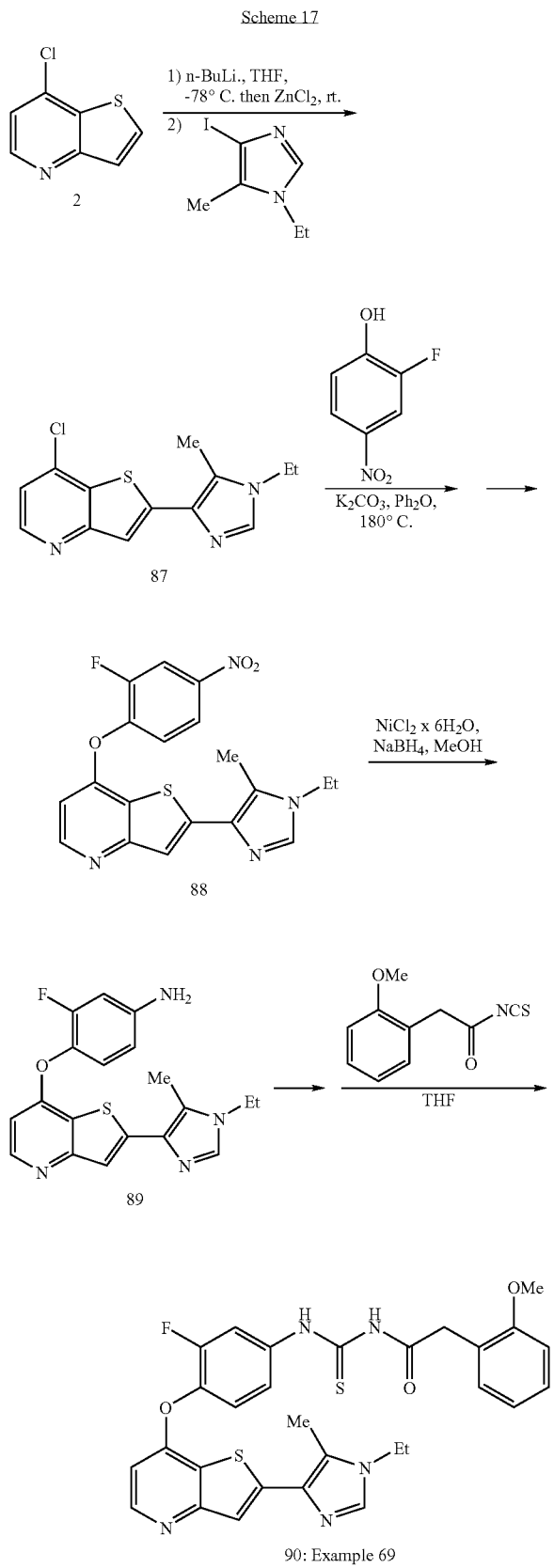

Example 69

1-(4-(2-(1-Ethyl-5-methyl-1H-imidazol-4-yl)thieno[3,2-b]pyridin-7-yloxy)-3-fluorophenyl)-3-(2-(2-methoxyphenyl)acetyl)thiourea (90)

Step 1. 7-Chloro-2-(1-ethyl-5-methyl-1H-imidazol-4-yl)-thieno[3,2-b]pyridine (87)

To a solution of 2 (1.14 g, 6.76 mmol) in THF (60 ml) was added, at −78° C., n-BuLi (3.38 ml, 2.5 M soln in hexanes) and the reaction mixture was stirred at the same temperature for 10 min. A solution of $ZnCl_2$ (16.9 ml, 2.5 ml, 0.5M in THF) was added and the reaction mixture was warmed to room temperature. Then a solution of 1-ethyl-4-iodo-5-methyl-1H-imidazole (800 mg, 3.38 mmol) (Pyne, S. G and Cliff, M. D. *Synthesis* 1994, 681) and $Pd(PPh_3)_4$ (390 mg, 0.34 mmol) in THF (15 ml) were added and the reaction mixture was refluxed for 3 hrs, cooled to room temperature, quenched with conc. ammonium hydroxide solution and made neutral with concentrated aqueous HCl. The neutral solution was extracted with EtOAc, the extract was collected, dried over anhydrous sodium sulfate, and filtered. The filtrate was evaporated and the residue was purified by column chromatography (eluent MeOH:EtOAc, 1:9) to afford the title compound 87 (1.1 g, 100% yield) as a brown oil. MS (m/z) 278.0/280.0 (M+H).

Step 2. 2-(1-Ethyl-5-methyl-1H-imidazol-4-yl)-7-(2-fluoro-4-nitro-phenoxy)-thieno[3,2-b]pyridine (88)

A suspension of 87 (650 mg, 2.35 mmol), potassium carbonate (970 mg, 7.04 mmol) and 2-fluoro-4-nitrophenol (738 mg, 4.7 mmol) were heated at 190° C. in diphenyl ether (15 ml) for 3 hrs. The mixture was cooled to room temperature, diluted with DCM and filtered. The filtrate was concentrated and the residue was purified by column chromatography (eluents EtOAc, then MeOH:EtOAc, 1:9) to afford title compound 88 (600 mg, 64%) as a yellow solid. MS (m/z) 399.0 (M+H).

Steps 3-4. 1-(4-(2-(1-Ethyl-5-methyl-1H-imidazol-4-yl)thieno[3,2-b]pyridin-7-yloxy)-3-fluorophenyl)-3-(2-(2-methoxyphenyl)acetyl)thiourea (90)

To a solution of 88 (200 mg, 0.5 mmol) in MeOH (8 ml) and THF (2 ml) at 0° C. was added $NiCl_2 \times 6H_2O$ (237 mg, 1 mmol) and $NaBH_4$ (74 mg, 2 mmol). The reaction mixture was allowed to stir for 1 hr, concentrated to dryness and the resultant solid was dissolved in 1 M HCl. The acidic solution was then made basic with concentrated aqueous ammonium hydroxide and extracted with EtOAc. The organic phase was collected, dried over anhydrous sodium sulfate and filtered. The solvent was evaporated under reduced pressure and the residue was triturated with $Et_2O$ to afford the crude amine 89 (184 mg, 100% yield) which was used immediately in the next step [without characterization].

To a solution of the amine 89 (180 mg, 0.49 mmol) in THF (10 ml) was added (2-methoxy-phenyl)-acetyl isothiocyanate (200 mg, 0.98 mmol). The reaction mixture was stirred for 10 min, concentrated and the residue was purified by column chromatography (eluents EtOAc, then to MeOH-EtOAc, 1:9), to afford title compound 90 (84 mg, 30% yield) as yellow solid. $^1$H NMR (400 MHz, DMSO-$d_6$) δ (ppm) 12.56 (s, 1H), 11.73 (s, 1H), 8.43 (d, J=5.5 Hz, 1H), 8.04 (d, J=12.3 Hz, 1H), 7.71 (s, 1H), 7.51 (m, 4H), 7.25 (m, 2H), 6.97 (d, J=8.2 Hz, 1H), 6.92 (t, J=7.2 Hz, 1H), 6.97 (d, J=8.2 Hz, 1H), 6.92 (t, J=7.2 Hz, 1H), 6.56 (d, J=5.5 Hz, 1H), 4.0 (q, J=3.2 Hz, 2H), 3.80 (s, 2H), 3.77 (s, 3H), 2.47 (s, 3H), 1.31 (t, J=3.2 Hz, 2H). MS (m/z) 576.1 (M+H).

Scheme 18
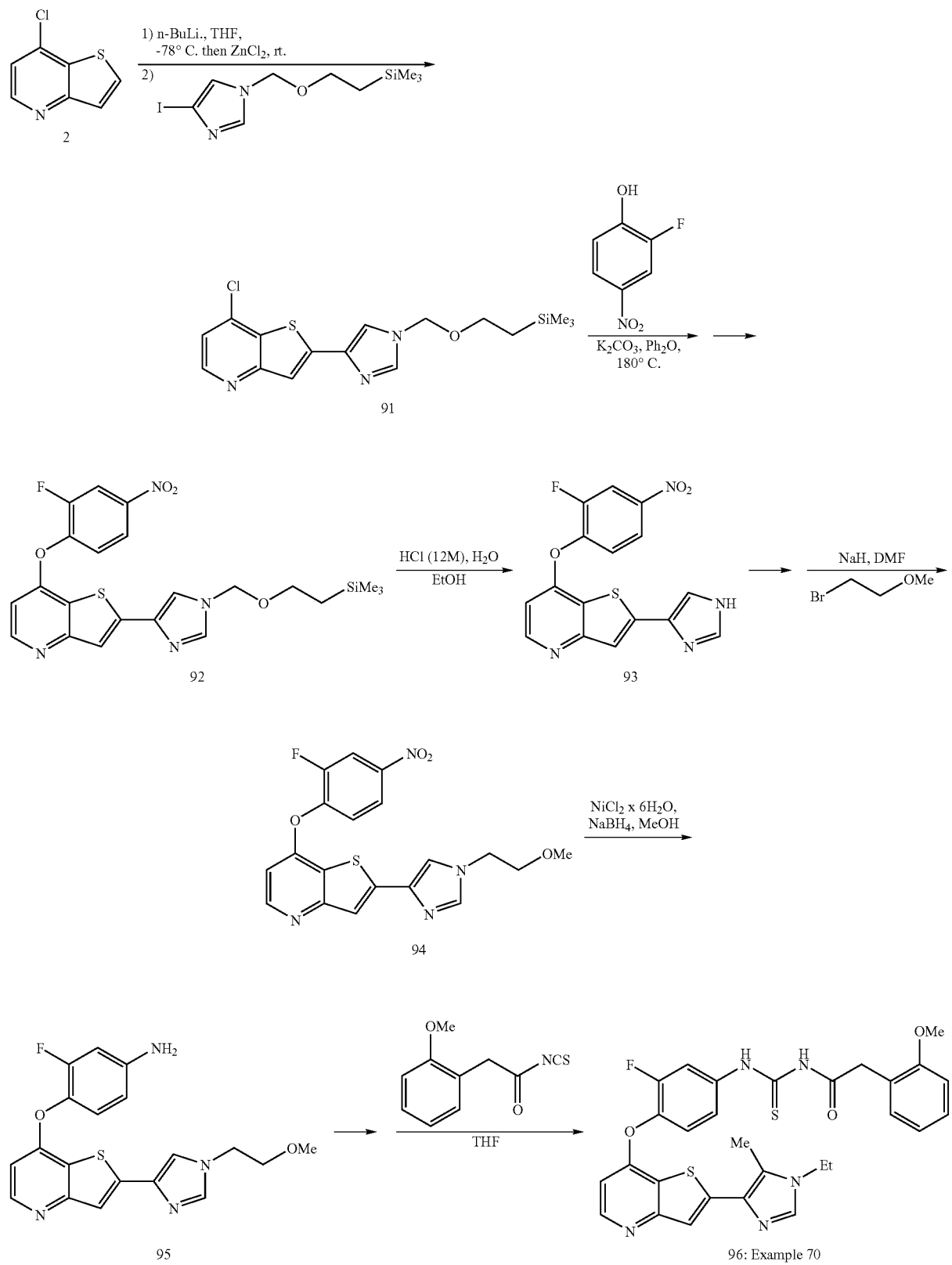

Example 70

N-(3-Fluoro-4-(2-(1-(2-methoxyethyl)-1H-imidazol-4-yl)thieno[3,2-b]pyridin-7-yloxy)phenylcarbamothioyl)-2-(2-methoxyphenyl)acetamide (96)

Step 1. 7-Chloro-2-(1-((2-(trimethylsilyl)ethoxy)methyl)-1H-imidazol-4-yl)thieno[3,2-b]pyridine (91)

To a solution of 2 (9.4 g, 56.0 mmol) in THF (150 ml) at −78° C. was added n-BuLi (28 ml, 70.0 mmol, 2.5 M soln in hexanes) and the reaction mixture was stirred at −78° C. for 45 mins. A solution of $ZnCl_2$ (140 ml, 70.0 mmol, 0.5M in THF) was added and the reaction mixture was warmed to room temperature. To the warmed mixture a solution of 4-iodo-1-(2-trimethylsilanyl-ethoxymethyl)-1H-imidazole [Carl J. Lovey et al, *Tetrahedron Lett.*, 2004, 45(28) 5529-5532] (9.0 g, 28.0 mmol) and $Pd(PPh_3)_4$ (2.5 g, 2.1 mmol) in THF (50 ml) were added. The reaction mixture was heated to reflux for 3 hrs, cooled to room temperature, quenched with aqueous ammonium hydroxide and made neutral with aqueous HCl. The neutral solution was extracted with EtOAc, the organic phase was collected, dried over anhydrous sodium sulfate and filtered. The filtrate was evaporated under reduced pressure and the residue was purified by column chromatography (eluent MeOH-EtOAc, 1:20) to afford the title compound 91 (7.5 g, 73% yield) as a brown oil. MS (m/z) 366.0/368.0 (M+H).

Step 2. 7-(2-Fluoro-4-nitrophenoxy)-2-(1-((2-(trimethylsilyl)ethoxy)methyl)-1H-imidazol-4-yl)thieno[3,2-b]pyridine (92)

A suspension of 91 (4.2 g, 11.5 mmol), potassium carbonate (7.95 g, 57.5 mmol) and 2-fluoro-4-nitrophenol (4.97 g, 31.6 mmol) was heated at 190° C. in diphenyl ether (15 ml) for 4.5 hrs, cooled to room temperature, diluted with DCM and filtered. The filtrate was concentrated under reduced pressure and purified by column chromatography (eluents hexane and acetone/hexane, 45:55) to afford title compound 92 (3.4 mg, 61% yield) as a yellow solid MS (m/z) 487.0 (M+H).

Step 3. 7-(2-Fluoro-4-nitrophenoxy)-2-(1H-imidazol-4-yl)thieno[3,2-b]pyridine (93)

To a suspension of 92 (3.3 g, 6.8 mmol) in EtOH (8 ml) was added concentrated HCl (7 ml) and distilled water (4 ml). The mixture was heated at 80-90° C. for 2.5 h, cooled to room temperature and concentrated under reduced pressure. The remaining residue was subjected to azeotropic distillation with EtOH followed by neutralization with saturated aqueous $NaHCO_3$. The solid that precipitated was filtered and washed with water, and the filtrate was extracted with EtOAc. The solid and EtOAc extract were combined, evaporated under reduced pressure and the residue was collected and dried to afford the title compound 93 (2.4 g, 100% yield) as a yellow solid. MS (m/z) 357.0 (M+H).

Step 4. 7-(2-Fluoro-4-nitrophenoxy)-2-(1-(2-methoxyethyl)-1H-imidazol-4-yl)thieno[3,2-b]pyridine (94)

To a solution of 93 (300 mg, 0.84 mmol) in dry DMF (3 ml) at 0° C. was added NaH (40 mg, 60% dispersion in oil, 1.0 mmol). The mixture was allowed to warm to room temperature over 0.5 h then re-cooled to 0° C. Bromoethylmethyl ether (123 mg, 0.88 mmol) was added and mixture was allowed to warm to room temperature over 20 hours, concentrated and partitioned between EtOAc and water. The EtOAc phase was dried over anhydrous $Na_2SO_4$, filtered, concentrated and purified by column chromatography (eluents hexane and acetone/hexane 75:25) to afford the title compound 94 (126 mg, 36% yield) as a pale yellow solid. MS (m/z) 415.1.0 (M+H).

Step 5. 3-Fluoro-4-(2-(1-(2-methoxyethyl)-1H-imidazol-4-yl)thieno[3,2-b]pyridin-7-yloxy)benzenamine (95)

Following the procedure described above for compound 89 (scheme 17) but replacing the nitro compound 88 with the nitro compound 94, title compound 95 was obtained as a beige solid (23 mg, 100% yield). MS (m/z) 385.2 (M+H).

Step 6. N-(3-Fluoro-4-(2-(1-(2-methoxyethyl)-1H-imidazol-4-yl)thieno[3,2-b]pyridin-7-yloxy)phenylcarbamothioyl)-2-(2-methoxyphenyl)acetamide (96)

Following the procedure described above for the compound 90 (scheme 17) but replacing the amine 89 with the amine 95 and using 2-(2-methoxyphenyl)acetyl isothiocyanate instead of 2-phenylacetyl isothiocyanate, title compound 96 was obtained as a beige solid (6 mg, 17% yield). $^1$H NMR (400 MHz, DMSO-$d_6$) δ (ppm) 12.57 (1H, s), 11.77 (1H, s), 8.53 (1H, d, J=5.48 Hz), 8.08 (1H, d, J=12.03 Hz), 8.02 (1H, s), 7.91 (1H, s), 7.76 (1H, s), 7.59-7.52 (2H, m), 7.28-7.21 (2H, m), 6.98 (1H, d, J=8.22 Hz), 6.91 (1H, d, J=7.44 Hz), 6.71 (1H, d, J=5.67 Hz), 4.21 (2H, t, J=4.89 Hz), 3.80 (2H, s), 3.77 (3H, s), 3.65 (2H, t, J=4.89 Hz), 3.26 (3H, s). MS (m/z) 592.1 (M+H).

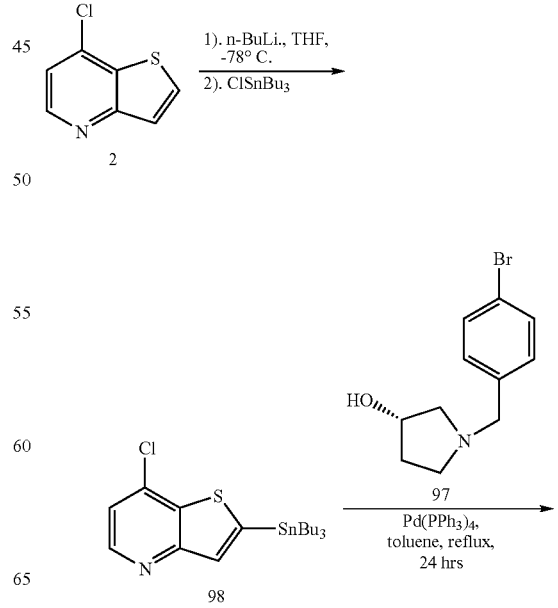

Scheme 19

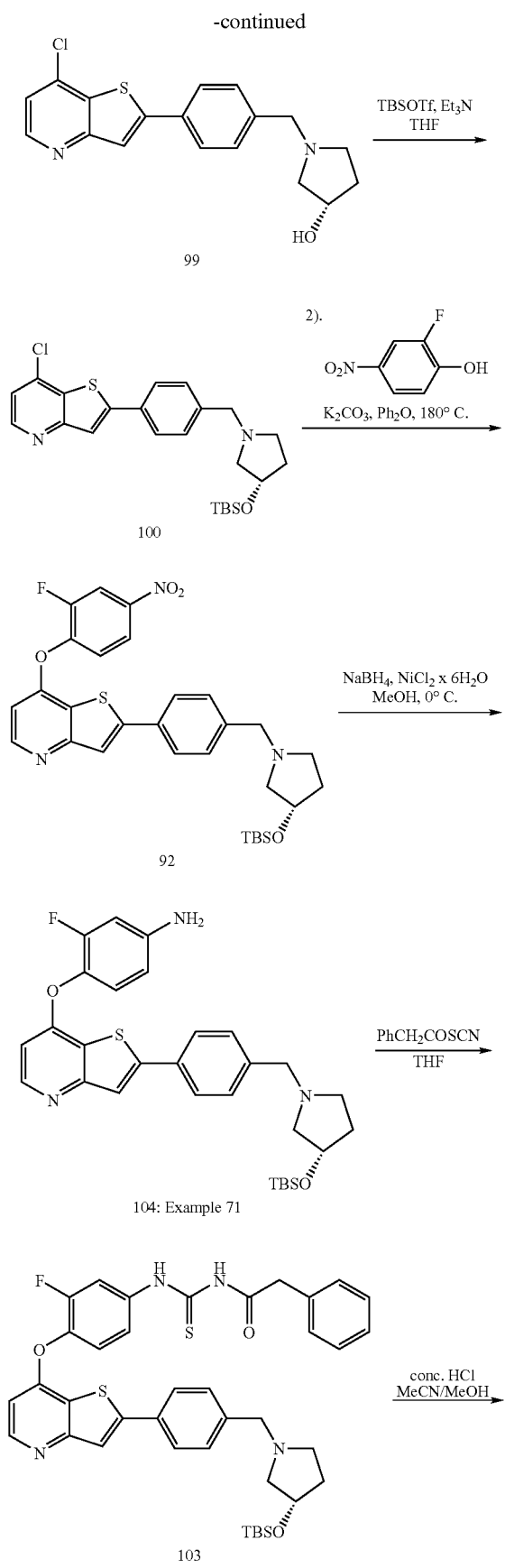

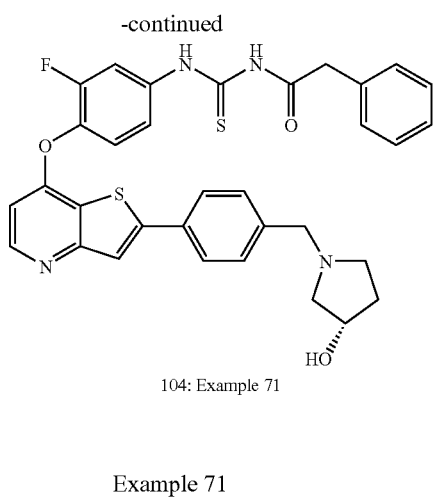

104: Example 71

Example 71

(S)—N-(3-Fluoro-4-(2-(4-((3-hydroxypyrrolidin-1-yl)methyl)phenyl)thieno[3,2-b]pyridin-7-yloxy)phenylcarbamothioyl)-2-phenylacetamide (104)

Step 1. (S)-1-(4-Bromobenzyl)pyrrolidin-3-ol (97)

Title compound 97 was obtained, according to the scheme 14 by reacting (S)-pyrrolidin-3-ol with 3-bromobenzylbromide, as a white solid (1.3 g 63% yield). LRMS 256.1/258.1 (M+1).

Step 2. 7-Chloro-2-(tributylstannyl)thieno[3,2-b]pyridine (98)

To a solution of the chloride 2 (18.72 g, 110 mmol) in THF (200 mL) at −78° C. n-BuLi (51 mL, 127 mmol) was added and the reaction mixture was stirred for about 30 minutes. The tributylchlorostannane (25.4 mL, 93 mmol) was added and the mixture was stirred at −78° C. for another 60 minutes, quenched with water [at the same temperature] and allowed to warm up to room temperature. The warmed mixture was extracted with EtOAc, the extract was dried over anhydrous sodium sulfate, filtered and evaporated under reduced pressure. The residue was purified by flash chromatography, eluents EtOAc-hexane (15:85), then EtOAc-hexane (25:75) to afford title compound 98 (30.2 g, 77% yield) as a yellow oil. LRMS (M+1) 459.1 (100%).

Step 3. (S)-1-(4-(7-Chlorothieno[3,2-b]pyridin-2-yl)benzyl)pyrrolidin-3-ol (99)

To a solution of 98 (2.44 g, 5.30 mmol) and bromide 97 (1.3 g, 5.07 mmol) in dry toluene (30 mL) was added Pd(PPh$_3$)$_4$ (290 mg, 0.25 mmol). The reaction mixture was heated to reflux for 1.5 h, cooled to room temperature and the solvent was removed under reduced pressure. The resultant solid was purified by column chromatography, eluents EtOAc-Hexane (1:1) then MeOH/EtOAc (20:80), to afford title compound 99 (1.24 g, 71% yield) as a white solid. MS (m/z): 345.1/347.1 (M+H).

Step 4. (S)-2-(4-((3-(tert-Butyldimethylsilyloxy) pyrrolidin-1-yl)methyl)phenyl)-7-chlorothieno[3,2-b]pyridine (100)

To a suspension of 99 (0.5 g, 1.45 mmol) in dry THF (7 ml) at 0° C. was added TBDMSOTf (0.5 ml, 2.2 mmol) and the reaction mixture was stirred for 20 min. Et$_3$N (0.61 ml, 4.4 mmol) was added and mixture was stirred at the same conditions for another hour, quenched by the addition of water (~2 ml) and concentrated to dryness. The remained solid was partitioned between EtOAc and water. Organic phase was collected, washed with brine, dried over anhydrous Na$_2$SO$_4$ and concentrated. The residue was purified by column chromatography, eluents EtOAc/hexane (1:1) then MeOH/EtOAc (5:95) to afford title compound 100 (637 mg, 96% yield) as a white solid. MS (m/z): 459.2/461.2 (M+H).

Step 5. (S)-2-(4-((3-(tert-Butyldimethylsilyloxy) pyrrolidin-1-yl)methyl)phenyl)-7-(2-fluoro-4-nitrophenoxy)thieno[3,2-b]pyridine (101)

To a solution of 100 (250.0 mg, 0.54 mmol) in Ph$_2$O (4 ml) was added 2-fluoro-4-nitrophenol (171 mg, 1.1 mmol) and potassium carbonate (304 mg, 2.2 mmol). The reaction mixture was heated to 195° C. for 3 hrs, cooled to room temperature, diluted with DCM, filtered and concentrated. The residue was purified by column chromatography, eluents EtOAc, then MeOH/EtOAc (20-80), to afford title compound 101 (94 mg, 30% yield) as a white solid. MS (m/z): 580.3 (M+H).

Step 6. (S)—N-(4-(2-(4-((3-(tert-Butyldimethylsilyloxy)pyrrolidin-1-yl)methyl)phenyl)thieno[3,2-b]pyridin-7-yloxy)-3-fluorophenylcarbamothioyl)-2-phenylacetamide (103)

To a solution of the nitro compound 101 (90 mg, 0.16 mmol) in MeOH (4 ml) at 0° C. was added NiCl$_2$×6H$_2$O (74 mg, 0.31 mmol) and NaBH$_4$ (23 mg, 0.62 mmol). The reaction mixture was allowed to stir for 1 hr, concentrated to dryness and the resultant solid was dissolved in 2 M HCl. The acidic solution was then made basic with aqueous ammonium hydroxide solution and extracted with EtOAc. The organic extract was dried over anhydrous sodium sulfate, filtered and evaporated to form the amine 102 (80 mg, 95% yield), which was used without further purification and characterization.

To a solution of the amine 102 (80 mg, 0.15 mmol) in THF (2 mL) was added 2-phenylacetyl isothiocyanate (64 mg, 0.36 mmol). The reaction mixture was stirred for 1 hr, concentrated and the residue was purified by column chromatography, eluents EtOAc:hexane (1:1), then EtOAc, to afford title compound 103 (34 mg, 30% yield) as a white solid. MS (m/z): 727.5 (M+H).

Step 7. (S)—N-(3-fluoro-4-(2-(4-((3-hydroxypyrrolidin-1-yl)methyl)phenyl)thieno[3,2-b]pyridin-7-yloxy)phenylcarbamothioyl)-2-phenylacetamide (104)

To a solution of 103 (34 mg, 0.047 mmol) in CH$_3$CN/MeOH (0.5 mL/2.0 mL), concentrated HCl (8 drops) was added and the reaction was allowed to stir 2 h. The solvents were removed under reduced pressure and the resultant solid was triturated with diethyl ether followed by purification by Gilson HPLC preparative system, column Aquasil C18 (25% MeOH in water to 100% MeOH), to afford title compound 104 (2.5 mg, 9% yield), as a white solid. $^1$H NMR (DMSO) δ (ppm): 11.82 (1H, s), 8.51 (1H, d, J=5.28 Hz), 8.23 (1H, s), 8.02-7.98 (2H, m), 7.82 (2H, d, J=7.83 Hz), 7.52 (2H, br), 7.41 (2H, d, J=7.83 Hz), 7.33-7.25 (5H, m), 6.64 (1H, d, J=5.09 Hz), 4.20 (1H, br), 3.83 (2H, s), 3.38 (2H, s), 2.34-2.32 (2H, m), 2.03-1.96 (2H, m), 1.56 (2H, br). MS (m/z) 613.3 (M+H).

Example 72

(S)-1-(4-(7-(2-Fluoro-4-(3-(2-phenylacetyl)thioureido)phenoxy)thieno[3,2-b]pyridin-2-yl)benzyl)pyrrolidine-2-carboxylic acid (106)

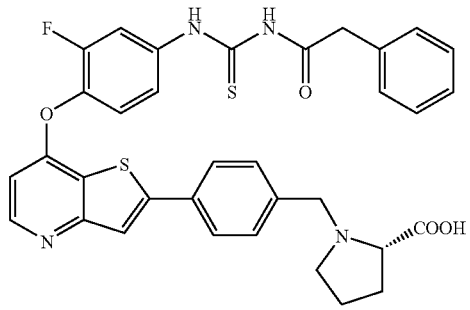

106: Example 72

Step 1. (S)-tert-Butyl 1-(4-bromobenzyl)pyrrolidine-2-carboxylate (105)

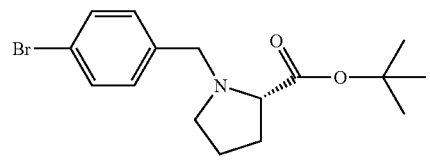

105

Title compound 105 was obtained, according to the scheme 14 by reacting (S)-tert-butyl pyrrolidine-2-carboxylate with 3-bromobenzylbromide, as a white solid (1.62 g, 94% yield). LRMS 340.1/342.1 (M+1).

(S)-1-(4-(7-(2-Fluoro-4-(3-(2-phenylacetyl)thioureido)phenoxy)thieno[3,2-b]pyridin-2-yl)benzyl)pyrrolidine-2-carboxylic acid (106)

Title compound 106 was obtained following the procedures similar to the ones described above for the synthesis of compound 104 (example 71, scheme 19), replacing bromide 97 with the bromide 105 in the second step, skipping the step 4 (TBS-protection) and using in the last step TFA/DCM mixture for tert-butyl ester de-protection. $^1$H NMR (400 MHz, DMSO-d$_6$): δ12.47 (1H, s), 11.82 (1H, s), 8.53 (1H, br), 8.13 (1H, s), 8.01 (1H, d, J=12.91 Hz), 7.96 (2H, d, J=7.02 Hz), 7.60 (2H, d, J=7.63 Hz), 7.54 (2H, br), 7.34-7.27 (5H, m), 6.67 (1H, d, J=5.09 Hz), 4.40 (1H, br), 4.23 (1H, br), 3.83 (2H, s), 3.38 (2H, s), 2.38 (1H, br), 2.00 (2H, br), 1.85 (1H, br). MS (m/z) 641.3 (M+H).

Examples 73-82

Compounds 13i-13r

Following the procedures described above for the synthesis of compound 13a (example 12, scheme 2) but substituting trimethyltin chloride in the step 1 for tributyltin chloride and 2-bromothiazole in the step 2 for heteroaryl bromides shown in the Table 9, title compounds 13i-13r were synthesized. Characterization of compounds 13i-13r (examples 73-82) is provided in the Table 10.

TABLE 9

Heteroaryl bromides used in the synthesis of compounds 13i-13r (examples 73-82)

| Heteroaryl bromide | Preparation |
|---|---|

McCullum, P., et al., Aust. J. Chem. 52(3), 1999, 159-166

McCullum, P., et al., Aust. J. Chem. 52(3), 1999, 159-166

Borai, M. El et al. Pol J. Chem. 55, 1981, 1659 a) Begtrup, M.; Larsen, P.; Acta Chem. Scand. 44, 10; 1990; 1050-1057.
b) Begtrup, M.; Bull. Soc. Chim. Belg.; 97; 8-9; 1988; 573-598.
c) Begtrup, M.; Larsen, P.; Chem. Pharm. Bull. 42, 9; 1994; 1784-& 1790.

a) Begtrup, M.; Larsen, P.; Acta Chem. Scand. 44, 10; 1990; 1050-1057.
b) Begtrup, M.; Bull. Soc. Chim. Belg.; 97; 8-9; 1988; 573-598.
c) Begtrup, M.; Larsen, P.; Chem. Pharm. Bull. 42, 9; 1994; 1784-& 1790.

a) Begtrup, M.; Larsen, P.; Acta Chem. Scand. 44, 10; 1990;
b) Begtrup, M.; Bull. Soc. Chim. Belg.; 97; 8-9; 1988; 573-598.
c) Begtrup, M.; Larsen, P.; Chem. Pharm. Bull. 42, 9; 1994; 1784-& 1790.

TABLE 9-continued

Heteroaryl bromides used in the synthesis of compounds 13i-13r(examples 73-82)

| Heteroaryl bromide | Preparation |
|---|---|

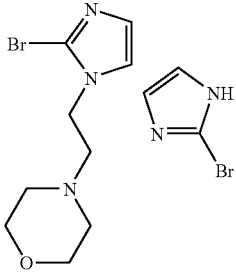

a) Begtrup, M.; Larsen, P.; Acta Chem. Scand. 44, 10; 1990; 1050-1057.
b) Begtrup, M.; Bull. Soc. Chim. Belg.; 97; 8-9; 1988; 573-598.
c) Begtrup, M.; Larsen, P.; Chem. Pharm. Bull. 42, 9; 1994; 1784-& 1790.
d) Reference where BrCN is being used for such a purpose

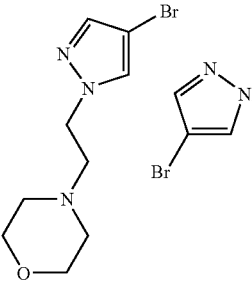

a) Begtrup, M.; Larsen, P.; Acta Chem. Scand. 44, 10; 1990; 1050-1057.
b) Begtrup, M.; Bull. Soc. Chim. Belg.; 97; 8-9; 1988; 573-598.
c) Begtrup, M.; Larsen, P.; Chem. Pharm. Bull. 42, 9; 1994; 1784-& 1790.

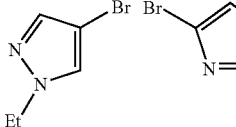

a) Begtrup, M.; Larsen, P.; Acta Chem. Scand. 44, 10; 1990; 1050-1057.
b) Begtrup, M.; Bull. Soc. Chim. Belg.; 97; 8-9; 1988; 573-598.
c) Begtrup, M.; Larsen, P.; Chem. Pharm. Bull. 42, 9; 1994; 1784-& 1790.

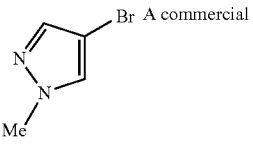 A commercial product

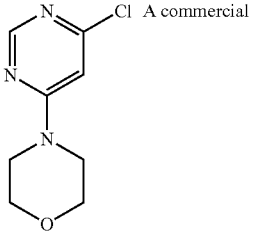 A commercial product

TABLE 10

Characterization of compounds 13i-13r(examples 73-82)

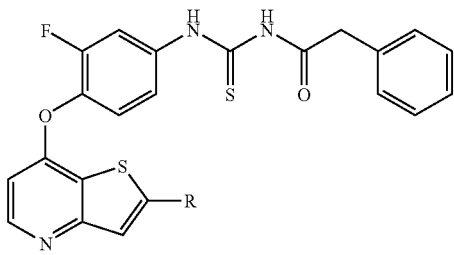

13i-13r: Examples 73-82

| Cpd | Ex | R | Name | Characterization |
|---|---|---|---|---|
| 13i | 73 | (1-Ethyl-imidazol-2-yl, N-Et) | N-(4-(2-(1-Ethyl-1H-imidazol-2-yl)thieno[3,2-b]pyridin-7-yloxy)-3-fluorophenylcarbamothioyl)-2-phenylacetamide | ¹H NMR(400 MHz, DMSO-d₆) δ ppm 12.48(1H, s), 11.81(1H, s), 8.52(1H, d, J=5.09 Hz), 8.02 (1H, d, J=12.13 Hz), 7.82(1H, s), 7.53-7.46(3H, m), 7.34-7.28(5H, m), 7.06(1H, s), 6.68(1H, d, J=5.48 Hz), 4.37(2H, q, J=6.85 Hz), 3.83(2H, s), 1.43(3H, t, J=7.24 Hz) MS(m/z) 532.3 (M + H) |
| 13j | 74 | (1-isopropyl-imidazol-2-yl) | N-(3-Fluoro-4-(2-(1-isopropyl-1H-imidazol-2-yl)thieno[3,2-b]pyridin-7-yloxy)phenylcarbamothioyl)-2-phenylacetamide | ¹H NMR(400 MHz,DMSO-d₆) δ ppm 12.48(1H, s), 11.82(1H, s), 8.53(1H, d, J=5.38 Hz), 8.02 (1H, d, J=12.13 Hz), 7.81(1H, s), 7.60(1H, s), 7.53(2H, d, J=5.28 Hz), 7.34-7.26(5H, m), 7.09(1H, s), 6.68(1H, d, J=5.28 Hz), 4.98 (1H, quintet, J=6.46 Hz), 3.83 (2H, s), 1.49(6H, d, J=6.46 Hz) MS(m/z) 546.3(M + H) |
| 13k | 75 | (4-methyl-triazol-3-yl) | N-(3-Fluoro-4-(2-(4-methyl-4H-1,2,4-triazol-3-yl)thieno[3,2-b]pyridin-7-yloxy)phenylcarbamothioyl)-2-phenylacetamide | ¹H NMR(400 MHz, DMSO-d₆) δ ppm 12.45(1H, s), 11.78(1H, s), 8.56(1H, d, J=5.28 Hz), 8.16(1H, s), 8.02(s, 1H), 7.98(1H, s), 7.52 (2H, s), 7.30-7.21(5H, m), 6.72 (1H, d, J=5.09), 4.16(3H, s), 3.78 (2H, s). MS(m/z) 519.2(M + H) |
| 13l | 76 | (1-methyl-imidazol-4-yl) | N-(3-Fluoro-4-(2-(1-methyl-1H-imidazol-4-yl)thieno[3,2-b]pyridin-7-yloxy)phenylcarbamothioyl)-2-phenylacetamide | ¹H NMR(400 MHz,DMSO-d₆) δ ppm 44(1H, d, J=5.67 Hz), 8.01 (1H, d, J=12.13 Hz), 7.85(1H, s), 7.71(1H, s), 7.68(1H, s), 7.51-7.50 (2H, m), 7.33-7.27(5H, m), 6.57 (1H, d, J=5.48 Hz), 3.83(2H, s), 3.72(3H, s). MS(m/z) 518.2 (M + H) |
| 13m | 77 | (1-Ethyl-imidazol-4-yl) | N-(4-(2-(1-Ethyl-1H-imidazol-4-yl)thieno[3,2-b]pyridin-7-yloxy)-3-fluorophenylcarbamothioyl)-2-phenylacetamide | ¹H NMR(400 MHz,DMSO-d₆) δ ppm 12.50(1H, s), 11.84(1H, s), 8.56(1H, d, J=5.87 Hz), 8.14 (1H, s), 8.11-8.04(2H, m), 7.78 (1H, s), 7.57-7.56(2H, m), 7.35-7.56(5H, m), 6.76(1H, d, J=5.48 Hz), 4.10(2H, q, J=7.24 Hz), 3.84(2H, s), 1.44(3H, t, J=7.24 Hz). MS(m/z) 532.2(M + H) |

TABLE 10-continued

Characterization of compounds 13i-13r(examples 73-82)

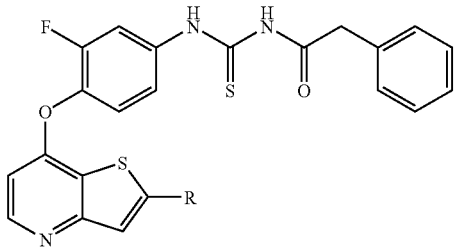

13i-13r: Examples 73-82

| Cpd | Ex | R | Name | Characterization |
|---|---|---|---|---|
| 13n | 78 | (1-(2-morpholinoethyl)-1H-imidazol-2-yl) | N-(3-Fluoro-4-(2-(1-(2-morpholinoethyl)-1H-imidazol-2-yl)thieno[3,2-b]pyridin-7-yloxy)phenylcarbamothioyl)-2-phenylacetamide | $^1$H NMR(400 MHz,DMSO-$d_6$) δ ppm 12.49(1H, s), 11.82(1H, s), 8.52(1H, d, J=5.09 Hz), 8.02 (1H, d, J=11.93 Hz), 7.90(1H, s), 7.54-7.48(3H, m), 7.33-7.24(5H, m), 7.06(1H, s), 6.69(1H, d, J=4.90 Hz), 4.44(2H, s), 3.83 (2H, s), 3.55-3.51(4H, m), 2.71 (2H, s), 2.50(2H, s). MS(m/z) 617.3(M + H) |
| 13o | 79 | (1-(2-morpholinoethyl)-1H-pyrazol-4-yl) | N-(3-Fluoro-4-(2-(1-(2-morpholinoethyl)-1H-pyrazol-4-yl)thieno[3,2-b]pyridin-7-yloxy)phenylcarbamothioyl)-2-phenylacetamide | $^1$H NMR(DMSO) δ(ppm): 12.46 (1H, s), 11.81(1H, s), 8.45(1H, d, J=5.48 Hz), 8.33(1H, s), 8.01-7.99 (2H, m), 7.69(1H, s), 7.51-7.49 (2H, m), 7.34-7.24(5H, m), 6.59 (1H, d, J=5.48 Hz), 4.26(2H, t, J=6.46 Hz), 3.82(2H, s), 3.54(4H, t, J=4.40 Hz), 2.74(2H, t, J=6.46 Hz), 2.42 (4H, br). MS(m/z) 617.3 (M + H). |
| 13p | 80 | (1-Ethyl-1H-pyrazol-4-yl) | N-(4-(2-(1-Ethyl-1H-pyrazol-4-yl)thieno[3,2-b]pyridin-7-yloxy)-3-fluorophenylcarbamothioyl)-2-phenylacetamide | $^1$H NMR(400 MHz, DMSO-$d_6$) δ ppm: 12.49(s, 1H), 11.84(s, 1H), 8.47(d, J=5.6 Hz, 1H), 8.36(s, 1H), 8.02-7.99(m, 2H), 7.70(s, 1H), 7.58-7.51(m, 2H), 7.39-7.32(m, 4H), 7.31-7.25(m, 1H), 6.60(d, J= 5.6 Hz, 1H), 4.18(q, J=7.2 Hz, 2H), 3.83(s, 2H), 1.41(t, J=7.2 Hz, 3H). |
| 13q | 81 | (1-methyl-1H-pyrazol-4-yl) | N-(3-Fluoro-4-(2-(1-methyl-1H-pyrazol-4-yl)thieno[3,2-b]pyridin-7-yloxy)phenylcarbamothioyl)-2-phenylacetamide | $^1$H NMR(400 MHz, DMSO-$d_6$) δ ppm: 12.50(s, 1H), 11.85(s, 1H), 8.47(d, J=5.6 Hz, 1H), 8.31(s, 1H), 8.02(d, J=12.0 Hz, 1H), 7.99(s, 1H), 7.70(s, 1H), 7.55-7.52(m, 2H), 7.38-7.32(m, 4H), 7.31-7.28(m, 1H), 6.60(d, J=5.6 Hz, 1H), 3.89(s, 3H), 3.83(s, 2H). |
| 13r | 82 | (6-morpholinopyrimidin-4-yl) | N-(3-Fluoro-4-(2-(6-morpholinopyrimidin-4-yl)thieno[3,2-b]pyridin-7-yloxy)phenylcarbamothioyl)-2-phenylacetamide | $^1$H NMR(400 MHz, DMSO-$d_6$) δ ppm: 12.48(s, 1H), 11.82(s, 1H), 8.60(s, 1H), 8.56(d, J=5.6 Hz, 1H), 8.55(s, 1H), 8.03(d, J=12.0 Hz, 1H), 7.66(s, 1H), 7.58-7.52(m, 2H), 7.37-7.31(m, 4H), 7.31-7.24(m, 1H), 6.70(d, J=5.6 Hz, 1H), 3.82(s, 2H), 3.78-3.68(m, 8H). |

Scheme 20

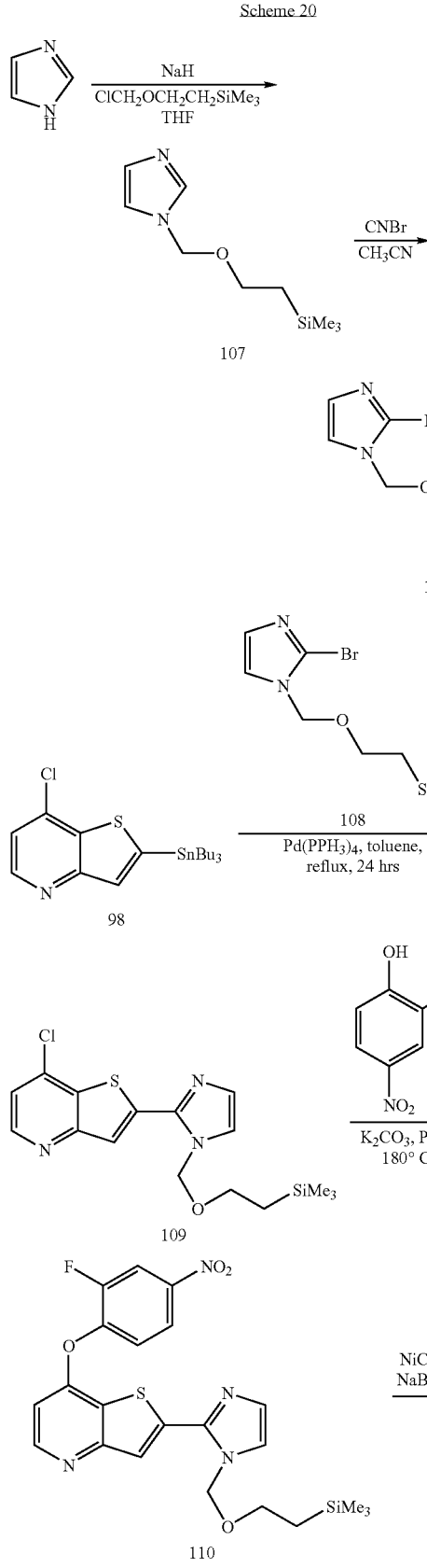

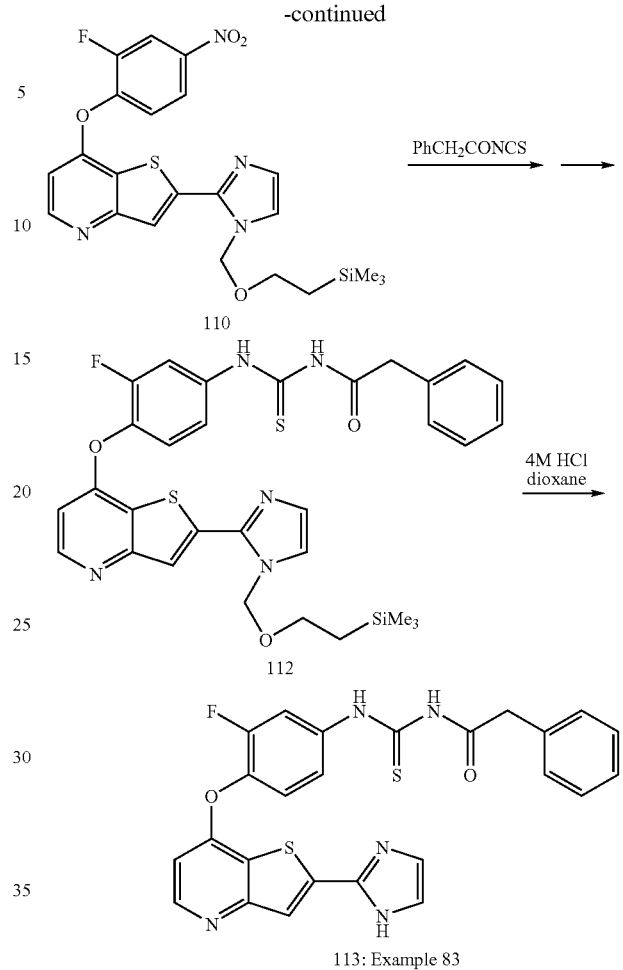

113: Example 83

Example 83

N-(4-(2-(1H-Imidazol-2-yl)thieno[3,2-b]pyridin-7-yloxy)-3-fluorophenylcarbamothioyl)-2-phenylacetamide (113)

Step 1. 1-((2-(Trimethylsilyl)ethoxy)methyl)-1H-imidazole (107)

To a stirred suspension of NaH (60% dispersion in oil, 0.65 g, 16.2 mmol) at 0° C. was added imidazole (1 g, 14.7 mmol) in THF (14 mL). The mixture was warmed to room temperature over 30 min, then re-cooled to 0° C. followed by an addition of (2-(chloromethoxy)ethyl)trimethylsilane (2.73 ml, 15.4 mmol). The combined mixture was warmed to room temperature over 1 h, quenched with saturated aqueous ammonium chloride, concentrated to dryness and partitioned between water and EtOAc. Organic phase was collected, dried over anhydrous sodium sulfate, filtered and evaporated. The residue was purified by column chromatography (eluents EtOAc, then MeOH/EtOAc 20:80), to afford the title compound (2.04 g, 70% yield) as a white solid. MS (m/z) 199.3 (M+H).

Step 2. 2-Bromo-1-((2-(trimethylsilyl)ethoxy)methyl)-1H-imidazole (108)

To a solution of 107 (100 mg, 0.50 mmol) in acetonitrile (1 mL) at room temperature was added cyanogen bromide (107 mg, 1.0 mmol) and the mixture was allowed to stir at room temperature for 3 h, concentrated to dryness and partitioned between EtOAc and water. The organic phase was collected, dried over anhydrous sodium sulfate and concentrated to dryness. The residue was purified by column chromatography (eluents EtOAc/hexane 25:75, then EtOAc), to afford the title compound 108 (45 mg, 32% yield) as a colorless oil. MS (m/z) 277.0/279.0 (M+H).

Step 3. 7-Chloro-2-(1-((2-(trimethylsilyl)ethoxy)methyl)-1H-imidazol-2-yl)thieno[3,2-b]pyridine (109)

Starting from the compound 98 (scheme 19) and following the procedure described above for the synthesis of compound 10 (example 12, scheme 2) but substituting 2-bromothiazole in the step 2 for the bromide 108, title compound 109 was obtained as a white solid (22 mg, 41% yield). MS (m/z) 366.1/368.1 (M+H).

Step 4. 7-(2-Fluoro-4-nitrophenoxy)-2-(1-((2-(trimethylsilyl)ethoxy)methyl)-1H-imidazol-2-yl)thieno[3,2-b]pyridine (110)

Following the procedure described above for the synthesis of compound 11 (example 12, step 3, scheme 2) but substituting compound 10 for compound 109, title compound 110 was obtained as a yellow solid (104 mg, 50% yield). MS (m/z) 487.3 (M+H).

Steps 5-6. N-(3-Fluoro-4-(2-(1-((2-(trimethylsilyl)ethoxy)methyl)-1H-imidazol-2-yl)thieno[3,2-b]pyridin-7-yloxy)phenylcarbamothioyl)-2-phenylacetamide (112)

Following the procedure described above for the synthesis of compound 13a (example 12, steps 4-5, scheme 2) but substituting compound 11 for compound 110 and using intermediate amine 111 (instead of amine 12), title compound 112 was obtained as a beige solid (48 mg, 33% yield). MS (m/z) 634.3 (M+H).

Step 7. N-(4-(2-(1H-Imidazol-2-yl)thieno[3,2-b]pyridin-7-yloxy)-3-fluorophenylcarbamothioyl)-2-phenylacetamide (113)

A solution of 112 (21 mg, 0.033 mmol) in 4N HCl in dioxane (3.5 mL) was allowed to stir at 55° C. for 1 h. The mixture was then cooled and solvent was removed under reduced pressure. The resultant gum was triturated with ether several times to form a solid material that was dried under high vacuum to afford the product 113 as a beige solid (5 mg, 28% yield). $^1$H NMR (400 MHz, DMSO-$d_6$) δ ppm 12.50 (1H, s), 11.84 (1H, s), 8.66 (1H, d, J=5.67 Hz), 8.39 (1H, s), 8.06 (1H, d, J=12.72 Hz), 7.68 (2H, s), 7.59-7.58 (2H, m), 7.36-7.30 (5H, m), 6.86 (1H, d, J=5.48 Hz), 3.83 (2H, s). MS (m/z) 504.1 (M+H).

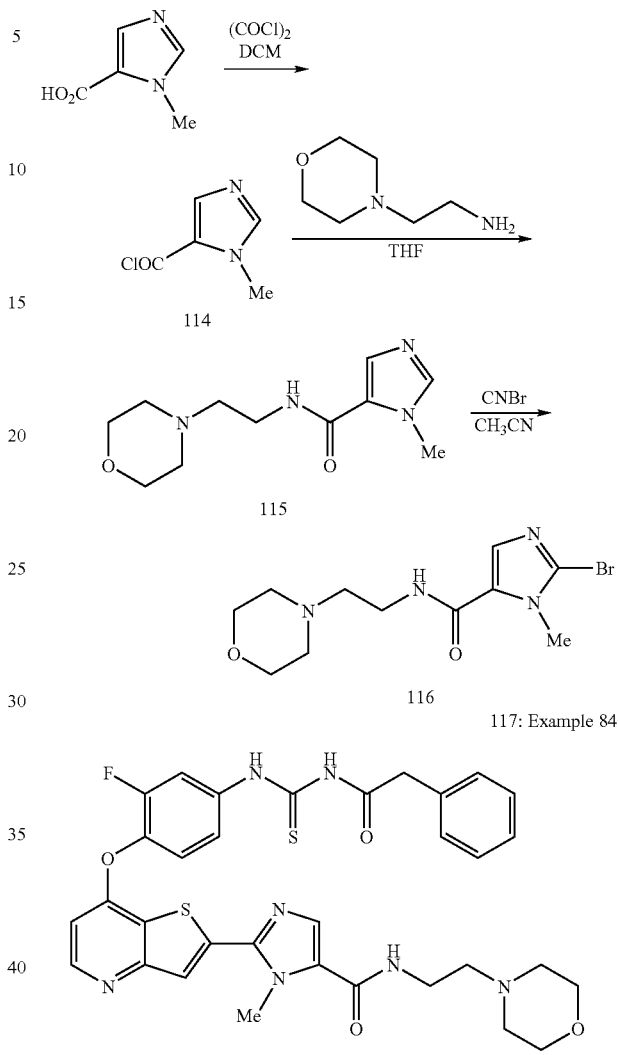

Example 84

2-(7-(2-Fluoro-4-(3-(2-phenylacetyl)thioureido)phenoxy)thieno[3,2-b]pyridin-2-yl)-1-methyl-N-(2-morpholinoethyl)-1H-imidazole-5-carboxamide (117)

Step 1. 1-Methyl-N-(2-morpholinoethyl)-1H-imidazole-5-carboxamide (115)

To a suspension of 1-methyl-1H-imidazole-5-carboxylic acid (0.92 g, 7.3 mmol) [Rapoport, H.; et al.; *Synthesis* 1988; 767.] in dichloromethane (10 ml), was added oxalyl chloride (2.6 ml, 29.2 mmol) and the reaction mixture was heated to reflux for 1 h, cooled, concentrated to dryness to form acid chloride 114 (1.05 g, 100%) which was used without characterization and further purification.

To a suspension of the acid chloride 114 (1.05 g, 7.3 mmol) in THF (10 mL) was added 2-morpholinoethanamine (2.38 g, 18.5 mmol). The mixture was stirred at room temperature for 1 h, concentrated to dryness and the residue was purified by column chromatography (eluent chloroform/MeOH/ammonium hydroxide, 100:2:0.5), to afford the title compound 115 (551 mg, 32% yield) as a white solid. MS (m/z) 239.1 (M+H).

Step 2. 2-Bromo-1-methyl-N-(2-morpholinoethyl)-1H-imidazole-5-carboxamide (116)

To a solution of 115 (550 mg, 2.31 mmol) in acetonitrile (5 mL) was added cyanogen bromide (489 mg, 4.6 mmol). The reaction flask was covered with aluminum foil and the mixture was allowed to stir at room temperature for 18 h. The solvent was removed under reduced pressure and the residue was purified by column chromatography (eluents 100% EtOAc to 30% MeOH/EtOAc), to afford title compound 116 as a beige solid (230 mg (31%). MS (m/z) 317.1/319.1 (M+H).

Step 3. 2-(7-(2-Fluoro-4-(3-(2-phenylacetyl)thioureido)phenoxy)thieno[3,2-b]pyridin-2-yl)-1-methyl-N-(2-morpholinoethyl)-1H-imidazole-5-carboxamide (117)

Following the procedures described above for the synthesis of compound 13a (example 12, scheme 2) but substituting trimethyltin chloride in the step 1 for tributyltin chloride and 2-bromothiazole in the step 2 for the bromide 116, title compound 117 was synthesized. $^1$H NMR (400 MHz, DMSO-$d_6$) δ ppm 8.55 (1H, d, J=5.28 Hz), 8.47 (1H, br), 8.04 (1H, s), 7.97 (1H, d, J=12.52 Hz), 7.67 (1H, s), 7.49 (2H, br), 7.33-7.32 (4H, m), 7.26 (1H, m), 6.70 (1H, d, J=5.09 Hz), 4.18 (3H, s), 3.84 (2H, s), 3.57 (4H, br), 2.47-2.33 (8H, m). MS (m/z) 674.3 (M+H).

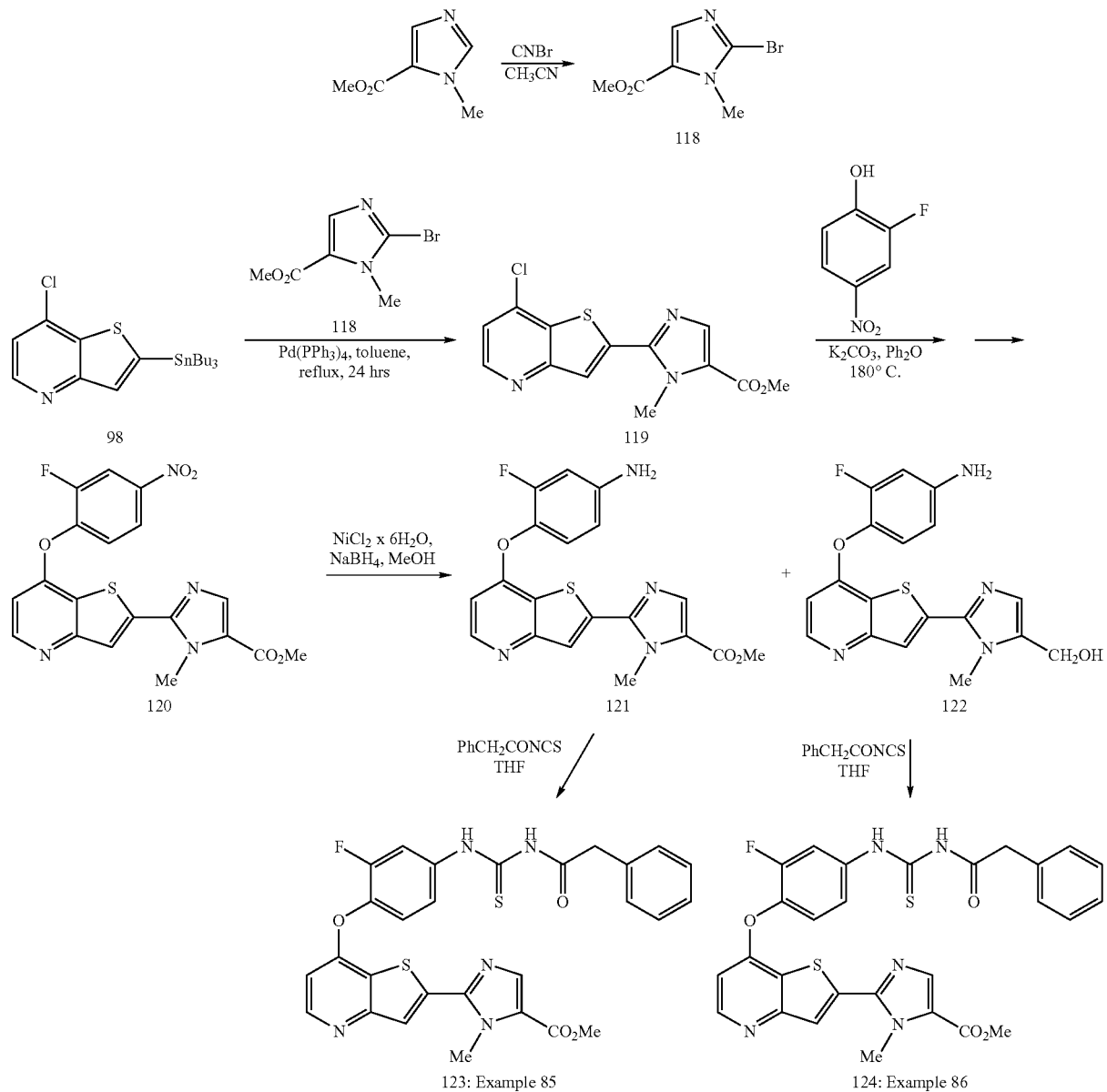

Examples 85 and 86

Methyl 2-(7-(2-fluoro-4-(3-(2-phenylacetyl)thioureido)phenoxy)thieno[3,2-b]pyridin-2-yl)-1-methyl-1H-imidazole-5-carboxylate (123), and N-(3-Fluoro-4-(2-(5-(hydroxymethyl)-1-methyl-1H-imidazol-2-yl)thieno[3,2-b]pyridin-7-yloxy)phenylcarbamothioyl)-2-phenylacetamide (124)

Step 1. Methyl 2-bromo-1-methyl-1H-imidazole-5-carboxylate (118)

Following the procedure described above for the compound 116 (scheme 21) but replacing compound 115 with methyl 1-methyl-1H-imidazole-5-carboxylate, title compound 118 was obtained as a beige solid (373 mg, 49% yield). MS (m/z) 219.1/221.1 (M+H).

Step 2. Methyl 2-(7-chlorothieno[3,2-b]pyridin-2-yl)-1-methyl-1H-imidazole-5-carboxylate (119)

Starting from the compound 98 (scheme 19) and following the procedure described above for the synthesis of compound 10 (example 12, scheme 2) but substituting 2-bromothiazole in the step 2 for the bromide 118, title compound 119 was obtained as a white solid (580 mg, 100% yield). MS (m/z) 308.1/310.0 (M+H).

Step 3. Methyl 2-(7-(2-fluoro-4-nitrophenoxy)thieno[3,2-b]pyridin-2-yl)-1-methyl-1H-imidazole-5-carboxylate (120)

Following the procedure described above for the synthesis of compound 11 (example 12, step 3, scheme 2) but substituting compound 10 for compound 119, title compound 120 was obtained as a yellow solid (254 mg, 31% yield). MS (m/z) 429.1 (M+H).

Step 4. Methyl 2-(7-(4-amino-2-fluorophenoxy)thieno[3,2-b]pyridin-2-yl)-1-methyl-1H-imidazole-5-carboxylate (121) and (2-(7-(4-amino-2-fluorophenoxy)thieno[3,2-b]pyridin-2-yl)-1-methyl-1H-imidazol-5-yl)methanol (122)

Following the procedure described above for the synthesis of compound 12 (example 12, step 4, scheme 2) but substituting compound 11 for compound 120, title compounds 121 and 122 were obtained as white solids (39 mg, 21% yield and 56 mg, 32% yield). MS (m/z) 399.1 (M+H) and MS (m/z) 371.1 (M+H) respectively.

Step 5. Methyl 2-(7-(2-fluoro-4-(3-(2-phenylacetyl)thioureido)phenoxy)thieno[3,2-b]pyridin-2-yl)-1-methyl-1H-imidazole-5-carboxylate (123)

Following the procedure described above for the synthesis of compound 13a (example 12, step 3, scheme 2) but substituting compound 12 for compound 121, title compound 123 was obtained as a beige solid (35 mg, 63% yield). $^1$H NMR (400 MHz, DMSO-$d_6$) δ ppm 12.48 (1H, s), 11.82 (1H, s), 8.58 (1H, dd, 5.48, 0.98 Hz), 8.13 (1H, d, J=0.98 Hz), 8.03 (1H, d, J=12.52 Hz), 7.81 (1H, d, J=1.17 Hz), 7.55-7.54 (2H, m), 7.36-7.31 (4H, m), 7.27 (1H, m), 6.74 (1H, d, J=5.48 Hz), 4.21 (3H, s), 3.83 (3H, s), 3.83 (2H, s). MS (m/z) 576.2 (M+H).

Step 5a. N-(3-Fluoro-4-(2-(5-(hydroxymethyl)-1-methyl-1H-imidazol-2-yl)thieno[3,2-b]pyridin-7-yloxy)phenylcarbamothioyl)-2-phenylacetamide (124)

Following the procedure described above for the synthesis of compound 13a (example 12, step 3, scheme 2) but substituting compound 12 for compound 122, title compound 124 was obtained as a beige solid (32 mg, 39% yield). $^1$H NMR (400 MHz, DMSO-$d_6$) δ ppm 12.48 (1H, s), 11.82 (1H, s), 8.58 (1H, dd, 5.48, 0.98 Hz), 8.13 (1H, d, J=0.98 Hz), 8.03 (1H, d, J=12.52 Hz), 7.81 (1H, d, J=1.17 Hz), 7.55-7.54 (2H, m), 7.36-7.31 (4H, m), 7.27 (1H, m), 6.74 (1H, d, J=5.48 Hz), 4.21 (3H, s), 3.83 (3H, s), 3.83 (2H, s). MS (m/z) 576.2 (M+H).

Scheme 23

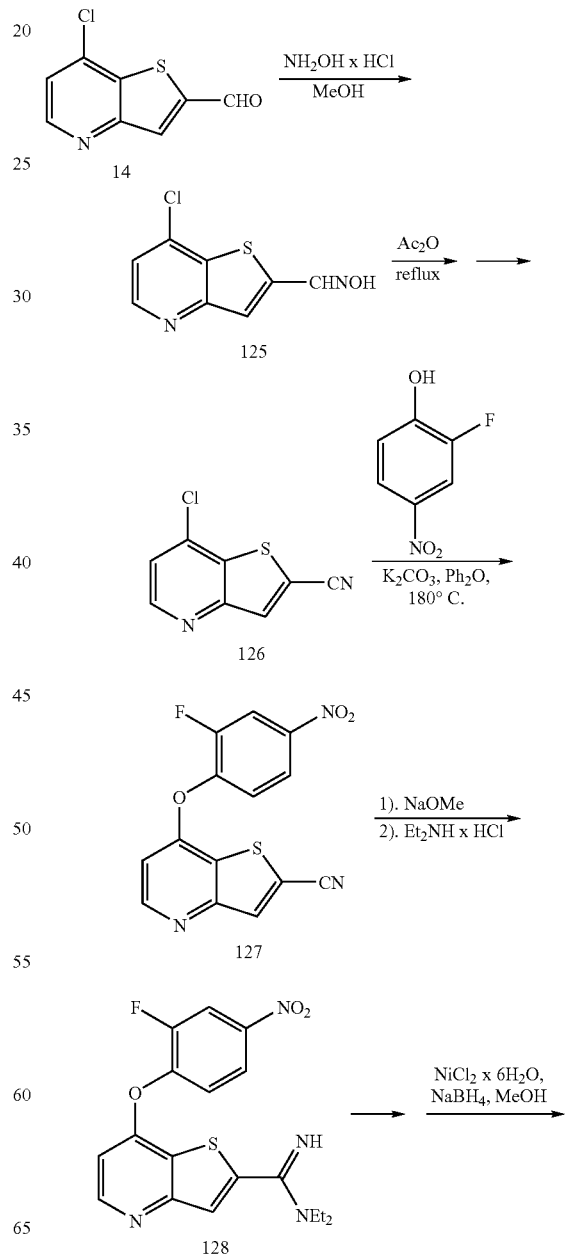

-continued

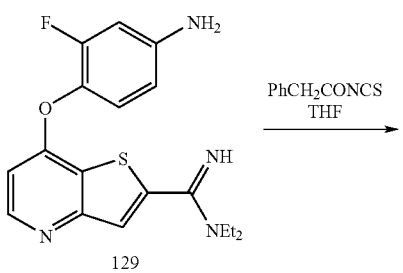

129

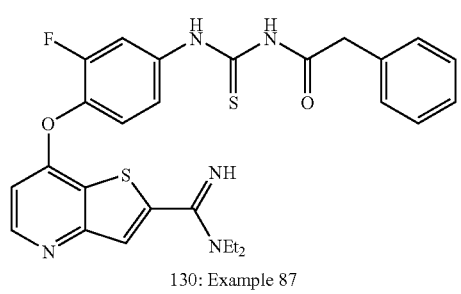

130: Example 87

Example 87

N-(4-(2-(N,N-Diethylcarbamimidoyl)thieno[3,2-b]pyridin-7-yloxy)-3-fluorophenylcarbamothioyl)-2-phenylacetamide (130)

Step 1. 7-Chlorothieno[3,2-b]pyridine-2-carbaldehyde oxime (125)

To a solution of aldehyde 14 (scheme 3) in MeOH was added NH$_2$OH×HCl (227 mg, 3.26 mmol) in water (0.5 mL) and the mixture was stirred at room temperature for 0.5 h. The solvents were removed by under reduced pressure and the residue was partitioned between EtOAc and water. The organic phase was dried over anhydrous sodium sulfate, filtered and evaporated to dryness to afford the title compound 125 (458 mg, 85% yield) as a white solid. MS (m/z) 213.1/215.1 (M+H).

Step 2. 7-Chlorothieno[3,2-b]pyridine-2-carbonitrile (126)

A solution of the oxime 125 (100 mg, 0.47 mmol) in acetic anhydride (2 ml) was set to reflux for 3 h and then at 90° C. for 48 h. The acetic anhydride was removed under reduced pressure and the residue was partitioned between a cold aqueous K$_2$CO$_3$ solution and EtOAc. The organic phase was dried over anhydrous sodium sulfate, concentrated to dryness and remained solid was purified by column chromatography, eluents 25% EtOAc/hexane (25:75), then 100% EtOAc, to afford the title compound 126 (65 mg, 71% yield). MS (m/z) 195.1/197.1 (M+H).

Step 3. 7-(2-Fluoro-4-nitrophenoxy)thieno[3,2-b]pyridine-2-carbonitrile (127)

Following the procedure described above for the synthesis of compound 11 (example 12, step 3, scheme 2) but substituting compound 10 for compound 126, title compound 127 was obtained as a yellow solid (114 mg, 60% yield). MS (m/z) 316.0 (M+H).

Step 4. N,N-Diethyl-7-(2-fluoro-4-nitrophenoxy)thieno[3,2-b]pyridine-2-carboximidamide (128)

To a solution of nitrile 127 (116 mg, 0.37 mmol) in MeOH (3 mL) was added NaOMe (25% in MeOH, 0.09 ml, 0.39 mmol) and the mixture was allowed to stir at room temperature for 18 h. Subsequently, Et$_2$NH×HCl (1.01 g, 9.25 mmol) was added and the mixture was heated to reflux for 12 h., cooled to room temperature and the solvent was removed under reduced pressure. The residue was partitioned between EtOAc and saturated aqueous ammonium chloride, the organic phase was dried over anhydrous sodium sulfate, filtered and concentrated to dryness. The remained solid was purified by column chromatography (eluents EtOAc then CHCl$_3$/MeOH/NH$_4$OH 44:5:0.5), to afford the title compound 128 (30 mg, 21% yield) as a white solid. MS (m/z) 389.2 (M+H).

Steps 4-5. N-(4-(2-(N,N-Diethylcarbamimidoyl)thieno[3,2-b]pyridin-7-yloxy)-3-fluorophenylcarbamothioyl)-2-phenylacetamide (130)

Following the procedure described above for the synthesis of compound 13a (example 12, steps 4-5, scheme 2) but substituting compound 11 for compound 128 and using intermediate amine 129 (instead of amine 12), title compound 130 was obtained as a beige solid (5 mg, 13% yield). $^1$H NMR (DMSO) δ (ppm): 8.58 (1H, d, J=5.48 Hz), 8.29 (1H, s), 8.02 (1H, d, J=11.35 Hz), 7.81 (1H, d, J=2.54 Hz), 7.53 (2H, br), 7.34-7.33 (5H, m), 6.74 (1H, d, J=5.28 Hz), 3.83 (2H, s), 3.40 (4H, q, J=6.91 Hz), 1.16 (6H, t, J=6.95 Hz). MS (m/z) 536.2 (M+H).

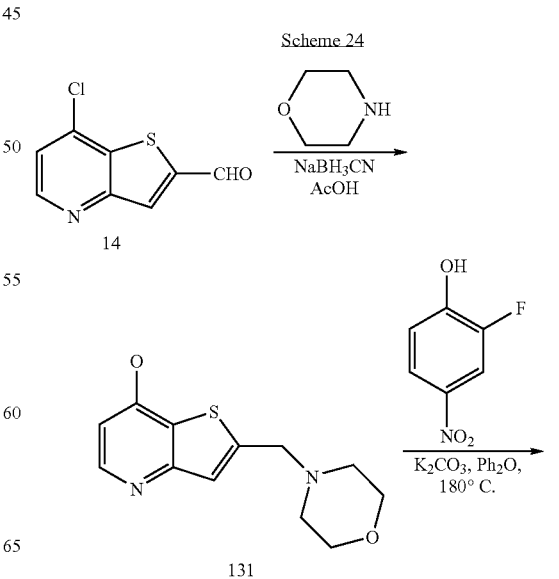

Scheme 24

131

-continued

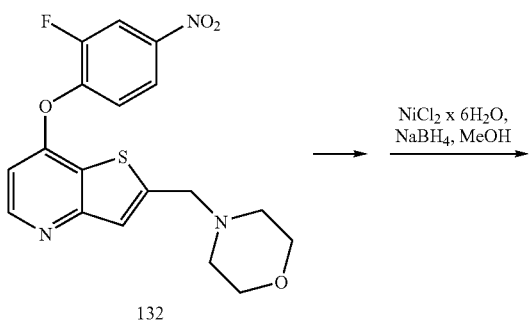

132

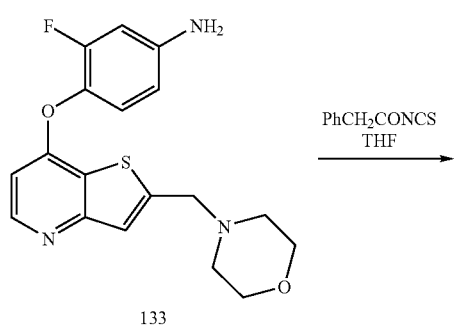

133

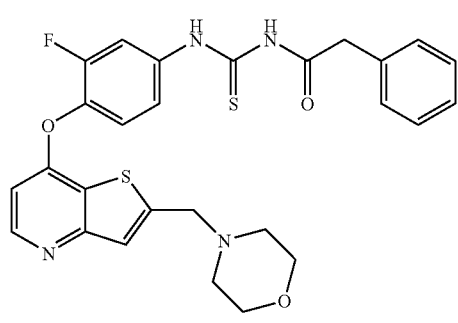

134: Example 88

Example 88

N-(3-Fluoro-4-(2-(morpholinomethyl)thieno[3,2-b] pyridin-7-yloxy)phenylcarbamothioyl)-2-phenylacetamide (134)

Step 1. 4-((7-Chlorothieno[3,2-b]pyridin-2-yl)methyl)morpholine (131)

To a solution of aldehyde 14 (scheme 3) (316 mg, 1.6 mmol) and morpholine (0.15 ml, 1.52 mmol) in MeOH (20 mL) was added acetic acid (0.88 ml, 15 mmol), followed by sodium cyanoborohydride (105 mg, 1.67 mmol). The resultant mixture was allowed to stir for 18 h, quenched with saturated aqueous potassium carbonate solution (5 mL), evaporated under reduced pressure and the residue was partitioned between EtOAc and water. The organic phase was dried over anhydrous sodium sulfate, concentrated to dryness and the remained solid was purified by column chromatography, eluents EtOAc/hexane (30:70), then MeOH/EtOAc (1:99), to afford the title compound 131 (120 mg, 29% yield). MS (m/z) 269.0/271.0 (M+H).

Step 2. 4-((7-(2-Fluoro-4-nitrophenoxy)thieno[3,2-b] pyridin-2-yl)methyl)morpholine (132)

Following the procedure described above for the synthesis of compound 11 (example 12, step 3, scheme 2) but substituting compound 10 for compound 131, title compound 132 was obtained as a yellow solid (110 mg, 69% yield). MS (m/z) 390.1 (M+H).

Steps 3-4. N-(3-Fluoro-4-(2-(morpholinomethyl) thieno[3,2-b]pyridin-7-yloxy)phenylcarbamothioyl)-2-phenylacetamide (134)

Following the procedure described above for the synthesis of compound 13a (example 12, steps 4-5, scheme 2) but substituting compound 11 for compound 132 and using intermediate amine 133 (instead of amine 12), title compound 134 was obtained as a white solid (38 mg, 27% yield). $^1$H NMR (DMSO) δ (ppm): 12.89 (1H, s), 12.24 (1H, s), 8.87 (1H, d, J=4.71 Hz), 8.42 (1H, d, J=12.13 Hz), 7.95-7.88 (3H, m), 7.76-7.68 (5H, m), 7.00 (1H, d, J=5.28 Hz), 4.26-4.25 (4H, m), 4.02 (4H, br), 3.76 (2H, s), 2.90 (2H, s). MS (m/z) 537.2 (M+H).

Examples 89-92

(S)-tert-Butyl 1-(7-(2-fluoro-4-(3-(2-phenylacetyl)thioureido)phenoxy)thieno[3,2-b]pyridine-2-carbonyl)pyrrolidine-2-carboxylate (135a)

(R)-tert-Butyl 3-((7-(2-fluoro-4-(3-(2-phenylacetyl)thioureido)phenoxy)thieno[3,2-b]pyridine-2-carboxamido)methyl)pyrrolidine-1-carboxylate (135b)

(R)—N-(4-(2-(3-(Dimethylamino)pyrrolidine-1-carbonyl) thieno[3,2-b]pyridin-7-yloxy)-3-fluorophenylcarbamothioyl)-2-phenylacetamide (135c), and N-(3-Fluoro-4-(2-(piperidine-1-carbonyl)thieno[3,2-b]pyridin-7-yloxy)phenylcarbamothioyl)-2-phenylacetamide (135d)

Compounds 135a-d (examples 89-92) were obtained following the procedures described above for the synthesis of compound 8a (example 1, scheme 1). Characterization of 135a-d is provided in Table 11.

TABLE 11

Characterization of compounds 135a-d (examples 89-92)

135 a-d: Examples 89-92

| Cpd | Ex | R | Name | Characterization |
|---|---|---|---|---|
| 135a | 89 | (tert-butyl pyrrolidine-2-carboxylate, S) | (S)-tert-Butyl 1-(7-(2-fluoro-4-(3-phenylacetyl)thioureido)phenoxy)thieno[3,2-b]pyridine-2-carbonyl)pyrrolidine-2-carboxylate | $^1$H NMR(400 MHz, DMSO-$d_6$) δ ppm: 12.48(s, 1H), 11.82(s, 1H), 8.61(d, J=5.6 Hz, 0.7H), 8.58(d, J=5.6 Hz, 0.3H), 8.10(s, 0.7H), 8.03(bd, J=12.0 (2Hz, 1H), 7.86(s, 0.3H), 7.57-7.51(m, 2H), 7.47-7.20(m, 5H), 6.77(d, J=5.6 Hz, 0.7H), 6.75(d, J=5.6 Hz, 0.3H), 5.02-4.97(m, 0.3H), 4.20(dd, J=3.2 and 8.4 Hz, 0.7H), 3.97(t, J=6.8 Hz, 1.4H), 3.82(s, 1.4H), 3.80(t, J=6.8 Hz, 0.6H), 3.55(s, 0.6H), 2.3-1.10(m, 5H), 1.41(s, 6.3H), 1.19(s, 2.7H). |
| 135b | 90 | (N-Boc pyrrolidine-3-yl aminomethyl, R) | (R)-tert-Butyl 3-((7-(2-fluoro-4-(3-(2-phenylacetyl)thioureido)phenoxy)thieno[3,2-b]pyridine-2-carboxamido)methyl)pyrrolidine-1-carboxylate | $^1$H NMR(400 MHz, DMSO-$d_6$) δ ppm: 12.48(s, 1H), 11.81(s,1H), 9.05-8.90(m, 1H), 8.58(d, J=5.6 Hz, 1H), 8.32-8.22(m, 1H), 8.02(d, J=11.6 Hz, 1H), 7.56-7.52(m, 2H), 7.36-7.30(m, 4H), 7.30-7.24(m, 1H), 6.73(d, J=5.6 Hz, 1H), 4.00-3.90(m, 1H), 3.82(s, 2H), 3.54-3.20(m, 4H), 1.91-1.74(m, 4H), 1.39(bs, 9H). |
| 135c | 91 | (3-dimethylaminopyrrolidine, R) | (R)-N-(4-(2-(3-(Dimethylamino)pyrrolidine-1-carbonyl)thieno[3,2-b]pyridin-7-yloxy)-3-fluorophenyl carbamothioyl)-2-phenylacetamide | $^1$H NMR(400 MHz CDCl3) δ ppm: 12.54(s, 1H), 8.80(s, 1H), 8.54(d, 1H, J=5.5 Hz), 8.14(s, 1H), 7.96(dd, 1H, J=11.4/2.1 Hz), 7.52-7.26(m, 6H), 6.63 (d, 1H, J=5.5 Hz), 4.35-3.52(m, 5H), 3.80(s, 2H), 2.79(s, 6H), 2.70-2.40(m, 2H). |
| 135d | 92 | (piperidine) | N-(3-Fluoro-4-(2-(piperidine-1-carbonyl)thieno[3,2-b]pyridin-7-yloxy)phenyl carbamothioyl)-2-phenylacetamide | LRMS(M + 1) 549.3(100%), 550.3 (32%). |

Example 93

N-(3-Fluoro-4-(2-(piperidine-1-carbonyl)thieno[3,2-b]pyridin-7-yloxy)phenylcarbamothioyl)-2-phenylacetamide hydrochloride (136a)

N-(3-Fluoro-4-(2-(piperidine-1-carbonyl)thieno[3,2-b]pyridin-7-yloxy)phenylcarbamothioyl)-2-phenylacetamide (135d, example 92) (686 mg, 1.25 mmol) was solubilized in THF (2 mL); dichloromethane (4 mL) and 1M hydrogen chloride in ether (1.5 mL, 1.5 mmol) were successfully added. The reaction mixture was stirred for 1 hour, the solvents were partially evaporated under reduced pressure to form a precipitate, which was collected by filtration, to afford the title compound 136a (380 mg, 65% yield) as a light-yellow solid. Characterization of this material is provided in Table 12.

Example 94

N-(3-Fluoro-4-(2-(pyrrolidine-1-carbonyl)thieno[3,2-b]pyridin-7-yloxy)phenylcarbamothioyl)-2-phenylacetamide hydrochloride (136b)

Following the procedure described above for the synthesis of compound 136a (example 93) but substituting compound 135d (example 92, table 11) for the compound 80 (example 37, table 6), title compound 136b was obtained. Characterization of this material is provided in Table 12.

Example 95

(S)-1-(7-(2-Fluoro-4-(3-(2-phenylacetyl)thioureido)phenoxy)thieno[3,2-b]pyridine-2-carbonyl)pyrrolidine-2-carboxylic acid hydrochloride (136c)

Following the procedure described above for the synthesis of compound 136a (Example 93) but substituting compound 135d (example 92, table 11) for the compound 135a (Example 89, Table 11), title compound 136c was obtained. Characterization of this material is provided in Table 12.

Example 96

N-(4-(2-(Azepane-1-carbonyl)thieno[3,2-b]pyridin-7-yloxy)-3-fluorophenylcarbamothioyl)-2-phenylacetamide hydrochloride (136d)

Title compound 136d was obtained following the procedures described above for the synthesis of compound 136a (example 93, table 12). Characterization of 136d is provided in Table 12.

TABLE 12

Characterization of compounds 136a-d (examples 93-96)

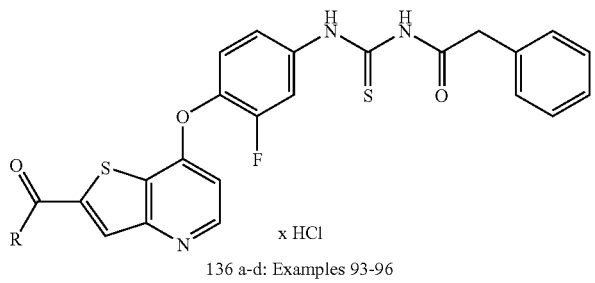

136 a-d: Examples 93-96

| Cpd | Ex | R | Name | Characterization |
|---|---|---|---|---|
| 136a | 93 | piperidine | N-(3-Fluoro-4-(2-(piperidine-1-carbonyl)thieno[3,2-b]pyridin-7-yloxy)phenylcarbamothioyl)-2-phenylacetamide hydrochloride | ¹H NMR(400 MHz DMSO-d₆) δ ppm: 12.49(s, 1H), 11.83(s, 1H), 8.65(d, 1H, J=5.7 Hz), 8.05(d, 1H, J=11.3 Hz), 7.82(s, 1H), 7.56-7.55 (m, 2H), 7.34-7.26(m, 5H), 6.84(d, 1H, J=5.7 Hz), 3.83(s, 2H), 3.61-3.58 (m, 4H), 1.65-1.09(m, 6H). |
| 136b | 94 | pyrrolidine | N-(3-Fluoro-4-(2-(pyrrolidine-1-carbonyl)thieno[3,2-b]pyridin-7-yloxy)phenylcarbamothioyl)-2-phenylacetamide hydrochloride | ¹H NMR(400 MHz, DMSO-d₆) δ ppm: 12.49(s, 1H), 11.82(s, 1H), 8.64(d, J=5.6 Hz, 1H), 8.08-8.01(m, 1H), 8.05(s, 1H), 7.58-7.53(m, 1H), 7.36-7.31(m, 4H), 7.30-7.24(m, 1H), 6.82(d, J=5.6 Hz, 1H), 3.85(t, J=6.4 Hz, 2H), 3.82(s, 2H), 3.54(t, J=6.4 Hz, 2H), 1.97(quin, J=6.4 Hz, 2H), 1.89(quin, J=6.4 Hz, 2H). |
| 136c | 95 | proline (HO₂C) | (S)-1-(7-(2-Fluoro-4-3-(2-phenylacetyl)thioureido)phenoxy)thieno[3,b]pyridine-2-carbonyl)pyrrolidine-2-carboxylic acid hydrochloride | ¹H NMR(400 MHz, DMSO-d₆) δ ppm: 12.49(s, 1H), 11.82(s, 1H), 8.67(d, J=5.6 Hz, 0.7H), 8.63(d, J=5.6 Hz, 0.3H), 8.12(s, 0.7H), 8.05(d, J=21.0 Hz, 1H), 7.88(s, 0.3H), 7.58-7.54(m, 2H), 7.37-7.10(m, 4H), 7.30-7.24(m, 1H), 6.85(d, J=5.6 Hz, 0.7H), 6.8 1(d, J=5.6 Hz, 0.3H), 5.03-4.99(m, 0.3H), 4.48(dd, J=4.4 and 8.0 Hz, 0.7H), 3.98(t, J=7.2 Hz, 1.4H), 3.82(s, 2H), 3.68-3.60(m, 0.6H), 2.32-2.25(m, 1H), 2.08-1.90(m, 3H). |
| 136d | 96 | azepane | N-(4-(2-(Azepane-1-carbonyl)thieno[3,2-b]pyridin-7-yloxy)-3-fluorophenylcarbamothioyl)-2-phenylacetamide hydrochloride | ¹H NMR(400 MHz DMSO-d₆) δ ppm: 12.49(s, 1H), 11.83(s, 1H), 8.64(d, 1H, J=5.7 Hz), 8.04(d, 1H, J=11.5 Hz), 7.85(s, 1H), 7.56-7.55 (m, 2H), 7.34-7.26(m, 5H), 6.81(d, 1H, J=5.5 Hz), 3.83(s, 2H), 3.67-3.56 (m, 4H), 1.76-1.57(m, 8H). |

Scheme 25
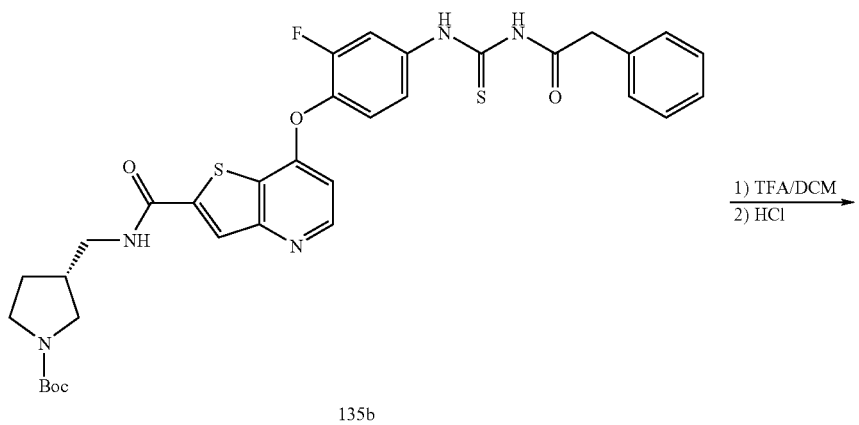
135b
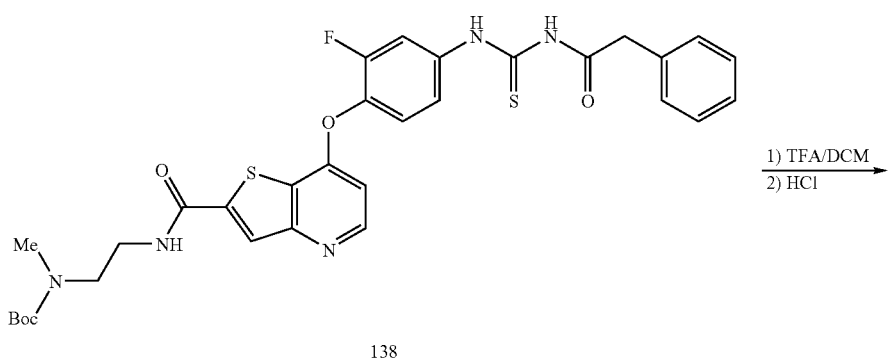
137a: Example 97
138
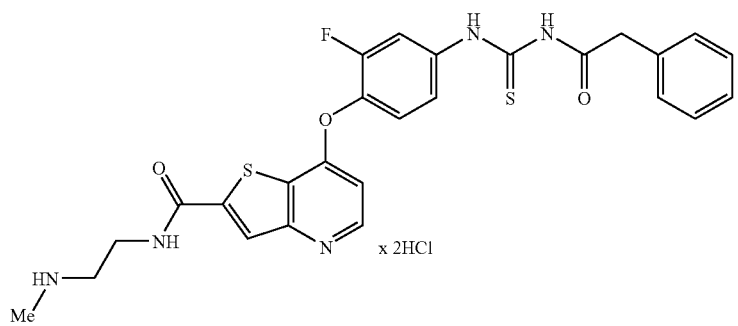
137b: Example 98

Example 97

(S)-7-(2-Fluoro-4-(3-(2-phenylacetyl)thioureido) phenoxy)-N-(pyrrolidin-3-ylmethyl)thieno[3,2-b] pyridine-2-carboxamide hydrochloride (137a)

To a solution of 135b (table 11) (16 mg, 0.028 mmol) in $CH_2Cl_2$ (15 mL) was added TFA (1 mL). The reaction mixture was stirred at room temperature until the reaction is complete, then the reaction mixture was quenched with saturated aqueous sodium bicarbonate solution a extracted with DCM. The extract was concentrated, the residue was dissolved in DCM (15 mL) and hydrogen chloride (0.5M in ether, 46 μL, 0.046 mmol) was added. The reaction mixture was stirred for one hour, the solvents were partially evaporated under reduced pressure to form a precipitate, which was collected by filtration, to afford the title compound 137a (10 mg, 87% yield) as a white solid. $^1$H NMR (400 MHz, DMSO-$d_6$) δ ppm: 12.48(s, 1H), 11.82 (s, 1H), 9.49-9.43 (m, 1H), 9.24(bs, 1H), 8.74(bs, 1H), 8.62(d, J=5.6 Hz, 1H), 8.38 (s, 1H), 8.03(d, J=12.0 Hz, 1H), 7.58-7.5 (m, 2H), 7.3-7.30 (m, 4H), 7.30-7.24 (m, 1H), 6.79(d, J=5.6 Hz, 1H), 3.80-3.54 (m, 3H), 3.30-3.20 (m, 1H), 3.20-3.10 (m, 1H), 2.12-2.02(m, 1H), 2.00-1.95 (m, 2H), 1.74-1.63 (m, 1H).

Example 98

7-(2-fluoro-4-(3-(2-phenylacetyl)thioureido)phenoxy)-N-(2-(methylamino)ethyl)thieno[3,2-b]pyridine-2-carboxamide hydrochloride (137b)

Steps 1-7. tert-Butyl 2-(7-(2-fluoro-4-(3-(2-phenylacetyl)thioureido)phenoxy)thieno[3,2-b]pyridine-2-carboxamido)ethyl(methyl)carbamate (138)

Following the procedures described above for the synthesis of compound 8a (Example 1, scheme 1) but replacing dimethyl amine with tert-butyl 2-aminoethyl(methyl)carbamate, title compound 138 was obtained (13%). LRMS (M+1) 638.2 (100%).

Step 8. 7-(2-Fluoro-4-(3-(2-phenylacetyl)thioureido) phenoxy)-N-(2-(methylamino)ethyl)thieno[3,2-b] pyridine-2-carboxamide hydrochloride (137b)

Following the procedure described above for the synthesis of 137a but replacing compound 135b with compound 138, title compound 137b was obtained as an HCl salt in 65% yield. $^1$H NMR (400 MHz, DMSO-$d_6$) δ ppm: 12.49 (s, 1H), 11.83 (s, 1H), 9.39(t, J=5.2 Hz, 1H), 8.80(bs, 1H), 8.62(d, J=5.6 Hz, 1H), 8.39 (s, 1H), 8.04(d, J=11.6 Hz, 1H), 7.97(bs, 1H), 7.58-7.50 (m, 2H), 7.37-7.31 (m, 4H), 7.31-7.24 (m, 1H), 6.80(d, J=5.6 Hz, 1H), 3.78-3.71(m, 0.5H), 3.61(q, J=6.0 Hz, 1H), 3.21-3.24 (m, 0.5H), 3.18-3.04 (m, 2H), 2.60 (t, J=4.8 Hz, 2H).

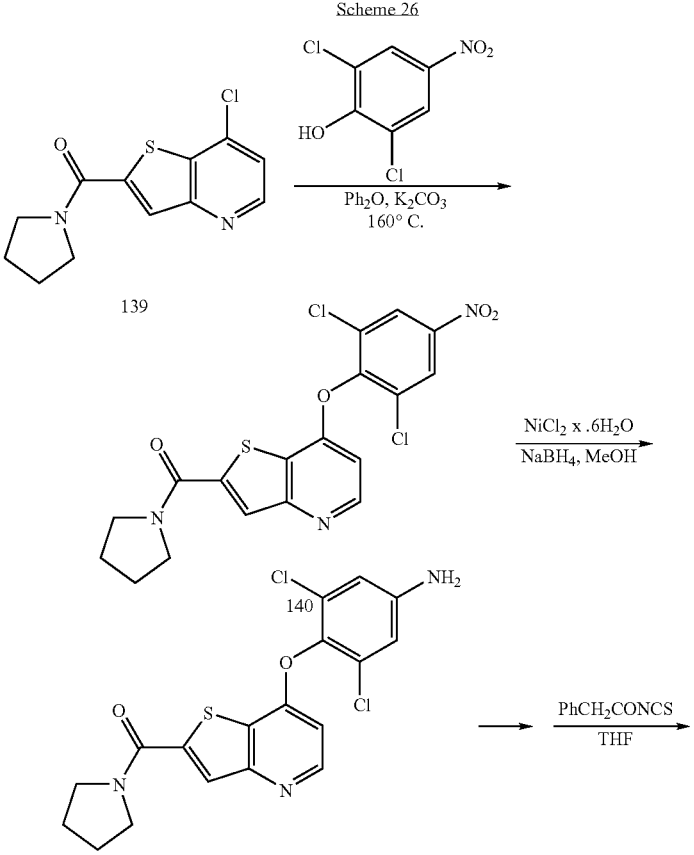

Scheme 26

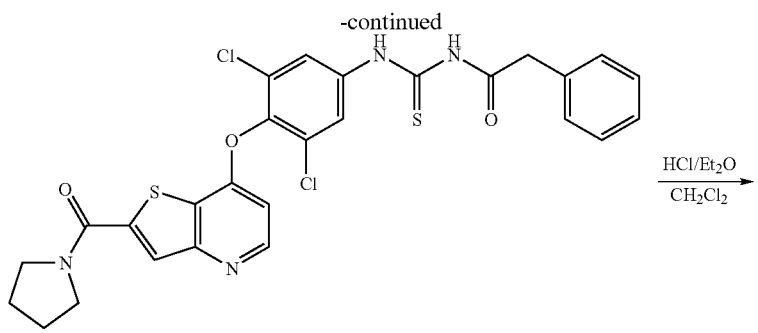

142: Example 99

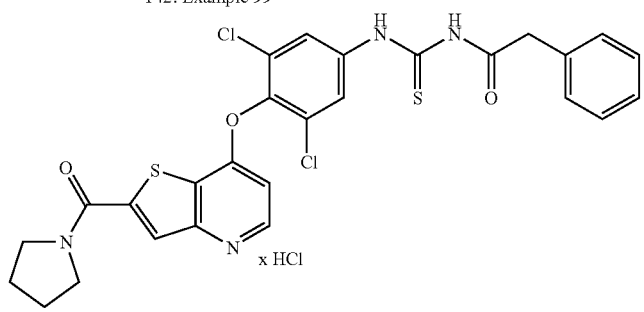

143: Example 100

Examples 99 and 100

N-(3,5-Dichloro-4-(2-(pyrrolidine-1-carbonyl)thieno[3,2-b]pyridin-7-yloxy)phenylcarbamothioyl)-2-phenylacetamide (142) and 7-(2,6-dichloro-4-(3-(2-phenylacetyl)thioureido)phenoxy)-2-(pyrrolidine-1-carbonyl)thieno[3,2-b]pyridin-4-ium chloride (143)

Steps 1-4. (7-Chlorothieno[3,2-b]pyridin-2-yl)(pyrrolidin-1-yl)methanone (139)

Following the procedures described above for the synthesis of compound 5 (scheme 1, example 1) but replacing dimethyl amine in the step 4 for pyrrolidine, title compound 139 was obtained. LRMS (M+1) 267.1 (100%).

Step 5. (7-(2,6-Dichloro-4-nitrophenoxy)thieno[3,2-b]pyridin-2-yl)(pyrrolidin-1-yl)methanone (140)

Starting from the compound 139 and following the procedure described above for the synthesis of compound 6 (scheme 1, example 1) but replacing 2-fluoro-4-nitrophenol with 2,6-dichloro-4-nitrophenol, title compound 140 was obtained in 69% yield. LRMS (M+1) 438.0 (100%), 439.1 (20%), 440.1 (70%).

Steps 6-7. N-(3,5-Dichloro-4-(2-(pyrrolidine-1-carbonyl)thieno[3,2-b]pyridin-7-yloxy)phenylcarbamothioyl)-2-phenylacetamide (142)

Starting from the nitro compound 140 and following the procedures described above for the synthesis of 8a (steps 6-7, scheme 1, example 1) title compound 142 was obtained in 49% yield. LRMS (M+1) 585.3 (100%), 586.2 (34%), 587.3 (72%).

7-(2,6-Dichloro-4-(3-(2-phenylacetyl)thioureido)phenoxy)-2-(pyrrolidine-1-carbonyl)thieno[3,2-b]pyridin-4-ium chloride (143)

Following the procedure described above for the synthesis of compound 136a (Table 12, Example 93) but replacing compound 135d with compound 142, title compound 143 was obtained in 42% yield. Characterization of 143 is provided in the Table 13.

Examples 101 and 102

N-(3-Chloro-4-(2-(pyrrolidine-1-carbonyl)thieno[3,2-b]pyridin-7-yloxy)phenylcarbamothioyl)-2-phenylacetamide hydrochloride (144) and N-(3-Methyl-4-(2-(pyrrolidine-1-carbonyl)thieno[3,2-b]pyridin-7-yloxy)phenylcarbamothioyl)-2-phenylacetamide hydrochloride (145)

Compounds 144-145 (examples 101-102) were obtained following the procedures described above for the synthesis of compound 143 (example 100). Characterization of compounds 144-145 is provided in the Table 13.

Examples 103 and 104

2-Phenyl-N-(4-(2-(pyrrolidine-1-carbonyl)thieno[3,2-b]pyridin-7-yloxy)phenylcarbamothioyl)acetamide (146) and N-(3-(Dimethylamino)-4-(2-(pyrrolidine-1-carbonyl)thieno[3,2-b]pyridin-7-yloxy)phenylcarbamothioyl)-2-phenylacetamide (147)

Compounds 146-147 (Examples 103-104) were obtained following the procedures described above for the synthesis of compound 142 (Example 99). Characterization of compounds 145-147 is provided in the Table 13.

TABLE 13

Characterization of compounds 143-146(examples 99-103)

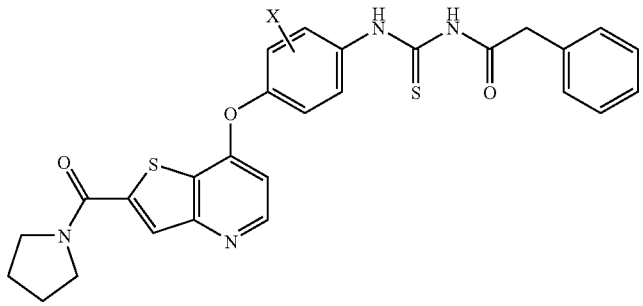

143-147: Examples 100-104

| Cpd | Ex | Ar | Name | Characterization |
|---|---|---|---|---|
| 143 | 100 | ![Cl,Cl-phenyl] | N-(3,5-Dichloro-4-(2-(pyrrolidine-1-carbonyl)thieno[3,2-b]pyridin-7-yloxy)phenylcarbamo-thioyl)-2-phenylacetamide hydrochloride | $^1$H NMR(400 MHz, DMSO-d$_6$) δ ppm: 12.44(s, 1H), 11.91(s, 1H), 8.61(d, 1H, J=5.5 Hz), 8.10 (s, 2H), 8.06(s, 1H), 7.34-7.27 (m, 5H), 6.68(d, 1H, J=5.5 Hz), 3.88-3.83(m, 4H), 3.70-3.40(m, 2H), 1.99-1.18(m, 4H). |
| 144 | 101 | ![Cl-phenyl] | N-(3-Chloro-4-(2-(pyrrolidine-1-carbonyl)thieno[3,2-b]pyridin-7-yloxy)phenylcarbamo-thioyl)-2-phenylacetamide hydrochloride | $^1$H NMR(400 MHz, DMSO-d$_6$) δ ppm: 12.43(s, 1H), 11.83(s, 1H), 8.65(d, 1H, J=5.7 Hz), 8.14 (d, 1H, J=2.3 Hz), 8.06(s, 1H), 7.70(dd, 1H, J=8.8/2.5 Hz), 7.55 (d, 1H, J=8.8 Hz), 7.34-7.26(m, 5H), 6.74(d, 1H, J=5.7 Hz), 3.87-3.83(m, 4H), 3.56-3.53(m, 2H), 1.99-1.88(m, 4H). |
| 145 | 102 | ![Me-phenyl] | N-(3-Methyl-4-(2-(pyrrolidine-1-carbonyl)thieno[3,2-b]pyridin-7-yloxy)phenylcarbamo-thioyl)-2-phenylacetamide hydrochloride | $^1$H NMR(400 MHz, DMSO-d$_6$) δ ppm: 12.43(s, 1H), 11.74(s, 1H), 8.62(d, 1H, J=5.7 Hz), 8.04 (s, 1H), 7.69-7.65(m, 2H), 7.43-7.26(m, 6H), 6.67(d, 1H, J=5.7 Hz), 3.87-3.82(m, 4H), 3.67-3.38 (m, 2H), 2.13(s, 3H), 1.99-1.18 (m, 4H). |
| 146 | 103 | ![phenyl] | 2-Phenyl-N-(4-(2-(pyrrolidine-1-carbonyl)thieno[3,2-b]pyridin-7-yloxy)phenylcarbamo-thioyl)acetamide | $^1$H NMR(400 MHz, DMSO-d$_6$) δ ppm: 12.41(s, 1H), 11.75(s, 1H), 8.68(d, J=5.6 Hz, 1H), 8.06(s, 1H), 7.77(d, J=8.8 Hz, 2H), 7.36(d, J=8.8 Hz, 2H), 7.34-7.31(m, 4H), 7.30-7.24(m, 1H), 6.85(d, J=5.6 Hz, 1H), 3.84(t, J=6.4 Hz, 2H), 3.82(s, 2H), 3.54(t, J=6.4 Hz, 2H), 1.97(quin, J=6.4 Hz, 2H), 1.89(quin, J=6.4 Hz, 2H). |
| 147 | 104 | ![NMe2-phenyl] | N-(3-(Dimethylamino)-4-(2-(pyrrolidine-1-carbonyl)thieno[3,2-b]pyridin-7-yloxy)phenylcarbamo-thioyl)-2-phenylacetamide | $^1$H NMR(400 MHz, CDCl$_3$) δ ppm: 8.48(d, 1H, J=6.1 Hz), 8.27(s, 1H), 7.56(m, 8H), 6.67 (m, 1H), 3.91(t, 2H, J=6.8 Hz), 3.78(s, 2H), 3.74(t, 2H, J=6.8 Hz), 2.73(s, 6H), 2.19-2.01(m, 4H). |

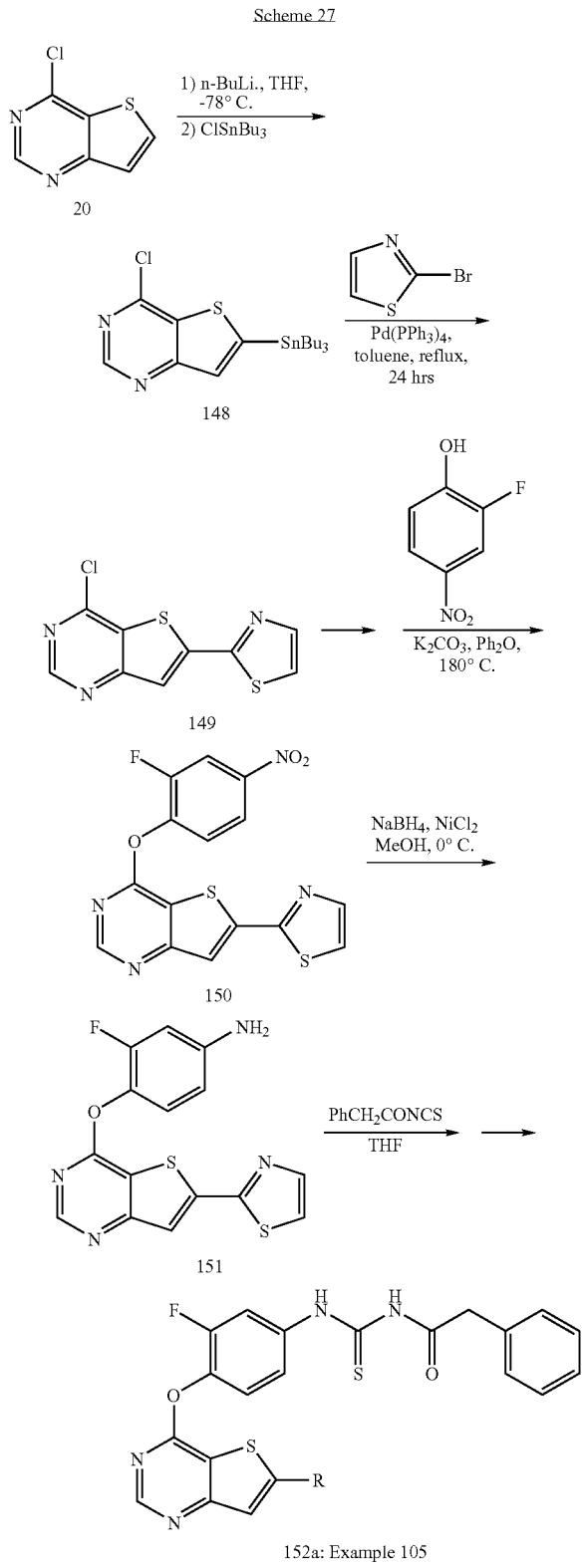

Example 105

N-(3-Fluoro-4-(6-(thiazol-2-yl)thieno[3,2-d]pyrimidin-4-yloxy)phenylcarbamothioyl)-2-phenylacetamide (152a)

Step 1. 4-Chloro-6-(tributylstannyl)thieno[3,2-d]pyrimidine (148)

Starting from 4-chloro-thieno[3,2-d]pyrimidine (20, scheme 4) and following the procedure described above for the synthesis of tributyltin compound 98 (scheme 19), title compound 148 was obtained in 79% yield. LRMS (M+1) 461.1 (100%).

Step 2.
4-Chloro-6-(thiazol-2-yl)thieno[3,2-d]pyrimidine (149)

Starting from the tributyltin compound 148 and following the procedure described above for the synthesis of compound 10 (scheme 2, example 12), title compound 149 was obtained in 81% yield. LRMS (M+1) 254.0 (100%).

Step 3. 4-(2-Fluoro-4-nitrophenoxy)-6-(thiazol-2-yl) thieno[3,2-d]pyrimidine (150)

Starting from the bis-aryl compound 149 and following the procedure described above for the synthesis of compound 11 (scheme 2, example 12) title compound 150 was obtained in 65% yield. LRMS (M+1) 375.0 (100%).

Steps 4-5. N-(3-Fluoro-4-(6-(thiazol-2-yl)thieno[3,2-d]pyrimidin-4-yloxy)phenylcarbamothioyl)-2-phenylacetamide (152a)

Starting from the nitro compound 150, following the procedure described above for the synthesis of compound 13a (via the intermediate amine 12, scheme 2, example 12), title compound 152a was obtained [via intermediate 3-fluoro-4-(6-(thiazol-2-yl)thieno[3,2-d]pyrimidin-4-yloxy)benzenamine (151)] in 7% yield. Characterization of 152a is provided in the Table 14.

Examples 106-108

N-(3-Fluoro-4-(6-(pyridin-2-yl)thieno[3,2-d]pyrimidin-4-yloxy)phenylcarbamothioyl)-2-phenylacetamide (152b)
N-(3-Fluoro-4-(6-(thiophen-2-yl)thieno[3,2-d]pyrimidin-4-yloxy)phenylcarbamothioyl)-2-phenylacetamide (152c), and
N-(3-Fluoro-4-(6-(thiophen-2-yl)thieno[3,2-d]pyrimidin-4-yloxy)phenylcarbamothioyl)-2-phenylacetamide (152d)
Compounds 152b-d (Examples 106-108) were synthesized according to the Scheme 27, similarly to the compound 152a (Example 105). Characterization of 152b-d is provided in the Table 14.

TABLE 14

Characterization of Compounds 152a-d (Examples 105-108)

| Cpd | Ex | R | Name | Characterization |
|---|---|---|---|---|
| 152a | 105 | thiazol-2-yl | N-(3-Fluoro-4-(6-(thiazol-2-yl)thieno[3,2-d]pyrimidin-4-yloxy)phenylcarbamothioyl)-2-phenylacetamide | $^1$H NMR(400 MHz, DMSO-$d_6$) δ ppm: 8.75(s, 1H), 8.32(s, 1H), 8.05(d, J=3.2 Hz, 1H), 8.03(d, J=3.2 Hz, 1H), 7.96-7.88(m, 1H), 7.58-7.50(m, 1H), 7.50-7.43(m, 1H), 7.36-7.30(m, 4H), 7.30-7.23(m, 1H), 3.83(s, 2H). |
| 152b | 106 | pyridin-2-yl | N-(3-Fluoro-4-(6-(pyridin-2-yl)thieno[3,2-d]pyrimidin-4-yloxy)phenylcarbamothioyl)-2-phenylacetamide | $^1$H NMR(400 MHz, DMSO-$d_6$) δ ppm: 12.44(s, 1H), 11.80(s, 1H), 8.73(s, 1H), 8.70-8.64(m, 1H), 8.47(s, 1H), 8.3 8(m, J=8.0 Hz, 1H), 8.00(td, J=2.0 and 8.0 Hz, 1H), 7.92(dd, J=2.0 and 12.0 Hz, 1H), 7.55(t, J=8.8 Hz, 1H), 7.53-7.46(m, 2H), 7.36-7.31(m, 4H), 7.30-7.24(m, 1H), 3.82(s, 2H). |
| 152c | 107 | thiophen-2-yl | N-(3-Fluoro-4-(6-(thiophen-2-yl)thieno[3,2-d]pyrimidin-4-yloxy)phenylcarbamothioyl)-2-phenylacetamide | $^1$H NMR(400 MHz, DMSO-$d_6$) δ ppm: 12.42(s, 1H), 11.80(s, 1H), 8.69(s, 1H), 7.92(dd, J=2.4 and 10.4 Hz, 1H), 7.91(s, 1H), 7.82(dd, J=1.2 and 4.8 Hz, 1H), 7.79(dd, J=1.2 and 3.6 Hz, 1H), 7.54(t, J=8.8 Hz, 1H), 7.47(dd, J=2.4 and 8.8 Hz, 1H), 7.36-7.30(m, 4H), 7.30-7.25(m, 1H), 7.24(dd, J=3.6 and 4.8 Hz, 1H), 3.82(s, 2H). |
| 152d | 108 | pyrimidin-2-yl | N-(3-Fluoro-4-(6-(pyrimidin-2-yl)thieno[3,2-d]pyrimidin-4-yloxy)phenylcarbamothioyl)-2-phenylacetamide | $^1$H NMR(400 MHz, DMSO-$d_6$) δ ppm: 12.44(s, 1H), 11.80(s, 1H), 9.00(s, 1H), 8.98(s, 1H), 8.77(s, 1H), 8.37(s, 1H), 7.94(dd, J=2.4 and 12.0 Hz), 7.61(t, J=5.2 Hz, 1H), 7.57(t, J=8.8 Hz, 1H), 7.49(dd, J=2.4 and 8.8 Hz, 1H), 7.38-7.31(m, 4H), 7.30-7.25(m 1H), 3.83(s, 2H). |

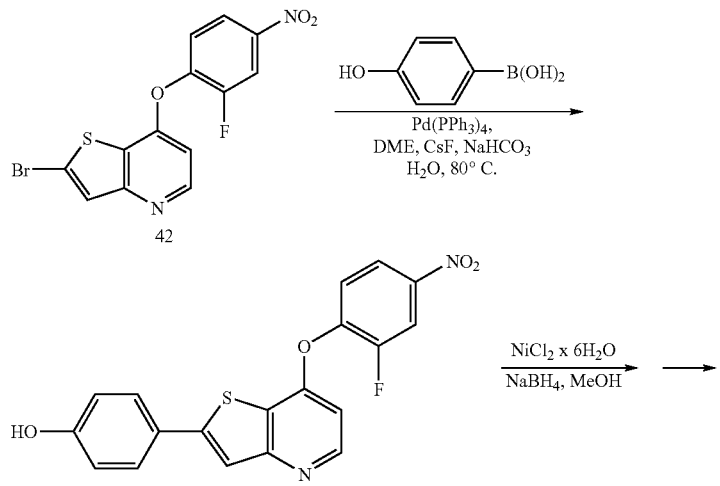

Scheme 28

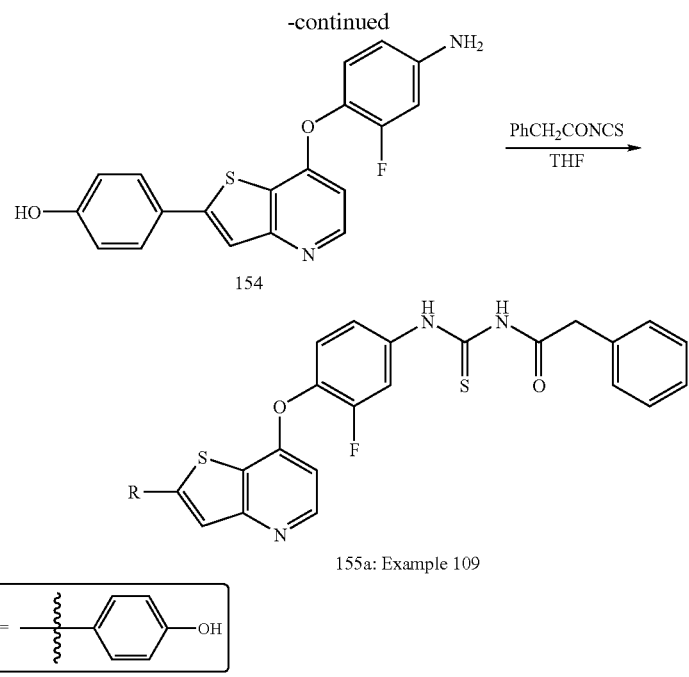

155a: Example 109

Example 109

N-(3-Fluoro-4-(2-(4-hydroxyphenyl)thieno[3,2-b]pyridin-7-yloxy)phenylcarbamothioyl)-2-phenylacetamide (155a)

Step 1. 4-(7-(2-Fluoro-4-nitrophenoxy)thieno[3,2-b]pyridin-2-yl)phenol (153)

To a solution of 2-bromo-7-(2-fluoro-4-nitrophenoxy)thieno[3,2-b]pyridine (42, scheme 8) (650 mg, 1.76 mmol) in ethylene glycol dimethyl ether (18 mL) were added 4-hydroxyphenylboronic acid (486 mg, 3.52 mmol), tetrakis-triphenylphosphine palladium(0) (203 mg, 0.18 mmol), cesium fluoride (802 mg, 5.28 mmol) and a solution of sodium bicarbonate (444 mg, 5.28 mmol) in water (1 mL). The reaction mixture was purged with nitrogen, heated at 80° C. for 4 hours, quenched with saturated aqueous ammonium chloride and extracted with EtOAc. The extract was washed with water and brine, dried over anhydrous magnesium sulfate, filtered and evaporated under reduced pressure. The residue was purified by trituration with methanol and ether to afford title compound 153 (418 mg, 62% yield) as a yellow solid. LRMS (M+1) 383.1 (100%).

Step 2. 4-(7-(4-Amino-2-fluorophenoxy)thieno[3,2-b]pyridin-2-yl)phenol (154)

Following the procedure described above for the synthesis of the amine 49 (scheme 10, example 55) but substituting nitro compound 48 for the nitro compound 153, title compound 154 was obtained in 99% yield (crude material, used in the next step without additional purification). LRMS (M+1) 353.1 (100%).

Step 3. N-(3-Fluoro-4-(2-(4-hydroxyphenyl)thieno[3,2-b]pyridin-7-yloxy)phenylcarbamothioyl)-2-phenylacetamide (155a)

Following the procedure described above for the synthesis of Compound 50 (Scheme 10, Example 55) but substituting amine 49 for the amine 154, title Compound 155a was obtained in 3% yield. Characterization of 155a is provided in the Table 14a.

Examples 110-118

N-(3-Fluoro-4-(2-(4-methoxyphenyl)thieno[3,2-b]pyridin-7-yloxy)phenylcarbamothioyl)-2-phenylacetamide (155b)

N-(3-Fluoro-4-(2-(3-methoxyphenyl)thieno[3,2-b]pyridin-7-yloxy)phenylcarbamothioyl)-2-phenylacetamide (155c)

N-(3-Fluoro-4-(2-(3-fluoro-4-methoxyphenyl)thieno[3,2-b]pyridin-7-yloxy)phenylcarbamothioyl)-2-phenylacetamide (155d)

N-(3-Fluoro-4-(2-(4-morpholinophenyl)thieno[3,2-b]pyridin-7-yloxy)phenylcarbamothioyl)-2-phenylacetamide (155e)

N-(3-Fluoro-4-(2-phenylthieno[3,2-b]pyridin-7-yloxy)phenylcarbamothioyl)-2-phenylacetamide (155f)

N-(3-Fluoro-4-(2-(2-morpholinopyrimidin-5-yl)thieno[3,2-b]pyridin-7-yloxy)phenylcarbamothioyl)-2-phenylacetamide (155g)

177

N-(3-Fluoro-4-(2-(2-(2-morpholinoethoxy)pyrimidin-5-yl)thieno[3,2-b]pyridin-7-yloxy)phenylcarbamothioyl)-2-phenylacetamide (155h)

N-(3-Fluoro-4-(2-(2-methoxyphenyl)thieno[3,2-b]pyridin-7-yloxy)phenylcarbamothioyl)-2-phenylacetamide (155i), and

178

N-(3-Fluoro-4-(2-(4-hydroxy-3-methoxyphenyl)thieno[3,2-b]pyridin-7-yloxy)phenylcarbamothioyl)-2-phenylacetamide (155j)

Compounds 155b-j (Examples 110-118) were prepared similarly to the Compound 155a (Example 109, Scheme 28). Characterization of 155b-j is provided in the Table 14a.

TABLE 14a

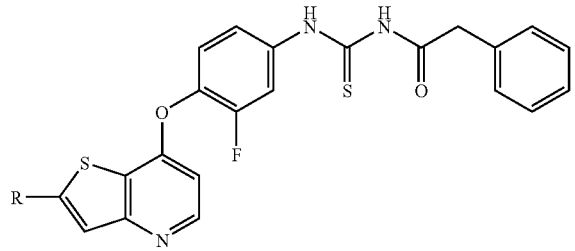

155a–j: Examples 109–118

Characterization of compounds 152a–j (examples 109–118)

| Cpd | Ex | R | Name | Characterization |
|---|---|---|---|---|
| 155a | 109 | ⁁–C₆H₄–OH (para) | N-(3-Fluoro-4-(2-(4-hydroxyphenyl)thieno[3,2-b]pyridin-7-yloxy)phenylcarbamothioyl)-2-phenylacetamide | $^1$H NMR (400 MHz, DMSO-d$_6$) δ ppm: 12.46(s, 1H), 11.82(s, 1H), 9.95(s, 1H), 8.46(d, 1H, J=5.3 Hz), 7.99(d, 1H, J=13.1 Hz), 7.83(s, 1H), 7.70(d, 2H, J=13.1 Hz), 7.52–7.51(m, 2H), 7.34–7.27(m, 5H), 6.86(d, 2H, J=8.6 Hz), 6.59(d, 1H, J=5.5 Hz), 3.83(s, 2H). |
| 155b | 110 | ⁁–C₆H₄–OMe (para) | N-(3-Fluoro-4-(2-(4-methoxyphenyl)thieno[3,2-b]pyridin-7-yloxy)phenylcarbamothioyl)-2-phenylacetamide | $^1$H NMR (400 MHz, DMSO-d$_6$) δ ppm: 12.46(s, 1H), 11.82(s, 1H), 8.48(d, J=5.6 Hz, 1H), 8.00(d, J=7.6 Hz, 1H), 7.91(s, 1H), 7.81(d, J=8.8 Hz, 2H), 7.66–7.60(m, 2H), 7.37–7.31(m, 4H), 7.31–7.24(m, 1H), 7.05(d, J=8.8 Hz, 2H), 6.61(d, J=5.6 Hz, 1H), 3.82(s, 3H). |
| 155c | 111 | ⁁–C₆H₄–OMe (meta) | N-(3-Fluoro-4-(2-(3-methoxyphenyl)thieno[3,2-b]pyridin-7-yloxy)phenylcarbamothioyl)-2-phenylacetamide | $^1$H NMR (400 MHz, DMSO-d$_6$) δ ppm: 12.46(s, 1H), 11.82(s, 1H), 8.52(d, J=5.6 Hz, 1H), 8.10(s, 1H), 8.01(d, J=12.4 Hz, 1H), 7.56–7.51(m, 2H), 7.46–7.37(m, 3H), 7.37–7.31(m, 4H), 7.31–7.24(m, 1H), 7.05–7.00(m, 1H), 6.65(d, J=5.6 Hz, 1H), 3.85(s, 3H), 3.82(s, 2H). |
| 155d | 112 | ⁁–C₆H₃(F)(OMe) (3-F, 4-OMe) | N-(3-Fluoro-4-(2-(3-fluoro-4-methoxyphenyl)thieno[3,2-b]pyridin-7-yloxy)phenylcarbamothioyl)-2-phenylacetamide | $^1$H NMR (400 MHz, DMSO-d$_6$) δ ppm: 12.46(s, 1H), 11.82(s, H), 8.49(d, J=5.6 Hz, 1H), 8.01(s, 1H), 8.2–7.76(m, 1H), 7.84(dd, J=2.4 and 12.0 Hz, 1H), 7.66–7.61(m, 1H), 7.55–7.51(m, 2H), 7.38–7.10(m, 6H), 6.63(d, J=5.6 Hz, 1H), 3.90(s, 3H), 3.82(s, 2H). |
| 155e | 113 | ⁁–C₆H₄–morpholino (para) | N-(3-Fluoro-4-(2-(4-morpholinophenyl)thieno[3,2-b]pyridin-7-yloxy)phenylcarbamothioyl)-2-phenylacetamide | $^1$H NMR (400 MHz, DMSO-d$_6$) δ ppm: 12.49(s, 1H), 11.85(s, 1H), 8.63(d, J=5.6 Hz, 1H), 8.03(d, J=11.6 Hz, 1H), 7.89(s, 1H), 7.79(d, J=8.8 Hz, 2H), 7.63–7.56(m, 2H), 7.36–7.31(m, 4H), 7.31–7.25(m, 1H), 7.05(d, J=8.8 Hz, 2H), 6.87(d, J=5.6 Hz, 1H), 3.83(s, 2H), 3.78–3.73(m, 4H), 3.30–3.24(m, 4H). |

TABLE 14a-continued

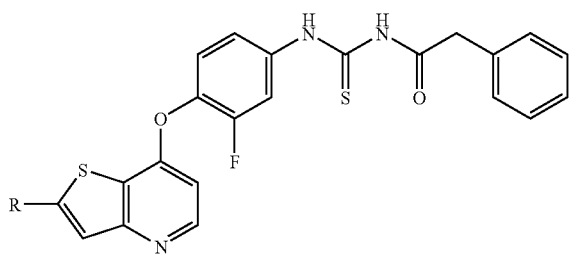

155a–j: Examples 109–118

Characterization of compounds 152a–j (examples 109–118)

| Cpd | Ex | R | Name | Characterization |
|---|---|---|---|---|
| 155f | 114 | phenyl | N-(3-Fluoro-4-(2-phenylthieno[3,2-b]pyridin-7-yloxy)phenylcarbamothioyl)-2-phenylacetamide | $^1$H NMR (400 MHz, DMSO-d$_6$) δ ppm: 12.46(s, H), 11.82(s, 1H), 8.52(d, J=5.6 Hz, 1H), 8.06(s, 1H), 8.01(d, J=12.4 hz, 1H), 7.88(d, J=6.8 Hz, 2H), 7.58–7.41(m, 5H), 7.38–7.31(m, 4H), 7.31–7.24(m, 1H), 6.65(d, J=5.6 Hz, 1H), 3.82(s, 2H). |
| 155g | 115 | 2-morpholinopyrimidin-5-yl | N-(3-Fluoro-4-(2-(2-morpholinopyrimidin-5-yl)thieno[3,2-b]pyridin-7-yloxy)phenylcarbamothioyl)-2-phenylacetamide | $^1$H NMR (400 MHz, DMSO-d$_6$) δ ppm: 12.46(s, 1H), 11.82(s, 1H), 8.89(s, 2H), 8.49(d, J=5.6 hz, 1H), 8.00(d, J=12.0 Hz, 1H), 7.98(s, 1H), 7.56–7.51(m, 2H), 7.37–7.31(m, 4H), 7.31–7.24(m, 1H), 6.61(d, J=5.6 Hz, 1H), 3.82(s, 2H), 3.82–3.76(m, 4H), 3.70–3.66(m, 4H). |
| 155h | 116 | 2-(2-morpholinoethoxy)pyrimidin-5-yl | N-(3-Fluoro-4-(2-(2-(2-morpholinoethoxy)pyrimidin-5-yl)thieno[3,2-b]pyridin-7-yloxy)phenylcarbamothioyl)-2-phenylacetamide | $^1$H NMR (400 MHz, DMSO-d$_6$) δ ppm: 12.49(s, 1H), 11.85(s, 1H), 9.13(s, 2H), 8.56(d, J=5.6 Hz, 1H), 8.18(s, 1H), 8.03(d, J=1.8 Hz, 1H), 7.60–7.54(m, 2H), 7.39–7.32(m, 4H), 7.32–7.25(m, 1H), 6.68(d, J=5.6 Hz, 1H), 4.50(t, J=5.6 Hz, 2H), 3.83(s, 2H), 3.57(t, J=4.4 Hz, 4H), 2.73(t, J=5.6 Hz, 2H), 2.51–2.44(m, 4H). |
| 155i | 117 | 2-methoxyphenyl | N-(3-Fluoro-4-(2-(2-methoxyphenyl)thieno[3,2-b]pyridin-7-yloxy)phenyl-carbamothioyl)-2-phenylacetamide | $^1$H NMR (400 MHz, DMSO-d$_6$) δ ppm: 12.51(s, 1H), 11.84(s, 1H), 8.67(d, 1H, J=6.1 Hz), 8.13 (s, 1H), 8.08(d, 1H, J=13.1 Hz), 8.02(dd, 1H, J=7.7/1.5 Hz), 7.61–7.60(m, 2H), 7.50(td, 1H, J=7.8/1.7 Hz), 7.35–7.32(m, 4H), 7.29–7.26(m, 2H), 7.13(td, 1H, J=7.6/1.1 Hz), 6.88(d, 1H, J=6.1 Hz), 4.00 (s, 3H), 3.83(s, 2H). |
| 155j | 118 | 4-hydroxy-3-methoxyphenyl | N-(3-Fluoro-4-(2-(4-hydroxy-3-methoxyphenyl)thieno[3,2-b]pyridin-7-yloxy)phenyl-carbamothioyl)-2-phenylacetamide | $^1$H NMR (400 MHz, DMSO-d$_6$) δ ppm: 12.49(s, 1H), 11.85(s, 1H), 9.57(s, 1H), 8.49(d, 1H, J=5.5 Hz), 8.01(d, 1H, J=13.5 Hz), 7.94(s, 1H), 7.54–7.53(m, 2H), 7.44(d, 1H, J=2.3 Hz), 7.38–7.27(m, 6H), 6.88(d, 1H, J=8.2 Hz), 6.61(d, 1H, J=4.9 Hz), 3.89(s, 3H), 3.83(s, 2H). |

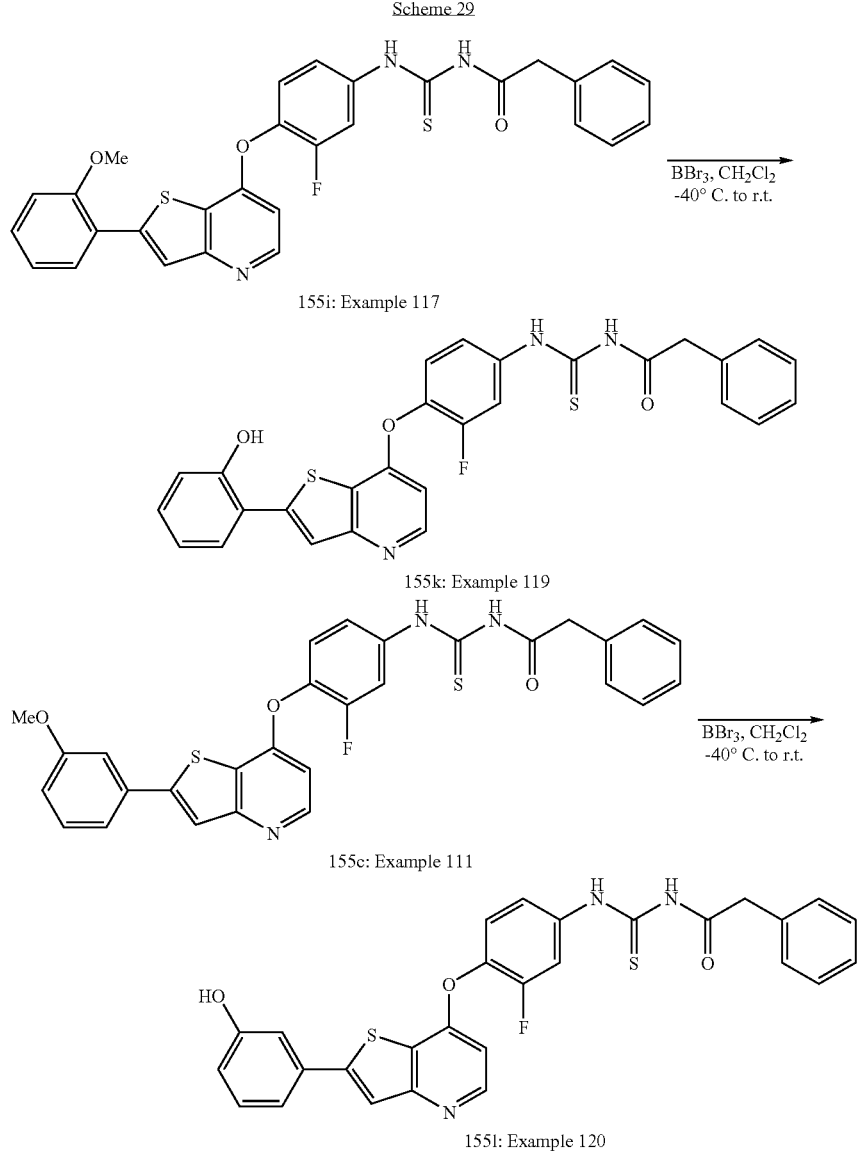

Example 119

N-(3-Fluoro-4-(2-(2-hydroxyphenyl)thieno[3,2-b]pyridin-7-yloxy)phenylcarbamothioyl)-2-phenylacetamide (155k)

To a cold (−40° C.) solution of the compound 155i (80 mg, 0.15 mmol) in DCM (3 mL) was added tribromoborane (1M in DCM, 0.60 mL, 0.60 mmol). The reaction mixture was stirred overnight at room temperature. Water and methanol were added and the mixture was stirred for additional 20 minutes. Organic phase was separated and the aqueous layer was extracted with EtOAc. Both organic phases were combined, washed with water and brine, dried over anhydrous magnesium sulfate, filtered and evaporated under reduced pressure. The residue was purified by flash chromatography (eluent MeOH-DCM, 2:98) then triturated with methanol, to afford the title compound 155k (6 mg, 7% yield), as a light yellow solid. $^1$H NMR (400 MHz, DMSO-$d_6$) δ ppm: 12.47 (d, 1H, J=0.4 Hz), 11.82 (s, 1H), 10.65 (s, 1H), 8.48 (d, 1H, J=5.5 Hz), 8.07 (s, 1H), 8.01 (d, 1H, J=11.5 Hz), 7.84 (d, 1H, J=7.8 Hz), 7.53-7.49 (m, 2H), 7.38-7.23 (m, 6H), 7.01 (d, 1H, J=8.2 Hz), 6.93 (t, 1H, J=7.4 Hz), 6.58 (d, 1H, J=5.5 Hz), 3.83 (s, 2H). LRMS (M+1) 530.2 (100%).

Example 120

N-(3-Fluoro-4-(2-(3-hydroxyphenyl)thieno[3,2-b]pyridin-7-yloxy)phenylcarbamothioyl)-2-phenylacetamide (155l)

Following the procedure described above for the synthesis of compound 155k (example 119, scheme 29) but substituting methoxy-compound 155i for the methoxy-compound 155c, title compound 155l was prepared in 62% yield. $^1$H NMR (400 MHz, DMSO-$d_6$) δ ppm: 12.49 (s, 1H), 11.84 (s, 1H), 8.68 (d, J=5.6 Hz, 1H), 8.07 (d, J=12.0 Hz, 1H), 7.99 (s, 1H), 7.64-7.56 (m, 2H), 7.38-7.24 (m, 8H), 6.96-6.88 (m, 2H), 3.83 (s, 2H).

Scheme 30
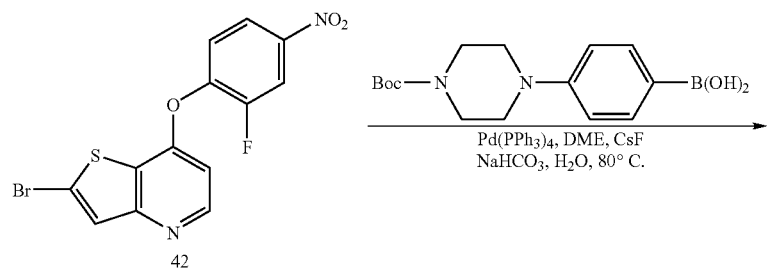
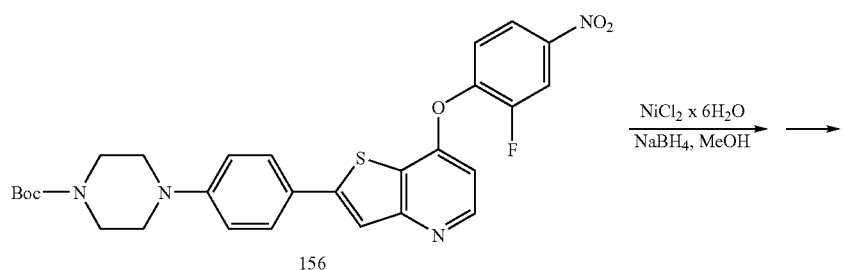
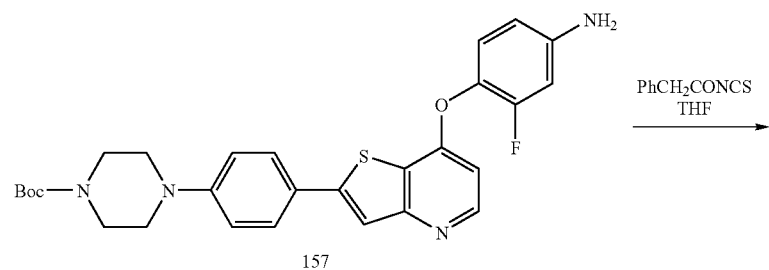
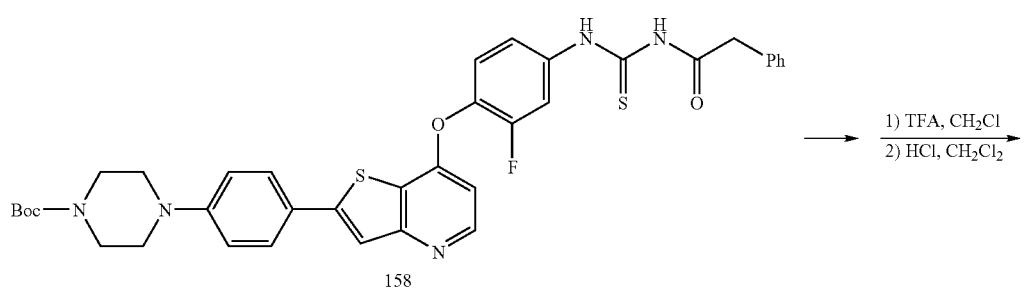
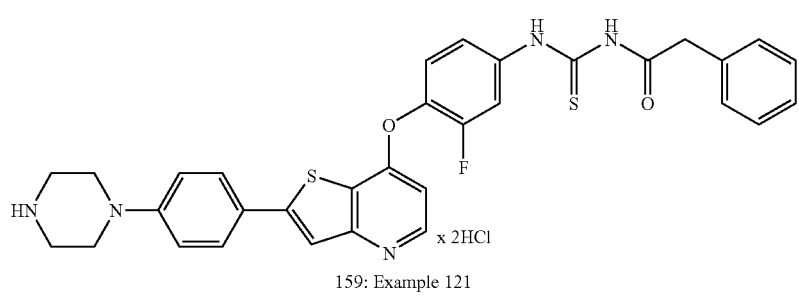
159: Example 121

Example 121

N-(3-Fluoro-4-(2-(4-(piperazin-1-yl)phenyl)thieno[3,2-b]pyridin-7-yloxy)phenylcarbamothioyl)-2-phenylacetamide di-hydrochloride (159)

Step 1. tert-Butyl 4-(4-(7-(2-fluoro-4-nitrophenoxy)thieno[3,2-b]pyridin-2-yl)phenyl)piperazine-1-carboxylate (156)

Starting from the nitro-bromo compound 42, following the procedure described above for the synthesis of compound 48 (scheme 10, example 55) but substituting 4,4,5,5-tetramethyl-2-(4-(methylsulfonyl)phenyl)-1,3,2-dioxaborolane for 4-(4-(tert-butoxycarbonyl)piperazin-1-yl)phenylboronic acid, title compound 156 was obtained in 70% yield. LRMS (M+1) 550.6 (100%).

Step 2. tert-Butyl 4-(4-(7-(4-amino-2-fluorophenoxy)thieno[3,2-b]pyridin-2-yl)phenyl)piperazine-1-carboxylate (157)

Following the procedure described above for the synthesis of amine 49 (scheme 10, example 55) but substituting nitro compound 48 for the nitro compound 156, title compound 157 was obtained in 99% yield (crude material, used in the next step without additional purification). LRMS (M+1) 520.2 (100%).

Step 3. tert-Butyl 4-(4-(7-(2-fluoro-4-(3-(2-phenylacetyl)thioureido)phenoxy)thieno[3,2-b]pyridine-2-yl)phenyl)piperazine-1-carboxylate (158)

Following the procedure described above for the synthesis of compound 50 (scheme 10, example 55) but substituting amine 49 for the amine 157, title compound 158 was obtained in 41% yield. LRMS (M+1) 697.2 (100%).

Step 4. N-(3-Fluoro-4-(2-(4-(piperazin-1-yl)phenyl)thieno[3,2-b]pyridin-7-yloxy)phenylcarbamothioyl)-2-phenylacetamide di-hydrochloride (159)

Following the procedure described above for the synthesis of compound 137a (scheme 25, example 97) but substituting compound 135b for the compound 158, title compound 159 was obtained in 21% yield. $^1$H NMR (400 MHz, DMSO-$d_6$) δ ppm: 12.48(s, 1H), 11.84 (s, 1H), 9.26(bs, 1H), 8.62(d, J=5.6 Hz, 1H), 8.05(d, J=12.0 Hz, 1H), 7.94 (s, 1H), 7.81(d, J=8.8 Hz, 2H), 7.62-7.55 (m, 2H), 7.37-7.31 (m, 4H), 7.31-7.24 (m, 1H), 7.10(d, J=8.8 Hz, 2H), 6.85(d, J=5.6 Hz, 1H), 3.83 (s, 2H), 3.58-3.51 (m, 4H), 3.26-3.18 (m, 4H). LRMS (M+1) 597.2 (100%).

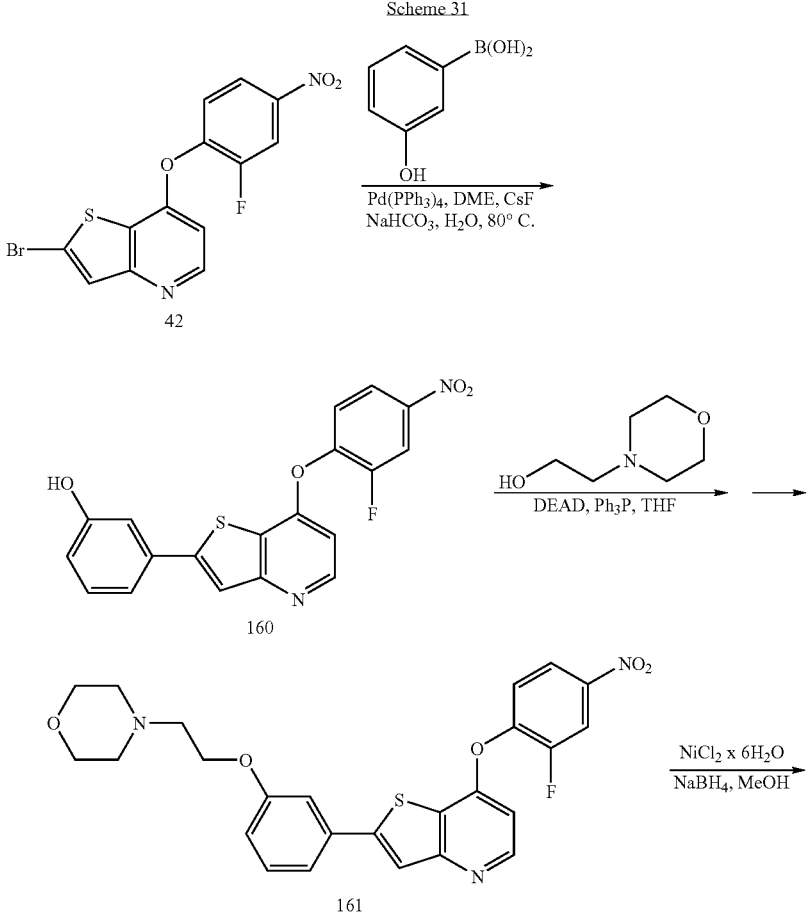

Scheme 31

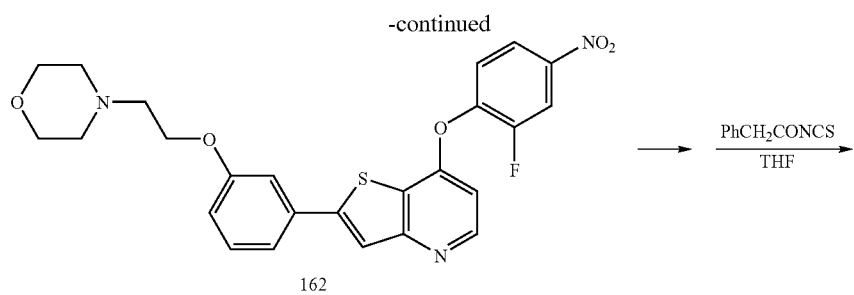

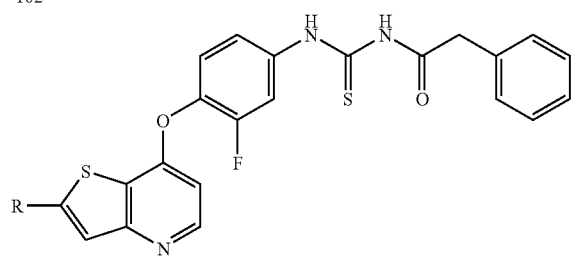

163a: Example 122

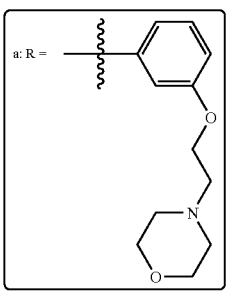

Example 122

N-(3-Fluoro-4-(2-(3-(2-morpholinoethoxy)phenyl)thieno[3,2-b]pyridin-7-yloxy)phenylcarbamothioyl)-2-phenylacetamide (163a)

Step 1. 3-(7-(2-Fluoro-4-nitrophenoxy)thieno[3,2-b]pyridin-2-yl)phenol (160)

Starting from the nitrobromo compound 42, following the procedure described above for the synthesis of compound 153 (scheme 28, example 109) but substituting 4-hydroxyphenylboronic acid for 3-hydroxyphenylboronic acid, title compound 160 was obtained in 66% yield as a gray solid. LRMS (M+1) 383.1 (100%).

Step 2. 4-(2-(3-(7-(2-Fluoro-4-nitrophenoxy)thieno[3,2-b]pyridin-2-yl)phenoxy)ethyl)morpholine (161)

Diethylazodicarboxylate (0.6 mL, 3.84 mmol) was added to the solution of 160 (1.05 g, 2.75 mmol), 2-morpholinoethanol (0.5 mL, 3.84 mmol) and triphenylphosphine (1.01 g, 3.84 mmol) in tetrahydrofuran (27 mL). The reaction mixture was stirred until its completion, quenched with saturated aqueous ammonium chloride and extracted with EtOAc. The organic phase was washed with water and brine, dried over anhydrous magnesium sulfate, filtered and evaporated under reduced pressure. The residue was purified by flash chromatography, eluent MeOH-DCM (2:98) to afford title compound 161 (906 mg, 66% yield) as a light-yellow solid. LRMS (M+1) 496.3 (100%).

Step 3. 3-Fluoro-4-(2-(3-(2-morpholinoethoxy)phenyl)thieno[3,2-b]pyridin-7-yloxy)benzenamine (162)

Following the procedure described above for the synthesis of amine 49 (scheme 10, example 55) but substituting nitro compound 48 for the nitro compound 161, title compound 162 was obtained in 91% yield (crude material, used in the next step without additional purification). LRMS (M+1) 466.2 (100%).

Step 4. N-(3-Fluoro-4-(2-(3-(2-morpholinoethoxy)phenyl)thieno[3,2-b]pyridin-7-yloxy)phenylcarbamothioyl)-2-phenylacetamide (163a)

Following the procedure described above for the synthesis of compound 50 (scheme 10, example 55) but substituting amine 49 for the amine 162, title compound 163a was obtained in 29% yield. Characterization of 163a is provided in the table 15. [LRMS (M+1) 643.3 (100%).

Examples 123-127

N-(3-Fluoro-4-(2-(4-(2-morpholinoethoxy)phenyl)thieno[3,2-b]pyridin-7-yloxy)phenylcarbamothioyl)-2-phenylacetamide (163b)

N-(3-Fluoro-4-(2-(4-(2-(piperidin-1-yl)ethoxy)phenyl)thieno[3,2-b]pyridin-7-yloxy)phenylcarbamothioyl)-2-phenylacetamide (163c)

N-(3-Fluoro-4-(2-(4-(2-(pyridin-2-yl)ethoxy)phenyl)thieno[3,2-b]pyridin-7-yloxy)phenylcarbamothioyl)-2-phenylacetamide hydrochloride (163d)

N-(3-Fluoro-4-(2-(4-(3-morpholinopropoxy)phenyl)
thieno[3,2-b]pyridin-7-yloxy)phenylcarbamothioyl)-
2-phenylacetamide (163e)

tert-Butyl 2-(4-(7-(2-fluoro-4-(3-(2-phenylacetyl)
thioureido)phenoxy)thieno[3,2-b]pyridin-2-yl)phe-
noxy)ethyl(methyl)carbamate (163f)

Starting from the phenol 153 (scheme 28, example 109) and following the procedures described above for the synthesis of 163a (Scheme 31, Example 122) title compounds 163b-f were obtained. Characterization of 163b-f is provided in the Table 15.

Examples 128-129

N-(3-Fluoro-4-(2-(3-methoxy-4-(2-morpholinoet-
hoxy)phenyl)thieno[3,2-b]pyridin-7-yloxy)phenyl-
carbamothioyl)-2-phenylacetamide (163g)

N-(3-Fluoro-4-(2-(2-(2-morpholinoethoxy)phenyl)
thieno[3,2-b]pyridin-7-yloxy)phenylcarbamothioyl)-
2-phenylacetamide hydrochloride (163h)

Following the procedures described above for the synthesis of 163a (Scheme 31, example 122) but replacing in the first step 3-hydroxyphenylboronic acid with 4-hydroxy-3-methoxyphenylboronic acid or 2-hydroxyphenylboronic acid, title compounds 163g-h were obtained. Characterization of 163g-h is provided in the table 15.

TABLE 15

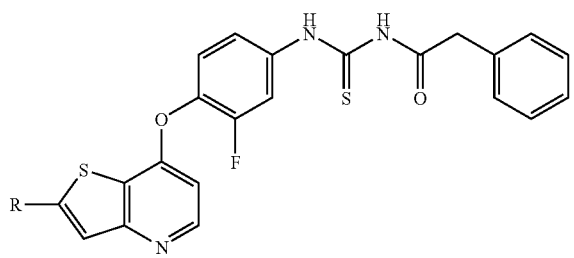

163a–h: Example 122–128

Characterization of compounds 163a–h (examples 122–128)

| Cpd | Ex | R | Name | Characterization |
|---|---|---|---|---|
| 163a | 122 | (3-position, -O-CH2CH2-N-morpholine on phenyl) | N-(3-Fluoro-4-(2-(3-(2-morpholinoethoxy)phenyl)thieno[3,2-b]pyridin-7-yloxy)phenyl-carbamothioyl)-2-phenylacetamide | $^1$H NMR (400 MHz, DMSO-d$_6$) δ ppm: 12.47 (s, 1H), 11.82 (s, 1H), 8.52 (d, 1H, J=5.5 Hz), 8.12 (s, 1H), 8.01 (d, 1H, J=12.1 Hz), 7.54–7.52(m, 2H), 7.45–7.26 (m, 8H), 7.04–7.01 (m, 1H), 6.65 (d, 1H, J=5.3 Hz), 4.20 (t, 2H, J=5.8 Hz), 3.83 (s, 2H), 3.57 (t, 4H, J=4.6 Hz), 2.73 (t, 2H, J=5.6 Hz), 2.51–2.49 (m, 4H). |
| 163b | 123 | (4-position, -O-CH2CH2-N-morpholine on phenyl) | N-(3-Fluoro-4-(2-(4-(2-morpholinoethoxy)phenyl)thieno[3,2-b]pyridin-7-yloxy)phenyl-carbamothioyl)-2-phenylacetamide | $^1$H NMR (400 MHz, DMSO-d$_6$) δ ppm: 12.46(s, 1H), 11.82(s, 1H), 8.49(s, J=5.6 Hz, 1H), 8.00(d, J=12.0 Hz, 1H), 7.94(s, 1H), 7.90–7.78(m, 2H), 7.56–7.38(m, 2H), 7.39–7.22(m, 5H), 7.16–7.02(m, 2H), 6.62(d, J=5.6 H, 1H), 4.34–3.90(m, 3H), 3.82(s, 2H), 3.76–2.40(m, 9H). |
| 163c | 124 | (4-position, -O-CH2CH2-N-piperidine on phenyl) | N-(3-Fluoro-4-(2-(4-(2-(piperidin-1-yl)ethoxy)phenyl)thieno[3,2-b]pyridin-yloxy)phenylcarbamothioyl)-2-phenylacetamide | $^1$H NMR (400 MHz, DMSO-d$_6$) δ ppm: 8.52(bs, 1H), 8.38(d, J=5.6 Hz, 1H), 8.0(dd, J=2.0 and 12.0 Hz, 1H), 7.75(d, J=8.4 Hz, 2H), 7.64(s, 1H), 7.44–7.40(m, 1H), 7.38–7.29(m, 5H), 7.29–7.24(m, 1H), 7.07(d, J=8.4 Hz, 2H), 6.60(d, J=5.6 Hz, 1H), 4.39–4.31(m, 2H), 3.75(s, 2H), 3.39–3.33(m, 2H), 3.20–3.05(m, 4H), 1.89–1.79(m, 4H), 1.70–1.60(m, 2H). |

TABLE 15-continued

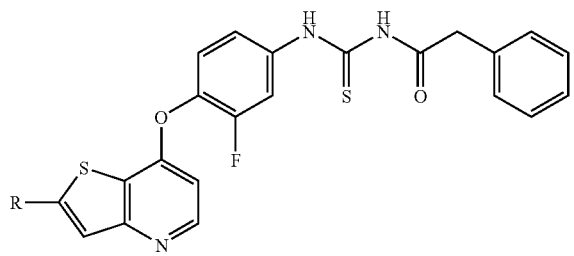

163a–h: Example 122–128

Characterization of compounds 163a–h (examples 122–128)

| Cpd | Ex | R | Name | Characterization |
|---|---|---|---|---|
| 163d | 125 | (4-(2-(pyridin-2-yl)ethoxy)phenyl) | N-(3-Fluoro-4-(2-(4-(2-(pyridin-2-yl)ethoxy)phenyl)thieno[3,2-b]pyridin-7-yloxy)phenylcarbamothioyl)-2-phenylacetamide hydrochloride | $^1$H NMR (400 MHz, DMSO-$d_6$) δ ppm: 12.48(s, 1H), 11.84(s, 1H), 8.81(d, J=4.8 Hz, 1H), 8.61(d, J=5.6 Hz, 1H), 8.44(t, J=7.6 Hz, 1H), 8.35–7.98(m, 2H), 7.97(s, 1H), 7.86(d, J=8.8 Hz, 2H), 7.61–7.55(m, 2H), 7.38–7.31(m, 4H), 7.31–7.24(m, 1H), 7.07(d, J=8.8 Hz, 2H), 6.82(d, J=5.6 Hz, 1H), 4.51(t, J=6.0 Hz, 2H), 3.83(s, 2H), 3.52(t, J=6.0 Hz, 2H). |
| 163e | 126 | (4-(3-morpholinopropoxy)phenyl) | N-(3-Fluoro-4-(2-(4-(3-morpholinopropoxy)phenyl)thieno[3,2-b]pyridin-7-yloxy)phenylcarbamothioyl)-2-phenylacetamide | $^1$H NMR (400 MHz, DMSO-$d_6$) δppm: 12.46(s, 1H), 11.82(s, 1H), 8.48(d, 1H, J=5.3 Hz), 8.00(d, 1H, J=12.5 Hz), 7.91(s, 1H), 7.80(d, 2H, J=8.8 Hz), 7.53 (m, 2H), 7.34–7.22(m, 5H), 7.04(d, 2H, J=8.6 Hz), 6.61(d, 1H, J=5.7 Hz), 4.10–4.07(m, 2H), 3.83(s, 2H), 3.59–3.55(m, 4H), 2.50–2.41(m, 6H), 1.92(m, 2H) |
| 163f | 127 | (4-(2-(N-Boc-methylamino)ethoxy)phenyl) | tert-Butyl 2-(4-(7-(2-fluoro-4-(3-(2-phenylacetyl)thioureido)phenoxy)thieno[3,2-b]pyridin-2-yl)phenoxy)ethyl(methyl)carbamate | $^1$H NMR(400 MHz, DMSO-$d_6$) δ ppm: 12.50(S, 1H), 11.85(s, 1H), 8.50(d, 1H, J=5.5 Hz), 8.02(d, 1H, J=13.3 Hz), 7.94(s, 1H), 7.83(d, 2H, J=8.8 Hz), 7.55–7.54(m, 2H), 7.38–7.26(m, 5H), 7.08(d, 2H, J=8.8 Hz), 6.63(d, 1H, J=5.3 Hz), 4.17(br s, 2H), 3.83(s, 2H), 3.56(m, 2H), 2.90–2.86(m, 3H), 1.40–1.36(m, 9H). |
| 163g | 128 | (3-methoxy-4-(2-morpholinoethoxy)phenyl) | N-(3-Fluoro-4-(2-(3-methoxy-4-(2-morpholinoethoxy)phenyl)thieno[3,2-b]pyridin-7-yloxy)phenylcarbamothioyl)-2-phenylacetamide | $^1$H NMR(400 MHz, DMSO-$d_6$) δ ppm: 8.51(d, 1H, J=5.5 Hz), 8.03–8.01(m, 2H), 7.55–7.53(m, 2H), 7.47(d, 1H, J=2.2 Hz), 7.39–7.24(m, 6H), 7.10(d, 1H, J=8.6 Hz), 6.63(d, 1H, J=5.5 Hz), 4.14(t, 2H, J=5.9 Hz), 3.88(s, 3H), 3.83(s, 2H), 3.58(t, 4H, J=4.6 Hz), 2.71(t, 2H, J=5.9 Hz), 2.46–2.43(m, 4H). |
| 163h | 129 | (2-(2-morpholinoethoxy)phenyl) | N-(3-Fluoro-4-(2-(2-(2-morpholinoethoxy)phenyl)thieno[3,2-b]pyridin-7-yloxy)phenylcarbamothioyl)-2-phenylacetamide hydrochloride | $^1$H NMR(400 MHz, DMSO-$d_6$) δ ppm: ppm: 12.50(s, 1H), 11.86(s, 1H), 11.66–11.50(brs, 1H), 8.79–8.76(m, 1H), 8.37(d, 1H, J=5.9 Hz), 8.08(dd, 1H, J=11.3/2.0 Hz), 7.93(dd, 1H, J=7.6/1.6 Hz), 7.63–7.52(m, 3H), 7.35–7.16(m, 7H), 6.99(t, 1H, J=4.8 Hz), 4.71(br s, 2H), 3.93–3.91(m, 2H), 3.84(s, 2H), 3.80–3.77(m, 4H), 3.53–3.50(m, 2H), 3.36–3.33(m, 2H). |

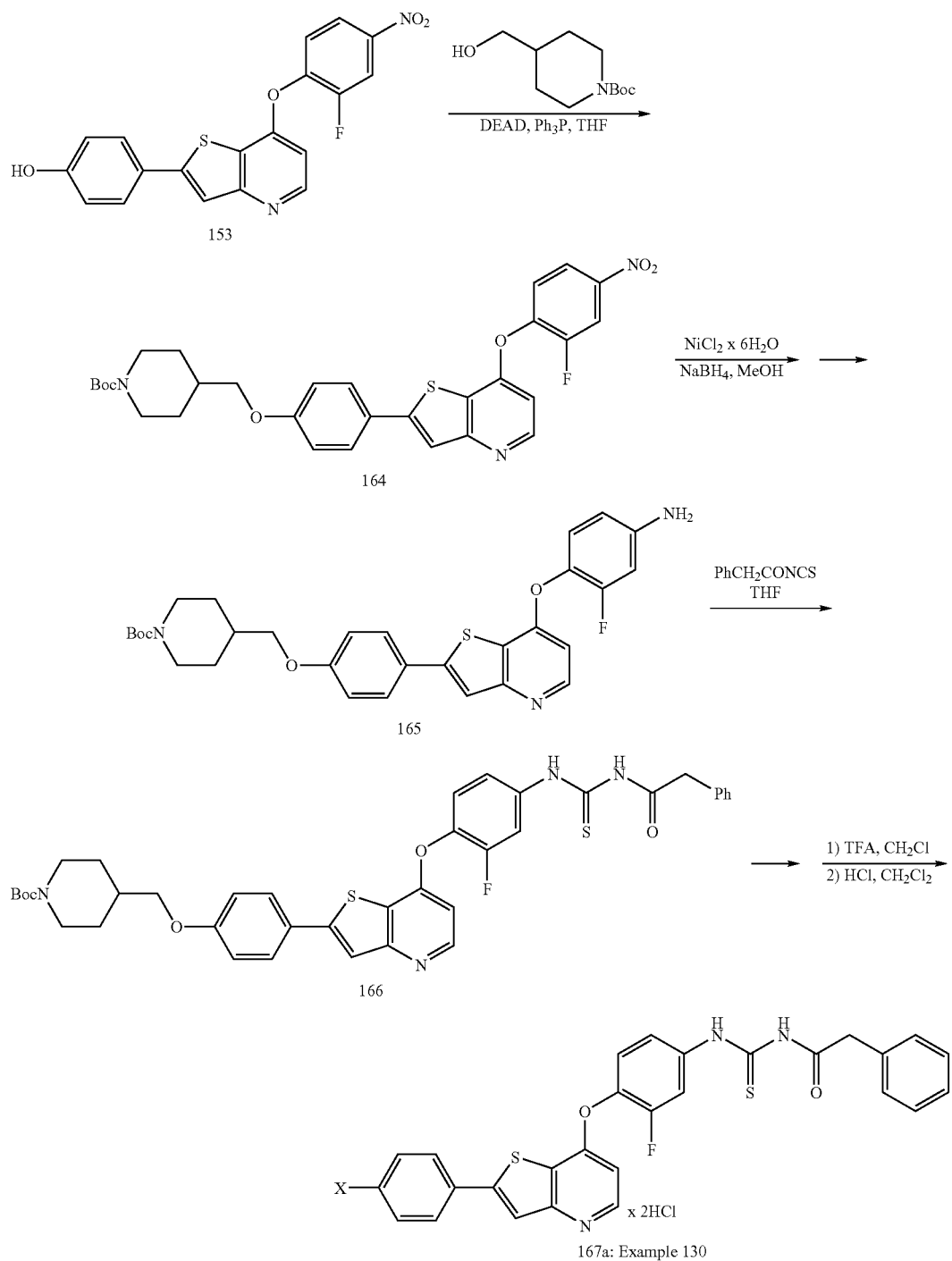

Example 130

N-(3-Fluoro-4-(2-(4-(piperidin-4-ylmethoxy)phenyl)thieno[3,2-b]pyridin-7-yloxy)phenylcarbamothioyl)-2-phenylacetamide (167a)

Step 1. tert-Butyl-4-((4-(7-(2-fluoro-4-nitrophenoxy)thieno[3,2-b]pyridin-2-yl)phenoxy)methyl)piperidine-1-carboxylate (164)

Starting from the compound 153 (shown in the scheme 28) and following the procedure described above for the synthesis of compound 161 (step 2, scheme 31, example 122), title compound 164 was obtained in 69% yield. LRMS (M+1) 579.2 (100%).

Step 2. tert-Butyl 4-((4-(7-(4-amino-2-fluorophenoxy)thieno[3,2-b]pyridin-2-yl)phenoxy)methyl)piperidine-1-carboxylate (165)

Following the procedure described above for the synthesis of amine 157 (scheme 30, example 121) but substituting nitro compound 156 for the nitro compound 164, title compound 165 was obtained in 99% yield (crude material, used in the next step without additional purification). LRMS (M+1) 549.2 (100%).

Step 3. tert-Butyl-4-((4-(7-(2-fluoro-4-(3-(2-phenylacetyl)thioureido)phenoxy)thieno[3,2-b]pyridin-2-yl)phenoxy)methyl)piperidine-1-carboxylate (166)

Following the procedure described above for the synthesis of compound 158 (scheme 30, example 121) but substituting amino compound 157 for the amino compound 165, title compound 166 was obtained in 31% yield. LRMS (M+1) 726.2 (100%).

Step 4. N-(3-Fluoro-4-(2-(4-(piperidin-4-ylmethoxy)phenyl)thieno[3,2-b]pyridin-7-yloxy)phenylcarbamothioyl)-2-phenylacetamide di-hydrochloride (167a)

Following the procedure described above for the synthesis of compound 159 (scheme 30, example 121) but substituting Boc-protected amino compound 158 for the Boc-protected amino compound 166, title compound 167a (presumably as a di-hydrochloride salt) was obtained in 15% yield. Characterization of 167a is provided in the table 16. LRMS (M+1) 626.2 (100%).

Example 131-132

(S)—N-(3-Fluoro-4-(2-(4-(pyrrolidin-2-ylmethoxy)phenyl)thieno[3,2-b]pyridin-7-yloxy)phenylcarbamothioyl)-2-phenylacetamide (167b) and

N-(4-(2-(4-(4-Aminobutoxy)phenyl)thieno[3,2-b]pyridin-7-yloxy)-3-fluorophenylcarbamothioyl)-2-phenylacetamide (167c)

Following the procedures described above for the synthesis of 167a (scheme 32, example 130) but replacing in the first step tert-butyl 4-(hydroxymethyl)piperidine-1-carboxylate with (S)-tert-butyl 2-(hydroxymethyl)pyrrolidine-1-carboxylate or tert-butyl 4-hydroxybutylcarbamate, title compounds 167b-c were obtained. Characterization of 167b-c is provided in the table 16.

TABLE 16

167a–c: Examples 130–132

Characterization of compounds 167a–c (examples 130–132)

| Cpd | Ex | X | Name | Characterization |
|---|---|---|---|---|
| 167a | 130 | 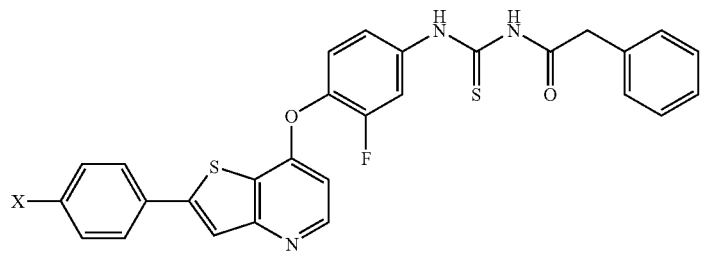 | N-(3-Fluoro-4-(2-(4-(piperidin-4-ylmethoxy)phenyl)thieno[3,2-b]pyridin-7-yloxy)phenyl-carbamothioyl)-2-phenylacetamide di-hydrochloride | $^1$H NMR (400 MHz, DMSO-d$_6$) δ ppm: 8.41(d, J=5.6 hz, 1H), 8.06(dd, J=3.2 and 12.4 Hz, 1H), 7.75(d, J=8.8 Hz, 2H), 7.65(s, 1H), 7.37–7.43(m, 1H), 7.39(d, J=8.4 Hz, 1H), 7.37–7.33(m, 4H), 7.33–7.25(m, 1H), 7.04(d, J=8.8 Hz, 2H), 6.64(d, J=5.6 Hz, 1H), 3.98(d, J=5.6 Hz, 2H), 3.76(s, 2H), 3.50–3.42(m, 2H), 3.12–3.01(m, 2H), 2.25–2.16(m, 1H), 2.16 2.06(m, 2H), 1.92–1.58(m, 2H). |

TABLE 16-continued

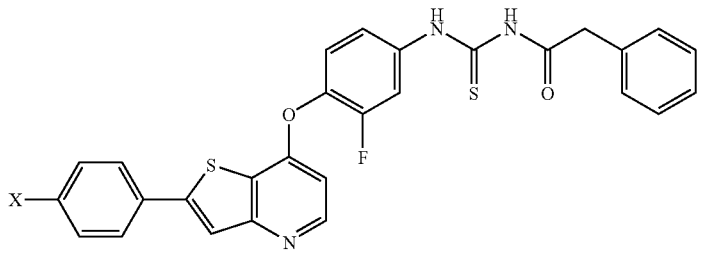

167a–c: Examples 130–132

Characterization of compounds 167a–c (examples 130–132)

| Cpd | Ex | X | Name | Characterization |
|---|---|---|---|---|
| 167b | 131 | (S)- pyrrolidin-2-ylmethoxy group | (S)-N-(3-Fluoro-4-(2-(4-(pyrrolidin-2-ylmethoxy)phenyl)thieno[3,2-b]pyridin-7-yloxy)phenylcarbamothioyl)-2-phenylacetamide di-hydrochloride | $^1$H NMR (400 MHz, DMSO-$d_6$) δ ppm: 12.46(s, 1H), 11.82(s, 1H), 8.49(d, J=5.6 Hz, 1H), 8.04–7.88(m, 1H), 7.96(s, 1H), 7.86(d, J=8.8 Hz, 1H), 7.56–7.51(m, 2H), 7.36–7.31(m, 4H), 7.31–7.24(m, 1H), 7.11(d, J=8.8 Hz, 2H), 6.63(d, J=5.6 Hz, 1H), 4.34(dd, J=4.4 and 10.8 Hz, 1H), 4.20–4.12(m, 1H), 4.00–3.90(m, 1H), 3.82(s, 2H), 3.28–3.18(m, 2H), 2.20–2.10(m, 1H), 2.05–1.88(m, 2H), 1.82–1.70(m, 1H). |
| 167c | 132 | —O(CH$_2$)$_4$NH$_2$ | N-(4-(2-(4-(4-Aminobutoxy)phenyl)thieno[3,2-b]pyridin-7-yloxy)-3-fluorophenylcarbamothioyl)-2-phenylacetamide di-hydrochloride | $^1$H NMR (400 MHz, DMSO-$d_6$) δ ppm: 8.40(d, J=5.6 Hz, 1H), 8.05(dd, J=3.2 and 12.0 Hz, 1H), 7.75(d, J=8.8 Hz, 2H), 7.64(s, H), 7.48–7.43(m, 1H), 7.39(d, J=8.8 Hz, 1H), 7.37–7.31(m, 4H), 7.31–7.24(m, 1H), 7.03(d, J=8.8 Hz, 2H), 6.64(d, j=5.6 Hz, 1H), 4.11(t, J=5.6 Hz, 2H), 3.76(s, 2H), 3.03(t, J=7.2 Hz, 2H), 1.99–1.83(m, 4H). |

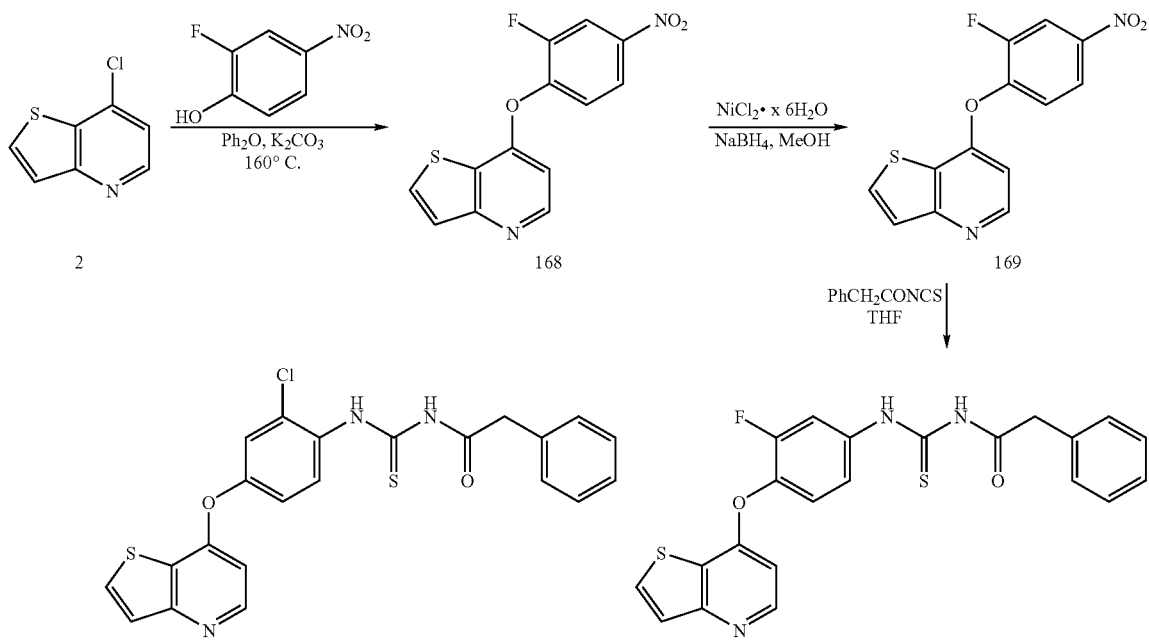

Scheme 33

170b: Example 134

170a: Example 133

Example 133

N-(3-Fluoro-4-(thieno[3,2-b]pyridin-7-yloxy)phenyl-carbamothioyl)-2-phenylacetamide (170a)

Step 1.
7-(2-Fluoro-4-nitrophenoxy)thieno[3,2-b]pyridine (168)

Starting from the chloride 2 (scheme 1) and following the procedure described above for the synthesis of compound 6 (scheme 1, example 1), title compound 168 was obtained in 45% yield. LRMS (M+1) 290.3 (100%).

Step. 3-Fluoro-4-(thieno[3,2-b]pyridin-7-yloxy)benzenamine (169)

Starting from the nitro compound 168 and following the procedure described above for the synthesis of amine 49 (scheme 10, example 55), title compound 169 was obtained in 41% yield. LRMS (M+1) 260.3 (100%).

Step 3. N-(3-Fluoro-4-(thieno[3,2-b]pyridin-7-yloxy) phenylcarbamothioyl)-2-phenylacetamide (170a)

Starting from the amine 169 and following the procedure described above for the synthesis of compound 50 (scheme 10, example 55), title compound 170a was obtained in 29% yield. $^1$H NMR (400 MHz, DMSO-d$_6$) δ ppm: 12.46 (s, 1H), 11.81 (s, 1H), 8.52(d, J=5.2 Hz, 1H), 8.17(d, J=5.2 Hz, 1H), 8.01(dd, J=2.0 and 11.2 Hz, 1H), 7.60(d, J=5.2 Hz, 1H), 7.58-7.48 (m, 2H), 7.36-7.30 (m, 4H), 7.30-7.22 (m, 1H), 6.64(d, J=5.2 Hz, 1H), 3.82 (s, 2H). LRMS (M+1) 437.5 (100%).

Example 134

N-(2-Chloro-4-(thieno[3,2-b]pyridin-7-yloxy)phenylcarbamothioyl)-2-phenylacetamide (170b)

Title compound 170b (example 134) was obtained according to the scheme 33 via a 3-step synthesis starting from the chloride 2 and replacing 2-fluoro-4-nitrophenol [in the step 1] with 3-chloro-4-nitrophenol. $^1$H NMR (400 MHz, DMSO-d$_6$) δ ppm: 12.36(s, H), 11.88(s, 1H), 8.55(d, J=5.6 Hz, 1H), 8.159d, J=5.6 Hz, 1H), 8.08(d, J=8.8 Hz, 1H), 7.61(d, J=2.8 Hz, 1H), 7.60(d, J=5.6 Hz, 1H), 7.36-7.30 (m, 4H), 7.32(m, J=2.8 Hz, 1H), 7.30-7.24 (m, 1H), 6.73(d, J=5.6 Hz, 1H), 3.84 (s, 2H).

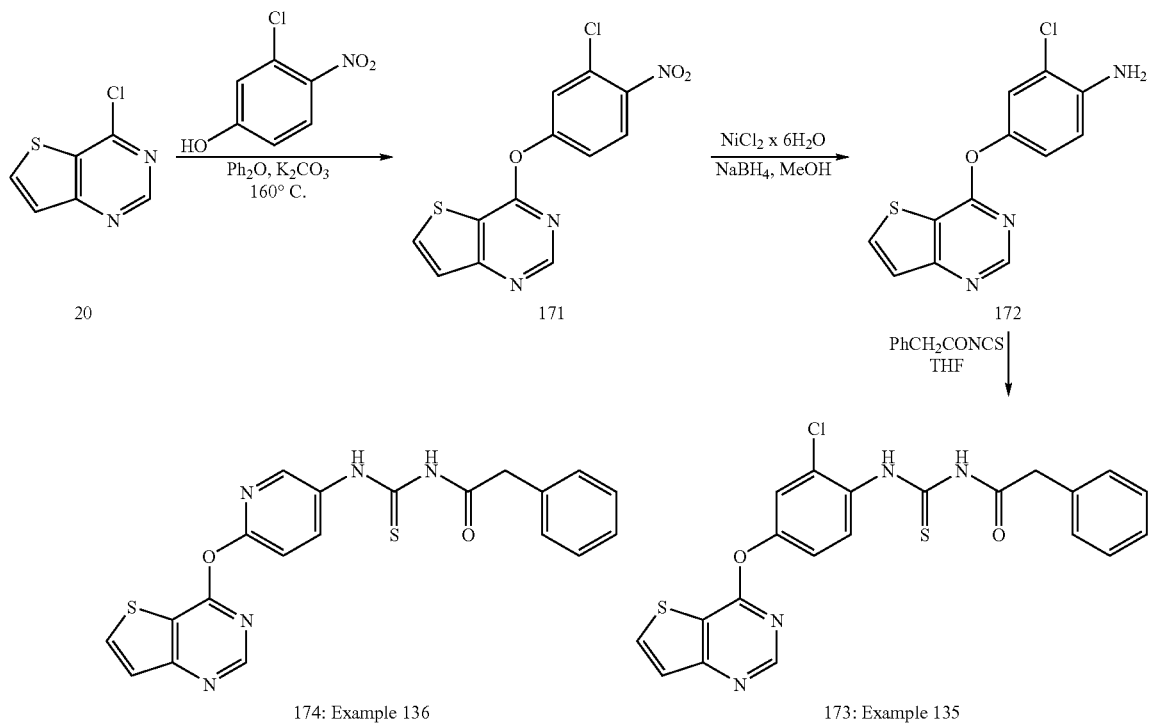

Scheme 34

174: Example 136

173: Example 135

Example 135

N-(2-Chloro-4-(thieno[3,2-d]pyrimidin-4-yloxy) phenylcarbamothioyl)-2-phenylacetamide (173)

Step 1.
4-(3-Chloro-4-nitrophenoxy)thieno[3,2-d]pyrimidine (171)

Starting from the chloride 20 (scheme 4) and following the procedure described above for the synthesis of compound 24 (scheme 4, example 22) replacing 2-fluoro-4-nitrophenol with 3-chloro-4-nitrophenol, title compound 171 was obtained in 72% yield. LRMS (M+1) 307.7 (100%).

Step 2. 2-Chloro-4-(thieno[3,2-d]pyrimidin-4-yloxy) benzenamine (172)

Starting from the nitro compound 171 and following the procedure described above for the synthesis of amine 25 (scheme 4, example 22), title compound 172 was obtained in 80% yield. LRMS (M+1) 277.7 (100%).

Step 3. N-(2-Chloro-4-(thieno[3,2-d]pyrimidin-4-yloxy)phenylcarbamothioyl)-2-phenylacetamide (173)

Starting from the amine 172 and following the procedure described above for the synthesis of compound 26a (scheme 4, example 22), title compound 173 was obtained in 9% yield. $^1$H NMR (400 MHz, DMSO-d$_6$) δ ppm: 12.35 (s, 1H), 11.89 (s, 1H), 8.72 (s, 1H), 8.48(d, J=5.6 Hz, 1H), 8.04(d, J=8.8 Hz, 1H), 7.69(d, J=2.8 Hz, 1H), 7.68(d, J=5.6 Hz, 1H), 7.40(dd, J=2.8 and 8.8 Hz, 1H), 7.36-7.30 (m, 4H), 7.30-7.24 (m, 1H), 3.84 (s, 2H). LRMS (M+1) (100%).

Example 136

2-Phenyl-N-(2-(thieno[3,2-d]pyrimidin-4-ylamino) pyrimidin-5-ylcarbamothioyl)acetamide (174)

Title compound 174 (example 136) was obtained according to the scheme 34 via a 3-step synthesis starting from the chloride 20 and replacing 3-chloro-4-nitrophenol [in the step 1] with 5-nitropyrimidin-2-amine. $^1$H NMR (400 MHz, DMSO-d$_6$) δ ppm: 11.85(bs, 2H), 10.91(bs, 1H), 8.71 (s, 1H), 8.64 (s, 2H), 8.63-8.61 (m, 1H), 8.25(d, J=5.6 Hz, 1H), 7.45 (d, J=5.6 Hz, 1H), 7.34-7.27 (m, 4H), 7.27-7.21 (m, 1H), 3.79 (s, 2H).

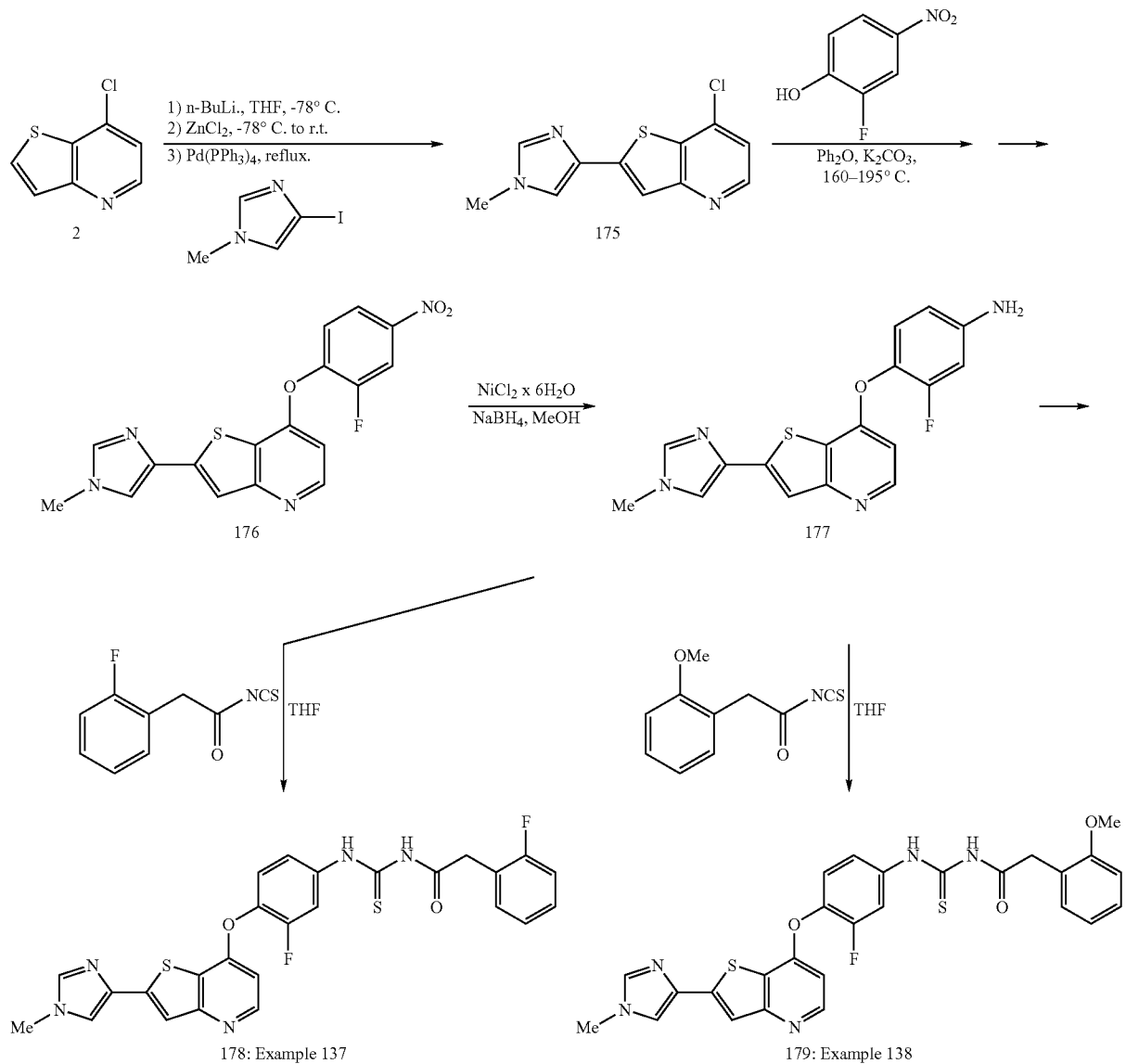

Example 137

N-(3-Fluoro-4-(2-(1-methyl-1H-imidazol-4-yl)thieno[3,2-b]pyridin-7-yloxy)phenylcarbamothioyl)-2-(2-fluorophenyl)acetamide (178)

Step 1. 7-Chloro-2-(1-methyl-1H-imidazol-4-yl)thieno[3,2-b]pyridine (175)

To a solution of chloride 2 (scheme 1) (2.45 g, 14.4 mmol) in THF (48 mL) at −78° C. was slowly added n-BuLi (2.5M in hexane, 7.2 mL, 18.0 mmol). The reaction mixture was stirred for one hour [at −78° C.] followed by slow addition of ZnCl (0.5M in THF, 36 mL, 18.0 mmol). In a few minutes the reaction mixture was allowed to warm to room temperature and stirred for one hour.

A solution of 4-iodo-1-methyl-1H-imidazole (1.50 g, 7.2 mmol) [*Tet. Lett.* 2004, 45, 5529] in THF (5 mL) and the tetrakis(triphenylphosphine)palladium (0) (0.83 g, 0.72 mmol) were added to the reaction mixture which was heated to reflux for 1 hour, cooled to room temperature, diluted with aqueous ammonium hydroxide and, finally neutralized with a 1N HCl solution. The acidic solution was extracted with DCM, the extract was washed with water and brine, dried over anhydrous magnesium sulfate, filtered and evaporated under reduced pressure. The residue was purified by flash chromatography (eluents DCM, then DCM-MeOH, 97:3) to afford title compound 175 (1.45 g, 81% yield) as a yellow solid. LRMS (M+1) 263.9 (100%), 265.9 (33%).

Step 2. 7-(2-Fluoro-4-nitrophenoxy)-2-(1-methyl-1H-imidazol-4-yl)thieno[3,2-b]pyridine (176)

Starting from the chloride 175 and following the procedure described above for the synthesis of compound 11 (scheme 2, example 12), title compound 176 was obtained in 47% yield. LRMS (M+1) 371.0 (100%).

Step 3. 3-Fluoro-4-(2-(1-methyl-1H-imidazol-4-yl)thieno[3,2-b]pyridin-7-yloxy)benzenamine (177)

Starting from the nitro compound 176 and following the procedure described above for the synthesis of amine 49 (scheme 10, example 55), title compound 177 was obtained in 74% yield. LRMS (M+1) 341.0 (100%).

Step 4. N-(3-Fluoro-4-(2-(1-methyl-1H-imidazol-4-yl)thieno[3,2-b]pyridin-7-yloxy)phenylcarbamothioyl)-2-(2-fluorophenyl)acetamide (178)

Starting from the amine 177, following the procedure described above for the synthesis of compound 50 (scheme 10, example 55) but replacing 2-phenylacetyl isothiocyanate with 2-(2-fluorophenyl)acetyl isothiocyanate, title compound 178 was obtained in 24% yield. $^1$H NMR (400 MHz, DMSO-$d_6$) δ ppm: 12.44 (s, 1H), 11.88 (s, 1H), 8.46 (d, 1H, J=5.5 Hz), 8.34 (dd, 1H, J=12.3/2.2 Hz), 7.87 (d, 1H, J=1.2 Hz), 7.72 (d, 1H, J=1.2 Hz), 7.69 (s, 1H), 7.57-7.49 (m, 2H), 7.43-7.31 (m, 2H), 7.23-7.15 (m, 2H), 6.59 (d, 1H, J=5.5 Hz), 3.94 (s, 2H), 3.73 (s, 3H). LRMS (M+1) 536.1 (100%).

Example 138

N-(3-Fluoro-4-(2-(1-methyl-1H-imidazol-4-yl)thieno[3,2-b]pyridin-7-yloxy)phenylcarbamothioyl)-2-(2-methoxyphenyl)acetamide (179)

Starting from the amine 177, following the procedure described above for the synthesis of compound 50 (scheme 10, example 55) but replacing 2-phenylacetyl isothiocyanate with 2-(2-methoxyphenyl)acetyl isothiocyanate, title compound 179 was obtained in 52% yield. $^1$H NMR (400 MHz, DMSO-$d_6$) δ ppm: 12.58 (s, 1H), 11.75 (s, 1H), 8.46 (d, 1H, J=5.5 Hz), 8.72 (dd, 1H, J=12.3/2.2 Hz), 7.86 (d, 1H, J=1.2 Hz), 7.72 (d, 1H, J=0.8 Hz), 7.70 (s, 1H), 7.57-7.49 (m, 2H), 7.30-7.23 (m, 2H), 7.00 (d, 1H, J=7.8 Hz), 6.92 (dt, 1H, J=7.3/0.9 Hz), 6.58 (d, 1H, J=5.1 Hz), 3.82 (s, 2H), 3.79 (s, 3H), 3.72 (s, 3H).

Scheme 26

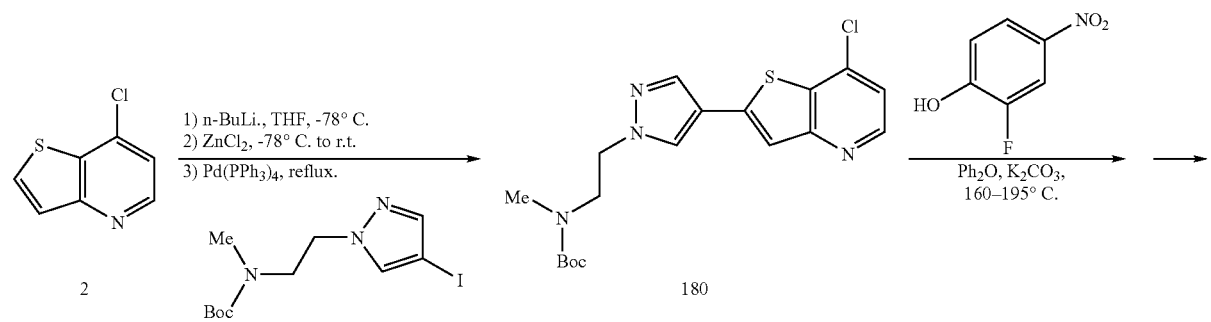

-continued
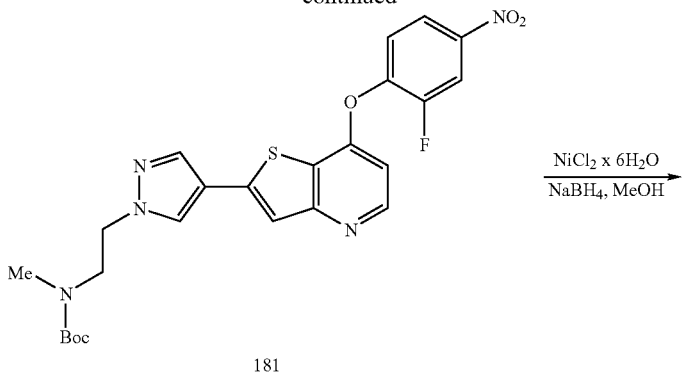
181
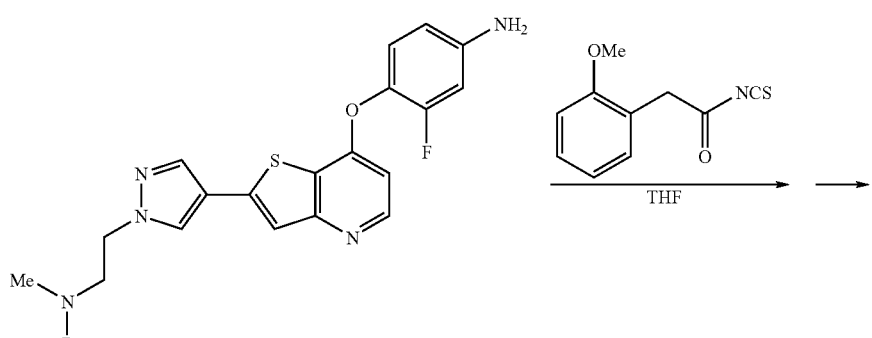
182
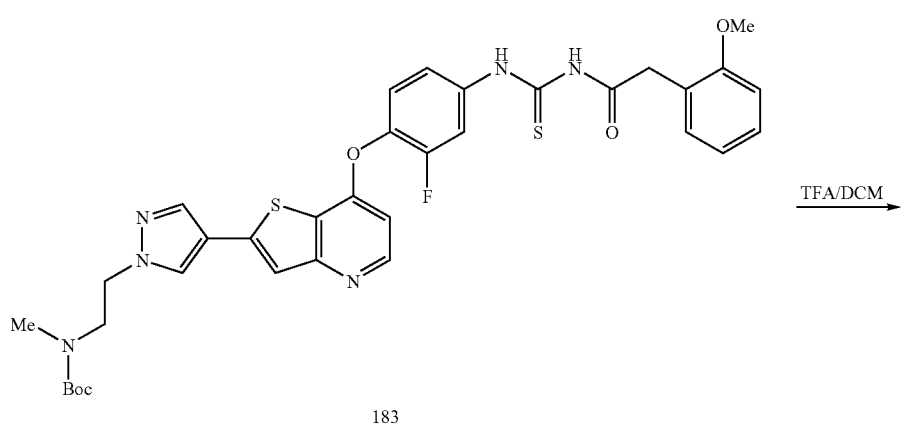
183
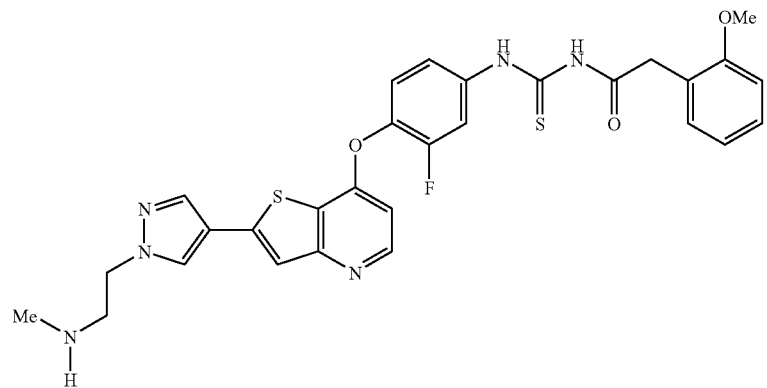
184: Example 139

Example 139

N-(3-Fluoro-4-(2-(1-(2-(methylamino)ethyl)-1H-pyrazol-4-yl)thieno[3,2-b]pyridin-7-yloxy)phenylcarbamothioyl)-2-(2-methoxyphenyl)acetamide (184)

Step 1. tert-Butyl 2-(4-(7-chlorothieno[3,2-b]pyridin-2-yl)-1H-pyrazol-1-yl)ethyl(methyl)carbamate (180)

Starting from the chloride 2 and following the procedure described above for the synthesis of 175 (scheme 35, example 138), but replacing 4-iodo-1-methyl-1H-imidazole with tert-butyl 2-(4-iodo-1H-pyrazol-1-yl)ethyl(methyl)carbamate, title compound 180 was obtained in 75% yield. LRMS (M+1) 393.1 (100%).

Step 2. tert-Butyl 2-(4-(7-(2-Fluoro-4-nitrophenoxy)thieno[3,2-b]pyridin-2-yl)-1H-pyrazol-1-yl)ethyl(methyl)carbamate (181)

Starting from the chloride 180 and following the procedure described above for the synthesis of compound 11 (scheme 2, example 12), title compound 181 was obtained in 37% yield. LRMS (M+1) 514.1 (100%).

Step 3. tert-Butyl 2-(4-(7-(4-amino-2-fluorophenoxy)thieno[3,2-b]pyridin-2-yl)-1H-pyrazol-1-yl)ethyl(methyl)carbamate (182)

Starting from the nitro compound 181 and following the procedure described above for the synthesis of amine 49 (scheme 10, example 55), title compound 182 was obtained in 22% yield. LRMS (M+1) 484.2 (100%).

Step 4. tert-Butyl 2-(4-(7-(2-fluoro-4-(3-(2-(2-methoxyphenyl)acetyl)thioureido)phenoxy)thieno[3,2-b]pyridin-2-yl)-1H-pyrazol-1-yl)ethyl(methyl)carbamate (183)

Starting from the amine 182, following the procedure described above for the synthesis of compound 50 (scheme 10, example 55) but replacing 2-phenylacetyl isothiocyanate with 2-(2-methoxyphenyl)acetyl isothiocyanate, title compound 183 was obtained in 90% yield. LRMS (M+1) 691.2 (100%).

Step 5. N-(3-Fluoro-4-(2-(1-(2-(methylamino)ethyl)-1H-pyrazol-4-yl)thieno[3,2-b]pyridin-7-yloxy)phenylcarbamothioyl)-2-(2-methoxyphenyl)acetamide (184)

Starting from the compound 183 and following the procedure described above for the synthesis of compound 159 (scheme 30, step 4, example 121), title compound 184 was obtained in 66% yield. $^1$H NMR (400 MHz, DMSO-d$_6$) δ ppm: 8.45(d, J=5.6 Hz, 1H), 8.33(s, 1H), 8.00 (s, 1H), 7.85-7.75 (m, 1H), 7.69 (s, 1H), 7.39(t, J=8.4 Hz, 1H), 7.35-7.28 (m, 1H), 7.28-7.22 (m, 1H), 7.22(d, J=7.6 Hz, 1H), 6.97(d, J=8.4 Hz, 1H), 6.89(t, J=7.6 Hz, 1H), 6.57(d, J=5.6 Hz, 1H), 4.19(t, J=6.4 Hz, 2H), 3.82 (s, 2H), 3.77 (s, 3H), 2.88(t, J=6.4 Hz, 2H), 2.28 (s, 3H).

Example 140

N-(3-Fluoro-4-(2-(1-(2-morpholinoethyl)-1H-imidazol-4-yl)thieno[3,2-b]pyridin-7-yloxy)phenylcarbamothioyl)-2-(2-methoxyphenyl)acetamide (185)

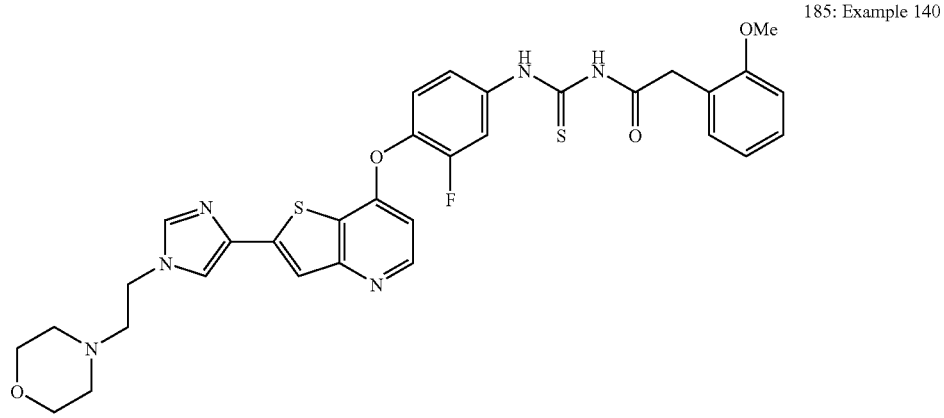

185: Example 140

Title compound 185 (example 140) was obtained following the procedures described above for compound 183 [according to the scheme 36] via a 4-step synthesis starting from chloride 2 and replacing tert-butyl 2-(4-iodo-1H-pyrazol-1-yl)ethyl(methyl)carbamate [in the step 1] with 4-(2-(4-iodo-1H-imidazol-1-yl)ethyl)morpholine [*Tet. Lett.* 2004, 45, 5529]. $^1$H NMR (400 MHz, DMSO-d$_6$) δ ppm: 12.56 (s, 1H), 11.75 (s, 1H), 8.55(d, J=5.6 Hz, 1H), 8.50-8.20 (m, 1H), 7.93(d, J=1.2 Hz, 1H), 7.78 (s, 1H), 7.60-7.55 (m, 2H), 7.35 (d, J=1.2 Hz, 1H), 7.32-7.25 (m, 1H), 7.23(dd, J=1.6 and 7.2 Hz, 1H), 7.00(d, J=7.6 Hz, 1H), 6.92(td, J=0.8 and 7.6 Hz, 1H), 6.69(d, J=5.6 Hz, 1H), 4.35(t, J=6.0 Hz, 2H), 3.81 (s, 2H), 3.78 (s, 3H), 3.48(t, J=4.4 Hz, 4H), 2.59(t, J=6.0 Hz, 2H), 2.35(t, J=4.4 Hz, 4H).

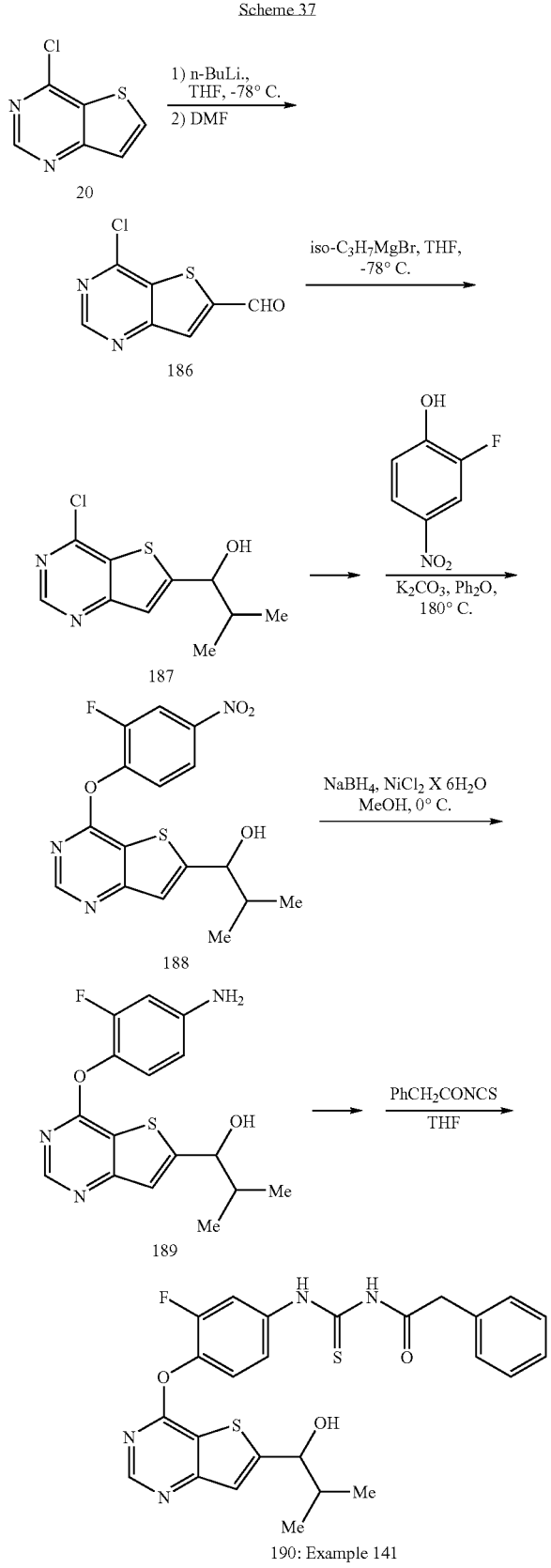

Scheme 37

Example 141

N-(3-Fluoro-4-(6-(1-hydroxy-2-methylpropyl)thieno[3,2-d]pyrimidin-4-yloxy)phenylcarbamothioyl)-2-phenylacetamide (190)

Step 1.
4-Chloro-thieno[3,2-d]pyrimidine-6-carbaldehyde (186)

Starting from 4-chloro-thieno[3,2-d]pyrimidine (20, scheme 4) and following procedure described above for the synthesis of aldehyde 14 (scheme 3, step 1, example 20), title compound 186 was obtained in 84% yield. LRMS (M+1) 199.0 (100%).

Steps 2-3. 1-[4-(2-Fluoro-4-nitro-phenoxy)-thieno[3,2-d]pyrimidin-6-yl]-ethanol (188)

Starting from the aldehyde 186 and following procedures described above for the synthesis of nitro compound 16 (scheme 3, steps 2-3, example 20), title compound 188 was obtained [via the intermediate alcohol 187], in 25% yield. LRMS (M+1) 336.0 (100%).

Steps 3-4. N-(3-Fluoro-4-(6-(1-hydroxy-2-methylpropyl)thieno[3,2-d]pyrimidin-4-yloxy)phenylcarbamothioyl)-2-phenylacetamide (190)

Starting from the nitro compound 188 and following procedures described above for the synthesis of compound 18a (scheme 3, steps 4-5, example 20), title compound 190 was obtained [via the intermediate amino alcohol 189], in 24% yield. $^1$H NMR (400 MHz, DMSO-$d_6$) δ ppm: 12.42 (s, 1H), 11.80 (s, 1H), 8.64 (s, 1H), 7.90(dd, J=2.0 and 12.0 Hz, 1H), 7.52(t, J=8.4 Hz, 1H), 7.48(d, J=0.8 Hz, 1H), 7.46(dd, J=2.0 and 8.4 Hz, 1H), 7.36-7.31 (m, 4H), 7.31-7.24 (m, 1H), 6.15 (d, 4.8 Hz, 1H), 4.82(td, J=0.8 and 5.2 Hz, 1H), 3.82 (s, 2H), 2.10-1.98 (m, 1H), 0.93(d, J=6.8 Hz, 3H), 0.90(d, J=6.8 Hz, 3H).

Examples 142-148

N-(3-Fluoro-4-(6-(pyrrolidine-1-carbonyl)thieno[3,2-d]pyrimidin-4-yloxy)phenylcarbamothioyl)-2-phenylacetamide (26f)

N-(4-(2-(Azetidine-1-carbonyl)thieno[3,2-b]pyridine-7-yloxy)-3-fluorophenylcarbamothioyl)-2-phenylacetamide hydrochloride (26g)

1-(4-(6-(N-Ethyl-N-methylcarbamoyl)thieno[3,2-d]pyrimidin-4-yloxy)-3-fluorophenyl)-3-(2-phenylacetyl)thiourea (26h)

N,N-Diethyl-4-(2-fluoro-4-(3-(2-phenylacetyl)thioureido)phenoxy)thieno[3,2-d]pyrimidine-6-carboxamide (26i)

(R)—N-(3-Fluoro-4-(6-(2-(hydroxymethyl)pyrrolidine-1-carbonyl)thieno[3,2-d]pyrimidin-4-yloxy)phenylcarbamothioyl)-2-phenylacetamide (26j)

(S)—N-(4-(6-(3-(tert-Butyldimethylsilyloxy)pyrrolidine-1-carbonyl)thieno[3,2-d]pyrimidin-4-yloxy)-3-fluorophenylcarbamothioyl)-2-phenylacetamide (26k)

tert-Butyl 1-(4-(2-fluoro-4-(3-(2-phenylacetyl)thio-ureido)phenoxy)thieno[3,2-d]pyrimidine-6-carbonyl)pyrrolidin-3-ylcarbamate (26l)

Compounds 26f-l (examples 142-148) were obtained by following the procedures described above for the compound 26a (example 22, scheme 4). Characterization of 26f-l is provided in the table 17.

TABLE 17

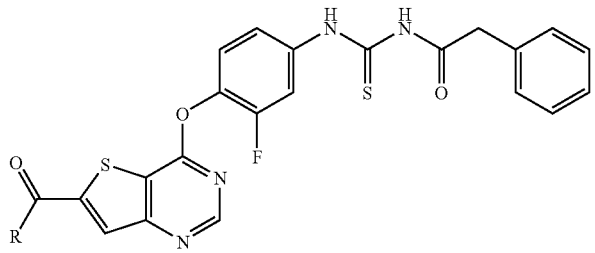

26f–l: Examples 142–148

Characterization of compounds 26f–l (examples 142–148)

| Cpd | Ex | R | Name | Characterization |
|---|---|---|---|---|
| 26f | 142 | | N-(3-Fluoro-4-(6-(pyrrolidine-1-carbonyl)thieno[3,2-d]pyrimidin-4-yloxy)phenylcarbamothioyl)-2-phenylacetamide | $^1$H NMR (400 MHz, DMSO-d$_6$) δ (ppm): 12.42(s, 1H), 11.79(s, 1H), 8.77(s, 1H), 8.11(s, 1H), 7.92(dd, J=2.0 and 11.6 Hz, 1H), 7.54(t, J=8.4 Hz, 1H), 7.47(dd, J=2.0 and 8.4 Hz, 1H), 7.36–7.31(m, 4H), 7.30–7.32(m, 1H), 3.85(t, J=6.4 Hz, 2H), 3.82(s, 2H), 3.55(t, J=6.4 Hz, 2H), 1.96(quin, J=6.4 Hz, 2H), 1.89(quin, J=6.4 Hz, 2H). |
| 26g | 143 | | N-(4-(2-(Azetidine-1-carbonyl)thieno[3,2-b]□yridine-7-yloxy)-3-fluorophenylcarbamothioyl)-2-phenylacetamide hydrochloride | $^1$H NMR (400 MHz, DMSO-d$_6$) δ (ppm): 12.48(s, 1H), 11.82(s, 1H), 8.64(d, J=5.6 Hz, 1H), 8.03(db, J=12.8 Hz, 1H), 7.91(s, 1H), 7.58–7.52(m, 2H), 7.37–7.31(m, 4H), 7.30–7.24(m, 1H), 6.82(d, J=5.6 Hz, 1H), 4.62(t, J=7.2 Hz, 2H), 4.11(t, J=7.2 Hz, 2H), 3.82(s, 2H), 2.35(quin, J=7.2 Hz, 2H). |
| 26h | 144 | | 1-(4-(6-(N-Ethyl-N-methylcarbamoyl)thieno[3,2-d]pyrimidin-4-yloxy)-3-fluorophenyl)-3-(2-phenylacetyl)thiourea | $^1$H NMR (400 MHz, DMSO-d$_6$) δ (ppm): 12.44(s, 1H), 11.81(s, 1H), 8.77(s, 1H), 8.03(s, 1/2H), 7.93(dd, 1H, J=11.9/2.3 Hz), 7.89(s, 1/2H), 7.54(t, 1H, J=8.5 Hz), 7.48(dd, 1H, J=8.8/2.2 Hz), 7.38–7.32(m, 4H), 7.30–7.25(m, 1H), 3.82(s, 2H), 3.52(m, 2H), 3.23(s, 3/2H), 3.04(s, 3/2H), 1.19(m, 3H). |
| 26i | 145 | | N,N-Diethyl-4-(2-fluoro-4-(3-(2-phenylacetyl)thioureido)phenoxy)thieno[3,2-d]pyrimidine-6-carboxamide | $^1$H NMR(400 MHz, DMSO-d$_6$) δ (ppm): 12.44(s, 1H), 11.80(s, 1H), 8.77(s, 1/3H), 8.77(s, 2/3H), 7.93(dd, 1H, J=2.2/11.9 Hz), 7.89(s, 1/3H), 7.89(s, 2/3H), 7.54(t, 1H, J=8.5 Hz), 7.48(dd, 1H, J=1.8/8.3 Hz), 7.34–7.33(m, 4H), 7.29–7.26(m, 1H), 3.83(s, 2H), 3.53–3.48(m, 4H), 1.21(m, 6H). |
| 26j | 146 | | ®-N-(3-Fluoro-4-(6-(2-(hydroxymethyl)pyrrolidine-1-carbonyl)thieno[3,2-d]pyrimidin-4-yloxy)phenylcarbamothioyl)-2-phenylacetamide | $^1$H NMR(400 MHz, DMSO-d$_6$) δ (ppm): 12.41(s, 1H); 11.80(s, 1H); 8.77 (s, 1H); 8.08(s, 1H); 7.92(d, J=11.6 Hz, 1H); 7.54(t, J=8.8 Hz, 1H); 7.49–7.45(m, 1H); 7.34–7.26(m, 5H); 4.84(t, J=4.4 Hz, 1H); 4.23–4.19(m, 1H); 3.91–3.78(m, 2H); 3.82(s, 2H); 3.62–3.51(m, 2H); 2.07–1.87(m, 4H). |

TABLE 17-continued

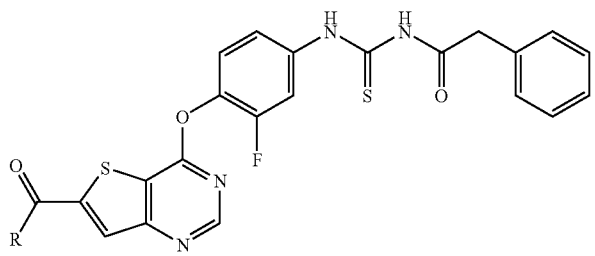

26f–l: Examples 142–148

Characterization of compounds 26f–l (examples 142–148)

| Cpd | Ex | R | Name | Characterization |
|---|---|---|---|---|
| 26k | 147 | ![pyrrolidine-OTBS] | (S)-N-(4-(6-(3-(tert-Butyldimethyl-silyloxy)pyrrolidine-1-carbonyl) thieno[3,2-d]pyrimidin-4-yloxy)-3-fluorophenylcarbamothioyl)-2-phenylacetamide | $^1$H NMR(400 MHz, CDCl$_3$) δ (ppm): 12.5(s, 1H), 8.79(s, 1H), 8.66(d, 1H, J=0.4 Hz), 8.03–7.91(m, 2H), 7.52–7.21(m, 6H), 4.60–4.52(m, 1H), 4.07–3.67(m, 4H), 2.13–1.97(m, 2H), 1.28–1.26(m, 2H), 0.93–0.89(m, 9H), 0.14–0.09(m, 6H). |
| 26l | 148 | ![pyrrolidine-NHBoc] | tert-Butyl 1-(4-(2-fluoro-4-(3-(2-phenylacetyl)thioureido)phenoxy) thieno[3,2-d]pyrimidine-6-carbonyl)pyrrolidin-3-ylcarbamate | 1H NMR (400 MHz, DMSO-d6) δ (ppm): 8.77(s, 1H), 8.09(s, 0.5H), 8.05(s, 0.5H), 7.96–7.93(m, 0.5H), 7.93–7.90(m, 0.5H), 7.58–7.50(m, 1H), 7.50–7.46(m, 1H), 7.38–7.31(nm, 4H), 7.31–7.24(m, 1H), 3.82(s, 2H), 4.15–1.20(m, 7H). |

Scheme 38

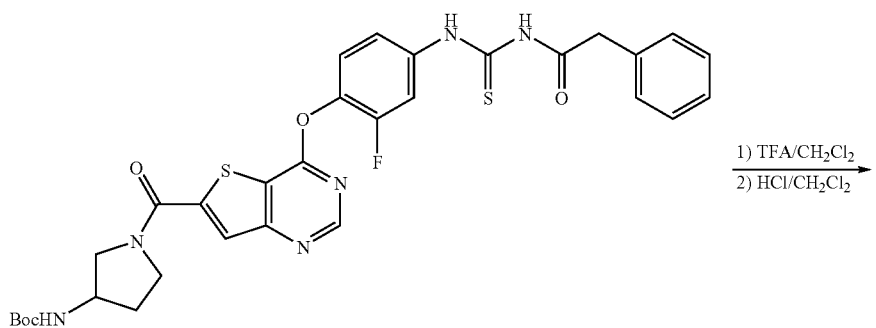

26l: Example 148

1) TFA/CH$_2$Cl$_2$
2) HCl/CH$_2$Cl$_2$

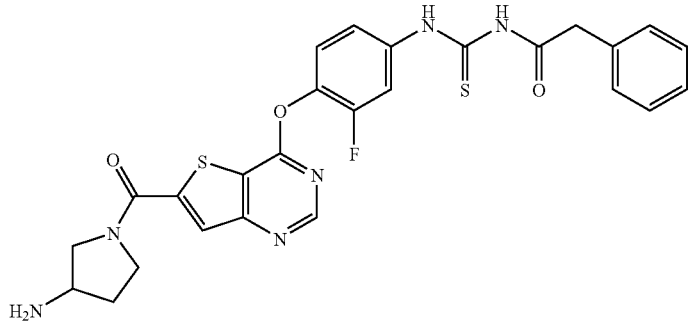

191: Example 149

Example 149

N-(4-(6-(3-Aminopyrrolidine-1-carbonyl)thieno[3,2-d]pyrimidin-4-yloxy)-3-fluorophenylcarbamothioyl)-2-phenylacetamide hydrochloride (191)

Following the procedure described above for the synthesis of compound 159 (scheme 30, example 121) but substituting Boc-protected amino compound 158 for the Boc-protected amino compound 26l, title compound 191 was obtained in 40% yield. $^1$H NMR (400 MHz, DMSO-$d_6$) δ (ppm): 8.77 (s, 1H), 8.12 (s, 0.5H), 8.06 (s, 0.5H), 7.92(dd, J=2.4 and 12.0 Hz, 1H), 7.54(t, J=8.4 Hz, 1H), 7.48(dd, J=2.4 and 8.4 Hz, 1H), 7.36-7.31 (m, 4H), 7.30-7.25 (m, 1H), 4.2-3.80 (m, 1H), 3.08 (s, 2H), 3.80-3.50 (m, 4H), 2.10-1.98 (m, 1H), 1.82-1.64 (m, 1H). LRMS (M+1) 550.6 (100%).

Scheme 39

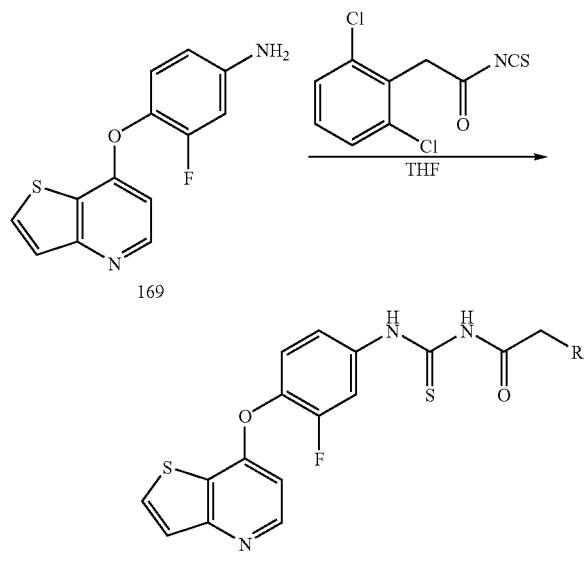

192a: Example 150

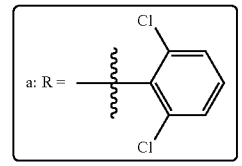

Example 150

2-(2,6-Dichlorophenyl)-N-(3-fluoro-4-(thieno[3,2-b]pyridin-7-yloxy)phenylcarbamothioyl)acetamide (192a)

Starting from the amine 169 (scheme 33), following the procedures described above for the synthesis of compound 170a (example 133) but replacing 2-phenylacetyl isothiocyanate with 2-(2,6-dichlorophenyl)acetyl isothiocyanate, title compound 192a was obtained in 7% yield. Characterization of 192a is provided in table 18.

Example 151

N-(3-Fluoro-4-(thieno[3,2-b]pyridin-7-yloxy)phenylcarbamothioyl)-2-(thiophen-2-yl)acetamide (192b)

Starting from the amine 169 (scheme 33), following the procedures described above for the synthesis of compound 170a (example 133) but replacing 2-phenylacetyl isothiocyanate with 2-(thiophen-2-yl)acetyl isothiocyanate, title compound 192b was obtained in 9% yield. Characterization of 192b is provided in table 18.

Example 152

2-(2,6-Difluorophenyl)-N-(3-fluoro-4-(thieno[3,2-b]pyridin-7-yloxy)phenylcarbamothioyl)acetamide (192c)

Starting from the amine 169 (scheme 33), following the procedures described above for the synthesis of compound 170a (example 133) but replacing 2-phenylacetyl isothiocyanate with 2-(2,6-difluorophenyl)acetyl isothiocyanate, title compound 192c was obtained in 23% yield. Characterization of 192c is provided in table 18.

Example 153

N-(3-Fluoro-4-(thieno[3,2-b]pyridin-7-yloxy)phenylcarbamothioyl)-1-phenylcyclopropanecarboxamide (192d)

Starting from the amine 169 (scheme 33), following the procedures described above for the synthesis of compound 170a (example 133) but replacing 2-phenylacetyl isothiocyanate with 1-phenylcyclopropanecarbonyl isothiocyanate, title compound 192d was obtained in 41% yield. Characterization of 192d is provided in table 18.

Example 154

N-(3-Fluoro-4-(thieno[3,2-b]pyridin-7-yloxy)phenyl-carbamothioyl)-2-phenylpropanamide (192e)

Starting from the amine 169 (scheme 33), following the procedures described above for the synthesis of compound 170a (example 133) but replacing 2-phenylacetyl isothiocyanate with 3-methyl-2-phenylbutanoyl isothiocyanate, title compound 192e was obtained in 49% yield. Characterization of 192e is provided in table 18.

Example 155

N-(3-Fluoro-4-(thieno[3,2-b]pyridin-7-yloxy)phenyl-carbamothioyl)-3-phenylpropanamide (192f)

Starting from the amine 169 (scheme 33), following the procedures described above for the synthesis of compound 170a (example 133) but replacing 2-phenylacetyl isothiocyanate with 3-phenylpropanoyl isothiocyanate, title compound 192f was obtained in 59% yield. Characterization of 192f is provided in table 18.

TABLE 18

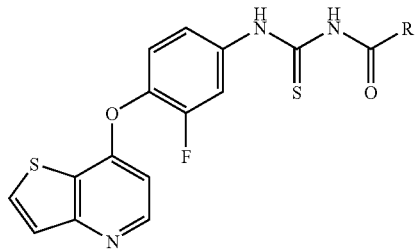

192a–f: Examples 150–155

Characterization of compounds 192a–f (examples 150–155)

| Cpd | Ex | R | Name | Characterization |
|---|---|---|---|---|
| 192a | 150 | 2,6-dichlorobenzyl (CH₂ linker) | 2-(2,6-Dichlorophenyl)-N-(3-fluoro-4-(thieno[3,2-b]pyridin-7-yloxy)phenylcarbamothioyl) acetamide | $^1$H NMR (400 MHz, DMSO-$d_6$) δ (ppm): 12.27(s, 1H), 12.01(s, 1H), 8.52(d, J=5.6 Hz, 1H), 8.35–8.00(m, J=12.0 Hz, 1H), 7.59(d, J=5.6 Hz, 1H), 7.58–7.47(m, 4H), 7.36(t, J=8.0 Hz, 1H), 6.64(d, J=5.6 Hz, 1H), 4.21(s, 2H). |
| 192b | 151 | thiophen-2-ylmethyl (CH₂ linker) | N-(3-Fluoro-4-(thieno[3,2-b]pyridin-7-yloxy)phenyl-carbamothioyl)-2-(thiophen-2-yl)acetamide | $^1$H NMR (400 MHz, DMSO-$d_6$) δ (ppm): 12.37(s, 1H), 11.80(s, 1H), 8.52(d, J=5.6 Hz, 1H), 8.17(d, J=5.6 Hz, 1H), 7.98(d, J=12.4 Hz, 1H), 7.60(d, J=5.6 Hz, 1H), 7.54–7.46(m, 2H), 7.42(dd, J=1.6 and 5.2 Hz, H), 7.20–6.97(m, 2H), 6.64(d, J= 5.6 Hz, 1H), 4.07(s, 2H). |
| 192c | 152 | 2,6-difluorobenzyl (CH₂ linker) | 2-(2,6-Difluorophenyl)-N-(3-fluoro-4-(thieno[3,2-b]pyridin-7-yloxy)phenyl-carbamothioyl)acetamide | $^1$H NMR (400 MHz, DMSO-$d_6$) δ (ppm): 12.28(s, H), 11.93(s, 1H), 8.52(d, J=5.6 Hz, H), 8.17(d, J=5.6 Hz, 1H), 8.03–7.98(m, 1H), 7.60(d, J=5.6 Hz, 1H), 7.57–7.48(m, 2H), 7.46–7.37(m, 1H), 7.12(t, J=7.6 Hz, 2H), 6.65(d, J=5.6 Hz, 1H), 3.96(s, 2H). |
| 192d | 153 | 1-phenylcyclopropyl | N-(3-Fluoro-4-(thieno[3,2-b]pyridin-7-yloxy)phenyl-carbamothioyl)-1-phenyl-cyclopropane carboxamide | $^1$H NMR (DMSO) δ (ppm): 12.31(1H, s), 9.26(1H, s), 8.52(1H, d, J=5.28 Hz), 8.17(1H, d, J=5.28 Hz), 7.96(1H, d, J= 11.93 Hz), 7.60(1H, d, J=5.28 Hz), 7.52–7.31(7H, m), 6.64(1H, d, J=5.09 Hz), 1.62(2H, brd, J=1.96 Hz), 1.33(2H, brd, J=2.35 Hz). MS (m/z) 464.2 (M + H). |

TABLE 18-continued

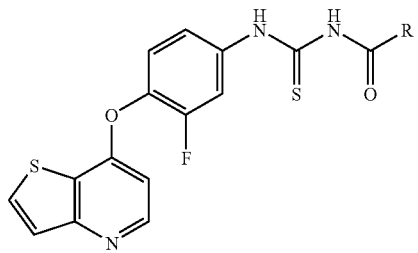

192a–f: Examples 150–155

Characterization of compounds 192a–f (examples 150–155)

| Cpd | Ex | R | Name | Characterization |
|---|---|---|---|---|
| 192e | 154 | Me, phenyl (CH(Me)Ph) | N-(3-Fluoro-4-(thieno[3,2-b]pyridin-7-yloxy)phenyl-carbamothioyl)-2-phenyl-propanamide | $^1$H NMR (400 MHz, DMSO-d$_6$) δ ppm 12.50(1H, s), 11.77(1H, s), 8.52(1H, d, J=5.28 Hz), 8.16(1H, d, J=5.48 Hz), 8.00(1H, d, J=11.74), 7.60(1H, d, J=5.48 Hz), 7.55–7.48(2H, m), 7.41–7.33(5H, m), 6.63(d, J=5.48 Hz), 4.10(1H, q, J=6.85 Hz), 1.44(3H, d, J=6.85 Hz). MS (m/z) 452.1 (M + H) |
| 192f | 155 | CH$_2$CH$_2$Ph | N-(3-Fluoro-4-(thieno[3,2-b]pyridin-7-yloxy)phenyl-carbamothioyl)-3-phenylpropanamide | $^1$H NMR(400 MHz, DMSO-d$_6$) δ ppm 12.58(2, 1H), 11.62(s, 1H), 8.53(1H, d, J=5.48 Hz), 8.17(1H, d, J=5.28 Hz), 8.03(1H, d, J=11.35 Hz), 7.60(1H, d, J=5.48 Hz), 7.53–7.52(2H, br), 7.31–7.21(5H, m), 6.66(1H, d, J=5.28 Hz), 2.92–2.87(2H, m), 2.83–2.79(2H, m). MS (m/z) 452.1 (M + H) |

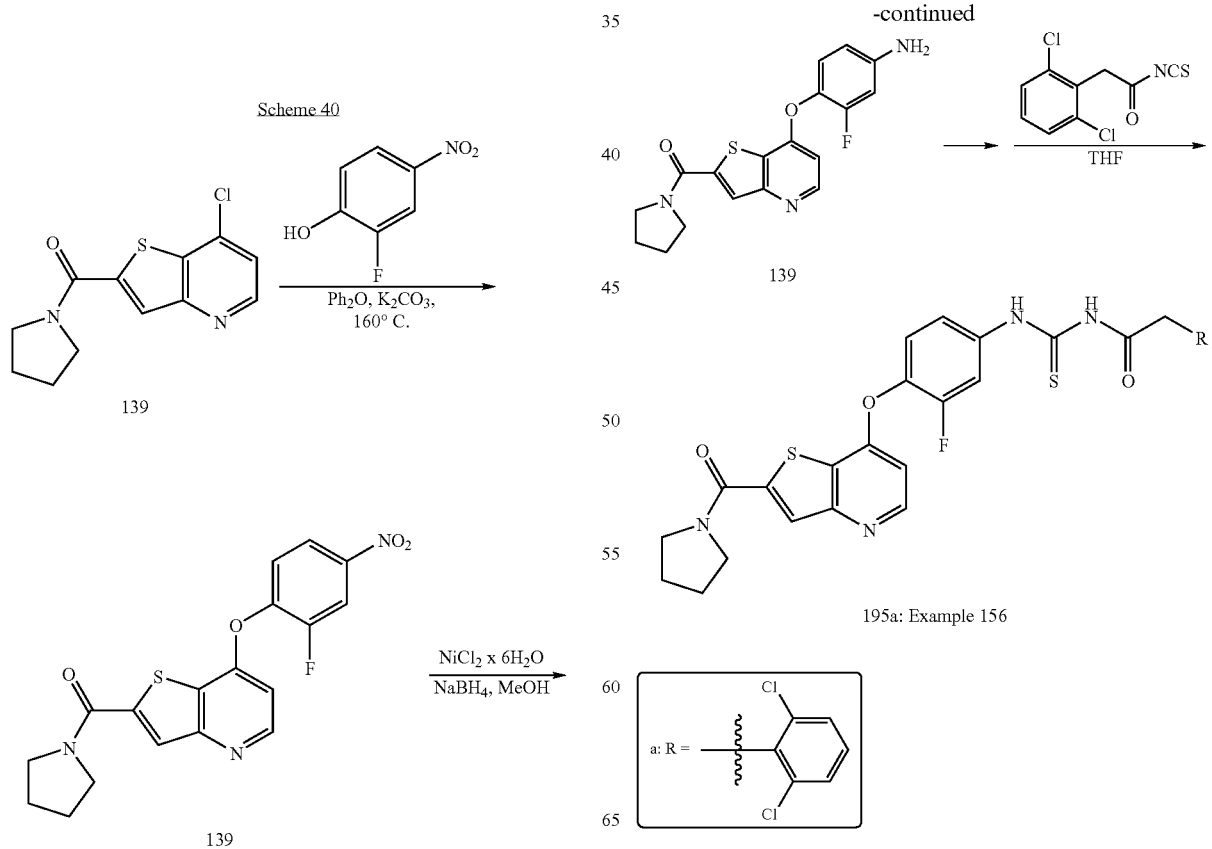

Example 156

2-(2,6-Dichlorophenyl)-N-(3-fluoro-4-(2-(pyrrolidine-1-carbonyl)thieno[3,2-b]pyridin-7-yloxy)phenylcarbamothioyl)acetamide (195a)

Step 1. (7-(2-Fluoro-4-nitrophenoxy)thieno[3,2-b]pyridin-2-yl)(pyrrolidin-1-yl)methanone (193)

Starting from (7-chlorothieno[3,2-b]pyridin-2-yl)(pyrrolidin-1-yl)methanone (139, scheme 26) and following the procedure described above for the synthesis of compound 6 (scheme 1, example 1), title compound 193 was obtained in (93% yield). LRMS (M+1) 387.4 (100%).

Step 2. (7-(4-Amino-2-fluorophenoxy)thieno[3,2-b]pyridin-2-yl)(pyrrolidin-1-yl)methanone (194)

Starting from the nitro compound 193 and following the procedures described above for the synthesis of amine 7, (scheme 1, example 1) title compound 194 was obtained in 92% yield. LRMS (M+1) 357.4 (100%).

Step 3. 2-(2,6-Dichlorophenyl)-N-(3-fluoro-4-(2-(pyrrolidine-1-carbonyl)thieno[3,2-b]pyridin-7-yloxy)phenylcarbamothioyl)acetamide (195a)

Starting from the amine 194 and following the procedure described above for the synthesis of compounds 50 (scheme 10), 170a (scheme 33) or 192a-f (scheme 39), title compound 195a was obtained in 70% yield. Characterization of 195a is provided in table 19.

Examples 157-181

Compounds 195b-q

Compounds 195b-q (examples 157-181) were obtained starting from the amine 194, following the procedure described above for the synthesis of compound 195a and replacing 2-(2,6-difluorophenyl)acetyl isothiocyanate with an appropriately substituted homologue. Characterization of 195b-q is provided in the table 19.

TABLE 19

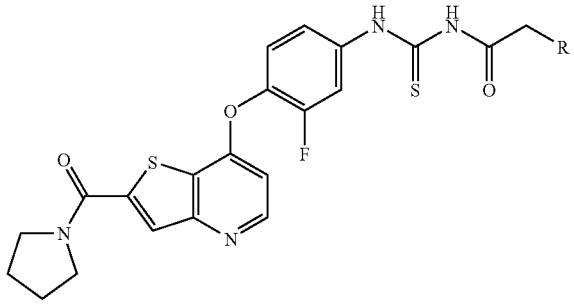

195a–q: Examples 156–181

Characterization of compounds 195 a–q (examples 156–181)

| Cpd | Ex | R | Name | Characterization |
|---|---|---|---|---|
| 195a | 156 | 2,6-dichlorophenyl | 2-(2,6-Dichlorophenyl)-N-(3-fluoro-4-(2-(pyrrolidine-1-carbonyl)thieno[3,2-b]pyridin-7-yloxy)phenylcarbamothioyl)acetamide hydrochloride | $^1$H NMR (400 MHz, DMSO-d$_6$) δ (ppm): 12.29(s, 1H), 12.02(s, 1H), 8.63(d, J=5.6 Hz, 1H), 8.08–8.02(m, 1H), 8.04(s, 1H), 7.62(m, 4H), 7.36(dd, J=7.2 and 8.4 Hz, 1H), 6.80(d, J=5.6 Hz, 1H), 4.21(s, 2H), 3.85(t, J=6.4 Hz, 2H), 3.54(t, J=6.4 Hz, 2H), 1.97(quint, J=6.4 Hz, 2H), 1.88(quint, J=6.4 Hz, 2H). |
| 195b | 157 | 2,6-difluorophenyl | 2-(2,6-Difluorophenyl)-N-(3-fluoro-4-(2-(pyrrolidine-1-carbonyl)thieno[3,2-b]pyridin-7-yloxy)phenylcarbamothioyl)acetamide hydrochloride | $^1$H NMR (400 MHz, DMSO-d$_6$) δ (ppm): 12.29(s, 1H), 11.94(s, 1H), 8.63(d, J=5.6 Hz, 1H), 8.07–8.01(m, 1H), 8.05(s, 1H), 7.60–7.51(m, 2H), 7.46–7.37(m, 1H), 7.18–709(m, 2H), 6.80(d, J=5.6 Hz, 1H), 3.97(s, 2H), 3.85(t, J=6.4 Hz, 2H), 3.54(t, J=6.4 Hz, 2H), 1.97(quin, J=6.4 Hz, 2H), 1.89(quin, J=6.4 Hz, 2H). |
| 195c | 158 | cyclohexyl | 2-Cyclohexyl-N-(3-fluoro-4-(2-(pyrrolidine-1-carbonyl)thieno[3,2-b]pyridin-7-yloxy)phenylcarbamothioyl)acetamide hydrochloride | $^1$H NMR (400 MHz, DMSO-d$_6$) δ (ppm): 12.67(s, 1H), 11.55(s, 1H), 8.65(d, J=5.6 Hz, 1H), 8.12–8.06(m, 1H), 8.06(s, 1H), 7.60–7.53(m, 2H), 6.82(d, J=5.6 Hz, 1H), 3.86(t, J=6.4 Hz, 2H), 3.54(t, J=6.4 Hz, 2H), 2.37(d, J=6.8 Hz, 2H), 1.97(quin, J=6.4 Hz, 2H), 1.89(quin, J=6.4 Hz, 2H), 1.71–1.58(m, 6H), 1.30–1.08(m, 3H), 1.07–0.92(m, 2H). |

TABLE 19-continued

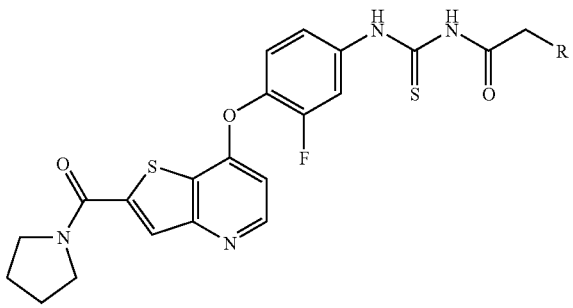

195a–q: Examples 156–181

Characterization of compounds 195 a–q (examples 156–181)

| Cpd | Ex | R | Name | Characterization |
|---|---|---|---|---|
| 195d | 159 | (4-methoxyphenyl) | N-(3-Fluoro-4-(2-(pyrrolidine-1-carbonyl)thieno[3,2-b]pyridin-7-yloxy)phenyl-carbamothioyl)-2-(4-methoxyphenyl)acetamide hydrochloride | $^1$H NMR (400 MHz, DMSO-d$_6$) δ (ppm): 12.50(s, 1H), 11.77(s, 1H), 8.64(d, J=5.6 Hz, 1H), 8.07–8.01(m, 1H), 8.05(s, H), 7.58–7.53(m, 2H), 7.28–7.22(m, 2H), 6.94–6.88(m, 2H), 6.81(d, J=5.6 Hz, 1H), 3.85(t, J=6.4 Hz, 2H), 3.73(s, 2H), 3.73(s, 3H), 3.54(t, J=6.4 Hz, 2H), 1.97(quin, J=6.4 Hz, 2H0, 1.89(quin, J=6.4 Hz, 2H). |
| 195e | 160 | (3-chlorophenyl) | 2-(3-Chlorophenyl)-N-(3-fluoro-4-(2-(pyrrolidine-1-carbonyl)thieno[3,2-b]pyridin-7-yloxy)phenylcarbamothioyl)acetamide hydrochloride | $^1$H NMR (400 MHz, DMSO-d$_6$) δ (ppm): 12.42(s, 1H), 11.83(s, 1H), 8.65(d, J=5.6 Hz, 1H), 8.07–8.01(m, 1H), 8.05(s, 1H), 7.59–7.52(m, 2H), 7.44–7.26(m, 4H), 6.82(d, J=5.6 Hz, 1H), 3.86(s, 2H), 3.85(t, J=6.4 Hz, 2H), 3.54(t, J=6.4 Hz, 2H), 1.97(quin, J=6.4 Hz, 2H), 1.89(quin, J=6.4 Hz, 2H). |
| 195f | 161 | (thiophen-2-yl) | N-(3-Fluoro-4-(2-(pyrrolidine-1-carbonyl)thieno[3,2-b]pyridin-7-yloxy)phenyl-carbamothioyl)-2-(thiophen-2-yl)acetamide hydrochloride | $^1$H NMR (400 MHz, DMSO-d$_6$) δ (ppm): 12.39(s, 1H), 11.82(s, 1H), 8.65(d, J=5.6 Hz, 1H), 8.08–8.00(m, 1H), 8.05(s, 1H), 7.60–.7.55(m, 2H), 7.46–7.42(m, 1H), 7.04–6.98(m, 2H), 6.83(d, J=5.6 Hz, 1H), 4.06(s, 2H), 3.85(t, J=6.4 Hz, 2H), 3.54(t, J=6.4 Hz, 2H), 1.98(quin, J=6.4 Hz, 2H), 1.89(quin, J=6.4 Hz, 2H). |
| 195g | 162 | (2-chloro-6-fluorophenyl) | 2-(2-Chloro-6-fluorophenyl)-N-(3-fluoro-4-(2-(pyrrolidine-1-carbonyl)thieno[3,2-b]pyridin-7-yloxy)phenyl-carbamothioyl)acetamide hydrochloride | $^1$H NMR (400 MHz, DMSO-d$_6$) δ (ppm): 12.30(s, 1H), 11.99(s, 1H), 8.63(d, J=5.6 Hz, 1H), 8.08–8.01(m, 1H), 8.05(s, 1H), 7.60–7.51(m, 2H), 7.44–7.36(m, 2H), 7.30–7.24(m, 1H), 6.80(d, J=5.6 Hz, 1H), 4.07(s, 2H), 3.85(t, J=6.4 Hz, 2H), 3.54(t, J=6.4 Hz, 2H), 1.95(quin, J=6.4 Hz, 2H), 1.89(quin, J=6.4 Hz, 2H). |
| 195h | 163 | (adamantan-1-yl) | 1-(2-Adamantan-1-yl-acetyl)-3-{3-fluoro-4-[2-(pyrrolidine-1-carbonyl)-thieno[3,2-b]pyridin-7-yloxy]-phenyl}-thiourea | $^1$H NMR (400 MHz, DMSO-d$_6$) δ (ppm): 12.75(s, 1H), 11.45(s, 1H), 8.67(d, J=5.6 Hz, 1H), 8.12(d, J=12.4 Hz, 1H), 8.06(s, 1H), 7.62–7.53(m, 2H), 6.86(d, J=5.6 Hz, 1H), 3.85(t, J=6.4 Hz, 2H), 3.54(t, J=6.4 Hz, 2H), 2.26(s, 2H), 2.02–1.92(m, 5H), 1.89(quin, J=6.4 Hz, 2H), 1.70–1.57(m, 12H). |
| 195i | 164 | (cyclopentyl) | 2-Cyclopentyl-N-(3-fluoro-4-(2-(pyrrolidine-1-carbonyl)thieno[3,2-b]pyridin-7-yloxy)phenylcarbamothioyl)acetamide hydrochloride | $^1$H NMR (400 MHz, DMSO-d$_6$) δ (ppm): 12.66(s, 1H), 11.55(s, 1H), 8.65(d, J=5.6 Hz, 1H), 8.10–8.03(m, 2H), 7.59–7.54(m, 2H), 6.82(d, J=5.6 Hz, 1H), 3.86(t, J=6.4 Hz, 2H), 3.54(t, J=6.4 Hz, 2H), 2.20(quin, J=7.6 Hz, 1H), 1.97(quin, J=6.4 Hz, 2H), 1.89(quin, J=6.4 Hz, 2H), 1.83–1.71(m, 2H), 1.68–1.47(m, 4H), 1.26–1.12(m, 2H). |

TABLE 19-continued

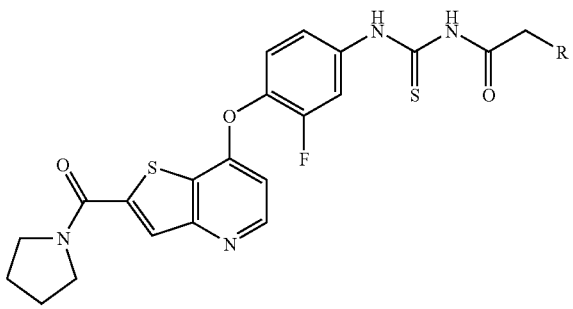

195a–q: Examples 156–181

Characterization of compounds 195 a–q (examples 156–181)

| Cpd | Ex | R | Name | Characterization |
|---|---|---|---|---|
| 195j | 165 | 3,4,5-trimethoxyphenyl (OMe, OMe, OMe) | N-(3-Fluoro-4-(2-(pyrrolidine-1-carbonyl)thieno[3,2-b]pyridin-7-yloxy)phenyl-carbamothioyl)-2-(3,4,5-trimethoxyphenyl)acetamide hydrochloride | $^1$H NMR (400 MHz, DMSO-$d_6$) δ (ppm): 12.49(s, 1H), 11.76(s, 1H), 8.60(d, J=5.6 Hz, 1H), 8.07–8.01(m, 2H), 7.58–7.54(m, 2H), 6.77(d, J=5.6 Hz, 1H), 6.65(s, 2H), 3.86(t, J=6.4 Hz, 2H), 3.76(s, 6H), 3.74(s, 2H), 3.63(s, 3H), 3.54(t, J=6.4 Hz, 2H), 1.97(quin, J=6.4 Hz, 2H), 1.89(quin, J=6.4 Hz, 2). |
| 195k | 166 | 4-(CO$_2$Me)phenyl | Methyl 4-(2-(3-(3-fluoro-4-(2-(pyrrolidine-1-carbonyl)thieno[3,2-b]pyridin-7-yloxy)phenyl)thioureido)-2-oxoethyl)benzoate hydrochloride | $^1$H NMR (400 MHz, DMSO-$d_6$) δ (ppm): 12.41(s, 1H), 11.86(s, 1H), 8.60(d, J=5.6 Hz, 1H), 8.04(s, 1H), 8.04–8.00(m, 1H), 7.93(d, J=8.0 Hz, 2H), 7.58–7.50(m, 2H), 7.47(d, J=8.0 Hz, 2H), 6.76(d, J=5.6 Hz, 1H), 3.94(s, 2H), 3.86(t, J=6.4 Hz, 2H), 3.84(s, H), 3.54(t, J=6.4 Hz, 2H), 1.97(quin, J=6.4 Hz, 2H), 1.89(quin, J=64 Hz, 2H). |
| 195l | 167 | (R)-2,2-dimethyl-5-oxo-1,3-dioxolan-4-yl | (R)-2-(2,2-Dimethyl-5-oxo-1,3-dioxolan-4-yl)-N-(3-fluoro-4-(2-(pyrrolidine-1-carbonyl)thieno[3,2-b]pyridin-7-yloxy)phenylcarbamoyl) ethanethioamide hydrochloride | $^1$H NMR (400 MHz, DMSO-$d_6$) δ (ppm): 12.32(s, 1H), 11.73(s, 1H), 8.64(d, J=5.6 Hz, 1H), 8.05(s, 1H), 8.04–8.00(m, 1H), 7.60–7.54(m, 2H), 6.81(d, J=5.6 Hz, 1H), 4.93(t, J=4.4 Hz, 1H), 3.86(t, J=6.4 Hz, 2H), 3.54(t, J=6.4 Hz, 2H), 3.16(dd, J=4.4 and 16.8 Hz, 1H), 2.99(dd, J=5.0 and 16.8 Hz, 1H), 1.97(quin, J=6.4 Hz, 2H), 1.89(quin, J=6.4 Hz, 2H). |
| 195m | 168 | 2-fluorophenyl | N-(3-Fluoro-4-(2-(pyrrolidine-1-carbonyl)thieno[3,2-b]pyridin-7-yloxy)phenyl-carbamothioyl)-2-(2-fluorophenyl)acetamide hydrochloride | $^1$H NMR (400 MHz, DMSO-$d_6$) δ (ppm): 12.42(s, 1H), 11.88(s, 1H), 8.67(d, J=5.6 Hz, 1H), 8.08–8.02(m, 1H), 8.06(s, H), 7.60–7.52(m, 2H), 7.43–7.30(m, 2H), 7.24–7.16(m, 2H), 6.85(d, J=5.6 Hz, 1H), 3.989s, 2H), 3.85(t, J=6.4 Hz, 2H), 3.54(t, J=6.4 Hz, 2H), 1.97(quin, J=6.4 Hz, 2H), 1.89(quin, J=6.4 Hz, 2H). |
| 195n | 169 | tetrahydro-2H-pyran-4-yl | N-(3-Fluoro-4-(2-(pyrrolidine-1-carbonyl)thieno[3,2-b]pyridin-7-yloxy)phenyl carbamothioyl)-2-(tetrahydro-2H-pyran-4-yl)acetamide hydrochloride | $^1$H NMR (400 MHz, DMSO-$d_6$) δ (ppm): 12.63(s, 1H), 11.59(s, 1H), 8.66(d, J=5.2 Hz, 1H), 8.11–8.02(m, 1H), 8.06(s, 1H), 7.60–7.54(m, 2H), 6.84(d, J=5.2 Hz, 1H), 3.85(t, J=6.8 Hz, 2H), 3.85–3.79(m, 2H), 3.54(t, J=6.8 Hz, 2H), 3.30(t, J=12.0 Hz, 2H), 2.43(d, J=6.8 Hz, 2H), 2.20–1.95(m, 1H), 1.97(quin, J=6.8 Hz, 2H), 1.89(quin, J=6.8 Hz, 2H), 1.61(d, J=12.8 Hz, 2H), 1.25(qd, J=4.0 and 12.0 Hz, 2H). |

TABLE 19-continued

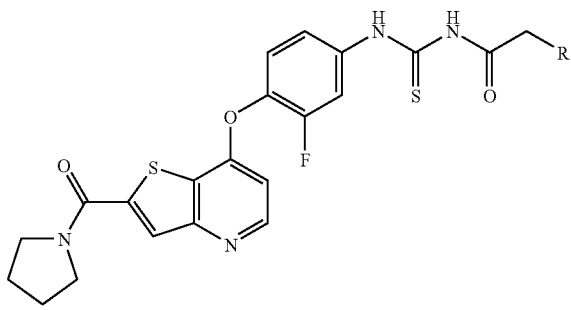

195a–q: Examples 156–181

Characterization of compounds 195 a–q (examples 156–181)

| Cpd | Ex | R | Name | Characterization |
|---|---|---|---|---|
| 195o | 179 | 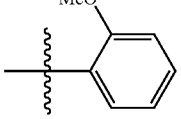 | N-(3-Fluoro-4-(2-(pyrrolidine-1-carbonyl)thieno[3,2-b]pyridin-7-yloxy)phenyl-carbamothioyl)-2-(2-methoxyphenyl)acetamide hydrochloride | $^1$H NMR (400 MHz, DMSO-d$_6$) δ (ppm): 12.55(s, 1H), 11.73(s, 1H), 8.63(d, J=5.6 Hz, 1H), 8.10–8.04(m, 2H), 7.60–7.51(m, 2H), 7.26(td, J=1.6 and 8.0 Hz, 1H), 7.21(dd, J=1.6 and 7.6 Hz, 1H), 6.99(d, J=8.0 Hz, H), 6.90(ts, J=1.2 and 7.6 Hz, 1H), 6.80(d, J=5.6 Hz, 1H), 3.86(t, J=6.4 Hz, 2H), 3.81(s, 2H), 3.78(s, 3H), 3.54(t, J=6.4 Hz, 2H), 1.97(quin, J=6.4 Hz, 2H), 1.89(quin, J=6.4 Hz, 2H). |
| 195p | 180 | 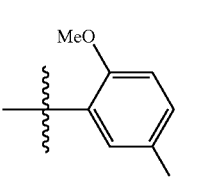 | 2-(2,5-Dimethoxyphenyl)-N-(3-fluoro-4-(2-(pyrrolidine-1-carbonyl)thieno[3,2-b]pyridin-7-yloxy)phenylcarbamothioyl)acetamide hydrochloride | $^1$H NMR (400 MHz, DMSO-d$_6$) δ (ppm): 12.53(s, 1H), 11.71 (s, 1H), 6.64(d, J=5.6 Hz, 1H)<8.10–8.04(m, 1H), 8.05(s, 1H), 7.60–7.52(m, 2H), 6.93–6.78(m, 4H), 3.85(t, J=6.4 Hz, 2H), 3.78(s, 2H), 3.72(s, 3H), 3.69(s, 3H), 3.54(t, J=6.4 Hz, 2H), 1.97(quin, J=6.4 Hz, 2H), 1.89(quin, J=6.4 Hz, 2H). |
| 195q | 181 | 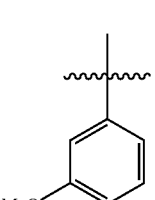 | 2-(3,4-Dimethoxyphenyl)-N-(3-fluoro-4-(2-(pyrrolidine-1-carbonyl)thieno[3,2-b]pyridin-7-yloxy)phenylcarbamothioyl)acetamide hydrochloride | $^1$H NMR (400 MHz, DMSO-d$_6$) δ (ppm): 12.51(s, 1H), 11.76(s, 1H), 8.69(d, J=5.6 Hz, 1H), 8.08–8.02(m, 1H), 8.07(s, 1H), 7.61–7.54(m, 2H), 6.98–6.82(m, 4H), 3.85(t, J=6.4 Hz, 2H), 3.78–3.70(m, 8H), 3.54(t, J=6.4 Hz, 2H), 1.97(quin, J=6.4 Hz, 2H), 1.89(quin, J=6.4 Hz, 2H). |

Scheme 41

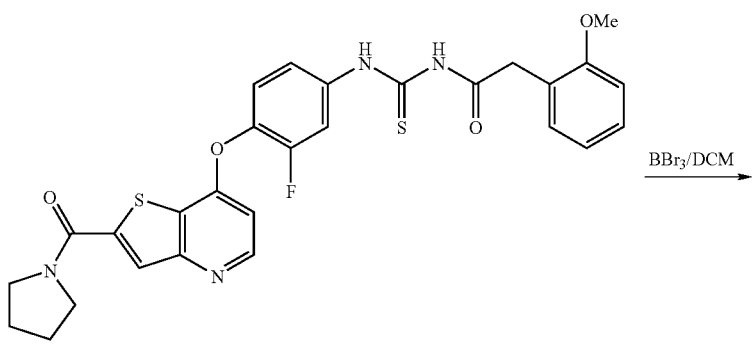

196o: Example 179

BBr$_3$/DCM

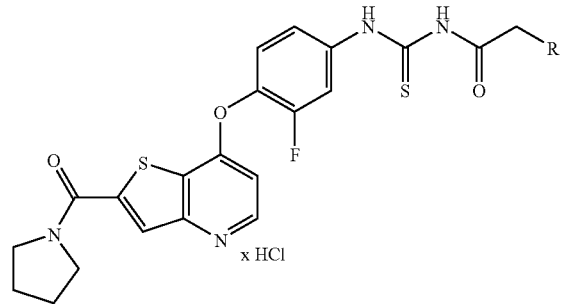

196a: Example 182

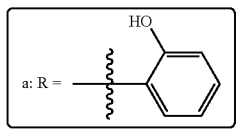

Example 182

N-(3-Fluoro-4-(2-(pyrrolidine-1-carbonyl)thieno[3,2-b]pyridin-7-yloxy)phenylcarbamothioyl)-2-(2-hydroxyphenyl)acetamide hydrochloride (196a)

Starting from the compound 195o and following the procedure described above for the synthesis of compound 155k (scheme 29, example 119), title compound 196a was obtained in 62% yield. Characterization of 196a is provided in table 20.

Example 183

2-(2,5-Dihydroxyphenyl)-N-(3-fluoro-4-(2-(pyrrolidine-1-carbonyl)thieno[3,2-b]pyridin-7-yloxy)phenylcarbamothioyl)acetamide hydrochloride (196b)

Starting from the compound 195p and following the procedure described above for the synthesis of 196a, title compound 196b was obtained in 83% yield. Characterization of 196b is provided in table 20.

Example 184

2-(3,4-Dihydroxyphenyl)-N-(3-fluoro-4-(2-(pyrrolidine-1-carbonyl)thieno[3,2-b]pyridin-7-yloxy)phenylcarbamothioyl)acetamide (196c)

Starting from the compound 195q and following the procedure described above for the synthesis of 196a, title compound 196c was obtained in 25% yield. Characterization of 196c is provided in table 20.

TABLE 20

Characterization of compounds 196a–c (examples 182–184)

| Cpd | Ex | R | Name | Characterization |
|---|---|---|---|---|
| 196a | 182 | HO-phenyl | N-(3-Fluoro-4-(2-(pyrrolidine-1-carbonyl)thieno[3,2-b]pyridin-7-yloxy)phenylcarbamothioyl)-2-(2-hydroxyphenyl)acetamide hydrochloride | $^1$H NMR (400 MHz, DMSO-$d_6$) δ (ppm): 12.60(s, 1H), 11.67(s, 1H), 9.63(bs, 1H), 8.63(d, J=5.6 Hz, 1H), 8.09–8.00(m, H), 8.05(s, 1H), 7.60–7.50(m, 2H), 7.13(d, J=7.6 Hz, 1H), 7.08(t, J=7.6 Hz, 1H), 6.83–6.77(m, 2H), 6.74(t, J=7.6 Hz, 1H), 3.85(t, J=6.4 Hz, 2H), 3.76(s, 2H), 3.54(t, J=6.4 Hz, 12H), 1.97(quin, J=6.4 Hz, 2H), 1.89(quin, J=6.4 Hz, 2H). |
| 196b | 183 | HO-phenyl-OH | 2-(2,5-Dihydroxyphenyl)-N-(3-fluoro-4-(2-(pyrrolidine-1-carbonyl)thieno[3,2-b]pyridin-7-yloxy)phenylcarbamothioyl)acetamide hydrochloride | $^1$H NMR (400 MHz, DMSO-$d_6$) δ (ppm): 12.59(s, 1H), 11.59(s, 1H), 8.60(d, J=5.6 Hz, 1H), 8.08–8.03(m, 1H), 8.04(s, 1H), 7.58–7.52(m, 2H), 6.77(d, J=5.6 Hz, 1H), 6.60(d, J=8.4 Hz, 1H), 6.57(d, J=2.8 Hz, 1H), 6.49(dd, J=2.8 and 8.4 Hz, 1H), 3.86(t, J=6.4 Hz, 2H), 3.54(t, j=6.54 Hz, 2H), 1.97(quin, J=6.4 Hz, 2H), 1.89(quin, J=6.4 Hz, 2H). |

TABLE 20-continued
Characterization of compounds 196a–c (examples 182–184)
| Cpd | Ex | R | Name | Characterization |
|---|---|---|---|---|
| 196c | 184 | [3,4-dihydroxyphenyl group, attached via CH] | 2-(3,4-Dihydroxyphenyl)-N-(3-fluoro-4-(2-(pyrrolidine-1-carbonyl)thieno[3,2-b]pyridin-7-yloxy)phenylcarbamothioyl)acetamide | $^1$H NMR (400 MHz, DMSO-d$_6$) δ (ppm): 8.53(d, J=5.6 Hz, 1H), 8.07(dd, J=2.4 and 12.0 Hz, 1H), 7.94(s, 1H), 7.50–7.44(m, 1H), 7.40(t, J=8.4 Hz, 1H), 6.82–6.71(m, 3H), 6.65(dd, J=2.4 and 8.4 Hz, 1H), 3.92(t, J=6.4 Hz, 2H), 3.67(t, J=6.4 Hz, 1H), 3.59(s, 2H), 2.09(quin, J=6.4 Hz, 2H), 2.02(quin, J=6.4 Hz, 2H). |
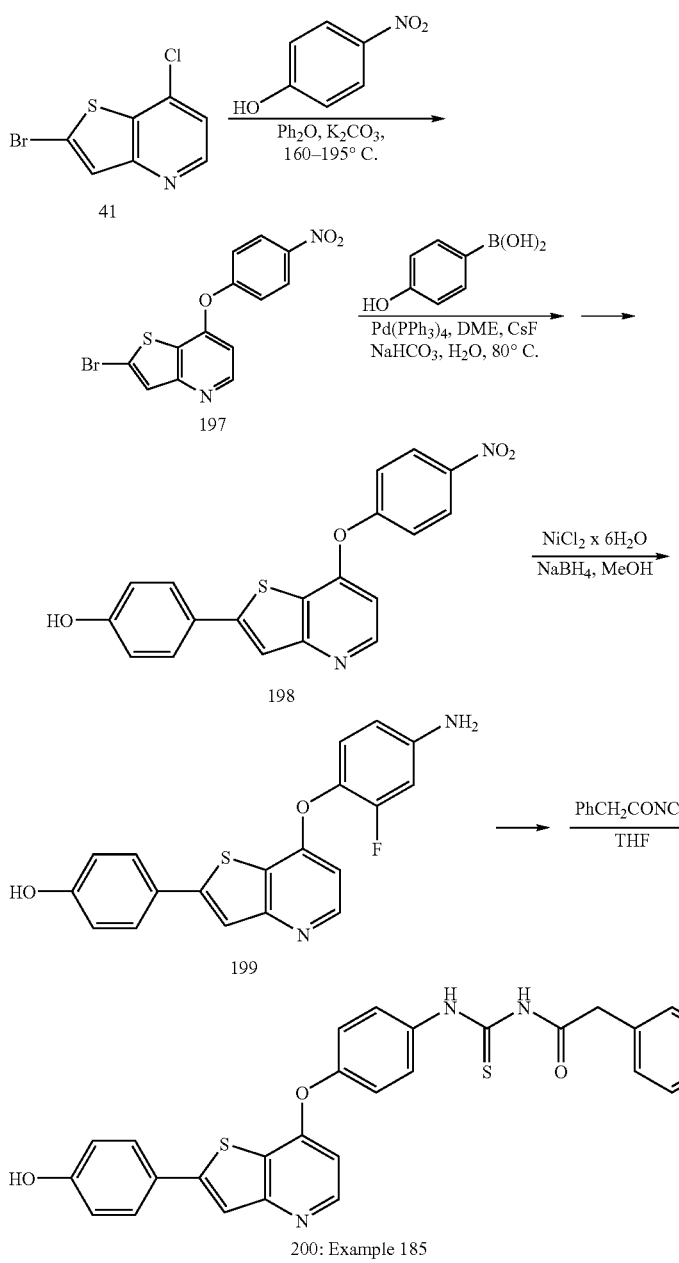
Scheme 42

Example 185

N-(4-(2-(4-Hydroxyphenyl)thieno[3,2-b]pyridin-7-yloxy)phenylcarbamothioyl)-2-phenylacetamide (200)

Step 1. 2-Bromo-7-(4-nitrophenoxy)thieno[3,2-b]pyridine (197)

Starting from the compound 41 (scheme 8) and following the procedure described above for the synthesis of compound 42 (scheme 8) but replacing 2-fluoro-4-nitrophenol for 4-nitrophenol, title compound 197 was obtained in 48% yield. LRMS (M+1) 350.9 (100%). 352.9 (100%).

Step 2. 4-(7-(4-Nitrophenoxy)thieno[3,2-b]pyridin-2-yl)phenol (198)

Starting from the compound 197 and following the procedure described above for the synthesis of compound 153 (scheme 28), title compound 198 was obtained in 81% yield. LRMS (M+1) 365.0 (100%).

Step 3. 4-(7-(4-Aminophenoxy)thieno[3,2-b]pyridin-2-yl)phenol (199)

Starting from the compound 198 and following the procedure described above for the synthesis of compound 154 (scheme 28), title compound 199 was obtained in 83% yield. LRMS (M+1) 335.0 (100%).

Step 4. N-(4-(2-(4-Hydroxyphenyl)thieno[3,2-b]pyridin-7-yloxy)phenylcarbamothioyl)-2-phenylacetamide (200)

Starting from the compound 199 and following the procedure described above for the compound 155a (scheme 28, example 109), title compound 200 was obtained in 3% yield. $^1$H NMR (400 MHz, DMSO-$d_6$) δ ppm: 12.38 (s, 1H), 11.74 (s, 1H), 9.94 (s, 1H), 8.46 (d, 1H, J=5.3 Hz), 7.81 (s, 1H), 7.72 (d, 2H, J=9.0 Hz), 7.69 (dd, 2H, J=6.7/1.8 Hz), 7.34-7.27 (m, 7H), 6.86 (dd, 2H, J=6.7/1.8 Hz), 6.61 (d, 1H, J=5.5 Hz), 3.82 (s, 2H). LRMS (M+1) 512.1 (100%).

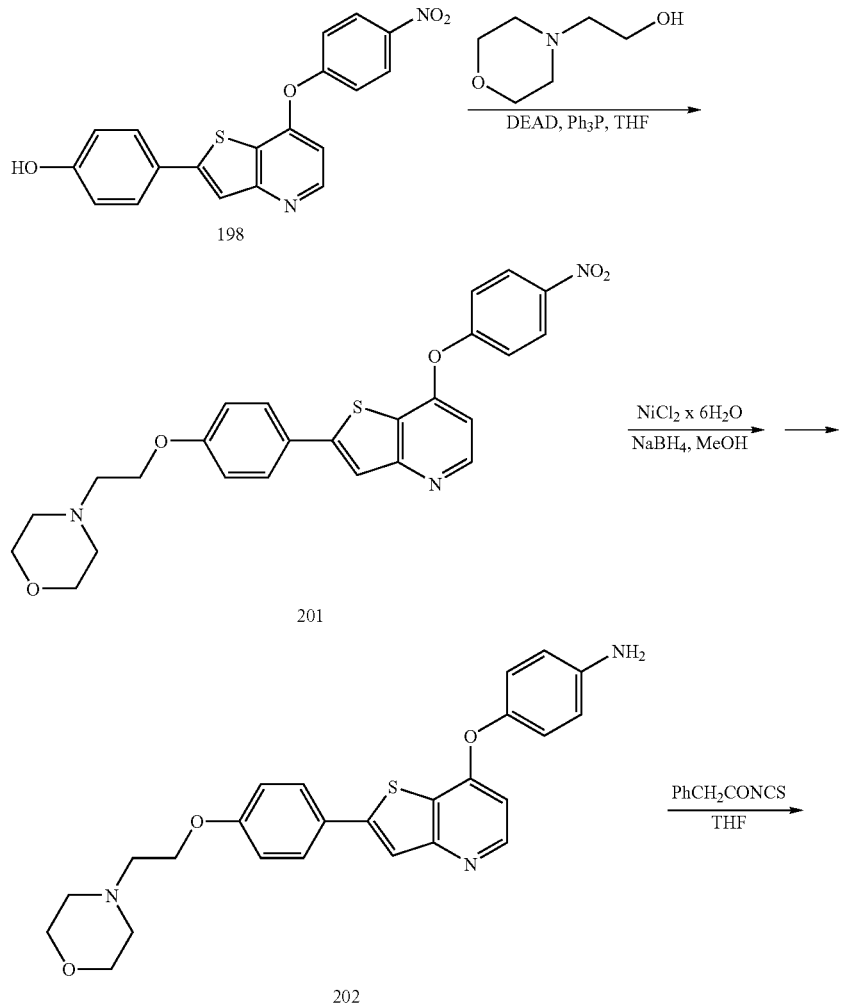

Scheme 43

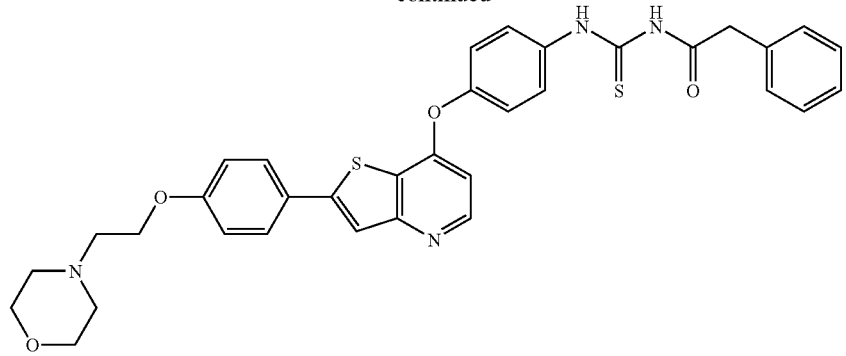

203: Example 186

Example 186

N-(4-(2-(4-(2-Morpholinoethoxy)phenyl)thieno[3,2-b]pyridin-7-yloxy)phenylcarbamothioyl)-2-phenylacetamide (203)

Step 1. 4-(2-(4-(7-(4-Nitrophenoxy)thieno[3,2-b]pyridin-2-yl)phenoxy)ethyl)morpholine (201)

Starting from the compound 198 (scheme 42) and following the procedure described above for the compound 161 (scheme 31), title compound 201 was obtained in 69% yield. LRMS (M+1) 478.1 (100%).

Step 2. 4-(2-(4-(2-Morpholinoethoxy)phenyl)thieno[3,2-b]pyridin-7-yloxy)benzenamine (202)

Starting from the compound 201 and following the procedure described above for the compound 162 (scheme 31), title compound 202 was obtained in 69% yield. LRMS (M+1) 448.2 (100%).

Step 3. N-(4-(2-(4-(2-Morpholinoethoxy)phenyl)thieno[3,2-b]pyridin-7-yloxy)phenylcarbamothioyl)-2-phenylacetamide (203)

Starting from the compound 202 and following the procedure described above for the compound 163a (scheme 31), title compound 203 was obtained in 30% yield. $^1$H NMR (400 MHz, DMSO-$d_6$) δ ppm: 12.38 (s, 1H), 11.73 (s, 1H), 8.47 (d, 1H, J=5.5 Hz), 7.90 (s, 1H), 7.79 (s, 2H, J=9.0), 7.36 (d, 2H, J=9.0 Hz), 7.43-7.27 (m, 7H), 7.05 (d, 2H, J=9.0 Hz), 6.63 (d, 1H, J=5.3 Hz), 4.15 (t, 2H, J=5.6 Hz), 3.82 (s, 2H), 3.58 (t, 4H, J=4.6 Hz), 2.71 (t, 2H, J=5.7 Hz), 2.51-2.46 (m, 4H). LRMS (M+1) 625.2 (100%).

Scheme 44

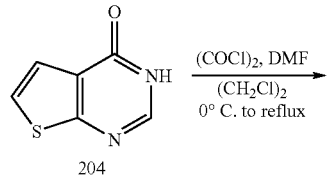

204

-continued

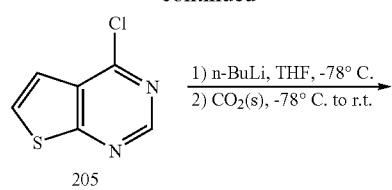

205

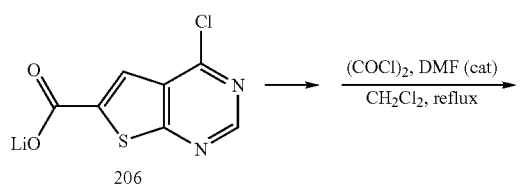

206

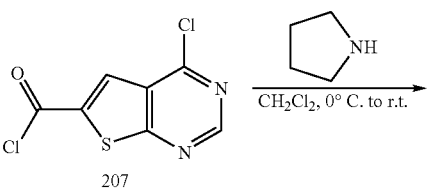

207

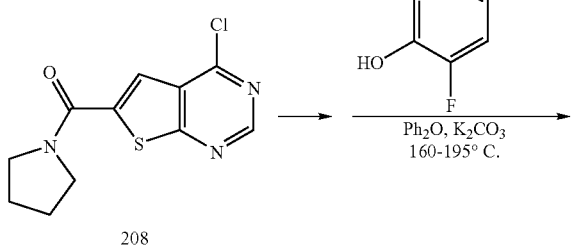

208

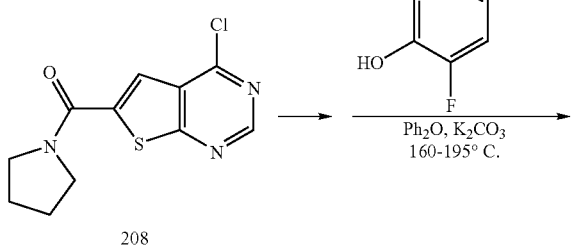

209

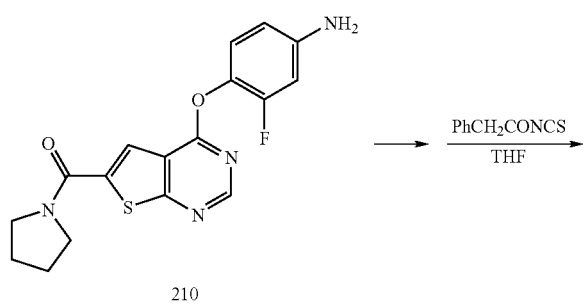

210

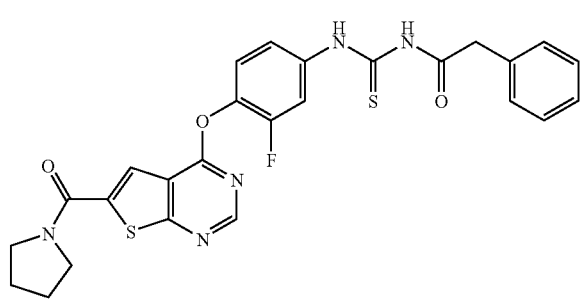

211: Example 187

Example 187

N-(3-fluoro-4-(6-(pyrrolidine-1-carbonyl)thieno[2,3-d]pyrimidin-4-yloxy)phenylcarbamothioyl)-2-phenylacetamide (211)

Step 1. 4-Chlorothieno[2,3-d]pyrimidine (205)

Starting from thieno[2,3-d]pyrimidin-4(3H)-one (204) [*J. Med. Chem.*, 1999, 42, 26, 5437-5447, *Bull. Soc. Chim. Fr.*, 1975, 587-591] and following the procedure described above for the synthesis of compound 20 (scheme 4, example 22), title compound 205 was obtained in 93% yield. LRMS (M+1) 169.1 (100%), 171.1 (32%).

Steps 2-4. (4-Chlorothieno[2,3-d]pyrimidin-6-yl)(pyrrolidin-1-yl)methanone (208)

Starting from the compound 205 and following the procedures described above for the synthesis of amide 5 (scheme 1, steps 2-4, example 1), title compound 208 was obtained [via intermediates 206 and 207], in 76% yield as dark-brown oil (crude material, was used for the next step without additional purification). LRMS (M+1) 268.2 (100%).

Step 5. (4-(2-Fluoro-4-nitrophenoxy)thieno[2,3-d]pyrimidin-6-yl)(pyrrolidin-1-yl)methanone (209)

Starting from the compound 208 and following the procedures described above for the synthesis of nitro compound 6 (scheme 1, step 5, example 1), title compound 209 was obtained in 24% yield. LRMS (M+1) 389.1 (100%).

Step 6. (4-(4-Amino-2-fluorophenoxy)thieno[2,3-d]pyrimidin-6-yl)(pyrrolidin-1-yl)methanone (210)

Starting from the compound 209 and following the procedures described above for the synthesis of amine 7 (scheme 1, step 6, example 1), crude title compound 210 was obtained. It was purified by flash chromatography, eluents DCM followed by DCM-MeOH-Et$_3$N (97.75:2:0.25), to afford title compound 210 in 54% yield as a yellow solid. LRMS (M+1) 359.1 (100%).

Step 7. N-(3-Fluoro-4-(6-(pyrrolidine-1-carbonyl)thieno[2,3-d]pyrimidin-4-yloxy)phenylcarbamothioyl)-2-phenylacetamide (211)

Starting from the compound 210 and following the procedures described above for the synthesis of compound 8a (scheme 1, step 7, example 1), crude title compound 211 was obtained. It was purified by flash chromatography, eluents DCM and DCM-MeOH-Et$_3$N (97.75:2:0.25) followed by trituration with a mixture of MeOH-EtOAc, to afford title compound 211 in 17% yield as a yellow solid. $^1$H NMR (400 MHz, DMSO-d$_6$) δ(ppm): 12.43 (s, 1H), 11.80 (s, 1H), 8.70 (s, 1H), 8.06 (s, 1H), 7.93 (d, 1H, J=11.7/2.3 Hz), 7.53-7.47 (m, 2H), 7.34-7.26 (m, 5H), 3.90 (t, 2H, J=6.7 Hz), 3.83 (s, 2H), 3.55 (t, 2H, J=6.7 Hz), 1.99-1.85 (m, 4H). LRMS (M+1) 536.2 (100%).

Scheme 45

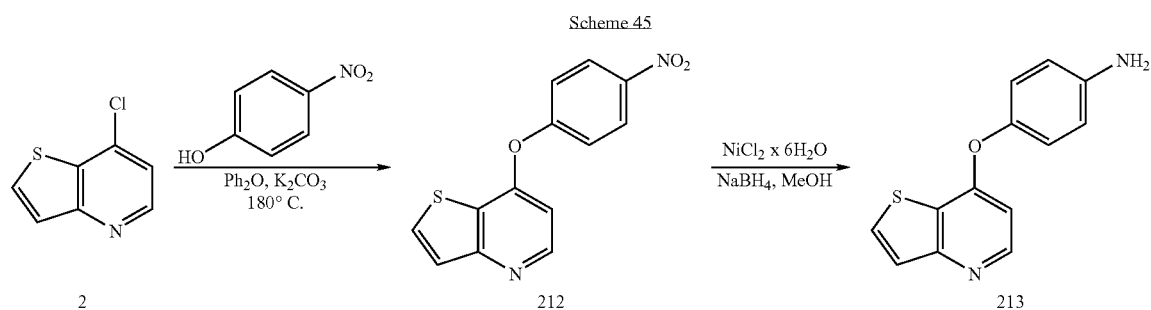

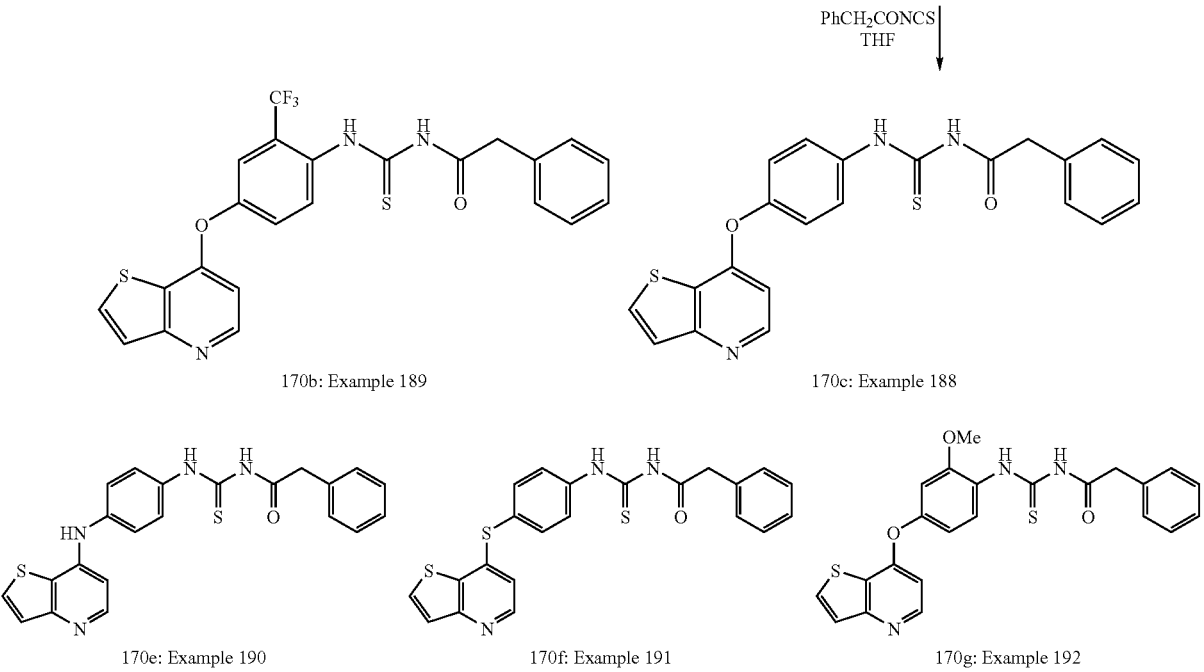

170b: Example 189
170c: Example 188
170e: Example 190
170f: Example 191
170g: Example 192

Example 188

2-Phenyl-N-(4-(thieno[3,2-b]pyridin-7-yloxy)phenylcarbamothioyl)acetamide (170c)

Step 1. 7-(4-Nitrophenoxy)thieno[3,2-b]pyridine (212)

Staring from the chloride 2, following the procedure described above for the synthesis of compound 6 (scheme 1, example 1) but substituting 2-fluoro-4-nitrophenol for 4-nitrophenol, title compound 212 was obtained in 89% yield. MS (m/z) 273.0 (M+H).

Step 2. 4-(Thieno[3,2-b]pyridin-7-yloxy)benzenamine (213)

Staring from the nitro compound 212, following the procedure described above for the synthesis of amine 49 (scheme 10, example 55), title compound 213 was obtained in 90% yield. MS (m/z) 243.1 (M+H).

Step 3. 2-Phenyl-N-(4-(thieno[3,2-b]pyridin-7-yloxy)phenylcarbamothioyl)acetamide (170c)

Staring from the amine 213, following the procedure described above for the synthesis of compound 50 (scheme 10, example 55), title compound 170c was obtained in 34% yield. $^1$H NMR (400 MHz, DMSO-$d_6$) δ ppm 12.35 (1H, s), 11.69 (1H, s), 8.47 (1H, d, J=5.28 Hz), 8.10 (1H, d, J=5.28 Hz), 7.70 (1H, s), 7.68 (1H, s), 7.54 (1H, d, J=5.28 Hz), 7.30-7.22 (7H, m), 6.61 (1H, d, J=5.28 Hz), 3.78 (2H, s). MS (m/z) 420.0 (M+H).

Example 189

2-Phenyl-N-(4-(thieno[3,2-b]pyridin-7-yloxy)-2-(trifluoromethyl)phenylcarbamothioyl)acetamide (170d)

Title compound 170d was obtained according to the scheme 45 via a three-step synthesis starting from the chloride 2 and replacing 4-nitrophenol [in the first step] with 4-nitro-3-(trifluoromethyl)phenol. $^1$H NMR (400 MHz, DMSO-$d_6$) δ (ppm): 12.29 (s, 1H), 11.99 (s, 1H), 8.56 (d, J=5.3 Hz, 1H), 8.17 (d, J=5.3 Hz, 1H), 7.84 (d, J=8.6 Hz, 1H), 7.74 (d, J=2.7 Hz, 1H), 7.63 (m, 2H), 7.34 (m, 4H), 7.26 (m, 2H), 6.75 (d, J=5.3 Hz, 1H), 3.85 (s, 1H). MS (m/z): 488.3 (M+H).

Example 190

2-Phenyl-N-(4-(thieno[3,2-b]pyridin-7-ylamino)phenylcarbamothioyl)acetamide (170e)

Title compound 170e was obtained according to the scheme 45 via a three-step synthesis starting from the chloride 2 and replacing 4-nitrophenol [in the first step] with 4-nitrobenzenamine. $^1$H NMR (400 MHz, DMSO-$d_6$) δ (ppm) 12.39 (s, 1H), 11.72 (s, 1H), 8.97 (s, 1H), 8.35 (d, J=5.1 Hz, 1H), 8.03 (d, J=5.5 Hz, 1H), 7.64 (d, J=8.4 Hz, 2H), 7.49 (d, J=5.3 Hz, 1H), 7.38 (m, 4H), 7.32 (d, J=8.4 Hz, 3H), 6.94 (d, J=5.5 Hz, 1H), 3.87 (s, 1H). MS (m/z): 419.2 (M+H).

Example 191

2-Phenyl-N-(4-(thieno[3,2-b]pyridin-7-ylthio)phenylcarbamothioyl)acetamide (170f)

Title compound 170f was obtained according to the scheme 45 via a three-step synthesis starting from the chloride 2 and replacing 4-nitrophenol [in the first step] with 4-nitrobenzenethiol. ¹H NMR (400 MHz, DMSO-d₆) δ ppm 12.65 (1H, s), 11.91 (1H, s), 8.62 (1H, d, J=4.70 Hz), 8.28 (1H, d, J=5.28 Hz), 8.01-7.90 (2H, m), 7.79-7.68 (5H, m), 7.23 (1H, m), 3.95 (2H, m). MS (m/z) 436.0 (M+H)

Example 192

N-(2-Methoxy-4-(thieno[3,2-b]pyridin-7-yloxy)phenylcarbamothioyl)-2-phenylacetamide (170g)

Title compound 170g was obtained according to the scheme 45 via a three-step synthesis starting from the chloride 2 and replacing 4-nitrophenol [in the first step] with 3-methoxy-4-nitrophenol [Hodgson, C., *J. Chem. Soc.*, 1929, 2778). ¹H NMR (DMSO) δ (ppm): 12.70 (1H, s), 11.71 (1H, s), 8.63 (1H, d, J=8.80 Hz), 8.51 (1H, d, J=5.28 Hz), 8.14 (1H, d, J=5.48 Hz), 7.50 (1H, dd, J=5.48, 0.78 Hz), 7.36-7.25 (5H, m), 7.13 (1H, d, J=2.54 Hz), 6.89 (1H, dd, J=8.80, 2.54 Hz), 6.69 (1H, d, J=5.48 Hz), 3.82 (5H, s). MS (m/z) 449.55 (M+H).

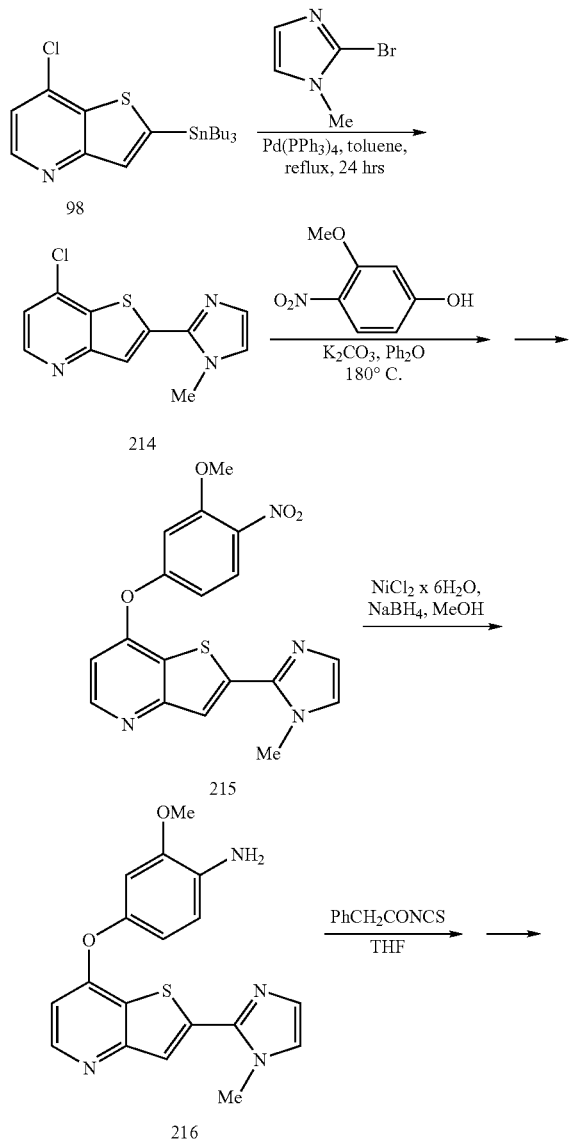

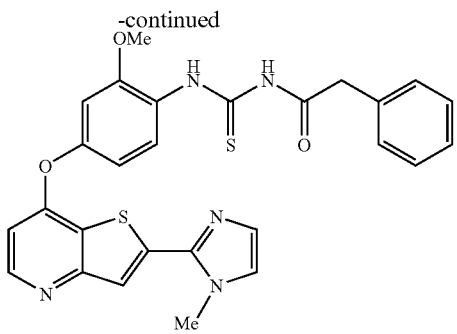

217: Example 193

Example 193

N-(2-Methoxy-4-(2-(1-methyl-1H-imidazol-2-yl)thieno[3,2-b]pyridin-7-yloxy)phenylcarbamothioyl)-2-phenylacetamide (217)

Step 1. 7-Chloro-2-(1-methyl-1H-imidazol-2-yl)thieno[3,2-b]pyridine (214)

Starting from tributyltin compound 98 (scheme 19) and following the procedure described above for the synthesis of compound 10 (scheme 2, step 2, example 12) but replacing 2-bromothiazole with 2-bromo-1-methyl-1H-imidazole, title compound 214 was obtained in 95% yield. MS (m/z) 250.1 (100%), 252.1 (37%), (M+H).

Step 2. 7-(3-Methoxy-4-nitrophenoxy)-2-(1-methyl-1H-imidazol-2-yl)thieno[3,2-b]pyridine (215)

Starting from compound 214, following the procedure described above for the synthesis of compound 11 (scheme 2, step 3, example 12) but replacing 2-fluoro-4-nitrophenol with 3-methoxy-4-nitrophenol [Hodgson, C., *J. Chem. Soc.*, 1929, 2778], title compound 215 was obtained in 9% yield. MS (m/z) 383.1 (M+H).

Step 3. 2-Methoxy-4-(2-(1-methyl-1H-imidazol-2-yl)thieno[3,2-b]pyridin-7-yloxy)benzenamine (216)

Starting from compound 215 and following the procedure described above for the synthesis of compound 12 (scheme 2, step 4, example 12), title compound 216 was obtained in 100% yield. MS (m/z) 353.1 (M+H).

Step 4. N-(2-Methoxy-4-(2-(1-methyl-1H-imidazol-2-yl)thieno[3,2-b]pyridin-7-yloxy)phenylcarbamothioyl)-2-phenylacetamide (217)

Starting from compound 216 and following the procedure described above for the synthesis of compound 13a (scheme 2, step 5, example 12), title compound 217 was obtained in 48% yield. ¹H NMR (400 MHz, DMSO-d₆) δ ppm 12.07 (1H, s), 11.59 (1H, s), 8.45 (1H, d, J=5.48 Hz), 7.91 (1H, d, J=8.80 Hz), 7.85 (1H, s), 7.41 (1H, s), 7.24-6.98 (8H, m), 6.66 (1H, d, J=5.67 Hz), 3.99 (3H, s), 3.78 (3H, s), 3.59 (2H, s). MS (m/z) 530.2 (M+H).

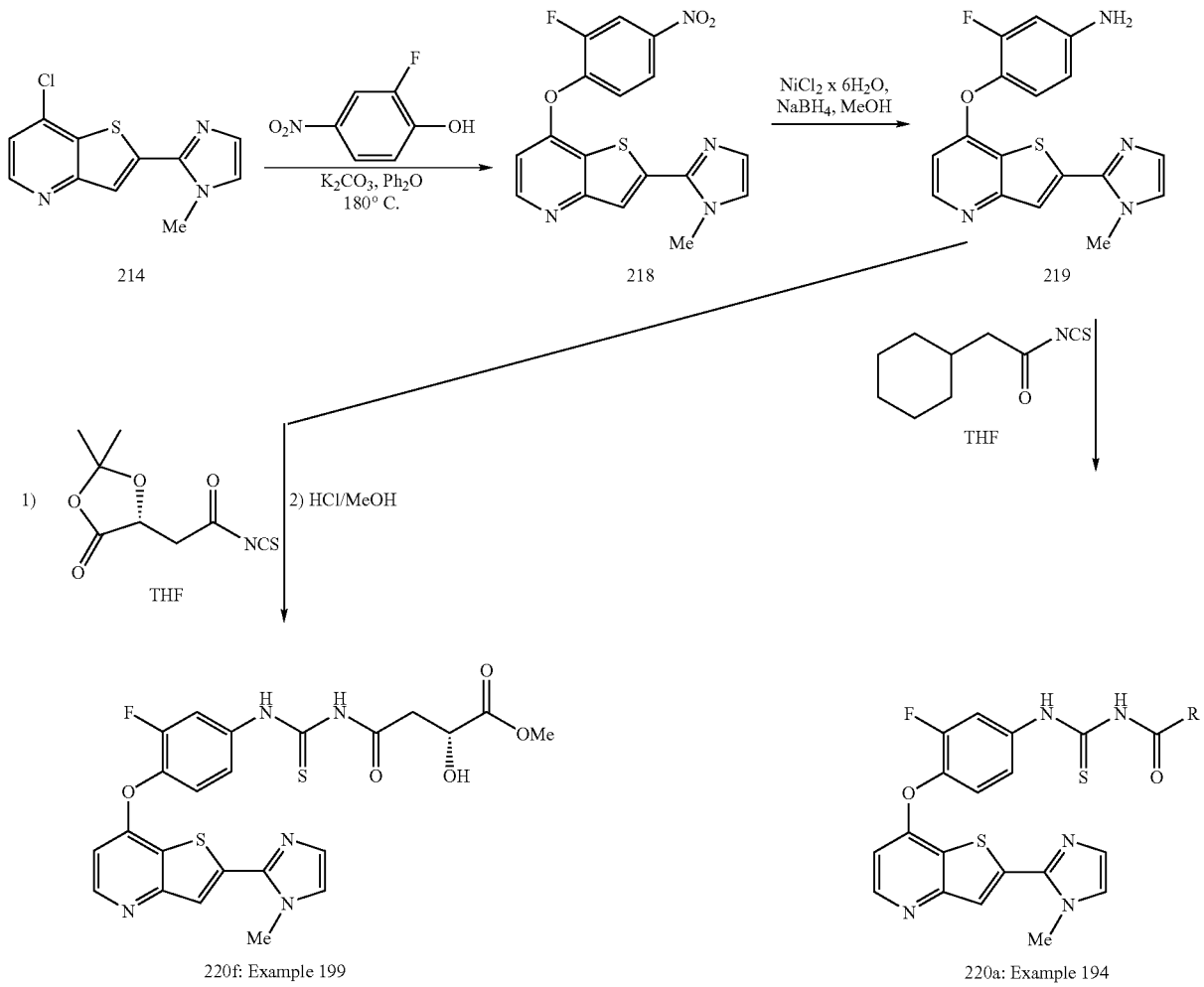

Scheme 47

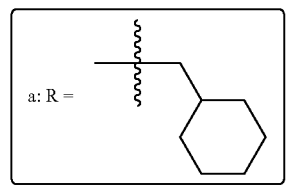

a: R =

Example 194

2-Cyclohexyl-N-(3-fluoro-4-(2-(1-methyl-1H-imidazol-2-yl)thieno[3,2-b]pyridin-7-yloxy)phenylcarbamothioyl)acetamide (220a)

Step 1. 7-(2-Fluoro-4-nitrophenoxy)-2-(1-methyl-1H-imidazol-2-yl)thieno[3,2-b]pyridine (218)

Starting from compound 214 (scheme 46) and following the procedure described above for the synthesis of compound 11 (scheme 2, step 3, example 12), title compound 218 was obtained in 45% yield. MS (m/z) 371.1 (M+H).

Step 2. 3-Fluoro-4-(2-(1-methyl-1H-imidazol-2-yl)thieno[3,2-b]pyridin-7-yloxy)benzenamine (219)

Starting from compound 218 and following the procedure described above for the synthesis of compound 12 (scheme 2, step 4, example 12), title compound 219 was obtained in 86% yield. MS (m/z) 341.1 (M+H).

Step 3: 2-Cyclohexyl-N-(3-fluoro-4-(2-(1-methyl-1H-imidazol-2-yl)thieno[3,2-b]pyridin-7-yloxy)phenylcarbamothioyl)acetamide (220a)

To a suspension of 219 (50 mg, 0.145 mmol) in THF (1.5 mL) was added 2-cyclohexylacetyl isothiocyanate (40 mg, 0.22 mmol) [P. A. S. Smith and R. O. Kan. *J. Org. Chem.*,

Example 195

2-Cyclopentyl-N-(3-fluoro-4-(2-(1-methyl-1H-imidazol-2-yl)thieno[3,2-b]pyridin-7-yloxy)phenylcarbamothioyl)acetamide (220b)

Title compound 220b was obtained similarly to the compound 220a from the amine 219 and 2-cyclopentylacetyl isothiocyanate [P. A. S. Smith and R. O. Kan. *J. Org. Chem.,* 1964, 2261] in 47% yield. Characterization of 220b is provided in the table 21.

Example 196

N-(3-Fluoro-4-(2-(1-methyl-1H-imidazol-2-yl)thieno[3,2-b]pyridin-7-yloxy)phenylcarbamothioyl)-2-(2-oxopyrrolidin-1-yl)acetamide (220c)

Title compound 220c was obtained similarly to the compound 220a from the amine 219 and 2-(2-oxopyrrolidin-1-yl)acetyl isothiocyanate [prepared according to the reference P. A. S. Smith and R. O. Kan. *J. Org. Chem.,* 1964, 2261] in 18% yield. Characterization of 220c is provided in the table 21.

Example 197

N-(3-Fluoro-4-(2-(1-methyl-1H-imidazol-2-yl)thieno[3,2-b]pyridin-7-yloxy)phenylcarbamothioyl)-2-(tetrahydro-2H-pyran-4-yl)acetamide (220d)

Title compound 220d was obtained similarly to the compound 220a from the amine 219 and 2-(tetrahydro-2H-pyran-4-yl)acetyl isothiocyanate [prepared according to the reference P. A. S. Smith and R. O. Kan. *J. Org. Chem.,* 1964, 2261] in 15% yield. Characterization of 220d is provided in the table 21.

Example 198

N-(3-Fluoro-4-(2-(1-methyl-1H-imidazol-2-yl)thieno[3,2-b]pyridin-7-yloxy)phenylcarbamothioyl)acetamide (220e)

Title compound 220f was obtained similarly to the compound 220a from the amine 219 and acetyl isothiocyanate in 28% yield. Characterization of 220f is provided in the table 21.

Example 199

(R)-Methyl 4-(3-(3-fluoro-4-(2-(1-methyl-1H-imidazol-2-yl)thieno[3,2-b]pyridin-7-yloxy)phenyl)thioureido)-2-hydroxy-4-oxobutanoate (220f)

To a suspension of 219 (60 mg, 0.186 mmol) in THF (1.9 mL) was added (R)-2-(2,2-dimethyl-5-oxo-1,3-dioxolan-4-yl)acetyl isothiocyanate (60 mg, 0,28 mmol) [P. A. S. Smith and R. O. Kan. *J. Org. Chem.,* 1964, 2261]. The reaction mixture was stirred for 3 hours, concentrated, purified by flash chromatography, eluent EtOAc-MeOH (19:1), to produce a solid material (29.5 mg) which was dissolved in MeOH, treated with HCl (1N in Et$_2$O, 0.1 mL) and the mixture was stirred for 10 min at room temperature. The solution was concentrated, and the residue was purified by preparative HPLC (Aquasil C18 column, gradient: 30% MeOH to 95% MeOH in water, 45 min), to afford title compound 220f (15 mg, 13% yield) as a white solid. Characterization of 220f is provided in the table 21.

TABLE 21

220a–f: Examples 194–199

Characterization of compounds 220a–f (examples 194–199)

| Cpd | Ex | R | Name | Characterization |
|---|---|---|---|---|
| 220a | 194 | 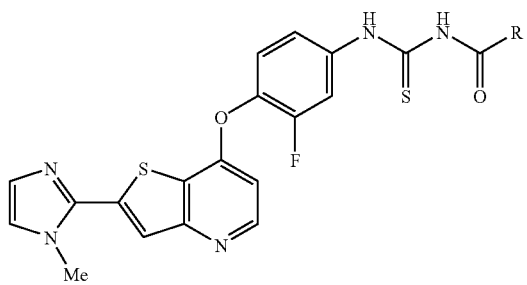 | 2-Cyclohexyl-N-(3-fluoro-4-(2-(1-methyl-1H-imidazol-2-yl)thieno[3,2-b]pyridin-7-yloxy)phenylcarbamothioyl)acetamide | $^1$HNMR: (DMSO-d$_6$) δ (ppm): 12.68(s, 1H), 11.57(s, 1H), 8.72(d, 5.5 Hz, 1H), 8.40(s, 1H), 8.1(m, 1H), 7.88(m, 1H), 7.75(s, 1H), 7.61(m, 2H), 6.90(d, J=5.5 Hz, 1H), 4.05(s, 3H), 2.37(d, J=6.8 Hz, H), 1.79–1.60(m, 6H), 1.28–1.12(m, 3H), 1.02–0.94(m, 2H). MS (m/z): 524.3 (M + 1). |

TABLE 21-continued

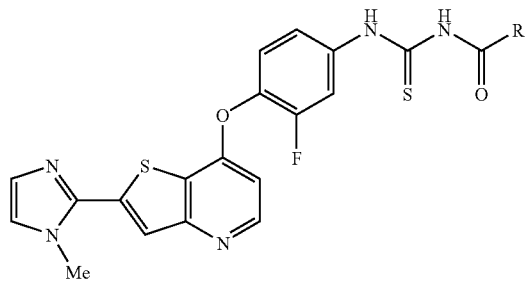

220a–f: Examples 194–199

Characterization of compounds 220a–f (examples 194–199)

| Cpd | Ex | R | Name | Characterization |
|---|---|---|---|---|
| 220b | 195 | ![cyclopentylmethyl] | 2-Cyclopentyl-N-(3-fluoro-4-(2-(1-methyl-1H-imidazol-2-yl)thieno[3,2-b]pyridin-7-yloxy)phenylcarbamothioyl)acetamide | $^1$H NMR (DMSO-$d_6$) δ (ppm): 12.66(s, 1H), 11.55(s, 1H), 8.5(m, 1H), 8.06(d, J=12.5 Hz, 1H), 7.9(s, 1H), 7.55 (m, 2H), 7.41(s, 1H), 7.05(s, 1H), 6.69(m, 1H), 4.0(s, 3H), 2.5(m, 2H), 2.2(m, 1H), 1.78(m, 2H), 1.61–1.52(m, 4H), 1.18(m, 2H). MS (m/z): 510.2 (M + 1) |
| 220c | 196 | ![(2-oxopyrrolidin-1-yl)methyl] | N-(3-Fluoro-4-(2-(1-methyl-1H-imidazol-2-yl)thieno[3,2-b]pyridin-7-yloxy)phenyl-carbamothioyl)-2-(2-oxopyrrolidin-1-yl)acetamide | $^1$NMR (DMSO-$d_6$) δ (ppm): 8.52 (d, J=5.4 Hz, 1H), 7.98(m, 1H), 7.89(m, 1H), 7.46(m, 2H), 7.40(s, 1H), 7.04(m, 1H), 6.68(d, J=5.3 Hz, 1H), 4.18(s, 2H), 3.99(s, 3H), 3.37(m, 2H), 2.27(m, 2H), 2.0(m, 2H). MS (m/z): 525.3 (M + 1). |
| 220d | 197 | ![cyclohexylmethyl] | N-(3-Fluoro-4-(2-(1-methyl-1H-imidazol-2-yl)thieno[3,2-b]pyridin-7-yloxy)phenyl-carbamothioyl)-2-(tetrahydro-2H-pyran-4-yl)acetamide | $^1$H NMR (DMSO-$d_6$) δ (ppm): 8.53 (d, J=5.3 Hz, 1H), 8.03(d, J=12.5 Hz, 1H), 7.89(s, 1H), 7.52(m, 2H), 7.41(m, 1H), 7.04(m, 1H), 6.69(d, J=5.4 Hz, 1H), 3.99(s, 3H), 3.82(m, 2H), 3.59(m, 1H), 3.3(m, 2H), 2.43(m, 2H), 1.76(m, 2H), 1.25(m, 2H). MS (m/z): 526.2 (M + 1). |
| 220e | 198 | CH$_3$ | N-(3-Fluoro-4-(2-(1-methyl-1H-imidazol-2-yl)thieno[3,2-b]pyridin-7-yloxy)phenyl-carbamothioyl)acetamide | $^1$H NMR (DMSO-$d_6$) δ (ppm): 12.55(br, 1H), 11.52(br, 1H), 8.53(m, 1H), 8.03(m, 1H), 7.90(s, 1H), 7.52(m, 2H), 7.41(s, 1H), 7.04(s, 1H), 6.69(m, 1H), 4.00(s, 3H), 2.18(s, 2H). MS (m/z): 442.1 (M + 1). |
| 220f | 199 | ![methyl 2-hydroxy-4-oxobutanoate fragment] | (R)-Methyl 4-(3-(3-fluoro-4-(2-(1-methyl-1H-imidazol-2-yl)thieno[3,2-b]pyridin-7-yloxy)phenyl)thioureido)-2-hydroxy-4-oxobutanoate | $^1$H NMR(DMSO-$d_6$) δ (ppm): 8.55(d, J=5.5 Hz, 1H), 8.04(m, 1H), 7.92(s, 1H), 7.55(m, 2H), 7.43(d, J=1 Hz, 1H), 7.06(d, J=1 Hz, 1H), 6.70(dd, J=5.5 Hz, J=1 Hz, 1H), 4.48(dd, J=5.2 Hz, J=7.2 Hz, 1H), 4.0(s, 3H), 3.67(s, 3H), 2.92(dd, J=5.2 Hz, J=15.5 Hz, 1H), 2.86(dd, J=7.4 Hz, J=15.5 Hz, 1H). MS (m/z): 530.2 (M + 1) |

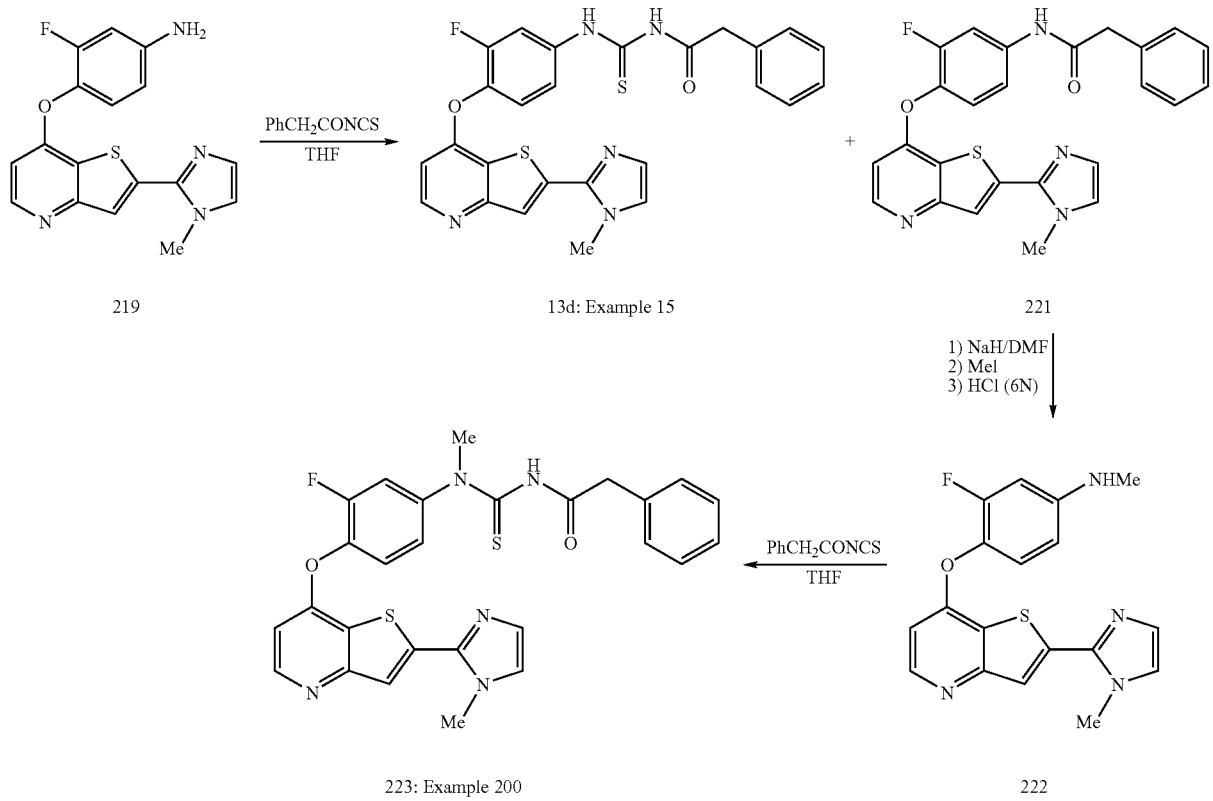

Scheme 48

219

13d: Example 15

221

223: Example 200

222

Example 200

N-((3-Fluoro-4-(2-(1-methyl-1H-imidazol-2-yl)thieno[3,2-b]pyridin-7-yloxy)phenyl)(methyl)carbamothioyl)-2-phenylacetamide (223)

Step 1: N-(3-Fluoro-4-(2-(1-methyl-1H-imidazol-2-yl)thieno[3,2-b]pyridin-7-yloxy)phenylcarbamothioyl)-2-phenylacetamide (13d) and N-(3-fluoro-4-(2-(1-methyl-1H-imidazol-2-yl)thieno[3,2-b]pyridin-7-yloxy)phenyl)-2-phenylacetamide (221)

To a suspension of 219 (400 mg, 1.18 mmol) in THF (12 mL) was added 2-2-phenylacetyl isothiocyanate (312 mg, 1.76 mmol) [P. A. S. Smith and R. O. Kan. *J. Org. Chem.*, 1964, 2261], the reaction mixture was stirred for 3 hours, transferred onto a flash chromatography column and eluted with EtOAc/MeOH mixture (98:2), to afford title compounds 13d (example 15, 254 mg, 42% yield) and 221 (96 mg, 17% yield).

Characterization of 13d (example 15) is provided in the table 2. Compound 221 is characterized by its mass-spectrum: MS (m/z): 459.1 (M+1).

Step 2. 3-Fluoro-N-methyl-4-(2-(1-methyl-1H-imidazol-2-yl)thieno[3,2-b]pyridin-7-yloxy)benzenamine (222)

To a solution of 221 (274.8 mg, 0.6 mmol) in DMF (6 mL) NaH (60% in mineral oil, 36 mg, 0.9 mmol) was added in one portion at 0° C. and the reaction mixture was stirred for 1 h, followed by addition of MeI (0.037 mL, 0.6 mmol). The reaction mixture was allowed to warm up to room temperature, stirred overnight, diluted with EtOAc, washed with water, dried over anhydrous $Na_2SO_4$ and concentrated under reduced pressure. The residue was treated with 6N HCl (3 mL), and heated at 100° C. for 3 h, cooled to room temperature and partitioned between water and DCM. Aqueous phase was collected, basified with 1N NaOH to pH 11 and extracted with EtOAc. The extract was dried over anhydrous $Na_2SO_4$ and concentrated. The residue was purified by flash chromatography (eluent EtOAc/MeOH, 9:1) to afford title compound 222 (102 mg, 46% yield) as a syrup. MS (m/z): 355.1 (M+1).

Step 3: N-((3-Fluoro-4-(2-(1-methyl-1H-imidazol-2-yl)thieno[3,2-b]pyridin-7-yloxy)phenyl)(methyl)carbamothioyl)-2-phenylacetamide (223)

To a suspension of the 222 (102 mg, 2.88 mmol) in THF (3 ml) was added 2-phenylacetyl isothiocyanate (51 mg, 0.288 mmol). The reaction mixture was stirred for 1 hr, transferred onto a chromatography column and eluted with a mixture EtOAc/MeOH (19:1) to afford title compound 223 (30 mg, 20% yield) as a white solid. $^1$HNMR: (DMSO-$d_6$) δ (ppm): 10.88 (s, 1H), 8.51 (d, J=5.3 Hz, 1H), 7.91 (s, 1H), 7.41-7.18 (m, 6H), 7.04 (m, 4H), 6.5 (d, J=5.3 Hz, 1H), 4.0 (s, 3H), 3.6 (s, 2H), 3.43 (s, 3H). MS (m/z): 532.3 (M+1).

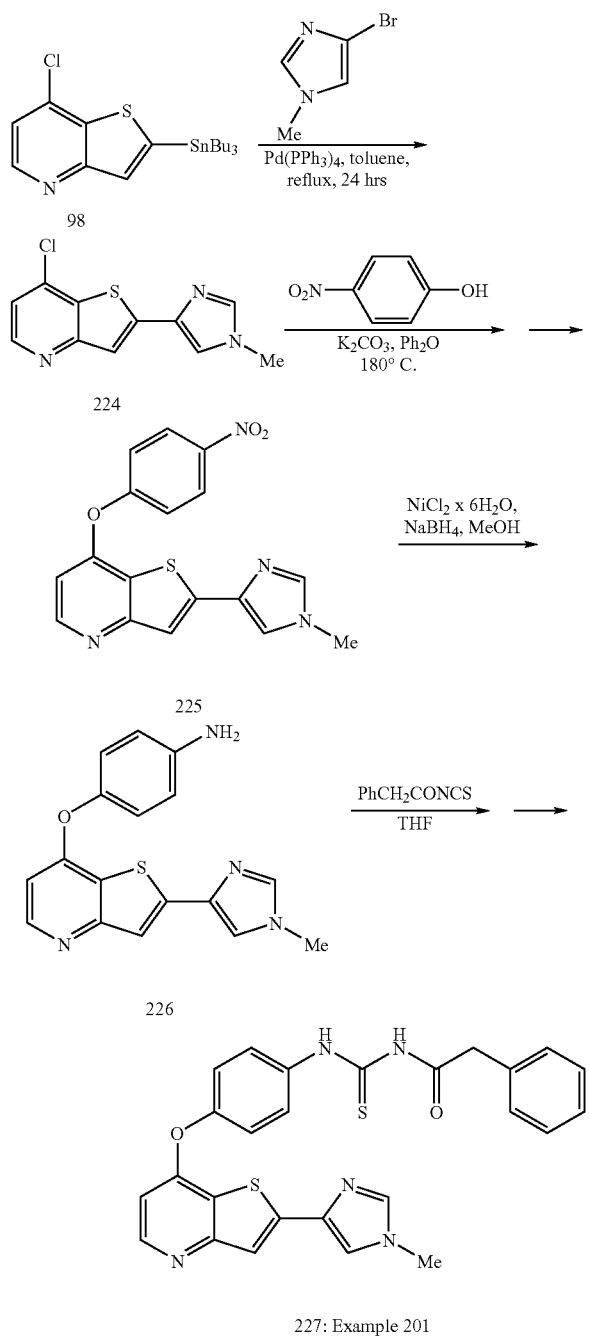

Example 201

N-(4-(2-(1-Methyl-1H-imidazol-4-yl)thieno[3,2-b]pyridin-7-yloxy)phenylcarbamothioyl)-2-phenylacetamide (227)

Step 1: 7-Chloro-2-(1-methyl-1H-imidazol-4-yl)thieno[3,2-b]pyridine (224)

Starting from the compound 98 (scheme 19), following the procedure described above for the synthesis of compound 10 (scheme 2, step 2, example 12) but replacing 2-bromothiazole with 4-bromo-1-methyl-1H-imidazole, title compound 224 was obtained in 29% yield. MS (m/z): 250.1 (100%), 252.1 (37%) (M+1).

Step 2: 2-(1-Methyl-1H-imidazol-4-yl)-7-(4-nitrophenoxy)thieno[3,2-b]pyridine (225)

A mixture of 224 (950 mg, 3.81 mmol), 4-nitrophenol (795 mg, 5.72 mmol), $K_2CO_3$ (1.05 g, 7.62 mmol) and $Ph_2O$ (5 mL) was stirred at 190° C. for 2 h in a sealed tube, cooled and treated with additional amount of 4-nitrophenol (795 mg, 5.72 mmol). The mixture was stirred for another hour at the same conditions, cooled to room temperature and diluted with DCM. The DCM solution was extracted with 2N HCl; the aqueous phase was collected, basified with concentrated ammonium hydroxide solution (pH~11) and extracted with EtOAc. The extract was dried over anhydrous $Na_2SO_4$ and concentrated under reduced pressure to afford 225 (860 mg, 64% yield) as an orange solid. MS (m/z): 353.1 (M+1).

Step 3: 4-(2-(1-Methyl-1H-imidazol-4-yl)thieno[3,2-b]pyridin-7-yloxy)benzenamine (226)

To a solution of 225 (860 mg, 2.44 mmol) and $NiCl_2 \times 6H_2O$ (1.16 mg, 4.88 mmol) in MeOH/THF (49/81 mL) $NaBH_4$ (278 mg, 7.32 mmol) was carefully added. The reaction mixture was stirred for 10 min, concentrated under reduced pressure and the residue was suspended in 10% HCl. The suspension was basified with concentrated $NH_4OH$ solution (pH ~11) and extracted with EtOAc.

The extract was dried over anhydrous $Na_2SO_4$ and concentrated under reduced pressure to produce a solid material. The aqueous phase (a suspension) was filtered; the precipitate was collected, washed with MeOH and dried under reduced pressure.

Both precipitate and the solid obtained from the organic phase, were combined to afford title compound 226 (947.4 mg, crude) as a brown solid that was used in the next step without further purification. MS (m/z): 323.1 (M+1).

Step 4: N-(4-(2-(1-Methyl-1H-imidazol-4-yl)thieno[3,2-b]pyridin-7-yloxy)phenylcarbamothioyl)-2-phenylacetamide (227)

To a suspension of the 226 (385 mg, 0.99 mmol) in THF (10 mL) was added 2-phenylacetyl isothiocyanate (263 mg, 1.49 mmol). The reaction mixture was stirred for 1 hr, transferred onto a chromatography column and eluted with EtOAc/MeOH (9:1) producing a solid material which was re-crystallized from MeCN to afford title compound 227 (74.3 mg, 15% yield) as a white solid. $^1$HNMR: (DMSO-$d_6$) d(ppm): 12.39 (s, 1H), 11.73 (s, 1H), 8.43 (d, J=5.3 Hz, 1H), 7.84 (s, 1H), 7.72 (m, 3H), 7.66 (s, 1H), 7.34-7.27 (m, 7H), 6.69 (d, J=5.3 Hz, 1H), 3.82 (s, 2H), 3.72 (s, 3H). MS (m/z): 500.1 (M+1).

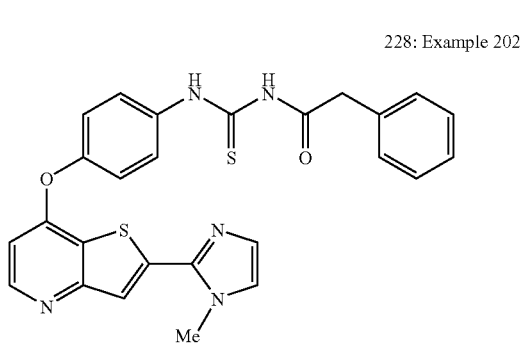

228: Example 202

Example 202

N-(4-(2-(1-Methyl-1H-imidazol-2-yl)thieno[3,2-b]pyridin-7-yloxy)phenylcarbamothioyl)-2-phenylacetamide (228)

Title compound 228 was obtained starting from the compound 214 (scheme 46) and following the procedures described above for the synthesis of compound 227 (scheme 49, example 201). $^1$H NMR (DMSO-$d_6$) δ (ppm): 12.42 (s, 1H), 11.77 (s, 1H), 8.74 (m, 1H), 8.37 (m, 1H), 7.87-7.78 (m, 1H), 7.70 (m, 1H), 7.42-7.20 (m, 7H), 6.90 (m, 1H), 4.05 (d, J=1 Hz, 3H), 3.83 (s, 2H). MS (m/z): 500.3.

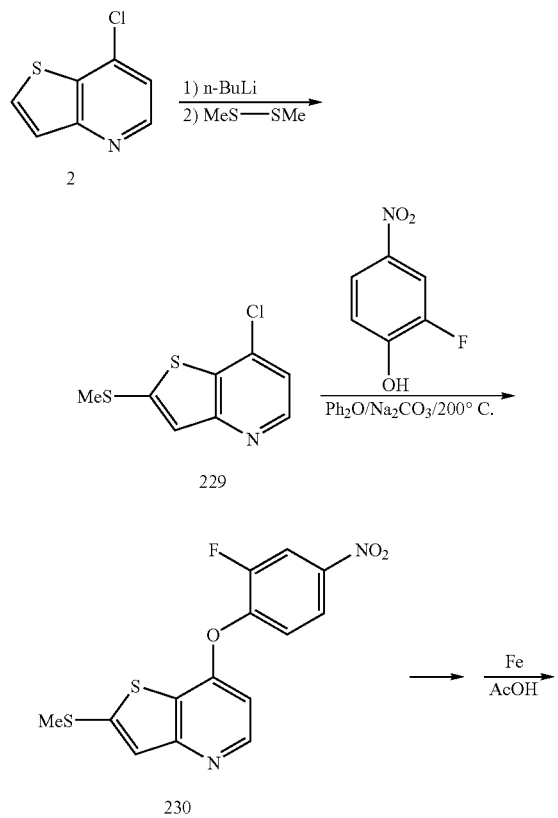

Scheme 50

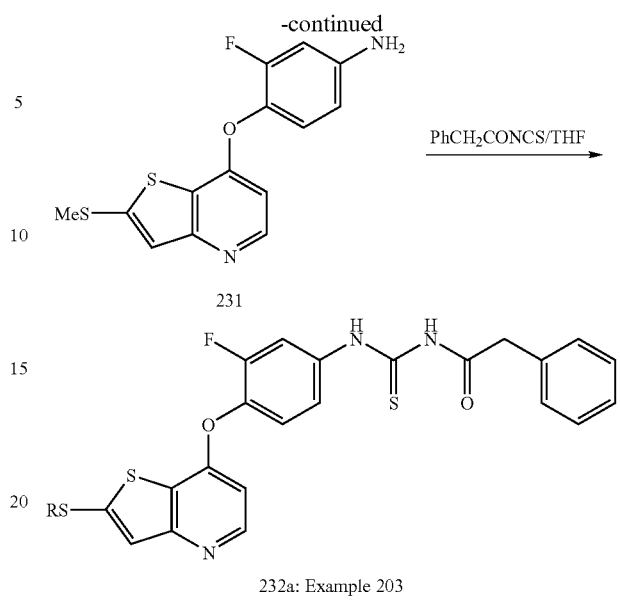

231

232a: Example 203 a: R = Me

Example 203

1-(4-(2-(Methylthio)thieno[3,2-b]pyridin-7-yloxy)-3-fluorophenyl)-3-(2-phenylacetyl)thiourea (232a)

Step 1: 7-Chloro-2-(methylthio)thieno[3,2-b]pyridine (229)

To a solution of 2 (200 mg, 1.18 mmol) in dry THF (11 ml) at −78° C. was added n-BuLi (0.57 mL, 2.5M solution on hexane, 1.41 mmol) and the resultant brown precipitate was stirred for 10 minutes. Methyl disulfide (0.16 ml, 1.77 mmol) was added slowly, the mixture was stirred at −78° C. for 3 hours and partitioned between DCM and water. Organic phase was separated, dried over anhydrous $Na_2SO_4$, filtered and concentrated under reduced pressure to afford title compound 229 (0.240 g, 94% yield, crude) as a yellow solid. MS (m/z): 216.1 (100%), 218.1 (39%) (M+1).

Step 2: 7-(2-Fluoro-4-nitrophenoxy)-2-(methylthio)thieno[3,2-b]pyridine (230)

To a suspension of 229 (100 mg, 0.463 mmol) in diphenyl ether (4 mL), was added 2-fluoro-4-nitrophenol (109 mg, 0.695 mmol) and sodium carbonate (147 mg, 1.39 mmol). The reaction mixture was heated at 200° C. overnight, cooled to room temperature, loaded onto a flash chromatography column and eluted with EtOAc/hexane (1:1) to afford title compound 230 (0.135 mg, 86% yield) as a yellow solid. MS (m/z): 337.0 (M+1).

Step 3: 4-(2-(Methylthio)thieno[3,2-b]pyridin-7-yloxy)-3-fluorobenzenamine (231)

To as solution of 230 (84 mg, 0.250 mmol) in acetic acid (5 mL) at 100° C., was added iron powder (0.069 g, 1.249 mmol). The reaction mixture was allowed to stir for 5 minutes, filtered through a celite pad and concentrated under reduced pressure. The residue was purified by column chromatography, eluent DCM/MeOH (50:1), to afford title compound 231 (61 mg, 80% yield) as yellow oil. MS (m/z): 307.1 (M+1).

Step 4: 1-(4-(2-(Methylthio)thieno[3,2-b]pyridin-7-yloxy)-3-fluorophenyl)-3-(2-phenylacetyl)thiourea (232a)

To a suspension of 231 (61 mg) in THF (2 mL) was added 2-phenylacetyl isothiocyanate (42 mg, 0.199 mmol). The reaction mixture was stirred for 3 hours, concentrated under reduced pressure and the residue was purified by column chromatography, eluent EtOAc/hexane (35:65), to produce yellow oil. Purification of this material by preparative HPLC (column C-18 Aquasil, gradient: 60% MeOH to 95% MeOH) afforded title compound 232a (25 mg, 26% yield) as a cream solid. Characterization of 232a is provided in the table 22.

Example 204

1-(4-(2-(Butylthio)thieno[3,2-b]pyridin-7-yloxy)-3-fluorophenyl)-3-(2-phenylacetyl)thiourea (232b)

Starting from the compound 2, following procedures described above for the synthesis of compound 232a (example 203, scheme 50) but replacing methyl disulfide with n-butyl disulfide in the step 1, title compound 232b was synthesized. Characterization of 232b is provided in the table 22.

Example 205

1-(4-(2-(Benzylthio)thieno[3,2-b]pyridin-7-yloxy)-3-fluorophenyl)-3-(2-phenylacetyl)thiourea (232c)

Starting from the compound 2, following procedures described above for the synthesis of compound 232a (example 203, scheme 50) but replacing methyl disulfide with benzyl disulfide in the step 1, title compound 232c was synthesized. Characterization of 232c is provided in the table 22.

Example 206

1-(4-(2-(Pyridin-2-ylthio)thieno[3,2-b]pyridin-7-yloxy)-3-fluorophenyl)-3-(2-phenylacetyl)thiourea (232d)

Starting from the compound 2, following procedures described above for the synthesis of compound 232a (example 203, scheme 50) but replacing methyl disulfide with 2-pyridyl disulfide in the step 1, title compound 232d was synthesized. Characterization of 232d is provided in the table 22.

TABLE 22

232a–d: Examples 203–206
Characterization of compounds 232a–d (examples 203–206)

| Cpd | Ex | R | Name | Characterization |
|---|---|---|---|---|
| 232a | 203 | Me | 1-(4-(2-(Methylthio)thieno[3,2-b]pyridin-7-yloxy)-3-fluorophenyl)-3-(2-phenylacetyl)thiourea | $^1$HNMR: (DMSO-d6) δ (ppm): 12.46(s, 1H), 11.81(s, 1H), 8.45(s, 1H), 7.99(d, J=12.5, 1H), 7.51(s, 1H), 7.50(s, 1H), 7.46(s, 1H), 7.34–7.30(m, 2H), 7.30–7.27(m, 3H), 6.61(d, J=5.5 Hz, 1H), 3.82(s, 2H), 2.71(s, 3H). MS (m/z): 484.1. |
| 232b | 204 | n-Bu | 1-(4-(2-(Butylthio)thieno[3,2-b]pyridin-7-yloxy)-3-fluorophenyl)-3-(2-phenylacetyl)thiourea | $^1$H NMR (DMSO-d$_6$) δ (ppm): 12.46(s, 1H), 11.81(s, 1H), 8.46(d, J=5.5 Hz, 1H), 7.98(d, J=12.44 Hz, 1H), 7.54(s, 1H), 7.53–7.47(m, 2H), 7.35–7.31(m, 4H), 7.31–7.24(m, 1H), 6.60(d, J=5.5 Hz, 1H), 3.82(s, 2H), 3.13(t, J=7.24 Hz, 2H), 1.64(q, J=7.43 Hz, 2H), 1.42(sextuplet, J=7.43 Hz, 2H), 0.90(t, J=7.24 Hz, 3H). MS (m/z): 526.2 |
| 232c | 205 | 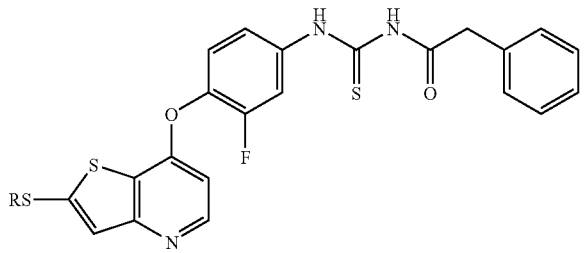 | 1-(4-(2-(Benzylthio)thieno[3,2-b]pyridin-7-yloxy)-3-fluorophenyl)-3-(2-phenylacetyl)thiourea | $^1$H NMR (DMSO-d$_6$) δ (ppm): 12.46 (s, 1H), 11.81(s, 1H), 8.44(d, J=5.5 Hz, 1H), 7.98(d, J=11.83 Hz, 1H), 7.52–7.45(m, 3H), 7.38–7.22(m, 10H), 6.60(d, J=5.5 Hz, 1H), 4.39(s, 2H), 3.82(s, 2H). MS (m/z): 560.2 |

TABLE 22-continued

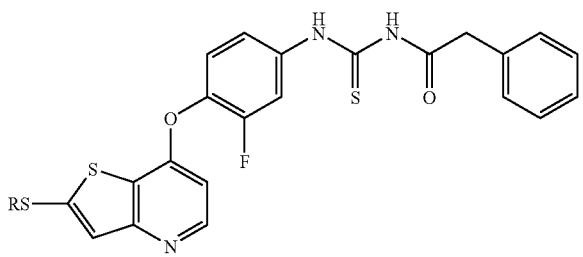

232a–d: Examples 203–206
Characterization of compounds 232a–d (examples 203–206)

| Cpd | Ex | R | Name | Characterization |
|---|---|---|---|---|
| 232d | 206 |  | 1-(4-(2-(Pyridin-2-ylthio)thieno[3,2-b]pyridin-7-yloxy)-3-fluorophenyl)-3-(2-phenylacetyl)thiourea | $^1$H NMR (DMSO-d6) δ (ppm): 8.55(d, J=5.3 Hz, 1H), 8.45(d, J=3.91 Hz, 1H), 8.00–7.95(m, 2H), 7.74(td, J=7.83 Hz; 1.76 Hz, 1H), 7.50(s, 2H), 7.35–7.23(m, 8H), 6.70(d, J=5.3 Hz, 1H), 3.82(s, 2H), 1.23(s, 1H). MS (m/z): 547.2 |

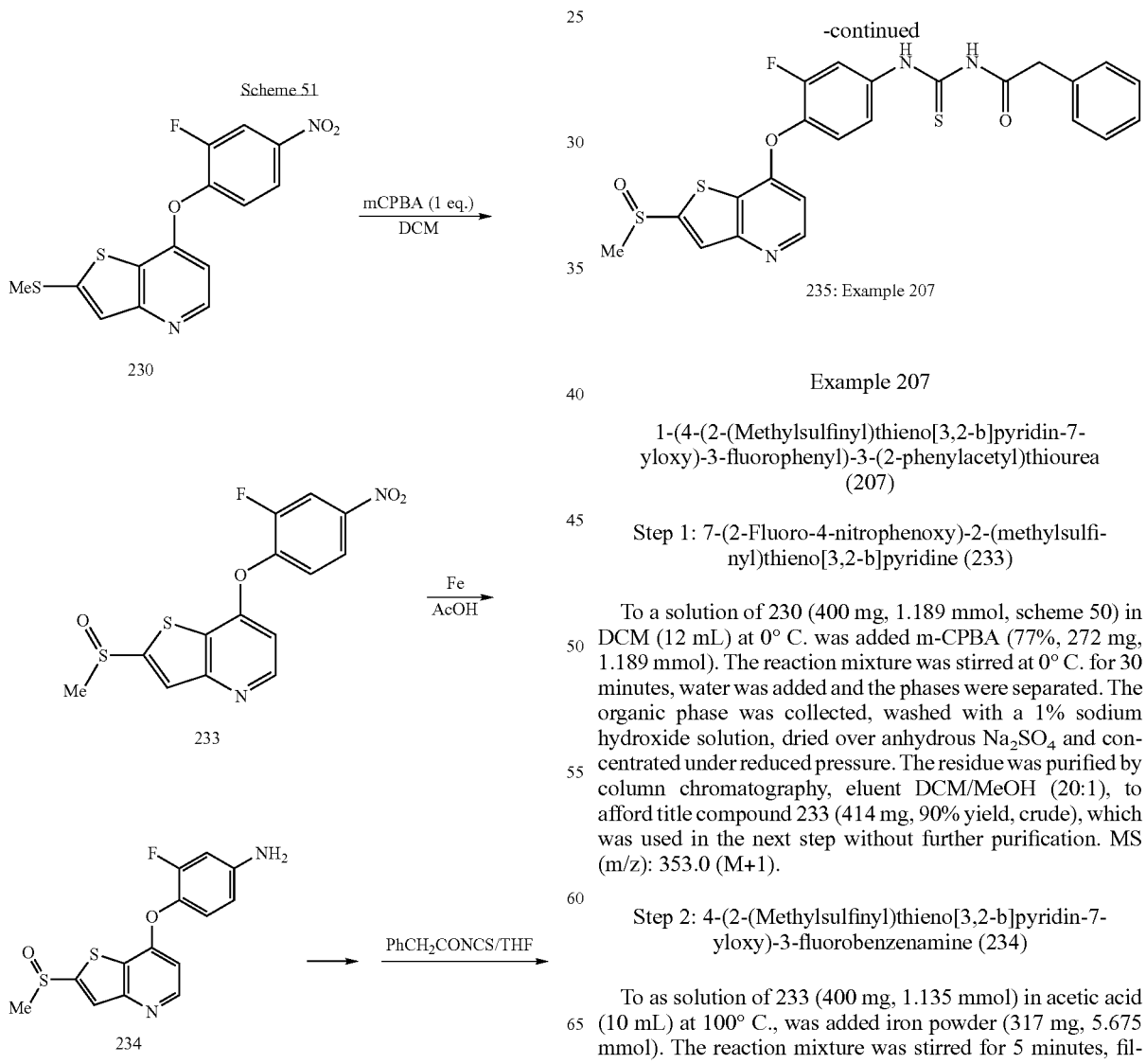

Example 207

1-(4-(2-(Methylsulfinyl)thieno[3,2-b]pyridin-7-yloxy)-3-fluorophenyl)-3-(2-phenylacetyl)thiourea (207)

Step 1: 7-(2-Fluoro-4-nitrophenoxy)-2-(methylsulfinyl)thieno[3,2-b]pyridine (233)

To a solution of 230 (400 mg, 1.189 mmol, scheme 50) in DCM (12 mL) at 0° C. was added m-CPBA (77%, 272 mg, 1.189 mmol). The reaction mixture was stirred at 0° C. for 30 minutes, water was added and the phases were separated. The organic phase was collected, washed with a 1% sodium hydroxide solution, dried over anhydrous $Na_2SO_4$ and concentrated under reduced pressure. The residue was purified by column chromatography, eluent DCM/MeOH (20:1), to afford title compound 233 (414 mg, 90% yield, crude), which was used in the next step without further purification. MS (m/z): 353.0 (M+1).

Step 2: 4-(2-(Methylsulfinyl)thieno[3,2-b]pyridin-7-yloxy)-3-fluorobenzenamine (234)

To as solution of 233 (400 mg, 1.135 mmol) in acetic acid (10 mL) at 100° C., was added iron powder (317 mg, 5.675 mmol). The reaction mixture was stirred for 5 minutes, filtered through a celite pad and concentrated under reduced pressure. The residue was purified by column chromatography, eluent EtOAc/hexane (4:1), to afford title compound 234 (0.285 g, 69% yield) as a yellow solid. MS (m/z): 323.0 (M+1).

Step 3: 1-(4-(2-(Methylsulfinyl)thieno[3,2-b]pyridin-7-yloxy)-3-fluorophenyl)-3-(2-phenylacetyl)thiourea (235)

To a suspension of 234 (280 mg, 0.868 mmol) in THF (8 mL) was added 2-phenyl acetyl isothiocyanate (185 mg, 1.04 mmol). The reaction mixture was stirred for 3 hours, concentrated; the solid residue washed with Et$_2$O and dried, to afford title compound 235 (229 mg, 53% yield) as a white-rose solid. $^1$HNMR: (DMSO-d6) δ (ppm): 12.41 (s, 1H), 11.75 (s, 1H), 8.54(d, J=5.3 Hz, 1H), 7.98 (s, 1H), 7.96(d, J=13.5 Hz, 1H), 7.48(d, J=5.0 Hz, 2H), 7.30-7.26(m, 2H), 7.26-7.18 (m, 3H), 6.69(d, J=5.5 Hz, 1H), 3.25 (s, 2H), 2.98 (s, 3H). MS (m/z): 500.1 (M+1).

Example 208

1-(4-(2-(Methylsulfonyl)thieno[3,2-b]pyridin-7-yloxy)-3-fluorophenyl)-3-(2-phenylacetyl)thiourea (238)

Step 1: 7-(2-Fluoro-4-nitrophenoxy)-2-(methylsulfonyl)thieno[3,2-b]pyridine (236)

To a solution of 233 (50 mg, 0.142 mmol) in DCM (2 mL), was added mCPBA (77%, 33 mg, 0.142 mmol) at 0° C. The mixture was stirred at 0° C. for 1 hour, water was added and the phases were separated. The organic layer was collected, washed with a 1% sodium hydroxide solution, dried over anhydrous Na$_2$SO$_4$ and concentrated under reduced pressure to afford title compound 236 (46 mg, 88% yield, crude) as a yellow solid which was used in the next step without additional purification. MS (m/z): 369.0 (M+1).

Step 2: 4-(2-(Methylsulfonyl)thieno[3,2-b]pyridin-7-yloxy)-3-fluorobenzenamine (237)

To a solution of 236 (45 mg, 0.122 mmol) in acetic acid (4 mL) at 100° C., was added iron powder (34 mg, 0.611 mmol). The reaction mixture was stirred for 5 minutes, filtered through a celite pad and concentrated under reduced pressure to afford title compound 237 (20 mg, 48% yield, crude) as a yellow oil that was used in the next step without further purification. MS (m/z): 339.0 (M+1).

Step 3. 1-(4-(2-(Methylsulfonyl)thieno[3,2-b]pyridin-7-yloxy)-3-fluorophenyl)-3-(2-phenylacetyl)thiourea (238)

To a suspension of 237 (20 mg, 0.059 mmol) in THF (10 mL) was added 2-phenylacetyl isothiocyanate (26 mg, 0.146 mmol). The reaction mixture was stirred for 2 hours, concentrated under reduced pressure and the residue was purified by column chromatography, eluent EtOAc/MeOH (19:1), to afford a solid material that was dissolved in a minimum MeOH and precipitated with hexane to afford title compound 238 (9.6 mg, 31%) as a white solid. $^1$HNMR: (DMSO-d$_6$) δ (ppm): 12.48 (s, 1H), 11.81 (s, 1H), 8.69(d, J=5.5 Hz, 1H), 8.36 (s, 1H), 8.03(d, J=12.13 Hz, 1H), 7.55 (s, 2H), 7.36-7.30 (m, 2H), 7.30-7.24 (m, 3H), 6.86(d, J=5.5 Hz, 1H), 3.83 (s, 2H), 3.54 (s, 3H). MS (m/z): 516.2.

Scheme 52

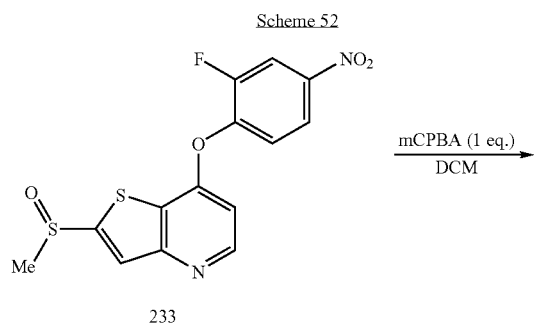
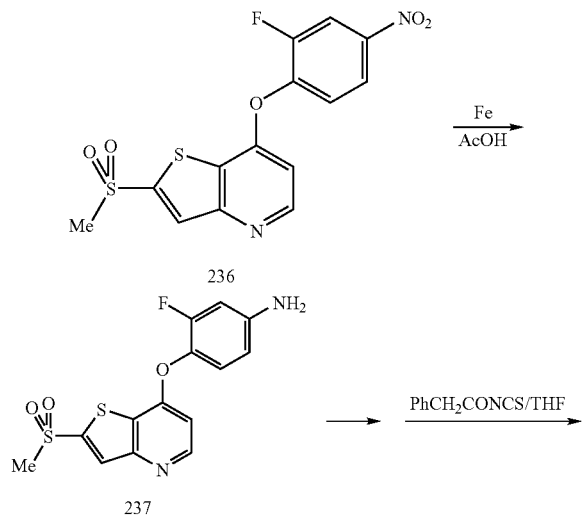

238: Example 208

Scheme 53

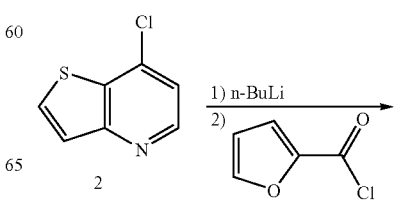

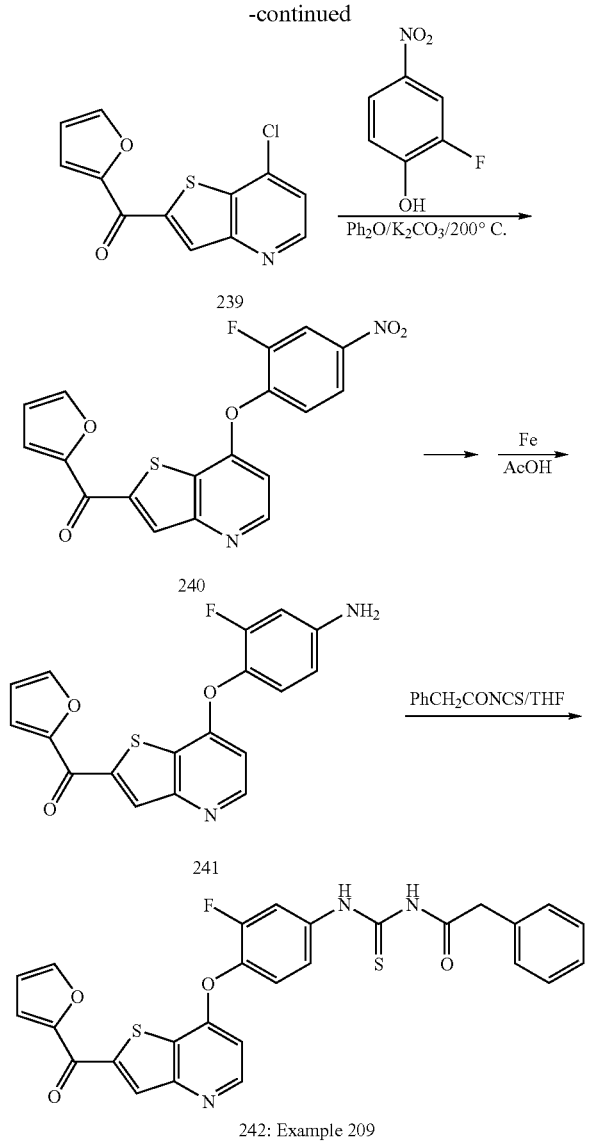

241

242: Example 209

Example 209

N-(3-Fluoro-4-(2-(furan-2-carbonyl)thieno[3,2-b]pyridin-7-yloxy)phenylcarbamothioyl)-2-phenylacetamide (242)

Step 1: (7-Chlorothieno[3,2-b]pyridin-2-yl)(furan-2-yl)methanone (239)

To a solution of 2 (100 mg, 0.589 mmol) in THF (6 mL) at −78° C., was added n-BuLi (2.5 M in hexane, 0.259 mL, 8.84 mmol) and the reaction mixture was stirred 15 minutes. 2-Furoyl chloride (0.087 mL, 0.884 mmol) was added drop wise; the mixture was stirred for additional 2 hours and partitioned between DCM and water. The organic layer was separated, dried over anhydrous $Na_2SO_4$ and concentrated under reduced pressure to afford title compound 239 (35 mg, 23% yield, crude) as a yellow solid, that was used in the next step without additional purification. MS (m/z): 264.0 (100%), 266.0 (40%) (M+1).

Step 2: (7-(2-Fluoro-4-nitrobenzyl)thieno[3,2-b]pyridin-2-yl)(furan-2-yl)methanone (240)

To a suspension of 239 (35 mg, 0.133 mmol) in $Ph_2O$ (2 mL) was added 2-fluoro-4-nitrophenol (42 mg, 0.265 mmol) and $K_2CO_3$ (73 mg, 0.530 mmol). The reaction mixture was heated at 180° C. in a sealed flask for 60 hrs, cooled down to room temperature, loaded onto a flash chromatography column and eluted with EtOAc/hexane mixture (1:1), to afford title compound 240 (20 mg 39% yield) as a yellow solid. MS (m/z): 385.1 (M+1).

Step 3: (7-(4-Amino-2-fluorobenzyl)thieno[3,2-b]pyridin-2-yl)(furan-2-yl)methanone (241)

To as solution of 240 (20 mg, 0.052 mmol) in acetic acid (2 mL) at 100° C., was added iron powder (15 mg, 0.260 mmol). The reaction mixture was stirred for 3 minutes, filtered through a celite pad and concentrated under reduced pressure. The residue was purified by flash chromatography, eluent EtOAc/hexane (3:7) to afford title compound 241 (3.3 mg, 18% yield) as a yellow solid. MS (m/z): 355.1 (M+1).

Step 4: N-(3-Fluoro-4-(2-(furan-2-carbonyl)thieno[3,2-b]pyridin-7-yloxy)phenylcarbamothioyl)-2-phenylacetamide (242)

To a solution of 241 (3.3 mg, 0.0093 mmol) in THF (1 mL) was added 2-phenylacetyl isothiocyanate (2 mg, 0.011 mmol). The reaction mixture was stirred for 3 hours, concentrated under reduced pressure and purified by column chromatography, eluent EtOAc/hexane (20:80), followed by precipitation from a mixture acetone/hexane. Thus, title compound 242 was obtained (2.2 mg, 44% yield) as a yellow solid. $^1$HNMR: 1HNMR: (DMSO-d6) δ (ppm): 12.49 (s, 1H), 11.82 (s, 1H), 8.67(d, J=5.5 Hz, 1H), 8.63 (s, 1H), 8.22(s, 1H), 8.03(d, J=13.1 Hz, 1H), 7.79(d, J=3.7 Hz, 1H), 7.60-7.55 (m, 2H), 7.55-7.25 (m, 5H), 6.89-6.87 (m, 1H), 6.83(d, J=5.5 Hz, 1H), 3.82 (s, 2H). MS (m/z): 532.1 (M+1).

Scheme 54

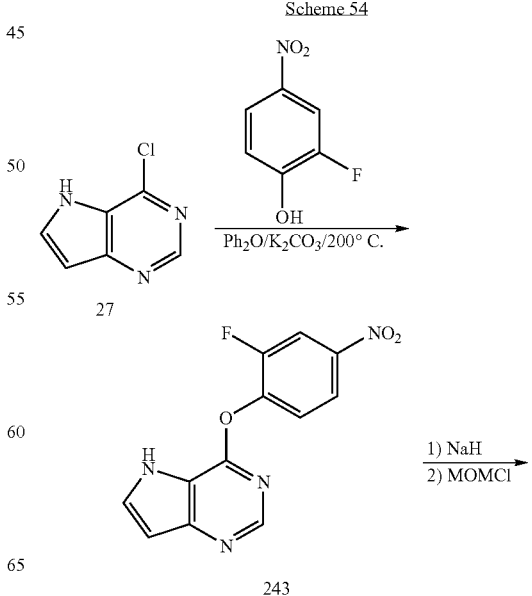

243

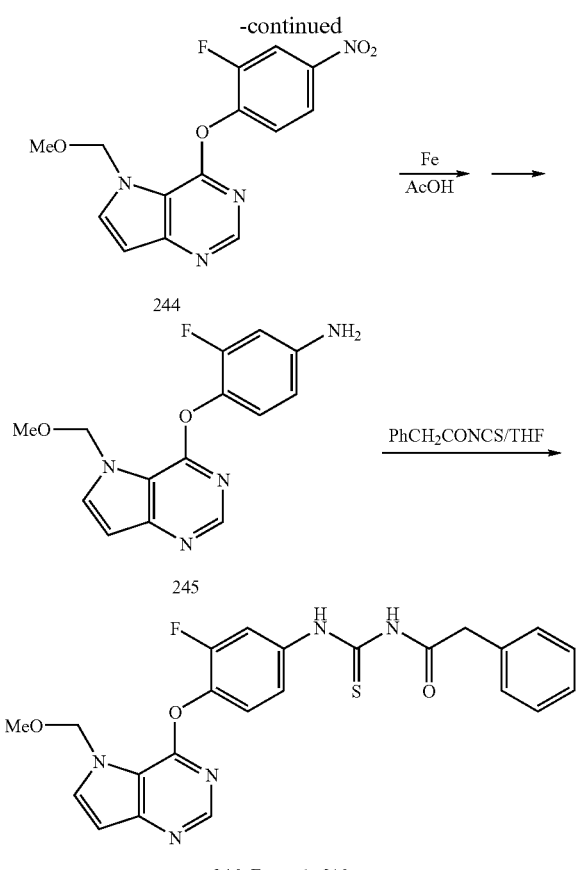

Example 210

N-(3-Fluoro-4-(5-(methoxymethyl)-5H-pyrrolo[3,2-d]pyrimidin-4-yloxy)phenylcarbamothioyl)-2-phenylacetamide (246)

Step 1. 4-(2-Fluoro-4-nitrophenoxy)-5H-pyrrolo[3,2-d]pyrimidine (243)

To a suspension of 27 (0.400 g, 2.60 mmol) [G. B. Evans, R. H. Furneaux, et. al *J. Org. Chem.*, 2001, 66, 17, 5723-5730] in diphenylether (25 ml) was added 2-fluoro-4-nitrophenol (614 mg, 3.90 mmol) and HCl (2N in $Et_2O$) (0.19 ml, 3.90 mmol). The reaction mixture was heated at 120° C. for 4 hours, cooled to room temperature and concentrated under reduced pressure, to afford title compound 243 (610 mg, 86% yield) as a black solid. MS (m/z): 274.1 (M+1).

Step 2: 4-(2-Fluoro-4-nitrophenoxy)-5-(methoxymethyl)-5H-pyrrolo[3,2-d]pyrimidine (244)

To a suspension of 243 (150 mg, 0.547 mmol in DMF (6 mL) was added NaH (66 mg, 1.64 mmol), and the reaction mixture was stirred at 0° C. for 1 hour. Chloromethyl methyl ester (132 mg, 1.641 mmol) was added drop wise and the mixture was stirred at room temperature overnight. MeOH (2 mL) was added and the mixture was stirred for an additional hour and partitioned between EtOAc and water. The organic phase was collected, dried over anhydrous sodium sulfate and concentrated under reduced pressure to afford title compound 244 (86 mg, 49% yield, crude) as an orange solid. MS (m/z): 319.1 (M+1).

Step 3: 3-Fluoro-4-(5-(methoxymethyl)-5H-pyrrolo[3,2-d]pyrimidin-4-yloxy)benzenamine (245)

To as solution of 244 (85 mg, 0.267 mmol) in acetic acid (8 mL) at 100° C., was added iron powder (75 mg, 1.34 mmol). The reaction mixture was stirred for 5 minutes, filtered through Celite® pad and concentrated to dryness; the residue was purified by flash chromatography, eluent DCM/MeOH (30:1) to afford title compound 245 (18 mg, 23% yield) as an orange solid. MS (m/z): 289.1 (M+1).

Step 4: N-(3-Fluoro-4-(5-(methoxymethyl)-5H-pyrrolo[3,2-d]pyrimidin-4-yloxy)phenylcarbamothioyl)-2-phenylacetamide (246)

To a suspension of 245 (18 mg, 0.062 mmol) in THF (1 mL) was added 2-phenylacetyl isothiocyanate (12 mg, 0.069 mmol). The reaction mixture was stirred for 3 hours, concentrated under reduced pressure and the residue was purified by flash chromatography, eluent hexane/EtOAc (3:2) followed by recrystallization (MeCN/water), and preparative HPLC (Aquasil C-18, gradient: 60% MeOH to 95% MeOH in water), to afford title compound 246 (9.2 mg, 33% yield) as a white solid. $^1$HNMR: ($CD_3OD$) δ (ppm): 8.35 (s, 1H), 8.03 (d, J=12.4 Hz, 1H), 7.96(d, J=3.13 Hz, 1H), 7.44-7.26 (m, 6H), 6.69 (d, J=3.13 Hz, 1H), 5.29 (quintuplet, J=6.65 Hz, 1H), 3.75 (s, 2H), 3.60 (d, J=10.96 Hz, 3H), 1.63(d, J=6.65 Hz, 6H). MS (m/z): 464.16 (M+1).

Scheme 55

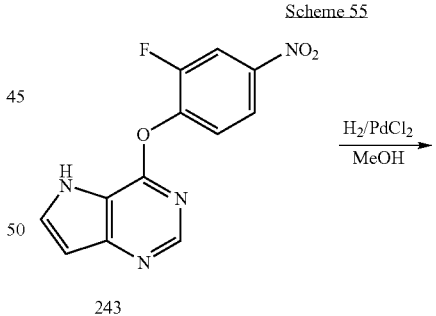

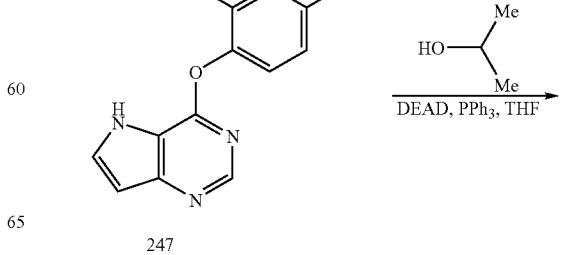

-continued

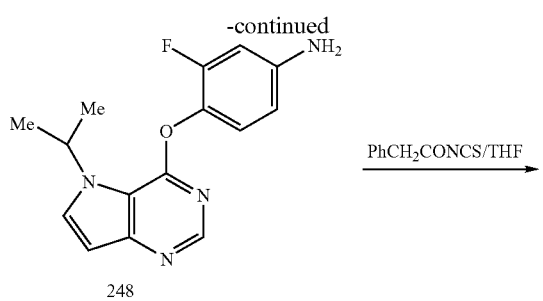

248

PhCH₂CONCS/THF

249: Example 211

Example 211

N-(3-Fluoro-4-(5-isopropyl-5H-pyrrolo[3,2-d]pyrimidin-4-yloxy)phenylcarbamothioyl)-2-phenylacetamide (249)

Step 1: 4-(5H-Pyrrolo[3,2-d]pyrimidin-4-yloxy)-3-fluorobenzenamine (247)

A solution of 243 (263 mg, 0.966 mmol, scheme 54) in MeOH (10 mL) and PdCl₂ (1.8 mg, 0.01 mmol) was stirred in the atmosphere of hydrogen for 60 hrs. The reaction mixture was filtered and the filtrate was concentrated under reduced pressure. Water was added to the residue and the aqueous solution was extracted with DCM. The extract was dried over anhydrous Na₂SO₄ and concentrated under reduced pressure, to afford title compound 247 (170 mg, 72% yield, crude) as a gray solid. MS (m/z): 243.08 (M+1).

Step 2: 3-Fluoro-4-(5-isopropyl-5H-pyrrolo[3,2-d]pyrimidin-4-yloxy)benzenamine (248)

To a suspension of 247 (80 mg, 0.327 mmol) in THF (4 mL), was added PPh₃ (258 mg, 0.983 mmol), DEAD (0.155 ml, 0.983 mmol) and isopropanol (0.075 ml, 0.983 mmol), and the reaction mixture was allowed to stir for 48 hours. 3N HCl solution (1.0 mL) was added and the mixture was extracted with DCM. Aqueous phase was collected, neutralized with NaOH 10% (pH ~11) and extracted with DCM. The organic phase was collected, dried over anhydrous sodium sulfate and concentrated under reduced pressure. The residue was purified twice by column chromatography: eluents EtOAc/hexane (3:7) and MeOH/DCM (1:20), to afford title compound 248 (19 mg, 31% yield) as yellow solid. MS (m/z): 287.1 (M+1).

Step 3: N-(3-Fluoro-4-(5-isopropyl-5H-pyrrolo[3,2-d]pyrimidin-4-yloxy)phenylcarbamothioyl)-2-phenylacetamide (249)

To a suspension of 248 (10 mg, 0.035 mmol) in THF (1 mL) was added 2-phenylacetyl isothiocyanate (0.007 mL, 0.038 mmol). The reaction mixture was stirred for 3 hours, concentrated under reduced pressure and the residue was purified by flash chromatography, eluent EtOAc/hexane (1:1) and preparative HPLC (C-18 Aquasyl column, gradient: 60% to 95% MeOH in water, 45 min), to afford title compound 249 (4 mg, 26% yield) as a white solid. ¹HNMR: (CD₃OD) δ (ppm): 8.35 (s, 1H), 8.03 (d, J=12.4 Hz, 1H), 7.96(d, J=3.13 Hz, 1H), 7.44-7.26 (m, 6H), 6.69 (d, J=3.13 Hz, 1H), 5.29 (quintuplet, J=6.65 Hz, 1H), 3.75 (s, 2H), 3.60 (d, J=10.96 Hz, 3H), 1.63(d, J=6.65 Hz, 6H). MS (m/z): 464.2 (M+1).

Scheme 56

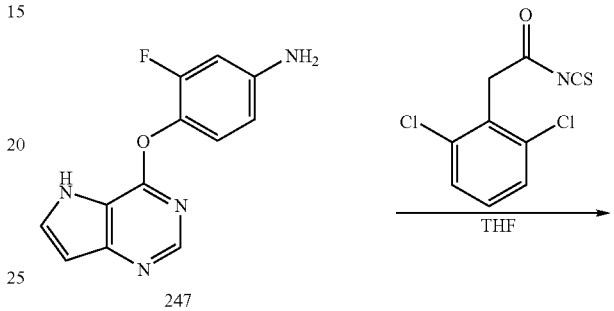

247

THF

250: Example 212

Example 212

N-(4-(5H-Pyrrolo[3,2-d]pyrimidin-4-yloxy)-3-fluorophenylcarbamothioyl)-2-(2,6-dichlorophenyl)acetamide (250)

Step 1: N-(4-(5H-pyrrolo[3,2-d]pyrimidin-4-yloxy)-3-fluorophenylcarbamothioyl)-2-(2,6-dichlorophenyl)acetamide (250)

To a solution of 247 (200 mg, 0.819 mmol, scheme 55) in THF (8.2 mL) 2-(2,6-dichlorophenyl)acetyl isothiocyanate (302 mg, 1.33 mmol) was added. The mixture was stirred for 1 h at room temperature, transferred onto a flash chromatography column and eluted with EtOAc/hexane (1:1). The solid material obtained was triturated with diethyl ether, filtered and dried under reduced pressure, to afford title compound 250 (200 mg, 0.408, 50% yield) as a light brown solid. ¹HNMR: (DMSO-d₆) δ (ppm) 12.69 (s, 1H), 12.26 (s, 1H), 12.04 (s, 1H), 7.94 (m, 2H), 7.53 (m, 4H), 7.39 (m, 1H), 6.72 (m, 1H), 4.22 (s, 2H). MS (m/z): 490.1 (100%, 492.1 (77%) (M+1).

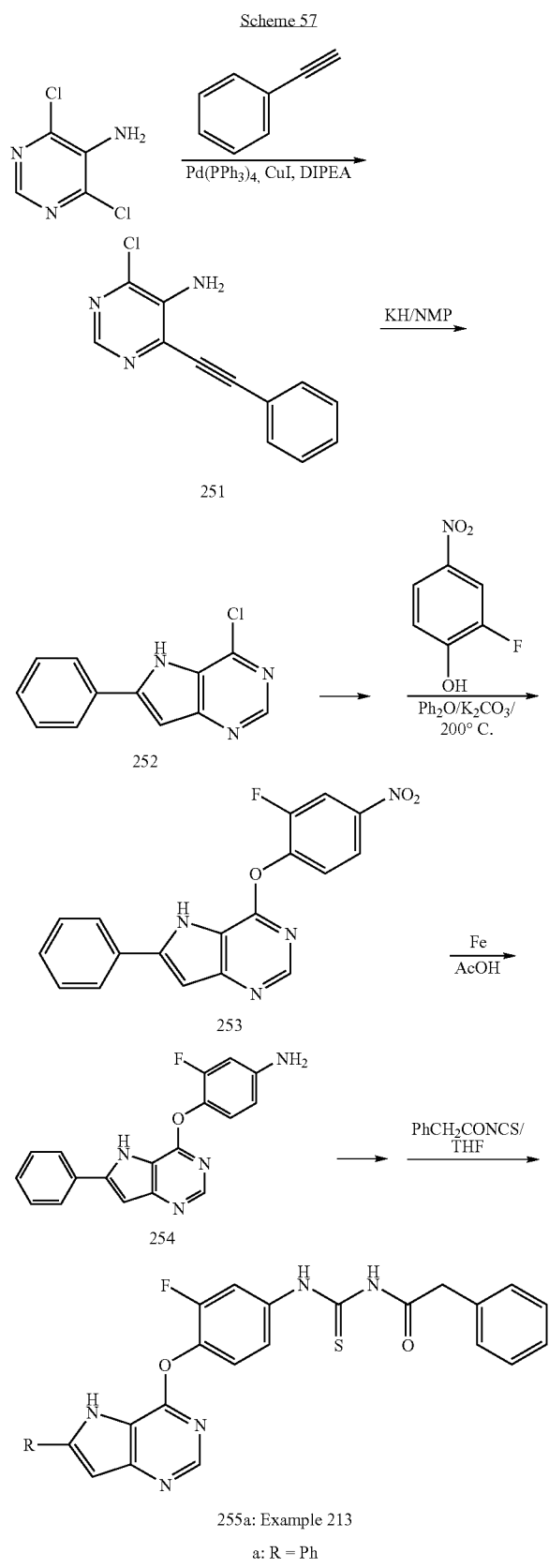

Example 213

N-(3-Fluoro-4-(6-phenyl-5H-pyrrolo[3,2-d]pyrimidin-4-yloxy)phenylcarbamothioyl)-2-phenylacetamide (255a)

Step 1:
4-Chloro-6-(phenylethynyl)pyrimidin-5-amine (251)

Ethynylbenzene (0.092 mL, 0.92 mmol) was added to a solution of 4,6-dichloropyrimidin-5-amine (100 mg, 0.61 mmol), Pd(PPh$_3$)$_4$ (140 mg, 0.12 mmol), CuI (116 mg, 0.61 mmol) and DIPEA (0.5 mL, 3.05 mmol) in DME (6.1 mL). The reaction mixture was stirred in the dark over night at room temperature, diluted with DCM, washed sequentially with dilute aqueous citric acid and water, dried over anhydrous Na$_2$SO$_4$ and concentrated under reduce pressure. The residue was purified by flash chromatography, eluent EtOAc/hexane (1:3), to afford title compound 251 (30.8 mg, 22% yield) as a yellow solid. MS (m/z): 230.1 (100.0%), 232.1 (33%) (M+1).

Step 2:
4-Chloro-6-phenyl-5H-pyrrolo[3,2-d]pyrimidine (252)

To a solution of 251 (30.8 mg, 0.134 mmol) in NMP (1.4 mL) a suspension of KH in mineral oil (35%, 31 mL, 0.268 mmol) was added in one portion. The mixture was stirred at room temperature overnight and partitioned between EtOAc and water. The organic phase was collected, dried over anhydrous Na$_2$SO$_4$ and concentrated. The residue was purified by flash chromatography, eluent EtOAc/hexane (1:2) to afford title compound affording 252 (22.7 mg, 74% yield). MS (m/z): 230.1 (100%) 232.1 (33%) (M+1).

Step 3: 4-(2-Fluoro-4-nitrophenoxy)-6-phenyl-5H-pyrrolo[3,2-d]pyrimidine (253)

A mixture of 252 (47.9 mg, 0.21 mmol), 4-nitrophenol (50 mg, 0.32 mmol), K$_2$CO$_3$ (58 mg, 0.42 mmol) and Ph$_2$O (4 mL) was stirred at 190° C. overnight in a sealed tube. The mixture was cooled down, more 4-nitrophenol (50 mg, 0.32 mmol) was added and the mixture was stirred at 190° C. for additional 8 h. It was cooled again, transferred onto a chromatography column and eluted sequentially with EtOAc/hexane (1:10) and EtOAc/hexane (1:3), to afford title compound 253 (71.4 mg, 97% yield) as a white foam. MS (m/z): 351.1 (M+1).

Step 4: 3-Fluoro-4-(6-phenyl-5H-pyrrolo[3,2-d]pyrimidin-4-yloxy)benzenamine (254)

To a solution of 253 (71.4 mg, 0.21 mmol) in acetic acid (2.1 mL) at 100° C., was added iron powder (59 mg, 1.05 mmol). The reaction mixture was stirred for 5 minutes, filtered through a Celite® pad and concentrated under reduced pressure. The residue was purified by column chromatography, eluent EtOAc/hexane (2:1), to afford title compound 254 (27.9 mg, 40% yield). MS (m/z): 321.1 (M+1).

Step 5: N-(3-Fluoro-4-(6-phenyl-5H-pyrrolo[3,2-d]pyrimidin-4-yloxy)phenylcarbamothioyl)-2-phenylacetamide (255a)

To a suspension of the 254 (26.8 mg, 0.84 mmol) in THF (1.6 ml) was added 2-phenylacetyl isothiocyanate (23 mg, 0.13 mmol). The mixture was stirred for 1 hr transferred onto a chromatography column and eluted sequentially with EtOAc/MeOH (9:1) and EtOAc/hexane (1:1), to afford title compound 255a (30 mg, 72% yield) as a white solid. ¹HNMR: (DMSO-d₆) δ (ppm): 12.65 (s, 1H), 12.43 (s, 1H), 11.79 (s, 1H), 8.31 (s, 1H), 8.06 (d, J=7.6 Hz, 2H), 7.91 (m, 1H), 7.52 (m, 4H), 7.43 (m, 1H), 7.34, (m, 4H), 7.27 (m, 1H), 7.18 (m, 1H), 3.83 (s, 2H). MS (m/z): 498.2 (M+1).

Example 214

N-(3-Fluoro-4-(6-(pyridin-2-yl)-5H-pyrrolo[3,2-d]pyrimidin-4-yloxy)phenylcarbamothioyl)-2-phenylacetamide (255b)

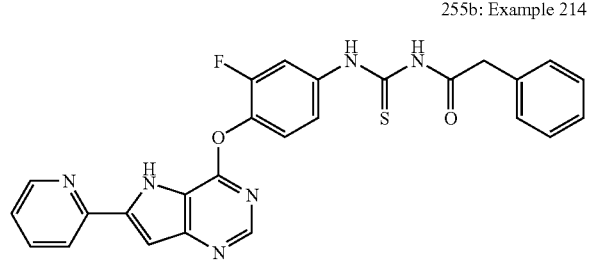

255b: Example 214

Following the procedures described above for the synthesis of compound 255a (example 213, scheme 57) but replacing ethynylbenzene in the step 1 with 2-ethynylpyridine, title compound 255b was obtained. ¹H NMR (DMSO-d₆) δ (ppm): 12.85 (br, 1H), 12.65 (br, 1H), 11.75 (br, 1H), 8.71 (m, 1H), 8.33 (s, 1H), 8.21 (d, J=8Hz, 1H), 7.96 (m, 1H), 7.89 (m, 1H), 7.52-7.42 (m, 3H), 7.34-7.32 (m, 5H), 7.28 (m, 1H), 3.83 (s, 2H). MS (m/z): 499.2 (M+1).

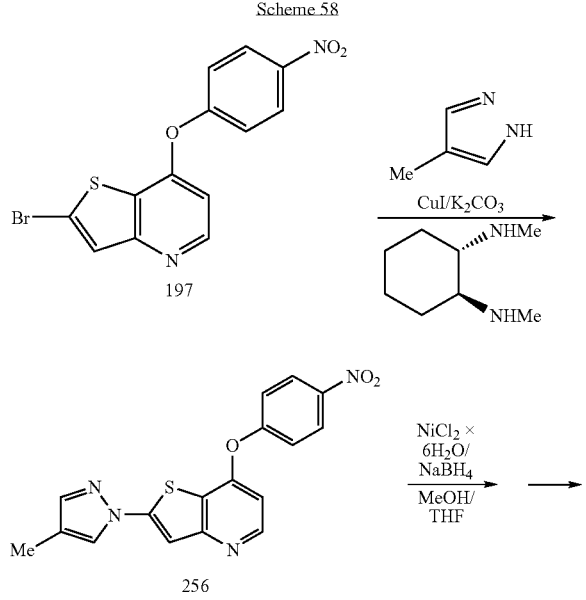

Scheme 58

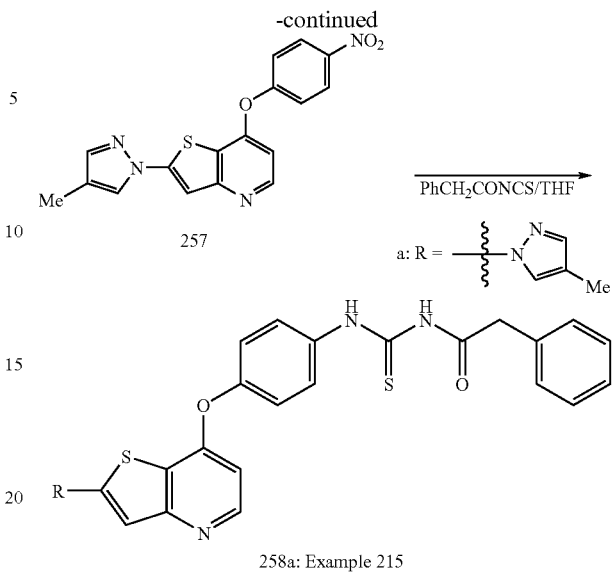

257 a: R = [pyrazole group]

258a: Example 215

Example 215

N-(4-(2-(4-Methyl-1H-pyrazol-1-yl)thieno[3,2-b]pyridin-7-yloxy) phenylcarbamothioyl)-2-phenylacetamide (258a)

Step 1: 2-(4-Methyl-1H-pyrazol-1-yl)-7-(4-nitrophenoxy)thieno[3,2-b]pyridine (256)

A mixture of 197 (300 mg, 0.86 mmol, scheme 42), 4-methyl-1H-pyrazole (69 mg, 0.86 mmol), CuI (16.4 mg, 0.086 mmol), trans-N¹,N²-dimethylcyclohexane-1,2-diamine (24.4 mg, 0.172 mmol) [J. C. Antilla, A. Klapars, et. al. *JACS*, 2002, 124, 11684-1688] and K₂CO₃ (238 mg, 1.72 mmol) in toluene (1.7 mL) was stirred at room temperature in an atmosphere of nitrogen overnight, diluted with EtOAc (100 mL), filtered through a Celite® pad, and concentrated under reduced pressure. The residue was purified by flash chromatography with gradient elution with EtOAc/hexane (1:1) to EtOAc/hexane (2:1) to afford title compound 256 (88.8 mg, 37% yield) as a white solid. MS (m/z): 352.06 (M+1).

Step 2: 4-(2-(4-Methyl-1H-pyrazol-1-yl)thieno[3,2-b]pyridin-7-yloxy)benzenamine (257)

To a solution of 256 (168.4 mg, 0.478 mmol) and NiCl₂× 6H₂O (226 mg, 0.956 mmol) in MeOH/THF (10/10 mL) NaBH₄ (72 mg, 1.92 mmol) was carefully added. The reaction mixture was stirred for 10 min, concentrated to dryness and the resultant solid was suspended in 10% HCl. The aqueous solution was basified (pH ~11) with concentrated aqueous NH₄OH and extracted with EtOAc. The organic extract was collected, dried over anhydrous Na₂SO₄ and concentrated under reduced pressure, to afford title compound 257 (134.6 mg, 87% yield) as a white solid. MS (m/z): 322.09 (M+1).

Step 3: N-(4-(2-(4-Methyl-1H-pyrazol-1-yl)thieno[3,2-b]pyridin-7-yloxy)phenylcarbamothioyl)-2-phenylacetamide (258a)

To a suspension of the 257 (134.6 mg, 0.418 mmol) in THF (4.2 mL) was added 2-phenylacetyl isothiocyanate (111 mg, 0.627 mmol). The reaction mixture was stirred for 1 hr at room temperature, transferred onto a chromatography column and eluted with a gradient of gradient EtOAc/hexane, 1:1 to 2:1, to provide a beige solid which was triturated with diethyl ether to afford title compound 258a (31 mg, 15% yield) as a white solid. Characterization of 258a is provided in the table 23.

Example 216

N-(4-(2-(1H-Pyrazol-1-yl)thieno[3,2-b]pyridin-7-yloxy)phenylcarbamothioyl)-2-phenylacetamide (258b)

Following the procedures described above for the synthesis of compound 258a (example 215, scheme 58) but replacing 4-methyl-1H-pyrazole in the step 1 with 1H-pyrazole, title compound 258b was obtained. Characterization of 258b is provided in the table 23.

Example 217

N-(4-(2-(3,5-Dimethyl-1H-pyrazol-1-yl)thieno[3,2-b]pyridin-7-yloxy)phenylcarbamothioyl)-2-phenylacetamide (258c)

Following the procedures described above for the synthesis of compound 258a (example 215, scheme 58) but replacing 4-methyl-1H-pyrazole in the step 1 with 3,5-dimethyl-1H-pyrazole, title compound 258c was obtained. Characterization of 258c is provided in the table 23.

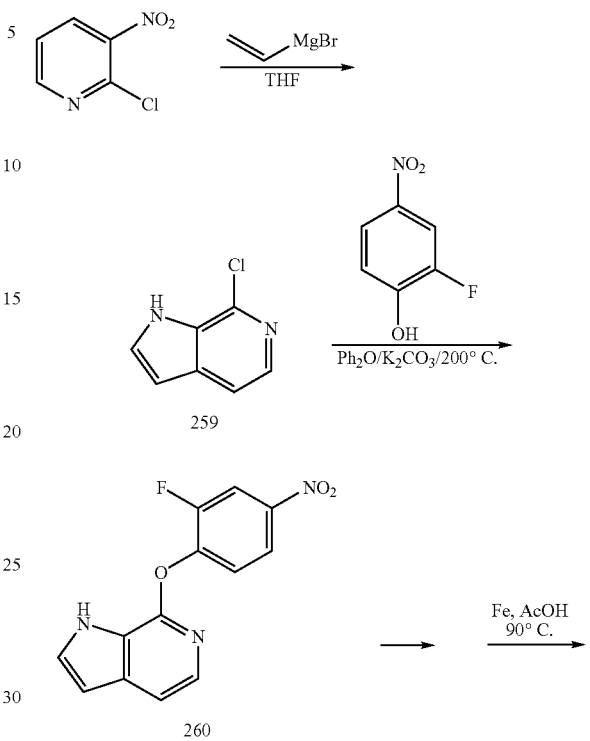

Scheme 59

TABLE 23

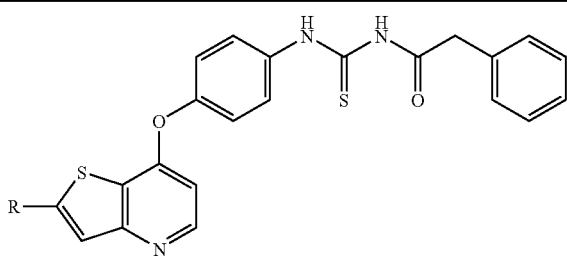

258a–c: Examples 215–217
Characterization of compounds 258a–c (examples 215–217)

| Cpd | Ex | R | Name | Characterization |
|---|---|---|---|---|
| 258a | 215 | 4-methyl-pyrazol-1-yl | N-(4-(2-(4-Methyl-1H-pyrazol-1-yl)thieno[3,2-b]pyridin-7-yloxy)phenylcarbamothioyl)-2-phenylacetamide | $^1$HNMR: (DMSO-$d_6$) δ (ppm): 12.42(br, 1H), 11.76(br, 1H), 8.5(m, 2H), 7.75(m, 2H), 7.65(s, 2H), 7.32(m, 7H), 6.65(m, 1H), 3.83(s, 2H), 2.12(s, 3H). MS (m/z): 500.0 (M + 1). |
| 258b | 216 | pyrazol-1-yl | N-(4-(2-(1H-Pyrazol-1-yl)thieno[3,2-b]pyridin-7-yloxy)phenylcarbamothioyl)-2-phenylacetamide | $^1$H NMR (DMSO-$d_6$) δ (ppm): 12.4(s, 1H), 11.73(s, 1H), 8.74(d, J=2.5 Hz, 1H), 8.45(d, J=5.7 Hz, 1H), 7.87(s, 1H), 7.81(m, 1H), 7.74(d, J=8.8 Hz, 1H), 7.34–7.31(m, 7H), 6.66(m, 2H), 3.82(s, 2H). MS (m/z): 486.1 |
| 258c | 217 | 3,5-dimethyl-pyrazol-1-yl | N-(4-(2-(3,5-Dimethyl-1H-pyrazol-1-yl)thieno[3,2-b]pyridin-7-yloxy)phenylcarbamothioyl)-2-phenylacetamide | $^1$H NMR (DMSO-$d_6$) δ (ppm): 12.44(s, 1H), 11.77(s, 1H), 8.6(d, J=5.8, 1H), 7.78(m, 2H), 7.49(s, 1H), 7.38–7.28(m, 7H), 6.80(d, J=5.8 Hz, 2H), 6.27(s, 1H), 3.83(s, 2H), 2.59(s, 3H), 2.21(s, 3H). MS (m/z): 514.1 |

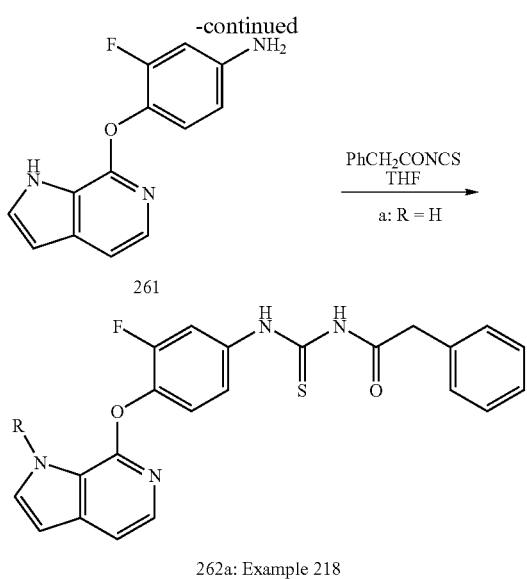

261

262a: Example 218

Example 218

N-(4-(1H-Pyrrolo[2,3-c]pyridin-7-yloxy)-3-fluorophenylcarbamothioyl)-2-phenylacetamide (262a)

Step 1. 7-Chloro-1H-pyrrolo[2,3-c]pyridine (259)

To a solution of 2-chloro-3-nitropyridine (5 g, 31.5 mmol)) in THF (200 mL) at −78° C., was added vinylmagnesium bromide (100 mL, 1.0M in THF) The reaction mixture was stirred at −20° C. for 8 hours, quenched with NH₄Cl solution (20%, 150 mL), extracted with EtOAc, dried over anhydrous Na₂SO₄ and concentrated. The residue was purified by flash chromatography, eluent EtOAc/hexane (1:5), to afford the title compound 259 (1.23 g, 26% yield) as a white solid [Z. Zhang, et al. *J. Org. Chem.*, 2002, 67, 2345-2347]. MS (m/z): 153.1 (M+H) (found).

Step 2. 7-(2-Fluoro-4-nitrophenoxy)-1H-pyrrolo[2,3-c]pyridine (260)

A mixture of 259 (420 mg, 2.76 mmol), 2-fluoro-4-nitrophenol (651 mg, 4.14 mmol) and K₂CO₃(1.14 g, 8.28 mmol) in Ph₂O (15 mL) was heated at 200° C. for 6 hours, cooled to room temperature and partitioned between EtOAc and water. Organic phase was collected, dried and concentrated. The residue was purified by flash column chromatography with gradient elution from hexane to hexane/EtOAc (3:1), to afford the title compound 260 (333 mg, 44% yield) as a yellowish solid. MS (m/z): 274. 1 (M+H) (found).

Step 3. 4-(1H-Pyrrolo[2,3-c]pyridin-7-yloxy)-3-fluorobenzenamine (261)

To a solution of 260 (100 mg, 0.36 mmol) in AcOH (4 mL) at 90° C., was added iron powder (102 mg, 2.1 mmol). The reaction mixture was vigorously stirred for 10 min, cooled, filtered through a Celite pad and concentrated. The residue was purified by flash column chromatography, eluent EtOAc/ hexane (1:1), to afford title compound 261 (87 mg, 99% yield) as an off-white solid. MS (m/z): 244.1 (M+H) (found).

Step 4. N-(4-(1H-Pyrrolo[2,3-c]pyridin-7-yloxy)-3-fluorophenylcarbamothioyl)-2-phenylacetamide (262a)

A mixture of 261 (44 mg, 0.18 mmol) and 2-phenylacetyl isothiocyanate (36 □L, 0.19 mmol) in THF (2 mL) was stirred at room temperature for 2 hours, and concentrated. The residue was purified by flash column chromatography, eluent EtOAc/hexane (1:1), to afford the title compound 262a (30 mg, 40%) as an off-white solid. ¹H NMR (DMSO-d₆) δ (ppm): 12.41 (s, 1H), 12.07 (s, 1H), 11.77 (s, 1H), 7.84(dd, 1H, J₁=10.95 Hz, J₂=2.0 Hz), 7.58(t, 1H, J₁=J₂=2.7 Hz), 7.51(d, 1H, J=5.7 Hz), 7.43-7.39 (m, 2H), 7.37-7.33(m, 4H), 7.31-7.26 (m, 2H), 6.55(dd, 1H, J₁=1.76 Hz, J₂=2.9 Hz), 3.84 (s, 2H), MS (m/z): 421.1 (M+H) (found).

Scheme 60

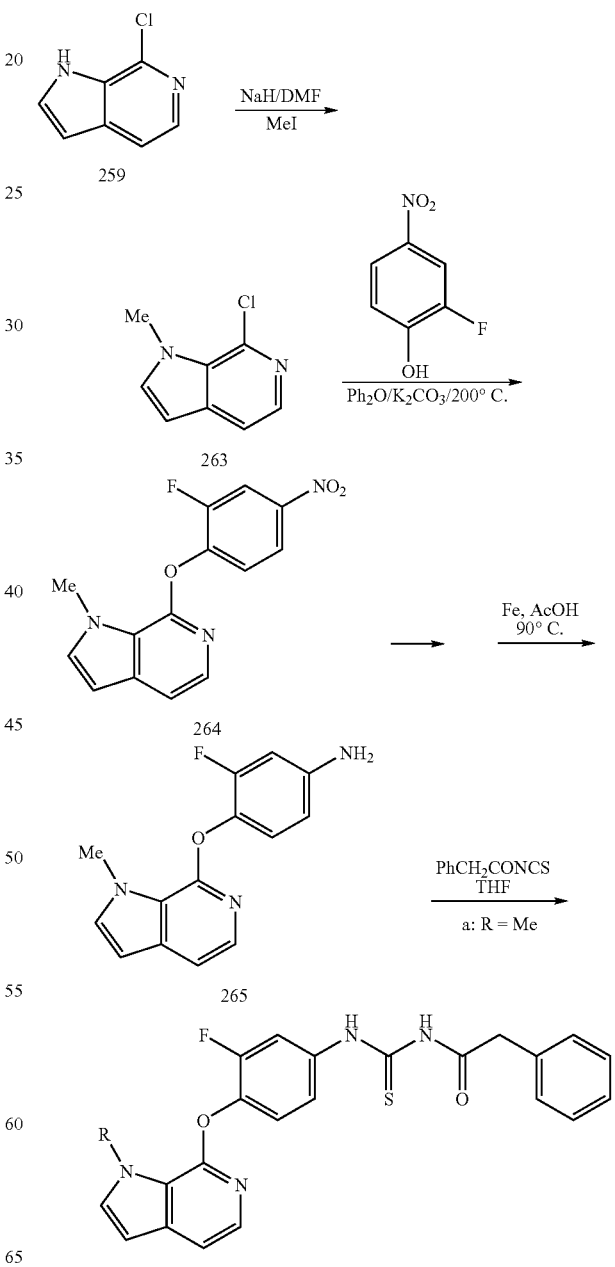

262b: Example 219

Example 219

N-(3-Fluoro-4-(1-methyl-1H-pyrrolo[2,3-c]pyridin-7-yloxy)phenylcarbamothioyl)-2-phenylacetamide (262b)

Step 1. 7-Chloro-1-methyl-1H-pyrrolo[2,3-c]pyridine (263)

To a solution of 259 (250 mg, 1.64 mmol) in DMF (16 mL) at 0° C. was added NaH (197 mg, 4.92 mmol, 60% in mineral oil), and the mixture was stirred for 30 min, followed by addition of MeI (112 □L, 1.80 mmol). The reaction mixture was stirred at room temperature for 2 h before acetic acid (1 mL) was added. Solvents were removed under reduced pressure, the residue was partitioned between water and EtOAc. Organic phase was collected, dried over anhydrous $Na_2SO_4$ and concentrated. The residue was purified by flash column chromatography, eluent EtOAc/hexane (1:1), to afford the title compound 263 (200 mg, 92% yield) as an off-white solid. MS (m/z): 167.1 (M+H) (found).

Step 2. 7-(2-Fluoro-4-nitrophenoxy)-1-methyl-1H-pyrrolo[2,3-c]pyridine (264)

Starting from the compound 263 and following the procedure described above for the synthesis of nitro compound 260 (scheme 59, step 2, example 218), title compound 264 was obtained in 91% yield as a yellow solid. MS (m/z): 288.1 (M+H) (found).

Step 3.-Fluoro-4-(1-methyl-1H-pyrrolo[2,3-c]pyridin-7-yloxy)benzenamine (265)

Starting from the compound 264 and following the procedure described above for the synthesis of amine 261 (scheme 59, step 3, example 218), title compound 265 was obtained in 89% yield as an off-white solid. MS (m/z): 258.1 (M+H) (found).

Step 4. N-(3-Fluoro-4-(1-methyl-1H-pyrrolo[2,3-c]pyridin-7-yloxy)phenylcarbamothioyl)-2-phenylacetamide (262b)

Starting from the compound 265 and following the procedure described above for the synthesis of compound 262a (scheme 59, step 4, example 218), title compound 262b was obtained in 87% yield as an off-white solid. $^1$H NMR (DMSO-$d_6$) δ (ppm): 12.40 (s, 1H), 11.78 (s, 1H), 7.83(dd, 1H, $J_1$=10.95 Hz, $J_2$=1.9 Hz), 7.56(d, 1H, 2.7 Hz), 7.49(d, 1H, J=5.5 Hz), 7.43-7.39 (m, 2H), 7.37-7.33 (m, 4H), 7.31-7.26 (m, 2H), 6.52(d, 1H, $J_2$=2.9 Hz), 4.11 (s, 3H), 3.84 (s, 2H), MS (m/z): 435.1 (M+H) (found).

Example 220

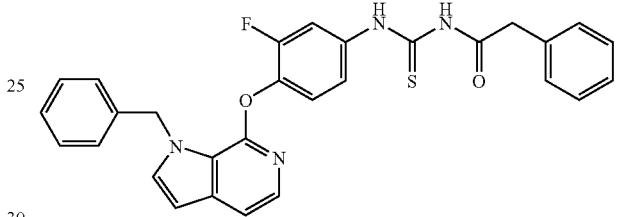

262c: Example 220

N-(4-(1-Benzyl-1H-pyrrolo[2,3-c]pyridin-7-yloxy)-3-fluorophenylcarbamothioyl)-2-phenylacetamide (262c)

Starting from the compound 259 and following the procedures described above for the synthesis of compound 262b (scheme 60, step 4, example 219) but using benzyl bromide in step 1 instead of methyl iodide, title compound 262c was obtained. $^1$H NMR (DMSO-$d_6$) δ (ppm): 12.36 (s, 1H), 11.76 (s, 1H), 7.78 (m, 1H), 7.58(t, 1H, $J_1$=$J_2$=2.7 Hz), 7.50(d, 1H, J=5.7 Hz), 7.34 (m, 5H), 7.30-7.221 (m, 5H), 7.15(dd, 1H, $J_1$=8.1 Hz, $J_2$=0.4 Hz), 7.10(t, 1H), 6.60(d, 1H, J=2.9 Hz), 5.68 (s, 2H), 3.82 (s, 2H). MS (m/z): 511.2 (M+H) (found).

Scheme 61

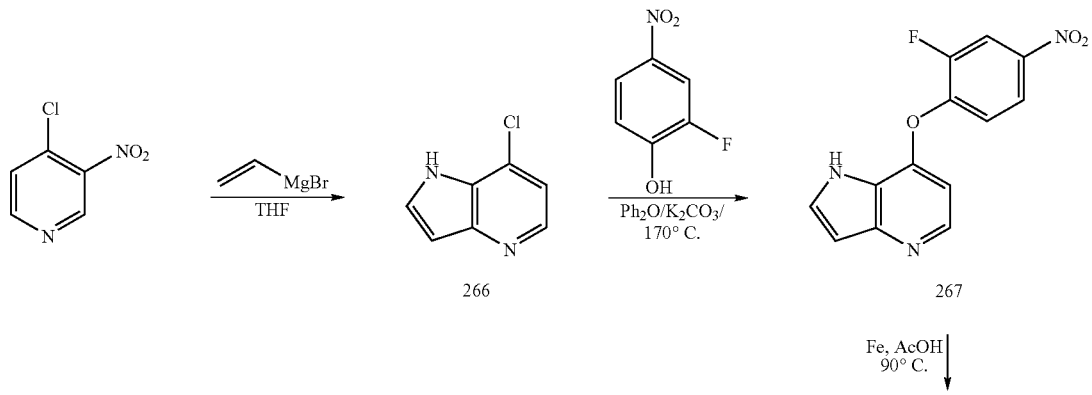

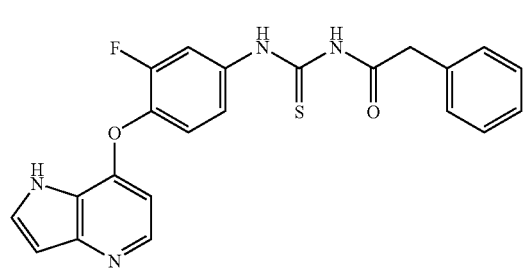

269a: Example 221

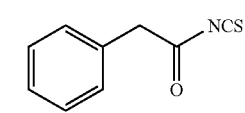

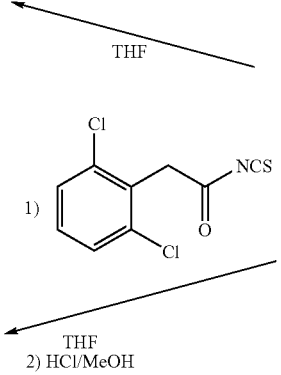

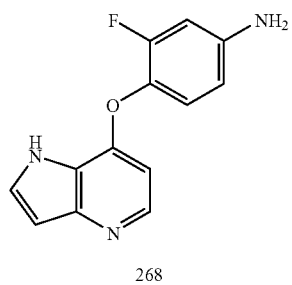
268

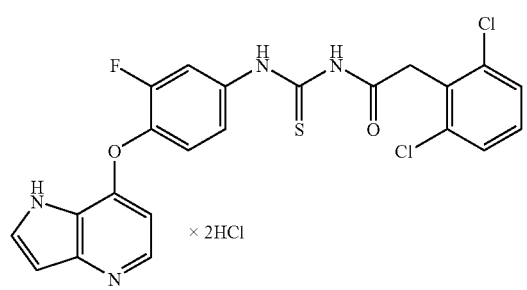

269b: Example 222

Example 221

N-(4-(1H-Pyrrolo[3,2-b]pyridin-7-yloxy)-3-fluorophenylcarbamothioyl)-2-phenyl acetamide (269a)

Step 1. 7-Chloro-1H-pyrrolo[3,2-b]pyridine (266)

To a solution of 2-chloro-3-nitropyridine (2.0 g, 12.6 mmol) [C. Almansa, et al. *J. Med. Chem.* 2001, 44, 350-361] in THF (80 mL) at −78° C., was added vinylmagnesium bromide (80 mL, 1.0M in THF), and the reaction mixture was stirred at −20° C. for 8 hours, quenched with $NH_4Cl$ solution (20%, 100 mL), extracted with EtOAc, dried over anhydrous $Na_2SO_4$ and concentrated. The residue was purified by flash column chromatography, eluent EtOAc/Hexane (1:1), to afford the title compound 266 (240 mg, 11%) as yellow crystals. MS (m/z): 153.1 (M+H) (found).

Step 2. 7-(2-Fluoro-4-nitrophenoxy)-1H-pyrrolo[3,2-b]pyridine (267)

A mixture of 266 (180 mg, 1.18 mmol), 2-fluoro-4-nitrophenol (558 mg, 3.55 mmol) and $K_2CO_3$ (981 mg, 7.10 mmol) in $Ph_2O$ (4 mL) was heated at 170° C. for 8 hours, cooled to room temperature and partitioned between EtOAc and water. Organic phase was collected, dried over anhydrous $Na_2SO_4$ and concentrated. The residue was purified by flash column chromatography with gradient elution of hexane, to hexane/EtOAc (1:1), to afford the title compound 267 (84 mg, 26% yield) as a yellowish solid. MS (m/z): 274.1 (M+H) (found).

Step 3. 4-(1H-Pyrrolo[3,2-b]pyridin-7-yloxy)-3-fluorobenzenamine (268)

To a solution of 267 (35 mg, 0.13 mmol) in AcOH (1 mL) at 90° C., was added iron powder (36 mg, 0.65 mmol). The reaction mixture was stirred vigorously for 10 min, cooled, filtered through a Celite pad and concentrated. The residue was partitioned between DCM and $NaHCO_3$ saturated solution. Phases were separated; the aqueous phase was neutralized with AcOH and extracted with DCM. Primary organic phase and the extract were combined and concentrated to give the title compound 268 (31 mg, 99%) as an off-white solid. MS (m/z): 244.1 (M+H) (found).

Step 4. N-(4-(1H-Pyrrolo[3,2-b]pyridin-7-yloxy)-3-fluorophenylcarbamothioyl)-2-phenyl acetamide (269a)

A mixture of 268 (20 mg, 0.08 mmol) and 2-phenylacetyl isothiocyanate (16 □L, 0.08 mmol) in THF (1 mL) was stirred at room temperature for 2 hours and concentrated. The residue was purified by flash column chromatography (eluent EtOAc) followed by preparative HPLC (column Aqusil C18, gradient elution with 60-95% MeOH in water, 45 min) to afford the title compound 269a (13 mg, 40% yield) as an off-white solid. $^1H$ NMR ($CD_3OD$) δ (ppm): 8.41 (s, 1H), 8.16 (d, 1H, J=5.6 Hz), 8.02 (dd, 1H, $J_1$=2.3Hz, $J_2$=12.2 Hz), 7.62 (d, 1H, J=3.3 Hz), 7.44 (m, 1H), 7.37-7.33 (m, 4H) 7.31-7.26 (m, 1H), 6.65(d, 1H, J=3.1 Hz), 6.52(d, 1H, J=5.7 Hz), 3.76 (s, 2H), MS (m/z): 421.1 (M+H) (found).

Example 222

N-(4-(1H-Pyrrolo[3,2-b]pyridin-7-yloxy)-3-fluorophenylcarbamothioyl)-2-(2,6-dichlorophenyl)acetamide dihydrochloride (269b)

Starting from the compound 268 and following the procedure described above for the synthesis of compound 269a (example 221) but replacing 2-phenylacethyl isothiocyanate with 2-(2,6-dichlorophenyl)acetyl isothiocyanate, a white solid was obtained. This material was dissolved in MeOH and treated with HCl (1 mL, 1.0M in ether). Solvents were removed under the reduced pressure and the residue was lyophilized, to afford the title compound 269b (48% yield) as a yellowish solid. $^1$H NMR (DMSO-d$_6$) δ (ppm): 13.29 (s, 1H), 12.32 (s, 1H), 12.05(s, 1H), 8.52(d, 1H), 8.14 (m, 2H), 7.64 (m, 2H), 7.51(d, 1H), 7.37(dd, 1H), 6.86 (m, 1H), 6.81 (dd, 1H), 4.22 (s, 2H), MS (m/z): 489.1 (M+H) (found).

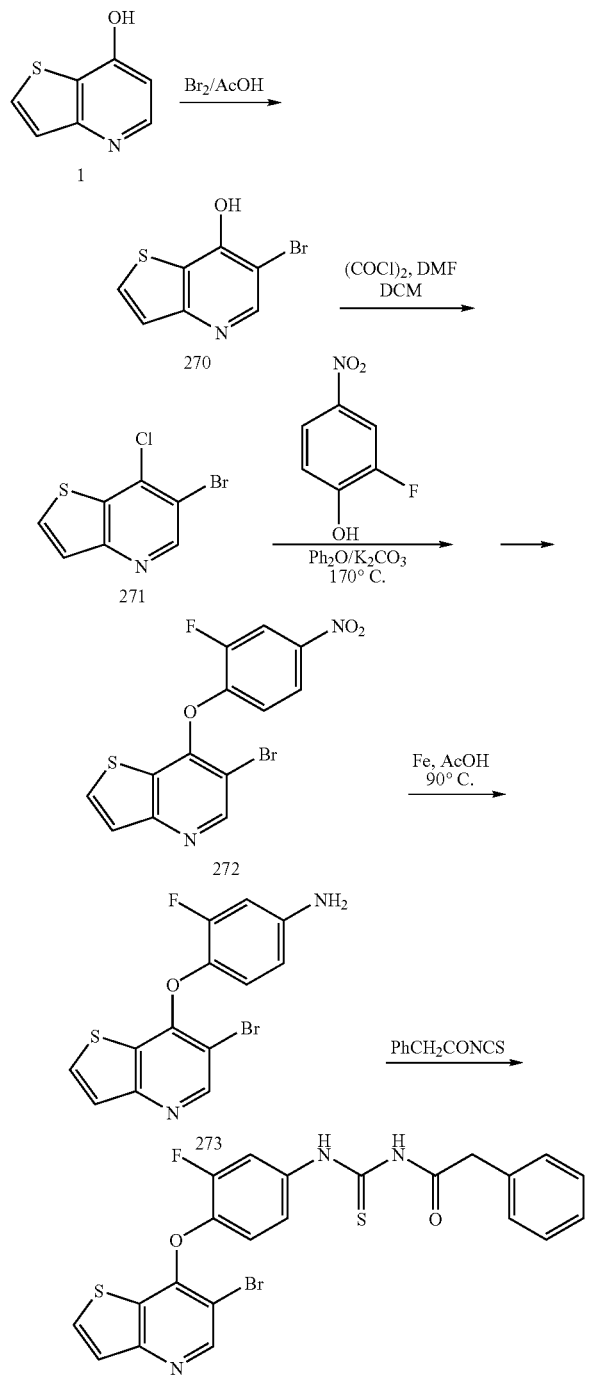

Scheme 62

274: Example 223

Example 223

N-(4-(6-Bromothieno[3,2-b]pyridin-7-yloxy)-3-fluorophenylcarbamothioyl)-2-phenylacetamide (274)

Step 1. 6-Bromothieno[3,2-b]pyridin-7-ol (270)

To a solution of thieno[3,2-b]pyridin-7-ol (1, 2.55 g, 16.87 mmol) in acetic acid (50 mL) was added bromine (1.7 mL, 32.72 mmol). The mixture was heated at 110° C. for 1 h, cooled and the resultant precipitate was separated by filtration, to afford the title compound 270 (4.47 g, crude) as a dark brown powder, which was used in next step without further purification. M/S (m/z): 231.9 (M+H) (found).

Step 2. 6-Bromo-7-chlorothieno[3,2-b]pyridine (271)

DMF (0.72 mL) was added slowly to a solution of (COCl)$_2$ in DCE at 0° C. and the mixture was stirred for 30 min, followed by addition of 270 (crude from above). The combined mixture was stirred for 10 min at the same conditions and was heated to reflux for 3 h. After cooling the mixture was concentrated and partitioned between DCM and water. Organic phase was collected and dried over anhydrous Na$_2$SO$_4$, filtered and concentrated. The residue was purified by flash column chromatography (eluent EtOAc), to afford the title compound 271 (0.66 g, 70% yield based on compound 1) as a yellowish solid. MS (m/z): 249.0 (M+H) (found).

Step 3. 6-Bromo-7-(2-fluoro-4-nitrophenoxy)thieno[3,2-b]pyridine (272)

Starting from the compound 271 and following the procedure described above for the synthesis of compound 260 (scheme 59, example 218, step 2), title compound 272 was obtained in 61% yield as an off-white solid. MS (m/z): 368.9 (M+H).

Step 4. 4-(6-Bromothieno[3,2-b]pyridin-7-yloxy)-3-fluorobenzenamine (273)

Starting from the compound 272 and following the procedure described above for the synthesis of compound 261 (scheme 59, example 218, step 3), title compound 273 was obtained in 92% yield as a light brown solid. MS (m/z): 340.0 (M+H).

Step 5. N-(4-(6-Bromothieno[3,2-b]pyridin-7-yloxy)-3-fluorophenylcarbamothioyl)-2-phenylacetamide (274)

Starting from the compound 273 and following the procedure described above for the synthesis of compound 262a (scheme 59, example 218, step 4), title compound 274 was obtained in 99% yield as a white solid. $^1$H NMR (DMSO-d$_6$) δ (ppm): 12.44 (s, 1H), 11.79(s, 1H), 8.82 (s, 1H), 8.03(d, 1H), 7.99(dd, 1H), 7.54(d, 1H), 7.41(dd, 1H), 7.32-7.24 (m, 6H), 3.80 (s, 2H). MS (m/z): 517.0 (M+H) (found).

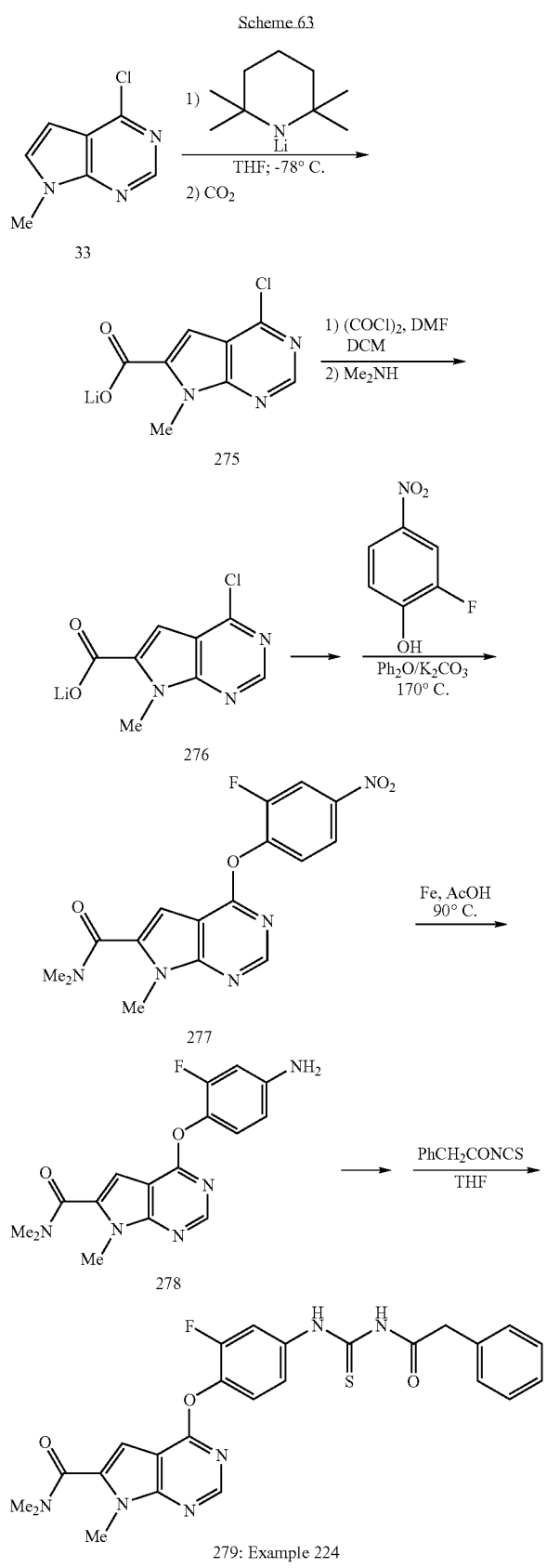

Scheme 63

279: Example 224

Example 224

4-(2-Fluoro-4-(3-(2-phenylacetyl)thioureido)phenoxy)-N,N,7-trimethyl-7H-pyrrolo [2,3-d]pyrimidine-6-carboxamide (279)

Step 1. Lithium 4-chloro-7-methyl-7H-pyrrolo[2,3-d]pyrimidine-6-carboxylate (275)

To a solution of 2,2,6,6-tetramethylpiperidine (92 µL, 0.54 mmol) in THF (4 mL) at −10° C., n-BuLi (338 µL, 1.6M in hexane, 0.54 mmol) was added drop wise and the reaction mixture was stirred at −10° C. for 10 min. Compound 33 (60 mg, 0.36 mmol) [G. B. Evans et al. *J. Org. Chem.* 2001, 66, 17, 5723-5730 and shown in the scheme 6] was added drop wise maintaining the temperature below −70° C. over a period of 15 min. Dried $CO_2$-gas was bubbled through the reaction mixture and stirred at room temperature overnight. The precipitate thus formed was collected by filtration and dried to afford the title compound 275 (78 mg, 100% yield) as a yellow solid. MS (m/z): 209.9 (RCOOH, M−H) (found).

Step 2. 4-Chloro-N,N,7-trimethyl-7H-pyrrolo[2,3-d]pyrimidine-6-carboxamide (276)

A reaction mixture containing carboxylate 275 (78 mg, 0.36 mmo), oxalyl chloride (63 uL, 0.72 mmol), and a drop of DMF in DCM was stirred for 2 h. Solvents were removed under reduced pressure and the residue was re-dissolved in DCM (4 mL). To this solution $Me_2NH$ (360 µL, 0.72 mmol, 2M in THF) in THF was added and the mixture was stirred at room temperature for 4 h. The solvent was removed under reduced pressure and the residue was purified by flash column chromatography (eluent EtOAc) to afford the title compound 276 (50 mg, 58% yield) as a yellowish solid. MS (m/z): 239.1 (M+H) (found).

Step 3. 4-(2-Fluoro-4-nitrophenoxy)-N,N,7-trimethyl-7H-pyrrolo[2,3-d]pyrimidine-6-carboxamide (277)

Starting from the compound 276 and following the procedure described above for the synthesis of compound 260 (scheme 59, example 218, step 2) title compound 277 was obtained in 77% yield as an off-white solid. MS (m/z): 360.1 (M+H) (found).

Step 4. 4-(4-Amino-2-fluorophenoxy)-N,N,7-trimethyl-7H-pyrrolo[2,3-d]pyrimidine-6-carboxamide (278)

Starting from the compound 277 and following the procedure described above for the synthesis of compound 261 (scheme 59, example 218, step 3) title compound 278 was obtained in 72% yield as an off-white solid. MS (m/z): 330.1 (M+H) (found).

Step 5. 4-(2-Fluoro-4-(3-(2-phenylacetyl)thioureido)phenoxy)-N,N,7-trimethyl-7H-pyrrolo [2,3-d]pyrimidine-6-carboxamide (279)

Starting from the compound 278 and following the procedure described above for the synthesis of compound 262a (scheme 59, example 218, step 4) title compound 279 was obtained in 98% yield as an off-white solid. 1H NMR (DMSO-d6) δ (ppm): 12.45 (s, 1H), 11.81 (s, 1H), 8.43 (s, 1H), 7.89 (m, 1H), 7.46 (m, 2H), 7.34 (m, 4H), 7.28(m, 1H), 6.93 (m, 1H), 4.03 (s, 3H), 3.82 (s, 2H), 3.81 (s, 3H), 3.14 (s, 3H), 3.06 (s, 3H). MS (m/z): 507.1 (M+H) (found).

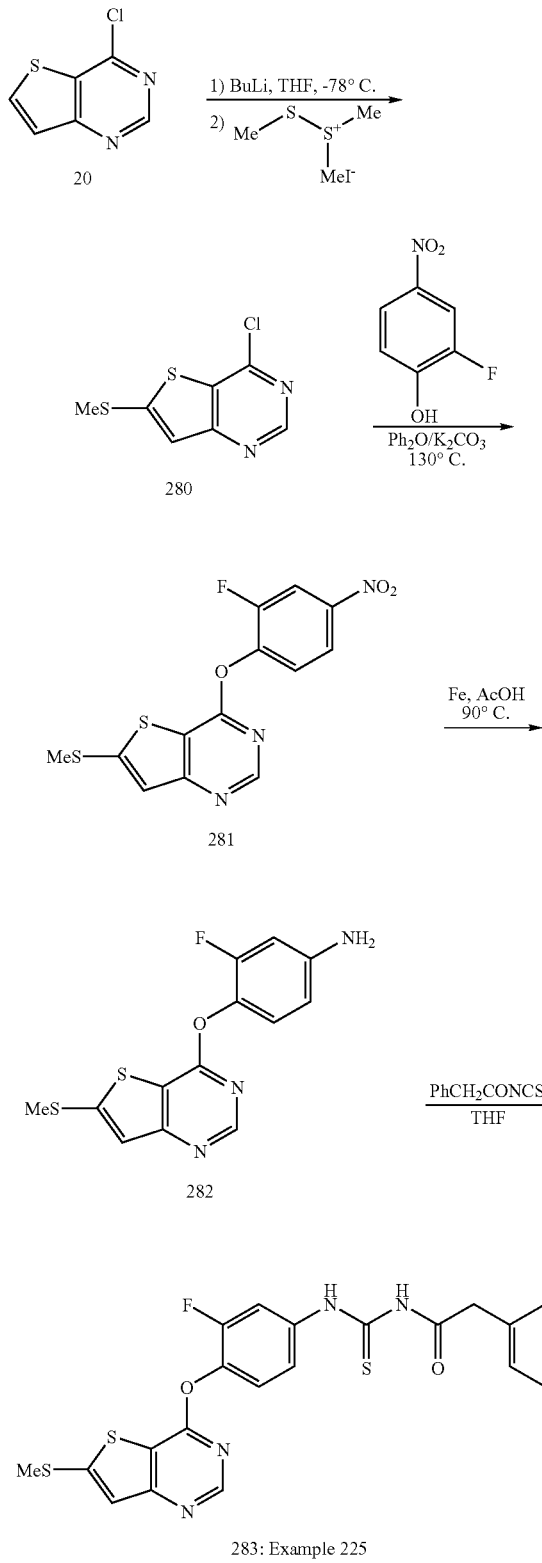

Example 225

N-(3-Fluoro-4-(6-(methylthio)thieno[3,2-d]pyrimidin-4-yloxy)phenylcarbamothioyl)-2-phenylacetamide (283)

Step 1.
4-chloro-6-(methylthio)thieno[3,2-d]pyrimidine (280)

To a solution of 20 (shown in the scheme 4) (200 mg, 1.18 mmol) in THF (11 mL) was added n-BuLi (566 μL, 1.42 mmol, 2.5M in THF) very slowly at −78° C. and the mixture was stirred for 15 min at the same conditions. A solutions of dimethyl disulfide (160 uL, 1.77 mmol) and MeI (110 μL, 1.77 mmol) in THF (1 mL) was added drop wise. The reaction mixture was stirred for 2 h at −78° C., quenched with saturated aqueous NH$_4$Cl solution, and extracted with DCM. The extract was dried over anhydrous Na$_2$SO$_4$ and concentrated to afford the title compound 280 (210 mg, 82% yield) as a yellowish solid. MS (m/z): 217.0 (M+H) (found).

Step 2. 4-(2-Fluoro-4-nitrophenoxy)-6-(methylthio) thieno[3,2-d]pyrimidine (281)

A mixture of 280 (210 mg, 0.97 mmol), 2-fluoro-4-nitrophenol (278 mg, 1.77 mmol) and K$_2$CO$_3$ (560 mg, 3.54 mmol) in Ph$_2$O (10 mL) was heated at 130° C. 60 hours, cooled to room temperature and partitioned between EtOAc and water. Organic phase was collected, dried over anhydrous Na$_2$SO$_4$, filtered, concentrated and purified by flash column chromatography with a gradient elution (hexane to hexane/EtOAc, 1:1) to afford the title compound 281 (288 mg, 88% yield) as a yellowish solid. MS (m/z): 338.1 (M+H) (found).

Step 3. 3-Fluoro-4-(6-(methylthio)thieno[3,2-d]pyrimidin-4-yloxy)benzenamine (282)

To a solution of 281 (288 mg, 0.94 mmol) in AcOH (25 mL) at 90° C., was added iron powder (238 mg, 4.25 mmol), and the reaction mixture was stirred vigorously at 90° C. for 10 min, cooled, filtered through a Celite pad and concentrated. The residue was purified by flash column chromatography (eluent EtOAc) to afford the title compound 282 (248 mg, 95%) as an off-white solid. MS (m/z): 308.1 (M+H) (found).

Step 4. N-(3-Fluoro-4-(6-(methylthio)thieno[3,2-d] pyrimidin-4-yloxy)phenylcarbamothioyl)-2-phenylacetamide (283)

A mixture of 282 (248 mg, 0.80 mmol) and 2-phenylacetyl isothiocyanate (214 mg, 1.20 mmol) in THF (8 mL) was stirred for 2 hours, and concentrated. The residue was purified by flash column chromatography, eluent EtOAc/hexane (3:7), to afford title compound 283 (200 mg, 52% yield) as an off-white solid. $^1$H NMR (DMSO-d$_6$) δ (ppm): 12.42 (s, 1H), 11.80(s, 1H), 8.63 (s, 1H), 7.85(d, 1H), 7.54-7.44 (m, 3H), 7.35 (m, 4H), 7.30 (m, 1H), 3.81 (s, 2H), MS (m/z): 485.1 (M+H) (found).

Scheme 65

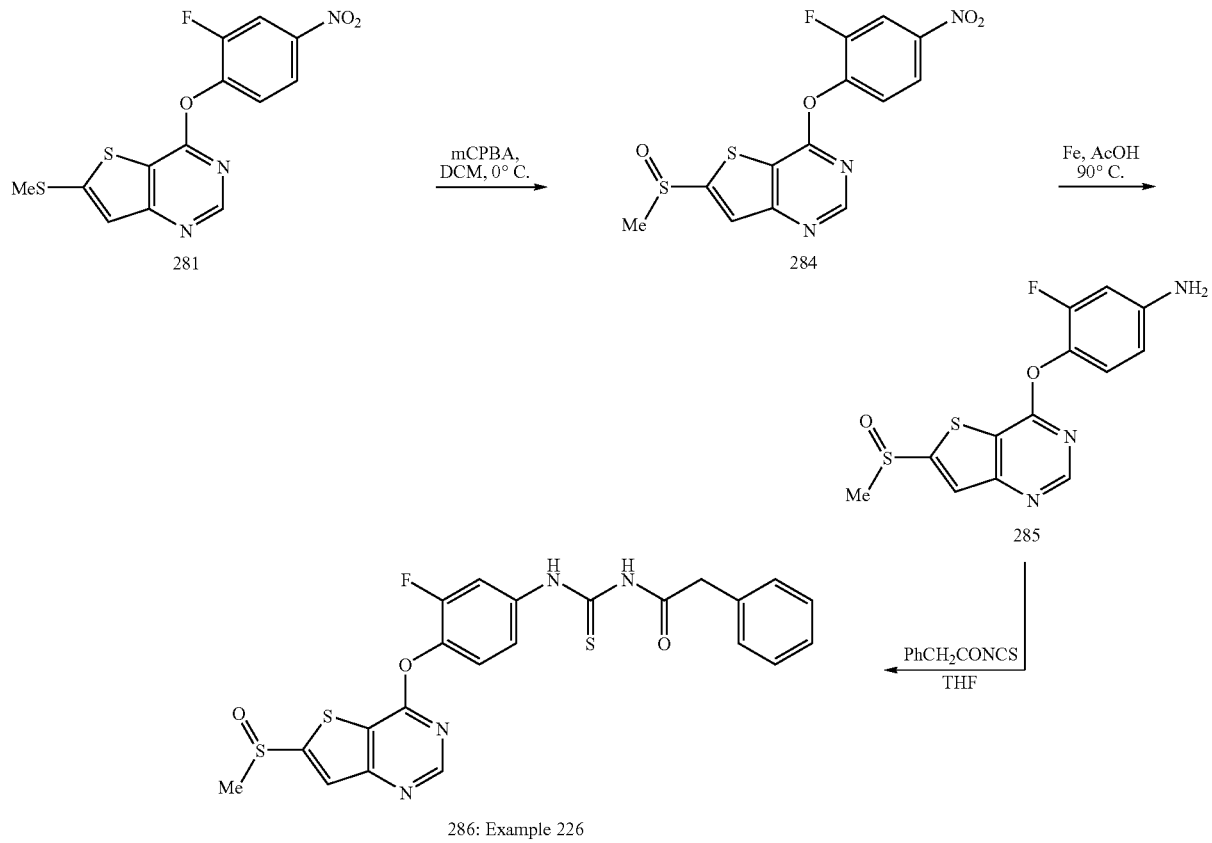

286: Example 226

Example 226

N-(3-Fluoro-4-(6-(methylsulfinyl)thieno[3,2-d]pyrimidin-4-yloxy)phenyl carbamothioyl)-2-phenylacetamide (286)

Step 1. 4-(2-Fluoro-4-nitrophenoxy)-6-(methylsulfinyl)thieno[3,2-d]pyrimidine (284)

A mixture of 281 (1.1 g, 3.2 mmol) and m-CPBA (77%, 890 mg, 12.8 mmol) in DCM at 0° C. was stirred for 2 hours, diluted with DCM, washed with ice water, NaHCO$_3$ solution and water again; dried and concentrated to give the title compound 284 (1.15 g, quantitative) as a yellowish solid. MS (m/z): 354.0 (M+H) (found).

Step 2. 4-(2-Fluoro-4-nitrophenoxy)-6-(methylsulfinyl)thieno[3,2-d]pyrimidine (285)

Starting from the compound 284 and following the procedure described above for the synthesis of compound 282 (scheme 64, step 3, example 225), title compound 285 was obtained in 34% yield as an off-white solid. MS (m/z): 324.0 (M+H) (found).

Step 3. N-(3-Fluoro-4-(6-(methylsulfinyl)thieno[3,2-d]pyrimidin-4-yloxy)phenyl carbamothioyl)-2-phenylacetamide (286)

Starting from the compound 285 and following the procedure described above for the synthesis of compound 283 (scheme 64, step 4, example 225), title compound 286 was obtained in 36% yield as an off-white solid. $^1$H NMR (DMSO-d$_6$) δ (ppm): 12.45 (s, 1H), 11.83 (s, 1H), 8.80 (s, 1H), 8.13 (s, 1H), 7.93(dd, 1H, J$_1$=2.3 Hz, J$_2$=10.9 Hz), 7.55 (t, 1H, J=8.6 Hz), 7.48 (m, 1H), 7.34-7.31 (m, 4H), 7.28-7.25 (m, 1H), 3.81 (s, 2H), 3.08 (s, 3H). MS (m/z): 501.0 (M+H) (found).

Scheme 66

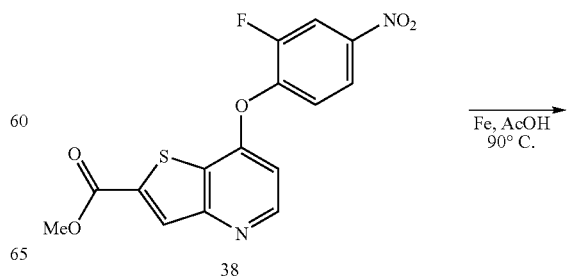

-continued

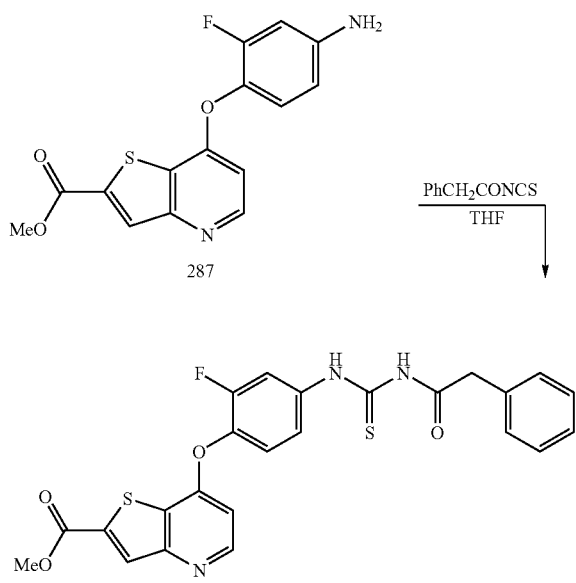

Example 227

Methyl 7-(2-fluoro-4-(3-(2-phenylacetyl)thioureido)phenoxy)thieno[3,2-b]pyridine-2-carboxylate hydrochloride (288)

Step 1. Methyl 7-(4-amino-2-fluorophenoxy)thieno[3,2-b]pyridine-2-carboxylate (287)

Starting from the nitro compound 38 (shown in the scheme 7) and following the procedure described above for the synthesis of compound 261 (scheme 59, step 3, example 218), title compound 287 was obtained in 86% yield as an off-white solid. MS (m/z): 319.0 (M+H) (found).

Step 2. Methyl 7-(2-fluoro-4-(3-(2-phenylacetyl)thioureido)phenoxy)thieno[3,2-b]pyridine-2-carboxylate hydrochloride (288)

Starting from the amine 287, following the procedure described above for the synthesis of compound 269b (scheme 561, example 222) and replacing 2-(2,6-dichlorophenyl)acetyl isothiocyanate with 2-phenylacetyl isothiocyanate, title compound 288 was obtained in 72% yield as a yellowish solid. $^1$H NMR (d-DMSO) δ (ppm): 12.51 (s, 1H), 11.84 (s, 1H), 8.64(dd, 1H, $J_1$=5.1 Hz, $J_2$=0.4 Hz), 8.24 (s, 1H, J=0.4Hz), 8.02(dd, 1H, $J_1$=1.8 Hz, $J_2$=13.4 Hz), 7.56-7.54 (m, 2H), 7.36-7.31 (m, 1H), 7.28-7.25 (m, 1H), 6.81 (d, 1H, J=5.5 Hz), 3.91 (s, 3H), 3.81 (s, 2H). MS (m/z): 496.3 (M+H) (found).

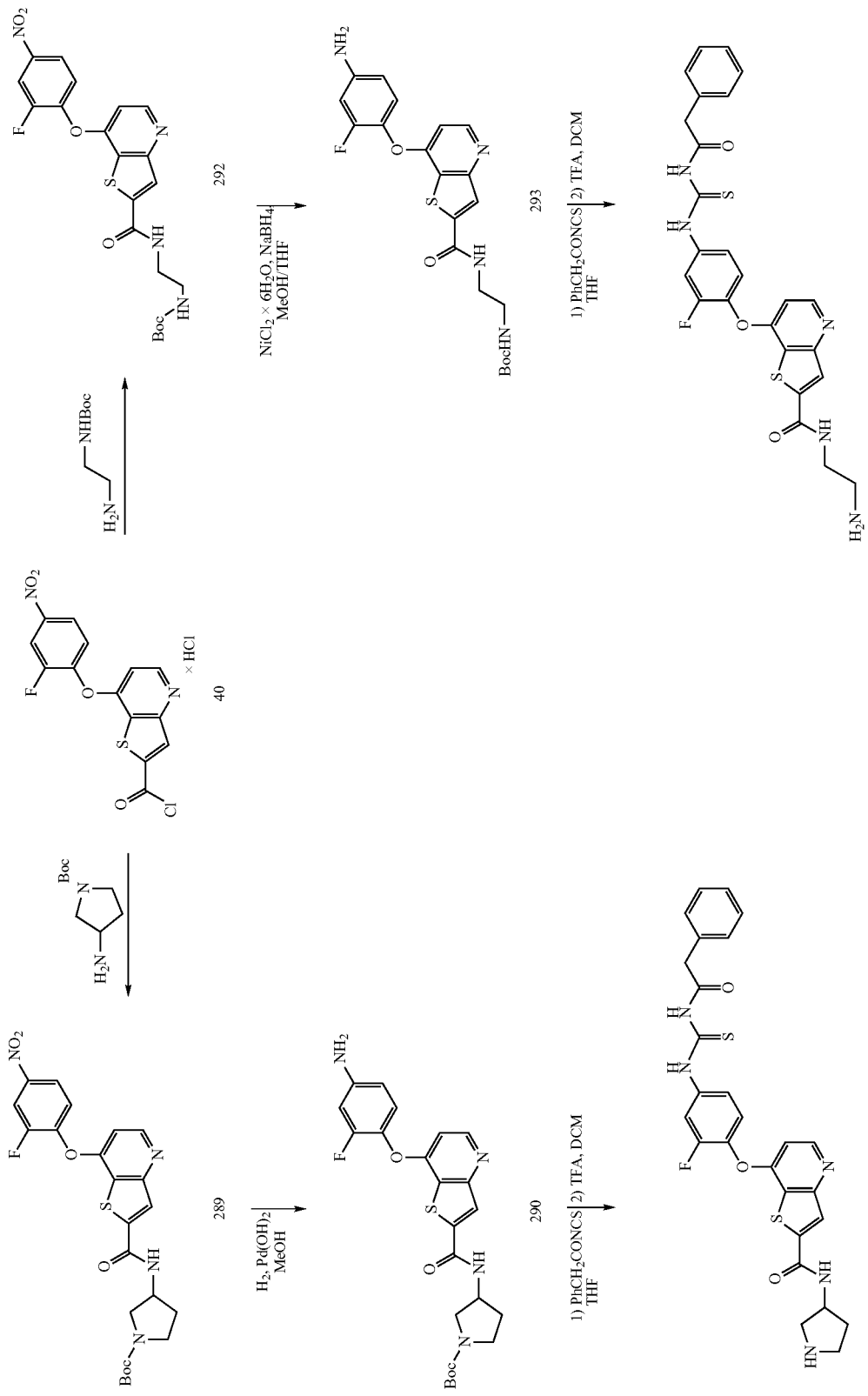

Example 228

7-(2-Fluoro-4-(3-(2-phenylacetyl)thioureido)phenoxy)-N-(pyrrolidin-3-yl)thieno[3,2-b]pyridine-2-carboxamide (291)

Step 1. tert-Butyl 3-(7-(2-fluoro-4-nitrophenoxy)thieno[3,2-b]pyridine-2-carboxamido)pyrrolidine-1-carboxylate (289)

A solution of 40 (shown in the scheme 7, 600 mg, 1.54 mmol), tert-butyl 3-aminopyrrolidine-1-carboxylate (369 mg, 2.0 mmol) in DCM (15 mL) was stirred overnight at room temperature. The solvent was removed under reduced pressure and the residue was purified by flash column chromatography, eluents EtOAc and EtOAc/MeOH (10:1), to afford the title compound 289 (160 mg, 20%) as an off-white solid. MS (m/z): 503.3 (M+H) (found).

Step 2. tert-Butyl 3-(7-(4-amino-2-fluorophenoxy)thieno[3,2-b]pyridine-2-carboxamido)pyrrolidine-1-carboxylate (290)

A mixture of 289 (90 mg, 0.18 mmol) and Pd(OH)$_2$ in MeOH (2 mL) was hydrogenated at 1 atm for 1 h. The catalyst was filtered off and the filtrate was concentrated to afford the title compound 290 (60 mg, 70% yield) as a yellowish solid. MS (m/z): 473.2 (M+H) (found).

Step 3. 7-(2-Fluoro-4-(3-(2-phenylacetyl)thioureido)phenoxy)-N-(pyrrolidin-3-yl)thieno[3,2-b]pyridine-2-carboxamide (291)

A solution of 290 (40 mg, 0.084 mmol) and 2-phenylacetyl isothiocyanate (22 mg, 0.126 mmol) in THF (2 mL) was stirred for 30 min. The solvent was removed under reduced pressure and the residue was purified by flash column chromatography (eluent EtOAc), to afford a solid material, which was dissolved in a mixture of TFA/DCM (0.5 mL/0.5 mL) and stirred at room temperature for 2 h. Solvents were removed under reduced pressure and the residue was purified by preparative HPLC (Aqusil C18, gradient eluent, 60-95% MeOH in water, 45 min) to afford the title compound 291 (8 mg, 80% yield) as an off-white solid. $^1$H NMR (d-DMSO) δ (ppm): 9.27(d, 1H), 8.57(d, 1H), 8.37 (s, 1H), 8.30 (s, 1H), 8.01(d, 1H), 7.53 (m, 2H), 7.33-7.31 (m, 4H), 7.29-7.25 (m, 1H), 6.74(d, 1H), 4.46 (m, 1H), 3.82 (s, 2H), 3.11-3.03 (m, 2H), 2.18-2.09 (m, 2H), 1.93-1.89 (m, 2H). MS (m/z): 550.2 (M+H) (found).

Example 229

N-(2-Aminoethyl)-7-(2-fluoro-4-(3-(2-phenylacetyl)thioureido)phenoxy)thieno[3,2-b]pyridine-2-carboxamide (294)

Step 1. tert-Butyl 2-(7-(2-fluoro-4-nitrophenoxy)thieno[3,2-b]pyridine-2-carboxamido)ethylcarbamate (292)

A solution of 40 (shown in the scheme 7, 100 mg, 0.26 mmol), N-Boc-N-methylethylenediamine hydrochloride (50 mg, 0.26 mmol) and Et$_3$N (36 μL, 0.52 mmol) in DCM (2 mL) was stirred for 4 h at room temperature and diluted with EtOAc (10 mL). The combined mixture was washed with brine and phases were separated. The aqueous phase was extracted with EtOAc, and the extract was combined with the organic phase, dried over anhydrous Na$_2$SO$_4$ and concentrated to afford title compound 292 (119 mg, 96%, crude) as yellowish solid. MS (m/z): 477.1 (M+H) (found).

Step 2. tert-Butyl 2-(7-(4-amino-2-fluorophenoxy)thieno[3,2-b]pyridine-2-carboxamido)ethylcarbamate (293)

To a solution of 292 (80 mg, 0.17 mmol) in MeOH/THF (1.7 mL/1.7 mL) at 0° C., was added NiCl$_2$×6H$_2$O (85 mg, 0.35 mmol), followed by addition of NaBH$_4$ (26 mg, 0.68 mmol), portion wise. The reaction mixture was stirred for 15 min, treated with 2N aqueous HCl (2 mL), filtered; the filtrate was neutralized with aqueous NH$_4$OH to pH 7 and partitioned between EtOAc and water. Organic phase was collected, dried over anhydrous Na$_2$SO$_4$ and concentrated. The residue (75 mg, quantitative yield, crude) was used directly in next step without further purification. MS (m/z): 447.1 (M+H) (found).

Step 3. N-(2-Aminoethyl)-7-(2-fluoro-4-(3-(2-phenylacetyl)thioureido)phenoxy)thieno[3,2-b]pyridine-2-carboxamide (294)

Following the procedure described above for the synthesis of compound 291 (example 228), title compound was obtained in 3% yield as an off-white solid. $^1$H NMR (d-DMSO) δ (ppm): 9.00(d, 1H), 8.50 (m, 1H), 8.30 (m, 1H), 8.20(d, 1H), 7.92(d, 1H, 7.44 (m, 2H), 7.26-7.25 (m, 3H), 7.21-7.18 (m, 1H), 6.66(d, 1H), 3.75 (s, 2H), 3.30-3.20 (m, 6H), MS (m/z): 524.3 (M+H).

Scheme 68

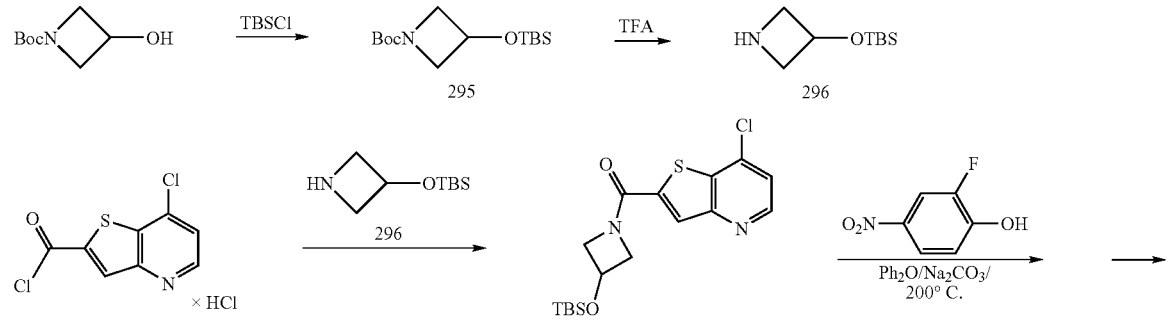

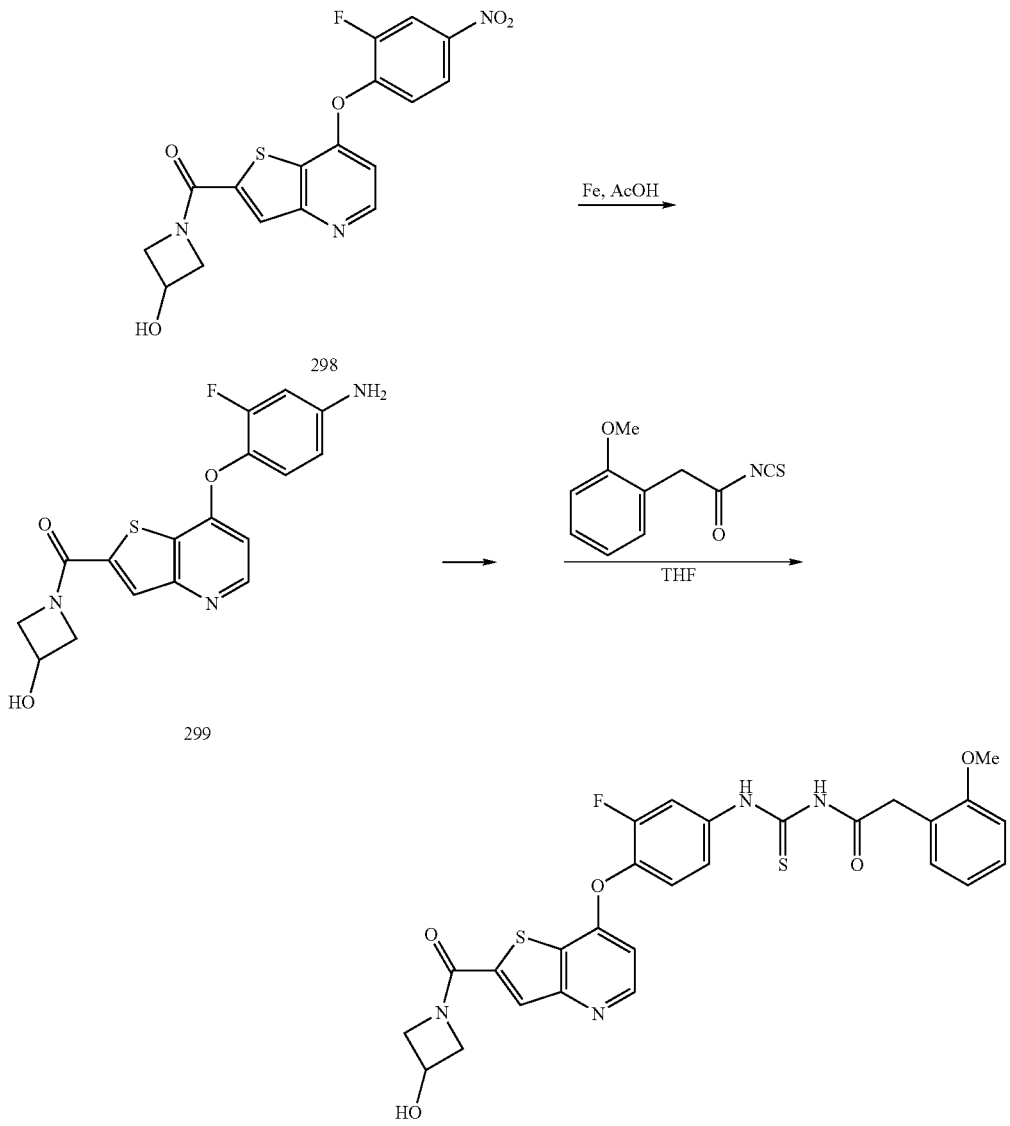

300: Example 230

Example 230

N-(3-Fluoro-4-(2-(3-hydroxyazetidine-1-carbonyl)thieno[3,2-b]pyridin-7-yloxy)phenylcarbamothioyl)-2-(2-methoxyphenyl)acetamide (300)

Step 1. tert-Butyl 3-(tert-butyldimethylsilyloxy)azetidine-1-carboxylate (295)

A solution of tert-butyl 3-hydroxyazetidine-1-carboxylate (1 g, 5.77 mmol), TBSCl (6.35 mmol, 956 mg) in DCM (11.5 mL), was stirred for 72 hrs at room temperature. The solvent was removed under reduced pressure, EtOAc was added to the residue, and the solid material was removed by filtration. The filtrate was concentrated under reduced pressure and the residue was purified by flash chromatography with gradient elution with EtOAc/hexane (9:1) to EtOAc/hexane (1:1), to afford title compound 295 (1.25 g, 75% yield) as a syrup. MS (m/z): 310.1 (M+23).

Step 2: 3-(tert-Butyldimethylsilyloxy)azetidine (296)

A mixture of 295 (200 mg, 0.696 mol), DCM (1 mL) and TFA (1 mL) was stirred for 1 h at room temperature, concentrated under reduced pressure; NaOH (1M, 15 mL) was added to the residue and the suspension was extracted with DCM, the extract was dried (anhydrous $Na_2SO_4$) and concentrated, to afford title compound 296 (90.4 mg, 69% yield) as a syrup. MS (m/z): 188.1 (M+1).

Step 3: (3-(tert-Butyldimethylsilyloxy)azetidin-1-yl)(7-chlorothieno[3,2-b]pyridin-2-yl)methanone (297)

Starting from the acyl chloride 4 (scheme 1), replacing dimethyl amine with the amine 296 and following the procedure described for the synthesis of amide 5 (scheme 1 as well), title compound 297 was obtained in 64% yield as a syrup. MS (m/z): 383.0 (M+1).

Step 4: (7-(2-Fluoro-4-nitrophenoxy)thieno[3,2-b]pyridin-2-yl)(3-hydroxyazetidin-1-yl)methanone (298)

Starting from the amide 297 and following the procedure described above for the synthesis of compound 230 (scheme 50, example 203), title compound 298 was obtained in 39% yield as a syrup. MS (m/z): 389.05 (M+1).

Step 5: (7-(4-Amino-2-fluorophenoxy)thieno[3,2-b]pyridin-2-yl)(3-hydroxyazetidin-1-yl)methanone (299)

Starting from the nitro compound 298 and following the procedure described above for the synthesis of the amine 231 (scheme 50, example 203), title compound 299 was obtained in 83% yield. MS (m/z): 359.07 (M+1).

Step 6: N-(3-Fluoro-4-(2-(3-hydroxyazetidine-1-carbonyl)thieno[3,2-b]pyridin-7-yloxy)phenylcarbamothioyl)-2-(2-methoxyphenyl)acetamide (300)

Starting from the amine 299, following the procedure described above for the synthesis of compound 232a (scheme 50, example 203) but replacing 2-phenylacetyl isothiocyanate with (2-methoxy-phenyl)-acetyl isothiocyanate and title compound 300 was obtained in 39% yield as a creamy solid. ¹HNMR: (CD₃OD) δ (ppm): 12.58 (s, 1H), 11.77 (s, 1H), 8.62 (m, 1H), 8.09 (d, J=12.3 Hz, 1H), 7.95 (s, 1H), 7.56 (m, 2H), 7.26 (m, 2H), 7.00 (m, 1H), 6.92 (m, 1H), 6.77 (m, 1H), 6.50 (d, J=5.9 Hz, 1H), 4.81 (m, 1H), 4.59 (m, 1H), 4.35 (m, 2H), 3.87-3.78 (m, 6H). MS (m/z): 567.0 (M+1).

-continued

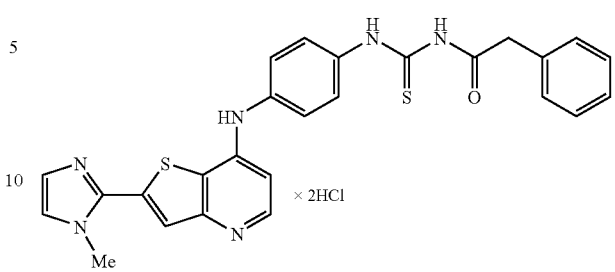

302: Example 231

Example 231

N-(4-(2-(1-methyl-1H-imidazol-2-yl)thieno[3,2-b]pyridin-7-ylamino)phenyl carbamothioyl)-2-phenylacetamide (302)

Step 1. N4-(2-(1-Methyl-1H-imidazol-2-yl)thieno[3,2-b]pyridin-7-yl)benzene-1,4-diamine (301)

A mixture of 214 (500 mg, 2.0 mmol, scheme 46) and benzene-1,4-diamine (500 mg, 4.62 mmol) in iso-PrOH (15 mL) was refluxed overnight, cooled to room temperature and filtered. The solid was collected, washed with iso-PrOH/H₂O mixture, to afford the title compound 301 (300 mg, 44% yield) as a yellowish solid. MS (m/z): 322.1 (M+H) (found).

Step 2. N-(4-(2-(1-Methyl-1H-imidazol-2-yl)thieno[3,2-b]pyridin-7-ylamino)phenyl carbamothioyl)-2-phenylacetamide (302)

Starting from the compound 301, following the procedures described above for the synthesis of compound 269b (scheme 61, example 222) but replacing 2-(2,6-dichlorophenyl)acetyl isothiocyanate with 2-phenylacethyl isothiocyanate, title compound 302 was obtained in 12% yield, as a yellow solid. ¹H NMR (d-DMSO) δ (ppm): 12.47 (s, 1H), 11.76 (s, 1H), 10.83 (s, 1H), 8.41(d, 1H, J=6.9Hz), 7.84 (s, 1H), 7.80 (s, 1H), 7.78 (s, 1H), 7.55(s, 1H), 7.46 (s, 1H), 7.43 (s, 1H), 7.32 (m, 4H), 7.28-7.20 (m, 1H), 7.20 (s, 1H), 6.94(d, 1H, J=6.8 Hz), 3.98 (s, 3H), 3.81 (s, 2H). MS (m/z): 499.1 (M+H) (found).

Scheme 69

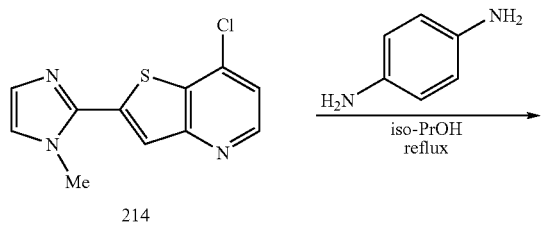

214

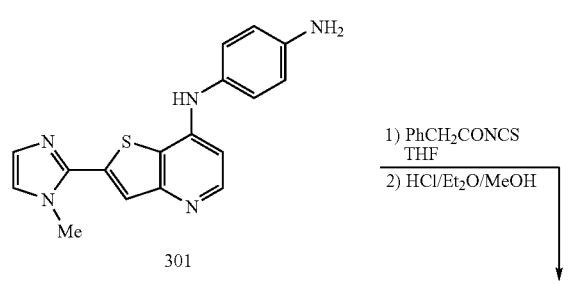

301

1) PhCH₂CONCS
THF
2) HCl/Et₂O/MeOH

Scheme 70

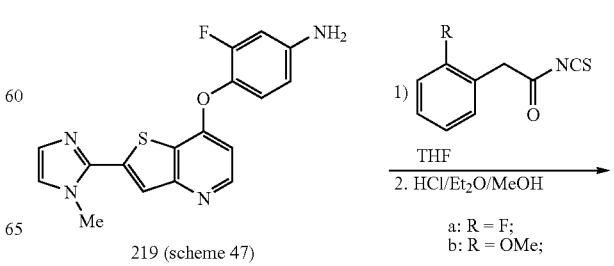

219 (scheme 47)

1)
THF
2. HCl/Et₂O/MeOH a: R = F;
b: R = OMe;

-continued

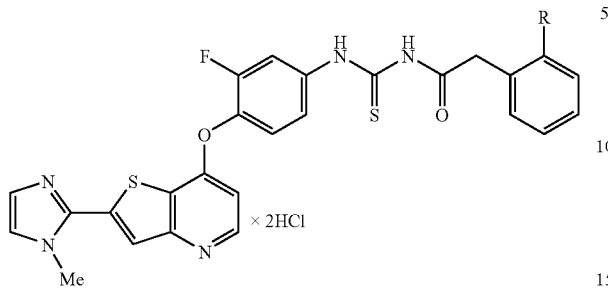

303a: Example 232
303b: Example 233

Example 232

N-(3-Fluoro-4-(2-(1-methyl-1H-imidazol-2-yl)thieno[3,2-b]pyridin-7-yloxy) phenyl carbamothioyl)-2-(2-fluorophenyl)acetamide di-hydrochloride (303a)

A mixture of aniline 219 (100 mg, 0.29 mmol, scheme 47) and 2-(2-fluorophenyl)acetyl isothiocyanate (115 mg, 0.58 mmol) in THF (3 mL) was stirred for 1 hour, loaded directly onto a column containing silica gel and eluted sequentially with EtOAc and EtOAc/MeOH (100:1), to produce a white solid. This material was suspended in MeOH (5 mL) and HCl (1.0M in ether, 1 mL) was added to form a clear solution that was evaporated to dryness. The residue was washed with ether, suspended in $H_2O$, and lyophilized to afford the title compound (80 mg, 45% yield) as a yellowish solid. $^1$H-NMR (DMSO-$d_6$) δ (ppm): 12.42(s, 1H), 11.88 (s, 1H), 8.65(d. 1H, J=5.5 Hz), 8.20 (s, 1H), 8.05(d, 1H, J=1.7Hz), 7.74 (s, 1H), 7.58-7.55 (m, 3H) 7.39-7.32 (m, 2H), 7.21-7.16 (m, 2H), 6.82(d, 1H, J=5.5 Hz), 4.02 (s, 3H), 3.93(s, 2H), MS (m/z): 536.2 (M+H) (found).

Example 233

N-(3-Fluoro-4-(2-(1-methyl-1H-imidazol-2-yl)thieno[3,2-b]pyridin-7-yloxy)phenylcarbamothioyl)-2-(2-methoxyphenyl)acetamide di-hydrochloride (303b)

Starting from the compound 219, following the procedure described above for the synthesis of 303a (example 232) but replacing 2-(2-fluorophenyl)acetyl isothiocyanate with 2-(2-methoxyphenyl)acetyl isothiocyanate, title compound 303b was obtained in 44% as an off-white solid. $^1$H NMR (d-DMSO) δ (ppm): 12.55 (s, 1H), 11.73 (s, 1H), 8.62 (m, 1H), 8.09(m, 1H), 7.65 (s, 1H), 7.57 (m, 1H), 7.43 (s, 1H), 7.27-7.20 (m, 1H), 6.98(d, 1H, J=8.2 Hz), 6.90(dt, 1H, $J_1$=10 Hz, $J_2$=7.4 Hz), 6.79 (m, 1H), 4.02 (s, 3H), 3.81 (s, 2H), 3.77 (s, 3H). MS (m/z): 548.3 (M+H) (found).

Example 234

2-(2-Fluorophenyl)-N-(4-(2-(1-methyl-1H-imidazol-2-yl)thieno[3,2-b]pyridin-7-yloxy)phenylcarbamothioyl)acetamide dihydrochloride (304)

304: Example 234

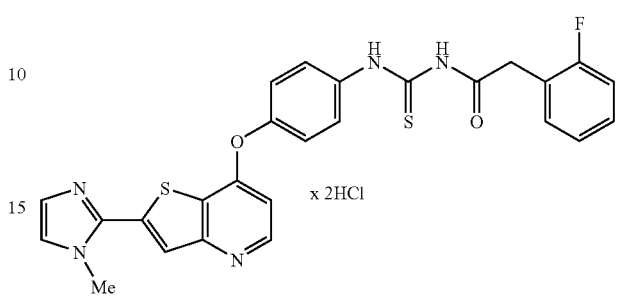

Starting from the compound 214 (scheme 46) and following the procedures described above for the synthesis of compound 228 (example 202) and 303a (example 232), title compound 234 was obtained in 31% yield as an off-white solid. $^1$H NMR (d-DMSO) δ (ppm): 12.34 (s, 1H), 11.81 (s, 1H), 8.68 (m, 1H), 8.24 (s, 1H), 7.79 (m, 3H), 7.62 (s, 1H), 7.40-7.13 (m, 6H), 6.86(d, 1H), 4.02 (s, 3H), 3.93 (s, 2H). MS (m/z): 518.1 (M+H) (found).

SCHEME 71

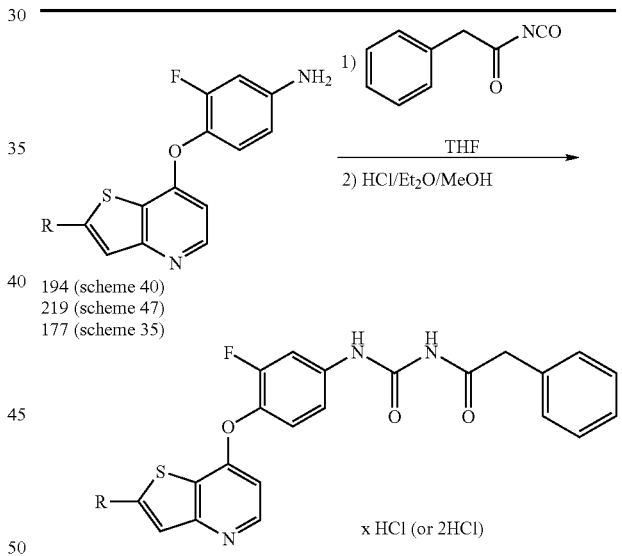

194 (scheme 40)
219 (scheme 47)
177 (scheme 35)

305a: Example 235
305b: Example 236
305c: Example 237

| R | Compound No |
|---|---|
| 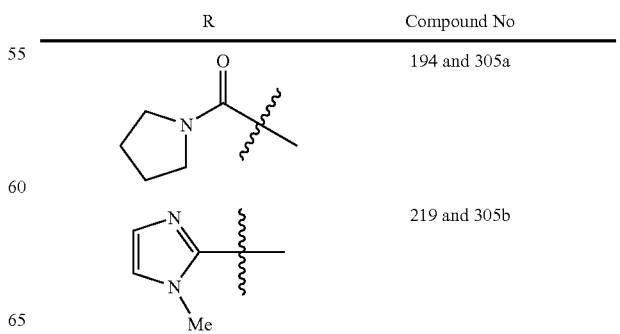 | 194 and 305a |
|  | 219 and 305b |

SCHEME 71-continued

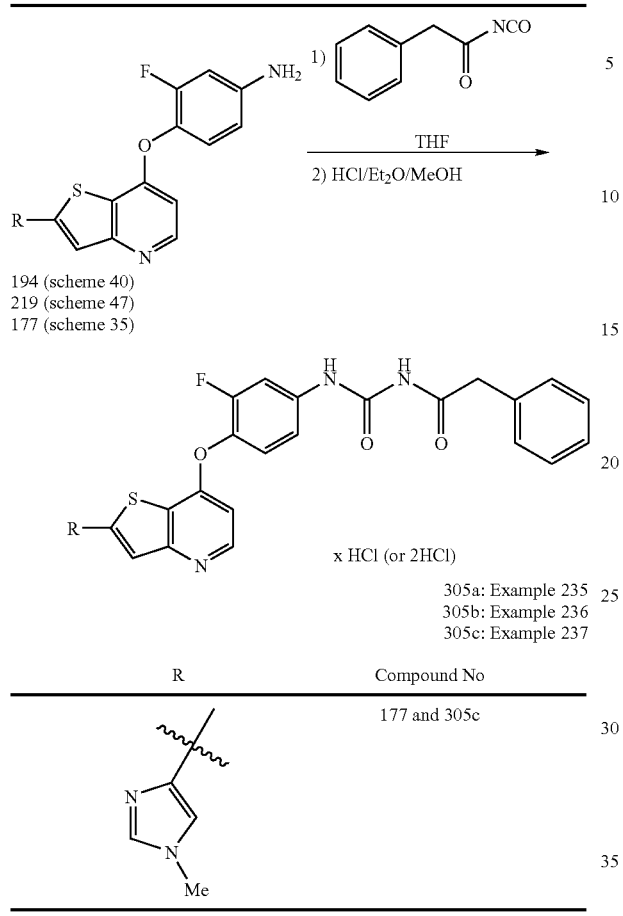

| R | Compound No |
|---|---|
| ![imidazole-Me] | 177 and 305c |

Examples 235

N-(3-Fluoro-4-(2-(pyrrolidine-1-carbonyl)thieno[3,2-b]pyridin-7-yloxy)phenyl carbamoyl)-2-phenylacetamide hydrochloride (305a)

A mixture of 194 (93 mg, 0.26 mmol, scheme 40) and 2-phenylacetyl isocyanate (83 mg, 0.62 mmoL) [J. Hill et al. *JACS,* 62; 1940; 1595] was stirred for 1 h at room temperature, loaded directly onto a flash chromatography column and eluted with EtOAc. A white solid was obtained, which was suspended in MeOH and treated with HCl (1 mL, 1.0M in Et$_2$O) to form a clear solution. The solution was concentrated to form a precipitate which was collected by filtration, to afford the title compound 305a (48 mg, 33% yield) as a white solid. $^1$H NMR (d-DMSO) δ (ppm): 11.05 (s, 1H), 10.62 (s, 1H), 8.57(d, 1H), 8.02 (s, 1H), 7.81(d, 1H), 7.48-7.43 (m, 2H), 7.33-7.25 (m, 5H), 6.74(d, 1H), 3.85(t, 2H), 3.78 (s, 2H), 3.51(t, 2H), 1.98-1.86(m, 2H). MS (m/z): 519.2 (M+H) (found).

Example 236

N-(3-Fluoro-4-(2-(1-methyl-1H-imidazol-2-yl)thieno[3,2-b]pyridin-7-yloxy)phenyl carbamoyl)-2-phenylacetamide dihydrochloride (305b)

Starting from the compound 219 (scheme 47) and following the procedure described above for the synthesis of compound 305a, title compound 305b was obtained in 15% yield as a white solid. $^1$H NMR (d-DMSO) δ (ppm): 11.07 (s, 1H), 10.66 (s, 1H), 8.67(d, 1H, J=5.5 Hz), 8.27 (s, 1H), 7.85-7.80 (m, 2H), 7.65 (s, 1H), 7.51(t, 1H, J=8.6Hz), 7.46(d, 1H), 7.34-7.28(m, 5H), 6.85(d, 1H, J=5.3 Hz), 4.03 (s, 3H), 3.74 (s, 2H). MS (m/z): 502.2 (M+H) (found).

Example 237

N-(3-Fluoro-4-(2-(1-methyl-1H-imidazol-4-yl)thieno[3,2-b]pyridin-7-yloxy)phenyl carbamoyl)-2-phenylacetamide dihydrochloride (305c)

Starting from the compound 177 (scheme 35) and following the procedure described above for the synthesis of compound 305a, title compound 305c was obtained in 54% yield as a white solid. $^1$H NMR (d-DMSO) δ (ppm): 11.08 (s, 1H), 10.67 (s, 1H), 8.66 (d, 1H, J=6.2 Hz), 8.26 (s, 1H), 8.21 (s, 1H), 7.93 (s, 1H), 7.85(dd, 1H, J$_1$=12.9 Hz, J$_2$=2.5 Hz), 7.53(t, 1H, J=8.8 Hz), 7.65 (s, 1H), 7.48-7.45 (m, 1H), 7.35-7.30 (m, 4H), 7.28-7.24 (m, 1H), 6.94(d, 1H, J=6.1 Hz), 3.79 (s, 3H), 3.75 (s, 2H). MS (m/z): 502.1 (M+H) (found).

Scheme 72

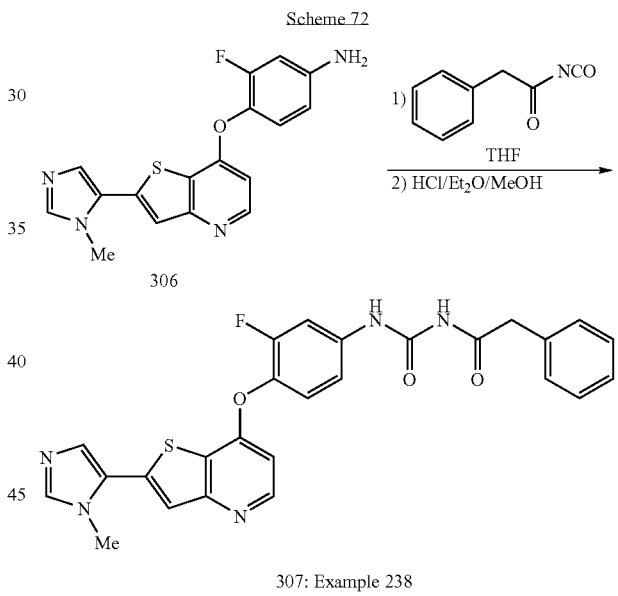

307: Example 238

Example 238

N-(3-Fluoro-4-(2-(1-methyl-1H-imidazol-5-yl)thieno[3,2-b]pyridin-7-yloxy)phenyl carbamoyl)-2-phenylacetamide (307)

3-Fluoro-4-[2-(1-methyl-1H-imidazol-5-yl)-thieno[3,2-b]pyridin-7-yloxy]-phenylamine (306)

Starting from the compound 98 (scheme 19) and following the procedures described above for the synthesis of compound 12 (scheme 2, steps 1-4) but replacing 2-bromothiazole at the Stille coupling stage with 5-bromo-1-methyl-1H-imidazole (Table 9), title compound 306 was obtained. MS (m/z): 341.0M+H) (found).

301

N-(3-Fluoro-4-(2-(1-methyl-1H-imidazol-5-yl)thieno [3,2-b]pyridin-7-yloxy)phenyl carbamoyl)-2-phenylacetamide (307)

A mixture of 306 (99 mg, 0.29 mmol) and 2-phenylacetyl isocyanate (97 mg, 0.60 mmoL) [A. J. Hill et al. *JACS*, 62; 1940; 1595] was stirred for 1 h at room temperature, loaded directly onto a flash chromatography column and gradient eluted with EtOAc, to MeOH/EtOAc (10:90) to afford the title compound 307 (42% yield) as a white solid. $^1$H NMR (d-DMSO) δ (ppm): 11.11 (s, 1H), 10.68 (s, 1H, J=5.5 Hz), 8.49(d), 7.85 (s, 1H), 7.82(dd, 1H, $J_1$=12.9 Hz, $J_2$=2.4 Hz), 7.76 (s, 1H), 7.43 (m, 2H), 7.40 (s, 1H), 7.32 (m, 4H), 7.28 (m, 1H), 6.61(d, 1H, J=5.5 Hz), 3.89 (s, 3H), 3.74 (s, 2H). MS (m/z): 502.4 (M+H) (found).

302

N-(4-(2-(1-Ethyl-1H-imidazol-4-yl)thieno[3,2-b] pyridin-7-yloxy)-3-fluorophenyl carbamoyl)-2-phenylacetamide (309a)

A mixture of 308 (300 mg, 0.85 mmol) and 2-phenylacetyl isocyanate (164 mg, 1.02 mmoL) [Arthur J. Hill et al. *JACS*, 62; 1940; 1595] was stirred for 1 h at room temperature, loaded directly onto a flash chromatography column and gradient eluted with EtOAc, to MeOH/EtOAc (20:80) to afford the title compound 309a (45% yield) as a white solid. $^1$H NMR (d-DMSO) δ (ppm): 11.07 (s, 1H), 10.63 (s, 1H), 8.41 (d, 1H, J=5.5 Hz), 7.94(d, 1H, J=1.4 Hz), 7.80(dd, 1H, $J_1$=13.1 Hz, $J_2$=2.4 Hz), 7.77(d, 1H, J=1.1 Hz), 7.65 (s, 1H), 7.46-7.39 (s, 2H), 7.35-7.19 (m, 4H), 7.28-7.24 (m, 1H), 6.54(dd, 1H, $J_1$=5.5 Hz, $J_2$=0.8 Hz), 4.03(q, 2H), 3.73 (s, 2H), 1.38(t, 3H). MS (m/z): 516.1 (M+H) (found).

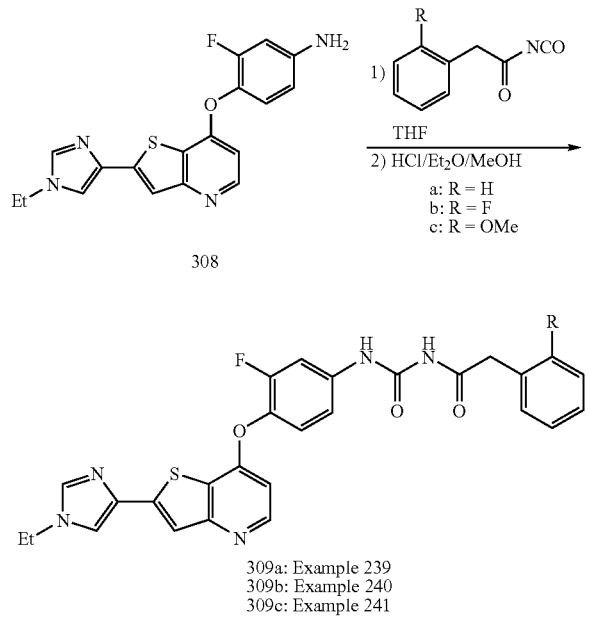

Scheme 73

309a: Example 239
309b: Example 240
309c: Example 241

Example 239

N-(4-(2-(1-Ethyl-1H-imidazol-4-yl)thieno[3,2-b] pyridin-7-yloxy)-3-fluorophenyl carbamoyl)-2-phenylacetamide (309a)

4-[2-(1-Ethyl-1H-imidazol-4-yl)-thieno[3,2-b]pyridin-7-yloxy]-3-fluoro-phenylamine (308)

Starting from the compound 98 (scheme 19) and following the procedures described above for the synthesis of compound 12 (scheme 2, steps 1-4) but replacing 2-bromothiazole at the Stille coupling stage with 4-bromo-1-ethyl-1H-imidazole (Table 9), title compound 308 was obtained. MS (m/z): 355.1 (M+H) (found).

Example 240

N-(4-(2-(1-Ethyl-1H-imidazol-4-yl)thieno[3,2-b] pyridin-7-yloxy)-3-fluorophenyl carbamoyl)-2-(2-fluorophenyl)acetamide (309b)

A mixture of 308 (320 mg, 0.90 mmol) and (2-fluorophenyl)-acetyl isocyanate (600 mg, 3.35 mmoL) [A. J. Hill et al. *JACS*, 62; 1940; 1595] was stirred for 1 h at room temperature, loaded directly onto a flash chromatography column and gradient eluted with EtOAc, to MeOH/EtOAc (20:80), to afford the title compound 309b in 42% yield as a white solid. $^1$H NMR (d-DMSO) δ (ppm): 11.10 (s, 1H), 10.58 (s, 1H), 8.42(d, 1H, J=5.5 Hz), 7.94(d, 1H, J=1.1 Hz), 7.82-7.77 (m, 2H), 7.65 (s, 1H), 7.45-7.30 (m, 4H), 7.19-7.16 (m, 2H), 6.54(dd, 1H, $J_1$=0.7 Hz, $J_2$=5.4 Hz), 4.04(q, 2H), 3.83 (s, 2H), 1.38(t, 3H). MS (m/z): 534.1 (M+H) (found).

Example 241

N-(4-(2-(1-Ethyl-1H-imidazol-4-yl)thieno[3,2-b] pyridin-7-yloxy)-3-fluorophenyl carbamoyl)-2-(2-methoxyphenyl)acetamide (309c)

A mixture of 308 (370 mg, 1.05 mmol) and (2-methoxyphenyl)-acetyl isocyanate (240 mg, 1.25 mmoL) [A. J. Hill et al. *JACS*, 62; 1940; 1595] was stirred for 1 h at room temperature, loaded directly onto a flash chromatography column and eluted with EtOAc, to afford the title compound 309c in 42% yield as a white solid. $^1$H NMR (d-DMSO) δ (ppm): 10.98 (s, 1H), 10.69 (s, 1H), 8.41(d, 1H, J=5.3 Hz), 7.94(d, 1H, J=1.2 Hz), 7.81(dd, 1H, $J_1$=13.1 Hz, $J_2$=2.4 Hz), 7.77(d, 1H, J=0.9 Hz), 7.65 (s, 1H), 7.45-7.40 (m, 2H), 7.26-7.19 (m, 2H), 6.97(d, 1H, J=8.0 Hz), 6.89(dt, 1H, $J_1$=0.8 Hz, $J_2$=8.2 Hz), 6.54(d, 1H, J=5.5 Hz), 4.04(q, 2H), 3.75 (s, 3H), 3.70 (s, 2H), 1.38(t, 3H). MS (m/z): 546.1 (M+H) (found).

Scheme 74

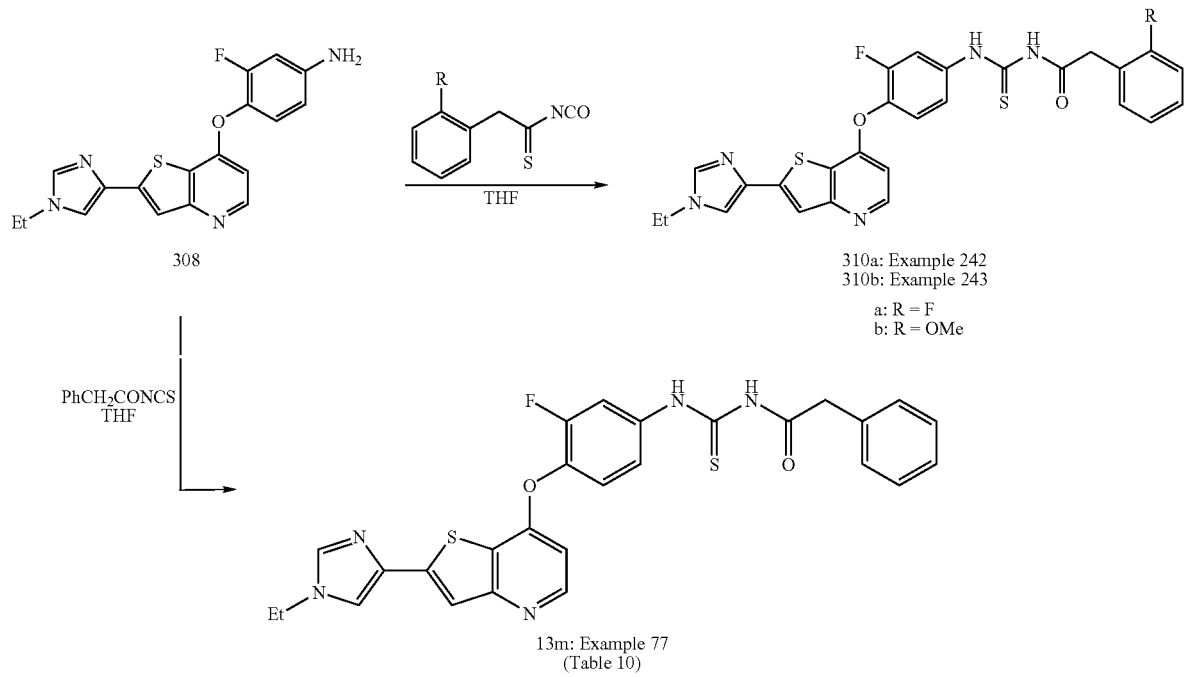

310a: Example 242
310b: Example 243
a: R = F
b: R = OMe

13m: Example 77
(Table 10)

Example 242

1-{4-[2-(1-Ethyl-1H-imidazol-4-yl)-thieno[3,2-b]pyridin-7-yloxy]-3-fluoro-phenyl}-3-[2-(2-fluorophenyl)-acetyl]-thiourea (310a)

To a suspension of the 308 (385 mg, 0.99 mmol) in THF (10 mL) was added 2-(2-fluorophenyl)acetyl isothiocyanate (263 mg, 1.49 mmol) and the reaction mixture was stirred for 1 hr, transferred onto a flash chromatography column and eluted with EtOAc/MeOH 19:1, to afford title compound 310a (366.9 mg, 67% yield) as a creamy solid. $^1$HNMR: (DMSO-$d_6$) δ (ppm): 12.42 (s, 1H), 11.87 (s, 1H), 8.44 (d, J=5.5 Hz, 1H), 8.02 (d, J=11.5 Hz, 1H), 7.95 (s, 1H), 7.78 (s, 1H), 7.67 (s, 1H), 7.52 (m, 2H), 7.42 (m, 2H), 7.25 (m, 2H), 7.06 (d, J=5.5 Hz, 1H), 4.04 (q, J=7.3 Hz, 2H), 3.92 (s, 2H), 7.4 (t, J=7.3 Hz, 3H). MS (m/z): 550.0 (M+1).

Example 243

1-{4-[2-(1-Ethyl-1H-imidazol-4-yl)-thieno[3,2-b]pyridin-7-yloxy]-3-fluoro-phenyl}-3-[2-(2-methoxyphenyl)-acetyl]-thiourea (310b)

Starting from the compound 308, following the procedure described above for the synthesis of 310a but replacing 2-(2-fluorophenyl)acetyl isothiocyanate with (2-methoxy-phenyl)-acetyl isothiocyanate, title compound 310b was obtained in 82% yield. $^1$H NMR (DMSO-$d_6$) δ (ppm): 12.57 (s, 1H), 11.76 (s, 1H), 8.45 (d, J=5.5 Hz, 1H), 8.07 (m, 1H), 7.96 (d, J=1 Hz, 1H), 7.79 (d, J=1 Hz, 1H), 7.69 (s, 1H), 7.6 (m, 2H), 7.26 (m, 2H), 7.0 (d, J=7.4 Hz, 1H), 6.92 (m, 1H), 6.59 (d, J=5.5 Hz, 1H), 4.06 (q, J=7.5 Hz, 2H), 3.82 (s, 2H), 3.79 (s, 3H), 1.4 (t, J=7.4 Hz, 3H). MS (m/z): 562.0 (M+1).

Example 244

311: Example 244

N-Ethyl-7-(2-fluoro-4-(3-(2-phenylacetyl)thioureido)phenoxy)-N-methylthieno[3,2-b]pyridine-2-carboxamide (311)

Title compound 311 was obtained by following the procedures described above for the synthesis of compound 8a (scheme 1, example 1) but replacing dimethylamine in the step 4 with N-methylethanamine. $^1$H NMR (400 MHz, DMSO-d6) (ppm) 12.49 (s, 1H), 11.82 (s, 1H), 8.64 (d, J=5.48 Hz, 1H), 8.03 (d, J=12.7 Hz, 1H) 7.85 (m, 1H), 7.54 (m, 2H), 7.32 (m, 4H), 7.24 (m, 1H), 6.82 (d, J=5.3 Hz, 1H), 3.83 (s, 2H), 3.53 (m, 2H), 3.38 (m, 2H), 3.05 (s, 1H), 1.10 m, 3H). MS (calcd.) 522.1, found 523.2 (M+H).

Example 245

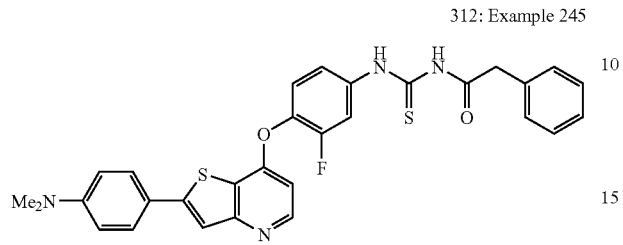

312: Example 245

N-(4-(2-(4-(Dimethylamino)phenyl)thieno[3,2-b]pyridin-7-yloxy)-3-fluorophenylcarbamothioyl)-2-phenylacetamide (312)

Title compound 312 was obtained by following the procedures described above for the synthesis of compound 50 (scheme 10, example 55) but replacing 4,4,5,5-tetramethyl-2-(4-(methylsulfonyl)phenyl)-1,3,2-dioxaborolane in the first step with 4-(dimethylamino)phenylboronic acid. $^1$H NMR (DMSO): 12.48 (1H, s), 11.83 (1H, s), 8.44 (1H, d, J=5.48 Hz), 7.99 (1H, d, J=12.91 Hz), 7.77 (1H, s), 7.68 (2H, d, J=8.41 Hz), 7.51 (2H, br), 7.33-7.28 (5H, m), 6.77 (2H, d, J=8.22 Hz), 6.56 (1H, d, J=4.89 Hz), 3.81 (2H, s), 2.96 (6H, s), MS: calcd: 556.7, found: 556.9 (M+H).

Example 246

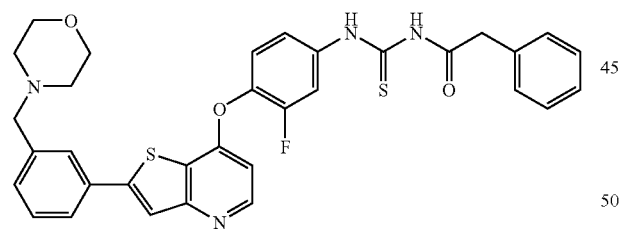

313: Example 246

N-(3-Fluoro-4-(2-(3-(morpholinomethyl)phenyl)thieno[3,2-b]pyridin-7-yloxy)phenylcarbamothioyl)-2-phenylacetamide (313)

Title compound 313 was obtained by following the procedures described above for the synthesis of compound 75 (scheme 15) but starting from 4-(3-bromobenzyl)morpholine instead of tert-butyl 3-bromobenzyl(2-methoxyethyl)carbamate (65). $^1$H NMR (DMSO): 12.49 (1H, s), 11.84 (1H, s), 8.52 (1H, d, J=5.48 Hz), 8.05 (1H, s), 8.01 (1H, d, J=12.72 Hz), 7.79-7.78 (2H, m), 7.53 (2H, br), 7.46 (1H, t, J=7.63 Hz), 7.39 (1H, d, J=7.63 Hz), 7.34-7.26 (5H, m), 6.66 (1H, d, J=5.28 Hz), 3.82 (2H, s), 3.57 (4H, br), 3.32 (2H, s), 2.38 (4H, br). MS calcd: 612.7, found: 613.3 (M+1).

Example 247

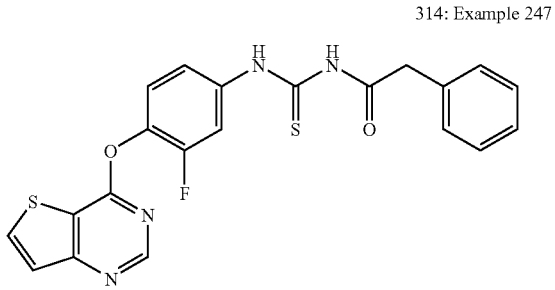

314: Example 247

N-(3-Fluoro-4-(thieno[3,2-d]pyrimidin-4-yloxy)phenylcarbamothioyl)-2-phenylacetamide (314)

Title compound 314 was obtained by following the procedures described above for the synthesis of compound 173 (scheme 34, example 135) but replacing 3-chloro-4-nitrophenol in the step 1 with 2-fluoro-4-nitrophenol. $^1$HNMR (DMSO-d$_6$) δ (ppm): 12.42 (bs, 1H), 11.79 (bs, 1H), 8.71 (s, 1H), 8.51 (d, J=5.2 Hz, 1H), 7.91 (dd, J=2.4 and 12.0 Hz, 1H), 7.70 (d, J=5.2 Hz, 1H), 7.53 (dd, J=8.4 Hz, 1H), 7.47 (dd, J=2.4 and 8.4 Hz, 1H), 7.38-7.30 (m, 4H), 7.30-7.27 (m, 1H), 3.82 (s, 2H). LRMS: 438.1(calc) 439.1 (found).

Example 248

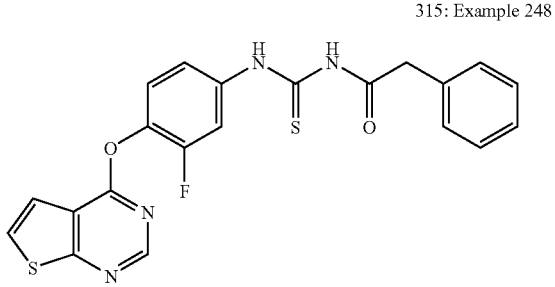

315: Example 248

N-(3-Fluoro-4-(thieno[2,3-d]pyrimidin-4-yloxy)phenylcarbamothioyl)-2-phenylacetamide (315)

Title compound 315 was obtained starting from the compound 205 (scheme 44) and following the procedures described above for the synthesis of compound 314. $^1$HNMR (DMSO-d$_6$) δ (ppm): 12.42 (s, 1H), 11.80 (s, 1H), 8.63 (s, 1H), 8.01 (d, J=5.6 Hz, 1H), 7.91 (dd, J=2.0 and 12.0 Hz, 1H), 7.70 (d, J=5.6 Hz, 1H), 7.50 (t, J=8.4 Hz, 1H), 7.46 (dd, J=2.4 and 8.4 Hz, 1H), 7.36-7.30 (m, 4H), 7.30-7.24 (m, 1H), 3.82 (s, 2H). LRMS: 438.4 (calc) 439.3 (found).

Example 249

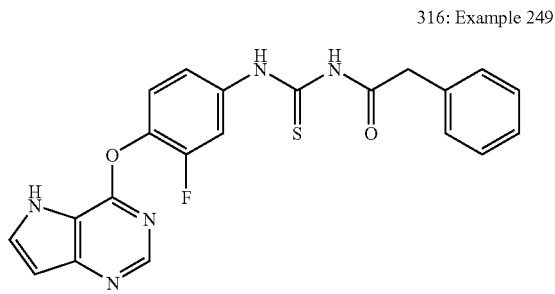

316: Example 249

N-(4-(5H-Pyrrolo[3,2-d]pyrimidin-4-yloxy)-3-fluorophenylcarbamothioyl)-2-phenylacetamide (316)

Title compound 316 was obtained by following the procedures described above for the synthesis of compound 31a (scheme 5, example 28) but skipping N-methylation step. $^1$HNMR (DMSO-d$_6$) δ(ppm): 12.41 (s, 1H), 8.32 (s, 1H), 7.91 (d, J=10 Hz, 1H), 7.48 (s, 1H), 7.56-7.42 (m, 2H), 7.39-7.32 (m, 4H), 7.30-7.22 (m, 1H), 6.66 (s, 1H), 3.83 (s, 2H). LRMS: 421.1 (calc) 422.1 (found).

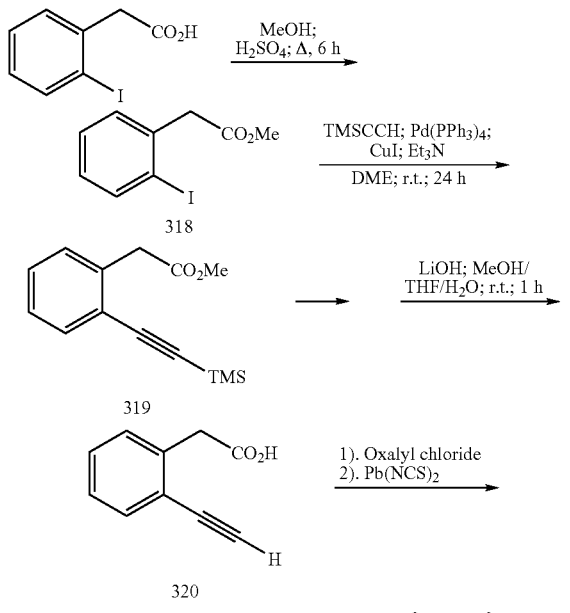

2-(2-Ethynylphenyl)acetyl isothiocyanate (317)

Step 1: Methyl 2-(2-iodophenyl)acetate (318)

A solution of 2-iodophenylacetic acid (5.05 g, 19.3 mmol) and sulfuric acid (0.5 mL) in methanol was heated under reflux for 6 h, then cooled and concentrated under reduced pressure. The residue was partitioned between ethyl acetate and water, organic phase was collected, washed with 1M NaOH, brine, dried (MgSO$_4$), filtered and concentrated to afford pure 318 (5.05 g, 95% yield). $^1$H NMR (400 MHz, CDCl$_3$) δ (ppm): 7.85 (dd, J=8.0, 1.2 Hz, 1H); 7.34-7.27 (m, 2H); 6.97 (dt, J=7.6, 2.2 Hz, 1H); 3.81 (s, 2H); 3.73 (s, 3H).

Step 2: Methyl 2-(2-((trimethylsilyl)ethynyl)phenyl)acetate (319)

To a solution of ester 318 (7.50 g, 27.2 mmol) in dry DME (125 mL) at 0° C. was added triethylamine (6.0 mL, 4.3 g, 43 mmol), copper (I) iodide (1.00 g, 5.25 mmol), and bis(triphenylphosphine) palladium (II) chloride (0.65 g, 0.93 mmol). The mixture was degassed with a stream of N$_2$ for 5 min, then trimethylsilylacetylene (5.8 mL, 4.1 g, 41 mmol) was added and the reaction mixture was warmed to room temperature and stirred for 24 h. It was concentrated under reduced pressure, partitioned between ethyl acetate and water, washed with brine, dried (anhydrous MgSO$_4$), filtered and concentrated. Flash chromatography of the residue (eluent 4% ethyl acetate/hexanes) afforded title compound 319 (4.65 g, 69% yield). $^1$H NMR (400 MHz, CDCl$_3$) δ (ppm): 7.22 (dd, J=7.4, 0.8 Hz, 1H); 7.07-6.95 (m, 3H); 3.58 (s, 2H); 3.45 (s, 3H); 0.00 (s, 9H). LCMS: (M+H) 247.1.

Step 3: 2-(2-Ethynylphenyl)acetic acid (320)

To a solution of ester 319 (4.65 g, 18.9 mmol) in 1:1 THF/methanol (100 mL) was added lithium hydroxide monohydrate (1.60 g, 38.1 mmol) in water (25 mL) and the mixture was stirred at r.t. for 30 min. It was then partially concentrated, the aqueous residue was washed with ether, then acidified with 3M HCl (aq) and extracted with ethyl acetate. The organic extract was washed with water, dried (anhydrous MgSO$_4$), filtered and concentrated. The residue was dissolved in ethyl acetate, run through a short plug of silica gel, and concentrated to provide 320 (2.77 g, 92% yield). $^1$H NMR (400 MHz, DMSO-d$_6$) δ (ppm): 12.40 (br s, 1H); 7.45 (d, J=8.0 Hz, 1H), 7.37-7.24 (m, 3H), 4.36 (s, 1H); 3.72 (s, 2H). LCMS: (M+Na) 183.1

Step 4: 2-(2-Ethynylphenyl)acetyl isothiocyanate (317)

To acid 319 (0.34 g, 2.1 mmol) in dry dichloromethane (25 mL) was added oxalyl chloride (0.39 mL, 0.57 g, 4.5 mmol) and dry DMF (0.05 mL). The mixture was stirred for 1 h, then concentrated under reduced pressure. The residue was re-dissolved in toluene (40 mL) and lead thiocyanate (0.75 g, 2.3 mmol) was added. The resulting suspension was heated to reflux with vigorous stirring for 3 h, then cooled, filtered through celite, and concentrated to afford crude 317 which was used without further purification.

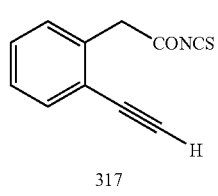

317

Scheme 76

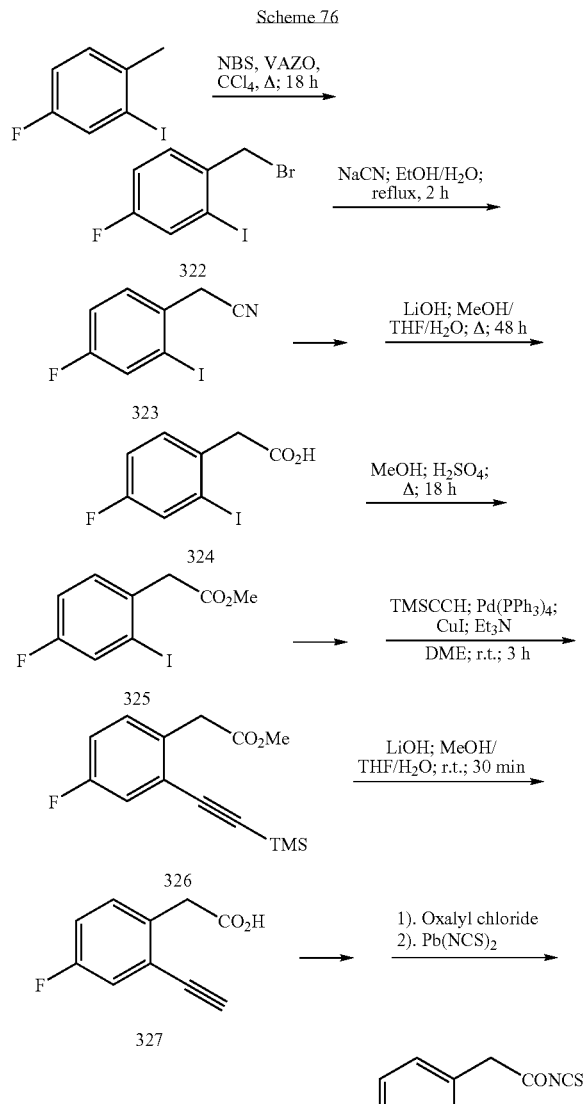

2-(2-Ethynyl-4-fluorophenyl)acetyl isothiocyanate (321)

Step 1: 1-(Bromomethyl)-4-fluoro-2-iodobenzene (322)

N-Bromosuccinimide (0.61 g, 3.4 mmol) and VAZO (0.10 g, 0.41 mmol) were added to a solution of 4-fluoro-2-iodotoluene (0.75 g, 3.2 mmol) in carbon tetrachloride (45 mL). The resulting suspension was stirred and heated under reflux for 18 hours. It was then cooled and filtered, the solid was rinsed with carbon tetrachloride (5 mL), and the combined filtrates were concentrated under reduced pressure. The residue was purified by flash column chromatography (eluting with hexanes) to provide 322 (0.58 g, 58% yield). $^1$H NMR (400 MHz, CDCl$_3$) δ (ppm): 7.51 (dd, J=8.0, 2.5 Hz, 1H); 7.38 (dd, J=8.4, 5.7 Hz, 1H); 7.00 (dt, J=8.2, 2.7 Hz, 1H); 4.54 (s, 2H).

Steps 2-3: 2-(4-Fluoro-2-iodophenyl)acetic acid (324)

To the benzylic bromide 322 (4.90 g, 15.6 mmol) in ethanol (50 mL) was added sodium cyanide (1. 60 g, 32.6 mmol) in water (10 mL) and the mixture was heated to reflux for 3 h. It was then concentrated, partitioned between diethyl ether and water; organic phase was collected, washed with brine, dried (MgSO$_4$), filtered and concentrated to afford crude nitrile 323. To this material in 1:1 THF/methanol (50 mL) was added lithium hydroxide monohydrate (1.75 g, 41.7 mmol), in water (12 mL) and the mixture was heated to reflux for 24 h. It was then cooled, partially concentrated and the aqueous residue was washed with ether, then acidified with 3M HCl (aq) and extracted with ether. The extract was washed with brine, dried (MgSO$_4$), filtered and concentrated to yield acid 324 (3.95 g, 90% yield over two steps). LCMS: (M+Na) 303.0.

Step 4: Methyl 2-(4-fluoro-2-iodophenyl)acetate (325)

A solution of the acid 324 (3.95 g, 14.1 mmol) and sulfuric acid (0.5 mL) in methanol (50 mL) was heated under reflux for 18 h, then cooled and concentrated under reduced pressure. The residue was partitioned between ethyl acetate and water; the organic phase was collected, dried (anhydrous MgSO$_4$), filtered and concentrated to afford pure 325 (3.93 g, 95% yield). $^1$H NMR (400 MHz, CDCl$_3$) δ (ppm): 7.57 (dd, J=8.2, 2.7 Hz, 1H); 7.25 (dd, J=8.6, 5.9 Hz, 1H); 7.05 (dt, J=8.2, 2.7 Hz, 1H); 3.78 (s, 2H); 3.72 (s, 3H). LCMS: (M+H) 295.0.

Step 5: Methyl 2-(4-fluoro-2-((trimethylsilyl)ethynyl)phenyl)acetate (326)

To a solution of ester 325 (3.80 g, 12.9 mmol) in dry DME (100 mL) at 0° C. was added triethylamine (4.5 mL, 3.3 g, 33 mmol), copper (I) iodide (0.50 g, 2.6 mmol), and bis(triphenylphosphine) palladium (II) chloride (0.38 g, 0.54 mmol). The mixture was degassed with a stream of N$_2$ for 5 min, then trimethylsilylacetylene (4.0 mL, 2.8 g, 29 mmol) was added and the reaction mixture was warmed to room temperature and stirred for 3 h. It was then concentrated under reduced pressure, re-dissolved in ether, filtered and concentrated. Silica gel chromatography of the residue (eluent 10% ethyl acetate/hexanes) afforded 326 (3.30 g, 97% yield). $^1$H NMR (400 MHz, CDCl$_3$) δ (ppm): 7.23 (dd, J=8.6, 5.7 Hz, 1H); 7.14 (dd, J=9.0, 2.7 Hz, 1H); 7.00 (dt, J=8.4, 2.7 Hz, 1H); 3.79 (s, 2H); 3.70 (s, 3H); 0.25 (s, 9H). LCMS: (M+H) 265.2.

Step 6. 2-(2-Ethynyl-4-fluorophenyl)acetic acid (327)

To a solution of ester 326 (3.30 g, 12.5 mmol) in 1:1 THF/methanol (100 mL) was added lithium hydroxide monohydrate (1.60 g, 38.1 mmol) in water (25 mL) and the mixture was stirred at r.t. for 30 min. It was then partially concentrated; the aqueous residue was washed with ether; then acidified with 3M HCl (aq), extracted with ethyl acetate. The organic extract was washed with water, dried (anhydrous MgSO$_4$), filtered and concentrated to provide acid 327 (2.10 g, 95% yield). $^1$H NMR (400 MHz, DMSO-d$_6$) δ (ppm): 7.36

(dd, J=8.6, 5.9 Hz, 1H); 7.30 (dd, J=9.2, 2.7 Hz, 1H); 7.21 (dt, J=8.6, 2.7 Hz, 1H); 4.48 (s, 1H); 3.70 (s, 2H). LCMS: (M+Na) 201.1.

Step 7: 2-(2-Ethynyl-4-fluorophenyl)acetyl isothiocyanate (321)

To a solution of acid 327 (2.10 g, 11.8 mmol) in dry dichloromethane (50 mL) was added oxalyl chloride (2.0 mL, 2.9 g, 23 mmol) and dry DMF (0.1 mL). The mixture was stirred for 1 h, then concentrated under reduced pressure. The residue was re-dissolved in toluene (75 mL) and lead thiocyanate (4.0 g, 12 mmol) was added. The resulting suspension was heated to reflux with vigorous stirring for 3 h, then cooled, filtered through celite, and concentrated to afford crude 321 which was used without further purification.

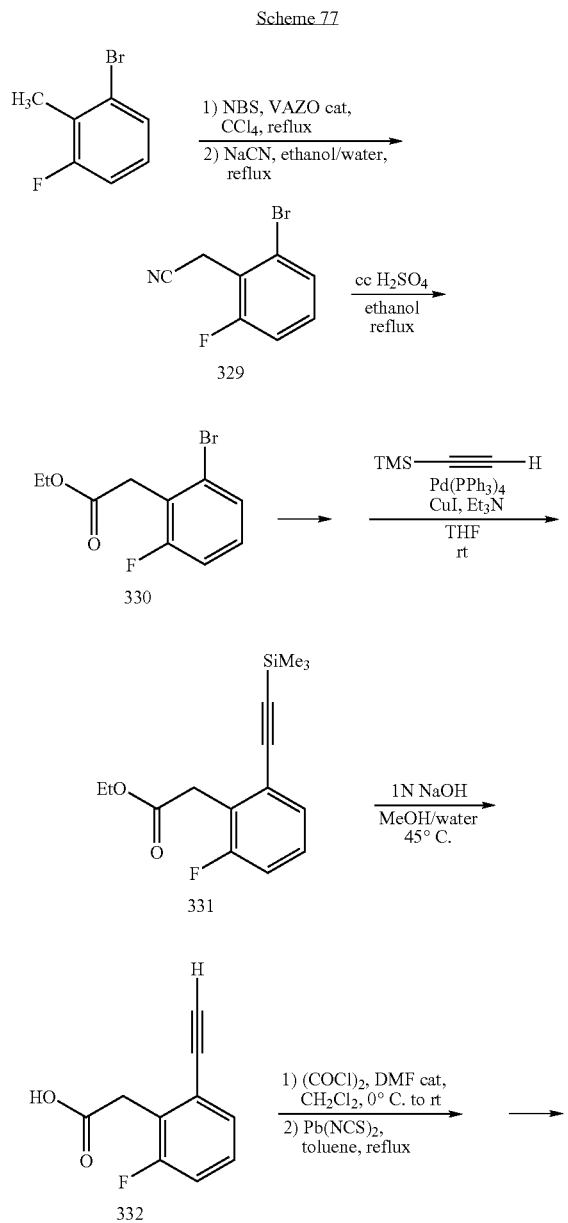

Scheme 77

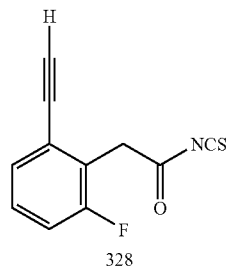

2-(2-Ethynyl-6-fluorophenyl)acetyl isothiocyanate (328)

Step 1. 2-(2-Bromo-6-fluorophenyl)acetonitrile (329)

A suspension of 2-bromo-6-fluorotoluene (5.00 g, 26.45 mmol), NBS (5.18 g, 29.10 mmol), and VAZO (323 mg, 1.32 mmol) in CCl$_4$ (100 mL) was heated to reflux under vigoroue stirring overnight. The reaction mixture was cooled to room temperature, concentrated and the residue was removed by filtration. The filtrate was concentrated and the residue was re-dissolved in ethanol (90 mL), treated with a solution of NaCN (2.59 g, 52.9 mmol) in water (20 mL) and the combined mixture was heated to reflux for 5 hrs. Ethanol was removed under reduced pressure, the aqueous residue was diluted with water and extracted with AcOEt. The organic layer was successively washed with water and brine, concentrated, adsorbed on silica gel and purified by flash column chromatography (eluents AcOEt/hexanes: 10/90 to 20/80) to afford title compound 329 (3.92 g, 69% yield over 2 steps, slightly contaminated) as a pale yellow sticky solid. $^1$H NMR (400 MHz, DMSO-d$_6$) δ (ppm): 7.62-7.57 (m, 1H), 7.45-7.35 (m, 2H), 4.08 (s, 2H).

Step 2. Ethyl 2-(2-bromo-6-fluorophenyl)acetate (330)

A solution of 329 (3.89 g, 18.17 mmol) and concentrated sulfuric acid (35 mL) in ethanol (80 mL) was heated to reflux overnight. The mixture was allowed to cool down to room temperature, and poured into a mixture of ice/water, shaken for 15 min, and extracted with AcOEt. The extract was successively washed with water, sat. NaHCO$_3$, water, dried over anhydrous magnesium sulfate, filtered, and concentrated to afford title compound 330 (4.86 g, quantitative yield, contaminated) as a yellow oily liquid. LCMS: 261.0 and 263.0 (M+H)$^+$.

Step 3. Ethyl 2-(2-fluoro-6-((trimethylsilyl)ethynyl)phenyl)acetate (331)

To a solution of 330 (4.85 g, 18.0 mmol) in anhydrous THF (100 ml) were added Pd(PPh$_3$)$_2$Cl$_2$ (632 mg, 0.9 mmol), CuI (343 mg, 1.8 mmol), TMSacetylene (3.24 mL, 23.4 mmol), respectively. The reaction mixture was degassed for 15 min with nitrogen, treated with Et$_3$N (7.53 mL, 54 mmol), stirred overnight under nitrogen and diluted with AcOEt. The AcOEt solution was successively washed with sat.NH$_4$Cl, dried over anhydrous MgSO$_4$, filtered, and concentrated. The crude product was purified by flash column chromatography (eluents AcOEt/hexanes: 2/98 to 10/90) to afford a mixture of 331 and 330 which was resubmitted to the same reaction conditions and work-up. The crude product was purified three times by flash column chromatography (eluents AcOEt/hexanes: 2/98) to afford title compound 331 (611 mg, 12% yield over 2 steps, slightly contaminated) as a brown oily liquid. ¹H NMR (400 MHz, DMSO-$d_6$) δ (ppm): 7.38-7.25 (m, 3H), 4.09 (q, J=7.2 Hz, 2H), 3.83 (d, J=7.8 Hz, 1H), 3.82 (d, J=7.4 Hz, 1H), 1.18 (t, J=7.0 Hz, 3H), 0.23 (s, 9H).

Step 4. 2-(2-Ethynyl-6-fluorophenyl)acetic acid (332)

A stirred solution of 331 (607 mg, 2.18 mmol) and 1N NaOH (5.5 mL) in methanol (15 mL) was heated at 45° C. for 16 h under nitrogen. The reaction mixture was allowed to cool to room temperature; it was then concentrated, diluted with water, and washed with hexanes. The aqueous layer was collected, acidified with 3N HCl and extracted twice with AcOEt. The organic extract was dried over anhydrous magnesium sulfate, filtered, and concentrated to afford title compound 332 (400 mg, 94% yield, mono-hydrate) as an orange sticky solid. LCMS: 201.1 (M+Na)⁺.

Step 5. 2-(2-Ethynyl-6-fluorophenyl)acetyl isothiocyanate (328)

To a stirred solution at 0° C. of 332 (390 mg, 2.19 mmol) in anhydrous $CH_2Cl_2$ (25 ml) were added oxalyl chloride (420 µL, 4.82 mmol) and anhydrous DMF (few drops). The reaction mixture was stirred under nitrogen at 0° C. for 40 min, and then at room temperature for 1 hr, concentrated and dried under high vacuum. The solid residue was dissolved in anhydrous toluene (50 mL) and $Pb(NCS)_2$ was added (780 mg, 2.41 mmol). The suspension was heated to reflux for 3.5 hrs under nitrogen, cooled to room temperature, filtered through celite, and rinsed with AcOEt. The filtrate was concentrated and dried under high vacuum to afford title compound 328 (474 mg, 98% yield) as a dark brown oily liquid.

T. *J. Org. Chem.* 2003, 68, 6354-6359) and LiOH×$H_2O$ (185 mg, 4.41 mmol) in $H_2O$/THF (1:1, 11 mL) was stirred overnight at room temperature. The THF was evaporated off under reduced pressure; the aqueous residue was diluted with water, washed with EtOAc, acidified to pH~3 by addition of 1N HCl and extracted with DCM. The organic extract was dried over anhydrous $Na_2SO_4$ and concentrated under reduced pressure affording 335 (557.2 mg, 77% yield) as a white solid. LCMS: (M−1) 187.1 (100%).

Step 2: 2-(2-(1-Fluorovinyl)phenyl)acetyl isothiocyanate (333)

To a solution of 2-(2-(1-fluorovinyl)phenyl)acetic acid (335, 557.2 mg, 3.9 mmol) in DCM (6.2 mL) oxalyl chloride (810 mL, 9.28 mmol) was added in one portion followed by one drop DMF. The mixture was stirred until no more bubbling occurred (~1 h), then concentrated under reduced pressure. The residue was re-dissolved in toluene (30.9 mL), $Pb(NCS)_2$ (999.6 mg, 3.09 mmol) was added and the mixture was heated to reflux under vigorous stirring for 3 h. The suspension was filtered through Celite®, the Celite® washed with toluene and the combined filtrates were concentrated under reduced pressure affording title compound 333 630.3 mg, 92% yield) as a red syrup that was used in the next step without further purification. LCMS: (M+MeOH+1) 254.1 (40%).

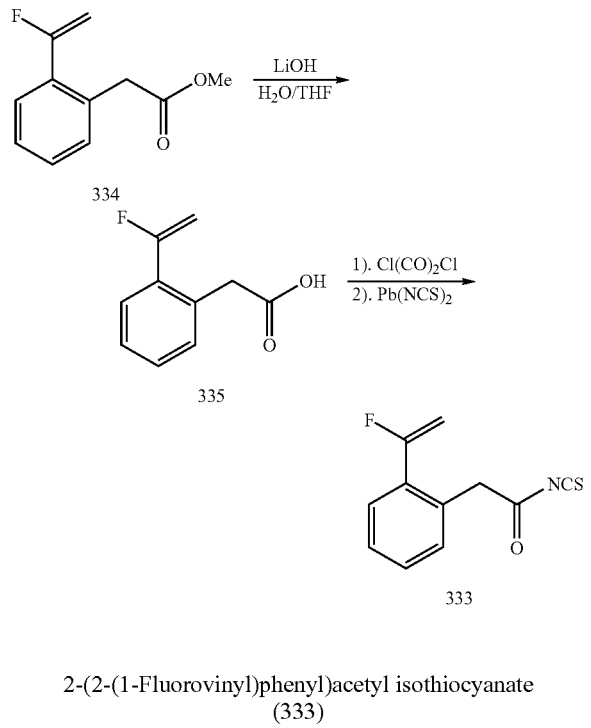

Scheme 78

2-(2-(1-Fluorovinyl)phenyl)acetyl isothiocyanate (333)

Step 1: 2-(2-(1-Fluorovinyl)phenyl)acetic acid (335)

A suspension of methyl 2-(2-(1-fluorovinyl)phenyl)acetate (334, 770.8 mg, 4.015 mmol) (Hakamoto T.; Kobavashi

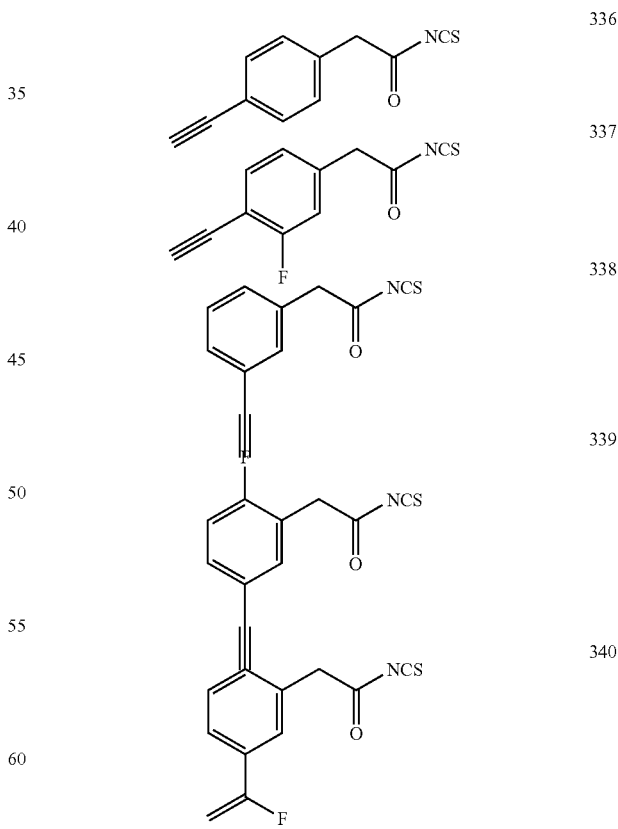

Scheme 79

Isothiocyanates 336-339 were synthesized similarly to the isothiocyanates 317, 321 and 328 (schemes 75-77). Compound 340 was prepared similarly to 333 (scheme 78).

TABLE 24

*Characterization of compounds 339–375 (examples 250–284) prepared according to the procedures similar to ones shown in the schemes 2, 17, 18, 20, 35, 49, 73 and 74.*

| Cpd | Ex. | Structure | Characterization |
|---|---|---|---|
| 341 | 250 | 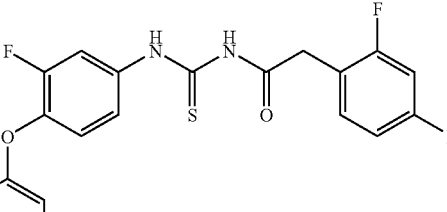<br>2-(2,4-Difluorophenyl)-N-(4-(2-(1-ethyl-1H-imidazol-2-yl)thieno[3,2-b]pyridin-7-yloxy)-3-fluorophenylcarbamothioyl)acetamide | $^1$H NMR(400 MHz, DMSO-d$_6$) δ (ppm): 12.38(s, 1H); 11.87(s, 1H); 8.54(d, J=5.5 Hz, 1H); 8.03(d, J=12.5 Hz, 1H); 7.83(s, 1H); 7.54–7.43(m, 4H); 7.25(dd, J=9.8, 2.7 Hz, 1H); 7.08(dd, J=8.6, 2.7 Hz, 1H); 7.07 (s, 1H); 6.69(d, J=5.7 Hz, 1H); 4.37(q, J= 7.2 Hz, 2H); 3.92(s, 2H); 1.42(t, J=7.2 Hz, 3H). LCMS: (M + H) 568.1. |
| 342 | 251 | 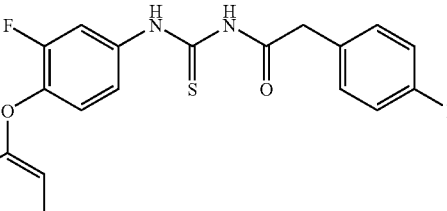<br>N-(4-(2-(1-Ethyl-1H-imidazol-2-yl)thieno[3,2-b]pyridin-7-yloxy)-3-fluorophenylcarbamothioyl)-2-(4-fluorophenyl)acetamide | $^1$H NMR(400 MHz, DMSO-d$_6$) δ (ppm): 12.48(s, 1H); 11.83(s, 1H); 8.54(d, J=5.5 Hz, 1H); 8.05–8.01(m, 1H); 7.85(s, 1H); 7.55–7.51(m, 2H); 7.49(s, 1H); 7.39–7.35 (m, 2H); 7.20–7.15(m, 2H); 7.09(s, 1H); 6.69(d, J=5.3 Hz, 1H); 4.37(q, J=7.2 Hz, 2H); 3.82(s, 2H); 1.42(t, J=7.2 Hz, 3H). LCMS: (M + H) 550.2 |
| 343 | 252 | 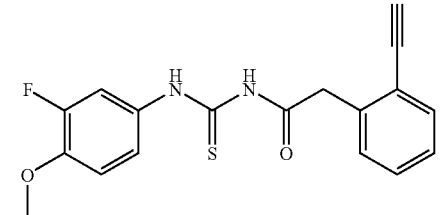<br>N-(4-(2-(1-Ethyl-1H-imidazol-2-yl)thieno[3,2-b]pyridin-7-yloxy)-3-fluorophenylcarbamothioyl)-2-(2-ethynylphenyl)acetamide | $^1$H NMR(400 MHz, DMSO-d$_6$) δ (ppm): 12.53(s, 1H); 11.90(s, 1H); 8.54(s, J=5.9 Hz, 1H); 8.06(d, J=11.9 Hz, 1H); 7.83(s, 1H); 7.58–7.52(m, 2H); 7.50–7.48(m, 2H); 7.40–7.38(m, 2H); 7.33–7.27(m, 1H); 7.07 (s, 1H); 6.69(d, J=5.3 Hz, 1H); 4.44(s, 1H); 4.37(q, J=7.4 Hz, 2H); 4.05(s, 2H); 1.42(t, J=7.4 Hz, 3H). LCMS: (M + H) 556.2 |
| 344 | 253 | 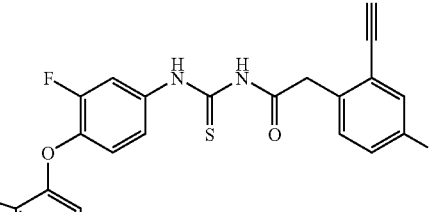<br>2-(2-ethynyl-4-fluorophenyl)-N-(3-fluoro-4-(2-(1-methyl-1H-imidazol-4-yl)thieno[3,2-b]pyridin-7-yloxy)phenylcarbamothioyl)acetamide | $^1$H NMR(400 MHz, DMSO-d$_6$) δ (ppm): 12.47(s, 1H); 11.90(s, 1H); 8.52(d, J=5.9 Hz, 1H); 8.06(dd, J=12.5, 2.3 Hz, 1H); 7.97 (s, 1H); 7.89(s, 1H); 7.74(s, 1H); 7.59–7.51 (s, 2H); 7.43(dd, J=8.6, 5.9 Hz, 1H); 7.35 (dd, J=9.2, 2.8 Hz, 1H); 7.26(dt, J=8.8, 2.7 Hz, 1H); 6.69(d, J=5.5 Hz, 1H); 4.57(s, 1H); 4.02(s, 2H); 3.73(s, 3H). LCMS: (M + H) 560.1. |

TABLE 24-continued

Characterization of compounds 339–375 (examples 250–284) prepared according to the procedures similar to ones shown in the schemes 2, 17, 18, 20, 35, 49, 73 and 74.

| Cpd | Ex. | Structure | Characterization |
|---|---|---|---|
| 345 | 254 | 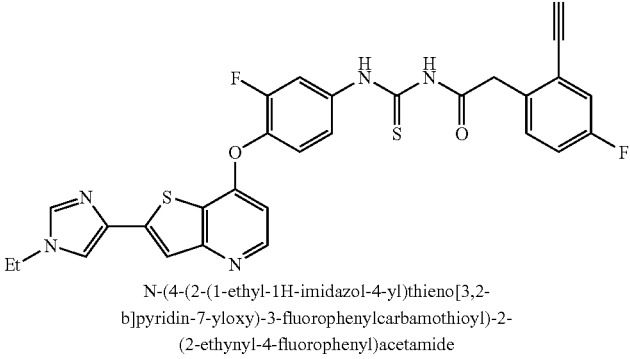<br>N-(4-(2-(1-ethyl-1H-imidazol-4-yl)thieno[3,2-b]pyridin-7-yloxy)-3-fluorophenylcarbamothioyl)-2-(2-ethynyl-4-fluorophenyl)acetamide | $^1$H NMR(400 MHz, DMSO-d$_6$) δ (ppm): 12.47(s, 1H); 11.90(s, 1H); 8.53(d, J=5.9 Hz, 1H); 8.10–8.02(m, 3H); 7.75(s, 1H); 7.59–7.51(m, 2H); 7.43(dd, J=8.8, 7.3 Hz, 1H); 7.35(dd, J=8.8, 2.9 Hz, 1H); 7.26(dt, J=8.8, 2.7 Hz, 1H); 6.71(d, J=5.5 Hz, 1H); 4.57(s, 1H); 4.08(q, J=7.2 Hz, 2H); 4.03(s, 2H); 1.40(t, J=7.4 Hz, 3H). LCMS:(M + H) 574.1 |
| 346 | 255 | 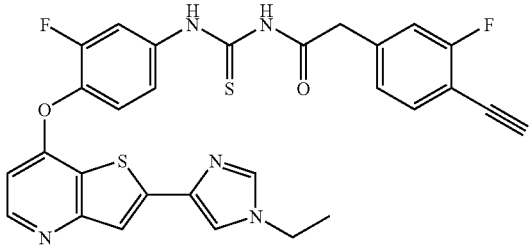<br>N-(4-(2-(1-ethyl-1H-imidazol-4-yl)thieno[3,2-b]pyridin-7-yloxy)-3-fluorophenylcarbamothioyl)-2-(4-ethynyl-3-fluorophenyl)acetamide | $^1$H NMR(400 MHz, DMSO-d$_6$) δ (ppm): 12.34(s, 1H), 11.89(s, 1H), 8.44(d, J=5.48 Hz, 1H), 8.02(m, 1H), 7.94(s, 1H), 7.77(s, 1H), 7.67(s, 1H), 7.51(m, 2H), 7.36(m, 3H), 6.57(d, J=5.48 Hz, 1H), 4.31(s, 1H), 4.03 (q, J=7.24 Hz, 2H), 3.94(s, 2H), 1.39(t, J=7.43 Hz, 3H). LCMS: 574.2(M + H). |
| 347 | 256 | 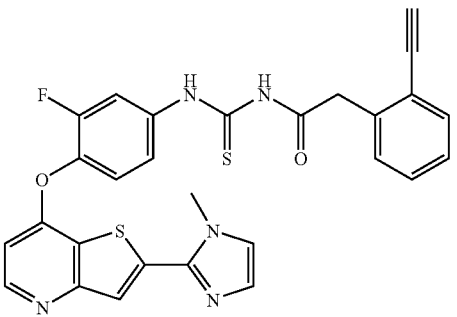<br>2-(2-ethynylphenyl)-N-(3-fluoro-4-(2-(1-methyl-1H-imidazol-2-yl)thieno[3,2-b]pyridin-7-yloxy)phenylcarbamothioyl)acetamide | $^1$H NMR(400 MHz, DMSO-d$_6$) δ (ppm): 12.51(s, 1H), 11.90(s, 1H), 8.53(d, J=5.48 Hz, 1H), 8.18(s, 1H), 8.07(m, 1H), 7.90(s, 1H), 7.38(m, 6H), 7.04(s, 1H), 6.68(d, J=5.48 Hz, 1H), 4.45(s, 1H), 4.05(s, 2H), 3.99 (s, 3H). LCMS: 542.2(M + H). (formate salt) |
| 348 | 257 | 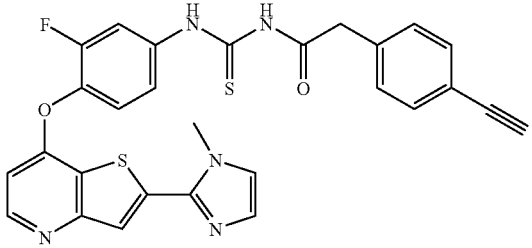<br>2-(4-ethynylphenyl)-N-(3-fluoro-4-(2-(1-methyl-1H-imidazol-2-yl)thieno[3,2-b]pyridin-7-yloxy)phenylcarbamothioyl)acetamide | $^1$H NMR(400 MHz, DMSO-d$_6$) δ (ppm): 12.47(s, 1H), 11.85(s, 1H), 8.54(d, J=5.48 Hz, 1H), 8.02(s, 1H), 7.91(s, 1H), 7.42(m, 7H), 7.06(s, 1H), 6.69(d, J=5.48 Hz, 1H), 4.17(s, 1H), 3.99(s, 3H), 3.86(s, 2H). LCMS: 542.1(M + H). |

TABLE 24-continued

Characterization of compounds 339–375 (examples 250–284) prepared according to the procedures similar to ones shown in the schemes 2, 17, 18, 20, 35, 49, 73 and 74.

| Cpd | Ex. | Structure | Characterization |
|---|---|---|---|
| 349 | 258 | 2-(4-ethynyl-3-fluorophenyl)-N-(3-fluoro-4-(2-(1-methyl-1H-imidazol-2-yl)thieno[3,2-b]pyridin-7-yloxy)phenylcarbamothioyl)acetamide | $^1$H NMR(400 MHz, DMSO-d$_6$) δ (ppm): 12.37(s, 1H), 11.90(s, 1H), 8.53(d, J=5.48 Hz, 1H), 8.16(s, 1H), 8.01(m, 1H), 7.89(s, 1H), 7.54(m, 2H), 7.31(m, 4H), 7.03(s, 1H), 6.68(d, J=5.48 Hz, 1H), 4.31(s, 1H), 3.98(s, 3H), 3.94(s, 2H). LCMS: 560.2 (M + H). (formate salt) |
| 350 | 259 | 2-(2-ethynyl-4-fluorophenyl)-N-(3-fluoro-4-(2-(1-methyl-1H-imidazol-2-yl)thieno[3,2-b]pyridin-7-yloxy)phenylcarbamothioyl)acetamide | $^1$H NMR(400 MHz, DMSO-d$_6$) δ (ppm): 12.47(s, 1H), 11.89(s, 1H), 8.44(d, J=5.48 Hz, 1H), 8.05(m, 1H), 7.89(s, 1H), 7.37(s, 6H), 7.03(s, 1H), 6.67(d, J=5.48 Hz, 1H), 4.58(s, 1H), 4.03(s, 2H), 3.98(s, 3H). LCMS: 560.2(M + H). |
| 351 | 260 | 2-(5-ethynyl-2-fluorophenyl)-N-(3-fluoro-4-(2-(1-methyl-1H-imidazol-2-yl)thieno[3,2-b]pyridin-7-yloxy)phenylcarbamothioyl)acetamide | $^1$H NMR(400 MHz, DMSO-d$_6$) δ (ppm): 12.48(s, 1H), 11.90(s, 1H), 8.52(m, 1H), 8.02(m, 1H), 7.89(s, 1H), 7.48(m, 4H), 7.40 (s, 1H), 7.23(t, J=9 Hz, 1H), 7.03(s, 1H), 6.69(d, J=5.48 Hz, 1H), 4.20(s, 1H), 3.98 (s, 3H), 3.92(s, 2H). LCMS: 560.1(M + H). |
| 352 | 261 | 2-(2,4-difluorophenyl)-N-(3-fluoro-4-(2-(1-methyl 1H-imidazol-2-yl)thieno[3,2-b]pyridin-7-yloxy)phenylcarbamothioyl)acetamide | $^1$H NMR(400 MHz, DMSO-d$_6$) δ (ppm): 12.42(s, 1H), 11.90(s, 1H), 8.54(m, 1H), 8.06(m, 1H), 7.91(s, 1H), 7.47(m, 4H), 7.23 (m, 1H), 7.09(m, 2H), 6.67(m, 1H), 4.0(s, 3H), 3.92(s, 2H). LCMS: 554.1(M + H). |

TABLE 24-continued

Characterization of compounds 339–375 (examples 250–284) prepared according to the
procedures similar to ones shown in the schemes 2, 17, 18, 20, 35, 49, 73 and 74.

| Cpd | Ex. | Structure | Characterization |
|---|---|---|---|
| 353 | 262 | N-(3-fluoro-4-(2-(1-methyl-1H-imidazol-2-yl)thieno[3,2-b]pyridin-7-yloxy)phenylcarbamothioyl)-2-o-tolylacetamide | $^1$H NMR(400 MHz, DMSO-d$_6$) δ (ppm): 12.53(s, 1H), 11.83(s, 1H), 8.53(d, J=5.28 Hz, 1H), 8.04(m, 1H), 7.90(s, 1H), 7.55(m, 2H), 7.41(s, 1H), 7.19(m, 4H), 7.05(s, 1H), 6.68(d, J=5.28 Hz, 1H), 3.99(s, 3H), 3.87 (s, 2H). LCMS: 532.2(M + H). |
| 354 | 263 | N-(3-fluoro-4-(2-(1-methyl-1H-imidazol-2-yl)thieno[3,2-b]pyridin-7-yloxy)phenylcarbamothioyl)-2-(4-fluorophenyl)acetamide | $^1$H NMR(400 MHz, DMSO-d$_6$) δ (ppm): 12.50(s, 1H), 11.84(s, 1H), 8.54(m, 1H), 8.03(m, 1H), 7.91(s, 1H), 7.55(m, 2H), 7.41 (s, 3H), 7.17(m, 3H), 7.05(s, 1H), 6.68(m, 1H), 3.99(s, 3H), 3.84(s, 2H). LCMS: 536.1 (M + H). |
| 355 | 264 | N-(3-fluoro-4-(2-(1-methyl-1H-imidazol-4-yl)thieno[3,2-b]pyridin-7-yloxy)phenylcarbamothioyl)-2-(2-(1-fluorovinyl)phenyl)acetamide | $^1$H NMR(400 MHz, DMSO-d$_6$) δ (ppm): 12.49(s, 1H), 11.84(s, 1H), 8.45(dd, J=5.2, 2.5 Hz, 1H), 8.06(d, J=12.5Hz, 1H), 7.87 (s, 1H), 7.72(s,1H), 7.70(s, 1H), 7.67–7.36 (m, 6H), 6.59(dd, J=1.7, 3.7 Hz, 1H), 5.08 (ddd, J=3, 2.9, 28.9 Hz, 1H), 5.00(ddd, J= 3.3, 2.9, 62.4 Hz, 1H), 4.01(s, 2H), 3.72(s, 3H). LCMS: 562.2(M + H) |
| 356 | 265 | N-(3-fluoro-4-(2-(1-methyl-1H-imidazol-4-yl)thieno[3,2-b]pyridin-7-yloxy)phenylcarbamothioyl)-2-(3-(1-fluorovinyl)phenyl)acetamide | $^1$H NMR(400 MHz, DMSO-d$_6$) δ (ppm): 12.47(s, 1H), 11.9(s, 1H), 8.45(d, J=5.5 Hz, 1H), 8.02(dd, J=2, 13.3 Hz, 1H), 7.87 (d, J=1.1 Hz, 1H), 7.72(d, J=0.8 Hz, 1H), 7.69(s, 1H), 7.61-7.39(m, 6 H), 6.58(dd, J= 5.5 Hz, J=0.8 Hz, 1H), 5.38(dd, J=3.9 Hz, J=52.2 Hz, 1H), 4.98(dd, J=3.9, 19.0 Hz, 1H), 3.89(s, 2H), 3.72(s, 3H). LCMS: 562.2 (M + H) |

TABLE 24-continued

Characterization of compounds 339–375 (examples 250–284) prepared according to the procedures similar to ones shown in the schemes 2, 17, 18, 20, 35, 49, 73 and 74.

| Cpd | Ex. | Structure | Characterization |
|---|---|---|---|
| 357 | 266 | 2-(3-ethynylphenyl)-N-(3-fluoro-4-(2-(1-methyl-1H-imidazol-4-yl)thieno[3,2-b]pyridin-7-yloxy)phenylcarbamothioyl)acetamide | $^1$H NMR(400 MHz, DMSO-d$_6$) δ (ppm): 12.4(br, 1H), 11.9(br, 1H), 8.46(d, J=5.5 Hz, 1H), 8.02(dd, J=11.8, 2.3 Hz, 1H), 7.87 (d, J=1.0 Hz, 1H), 7.26(d, J=1Hz, 1H), 7.72(s, 1H), 7.69–7.48(m, 3H), 7.42–7.37 (m, 3H), 6.58(dd, J=0.8, 5.5 Hz, 1H), 4.22 (s, 1H), 3.85(s, 2H), 3.72(s, 3H). LCMS: (M + H) 542.10 |
| 358 | 267 | 2-(5-ethynyl-2-fluorophenyl)-N-(3-fluoro-4-(2-(1-methyl-1H-imidazol-4-yl)thieno[3,2-b]pyridin-7-yloxy)phenylcarbamothioyl)acetamide | $^1$H NMR(400 MHz, DMSO-d$_6$) δ (ppm): 12.39(s, 1H), 11.91(s, 1H), 8.48(d, J=5.5 Hz, 1H), 8.04(dd, J=1.8, 12.1 Hz, 1H), 7.90 (d, J=1.8 Hz, 1H), 7.76(s, 1H), 7.71(s, 1H), 7.59–7.46(m, 4H), 7.30(dd, J=8.6 Hz, 9.6 Hz, 1H), 6.61(d, J=5.5 Hz, 1H), 4.21(s, 1H), 3.94(s, 2H), 3.73(s, 3H). LCMS: (M + H) 560.2 |
| 359 | 268 | 2-(2-Ethynylphenyl)-N-(3-fluoro-4-(2-(1-methyl-1H-imidazol-4-yl)thieno[3,2-b]pyridin-7-yloxy)phenylcarbamothioyl)acetamide | $^1$H NMR(400 MHz, DMSO-d$_6$) δ (ppm): 12.51(s, 1H), 11.90(s, 1H), 8.46(d, J=5.4 Hz, 1H), 8.06(dd, J=12.4, 2.1 Hz, 1H), 7.87 (s, 1H), 7.72(s, 1H), 7.69(s, 1H), 7.60–7.47 (m, 3H), 7.43–7.37(m, 2H), 7.35–7.28(m, 1H), 6.59(d, J=5.5 Hz, 1H), 4.46(s, 1H), 4.06(s, 2H), 3.72(s, 3H). LCMS: 542.1 (M + H)$^+$. |
| 360 | 269 | 2-(2-Ethynyl-6-fluorophenyl)-N-(3-fluoro-4-(2-(1-methyl-1H-imidazol-4-yl) thieno[3,2-b]pyridin-7-yloxy)phenylcarbamothioyl)acetamide | $^1$H NMR(400 MHz, DMSO-d$_6$) δ (ppm): 12.35(bs, 1H), 11.99(bs, 1H), 8.45(d, J= 5.5 Hz, 1H), 8.08–7.98(m, 1H), 7.87(d, J= 1.2 Hz, 1H), 7.72(d, J=1.0 Hz, 1H), 7.69(s, 1H), 7.60–7.46(m, 2H), 7.41–7.27(m, 3H), 6.58(d, J=5.5 Hz, 1H), 4.59(s, 1H), 4.09 (bs, 2H), 3.72(s, 3H). LCMS: 560.2 (M + H)$^+$. |

TABLE 24-continued

Characterization of compounds 339–375 (examples 250–284) prepared according to the procedures similar to ones shown in the schemes 2, 17, 18, 20, 35, 49, 73 and 74.

| Cpd | Ex. | Structure | Characterization |
|---|---|---|---|
| 361 | 270 | 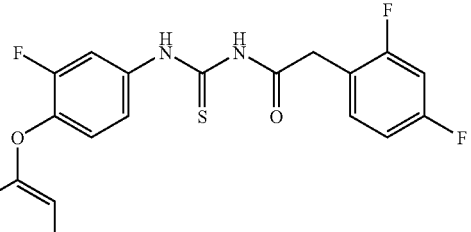<br>2-(2,4-difluorophenyl)-N-(3-fluoro-4-(2-(1-methyl-1H-imidazol-4-yl)thieno[3,2-b]pyridin-7-yloxy)phenylcarbamothioyl)acetamide | $^1$H NMR(400 MHz, DMSO-d$_6$) δ (ppm): 12.40(s, 1H), 11.89(s, 1H), 8.46(d, J=5.6 Hz, 1H), 8.03(dd, J=12.8, 2.4 Hz, 1H), 7.87 (d, J=0.8 Hz, 1H), 7.72(s, 1H), 7.69(s, 1H), 7.58–7.43(m, 3H), 7.26(td, J=10.0, 2.4 Hz, 1H), 7.09(td, J=8.4, 2.0 Hz, 1H), 6.58(d, J=5.6 Hz, 1H), 3.92(s, 2H), 3.73(s, 3H). LCMS:(M + H) 554.1 |
| 362 | 271 | 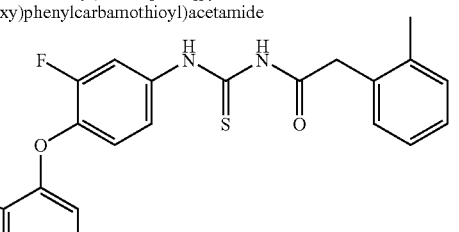<br>N-(3-fluoro-4-(2-(1-methyl-1H-imidazol-4-yl)thieno[3,2-b]pyridin-7-yloxy)phenylcarbamothioyl)-2-o-tolylacetamide | $^1$H NMR(400 MHz, DMSO-d$_6$) δ (ppm): 12.52(s, 1H), 11.83(s, 1H), 8.46(d, J=5.2 Hz, 1H), 8.05(dd, J=12.4, 2.4 Hz, 1H), 7.87 (d, J=1.2 Hz, 1H), 7.72(d, J=1.2 Hz, 1H), 7.69(s, 1H), 7.58–7.48(m, 2H), 7.28–7.23 (m, 1H), 7.22–7.13(m, 3H), 6.59(d, J=5.2 Hz, 1H), 3.88(s, 2H), 3.72(s, 3H), 2.29(s, 3H). LCMS:(M + H) 532.2 |
| 363 | 272 | 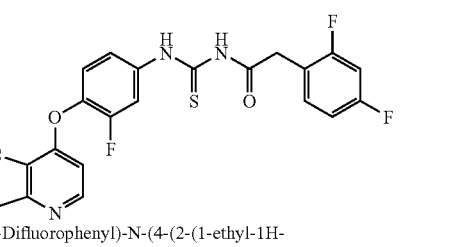<br>2-(2,4-Difluorophenyl)-N-(4-(2-(1-ethyl-1H-imidazol-4-yl)thieno[3,2-b]pyridin-7-yloxy)-3-fluorophenylcarbamothioyl)acetamide | $^1$H NMR(400 MHz, DMSO-d$_6$) δ (ppm): 12.44(s, 1H), 11.92(s, 1H), 8.65(d, J=6.0 Hz, 1H), 8.31(s, 1H), 8.26(s, 1H), 8.09(d, J=13.3 Hz, 1H), 7.85(s, 1H), 7.61–7.58(m, 2H), 7.47(q, J=7.6 Hz, 1H), 7.27 (td, J=2.5, 9.7 Hz, 1H), 7.01(td, J=2.5, 8.6 Hz, 1H), 6.88(d, J=5.9 Hz, 1H), 4.14(q, J=7.3 Hz, 2H), 3.93(s, 2H), 1.44(t, J=7.3 Hz, 3H). LCMS: 567.2(M + H). |
| 364 | 273 | 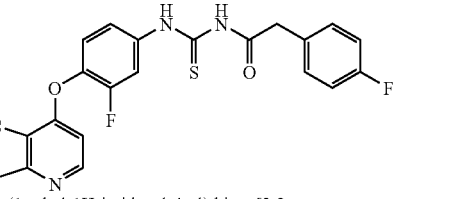<br>N-(4-(2-(1-ethyl-1H-imidazol-4-yl)thieno[3,2-b]pyridin-7-yloxy)-3-fluorophenylcarbamothioyl)-2-(4-fluorophenyl)acetamide | $^1$H NMR(400 MHz, DMSO-d$_6$) δ (ppm): 12.48(s, 1H), 11.83(s, 1H), 8.46(d, J=5.3 Hz, 1H), 8.02(d, J=12.1 Hz, 1H), 7.96(s, 1H), 7.79(s, 1H), 7.69(s, 1H), 7.53–7.50(m, 2H), 7.38(t, J=6.5 Hz, 2H), 7.18(t, J=8.6 Hz, 2H), 6.58(d, J=5.5Hz, 1H), 4.06(q, J=7.2 Hz, 2H), 3.83(s, 2H), 1.40(t, J=7.2 Hz, 3H). |
| 365 | 274 | 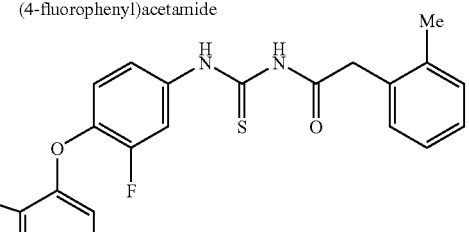<br>N-(4-(2-(1-ethyl-1H-imidazol-4-yl)thieno[3,2-b]pyridin-7-yloxy)-3-fluorophenylcarbamothioyl)-2-o-tolylacetamide | $^1$H NMR(400 MHz, DMSO-d$_6$) δ (ppm): 12.54(s, 1H), 11.85(s, 1H), 8.56(d, J=5.7 Hz, 1H), 8.13–8.07(m, 3H), 7.78(s, 1H), 7.58–7.54(m, 2H), 7.27–7.17(m, 4H), 6.75 (d, J=5.5 Hz, 1H), 4.10(q, J=7.2 Hz, 2H), 3.89(s, 2H), 2.29(s, 3H), 1.42(t, J=7.2 Hz, 3H). |

TABLE 24-continued

Characterization of compounds 339–375 (examples 250–284) prepared according to the procedures similar to ones shown in the schemes 2, 17, 18, 20, 35, 49, 73 and 74.

| Cpd | Ex. | Structure | Characterization |
|---|---|---|---|
| 366 | 275 | 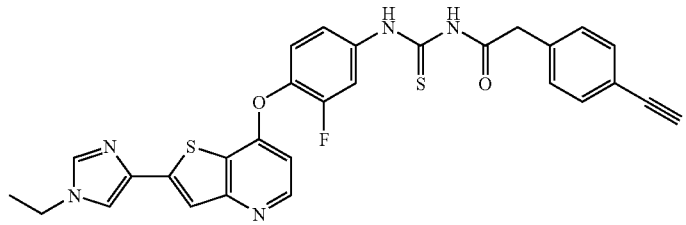<br>N-(4-(2-(1-ethyl-1H-imidazol-4-yl)thieno[3,2-b]pyridin-7-yloxy)-3-fluorophenylcarbamothioyl)-2-(4-ethynylphenyl)acetamide | $^1$H NMR(400 MHz, DMSO-d$_6$) δ (ppm): 12.46(s, 1H), 11.86(s, 1H), 8.46(d, J=5.5 Hz, 1H), 8.02(dd, J=2.1, 12.2 Hz, 1H), 7.96 (s, 1H), 7.80(d, J=0.8 Hz, 1H), 7.69(s, 1H), 7.53–7.52(m, 2H), 7.47(d, J=8.0 Hz, 2H), 7.36(d, J=8.0 Hz, 2H), 6.58(d, J=5.5 Hz, 1H), 4.19(s, 1H), 4.06(q, J=7.2 Hz, 2H), 3.87(s, 2H), 1.40(t, J=7.2 Hz, 3H). |
| 367 | 276 | 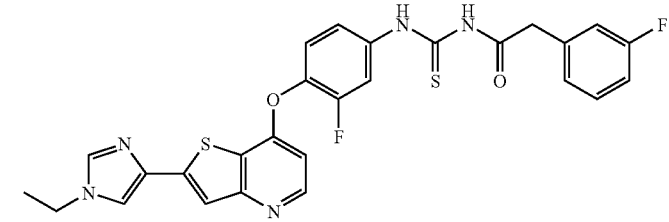<br>N-(4-(2-(1-ethyl-1H-imidazol-4-yl)thieno[3,2-b]pyridin-7-yloxy)-3-fluorophenylcarbamothioyl)-2-(3-fluorophenyl)acetamide | $^1$H NMR(400 MHz, DMSO-d$_6$) δ (ppm): 12.45(s, 1H), 11.85(s, 1H), 8.46(d, J=5.6 Hz, 1H), 8.03(d, J=12.0 Hz, 1H), 7.96(s, 1H), 7.79(s, 1H), 7.68(s, 1H), 7.60–7.48(m, 2H), 7.44–7.36(m, 1H),. 7.24–7.09(m, 3H), 6.58(d, J=5.6 Hz, 1H), 4.06(q, J=7.2 Hz, 2H), 3.87(s, 2H), 1.40(t, J=7.2 Hz, 3H). |
| 368 | 277 | 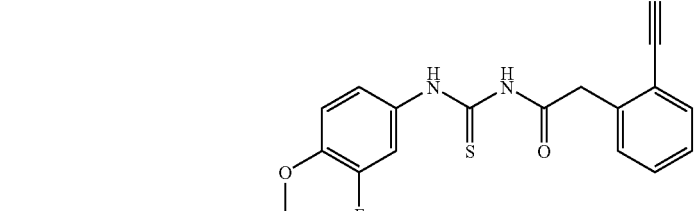<br>N-(4-(2-(1-ethyl-1H-imidazol-4-yl)thieno[3,2-b]pyridin-7-yloxy)-3-fluorophenylcarbamothioyl)-2-(2-ethynylphenyl)acetamide | $^1$H NMR(400 MHz, DMSO-d$_6$) δ (ppm): 12.50(s, 1H), 11.90(s, 1H), 8.45(d, J=5.6 Hz, 1H), 8.07(dd, J=2.4, 12.0 Hz, 1H), 7.96(d, J=1.2 Hz, 1H), 7.79(d, J=1.2 Hz, 1H), 7.68(s, 1H), 7.59–7.48(m, 3H), 7.42–7.38(m, 2H), 7.35–7.18(m, 1H), 6.58 (d, J=5.6 Hz, 1H), 4.45(s, 1H), 4.06(q, J=7.2 Hz, 2H), 4.05(s, 2H), 1.40(t, J=7.2 Hz, 3H). |
| 369 | 278 | 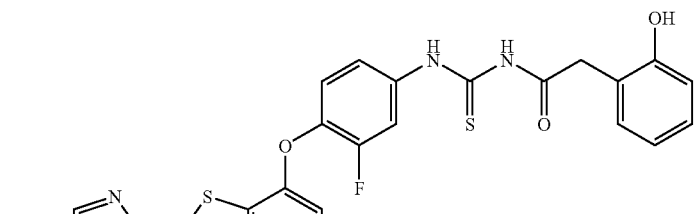<br>N-(4-(2-(1-ethyl-1H-imidazol-4-yl)thieno[3,2-b]pyridin-7-yloxy)-3-fluorophenylcarbamothioyl)-2-(2-hydroxyphenyl)acetamide | $^1$H NMR(400 MHz, DMSO-d$_6$) δ (ppm): 8.45(d, J=5.6 Hz, 1H), 8.06 (dd, J=2.4, 12.8 Hz, 1H), 7.96(d, J=1.2 Hz, 1H), 7.79(d, J=1.2 Hz, 1H), 7.68 (s, 1H), 7.56–7.48(m, 2H), 7.15(dd, J=1.6, 6.0 Hz, 1H), 7.09(td, J=1.2, 8.0 Hz, 1H), 6.80(d, J=8.0 Hz, 1H), 6.76(t, J=8.0 Hz, 1H) 6.58(d, J=5.6 Hz, 1H), 4.06 (q, J=7.2 Hz, 2H), 3.76(s, 2H), 1.40(t, J=7.2 Hz, 3H). LCMS: 518.1(M + H). |

TABLE 24-continued

Characterization of compounds 339–375 (examples 250–284) prepared according to the procedures similar to ones shown in the schemes 2, 17, 18, 20, 35, 49, 73 and 74.

| Cpd | Ex. | Structure | Characterization |
|---|---|---|---|
| 370 | 279 | 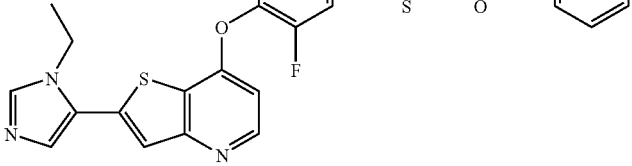<br>N-(4-(2-(1-ethyl-1H-imidazol-5-yl)thieno[3,2-b]pyridin-7-yloxy)-3-fluorophenylcarbamothioyl)-2-(2-methoxyphenyl)acetamide | $^1$H NMR(400 MHz, DMSO-d$_6$) δ (ppm): 12.56(s, 1H), 11.74 (s, 1H), 8.54(d, J=5.69 Hz, 1H), 8.06(dd, J=2.4, 13.2 Hz, 1H), 7.94(d, J=1.2 Hz, 1H), 7.74(s, 1H), 7.60–7.52 (m, 2H), 7.40(d, J=1.2 Hz, 1H), 7.31–7.25(m, 1H), 7.23 (dd, J=1.6, 7.6 Hz, 1H), 7.00(d, J=7.6 Hz, 1H), 6.92 (td, J=1.2, 7.6 Hz, 1H) 6.67(d, J=5.6 Hz, 1H), 4.29 (q, J=7.2 Hz, 2H), 3.81(s, H), 3.78(s, 3H), 1.34(t, J= 7.2 Hz, 3H). LCMS: 561.1 (M + H). |
| 371 | 280 | 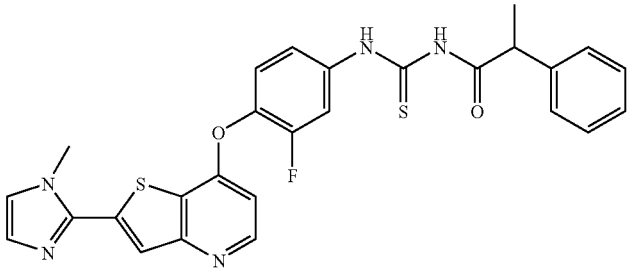<br>N-(3-fluoro-4-(2-(1-methyl-1H-imidazol-2-yl)thieno[3,2-b]pyridin-7-yloxy)phenyl carbamothioyl)-2-phenylpropanamide | $^1$H NMR(400 MHz, DMSO-d$_6$) δ (ppm): 12.5(s, 1H), 11.78(s, 1H), 8.53(d, d, 1H, J= 5.5 Hz), 8.01(d, 1H, J=12.7 Hz), 7.89(s, 1H), 7.52(m, 2H), 7.3–7.41(m, 5H), 7.27(m, 1H), 7.03(d, 1H, J=1.0 Hz), 6.67(d, 1H, J= 5.5 Hz), 4.09(q, 1H, J=7.1 Hz), 3.97(s, 3H), 1.42(d, 3H, J=7.0 Hz). LCMS:(M + H) 532.0 |
| 372 | 281 | 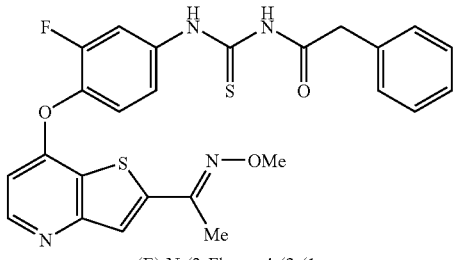<br>(E)-N-(3-Fluoro-4-(2-(1-(methoxyiinino)ethyl)thieno[3,2-b]pyridin-7-yloxy)phenylcarbainothioyl)-2-phenylacetainide | $^1$H NMR(400 MHz, DMSO-d$_6$) δ (ppm): 12.47(s, 1H), 11.82(s, 1H), 8.59(d, J=5.48 Hz, 1H), 8.02(m, 1H), 7.94(s, 1H), 7.51(m, 2H), 7.34(m, 5H), 6.67(m, 1H), 3.94(s, 3H), 2.30(s, 3H). LCMS: 509.0(M + H) |
| 373 | 282 | 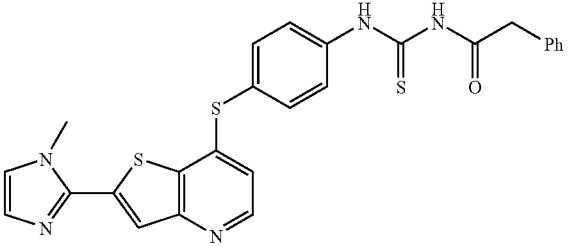<br>N-(4-(2-(1-Methyl-1H-imidazol-2-yl)thieno[3,2-b]pyridin-7-ylthio)phenylcarbamothioyl)-2-phenylacetamide | $^1$H NMR(400 MHz, DMSO-d$_6$) δ (ppm): 12.52(s,1H); 11.77(s, 1H); 8.50(d, J=5.1, 1H); 7.87(s, 1H); 7.82(d, J=8.6, 2H); 7.60 (d, J=8.6, 2H); 7.39(s, 1H); 7.33–7.24(m, 5H); 7.03(s, 1H); 6.87(d, J=5.1, 1H); (s, 3H); 3.80(s, 2H). LCMS:(M + H) 516.0 |

TABLE 24-continued

Characterization of compounds 339–375 (examples 250–284) prepared according to the procedures similar to ones shown in the schemes 2, 17, 18, 20, 35, 49, 73 and 74.

| Cpd | Ex. | Structure | Characterization |
|---|---|---|---|
| 374 | 283 | (S)-N-(4-(2-(3-(dimethylamino)pyrrolidine-1-carbonyl)thieno[3,2-b]pyridin-7-yloxy)-3-fluorophenylcarbamothioyl)-2-(4-fluorophenyl)acetamide | $^1$H NMR(400 MHz, CD$_3$OD) δ (ppm): 8.52 (d, J=5.5 Hz, 1H), 8.36(bs, 1H), 8.04(dd, J=2.2, 12.1 Hz, 1H), 7.88–7.98(bm, 1H), 7.42(m, 1H), 7.33–7.38(m, 3 H), 7.03–7.07 6.73(dd, J=0.8, 5.5 Hz H), 3.88–4.40(3 bs, 3H), 3.58–3.82(2bs, 4H), 2.68–2.84(2 bs, 6H), 2.36–2.56(bs, 1H), 2.08–2.36(2bs, 1H). |
| 375 | 284 | N-(4-(2-(1-(2-Amino-2-oxoethyl)-1H-imidazol-4-yl)thieno[3,2-b]pyridin-7-yloxy)-3-fluorophenylcarbamothioyl)-2-(2-methoxyphenyl)acetamide | LCMS: 591.1(M + H). |

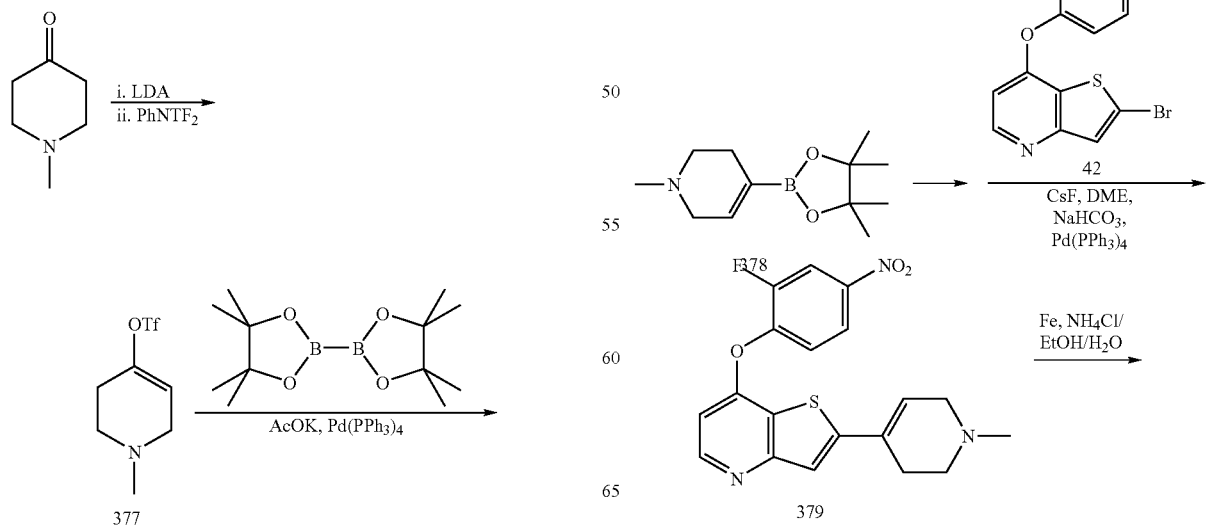

Scheme 80

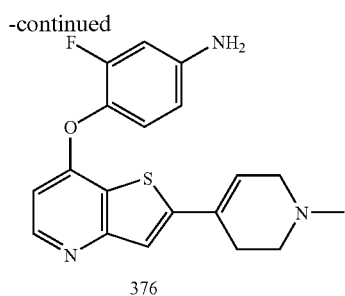

3-Fluoro-4-(2-(1-methyl-1,2,3,6-tetrahydropyridin-4-yl)thieno[3,2-b]pyridin-7-yloxy)aniline (376)

Step 1: 1-Methyl-1,2,3,6-tetrahydropyridin-4-yl trifluoromethanesulfonate (377)

LDA (1.5 N in THF, 8.1 mL, 12.17 mmol) was added to a solution of 1-methylpiperidin-4-one (1.4 mL, 12.17 mmol) in THF (16 mL) at −78° C., the mixture was allowed to warm to room temperature and stirred for 30 min. The solution was cooled again to −78° C. and PhNTf$_2$ (5 g, 18.12 mmol) was added in one portion; the reaction mixture was allowed to warm to room temperature and stirred for 3 h, poured into water, extracted with ether, the extract was dried over anhydrous Na$_2$SO$_4$ and concentrated under reduced pressure. The residue was purified by flash chromatography (EtOAc/Hexanes 1:5) affording 377 (2.38 g, 80% yield) as orange oil. LCMS:(M+H) 245.9.

Step 2: 7-(2-Fluoro-4-nitrophenoxy)-2-(1-methyl-1,2,3,6-tetrahydropyridin-4-yl)thieno[3,2-b]pyridine (379)

To a mixture of the triflate 377 (450 mg, 1.84 mmol), bis(pinacolato)diboron (477 mg, 2.02 mmol) and K$_2$CO$_3$ (541 mg, 5.52 mmol) in DME (3.7 mg), Pd(PPh$_3$)$_4$ (106 mg, 0.092 mmol) was added in one portion and the system was heated to reflux for 2 h under N$_2$. The reaction mixture was cooled and filtered. To the filtrate containing the intermediate 378 were added bromide 42 (435 mg, 1.84 mmol, scheme 8), CsF (838 mg, 5.52 mmol), NaHCO$_3$ (463 mg, 5.52 mmol) and water (0.8 mL), and the mixture was heated to reflux for additional 2 h. It was then diluted with water and extracted with DCM; the organic solution was extracted with 1N HCl, the aqueous phase was basified to pH~11 by addition of 2N aqueous NaOH, extracted with DCM; the extract was dried over anhydrous Na$_2$SO$_4$ and concentrated under reduced pressure affording 379 (279 mg, 39% yield) as a brown solid. LCMS:(M+H) 385.9.

Step 3: 3-Fluoro-4-(2-(1-methyl-1,2,3,6-tetrahydropyridin-4-yl)thieno[3,2-b]pyridin-7-yloxy)aniline (376)

To a mixture of nitro compound 379 (279 mg, 0.72 mmol) and NH$_4$Cl (33 mg, 0.612 mmol) in EtOH (7.2 mL)/water (3.6 mL) at 100° C. Fe powder (342 mg, 6.2 mmol) was added in one portion and the mixture was heated to reflux with vigorous stirring for 40 min. The mixture was filtered through Celite®, the Celite® washed with EtOH and the combined filtrates were concentrated under reduced pressure. The residue was dissolved in MeOH and purified by flash chromatography (DCM/MeOH 5:1) providing 376 (171.3 mg, 0.48 mmol, 67% yield) as a yellow solid. LCMS:(M+H) 356.0.

TABLE 25

Compounds 380–384 (examples 285–289) prepared from the amine 376 (scheme 80)

| Cpd | Ex. | Structure | Characterization |
|---|---|---|---|
| 380 | 285 | N-(3-fluoro-4-(2-(1-methyl-1,2,3,6 tetrahydropyridin-4-yl)thieno[3,2-b]pyridin-7 yloxy)phenylcarbamothioyl)-2-(4-fluorophenyl)acetamide | $^1$H NMR(400 MHz, DMSO-d$_6$) δ (ppm): 12.64(s, 1H), 11.84(s, 1H), 8.49(d, J=5.4Hz, 1H), 8.0(dd, J=11.2, 2Hz, 1H), 7.53(m, 3H), 7.38(m, 2H), 7.18(m, 2H), 6.64(d, J=5.4 Hz, 1H), 6.39(s, 1H), 3.83(s, 2H), 3.3(m, 2H), 2.83(m, 2H), 2.69(m, 2H), 2.46(s, 3H). LCMS:(M + H) 551.1 |
| 381 | 286 | N-(3-fluoro-4-(2-(1-methyl-1,2,3,6-tetrahydropyridin-4-yl)thieno[3,2-b]pyridin-7-yloxy)phenyl carbamothioyl)-2-o-tolylacetamide | $^1$H NMR(400 MHz, DMSO-d$_6$) δ (ppm): 12.5 (s, 1H), 11.84(s, 1H), 8.48(1H, J=5.5 Hz, 1H), 8.03(dd, J=1.8, 12.1 Hz, 1H), 7.56–7.51 (m, 3H), 7.37(m, 1H), 7.21–7.15(m, 3H), 6.63 (d, J=5.5 Hz, 1H), 6.38(t, J=3 Hz, 1H), 3.88 (s, 2H), 3.14(m, 2H), 2.66(m, 4H), 2.35(s, 3H), 2.9(s, 3H). LCMS:(M + H) 547.2 |

TABLE 25-continued

Compounds 380–384(examples 285–289) prepared from the amine 376(scheme 80)

| Cpd | Ex. | Sctructure | Characterization |
|---|---|---|---|
| 382 | 287 | 2-(2-ethynyl-4-fluorophenyl)-N-(3-fluoro-4-(2-(1-methyl-1,2,3,6-tetrahydropyridin-4-yl)thieno[3,2-b]pyridin-7-yloxy)phenylcarbamothioyl)acetamide | $^1$H NMR(400 MHz, DMSO-$d_6$) δ (ppm): 12.46(s, 1H), 11.91(s, 1H), 8.49(d, J=5.3 Hz, 1H), 8.15(s, 1H), 8.04(dd, J=12.1, 1.8 Hz, 1H), 7.56–7.49(m, 3H), 7.44(m, 1H), 7.36 (m, 1H), 7.27(m, 1H), 6.64(d, J=5.3 Hz, 1H), 6.39(s, 1H), 4.59(s, 1H), 4.04(s, 2H), 3.32(m, 2H), 2.85(m, 2H), 2.70(m, 2H), 2.47 (s, 3H). LCMS: 575.2 |
| 383 | 288 | N-(3-fluoro-4-(2-(1-methyl-1,2,3,6-tetrahydropyridin-4-yl)thieno[3,2-b]pyridin-7-yloxy)phenylcarbamothioyl)-2-phenylacetamide | $^1$H NMR(400MHz, DMSO-$d_6$) δ (ppm): 12.47 (s, 1H), 11.82(s, 1H), 8.45(d, 1H, J=5.5 Hz), 7.98(dd, 1H, J=1.3, 13.3 Hz), 7.50–7.48(m, 3H), 7.33–7.31(m, 4H), 7.28–7.26(m, 1H), 6.60(d, 1H, J=5.3Hz), 6.36(t, 1H, J=3.3 Hz), 3.80(s, 2H), 3.07(s, 2H), 2.60(s, 4H), 2.29(s, 3H). LCMS: 533.1(M + H). |
| 384 | 289 | 2-(2-Ethynylphenyl)-N-(3-fluoro-4-(2-(1-methyl-1,2,3,6-tetrahydropyridin-4-yl)thieno[3,2-b]pyridin-7-yloxy)phenylcarbamothioyl)acetamide | $^1$H NMR(400 MHz, DMSO-$d_6$) δ (ppm): 12.42(s, 1H), 11.83(s, 1H), 8.41(d, J=5.3 Hz, 1H), 7.97(dd, J=2.1, 12.1 Hz, 1H), 7.49–7.42(m, 4H), 7.34–7.32(m, 2H), 7.27–7.24 (m, 1H), 6.58(d, 1H,J=5.5 Hz), 6.32(t, 1H,J= 3.3 Hz),4.38(s, 1H), 3.98(s, 2H), 3.15(s, br, 2H), 2.69(s, br, 2H, 2.60(s, br, 2H), 3.39 (s, 3H). LCMS:(M + H) 557.1 |

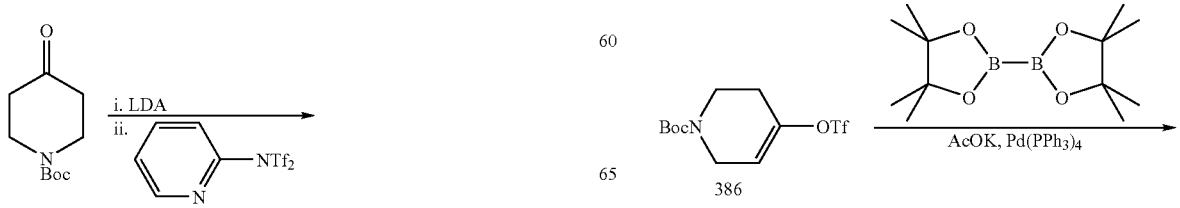

Scheme 81

-continued

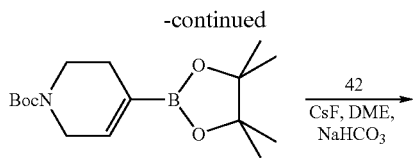

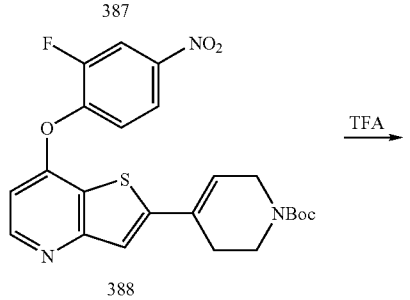

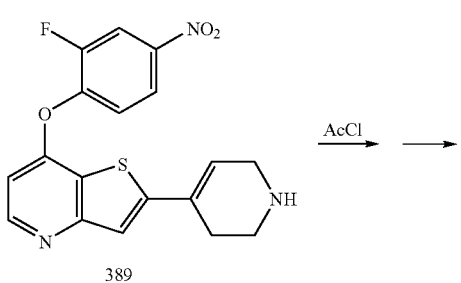

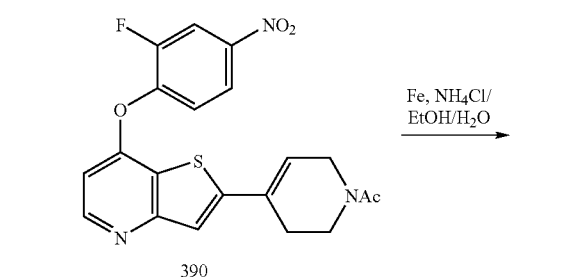

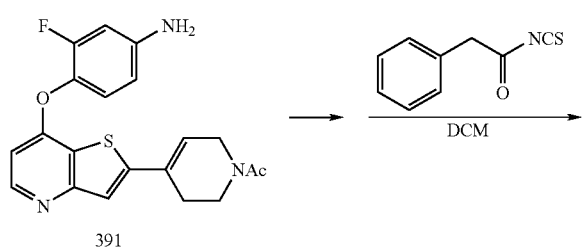

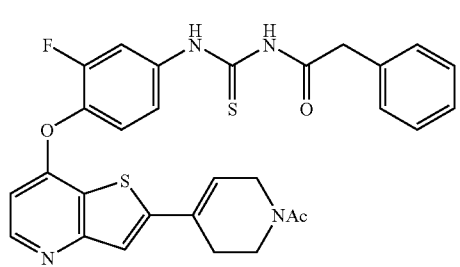

385: Example 290

Example 290

N-(4-(2-(1-Acetyl-1,2,3,6-tetrahydropyridin-4-yl)
thieno[3,2-b]pyridin-7-yloxy)-3-fluorophenylcar-
bamothioyl)-2-phenylacetamide (385)

Step 1: tert-Butyl 4-(trifluoromethylsulfonyloxy)-5,
6-dihydropyridine-1(2H)-carboxylate (386)

LDA (1.5 N in THF, 7.2 mL, 10.68 mmol) was added to a solution of tert-butyl 4-oxopiperidine-1-carboxylate (1.94 mL, 9.74 mmol) in THF (13 mL) at −78° C., the mixture was allowed to warm to room temperature and stirred for 30 min. The solution was cooled to −78° C. and 1,1,1-trifluoro-N-(pyridin-2-yl)-N-(trifluoromethylsulfonyl) methanesulfonamide (4 g, 11.2 mmol) was added in one portion. The reaction mixture was warmed to room temperature and stirred for an additional hour, diluted with EtOAc, washed with 1N HCl, water, brine and concentrated under reduced pressure to a minimum volume. The white precipitate thus formed was removed by filtration, the filtrate was concentrated and the residue was distilled under reduced pressure affording 386 (2.80 g, 86% yield) as brown liquid. LCMS:(M−Boc+H) 232.1 (26%).

Steps 2-3: tert-Butyl 4-(7-(2-fluoro-4-nitrophenoxy)
thieno[3,2-b]pyridin-2-yl)-5,6-dihydropyridine-1
(2H)-carboxylate (388)

Following the procedure described above for compound 379 (scheme 80) but replacing triflate 377 with triflate 386 the title compound 388 was obtained in 56% yield. LCMS: (M+H) 472.5 (via the intermediate boronate 387 which was not isolated from the reaction mixture).

Step 4: 7-(2-Fluoro-4-nitrophenoxy)-2-(1,2,3,6-tet-
rahydropyridin-4-yl)thieno[3,2-b]pyridine (389)

To a solution of the carboxylate 388 (1 g, 2.13 mmol) in DCM (4.3 mL) TFA (4.3 mL) was added and the reaction mixture was stirred 2 h at room temperature. The solvent was removed under reduced pressure, the residue was suspended in aqueous sodium bicarbonate, the mixture was extracted with DCM, EtOAc and DCM; the combined extracts were filtered and the recovered solids were collected and dried. The filtrate was dried over anhydrous $Na_2SO_4$, concentrated under reduced pressure and the residue was combined with the solid material obtained upon filtration, to afford 389 (806 mg, 100% yield) as a yellow solid. LCMS:(M+H) 372.1.

Step 5:1-(4-(7-(2-Fluoro-4-nitrophenoxy)benzo[b]
thiophen-2-yl)-5,6-dihydropyridin-1(2H)-yl)etha-
none (390)

To a suspension of the nitro amine 389 (400 mg, 1.08 mmol) and DIPEA (0.207 mL, 1.19 mmol) in DCM acetyl chloride (0.15 mL, 2.16 mmol) was added at room temperature and the mixture was stirred for 1 h. It was then concentrated under reduced pressure and the residue was purified by flash chromatography (eluent 5% MeOH to 10% MeOH in DCM) affording 390 (358.2 mg, 80% yield) as a white solid. LCMS: (M+H) 414.4.

Step 6: 1-(4-(7-(4-Amino-2-fluorophenoxy)thieno[3,2-b]pyridin-2-yl)-5,6-dihydropyridin-1(2H)-yl)ethanone (391)

To a mixture of the nitro compound 390 (358.2 mg, 0.87 mmol) and NH$_4$Cl (39.4 mg, 0.74 mmol) in EtOH (8.7 mL)/water (4.3 mL) at 100° C. Fe powder (411.3 mg, 7.36 mmol) was added in one portion and the mixture was heated to reflux under vigorous stirring for 40 min. It was then filtered through Celite®, the Celite® was washed with EtOH and the combined filtrates were concentrated under reduced pressure. The residue was dissolved in DCM, washed with water, dried (anhydrous Na$_2$SO$_4$) and concentrated under reduced pressure affording 391 (256.5 mg, 77% yield) as a white solid. LCMS:(M+H) 384.2.

Step 7: N-(4-(2-(1-Acetyl-1,2,3,6-tetrahydropyridin-4-yl)thieno[3,2-b]pyridin-7-yloxy)-3-fluorophenylcarbamothioyl)-2-phenylacetamide (385)

Starting from compound 391 and following the procedure described for compound 31b (Scheme 5, step 4, example 28); title compound 385 was obtained in 70% yield. $^1$H NMR (400 MHz, DMSO-d$_6$) δ (ppm): 12.45 (s, 1H), 11.83 (s, 1H), 8.49 (dd, J=5.5 Hz, J=0.8 Hz, 1H), 8.00 (d, J=11.9 Hz, 1H), 7.58-7.49 (m, 3H), 7.41-7.35 (m, 2H), 7.21-7.13 (m, 2H), 6.65 (dd, J=5.5, 1 Hz, 1H), 6.50 (m, 1H), 4.2 (m, 1H), 4.15 (m, 1H), 3.83 (s, 2H), 3.70-3.67 (m, 2H), 2.68 (m, 1H), 2.59 (m, 1H), 2.09 (s, 1.5H), 2.04 (s, 1.5H). LCMS: 579.2 (M+H).

TABLE 26

Compounds 392–405(examples 291–304) prepared according to the procedures similar to ones shown in the schemes 10, 11, 13–15, 19

| Cpd | Ex. | Structure | Characterization |
|---|---|---|---|
| 392 | 291 | 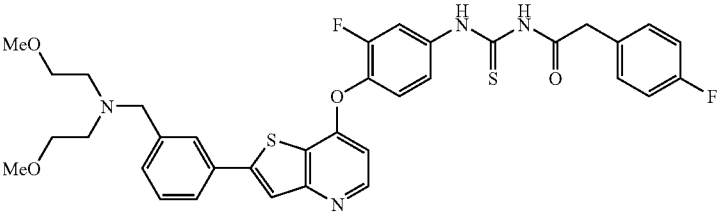<br>N-(4-(2-(3-((Bis(2-methoxyethyl)amino)methyl)phenyl)thieno[3,2-b]pyridin-7-yloxy)-3-fluorophenylcarbamothioyl)-2-(4-fluorophenyl)acetamide | $^1$H NMR(400 MHz, DMSO-d$_6$) δ (ppm): &12.46(s, 1H); 11.83(s, 1H); 8.52(d, J=&5.5 Hz, 1H); 8.02(s, 1H); 8.02–7.99 (m,&1H); 7.83(s, 1H); 7.77–7.74(m, 1H); &7.56–7.51(m, 2H); 7.44(t, J=7.6 Hz,&1H); 7.39–7.34(m, 3H), 7.19–7.14 (m,&2H); 6.66(d, J=5.5 Hz, 2H); 3.82(s, &2H); 3.72(s, 2H); 3.41(t, J=5.9 Hz,&4H); 3.20(s, 6H); 2.66(t, J=5.9 Hz,&4H). LCMS:(M + H) 677.3 |
| 393 | 292 | 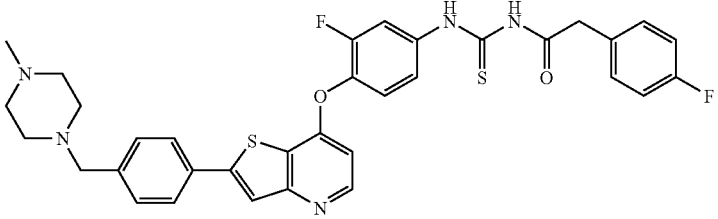<br>N-(3-Fluoro-4-(2-(4-((4-methylpiperazin-1-&yl)methyl)phenyl)thieno[3,2-b]pyridin-7-&yloxy)phenylcarbamothioyl)-2-(4-fluorophenyl)acetamide | $^1$H NMR(400 MHz, DMSO-d$_6$) δ (ppm): &12.46(s, 1H); 11.83(s, 1H); 8.52(d, J=&5.5 Hz, 1H); 8.03(s, 1H); 8.00(d. J=11.5&Hz, 1H); 7.84(d, J=8.2 Hz, 2H); 7.55–&7.51(m, 2H); 7.42–7.35(m, 4H); 7.20–&7.15(m, 2H); 6.65(d, J=5.3 Hz, 1H);&3.82(s, 2H); 3.50(s, 2H); 2.46–2.20 (m,&8H); 2.14(s, 3H). LCMS:(M + H) 644.2 |
| 394 | 283 | 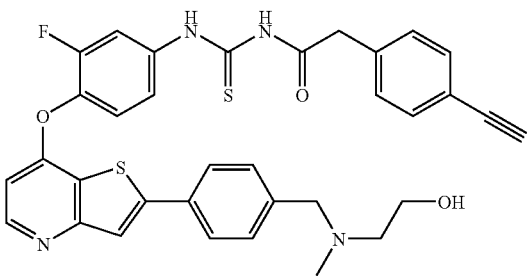<br>2-(4-ethynylphenyl)-N-(3-fluoro-4-(2-(4-(((2-hydroxyethyl)(methyl)amino)methyl)phenyl)thieno[3,2-b]pyridin-7-yloxy)phenylcarbamothioyl)acetamide | $^1$H NMR(400 MHz, DMSO-d$_6$) δ (ppm): &12.48(s, 1H), 11.86(s, 1H), 8.53(d, J=&5.3 Hz, 1H), 8.03(m, 3H), 7.86(m, 2H),&7.47(m, 9H), 6.65(d, J=5.28 Hz, 1H),&4.1(s, 1H), 3.86(s, 2H), 3.70(s, 2H), &3.56(s, 2H), 3.83(s, 2H), 3.33(s, 2H), &2.29(s, 3H). LCMS: 625.2(M + H). |

TABLE 26-continued

Compounds 392–405 (examples 291–304) prepared according to the procedures similar to ones shown in the schemes 10, 11, 13–15, 19

| Cpd | Ex. | Structure | Characterization |
|---|---|---|---|
| 395 | 294 | 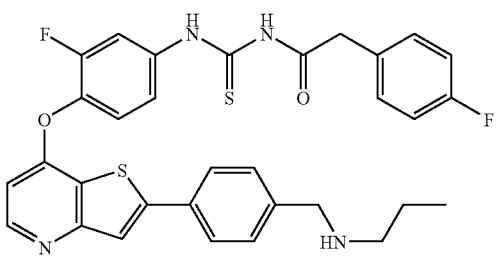<br>N-(3-fluoro-4-(2-(4-((propylamino)methyl)phenyl)thieno[3,2-b]pyridin-7-yloxy)phenylcarbamothioyl)-2-(4-fluorophenyl)acetamide | $^1$H NMR(400 MHz, DMSO-d$_6$) δ (ppm): 12.46(s, 1H), 11.83(s, 1H), 8.86(s, 2H), &8.54(d, J=5.28 Hz, 1H), 8.13(s, 1H), 8.03(m, 3H), 7.98(d, J=8.0 Hz, 2H), &7.62(d, J=8.0 Hz, 2H), 7.53(m, 9H), &7.35(m, 2H), 7.16(t, J=9 Hz, 1H), 6.68&(d, J=5.3 Hz, 1H), 4.2(s, 2H), 3.81(s, &2H), 3.70(s, 2H), 3.56(s, 2H), 3.83(s, &2H), 2.89(m, 2H), 1.61(m, 2H), 0.9(t, J=&7.24 Hz, 3H). LCMS: 603.2(M + H). |
| 396 | 295 | 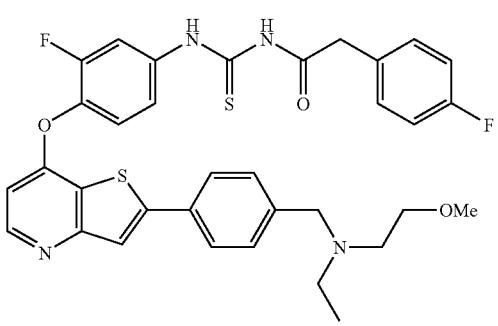<br>N-(4-(2-(4-((ethyl(2-methoxyethyl)amino)methyl)phenyl)thieno[3,2-b]pyridin-7-yloxy)-3-fluorophenylcarbamothioyl)-2-(4-fluorophenyl)acetamide | $^1$H NMR(400 MHz, DMSO-d$_6$) δ (ppm): &12.46(s, 1H), 11.83(s, 1H), 8.54(d, J=&5.1 Hz, 1H), 8.15(s, 1H), 7.99(m, 3H),&7.68(m, 1H), 7.55(d, J=8.8 Hz, 2H), &7.35(m, 2H), 7.11(m, 2H) 6.67(d, J=&5.1 Hz, 1H), 4.38(m, 1H), 3.82(s, 3H),&1.25(m, 3H). LCMS: 647.3(M + H). |
| 397 | 296 | 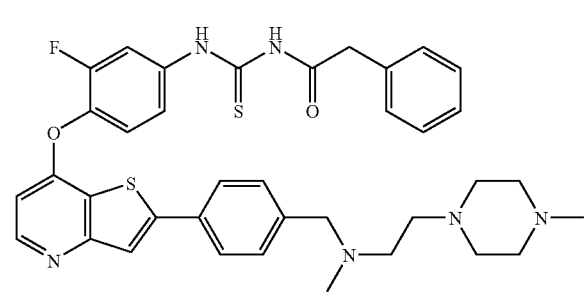<br>N-(3-fluoro-4-(2-(4-((methyl(2-(4-methylpiperazin-1-yl)ethyl)amino)methyl)phenyl)thieno[3,2-b]pyridin-7-yloxy)phenylcarbamothioyl)-2-phenylacetamide | $^1$H NMR(400 MHz, DMSO-d$_6$) δ (ppm): &12.50(s, 1H), 11.85(s, 1H), 8.50(d, J=&5.3 Hz, 1H), 8.20(m, 1H), 8.18(s, 1H),&8.04(s, 1H), 7.83(d, J=8.4 Hz, 1H), &7.53(m, 1H), 7.29(m, 6H), 6.62(d, J=&5.3 Hz, 1H), 3.81(s, 2H), 3.52(s, 1H), &2.31(m, 15H), 2.16(s, 3H), 2.15(s, 3H).&LCMS: 683.1(M + H). |
| 398 | 297 | 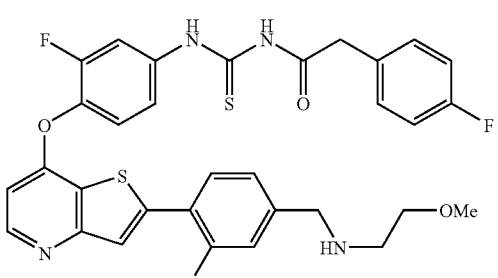<br>N-(3-fluoro-4-(2-(2-fluoro-4-((2-methoxyethylamino)methyl)phenyl)thieno[3,2-b]pyridin-7-yloxy)phenylcarbamothioyl)-2-(4-fluorophenyl)acetamide | $^1$H NMR(400 MHz, DMSO-d$_6$) δ (ppm): &12.47(s, 1H), 11.84(s, 1H), 8.53(d, J=&5.5 Hz, 1H), 8.19(s, 1H), 8.13(s, 1H), &8.01(d, J=12.1 Hz, 1H), 7.84(d, J=&11.7Hz, 1H), 7.73(d, J=8.0 Hz, 1H), &7.62(t, J=7.8 Hz, 2H), 7.52(m, 2H), &7.37(m, 2H), 7.17(t, J=8.8 Hz, 2H), &6.67(d, J=5.5 Hz, 1H), 3.93(s, 2H), &3.62(t, J=5.9 Hz, 2H), 2.76(m, 2H), &2.43(s, 3H). LCMS: 637.2(M + H). |

TABLE 26-continued

Compounds 392–405(examples 291–304) prepared according to the procedures similar to ones shown in the schemes 10, 11, 13–15, 19

| Cpd | Ex. | Structure | Characterization |
|---|---|---|---|
| 399 | 298 | N-(3-fluoro-4-(2-(4-((2-methoxyethylamino)methyl)phenyl)thieno[3,2-b]pyridin-7-yloxy)phenylcarbamothioyl)-2-(4-fluorophenyl)acetamide | $^1$H NMR(400 MHz, DMSO-d$_6$) δ (ppm): 12.42(s, 1H), 11.84(s, 1H), 8.51(d, J=5.5 Hz, 1H), 8.16(s, 1H), 8.03(s, 1H), 8.00(dd, J=1.9, 13.3 Hz, 1H), 7.84(dd, J=1.8, 6.5 Hz, 2H), 7.53–7.52(m 2H), 7.46(d, J=8.2 Hz, 2H), 7.38–7.34(m, 2H), 7.19–7.16(m, 2H), 6.64(dd, J=1.0, 6.5 Hz, 1H), 3.82(s, 2H), 3.8 0(s, 2H), 3.41(t, J=5.7 Hz, 2H), 3.23(s, 3H), 2.70(t, 2H, J=5.7 Hz). LCMS:(M + H) 619.1 |
| 400 | 299 | N-(3-fluoro-4-(2-(4-((2-methoxyethylamino)methyl) phenyl) thieno [3,2-bipyridin-7-yloxy)phenylcarbamoyl)-2-(4-fluorophenyl) acetamide | $^1$H NMR(400 MHz, DMSO-d$_6$) δ (ppm): 11.05(s, 1H), 10.61(s, 1H), 8.93(m, 2H), 8.52(d, J=5.5 Hz, 1H), 8.12(s, 1H), 7.97(d, J=8.4 Hz, 2H), 7.82(dd, J=2.4, 12.9 Hz, 2H), 7.62(d, J=8.2 Hz, 1H), 7.49–7.41(m, 2H), 7.36–7.33(m, 2H), 7.18–7.16(m, 2H), 6.64(dd, J=0.8, 5.3 Hz, 1H). LCMS:(M + H)603.2. |
| 401 | 300 | N-(3-fluoro-4-(2-(4-(methylsulfonyl)phenyl)thieno[3,2-b]pyridin-7-yloxy)phenylcarbamothioyl)-2-(4-fluorophenyl)acetamide | $^1$H NMR(400 MHz, DMSO-d$_6$) δ (ppm): 12.48(s, 1H), 11.85(s, 1H), 8.59(d, J=5.2 Hz, 1H), 8.31(s, 1H), 8.19(d, J=8.4 Hz, 2H), 8.04(d, J=8.4 Hz, 2H), 8.07–8.00(m, 1H), 7.61–7.53(m, 2H), 7.38(dd, J=8.8, 5.6 Hz, 2H), 7.19(tt, J=8.8, 2.0 Hz, 2H), 6.73(d, J=5.2 Hz, 1H), 3.84(s, 2H), 3.29(s, 3H). LCMS:(M + H) 610.1. |
| 402 | 301 | 4-(7-(2-fluoro-4-(3-(2-(4-fluorophenyl)acetyl)thioureido)phenoxy)thieno[3,2-b]pyridin-2-yl)-N,N-dimethylbenzamide | $^1$H NMR(400 MHz, DMSO-d$_6$) δ (ppm): 12.47(s, 1H), 11.83(s, 1H), 8.56(d, J=5.6 Hz, 1H), 8.16(s, 1H), 8.03(d, J=12.4 Hz, 1H), 7.96(d, J=8.0 Hz, 2H), 7.61–7.49(m, 4H), 7.38(dd, J=8.4, 5.6 Hz, 2H), 7.19(t, J=9.2 Hz, 2H), 6.69 (d, J=5.6 Hz, 1H), 3.84(s, 2H), 3.01(s, 3H), 2.96(s, 3H). LCMS:(M + H) 603.2 |

TABLE 26-continued

Compounds 392–405 (examples 291–304) prepared according to the procedures similar to ones shown in the schemes 10, 11, 13–15, 19

| Cpd | Ex. | Structure | Characterization |
|---|---|---|---|
| 403 | 302 | N-(3-fluoro-4-(2-(4-((4-methylpiperazin-1-yl)methyl)phenyl)thieno[3,2-b]pyridin-7-yloxy)phenylcarbamothioyl)-2-phenylacetamide | $^1$H NMR(400 MHz, CD$_3$CN) δ (ppm): &8.51(d, J=5.5Hz, 1H), 7.99(dd, J=& 2.5, 12.3 Hz, 1H), 7.84(s, 1H), 7.82(d,&J=8.2 Hz, 2H), 7.32–7.53(m, 9H),&6.62(d, J=4.5 Hz, 1H), 3.81(s, 2H),&3.54(s, 2 H), 2.30–2.53(bs, 8H), 2.22&(s, 3 H). |
| 404 | 303 | 2-(4-ethynylphenyl)-N-(3-fluoro-4-(2-(4-((4-methylpiperazin-1-yl)methyl)phenyl)thieno[3,2-b]pyridin-7-yloxy)phenylcarbamothioyl)acetamide | $^1$H NMR(400 MHz, DMSO-d$_6$) δ (ppm): &12.43(s, 1H), 11.84(s, 1H), 8.51(d, J=&5.5 Hz, 1H), 7.98–8.03(m, 2H), 7.83&(dd, J=1.8, 6.5 Hz, 2H), 7.54(m, 2H),&7.44–7.47(m, 2H), 7.41(d, J=8.4 Hz,&2H), 7.34(dd, J=2.0, 6.5 Hz, 2H), 6.64&(m, 1H), 4.17(s, 1H), 3.85(s, 2H), 3.49&(s, 2H), 2.37(bs, 6H), 2.17(s, 3H). (A&signal corresponding to 2H is hidden by&the residual DMSO signal). |
| 405 | 304 | 2-(2-ethynyl-4-fluorophenyl)-N-(3-fluoro-4-(2-(4-((4-methylpiperazin-1-yl)methyl)phenyl)thieno[3,2-b]pyridin-7-yloxy)phenylcarbamothioyl)acetamide | $^1$H NMR(400 MHz, DMSO-d$_6$) δ (ppm): &12.45(s, 1H), 11.90(s, 1H), 8.52(d, J=&5.5 Hz, 1H), 8.04(m, 2H), 7.85(d, J=&8.2 Hz, 2H), 7.54(m, 2H), 7.43(m, 3H),&7.36(dd, J=2.8, 9.3 Hz, 1H), 7.26 (m,&1H), 6.65(dd, J=0.8, 5.3 Hz, 1H), 4.58&(s, 1H), 4.03(s, 2H), 3.53(s, 2H), 2.31&(bs, 3H), (A part of the NMR spectrum is&hidden by the residual DMSO signal). |

Example 304

N-(4-(2-Ethynylthieno[3,2-b]pyridin-7-yloxy)-3-fluorophenylcarbamothioyl)-2-phenylacetamide (406)

Step 1: 7-(2-Fluoro-4-nitrophenoxy)-2-iodothieno[3,2-b]pyridine (408)

A mixture of the chloride 407 (Ragan J. A. et al, Organic Process Research and Development 2003, 7, 676-683) (7.0 g, 23.7 mmol), the phenol (11.15 g, 3 eq, 71.1 mmol), $K_2CO_3$ (13.08 g, 4 eq, 94.8 mmol) in $Ph_2O$ (30 ml) was heated to 200° C. for 3 hrs. The reaction mixture was cooled to RT, diluted with DCM, filtered and then concentrated. The resultant solid was triturated with diethyl ether, collected by filtration to afford 408 (7.3 g, 74% yield) which was used directly in the next step with no additional purification. LCMS: 417.0 (M+H).

Step 2: 7-(2-Fluoro-4-nitrophenoxy)-2-((trimethylsilyl)ethynyl)thieno[3,2-b]pyridine (409)

To a solution of the iodide 408 (4.5 g, 10.8 mmol) in dry THF (120 ml) at was added CuI (205 mg, 0.1 eq, 1.08 mmol), TEA (2.73 g, 2.5 eq, 27 mmol), ethynyltrimethylsilane (2.12 g, 2 eq, 21.6 mmol) and $Pd(PPh_3)_2Cl_2$ (212 mg, 0.028 eq, 0.30 mmol) and the reaction mixture was heated to reflux for 2 hours. It was then cooled to RT and partitioned between EtOAc and water. The organic phase was collected, dried over anhydrous sodium sulfate, filtered and adsorbed onto silica gel. Purification by column chromatography (30% EtOAc/hexane) afforded 409 (2.2 g, 53% yield). LCMS: 387.1 (M+H).

Step 3: 2-Ethynyl-7-(2-fluoro-4-nitrophenoxy)thieno[3,2-b]pyridine (410)

To a solution of the alkyne 409 (2.2 g, 5.69 mmol) in THF (30 ml) was added a solution of TBAF (8.53 mL, 1.5 eq, 1M soln in THF) in HOAc (30 ml), and the reaction mixture was stirred at RT overnight. It was then concentrated to dryness and partitioned between water and EtOAc. The organic phase was washed well with satd. $NaHCO_3$ soln, collected, dried over anhydrous $Na_2SO_4$, filtered and concentrated. The crude mixture was adsorbed onto silica gel then purified by column chromatography (30% EtOAc in hexane) to afford 410 (1.4 g, 72% yield). LCMS: 415.2 (M+H).

Steps 4-5: N-(4-(2-Ethynylthieno[3,2-b]pyridin-7-yloxy)-3-fluorophenylcarbamothioyl)-2-phenylacetamide (406)

To a solution of the alkyne 410 (200 mg, 0.64 mmol) in MeOH (10 ml) was added $SnCl_2 \times 2H_2O$ (574 mg, 4 eq, 2.54 mmol) and the reaction mixture was heated to reflux for 3 hours. It was then cooled to RT, concentrated and crude amine 411 was used directly in the next step with no additional purification (182 mg, 100%). To a solution of 411 (182 mg, 0.64 mmol) in EtOH (2 ml) and toluene (6 ml) was added 2-phenylacetyl isothiocyanate (227 mg, 2 eq, 1.28 mmol) and the reaction mixture was stirred at RT for 2 hrs, concentrated under reduced pressure and the residue was purified by column chromatography (1:3 EtOAc:hexane) to afford 406 as a white solid (25 mg, 9% yield). $^1$H NMR (400 MHz, DMSO-$d_6$) δ (ppm): 12.49 (s, 1H), 11.82 (s, 1H), 8.58 (d, J=5.48 Hz,

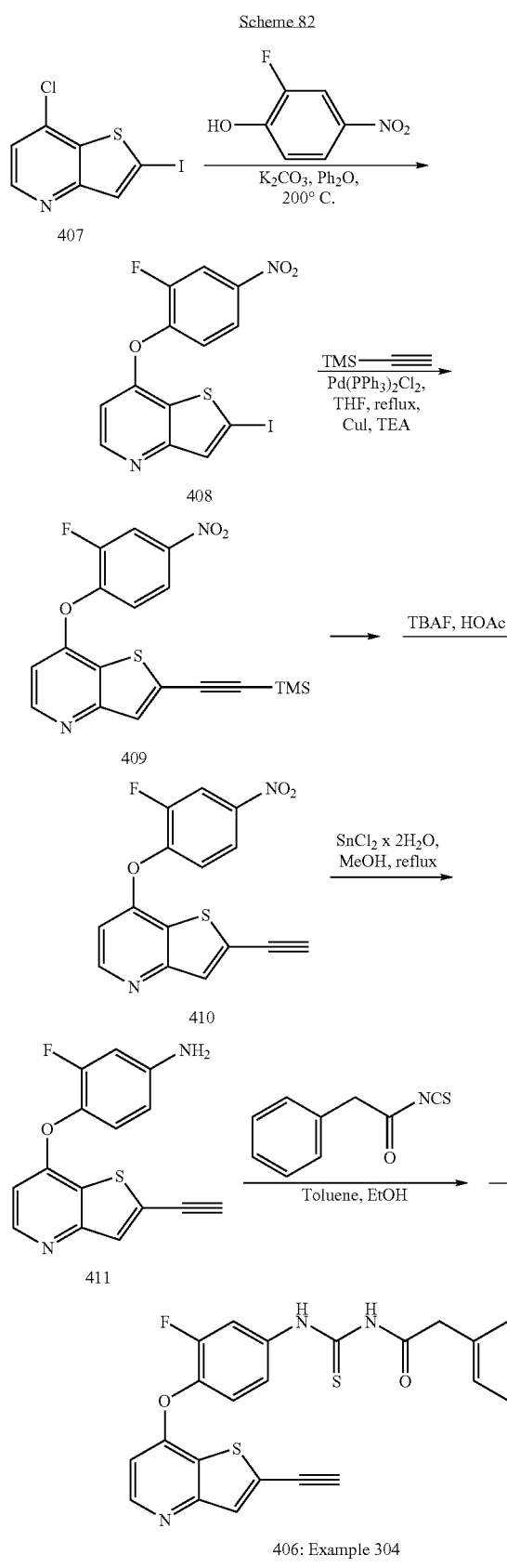

Scheme 82

1H), 8.01 (m, 1H), 7.88 (s, 1H), 7.50 (m, 2H), 7.25 (m, 5H), 6.73 (d, J=5.48 Hz, 1H), 5.01 (s, 1H), 3.81 (s, 2H). LCMS: 462.2 (M+H).

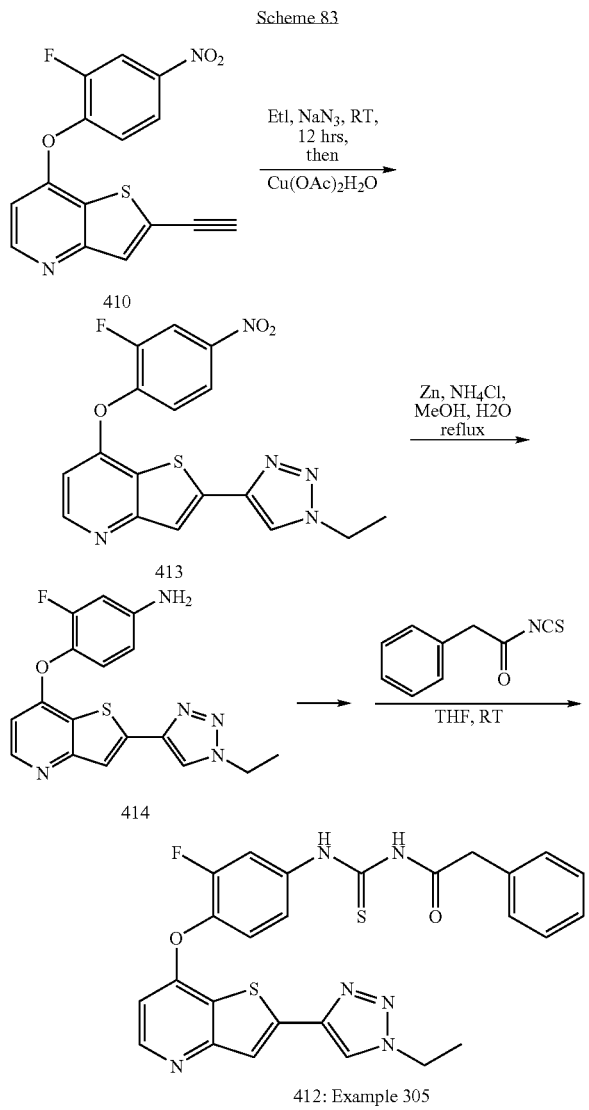

Example 305

N-(4-(2-(1-Ethyl-1H-1,2,3-triazol-4-yl)thieno[3,2-b]pyridin-7-yloxy)-3-fluorophenylcarbamothioyl)-2-phenylacetamide (412)

Step 1: 2-(1-Ethyl-1H-1,2,3-triazol-4-yl)-7-(2-fluoro-4-nitrophenoxy)thieno[3,2-b]pyridine (413)

To a solution of NaN$_3$ (107.3 mg, 1.65 mmol) in DMSO (5 ml) was added ethyl iodide (257 mg, 1.65 mmol) and the reaction mixture was stirred for 12 hrs at RT. The alkyne 410 (520 mg, 1.65 mmol) and Cu(OAc)$_2$×H$_2$O (66 mg, 0.2 eq, 0.331 mmol) were added and the deep red reaction mixture was allowed to stir at RT overnight. After 72 hrs, an orange precipitate had formed. The mixture was diluted with water and the solid was collected by filtration. The orange solid 413 was used directly in the next step with no additional purification (620 mg, 97% yield). LCMS: 386.2 (M+H).

Steps 2-3: N-(4-(2-(1-Ethyl-1H-1,2,3-triazol-4-yl)thieno[3,2-b]pyridin-7-yloxy-3-fluorophenylcarbamothioyl)-2-phenylacetamide (412)

To a suspension of the nitro compound 413 (300 mg, 0.78 mmol) in MeOH (20 ml), THF (20 ml) and water (4 ml) was added zinc (456 mg, 9 eq, 7.01 mmol.) followed by NH$_4$Cl (83 mg, 2 eq, 1.56 mmol) and the reaction mixture was heated to reflux for 4 hrs. The reaction mixture was concentrated to dryness and the resultant solid was triturated with diethyl ether to afford the amine 414 as a white solid (mixture with ZnCl$_2$) which was used crude in the next step (198 mg, 71% yield). To a suspension of the amine 414 (198 mg, 0.57 mmol) in EtOH (~2 ml) and toluene (~6 ml) was added the 2-phenylacetyl isothiocyanate (197 mg, 2 eq, 1.11 mmol) and the reaction mixture was stirred at RT for 3 hrs. The mixture was concentrated to dryness and the residue was purified by column chromatography (EtOAc) to afford 412 as a pale yellow solid (115 mg, 38% yield). $^1$H NMR (400 MHz, DMSO-d$_6$) δ (ppm): 12.51 (s, 1H), 11.84 (s, 1H), 8.84 (s, 1H), 8.51 (d, J=5.48 Hz, 1H), 8.03 (m, 1H), 7.91 (s, 1H), 7.53 (m, 2H), 7.28 (m, 7H), 6.65 (d, J=5.48 Hz, 1H), 4.46 (q, J=7.24 Hz, 2H), 4.03 (q, J=7.24 Hz, 2H), 3.82 (s, 2H), 1.49 (t, J=7.43 Hz, 3H). LCMS: 574.2 (M+H).

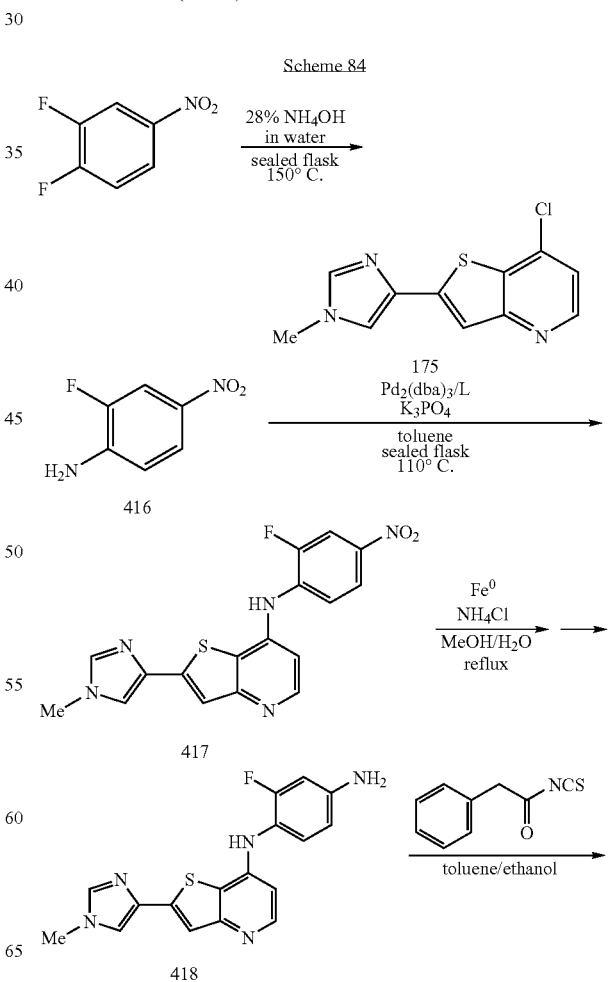

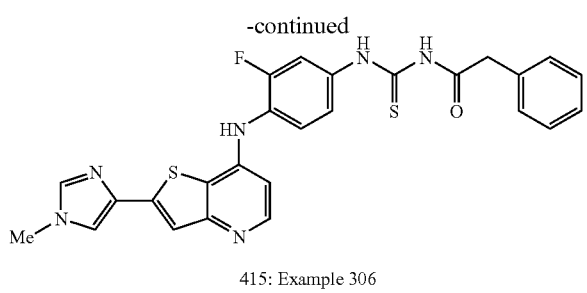

415: Example 306

Example 306

N-(3-Fluoro-4-(2-(1-methyl-1H-imidazol-4-yl)thieno[3,2-b]pyridin-7-ylamino)phenyl carbamothioyl)-2-phenylacetamide (415)

Step 1. 2-Fluoro-4-nitroaniline (416)

A stirred solution of 3,4-difluoronitrobenzene (2.00 g, 12.57 mmol) in ammonium hydroxide (20 ml, 28% in water) was heated at 150° C. in a sealed flask for 3.5 hrs. It was then cooled to room temperature, and the resulting suspension was diluted with water, shaken for 15 min. The resultant precipitate was collected by filtration, rinsed with water, air-dried, and dried under high vacuum to afford title compound 416 (1.76 g, 90% yield) as a yellow crystalline solid. LCMS: 157.0 $(M+H)^+$ and 179.0 $(M+Na)^+$.

Step 2. N-(2-Fluoro-4-nitrophenyl)-2-(1-methyl-1H-imidazol-4-yl)thieno[3,2-b]pyridin-7-amine (417)

A suspension of 175 (500 mg, 2.00 mmol, scheme 35), 416 (406 mg, 2.60 mmol), $Pd_2(dba)_3$ (73 mg, 0.08 mmol), (2-biphenyl)dicyclohexylphosphine (56 mg, 0.16 mmol), and $K_3PO_4$ (638 mg, 3.00 mmol) in toluene (20 ml) was degassed for 15 min with nitrogen, and then heated at 110° C. for 22 hrs in a sealed flask [ J. P. Wolfe, H. Tomori J. P. Sadighi J. Yin, S. L. Buchwald *J. Org. Chem.* 2000, 65, 1158-1174]. After cooling to room temperature the reaction mixture was filtered, the filtrate was concentrated and the residue was adsorbed on silica gel and subjected to flash column chromatography (eluents $MeOH/CH_2Cl_2$: 2/98 to 10/90). Fractions containing the product were combined, concentrated and treated with AcOEt/hexanes to afford title compound 417 (370 mg, 50% yield) as a yellow-orange solid. $^1$H NMR (400 MHz, DMSO-$d_6$) δ (ppm): 9.57 (bs, 1H), 8.45 (d, J=5.1 Hz, 1H), 8.22 (dd, J=11.3, 2.5 Hz, 1H), 8.06 (dd, J=8.9, 2.3 Hz, 1H), 7.83 (d, J=1.2 Hz, 1H), 7.70 (d, J=1.2 Hz, 1H), 7.63 (s, 1H), 7.24 (t, J=8.7 Hz, 1H), 6.94 (bd, J=4.7 Hz, 1H), 3.71 (s, 3H). LCMS: 370.0 $(M+H)^+$.

Step 3. 2-Fluoro-N1-(2-(1-methyl-1H-imidazol-4-yl)thieno[3,2-b]pyridin-7-yl)benzene-1,4-diamine (418)

To a stirred suspension of nitro compound 417 (370 mg, 1.00 mmol) in a mixture of MeOH (20 mL) and water (10 mL) were added iron powder (280 mg, 5.01 mmol) and $NH_4Cl$ (107 mg, 2.00 mmol). The reaction mixture was heated to reflux for 2 hrs, cooled to room temperature and filtered through celite. The filtrate was concentrated, diluted with minimal amount of methanol and treated with AcOEt/hexanes, to afford title compound 418 (463 mg, quantitative yield, ammonium salt) as a yellow solid. LCMS: 340.0 $(M+H)^+$.

Step 4. N-(3-Fluoro-4-(2-(1-methyl-1H-imidazol-4-yl)thieno[3,2-b]pyridin-7-ylamino)phenyl carbamothioyl)-2-phenylacetamide (415)

To a stirred solution of 418 (200 mg, 0.59 mmol) in a mixture of anhydrous toluene/ethanol (15mL/15mL) was slowly added a solution of 2-phenylacetyl isothiocyanate (522 mg, 2.95 mmol) in a mixture of anhydrous toluene/ethanol (5mL/5mL). The reaction mixture was stirred at room temperature for 4 hrs under nitrogen, concentrated, and adsorbed on silica gel. The crude material was purified by flash column chromatography (eluents 2% of $NH_4OH$ in methanol/$CH_2Cl_2$ from 5/95 to 10/90) followed by trituration with AcOEt (with traces of acetone)/hexanes, to afford title compound 415 (183 mg, 60% yield) as a pink solid. $^1$H NMR (400 MHz, DMSO-$d_6$) δ (ppm): 12.51 (s, 1H), 11.81 (s, 1H), 8.82 (bs, 1H), 8.22 (d, J=5.5 Hz, 1H), 7.91 (dd, J=12.4, 2.3 Hz, 1H), 7.79 (d, J=1.1 Hz, 1H), 7.69 (d, J=0.8 Hz, 1H), 7.53 (s, 1H), 7.44 (dd, J=8.6, 2.2 Hz, 1H), 7.40-7.24 (m, 6H), 6.42 (dd, J=5.55, 2.22 Hz, 1H), 3.83 (s, 2H), 3.71 (s, 3H). LCMS: 517.0 $(M+H)^+$.

Example 307

N-(3-Fluoro-4-(thieno[3,2-b]pyridin-7-ylamino)phenylcarbamothioyl)-2-phenylacetamide (419)

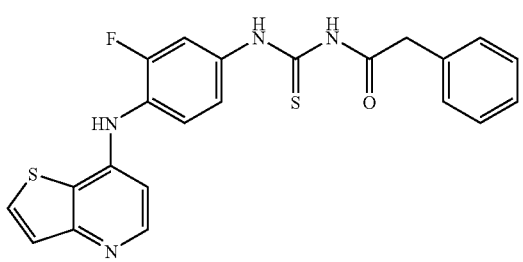

419: Example 307

The title compound 419 (example 307) was obtained in three steps from 2 and 416 as a beige solid following the same procedure as for the example 306, steps 2-4 (scheme 84). $^1$H NMR (400 MHz, DMSO-$d_6$) δ (ppm): 12.49 (s, 1H), 11.81 (s, 1H), 8.81 (s, 1H), 8.28 (d, J=5.5 Hz, 1H), 7.98 (d, J=5.5 Hz, 1H), 7.89 (dd, J=12.3, 2.2 Hz, 1H), 7.50-7.20 (m, 8H), 6.45 (dd, J=5.4, 2.3 Hz, 1H), 3.83 (s, 2H). LCMS: 437.0 $(M+H)^+$.

Scheme 85

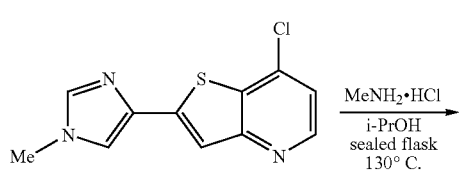

175

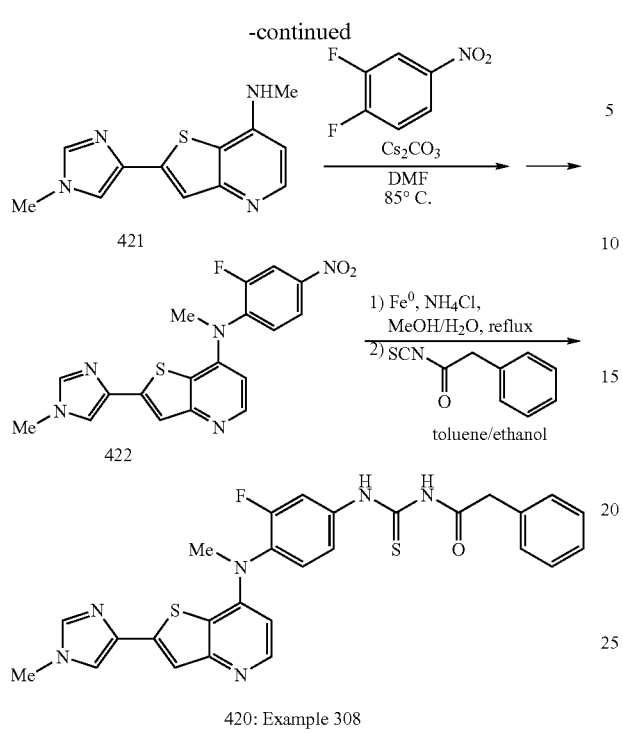

420: Example 308

Example 308

N-(3-Fluoro-4-(methyl(2-(1-methyl-1H-imidazol-4-yl)thieno[3,2-b]pyridin-7-yl)amino)phenylcarbamothioyl)-2-phenylacetamide (324)

Step 1. N-Methyl-2-(1-methyl-1H-imidazol-4-yl)thieno[3,2-b]pyridin-7-amine (421)

A stirred suspension of 175 (500 mg, 2 mmol) and methylamine hydrochloride (15 g, 222 mmol) in iso-propanol (50 ml) was heated at 130° C. in a sealed flask for four days. It was then cooled to room temperature, poured in water, and the pH was adjusted to 10 with 1N NaOH. After extraction of the aqueous phase with AcOEt, the combined organic phase was concentrated and purified by flash column chromatography (eluents 2% of $NH_4OH$ in methanol/$CH_2Cl_2$: 10/90 to 40/60) to afford title compound 421 (487 mg, 99% yield, hydrate form) as a beige solid. LCMS: 245.0 $(M+H)^+$.

Step 2. N-(2-Fluoro-4-nitrophenyl)-N-methyl-2-(1-methyl-1H-imidazol-4-yl)thieno[3,2-b]pyridin-7-amine (422)

A stirred suspension of 421 (500 mg, 2 mmol), 3,4-difluoronitrobenzene (795 mg, 5 mmol) and cesium carbonate (1.63 g, 5 mmol) in anhydrous DMF (50 ml) was heated at 85° C. under nitrogen for 7 hrs. It was then cooled down to room temperature poured in water, and extracted with dichloromethane. The combined organic extracts was concentrated and purified twice by flash column chromatography (eluents 2% of $NH_4OH$ in methanol/$CH_2Cl_2$: 5/95 to 10/90) to afford title compound 422 (144 mg, 19% yield) as a sticky yellow solid. LCMS: 384.0 $(M+H)^+$.

Step 3. N-(3-Fluoro-4-(methyl(2-(1-methyl-1H-imidazol-4-yl)thieno[3,2-b]pyridin-7-yl)amino)phenylcarbamothioyl)-2-phenylacetamide (420)

The title compound 420 was obtained in two steps from 422 as a pale brown solid following the same procedure as in example 306, steps 3 and 4 (scheme 84). $^1$H NMR (400 MHz, DMSO-$d_6$) δ (ppm): 12.68 (s, 1H), 11.86 (s, 1H), 8.37 (d, J=5.7 Hz, 1H), 8.05 (dd, J=12.6, 2.3 Hz, 1H), 7.64 (d, J=1.2 Hz, 1H), 7.58 (d, J=0.8 Hz, 1H), 7.53 (dd, J=8.7, 2.1 Hz, 1H), 7.47-7.40 (m, 2H), 7.38-7.26 (m, 5H), 6.82 (d, J=5.7 Hz, 1H), 3.83 (s, 2H), 3.64 (s, 3H), 3.38 (s, 3H). LCMS: 531.0 $(M+H)^+$.

Example 309

N-(3-Fluoro-4-(methyl(2-(1-methyl-1H-imidazol-2-yl)thieno[3,2-b]pyridin-7-yl)amino)phenylcarbamothioyl)-2-phenylacetamide (423)

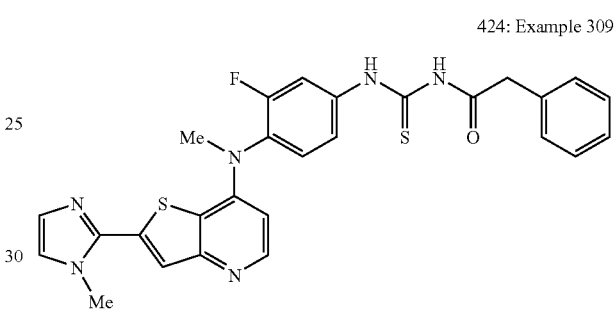

424: Example 309

The title compound 423 was obtained in four steps from 214 (scheme 46) as a beige solid following the same procedure as in example 308, steps 1-3 (scheme 85). $^1$H NMR (400 MHz, DMSO-$d_6$) δ (ppm): 12.69 (s, 1H), 11.84 (s, 1H), 8.45 (d, J=5.5 Hz, 1H), 8.07 (dd, J=12.6, 2.2 Hz, 1H), 7.65 (s, 1H), 7.56 (dd, J=8.7, 2.2 Hz, 1H), 7.46 (t, J=8.8 Hz, 1H), 7.38-7.25 (m, 6H), 6.92-6.87 (m, 2H), 3.87 (s, 3H), 3.83 (s, 2H), 3.39 (s, 3H). LCMS: 531.0 $(M+H)^+$.

Example 310

N-(3-Fluoro-4-(methyl(thieno[3,2-b]pyridin-7-yl)amino)phenylcarbamothioyl)-2-phenylacetamide (424)

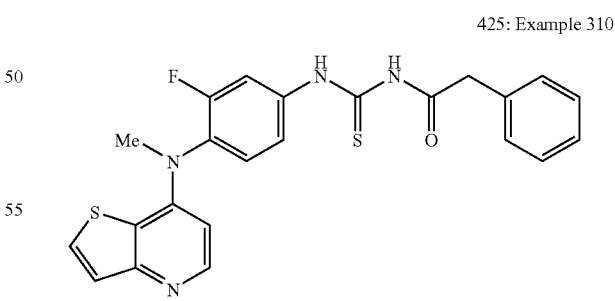

425: Example 310

The title compound 424 was obtained in four steps from 2 as a beige solid following the same procedure as in example 308, steps 1-3 (scheme 85). $^1$H NMR (400 MHz, DMSO-$d_6$) δ (ppm): 12.62 (s, 1H), 11.86 (s, 1H), 8.43 (d, J=5.5 Hz, 1H), 7.99 (dd, J=12.5, 2.2 Hz, 1H), 7.76 (d, J=5.7 Hz, 1H), 7.52 (dd, J=8.8, 2.3 Hz, 1H), 7.46 (t, J=8.7 Hz, 1H), 7.39-7.25 (m, 6H), 6.87 (d, J=5.7 Hz, 1H), 3.83 (s, 2H), 3.39 (s, 3H). LCMS: 451.0 $(M+H)^+$.

TABLE 27

Compounds 426–429(examples 311–314) prepared from the amine 425 similarly to the compounds 184 and 185(examples 139–140, scheme 36)

| Cpd | Ex. | Sctructure | Characterization |
|---|---|---|---|
| 426 | 311 | N-(3-Fluoro-4-(2-(1-(2-(pyrrolidin-1-yl)ethyl)-1H-imidazol-4-yl)thieno[3,2-b]pyridin-7-yloxy)phenylcarbainothioyl)-2-phenylacetainide | $^1$H NMR(400 MHz, DMSO-d$_6$) δ (ppm): 12.52(s, 1H), 11.86(s, 1H), 9.57(bs, 1H), 8.47(d, J=5.6 Hz, 1H), 8.06–7.98(m, 2H), 7.91(s, 1H), 7.71(s, 1H), 7.58–7.49(m, 2H), 7.39–7.26(m, 5H), 6.61(d, J=5.6 Hz, 1H), 4.43(t, J=6.0 Hz, 2H), 3.83(s, 2H), 3.71–3.63(m, 2H), 3.62–3.42(m, 2H), 3.13–3.02(m, 2H), 2.08–1.96(m, 2H), 1.92–1.78 (m, 2H). LCMS: 601.1(M + H) (formate salt). |
| 427 | 312 | 2-(2-Ethynylphenyl)-N-(3-fluoro-4-(2-(1-(2-(pyrrolidin-1-yl)ethyl)-1H-imidazol-4-yl)thieno[3,2-b]pyridin-7-yloxy)phenylcarbamothioyl)acetamide formate | $^1$H NMR(400 MHz, DMSO-d$_6$) δ (ppm): 12.51(s, 1H), 11.91(s, 1H), 8.47(d, J=5.6 Hz, 1H), 8.56(dd, J=12.4, 2.0 Hz, 1H), 7.97(s, 1H), 7.85(bs, 1H), 7.69(s, 1H), 7.60–7.48(m, 3H), 7.40(d, J=4.0 Hz, 2H), 7.36–7.29(m, 1H), 6.60(d, J=5.6 Hz, 1H), 4.46(s, 1H), 4.45–4.12(m, 2H), 4.06(s, 2H), 3.80–2.20(m, 6H), 2.00–1.60(m, 4H). LCMS:(M + H) 625.2 |
| 428 | 313 | 2-(4-Ethynylphenyl)-N-(3-fluoro-4-(2-(1-(2-(pyrrolidin-1-yl)ethyl)-1H-imidazol-4-yl)thieno[3,2-b]pyridin-7-yloxy)phenylcarbamothioyl)acetamide formate | $^1$H NMR(400 MHz, DMSO-d$_6$) δ (ppm): 12.46(s, 1H), 11.85(s, 1H), 8.46(d, J=5.2 Hz, 1H), 8.17(s, 1H), 8.02(dd, J=12.4, 2.0 Hz, 1H), 7.94(d, J=1.2 Hz, 1H), 7.79(d, J=1.2 Hz, 1H), 7.68(s, 1H), 7.56–7.51(m, 2H), 7.50–7.44(m, 2H), 7.38–7.34(m, 2H), 6.59(dd, J=5.2, 0.8 Hz, 1H), 4.19(s, 1H), 4.13(t, J=6.4 Hz, 2H), 3.87(s, 2H), 3.58–3.05(m, 4H), 2.80(t, J=6.4 Hz, 2H), 1.68 (q, J=3.2 Hz, 4H). LCMS:(M + H) 625.1 |
| 429 | 314 | 2-(2-Ethynyl-4-fluorophenyl)-N-(3-fluoro-4-(2-(1-(2-(pyrrolidin-1-yl)ethyl)-1H-imidazol-4-yl)thieno[3,2-b]pyridin-7-yloxy)phenylcarbamothioyl)acetamide | $^1$H NMR(400 MHz, DMSO-d$_6$) δ (ppm): 12.47(s, 1H), 11.90(s, 1H), 8.46(d, J=5.6 Hz, 1H), 8.06(dd, J=12.4, 2.4 Hz, 1H), 7.94(d, J=1.2 Hz, 1H), 7.79(d, J=1.2 Hz, 1H), 7.68(s, 1H), 7.56(dd, J=8.8, 2.4 Hz, 1H), 7.52(t, J=8.8 Hz, 1H), 7.45(dd, J=8.4, 5.6 Hz, 1H), 7.37(dd, J=9.2, 2.8 Hz, 1H), 7.28(td, J=8.4, 2.4 Hz, 1H), 6.59 4.8 Hz, 1H), 4.60(s, 1H), 4.14(t, J=6.0 Hz, 2H), 4.04(s, 2H), 2.80(t, J=6.0 Hz, 2H), 2.60–2.30(m, 4H, hidden under DMSO), 1.72–1.65(m, 4H). LCMS:(M + H) 643.3 |

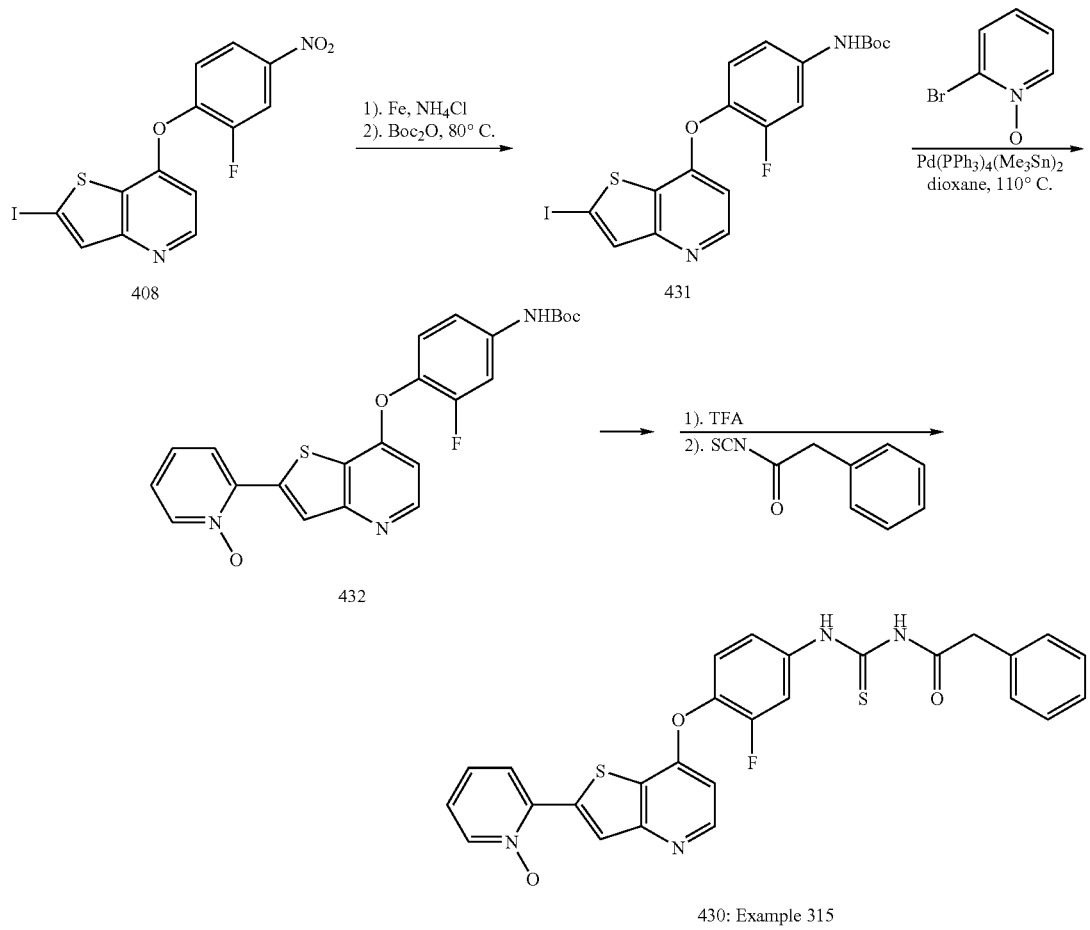

Scheme 86

430: Example 315

Example 315

2-(7-(2-Fluoro-4-(3-(2-phenylacetyl)thioureido)phenoxy)thieno[3,2-b]pyridin-2-yl)pyridine 1-oxide (430)

Step 1: tert-Butyl 3-fluoro-4-(2-iodothieno[3,2-b]pyridin-7-yloxy)phenylcarbamate (431)

A solution of 408 (2 g, 4.81 mmol) and NH$_4$Cl (220 mg, 4.1 mmol) in 2:1 mixture of EtOH/water (75 mL) was treated with iron powder (2.28 g, 40.8 mmol) and heated to reflux under vigorous stirring for 1 hour. The reaction mixture was filtered through celite and concentrated. The residue was mixed with Boc$_2$O (5 g, 22.9 mmol) in THF (10 mL) and was heated to reflux for 3 days. The reaction mixture was concentrated and the crude product was purified by flash chromatography using 40% EtOAc in hexanes as an eluent yielding 1.5 g of 431 (60% yield). LCMS: (M+H) 487.0.

Step 2: 2-(7-(4-(tert-Butoxycarbonylamino)-2-fluorophenoxy)thieno[3,2-b]pyridin-2-yl)pyridine 1-oxide (432)

A solution of 431 (460 mg, 0.94 mmol), 2-bromopyridine N-oxide (420 mg, 2.41 mmol), bistrimethyltin (294 µL, 465 mg, 1.42 mmol) and Pd(PPh$_3$)$_4$ (109 mg, 0.09 mmol) in dioxane (10 mL) was heated to reflux for 8 hrs under nitrogen. The reaction mixture was concentrated and purified by flash chromatography using the gradient 5-20% MeOH in EtOAc as an eluent yielding 432 (243 mg, 57% yield). LCMS: (M+H) 454.1.

Steps 3-4: 2-(7-(2-Fluoro-4-(3-(2-phenylacetyl)thioureido)phenoxy)thieno[3,2-b]pyridin-2-yl)pyridine 1-oxide (430)

A mixture of 432 (243 mg, 0.53 mmol) in 3:1 mixture of DCM/TFA (8 mL) was stirred at room temperature for 1 hour and concentrated under reduced pressure. The resultant solid was dissolved in 1:1 mixture of EtOH/toluene (10 mL) and treated with 2-phenylacetyl isothiocyanate (140 mg, 0.8 mmol). The reaction mixture was stirred for 1 hour at room temperature and concentrated. The residue was purified by flash chromatography using the gradient 0-20% MeOH in EtOAc as an eluent yielding 430 (101 mg, 36% yield). MeOH-d4/CDCl$_3$ (1:1) 8.5 (d, 1H, J=5.4 Hz), 8.38 (m, 3H), 8.0 (d, 1H, 11.9 Hz), 7.62 (t, 1H, J=7.7 Hz), 7.45 (m, 2H), 7.2-7.4 (m, 6H), 6.64 (5.1 Hz), 3.75 (s, 2H). LCMS: (M+H) 531.2.

TABLE 28

Compounds 433–324(examples 316–319) prepared according to the scheme 86

| Cpd | Ex. | Structure | Characterization |
|---|---|---|---|
| 433 | 316 | 2-(7-(2-Fluoro-4-(3-(2-(4-fluorophenyl)acetyl)thioureido)phenoxy)thieno[3,2-b]pyridin-2-yl)pyridine 1-oxide | $^1$H NMR(400 MHz, DMSO-d$_6$) δ (ppm): 8.70(s, 1H), 8.64(dd, J=1.8, 8.2 Hz, 1H), 8.59(d, J=5.2 Hz, 1H), 8.48(dd, J=1.0, 5.5 Hz, 1H), 7.99(d, J=12.5 Hz, 1H), 7.45–7.60 (m, 4H). 7.36(m, 2H), 7.15(m, 2H), 6.65(d, J=5.5 Hz, 1H), 3.82(s, 2H). LCMS: (M + H) 549.1 (100 %) |
| 434 | 317 | 4-(7-(2-Fluoro-4-(3-(2-(4-fluorophenyl)acetyl) thioureido)phenoxy)thieno[3,2-b]pyridin-2-yl)pyridine 1-oxide | $^1$H NMR(400 MHz, DMSO-d$_6$) δ (ppm): 12.46(s, 1H), 11.82(s, 1H), 8.55(d, J=5.3 Hz, 1H), 8.28(m, 3H), 8.01(d, J=12.7 Hz, 1H), 7.92(d, J=7.2 Hz, 2H), 7.53(m, 2H), 7.36(m, 2H), 7.16(t, J=9.0 Hz, 2H), 6.69(d, J=5.1 Hz, 1H), 3.81(s, 2H). LCMS:(M + H) 549.2 |
| 435 | 318 | 2-(7-(4-(3-(2-(2-Ethynylphenyl)acetyl)thioureido)-2-fluorophenoxy)thieno[3,2-b]pyridin-2-yl)pyridine 1-oxide | $^1$H NMR(400 MHz, DMSO-d$_6$) δ (ppm): 12.49(s, 1H), 11.88(s, 1H), 8.70(s, 1H), 8.65 (dd,J=1.6 Hz, J=8.4 Hz, 1H), 8.59(d, J=5.3 Hz, 1H), 8.48(m, 1H), 8.06(dd, J=2.1, 13.1 Hz, 1H), 7.45-7.60(m, 5H), 7.38(m, 2H), 7.30 (m, 1H), 6.66(dd, J=1.0, 5.3 Hz, 1H), 4.44(s, 1H), 4.04(s, 2H). LCMS:(M + H) 555.1 (100%) |

TABLE 28-continued
Compounds 433–324(examples 316–319) prepared according to the scheme 86
| Cpd | Ex. | Sctructure | Characterization |
|---|---|---|---|
| 436 | 319 | 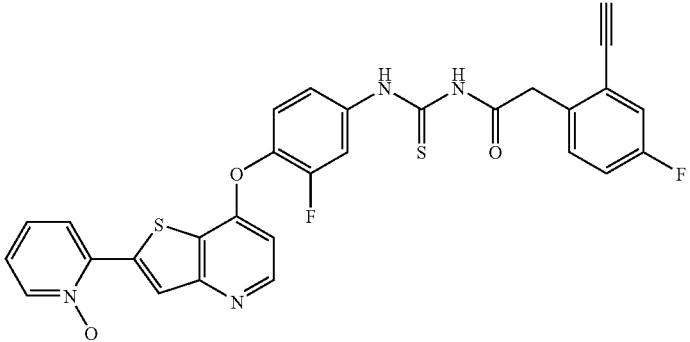<br>2-(7-(4-(3-(2-(2-Ethynyl-4-fluorophenyl)acetyl)thioureido)-2-fluorophenoxy)thieno[3,2-b]pyridin-2-yl)pyridine 1-oxide | $^1$H NMR(400 MHz, DMSO-d$_6$) δ (ppm): 12.46(s, 1H), 11.89(s, 1H), 8.70(s, 1H), 8.64 (d, J=6.7 Hz, 1H), 8.59(d, J=5.3 Hz, 1H), 8.48(d, J=6.4 Hz, 1H), 8.06(d, J=11.1 Hz, 1H), 7.54(m, 4H), 7.43(m, 1H), 7.35(dd, J= 2.7, 9.3 Hz, 1H), 7.26(m, 1H), 6.66(d, J= H, 1H z), 4.57(s, 1H), 4.02(s, 2H). LCMS: (M + H) 573.2 |
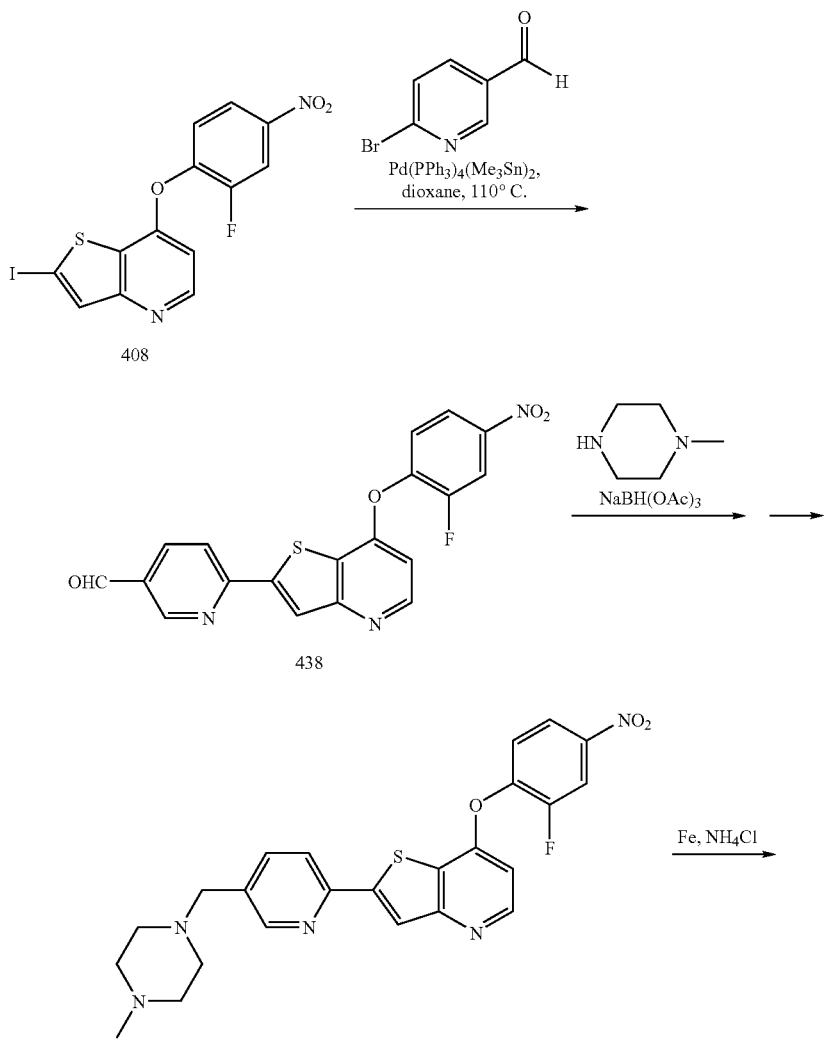
Scheme 87

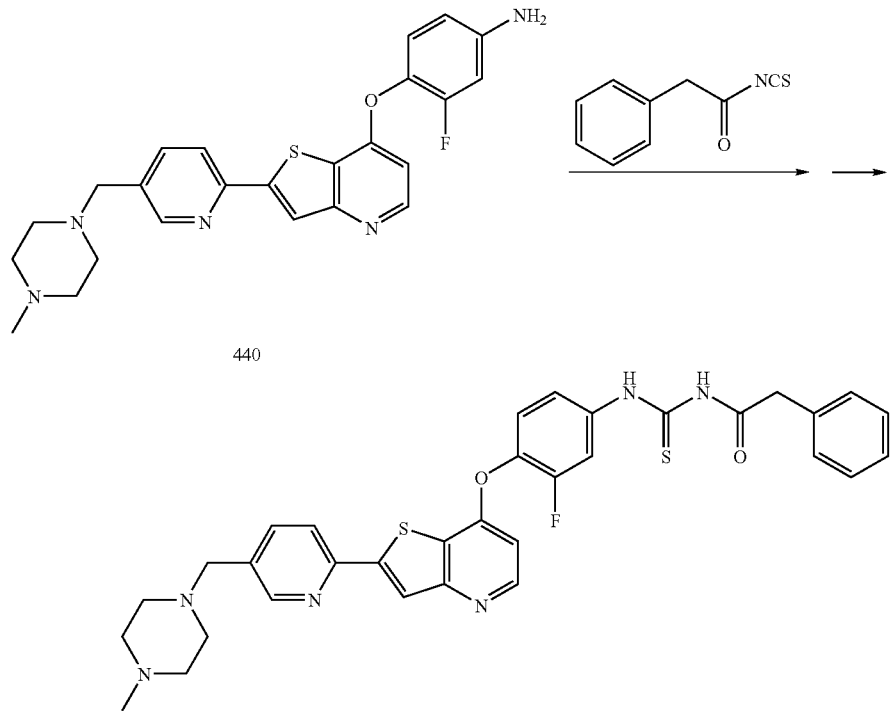

437: Example 320

Example 320

N-(3-Fluoro-4-(2-(5-((4-methylpiperazin-1-yl)methyl)pyridin-2-yl)thieno[3,2-b]pyridin-7-yloxy)phenylcarbamothioyl)-2-phenylacetamide (437)

Step 1: 6-(7-(2-Fluoro-4-nitrophenoxy)thieno[3,2-b]pyridin-2-yl)nicotinaldehyde (438)

A solution of 408 (1 g, 2.40 mmol) and 6-bromonicotinaldehyde (450 mg, 2.40 mmol) in dioxane (10 mL) was treated sequentially with bistirmethyl tin (500 μL, 787 mg, 2.40 mmol) and Pd(PPh$_3$)$_4$ (270 mg, 0.24 mmol). The reaction mixture was heated to reflux under nitrogen overnight and concentrated. The residue was purified by flash chromatography using the gradient 5%-10% MeOH in DCM as an eluent and subsequent trituration with MeOH, yielding pure 438 (494 mg, 52% yield). $^1$H NMR (400 MHz, DMSO-d$_6$) δ (ppm): 10.11 (s, 1H), 9.10 (m, 1H), 8.65 (d, 1H, J=5.2 Hz), 8.62 (s, 1H), 8.51 (d, 1H, J=8.8 Hz), 8.48 (dd, 1H, J=2.8 Hz, J=10.4 Hz), 8.38 (dd, 1H, J=2.1 Hz, J=8.2 Hz), 8.20 (m, 1H), 7.73 (t, 1H, J=9.0 Hz), 7.01 (d, 1H, J=5.5 Hz). LCMS: (M+H) 395.9.

Step 2: 7-(2-Fluoro-4-nitrophenoxy)-2-(5-((4-methylpiperazin-1-yl)methyl)pyridin-2-yl)thieno[3,2-b]pyridine (439)

A mixture of 438 (451 mg, 1.14 mmol) and 1-methylpiperazine (152 μL, 137 mg, 1.37 mmol) in DCM (7 mL) was stirred at room temperature for 10 min. It was then treated with NaBH(OAc)$_3$ (340 mg, 1.60 mmol) and stirred at room temperature overnight. The reaction mixture was the diluted with DCM (20 mL) and washed with saturated NaHCO$_3$ solution (20 mL). It was then dried over anhydrous Na$_2$SO$_4$, filtered and concentrated. The residue was purified by flash chromatography using the gradient 30-50% MeOH (with 2% Et$_3$N) in EtOAc as an eluent, yielding 439 of (308 mg, 52% yield). LCMS: (M+H) 480.0 (100%).

Step 3: 3-Fluoro-4-(2-(5-((4-methylpiperazin-1-yl)methyl)pyridin-2-yl)thieno[3,2-b]pyridin-yloxy)aniline (440)

A solution of 439 (306 mg, 0.64 mmol) and NH$_4$Cl (30 mg, 0.54 mmol) in 2:1 mixture of EtOH/water (10.5 mL) was treated with iron powder (304 mg, 5.43 mmol) and heated to reflux for 1 hour. The reaction mixture was then filtered through celite and concentrated yielding 440 (343 mg, 100% yield) which was used without further purification. LCMS: (M+H) 450.0 (100%).

Step 4: N-(3-Fluoro-4-(2-(5-((4-methylpiperazin-1-yl)methyl)pyridin-2-yl)thieno[3,2-b]pyridin-7-yloxy)phenylcarbamothioyl)-2-phenylacetamide (437)

A solution of 440 (100 mg, 0.22 mmol), in 1:1 mixture of EtOH/toluene (2 mL) was treated with 2-phenylacetyl isothiocyanate (394 mg, 2.22 mmol) and stirred at room temperature for 2 hours. The reaction mixture was then concentrated and purified by flash chromatography using the gradient 10-30% MeOH (containing 2% NH$_4$OH) in DCM as an eluent, yielding 437 (39 mg, 28% yield). DMSO-d6 8.53 (s, 1H), 8.51 (s, 1H), 8.33 (s, 1H), 8.23 (d, 1H, J=8.1 Hz), 8.02 (d, 1H, J=11.7 Hz), 7.83 (d, 1H, J=6.6 Hz), 7.53 (s, 1H0, 7.2-7.4 (m, 5H), 6.66 (d, 1H, J=5.5 Hz), 3.81 (s, 2H), 3.52 (s, 2H), 2.4 (m, 8H), 2.13 (s, 3H), LCMS: (M+H) 627.0 (100%).

TABLE 29

Compounds 329–333(examples 321–326) prepared according to the scheme 87

| Cpd | Ex. | Sctructure | Characterization |
|---|---|---|---|
| 441 | 321 | N-(4-(2-(5-((Dimethylamino)methyl)pyridin-2-yl)thieno[3,2-b]pyridin-7-yloxy)-3-fluorophenylcarbamothioyl)-2-phenylacetamide | $^1$H NMR(400 MHz, DMSO-d$_6$) δ (ppm): 12.51(s, 1H), 11.84(s, 1,H), 8.54(d, J=5.3 Hz, 2H), 8.35(s, 1H), 8.25(d, J=8.2 Hz, 1H), 8.03(d, J=13.5 Hz, 1H), 7.86(d, J=7.3 Hz, 1H), 7.53(m, 2H), 7.25–7.35(m, 5H), 6.68(d, J=5.3 Hz, 1H), 3.82(s, 2H), 3.51(s br, 2H), 2.20(s, 6H). LCMS:(M + H) 572.2 |
| 442 | 322 | N-(3-Dluoro-4-(2-(5-((2-methoxyethylamino)methyl)pyridin-2-yl)thieno[3,2-b]pyridin-7-yloxy)phenylcarbamothioyl)-2-(4-fluorophenyl)acetamide | $^1$H NMR(400 MHz, DMSO-d$_6$) δ (ppm): 12.49(s, 1H), 11.89(s, 1H), 9.01(sbr, 2H), 8.70(m, 1H), 8.55(d, 5.4 Hz, 1H), 8.42(s, 1H), 8.36(d, J=8.2 Hz, 1H), 8.06(m, 2H), 7.3–7.6(m, 4H), 6.70(ddJ=0.8, 5.3 Hz, 1H,), 4.43(s, 1H), 4.25(m, 2H), 4.04(s, 2H), 3.30(s, 3H), 3.15(m, 2H). LCMS: (M + H) 626.2 |
| 443 | 323 | 2-(2-Ethynylphenyl)-N-(3-fluoro-4-(2-(5-((2-methoxyethylamino)methyl)pyridin-2-yl)thieno[3,2-b]pyridin-7-yloxy)phenylcarbamothioyl)acetamide | $^1$H NMR(400 MHz, DMSO-d$_6$) δ (ppm): 12.49(s, 1H), 11.88(s, 1H), 8.70(s, 1H), 8.65(dd, J=1.6, 8.4 Hz, 1H), 8.59(d, J=5.3 Hz, 1H), 8.48(m, 1H), 8.06(dd, J=2.1 Hz, J=13.1 Hz, 1H), 7.45–7.60(m, 5H), 7.38 (m, 2H), 7.30(m, 1H), 6.66(dd, J=1.0, 5.3 Hz, 1H), 4.44(s, 1H), 4.04(s, 2H). LCMS: (M + H) 555.1 |
| 444 | 324 | N-(3-Fluoro-4-(2-(5-(((2-hydroxyethyl)(methyl)amino)methyl)pyridin-2-yl)thieno[3,2-b]pyridin-7-yloxy)phenylcarbamothioyl)-2-(4-fluorophenyl)acetamide | $^1$H NMR(400 MHz, DMSO-d$_6$) δ (ppm): 8.54(br.s, 1H), 8.53(d, J=5.4 Hz, 1H), 8.32(s, 1H), 8.22(d, J=8.0 Hz, 1H), 8.00 (d, J=12.5 Hz, 1H), 7.86(dd, J=2.0, 8.2 Hz, 1H), 7.50(m, 2H), 7.36(m, 2H), 7.25 (m, 1H), 7.16(t, J=8.8 Hz, 2H), 7.05(t, J=8.8 Hz, 1H), 6.66(d, 1H, J=5.5 Hz), 3.82 (s, 2H0, 3.57(s, 2H), 3.50(m, 2H), 2.43(t, J=6.3 Hz, 2H), 2.17(s, 3H). LCMS: (M + H) 620.2 |

TABLE 29-continued

Compounds 329–333(examples 321–326) prepared according to the scheme 87

| Cpd | Ex. | Sctructure | Characterization |
|---|---|---|---|
| 445 | 325 | N-(3-Fluoro-4-(2-(6-((2-methoxyethylamino)methyl)pyridin-2-yl)thieno[3,2-b]pyridin-7-yloxy)phenyl carbamothioyl)-2-(4-fluorophenyl)acetamide | $^1$H NMR(400 MHz, DMSO-d$_6$) δ (ppm): 12.48(s, 1H), 11.84(s, 1H), 9.33(br.s, 12H), 8.63(d, J=5.9 Hz, 1H), 8.49(s, 1H), 8.31(d, J=7.9 Hz, 1H), 8.05(m, 2H), 7.57 (m, 2H), 7.37(m, 2H), 7.17(t, J=9.0 Hz, 2H), 6.79(d, J=5.7 Hz, 1H), 4.41(m, 2H), 3.82(s, 3H), 3.68(m, 2H0, 3.28(m, 4H). LCMS:(M + H) 620.2 |
| 446 | 326 | N-(3-Fluoro-4-(2-(5-(pyrrolidin-1-ylmethyl)pyridin-2-yl)thieno[3,2-b]pyridin-7-yloxy)phenylcarbamothioyl)-2-phenylacetamide | δ (400 MHz, DMSO-d$_6$): 12.51(s, 1H), 11.81(s, 1H), 8.54(m, 2H), 8.33(s, 1H), 08.23(d, J=8.0 Hz, 1H), 8.01–8.05(m, 1H), 7.86(dd, J=1.8, 8.0 Hz, 1 H), 7.50–7.57(m, 2H), 7.32–7.37(m, 4H), 7.24–7.32(m, 1H), 6.68(d, J=5.3 Hz, 1H), 3.83(s, 2H), 3.64(s, 2H), 2.46(m, 4H), 1.70(m, 4H). |

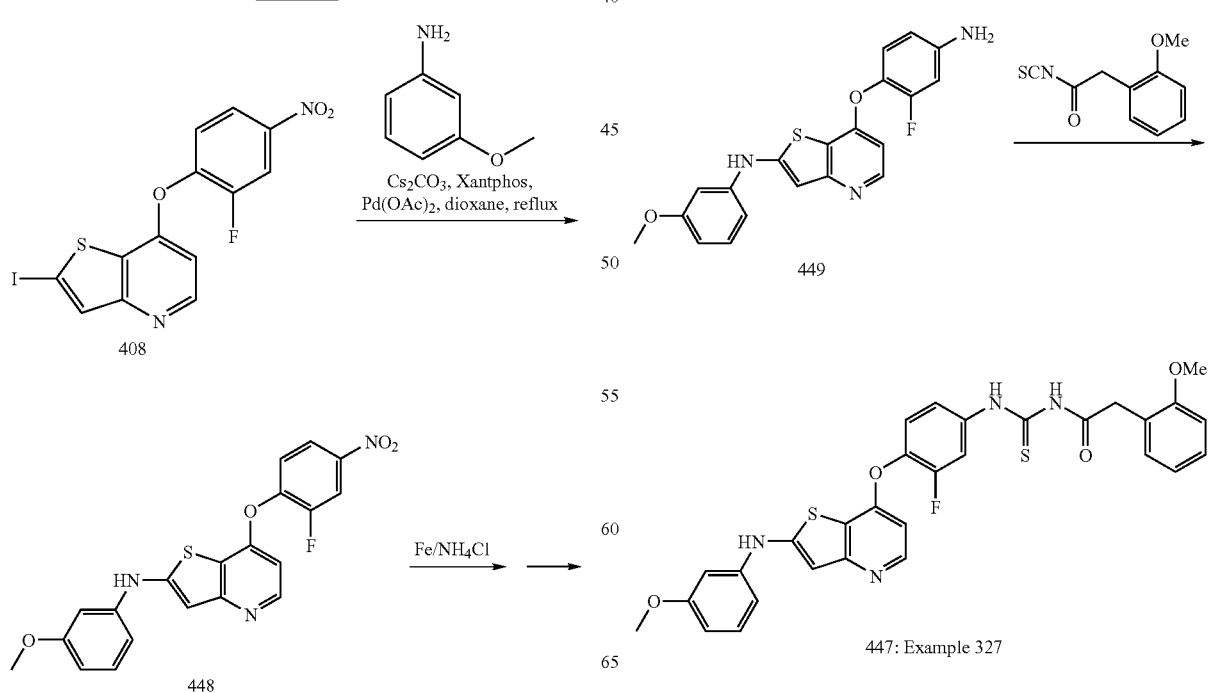

Scheme 88

Example 260

N-(3-Fluoro-4-(2-(3-methoxyphenylamino)thieno[3,2-b]pyridin-7-yloxy)phenylcarbamothioyl)-2-(2-methoxyphenyl)acetamide (447)

Step 1: 7-(2-Fluoro-4-nitrophenoxy)-N-(3-methoxyphenyl)thieno[3,2-b]pyridin-2-amine (448)

A solution of 408 (700 mg, 1.68 mmol), Cs$_2$CO$_3$ (1.12 g, 3.43 mmol), 3-methoxyaniline (190 μL, 206 mg, 1.68 mmol), Pd(OAc)$_2$ (70 mg, 0.17 mmol) and Xantphos (1.43 g, 2.52 mmol) (*J. Org. Chem.* 1999, 64, 6019-6022) in dioxane (15 mL) was heated to reflux for 5 hrs. The reaction mixture was then concentrated and purified by flash chromatography using 80% EtOAc in hexanes as an eluent yielding 448 of (408 mg, 59% yield). LCMS: (M+H) 412.0.

Step 2: 7-(4-Amino-2-fluorophenoxy)-N-(3-methoxyphenyl)thieno[3,2-b]pyridin-2-amine (449)

A solution of 448 (408 mg, 0.99 mmol) and NH$_4$Cl (45 mg, 084 mmol) in 2:1 mixture of EtOH/water (15 mL) was treated with iron powder (472 mg, 8.43 mmol) and heated to reflux under vigorous stirring for 1 hour. The reaction mixture was then filtered through celite and concentrated yielding 449 which was used without further purification (278 mg, 74% yield). LCMS: (M+H) 382.0.

Steps 3: N-(3-Fluoro-4-(2-(3-methoxyphenylamino)thieno[3,2-b]pyridin-7-yloxy)phenylcarbamothioyl)-2-(2-methoxyphenyl)acetamide (447)

A solution of 449 (40 mg, 0.10 mmol) in 1:1 mixture of EtOH/toluene (2 mL) was treated with 2-(2-methoxyphenyl)acetyl isothiocyanate (394 mg, 2.22 mmol) and stirred at room temperature for 2 hours. The reaction mixture was then concentrated and purified by flash chromatography using the gradient 75-100% EtOAc in hexanes as an eluent, yielding 447 (15 mg, 24% yield). CDCl$_3$ 12.39 (s, 1H), 9.47 (s, 1H), 8.34 (d, J=5.7 Hz, 1H), 7.92 (dd, J=2.0, 11.8 Hz, 1H), 7.36 (m, 2H), 7.22 (m, 2H), 7.01 (m, 3H), 6.80 (s, 2H), 6.59 (d, J=7.4 Hz, 2H), 6.39 (d, J=5.6 Hz, 1H), 4.00 (s, 3H), 3.80 (s, 3H), 3.72 (s, 2H) LCMS: (M+H) 589.0

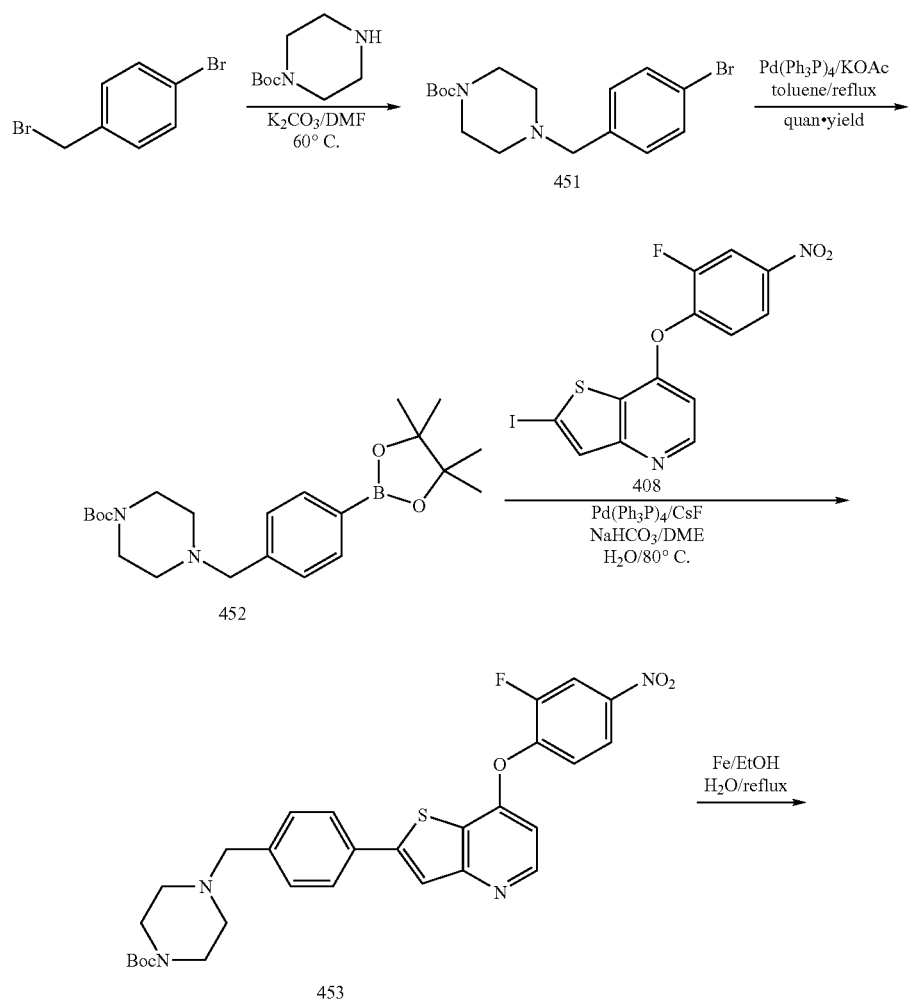

Scheme 89

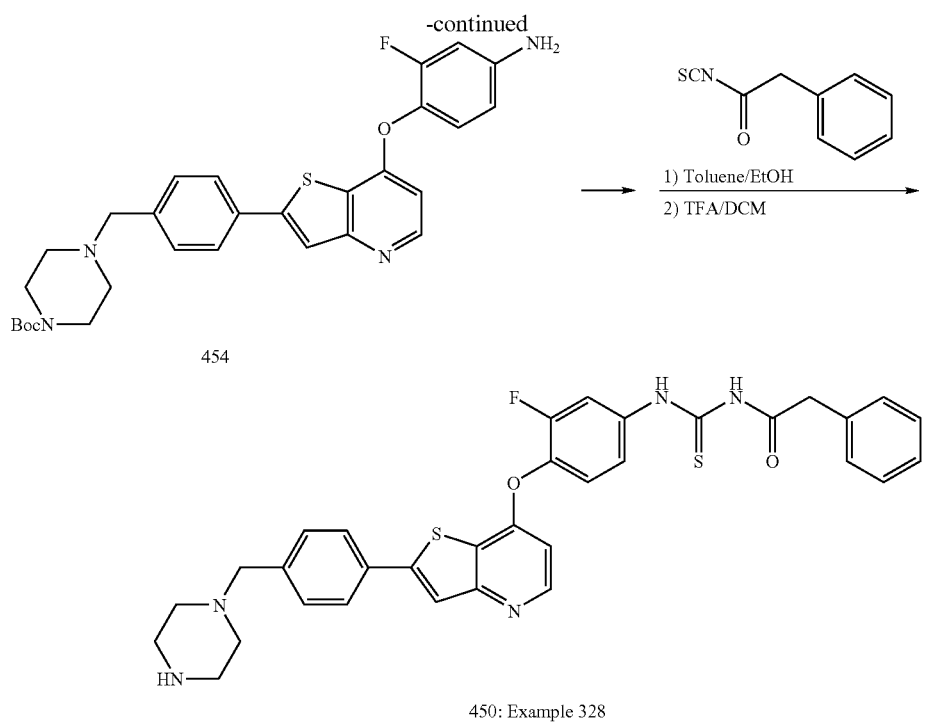

450: Example 328

Example 328

N-(3-Fluoro-4-(2-(4-(piperazin-1-ylmethyl)phenyl)thieno[3,2-b]pyridin-7-yloxy)phenyl)-2-oxo-3-phenylimidazolidine-1-carboxamide (450)

Step 1. tert-Butyl 4-(4-bromobenzyl)piperazine-1-carboxylate (451)

1-Bromo-4-(bromomethyl)benzene (8.078 g, 32.3 mmol) and tert-butyl piperazine-1-carboxylate (6.625 g, 35.6 mmol) were dissolved in DMF (40 ml) and $K_2CO_3$ (8.93 g, 64.6 mmol) was added. The reaction mixture was heated to 60° C. for 4 h and then filtered through a pad of celite. The filtrate was evaporated and the residue was triturated in hexanes to produce compound 451 as white solid (9.46 g, 82% yield). LCMS: 255.0 $(M+H)^+$.

Step 2. tert-Butyl 4-(4-(4,4,5,5-tetramethyl-1,3,2-dioxaborolan-2-yl)benzyl)piperazine-1-carboxylate (452)

Compound 451 (9.46 g, 26.63 mmol), KOAc (7.84 g, 79.88 mmol), 4,4,4',4',5,5,5',5'-octamethyl-2,2'-bi(1,3,2-dioxaborolane) (10.14 g, 39.95 mmol), $Pd(PPh_3)_4$ (3.07 g, 2.663 mmol) and toluene (133 mL) were placed into a 250 mL round bottom flask. The reaction mixture was purged with nitrogen for a half-an-hour and heated to reflux for 4 h. It was then cooled to RT, diluted with EtOAc (400 mL) and washed with $H_2O$ (100 mL), dried over $Na_2SO_4$, filtered, concentrated to afford title compound 452 as brown oil (22.36 g, >100% yield). LCMS: 403 $(M+H)^+$. This material was used in the next step with no additional purification.

Step 3. tert-Butyl 4-(4-(7-(2-fluoro-4-nitrophenoxy)thieno[3,2-b]pyridin-2-yl)benzyl)piperazine-1-carboxylate (453)

Compound 452 (22.36 g, 26.6 mmol), iodide 408 (7.904 g, 19.0 mmol), CsF (8.658 g, 57 mmol), $NaHCO_3$ (4.788 g, 57 mmol) and $Pd(PPh_3)_4$ (2.195 g, 1.9 mmol) were combined with a mixture of $H_2O$ (25 mL) and DME (100 mL) which was with nitrogen for a half-an-hour and heated to reflux overnight. It was then was cooled to RT, diluted with EtOAc (200 ml), washed with aqueous $NaHCO_3$ (50 mL) and brine (50 mL), and concentrated. The residue was purified by flash column chromatography (eluent pure EtOAc to 5% MeOH/EtOAc) followed by trituration with EtOAc/ether, to produce compound 453 as an off-white solid (5.4 g, 50% yield). LCMS: 565 $(M+H)^+$.

Step 4. tert-Butyl 4-(4-(7-(4-amino-2-fluorophenoxy)thieno[3,2-b]pyridin-2-yl)benzyl)piperazine-1-carboxylate (454)

Compound 453 (5.4 g, 9.56 mmol), iron powder (1.602 g, 28.69 mmol) and $NH_4Cl$ (0.78 g, 14.34 mmol) were placed in a mixture of $H_2O$ (24mL) and EtOH (48 mL). The reaction mixture was heated to reflux for 5 h. It was then cooled to RT, diluted with MeOH and filtered through a pad of celite. The filtrate was concentrated to dryness and the residue was dissolved in dichloromethane, washed with aqueous $NaHCO_3$ and brine, dried over $Na_2SO_4$, and filtered. The filtrate was concentrated to dryness to give compound 454 as white solid (4.2 g, 83% yield). LCMS: 535 $(M+H)^+$.

Step 5. N-(3-Fluoro-4-(2-(4-(piperazin-1-ylmethyl) phenyl)thieno[3,2-b]pyridin-7-yloxy)phenylcarbamothioyl)-2-phenylacetamide (450)

Compound 454 (0.3323 g, 0.62 mmol) was suspended in EtOH/toluene (3 mL/3 mL) at RT and stirred for 30 min. 2-Phenylacetyl isothiocyanate (0. 165 g, 0.93 mmol) was added and the reaction mixture was stirred at RT for 1 h, quenched with MeOH (2 mL) and concentrated to dryness. The residue was purified by flash chromatography (eluent 9/1/90 MeOH/NH$_4$OH/DCM) to give compound 450 as a white solid (60 mg, 16% yield). $^1$H NMR δ(400 MHz, CD$_3$CN): 8.51 (d, J=5.5 Hz, 1H), 7.99 (dd, J=2.5, 12.3 Hz, 1H), 7.84 (s, 1H), 7.82 (d, J=8.2 Hz, 2H), 7.32-7.53 (m, 9H), 6.62 (d, J=4.5 Hz, 1H), 3.81 (s, 2H), 3.54 (s, 2H), 2.30-2.53 (bs, 8H), 2.22 (s, 3H). LCMS: 613 (M+H)$^+$.

stirred for 10 min at 0° C. The reaction mixture was then warmed to RT over a 30 min period, and then was quenched with MeOH. It was then concentrated to dryness and the residue was purified by flash chromatography (eluent 9/1/10 MeOH/NH$_4$Cl/DCM) to give title compound 455 as a pale yellow solid (0.16 g, 39% yield). $^1$H NMR δ (400 MHz, DMSO-d6): 12.48 (s, 1H), 11.83 (s, 1 H), 8.51 (dd, J=1.2, 5.5 Hz, 1H), 8.01 (m, 2H), 7.84 (m, 2H), 7.53 (m, 2H), 7.42 (d, J=8.4 Hz, 2H), 7.23-7.38 (m, 5H) 6.65 (dd, J=0.8, 5.5 Hz, 1H), 6.39 (q, J=4.2 Hz, 1 H), 3.81 (s, 2 H), 3.51 (s, 2H), 3.25 (m, 4H), 2.53 (d, J=4.3 Hz, 3H), 2.31 (m, 4H). LCMS: 669 (M+H)$^+$.

Scheme 90

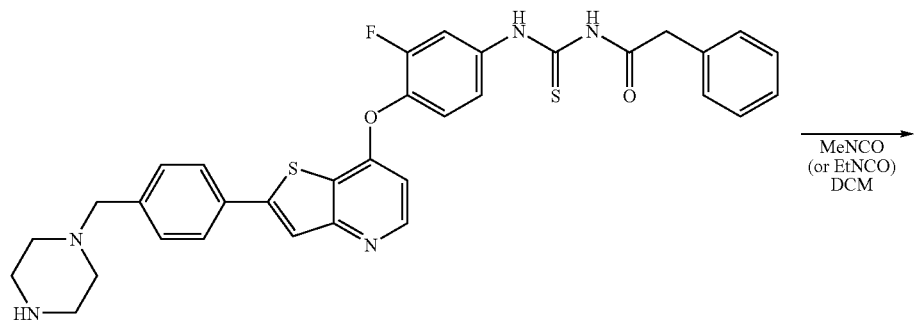

450: Example 328

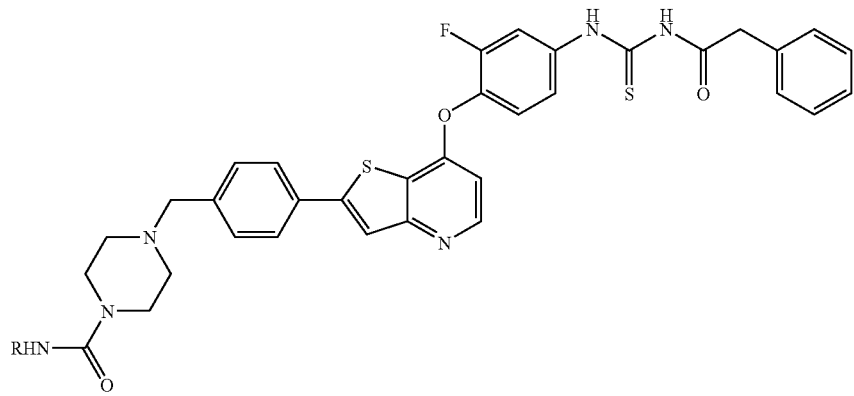

455: Example 329 (R = Me)
456: Example 330 (R = Et)

Example 329

4-(4-(7-(2-Fluoro-4-(3-(2-phenylacetyl)thioureido) phenoxy)thieno[3,2-b]pyridin-2-yl)benzyl)-N-methylpiperazine-1-carboxamide (455)

Compound 450 (0.367 g, 0.60 mmol) was dissolved in dichloromethane (2 mL) at RT and then Et$_3$N (0.25 mL, 1.803 mmol) was added. The reaction mixture was cooled to 0° C., treated with isocyanatomethane (0. 16 mL, 3.43 mmol) and

Example 330

N-Ethyl-4-(4-(7-(2-fluoro-4-(3-(2-phenylacetyl)thioureido)phenoxy)thieno[3,2-b]pyridin-2-yl)benzyl) piperazine-1-carboxamide (456)

Title compound 456 was obtained similarly to the compound 455 according to the scheme 90, in 82% yield. $^1$H NMR δ (400 MHz, DMSO-d6): ): 8.53 (dd, J=0.5, 5.4 Hz, 1H), 8.05 (s, 1H), 8.01 (d, J=12.5 Hz, 1H), 7.85 (d, J=8.2 Hz, 2H), 7.50-7.58 (m, 2H), 7.44 (d, J=8.0 Hz, 2H), 7.32-7.38 (m, 4H), 7.24-7.32 (m, 1H), 6.65 (d, J=5.3 Hz, 1H), 6.44 (t, J=5.5

Hz, 1H), 3.83 (s, 2H), 3.52 (s, 2H), 3.27 (m, 4H), 2.97-3.60 (m, 2H), 2.32 (m, 4H), 0.98 (t, J=7.1 Hz, 3H). LCMS: 683 (M+H)$^+$.

ASSAY EXAMPLES

Assay Example 1

Inhibition of c-met and VEGF Activity

The following protocols were used to assay the compounds of the invention.

In Vitro Receptor Tyrosine Kinase Assays (c-Met/HGF Receptor and VEGF Receptor KDR)

These tests measure the ability of compounds to inhibit the enzymatic activity of recombinant human c-Met/HGF receptor and VEGF receptor enzymatic activity.

A 1.3-kb cDNA corresponding to the intracellular domain of c-Met or c-Met IC (Genbank accession number NP000236-1 amino acid 1078 to 1337) was cloned into the BamHI/XhoI sites of the pBlueBacHis2A vector (Invitrogen) for the production of a histidine-tagged version of that enzyme. This constuct was used to generate recombinant baculovirus using the Bac-N-Blue™ system according to the manucfacturer's instructions (Invitrogen)

The c-Met IC protein was expressed in Hi-5 cells (Trichoplusia Ni) upon infection with recombinant baculovirus construct. Briefly, Hi-5 cells grown in suspension and maintained in serum-free medium (Sf900 II supplemented with gentamycin) at a cell density of about 2×10$^6$ cells/ml were infected with the abovementioned viruses at a multiplicity of infection (MOI) of 0.2 during 72 hours at 27° C. with agitation at 120 rpm on a rotary shaker. Infected cells were harvested by centrifugation at 398 g for 15 min. Cell pellets were frozen at −80° C. until purification was performed.

All steps described in cell extraction and purification were performed at 4° C. Frozen Hi-5 cell pellets infected with the C-Met IC recombinant baculovirus were thawed and gently resuspended in Buffer A (20 mM Tris pH 8.0, 10% glycerol, 1 µg/ml pepstatin, 2 µg/ml Aprotinin and leupeptin, 50 µg/ml PMSF, 50 µg/ml TLCK and 10 µM E64, 0.5 mM DTT and 1 mM Levamisole) using 3 ml of buffer per gram of cells. The suspension was Dounce homogenized after which it was centrifuged at 22500 g, 30 min., 4° C. The supernatant (cell extract) was used as starting material for purification of c-Met IC.

The supernatant was loaded onto a QsepharoseFF column (Amersham Biosciences) equilibrated with Buffer B (20 mM Tris pH 8.0, 10% glycerol) supplemented with 0.05M NaCl. Following a ten column volume (CV) wash with equilibration buffer, bound proteins were eluted with a 5 CV salt linear gradient spanning from 0.05 to 1M NaCl in Buffer B. Typically, the conductivity of selected fractions ranked between 6.5 and 37 mS/cm. This Qsepharose eluate had an estimated NaCl concentration of 0.33M and was supplemented with a 5M NaCl solution in order to increase NaCl concentration at 0.5M and also with a 5M Imidazole (pH 8.0) solution to achieve a final imidazole concentration of 15mM. This material was loaded onto a HisTrap affinity column (GE Healthcare) equilibrated with Buffer C (50 mM NaPO$_4$ pH 8.0, 0.5M NaCl, 10% glycerol) supplemented with 15mM imidazole. After a 10 CV wash with equilibration buffer and an 8 CV wash with buffer C+40 mM imidazole, bound proteins were eluted with an 8 CV linear gradient (15 to 500 mM) of imidazole in buffer C. C-Met IC enriched fractions from this chromatography step were pooled based on SDS-PAGE analysis. This pool of enzyme underwent buffer exchange using PD-1I column (GE Healthcare) against buffer D (25 mM HEPES pH 7.5, 0.1M NaCl, 10% glycerol and 2mM □-mercaptoethanol) Final C-Met IC protein preparations concentrations were about 0.5 mg/ml with purity approximating 80%. Purified c-Met IC protein stocks were supplemented with BSA at 1 mg/ml, aliquoted and frozen at −80° C. prior to use in enzymatic assay.

In the case of VEGF receptor KDR a 1.6-kb cDNA corresponding to the catalytic domain of VEGFR2 or KDR (Genbank accession number AF035121 amino acid 806 to 1356) was cloned into the Pst I site of the pDEST20 Gateway vector (Invitrogen) for the production of a GST-tagged version of that enzyme. This constuct was used to generate recombinant baculovirus using the Bac-to-Bac™ system according to the manucfacturer's instructions (Invitrogen)

The GST-VEGFR2$_{806-1356}$ protein was expressed in Sf9 cells (*Spodoptera frugiperda*) upon infection with recombinant baculovirus construct. Briefly, Sf9 cells grown in suspension and maintained in serum-free medium (Sf900 II supplemented with gentamycin) at a cell density of about 2×10$^6$ cells/ml were infected with the abovementioned viruses at a multiplicity of infection (MOI) of 0.1 during 72 hours at 27° C. with agitation at 120 rpm on a rotary shaker. Infected cells were harvested by centrifugation at 398 g for 15 min. Cell pellets were frozen at −80° C. until purification was performed.

All steps described in cell extraction and purification were performed at 4° C. Frozen Sf9 cell pellets infected with the GST-VEGFR2$_{806-1356}$ recombinant baculovirus were thawed and gently resuspended in Buffer A (PBS pH 7.3 supplemented with 1 µg/ml pepstatin, 2 µg/ml Aprotinin and leupeptin, 50 µg/ml PMSF, 50 µg/ml TLCK and 10 µM E64 and 0.5 mM DTT) using 3 ml of buffer per gram of cells. Suspension was Dounce homogenized and 1% Triton X-100 was added to the homogenate after which it was centrifuged at 22500 g, 30 min., 4° C. The supernatant (cell extract) was used as starting material for purification of GST-VEGFR2$_{806-1356}$.

The supernatant was loaded onto a GST-agarose column (Sigma) equilibrated with PBS pH 7.3. Following a four column volume (CV) wash with PBS pH 7.3+1% Triton X-100 and 4 CV wash with buffer B (50 mM Tris pH 8.0, 20% glycerol and 100 mM NaCl), bound proteins were step eluted with 5 CV of buffer B supplemented with 5mM DTT and 15 mM glutathion. GST-VEGFR2$_{806-1356}$ enriched fractions from this chromatography step were pooled based on U.V. trace i.e. fractions with high O.D.$_{.280}$. Final GST-VEGFR2$_{806-1356}$ protein preparations concentrations were about 0.7 mg/ml with purity approximating 70%. Purified GST-VEGFR2$_{806-1356}$ protein stocks were aliquoted and frozen at −80° C. prior to use in enzymatic assay.

Inhibition of c-Met/HGF receptor and VEGFR/KDR was measured in a DELFIA™ assay (Perkin Elmer). The substrate poly(Glu$_4$,Tyr) was immobilized onto black high-binding polystyrene 96-well plates. The coated plates were washed and stored at 4° C. During the assay, enzymes were pre-incubated with inhibitor and Mg-ATP on ice in polypropylene 96-well plates for 4 minutes, and then transferred to the coated plates. The subsequent kinase reaction took place at 30° C. for 10-30 minutes. ATP concentrations in the assay were 10 uM for C-Met (5× the K$_m$) and 0.6 uM for VEGFR/KDR (2× the K$_m$). Enzyme concentration was 25 nM (C-Met) or 5 nM (VEGFR/KDR). After incubation, the kinase reactions were quenched with EDTA and the plates were washed. Phosphorylated product was detected by incubation with Europium-labeled anti-phosphotyrosine MoAb. After washing the plates, bound MoAb was detected by time-resolved fluorescence in a Gemini SpectraMax reader (Molecular Devices). Compounds were evaluated over a range of concentrations and IC$_{50}$'s (concentration of compounds giving 50% inhibition of enzymatic activity) were determined.

C-Met Phosphorylation Cell-Based Assay

This test measures the ability of compounds to inhibit HGF stimulated auto-phosphorylation of the c-Met/HGF receptor itself in a whole cell system.

MNNGHOS cell line expressing TPR-MET fusion protein were purchased from ATCC. The TPR-MET is the product of a chromosomal translocation placing the TPR locus on chromosome 1 upstream of the MET gene on chromosome 7 encoding for it's cytoplasmic region catalytic domain. Dimerization of the M$_r$ 65,000 TPR-Met oncoprotein through a leucine zipper motif encoded by the TPR portion leads to constitutive activation of the met kinase. Constitutive autophosphorylation occurs on residues Tyr361/365/366 of TPR-Met. These residues are homologous to Tyr1230/1234/1235 of MET which become phosphorylated upon dimerization of the receptor upon HGF binding.

Inhibitor of c-Met formulated as 30 mM stocks in DMSO. For MNNGHOS treatments, cells, compounds were added to tissue culture media at indicated doses for 3 hours prior to cell lysis. Cells were lysed in ice-cold lysis buffer containing 50 mM HEPES (pH 7.5), 150 mM NaCl, 1.5 mM MgCl2, 10% glycerol, 1% Triton X-100, 1 mM 4-(2-Aminoethyl)benzenesulfonyl fluoride hydrochloride, 200 μM sodium orthovanadate, 1 mM sodium fluoride, 10 μg/ml of leupeptin, 10 μg/ml of aprotinin/ml, 1 ug/ml of pepstatin and 50 ug/ml Na-p-Tosyl-L-lysine chloromethyl ketone hydrochloride.

Lysate were separated on 5-20% PAGE-SDS and immunoblots were performed using Immobilon P polyvinylidene difluoride membranes (Amersham) according to the manufacturer's instructions for handling. The blots were washed in Tris-buffered saline with 0.1% Tween 20 detergent (TBST). Tyr361/365/366 of TPR-Met were detected with polyclonal rabbit antibodies against tyrosine phosphorylated Met (Biosource International) and secondary antibodies anti-rabbit-horseradish peroxidase (Sigma) by chemiluminescence assays (Amersham, ECL) were performed according to the manufacturer's instructions and followed by film exposure. Signal was quantitated by densitometry on Alpha-Imager. IC$_{50}$ values were defined as the dose required to obtain 50% inhibition of the maximal HGF stimulated phosphorylated c-Met levels.

In Vivo Solid Tumor Disease Model

This test measures the capacity of compounds to inhibit solid tumor growth.

Tumor xenografts were established in the flank of female athymic CD1 mice (Charles River Inc.), by subcutaneous injection of 1×10$^6$ U87, A431 or SKLMS cells/mouse. Once established, tumors were then serially passaged s.c. in nude mice hosts. Tumor fragments from these host animals were used in subsequent compound evaluation experiments. For compound evaluation experiments female nude mice weighing approximately 20 g were implanted s.c. by surgical implantation with tumor fragments of ~30 mg from donor tumors. When the tumors were approximately 100 mm$^3$ in size (~7-10 days following implantation), the animals were randomized a separated into treatment and control groups. Each group contained 6-8 tumor-bearing mice, each of which was ear-tagged and followed individually throughout the experiment Mice were weighed and tumor measurements are taken by calipers three times weekly, starting on Day 1. These tumor measurements were converted to tumor volume by the well-known formula (L+W/4)$^3$ 4/37π. The experiment was terminated when the control tumors reached a size of approximately 1500 mm$^3$. In this model, the change in mean tumor volume for a compound treated group/the change in mean tumor volume of the control group (non-treated or vehicle treated)×100 (ΔT/ΔC) was subtracted from 100 to give the percent tumor growth inhibition (% TGI) for each test compound. In addition to tumor volumes, body weight of animals were monitored twice weekly for up to 3 weeks.

The activities of a number of compounds according to the invention measured by various assays are displayed in the following tables, Table 30 and Table 31. In these tables, "a" indicates inhibitory activity at a concentration of less than 50 nanomolar; "b" indicates inhibitory activity at a concentration ≧50 but <250 nanomolar, "c" indicates inhibitory activity at ≧250 but <500 and "d" indicates inhibitory activity at a concentration of ≧500 nanomolar; and "e" indicates no activity as measured by that assay.

HGF has well known activity in terms of inducing scattering and migration (wound healing) (Wells et al., Cell Motil Cytoskeleton. 2005 November 62(3):180-94; Miura et al., Urology December 2001 December 58(6):1064-9; Nishimura et al., Int J Urol. 1998 May 5(3):276-81; Wang et Cancer Ther. November 2003; 2(11):1085-92; and Christensen et al., Cancer Res. November 2003 1; 63(21):7345-55). Assays to evaluate inhibitor ability to block these HGF dependent activities have been employed and follow the methods employed in Christensen et al. For Table 31, for columns directed to A549 wound healing inhibition and DU145 scattering inhibition, IC$_{50}$ with "A" indicating IC$_{50}$ of less than 1 mM, "B" indicating IC$_{50}$ of >1 mM indicating IC$_{50}$ of ≧5 mM but <10 mM, and "D" indicating IC$_{50}$ of ≧10 mM.

TABLE 30

| Example No | Compound No | C-Met (enz.) (IC$_{50}$, nM) | VEGF(enz.) (IC$_{50}$, nM) | C-Met cell-based Y1230-34-35 tpr-met inhibition (IC$_{50}$, nM) |
|---|---|---|---|---|
| 1 | 8a | b | a | a |
| 2 | 8b | b | a | b |
| 3 | 8c | b | c | b |
| 5 | 8e | b | b | b |
| 7 | 8g | b | c | b |
| 9 | 8i | b | b | c |
| 10 | 8j | b | b | b |
| 11 | 8k | b | d | b |
| 12 | 13a | b | a | a |
| 13 | 13b | b | a | a |
| 14 | 13c | b | b | b |
| 15 | 13d | b | a | a |
| 133 | 170a | b | b | b |
| 16 | 13e | b | a | c |
| 18 | 13g | b | b | b |
| 20 | 18a | b | d | e |
| 22 | 26a | b | b | a |
| 23 | 26b | b | a | b |
| 24 | 26c | b | c | d |
| 25 | 26d | b | b | e |
| 26 | 26e | b | b | e |
| 27 | 26f | b | b | e |
| 28 | 31a | b | d | e |
| 29 | 31b | c | d | e |
| 35 | 8m | b | b | a |
| 36 | 8n | b | d | b |
| 37 | 8o | b | a | a |
| 40 | 8r | b | a | b |
| 75 | 13k | b | a | a |
| 142 | 26f | b | a | a |
| 188 | 170c | c | d | d |
| 221 | 269a | a | d | d |

TABLE 31

| Structure | CMet ic50 (nM) | VEGFR IC50 (nM) | A549 wound healing inhib IC50 (mM) | DU145 scattering inhib IC50 (mM) |
|---|---|---|---|---|
| | b | b | D | B |
| | a | a | B | B |
| | a | | B | A |
| | a | b | B | B |
| | b | b | A | A |

TABLE 31-continued

| Structure | CMet ic50 (nM) | VEGFR IC50 (nM) | A549 wound healing inhib IC50 (mM) | DU145 scattering inhib IC50 (mM) |
|---|---|---|---|---|
| 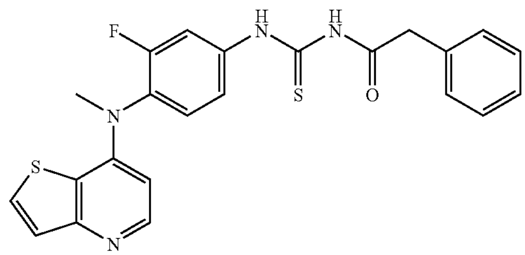 | c | d | C | C |
| | a | d | A | A |
| 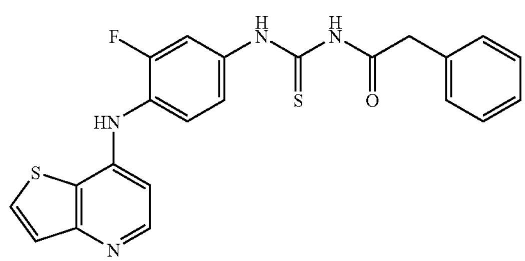 | b | d | A | B |
| | a | d | A | A |
| | a | a | A | A |

TABLE 31-continued

| Structure | CMet ic50 (nM) | VEGFR IC50 (nM) | A549 wound healing inhib IC50 (mM) | DU145 scattering inhib IC50 (mM) |
| --- | --- | --- | --- | --- |
| | a | d | A | A |
| | a | a | A | A |
| | a | a | C | A |
| 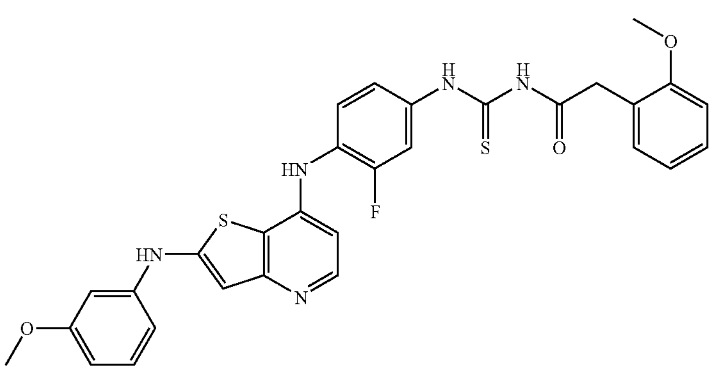 | b | d | B | B |

TABLE 31-continued
| Structure | CMet ic50 (nM) | VEGFR IC50 (nM) | A549 wound healing inhib IC50 (mM) | DU145 scattering inhib IC50 (mM) |
|---|---|---|---|---|
| 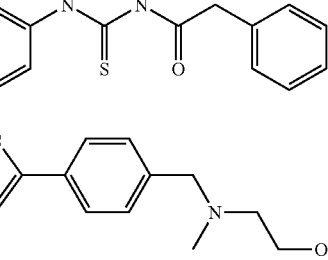 | a | a | A | A |
| 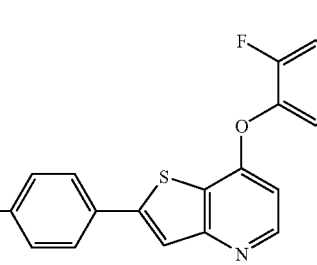 | a | a | A | A |
| 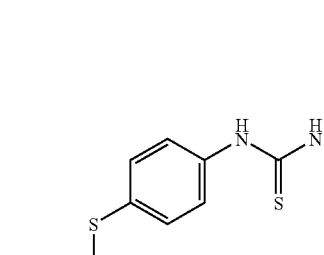 | a | d | A | A |
| 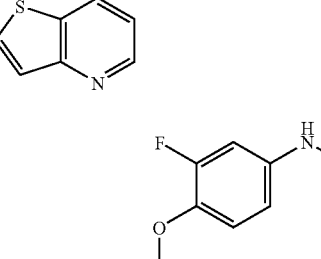 | a | c | A | A |
| 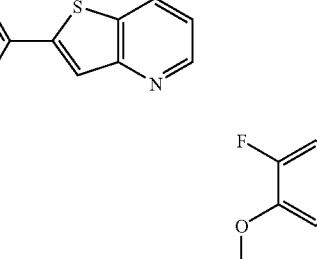 | a | a | B | A |

TABLE 31-continued

| Structure | CMet ic50 (nM) | VEGFR IC50 (nM) | A549 wound healing inhib IC50 (mM) | DU145 scattering inhib IC50 (mM) |
|---|---|---|---|---|
| (structure) | a | a | A | A |
| (structure) | a | a | B | A |
| (structure) | a | c | A | A |
| (structure) | a | a | A | A |

TABLE 31-continued

| Structure | CMet ic50 (nM) | VEGFR IC50 (nM) | A549 wound healing inhib IC50 (mM) | DU145 scattering inhib IC50 (mM) |
| --- | --- | --- | --- | --- |
| | a | a | A | A |
| | a | b | A | A |
| | a | a | A | A |
| | a | a | A | A |
| | a | a | A | A |

TABLE 31-continued
| Structure | CMet ic50 (nM) | VEGFR IC50 (nM) | A549 wound healing inhib IC50 (mM) | DU145 scattering inhib IC50 (mM) |
|---|---|---|---|---|
| 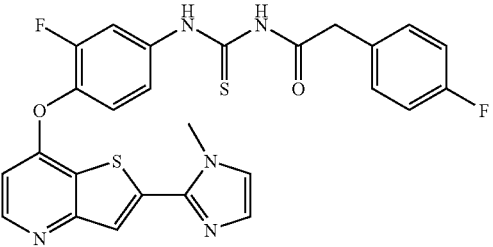 | a | a | A | A |
| 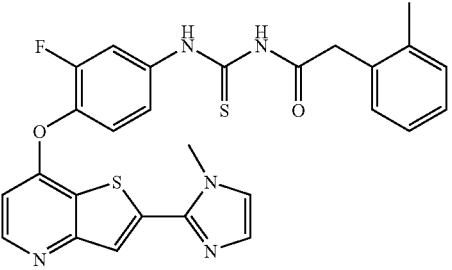 | a | a | A | A |
| 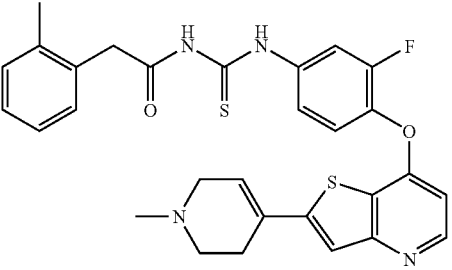 | a | c | A | A |
| 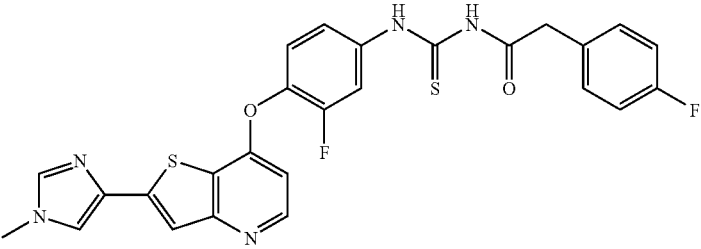 | a | a | A | A |
| 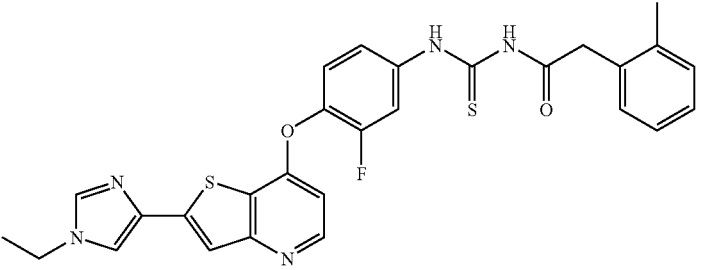 | a | a | A | A |

TABLE 31-continued
| Structure | CMet ic50 (nM) | VEGFR IC50 (nM) | A549 wound healing inhib IC50 (mM) | DU145 scattering inhib IC50 (mM) |
| --- | --- | --- | --- | --- |
| 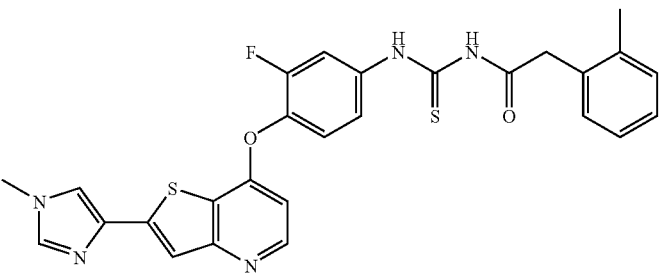 | a | a | A | |
| 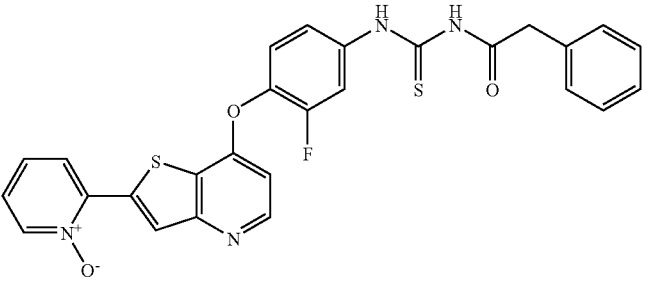 | a | b | A | A |
| 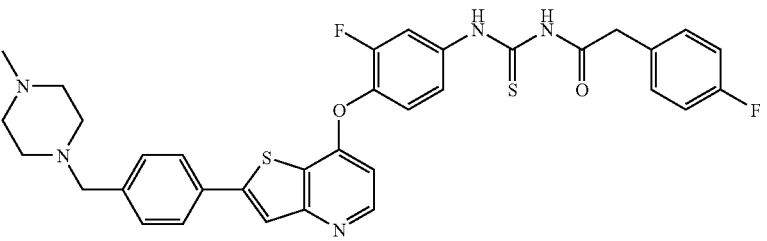 | a | a | A | A |
| 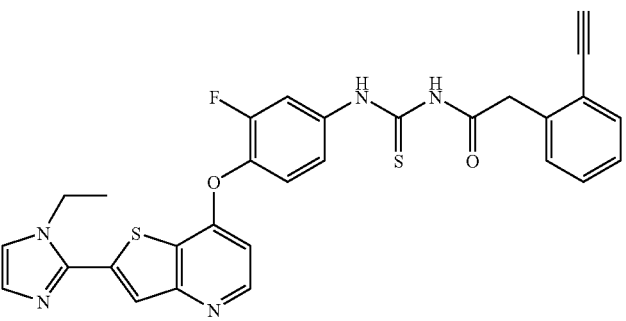 | a | a | A | A |
| 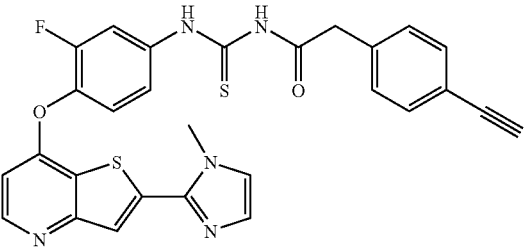 | b | b | B | D |

TABLE 31-continued
| Structure | CMet ic50 (nM) | VEGFR IC50 (nM) | A549 wound healing inhib IC50 (mM) | DU145 scattering inhib IC50 (mM) |
| --- | --- | --- | --- | --- |
| 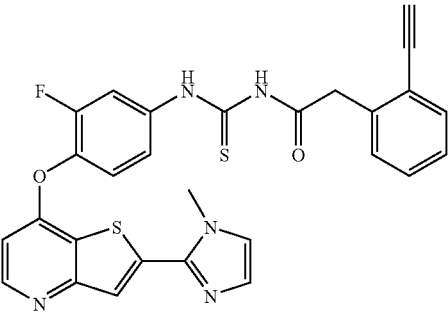 | a | a | A | A |
| 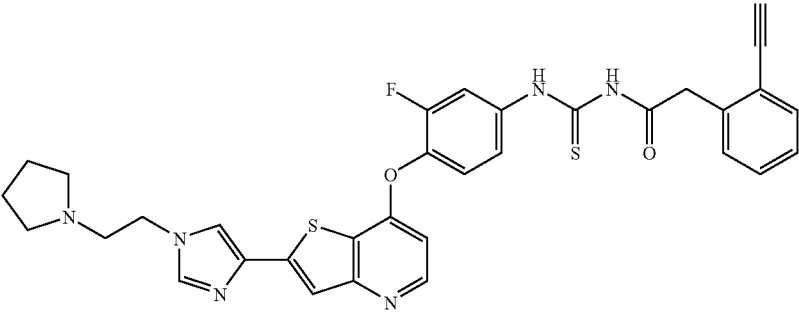 | a | a | A | A |
| 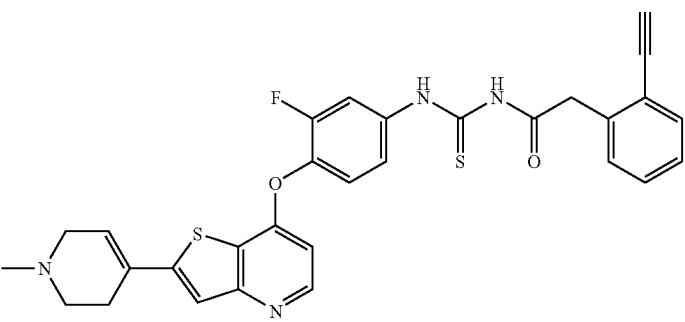 | a | b | A | A |
| 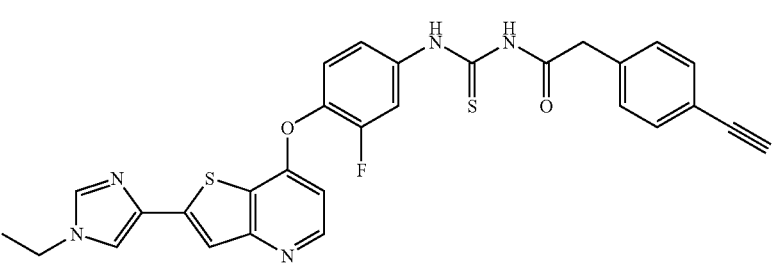 | b | a | B | B |

TABLE 31-continued

| Structure | CMet ic50 (nM) | VEGFR IC50 (nM) | A549 wound healing inhib IC50 (mM) | DU145 scattering inhib IC50 (mM) |
|---|---|---|---|---|
| | a | a | A | A |
| 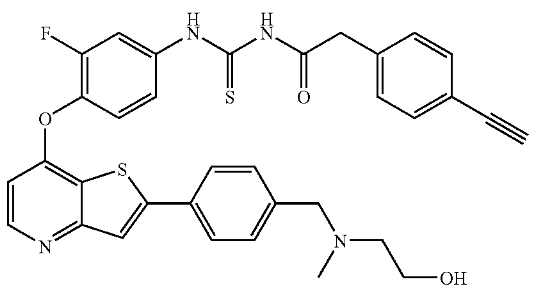 | b | a | D | D |
| | a | a | A | A |
| | a | b | A | A |
| | a | a | A | A |

TABLE 31-continued

| Structure | CMet ic50 (nM) | VEGFR IC50 (nM) | A549 wound healing inhib IC50 (mM) | DU145 scattering inhib IC50 (mM) |
| --- | --- | --- | --- | --- |
| | a | a | B | B |
| | b | a | D | D |
| | b | a | D | B |
| | b | a | A | B |
| | a | a | B | B |

TABLE 31-continued
| Structure | CMet ic50 (nM) | VEGFR IC50 (nM) | A549 wound healing inhib IC50 (mM) | DU145 scattering inhib IC50 (mM) |
|---|---|---|---|---|
| 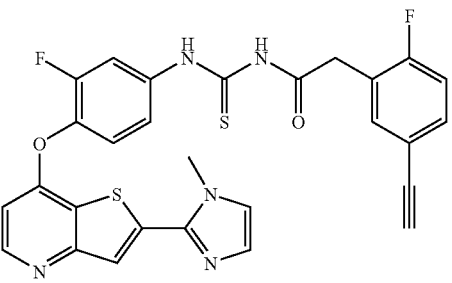 | a | a | B | B |
| 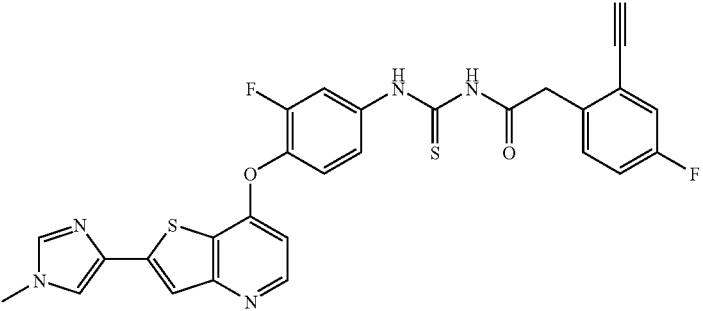 | a | a | A | A |
| 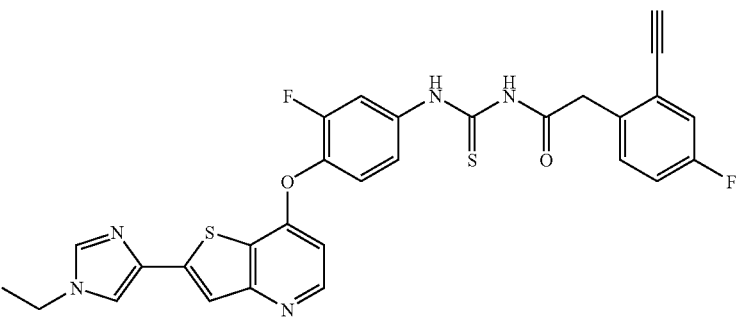 | a | a | A | A |
| 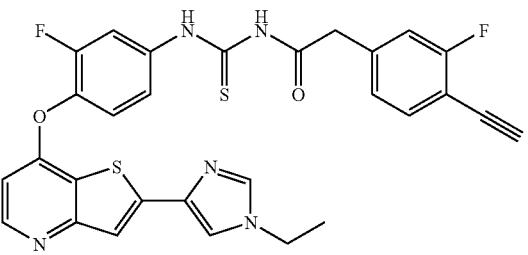 | b | a | D | B |

TABLE 31-continued

| Structure | CMet ic50 (nM) | VEGFR IC50 (nM) | A549 wound healing inhib IC50 (mM) | DU145 scattering inhib IC50 (mM) |
|---|---|---|---|---|
| | a | a | A | A |
| 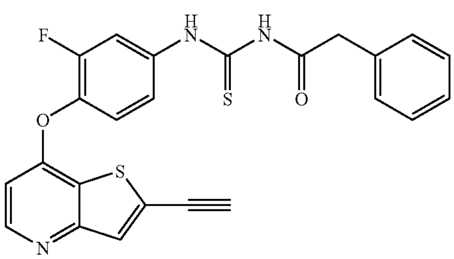 | b | d | D | B |
| | a | a | A | A |
| | a | a | A | A |

TABLE 31-continued

| Structure | CMet ic50 (nM) | VEGFR IC50 (nM) | A549 wound healing inhib IC50 (mM) | DU145 scattering inhib IC50 (mM) |
| --- | --- | --- | --- | --- |
| | a | a | B | A |
| | a | a | A | A |
| | a | a | A | A |
| | a | b | A | A |

TABLE 31-continued
| Structure | CMet ic50 (nM) | VEGFR IC50 (nM) | A549 wound healing inhib IC50 (mM) | DU145 scattering inhib IC50 (mM) |
|---|---|---|---|---|
| 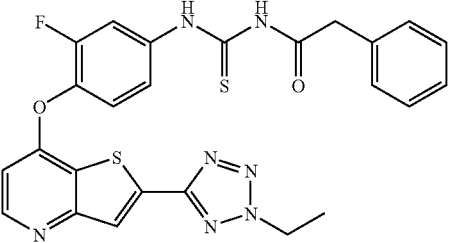 | a | c | A | A |
| 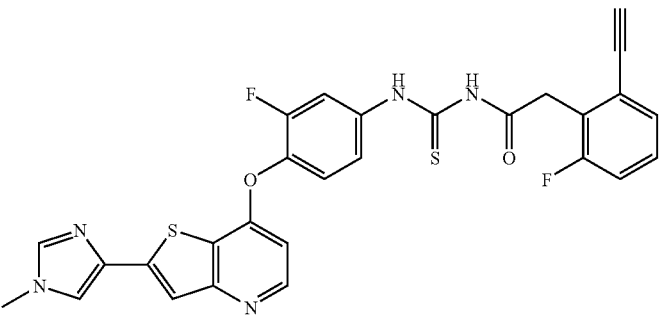 | a | a | A | A |
| 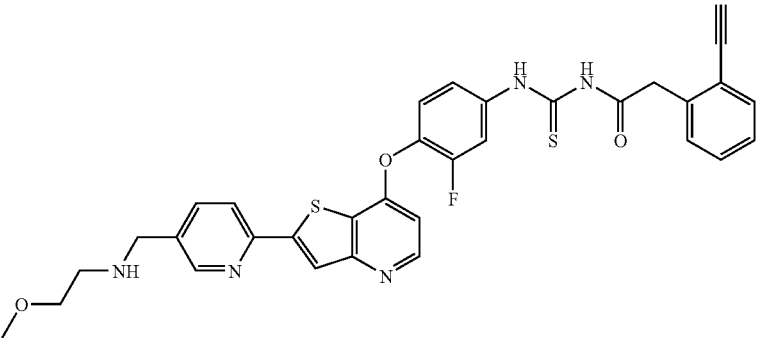 | a | a | A | A |
| 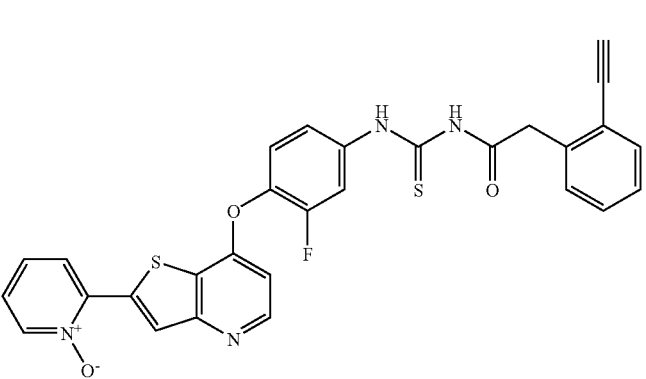 | a | a | A | A |

TABLE 31-continued

| Structure | CMet ic50 (nM) | VEGFR IC50 (nM) | A549 wound healing inhib IC50 (mM) | DU145 scattering inhib IC50 (mM) |
|---|---|---|---|---|
| | a | a | A | A |
| | a | b | A | A |
| | a | a | A | A |
| | a | a | A | A |

TABLE 31-continued
| Structure | CMet ic50 (nM) | VEGFR IC50 (nM) | A549 wound healing inhib IC50 (mM) | DU145 scattering inhib IC50 (mM) |
|---|---|---|---|---|
| 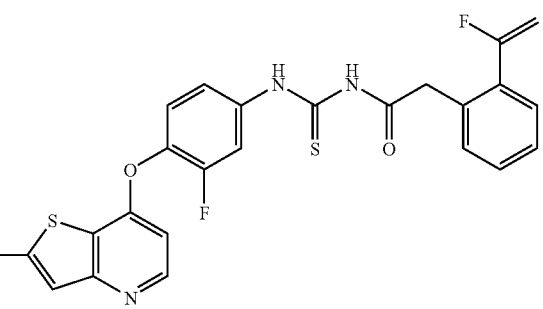 | a | a | A | A |
| 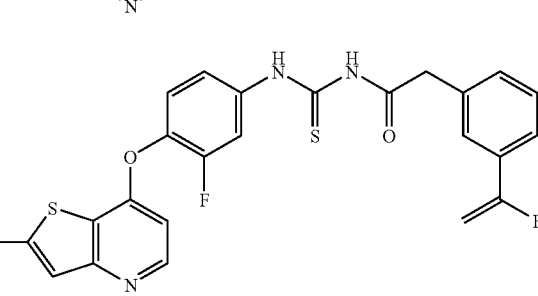 | b | b | B | B |
| 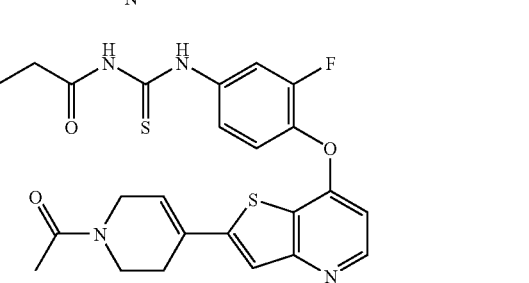 | a | a | A | A |
| 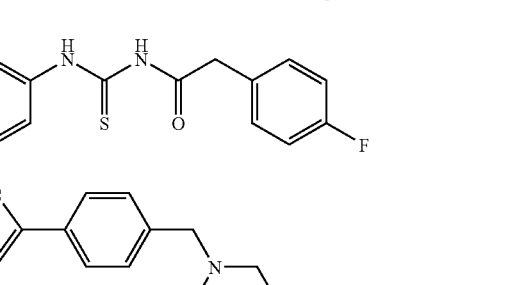 | a | a | A | A |
| 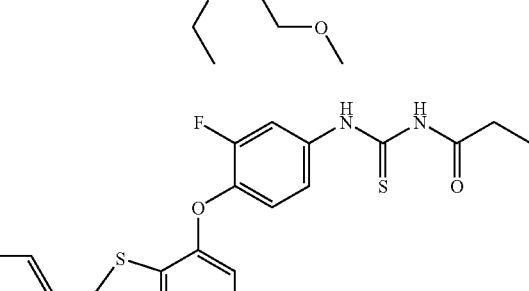 | a | b | A | A |

TABLE 31-continued

| Structure | CMet ic50 (nM) | VEGFR IC50 (nM) | A549 wound healing inhib IC50 (mM) | DU145 scattering inhib IC50 (mM) |
|---|---|---|---|---|
| | a | a | A | A |
| | a | | A | A |
| | a | c | A | A |
| | a | a | | A |
| | a | b | A | A |

TABLE 31-continued

| Structure | CMet ic50 (nM) | VEGFR IC50 (nM) | A549 wound healing inhib IC50 (mM) | DU145 scattering inhib IC50 (mM) |
|---|---|---|---|---|
| 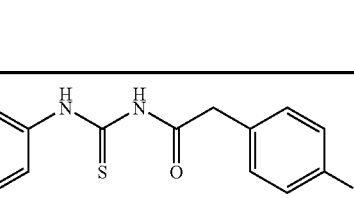 | | | A | A |
| 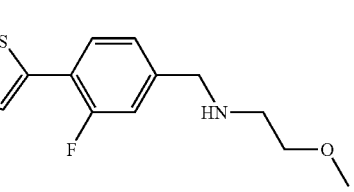 | | | A | A |

In the following tables, Table 32 and Table 33, "a" indicates % TGI in the range of 75-100; "b" indicates % TGI in the range of 50-74; "c" indicates % TGI in the range of 25-49, and "d" indicates % TGI in the range of 0-24. Regiment of administration was once daily.

TABLE 32

| Ex (Cpd) | Dosage mg/kg (once daily) | Vehicle | Tumor type | Duration of experiment (days) | Route of administration | Tumor Growth Inhibition (%) |
|---|---|---|---|---|---|---|
| 1 (8a) | 30 | DMSO | A431 | 14 | IP | d |
|  | 30 | DMSO | A549 | 14 | IP | b |
|  | 100 | 5% DMSO - 1% Tween-80 in water | U87MG | 14 | PO | c |
|  | 15 | DMSO | MKN74 | 10 | IP | d |
|  | 30 | DMSO | MKN74 | 10 | IP | c |
|  | 15 | DMSO | U87MG | 10 | IP | c |
|  | 30 | DMSO | U87MG | 7 | IP | c |
|  | 30 | DMSO | A431 | 14 | IP | c |
|  | 30 | DMSO | U87MG | 14 | IP | c |
|  | 30 | DMSO | SKLMS40 | 14 | IP | b |
|  | 30 | DMSO | SW48 | 14 | IP | b |
|  | 30 | DMSO | U87MG | 14 | IP | a* |
|  | 30 | DMSO | HCT116 | 14 | IP | c |
| 7 (8g) | 30 | DMSO | SW48 | 14 | IP | c |
|  | 30 | DMSO | HCT116 | 14 | IP | b |
| 12 (13a) | 30 | DMSO | SW48 | 14 | IP | b |
|  | 30 | DMSO | U87MG | 14 | IP | b |
|  | 30 | DMSO | HST116 | 14 | IP | c |
|  | 30 | DMSO | SW48 | 14 | IP | d |
| 13 (13b) | 30 | DMSO | A431 | 7 | IP | b |
|  | 30 | DMSO | SW48 | 14 | IP | d |
|  | 30 | DMSO | U87MG | 14 | IP | a |
|  | 30 | DMSO | DU145 | 10 | IP | d |
|  | 30 | DMSO | SKLMS40 | 10 | IP | b |
| 37 (8o) | 15 | DMSO | DU145 | 10 | IP | d |

TABLE 32-continued

| Ex (Cpd) | Dosage mg/kg (once daily) | Vehicle | Tumor type | Duration of experiment (days) | Route of administration | Tumor Growth Inhibition (%) |
|---|---|---|---|---|---|---|
| | 30 | DMSO | DU145 | 10 | IP | d |
| | 30 | DMSO | A431 | 14 | IP | b |
| | 30 | DMSO | A549 | 14 | IP | c |
| | 15 | 50/50 DMSO:40/60 PEG/0.2 N HCl in saline | U87MG | 10 | IV | b |
| | 30 | 50/50 DMSO:40/60 PEG/0.2 N HCl in saline | U87MG | 10 | IV | c |
| 15 (13d) | 30 | DMSO | DU145 | 10 | IP | b |
| | 30 | DMSO | SKLMS40 | 10 | IP | b |
| | 30 | DMSO | A431 | 14 | IP | b |
| | 30 | DMSO | A549 | 14 | IP | b |
| | 15 | DMSO | DU145 | 10 | IP | d |
| | 30 | DMSO | DU145 | 10 | IP | d |
| | 15 | 50/50 DMSO:40/60 PEG/0.2 N HCl in saline | U87MG | 10 | IV | b |
| | 30 | 50/50 DMSO:40/60 PEG/0.2 N HCl in saline | U87MG | 10 | IV | b |
| | 100 | 5% DMSO - 1% Tween-80 in water | U87MG | 14 | PO | a |
| | 30 | DMSO | U87MG | 14 | IP | b |
| | 75 | 5% DMSO - 1% Tween-80 in water | A549 | 12 | PO | c |
| | 50 | 5% DMSO - 1% Tween-80 in water | A549 | 11 | PO | c |
| | 75 | 5% DMSO - 1% Tween-80 in water | A549 | 10 | PO | b |
| | 15 | DMSO | MKN74 | 10 | IP | c |
| | 30 | DMSO | MKN74 | 10 | IP | c |
| | 15 | DMSO | U87MG | 10 | IP | b |
| | 30 | DMSO | U87MG | 10 | IP | b |
| | 15 | DMSO | HCT116 | 10 | IP | c |
| | 30 | DMSO | HCT116 | 10 | IP | c |
| 75 (13k) | 15 | DMSO | DU145 | 10 | IP | c |
| | 15 | DMSO | SKLMS40 | 10 | IP | b |
| | 100 | 5% DMSO - 1% Tween-80 in water | U87MG | 14 | PO | b |
| | 30 | DMSO | U87MG | 14 | IP | c |
| | 75 | 5% DMSO - 1% Tween-80 in water | A549 | 12 | PO | b |
| | 30 | DMSO | U87MG | 10 | IP | c |
| | 15 | DMSO | U87MG | 10 | IP | d |
| 73 (13i) | 100 | 5% DMSO - 1% Tween-80 in water | U87MG | 14 | PO | c |
| 38 (8p) | 30 | DMSO | A431 | 14 | IP | c |
| | 30 | DMSO | A549 | 14 | IP | c |
| 39 (8q) | 30 | DMSO | A549 | 14 | IP | b |
| 148 (26l) | 30 | DMSO | DU145 | 10 | IP | c |
| | 30 | 50/50 DMSO:40/60 PEG/0.2 N HCl in saline | U87MG | 10 | IP | c |
| 76 (13l) | 75 | 5% DMSO - 1% Tween-80 in water | A549 | 10 | PO | b |
| | 75 | 5% DMSO - 1% Tween-80 in water | DU145 | 10 | PO | c |
| | 30 | DMSO | A549 | 14 | IP | b |
| | 75 | 5% DMSO - 1% Tween-80 in water | A549 | 14 | PO | c |
| 157 (195b) | 30 | DMSO | A341 | 14 | IP | c |
| | 30 | DMSO | A549 | 14 | IP | c |
| 56 (55) | 30 | DMSO | A549 | 12 | IP | c |
| 63 (76c) | 30 | DMSO | A549 | 10 | IP | b |
| | 30 | DMSO | DU145 | 10 | IP | c |
| 77 (13m) | 30 | DMSO | A549 | 10 | IP | b |
| | 75 | 5% DMSO - 1% Tween-80 in water | A549 | 10 | PO | b |
| | 75 | 5% DMSO - 1% Tween-80 in water | U87MG | 14 | PO | b |
| | 75 | 5% DMSO - 1% Tween-80 in water | SKLMS40 | 6 | PO | d |
| 201 (227) | 30 | DMSO | A549 | 10 | IP | c |
| | 75 | 5% DMSO - 1% Tween-80 in water | A549 | 10 | PO | c |
| 81 (13q) | 75 | 5% DMSO - 1% Tween-80 in water | SKLMS40 | 14 | PO | c |
| 242 (310a) | 75 | 5% DMSO - 1% Tween-80 in water | U87MG | 14 | PO | a |
| | 75 | 5% DMSO - 1% Tween-80 in water | HCT116 | 14 | PO | b |
| 243 (310b) | 75 | 5% DMSO - 1% Tween-80 in water | U87MG | 14 | PO | b |
| | 75 | 5% DMSO - 1% Tween-80 in water | SKLMS40 | 11 | PO | b |
| 137 (178) | 75 | 0.5% CMC in acetate buffer (pH 4.0) | MDA-MB-231 | 14 | PO | b |
| 138 (179) | 75 | 0.5% CMC in acetate buffer (pH 4.0) | MDA-MB-231 | 14 | PO | b | a* - greater than 100% tumor growth inhibition (i.e., tumor shrinkage)

TABLE 33

| Structure | Dosage mg/kg (once daily) | Tumor type | Duration of experiment (days) | Tumor Growth Inhibition (%) |
|---|---|---|---|---|
| | 40 (p.o.) | MNNG-HOS | 14 | a |
| 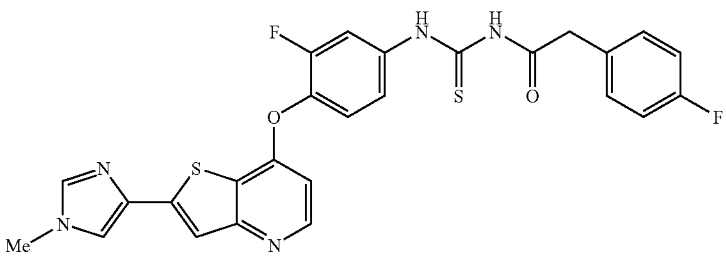 | 75 (p.o.) | MNNG-HOS | 14 | a* |
| | 20 (p.o.) | MNNG-HOS | 14 | c |
| | 40 (p.o.) | A549 | 14 | b |
| | 20 (p.o.) | MV4-11 | 14 | a | a* - greater than 100% tumor growth inhibition (i.e., tumor shrinkage)

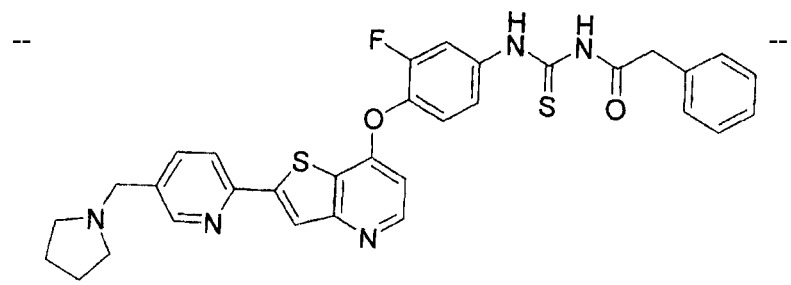

What is claimed is:
1. A compound selected from the group consisting of
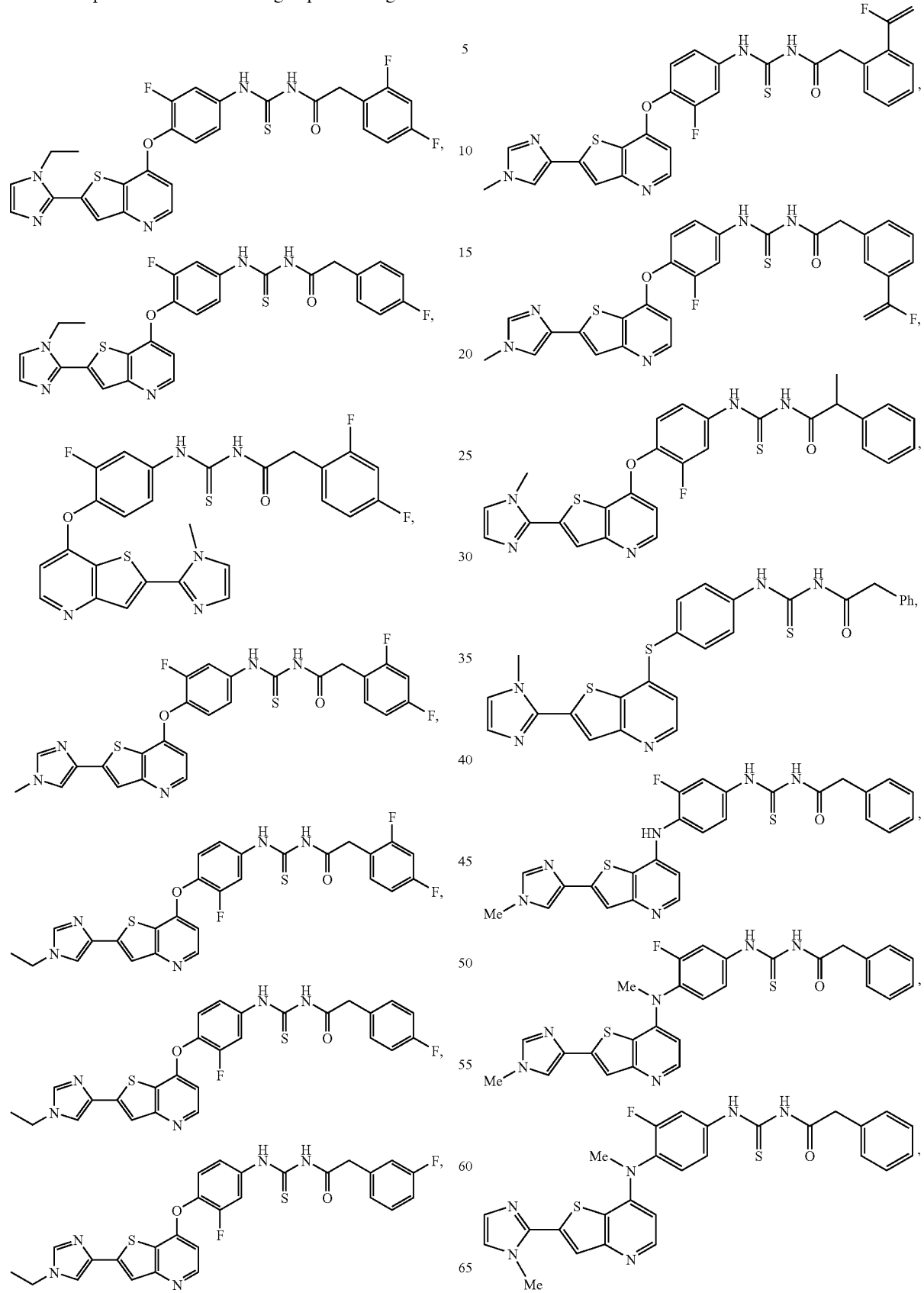

-continued
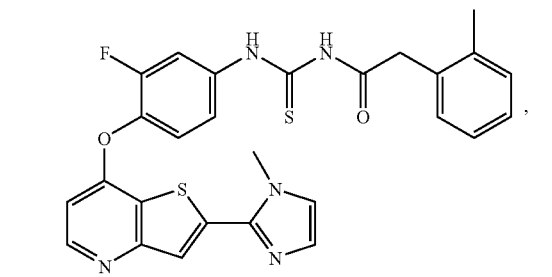
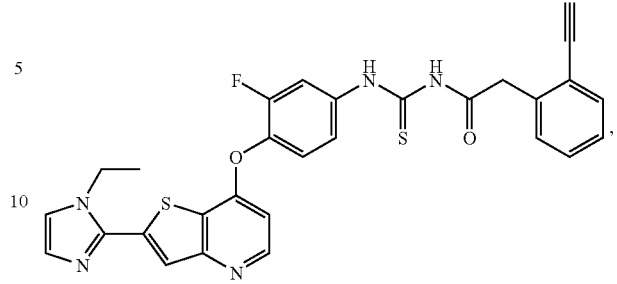
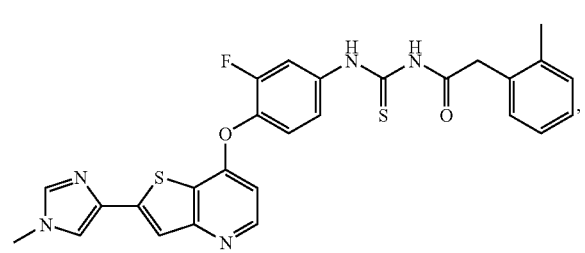
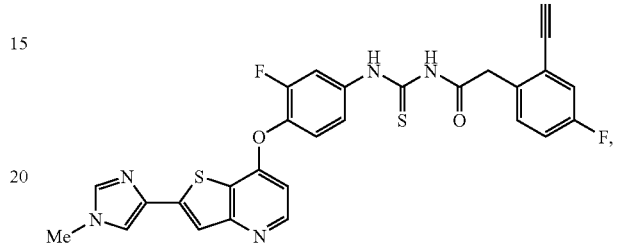
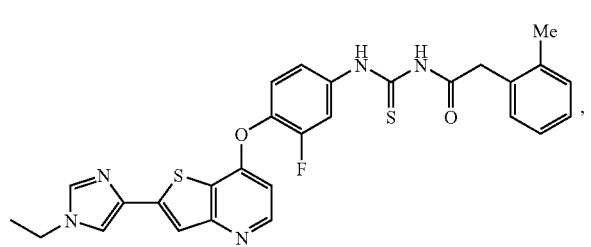
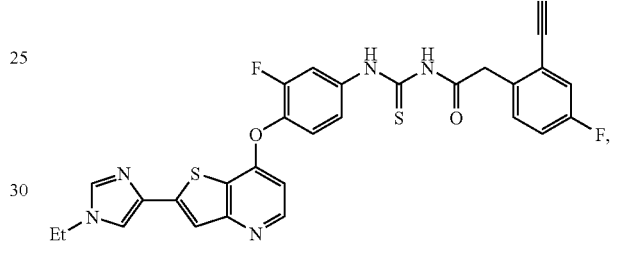
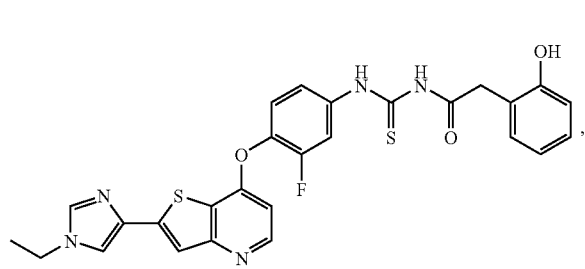
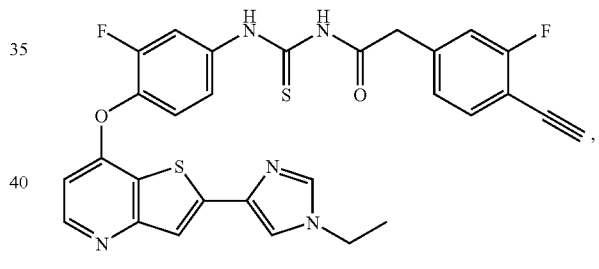
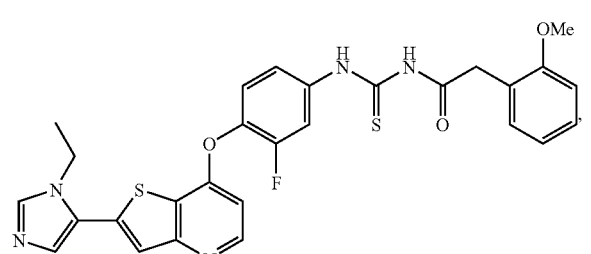
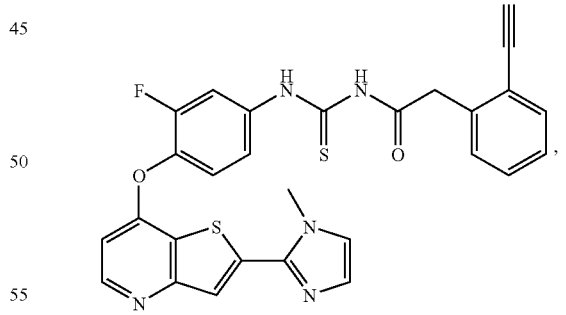
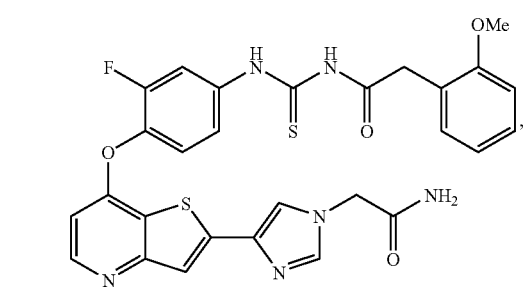
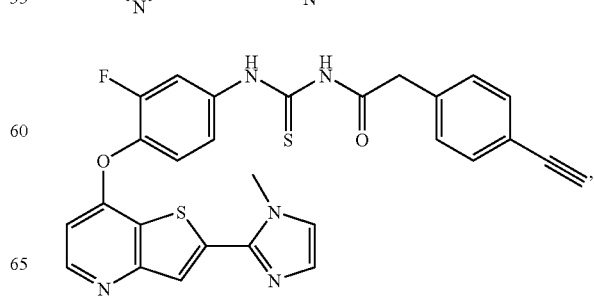

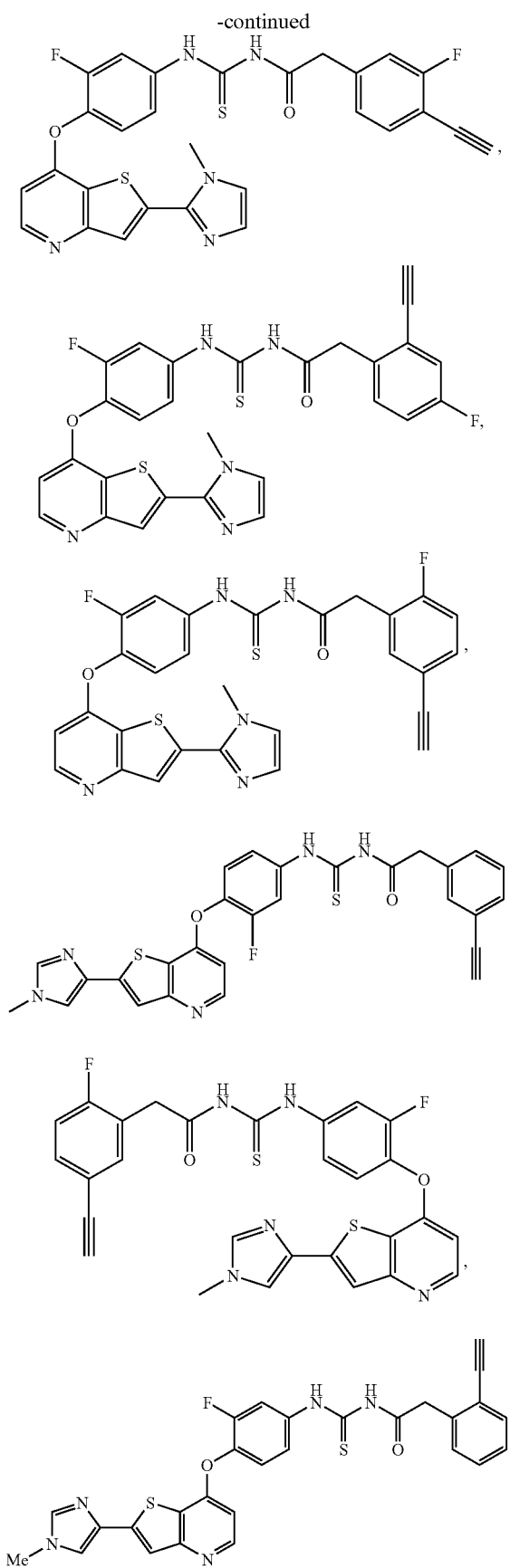

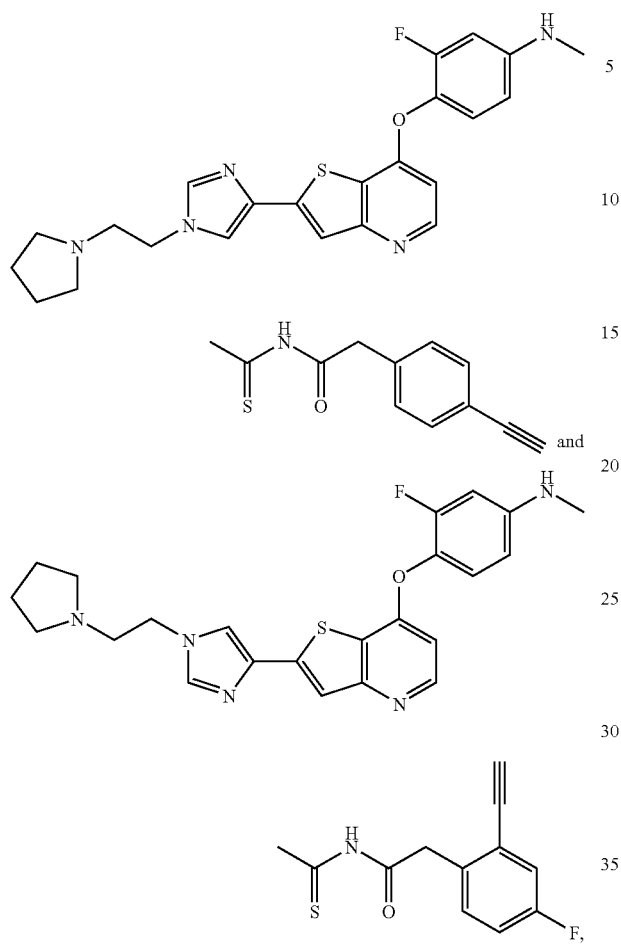
and pharmaceutically acceptable salts thereof.
2. A compound selected from the group consisting of
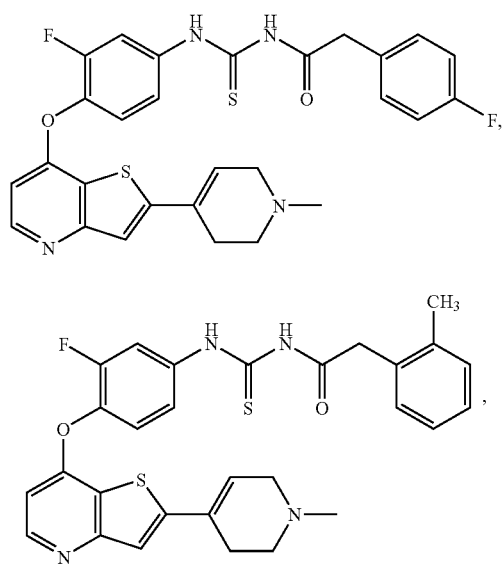
and pharmaceutically acceptable salts thereof.
3. A compound selected from the group consisting of -continued
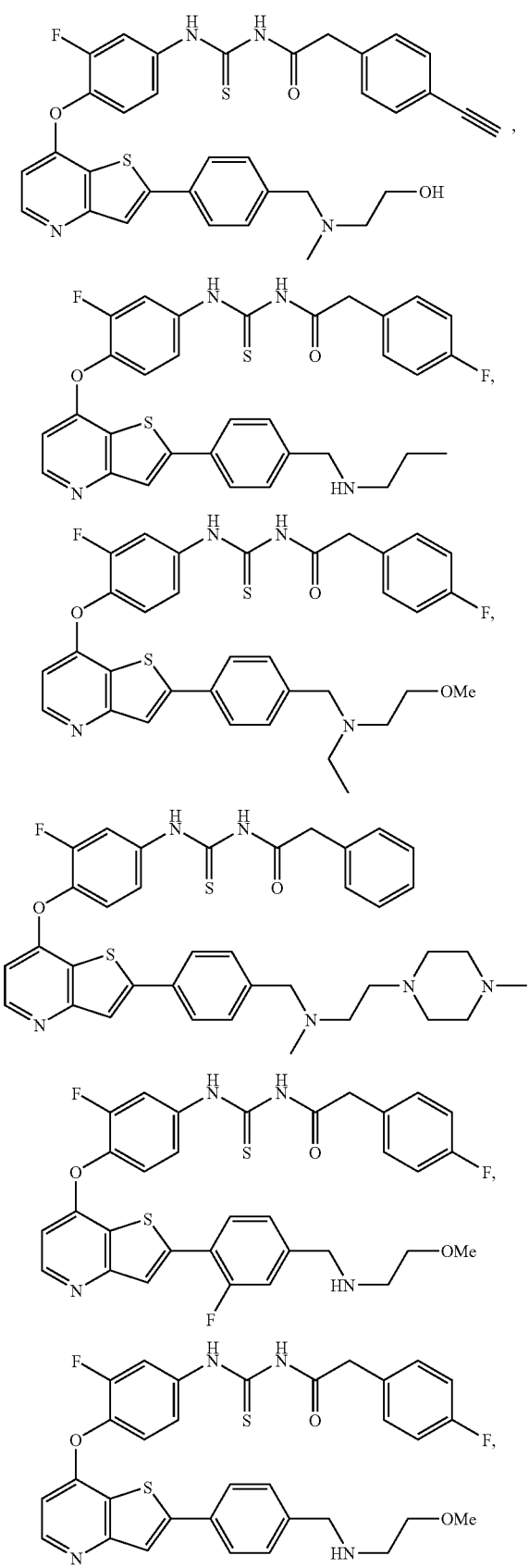
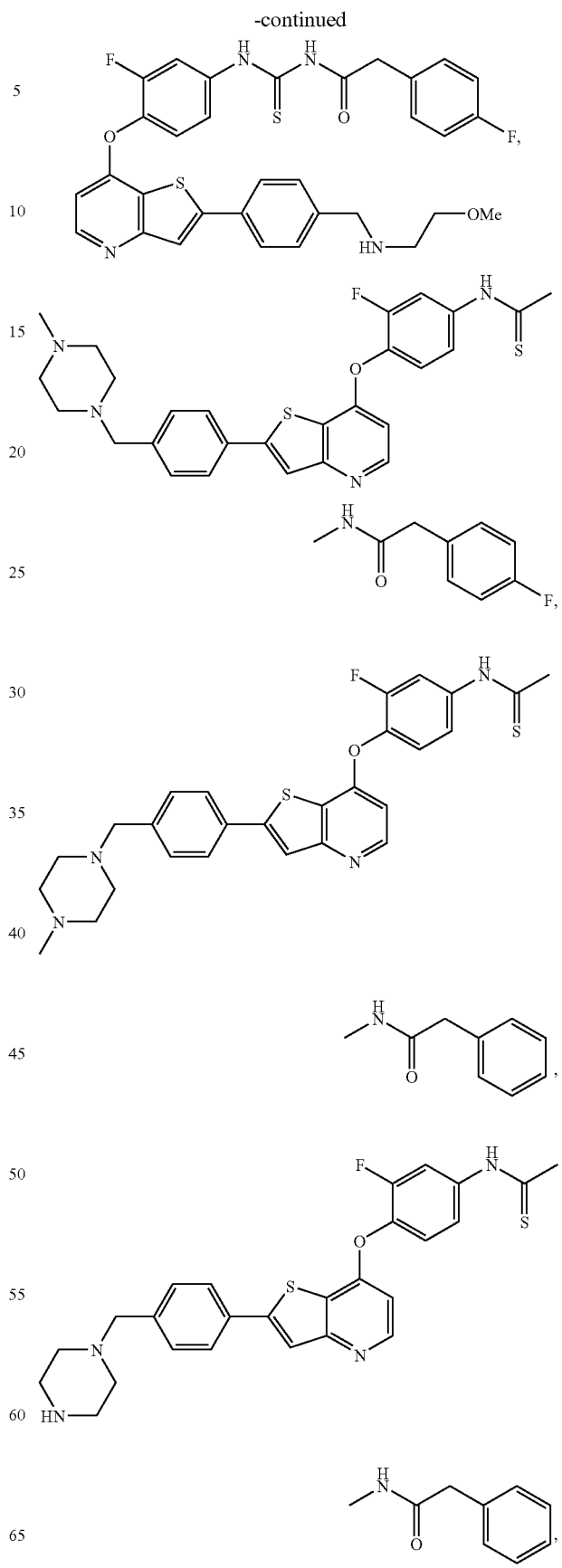

431
-continued
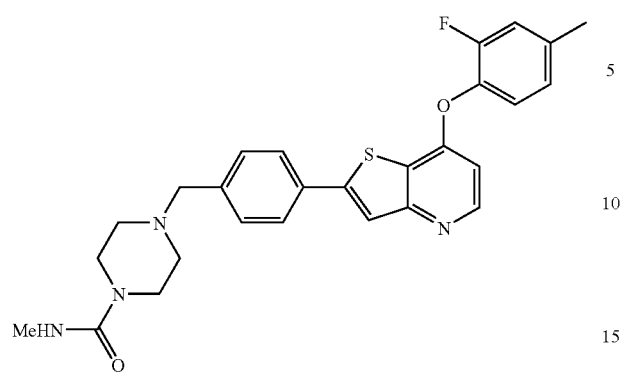
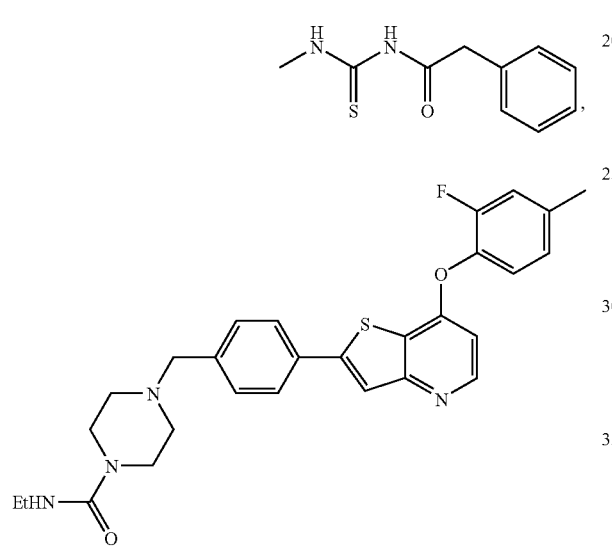
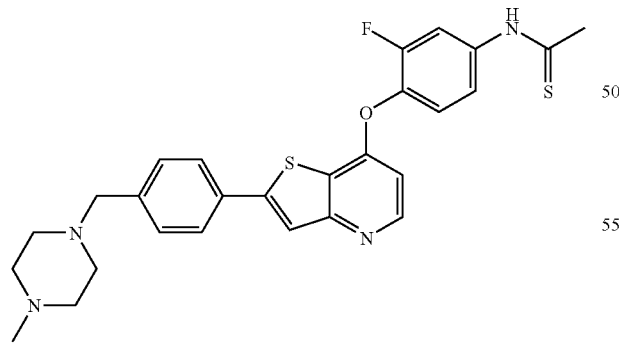
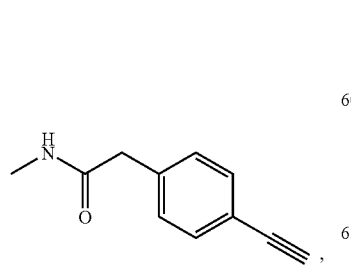
432
-continued
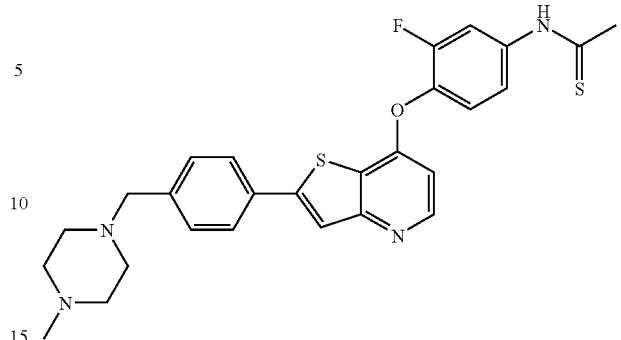
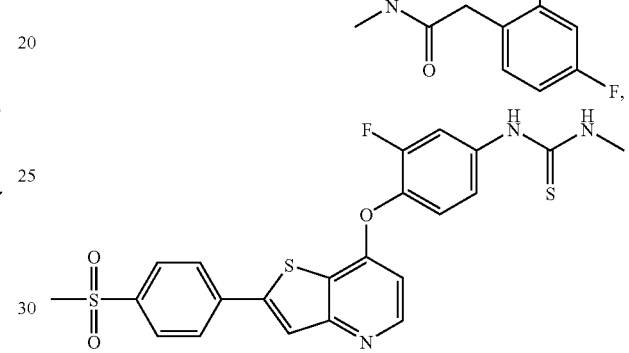
 and
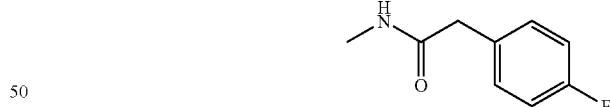
and pharmaceutically acceptable salts thereof.
4. A compound selected from the group consisting of
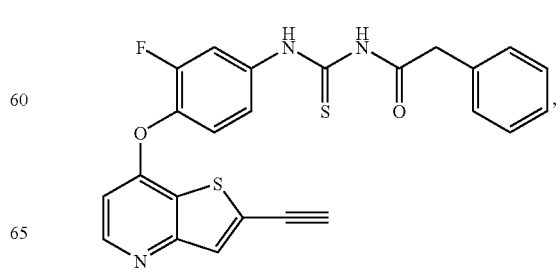

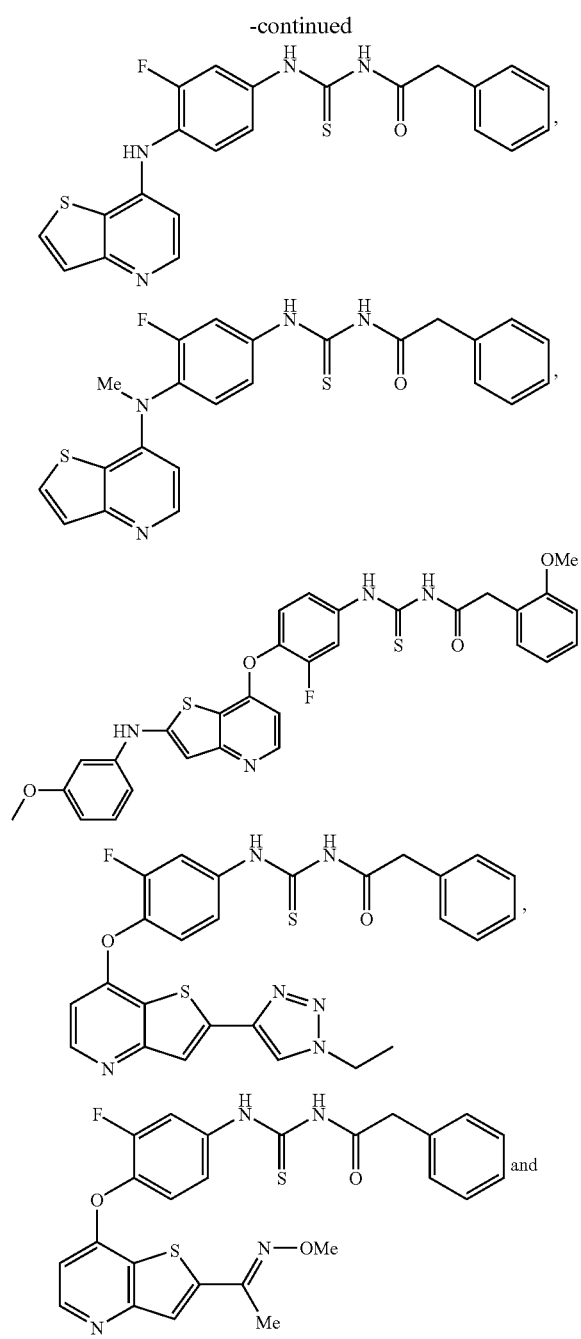
and pharmaceutically acceptable salts thereof.
5. A compound selected from the group consisting of
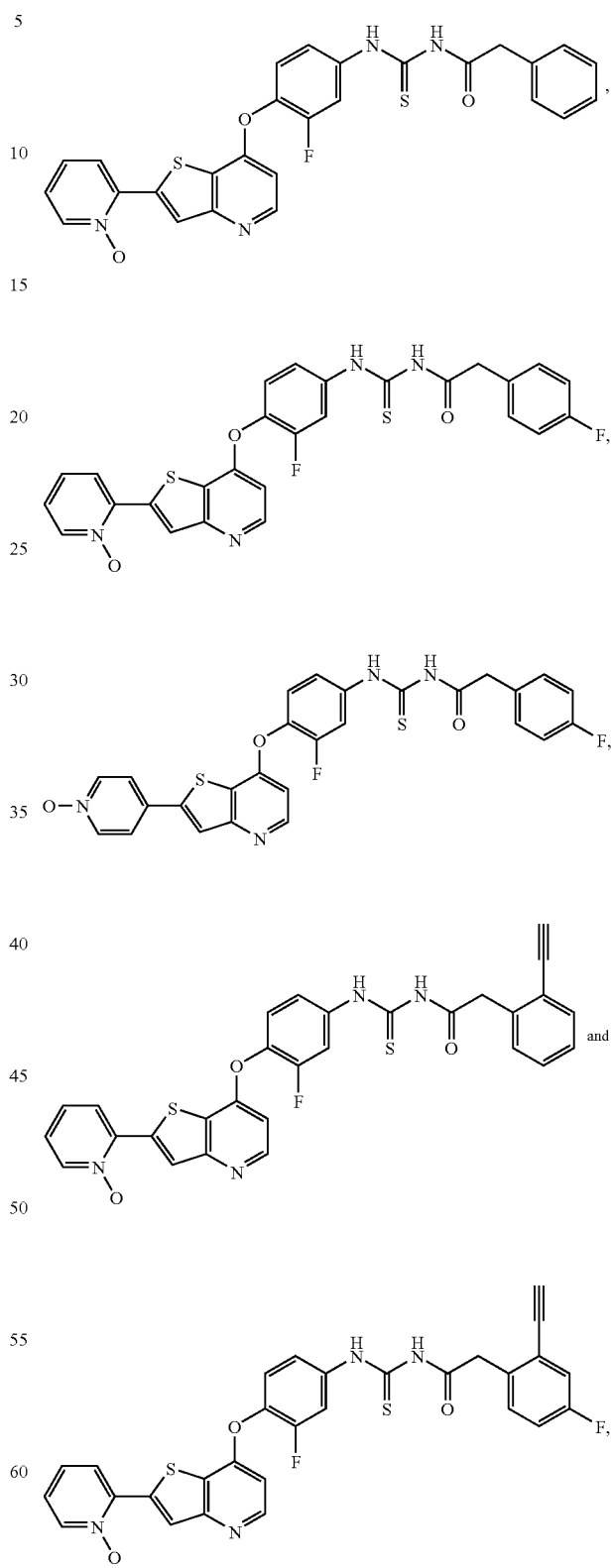
and pharmaceutically acceptable salts thereof.

6. A compound selected from the group consisting of
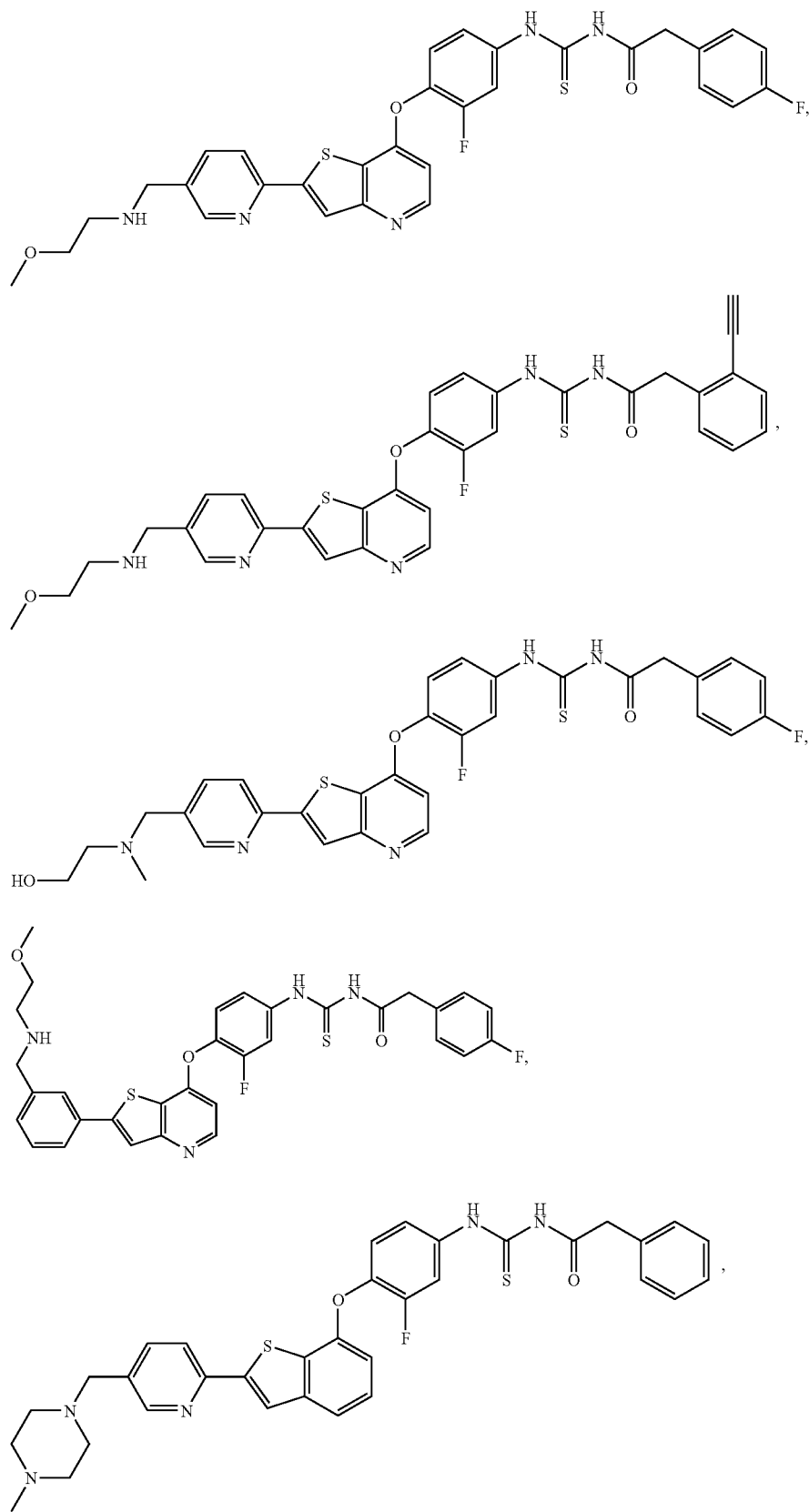

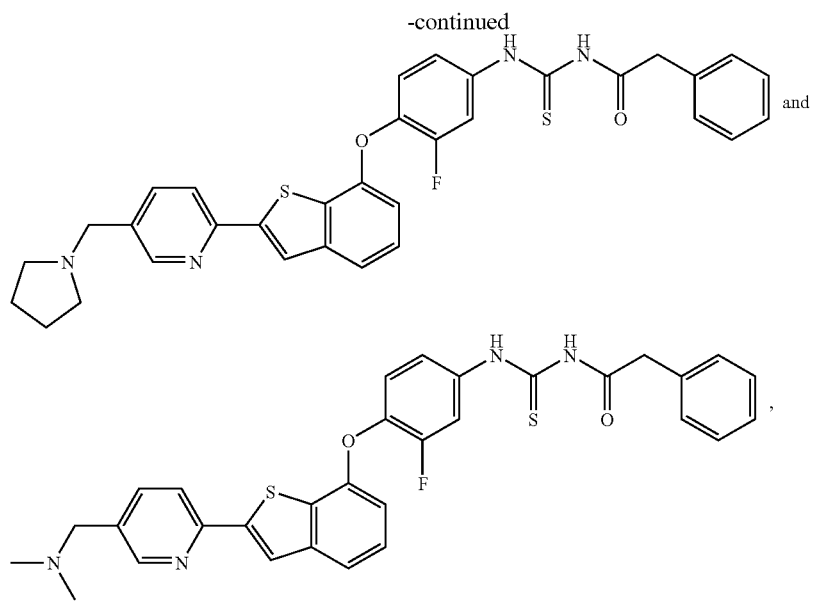

and pharmaceutically acceptable salts thereof.

7. The compound according to claim 1, having the structure

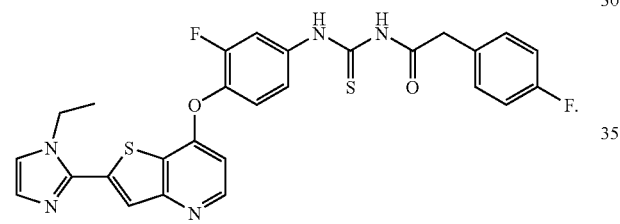

8. The compound according to claim 1, having the structure

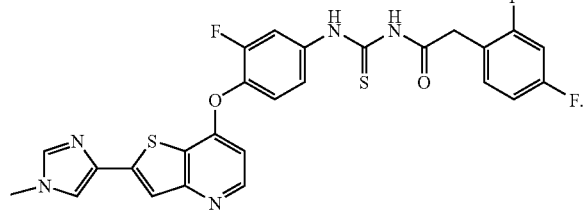

9. The compound according to claim 1, having the structure

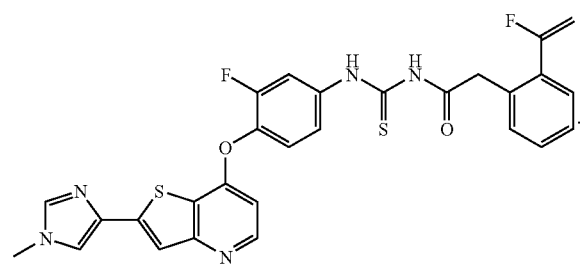

10. The compound according to claim 1, having the structure

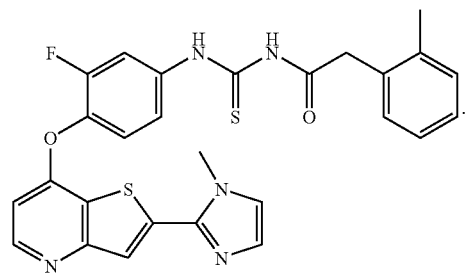

11. The compound according to claim 1, having the structure

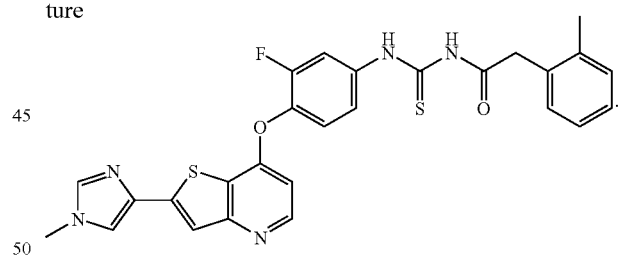

12. The compound according to claim 1, having the structure

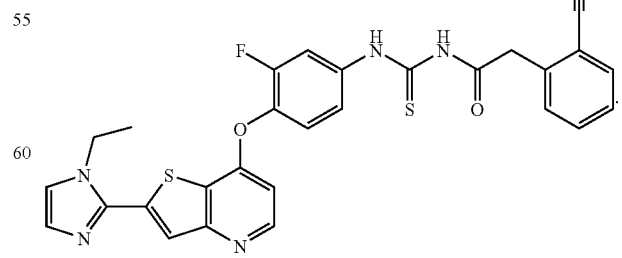

13. The compound according to claim 1, having the structure

15. The compound according to claim 1, having the structure
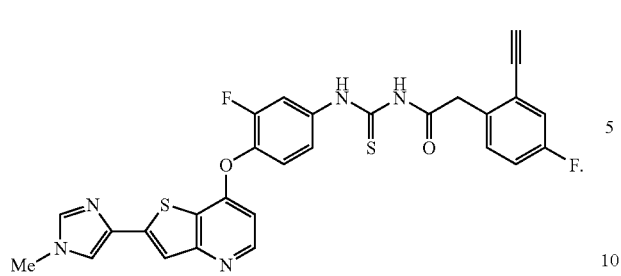
14. The compound according to claim 1, having the structure
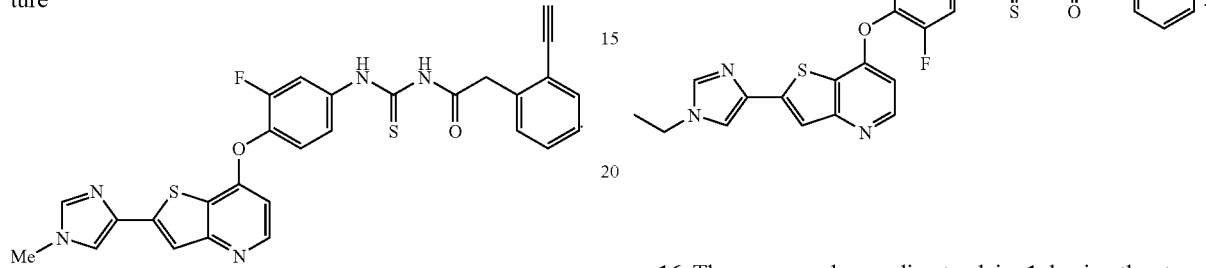
16. The compound according to claim 1, having the structure
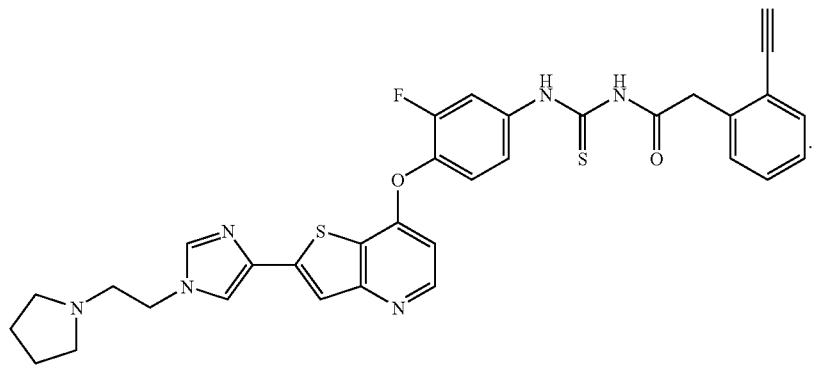
17. The compound according to claim 1, having the structure
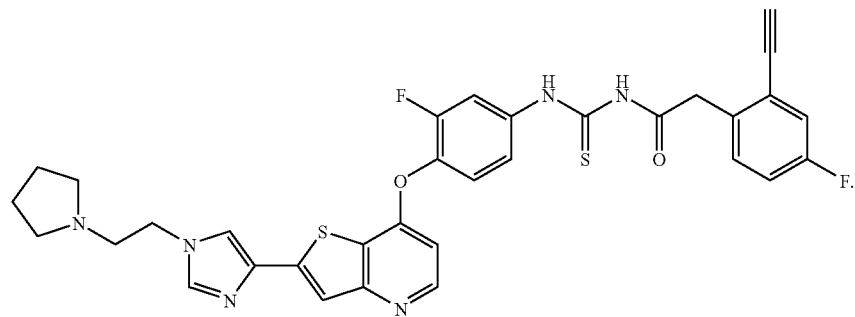

18. The compound according to claim 2, having the structure
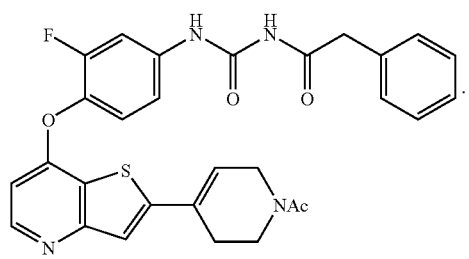
19. The compound according to claim 3, having the structure
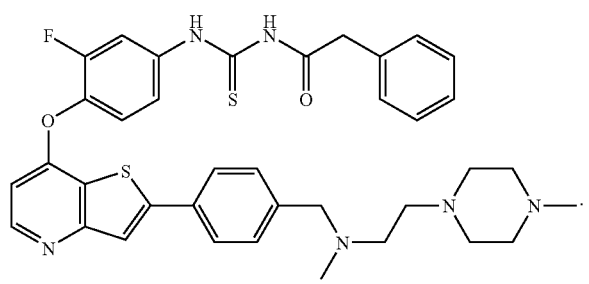
20. The compound according to claim 3, having the structure
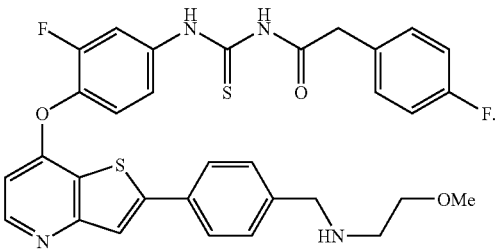
21. The compound according to claim 3, having the structure
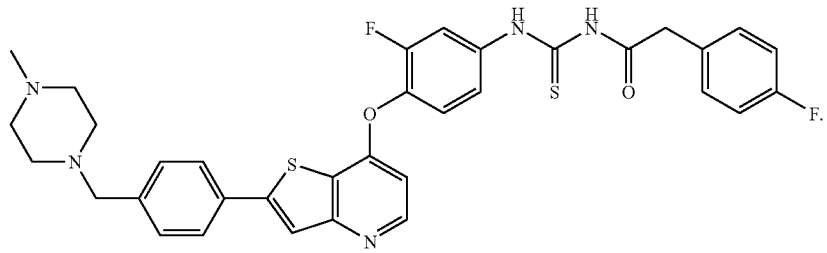
22. The compound according to claim 3, having the structure
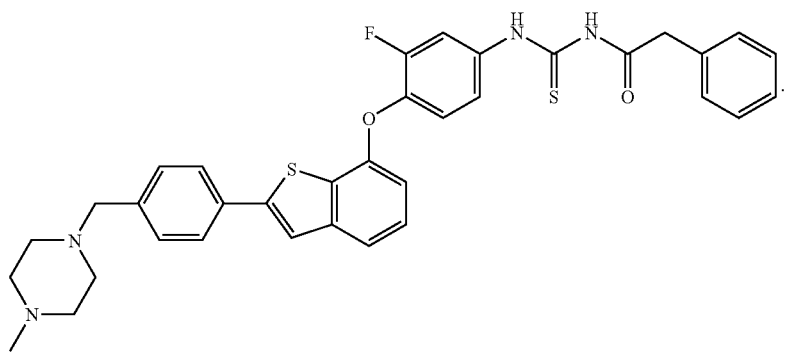

23. The compound according to claim 3, having the structure
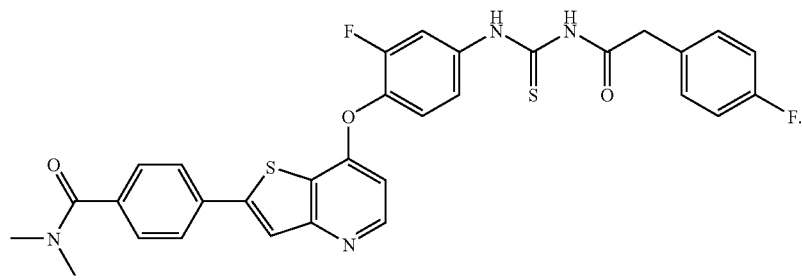
24. The compound according to claim 5, having the structure
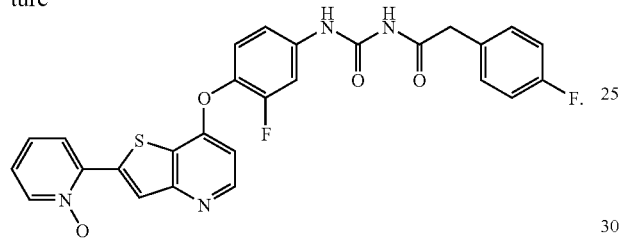
25. The compound according to claim 5, having the structure
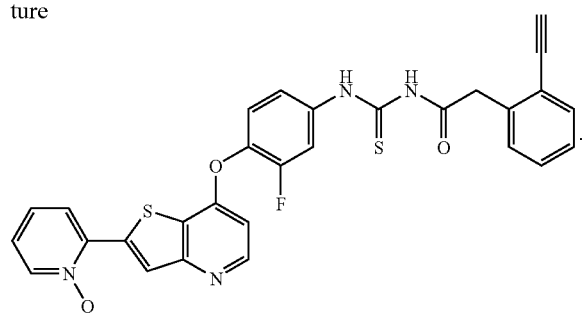
26. The compound according to claim 5, having the structure
27. The compound according to claim 6, having the structure
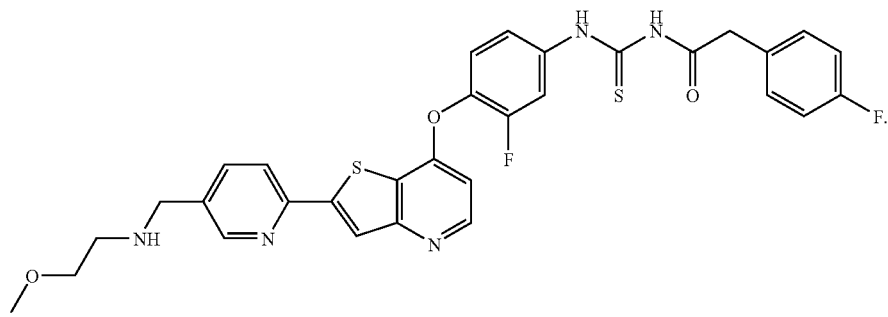

28. The compound according to claim 6, having the structure
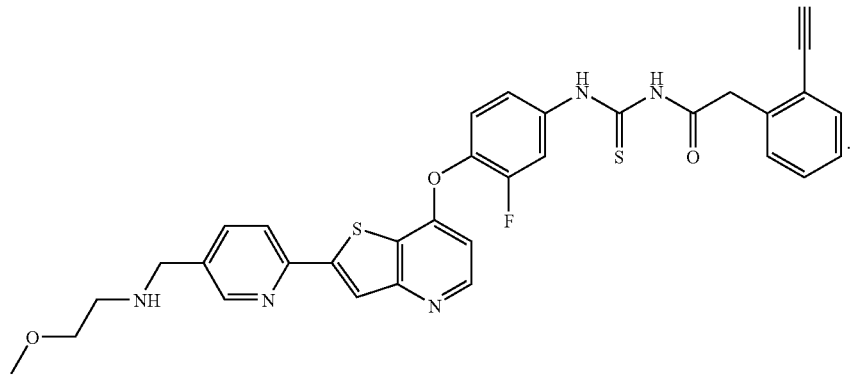
29. The compound according to claim 6, having the structure
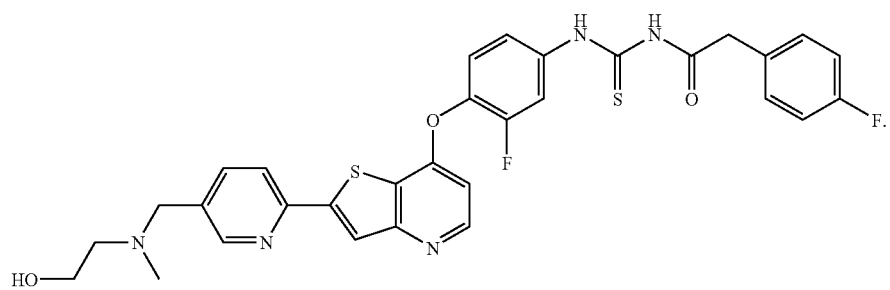
30. The compound according to claim 6, having the structure
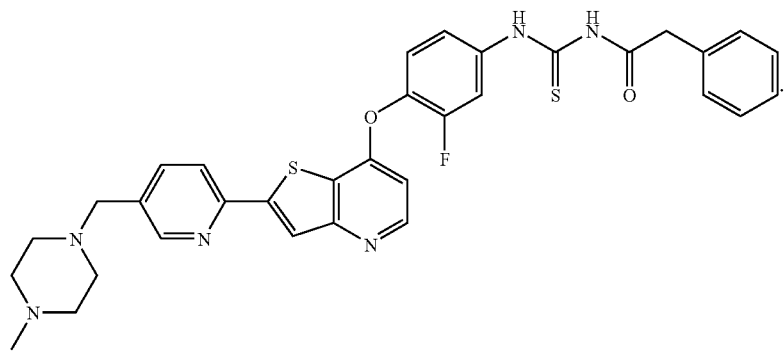

31. The compound according to claim 6, having the structure

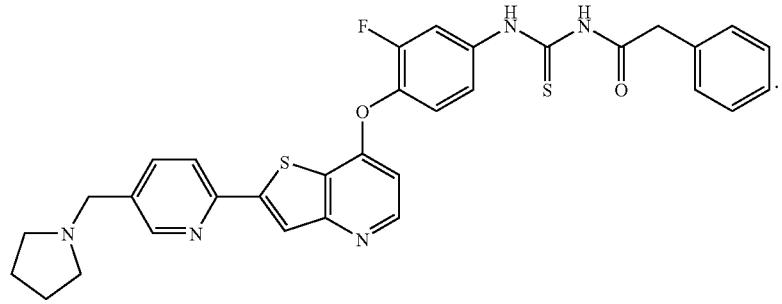

32. An N-oxide of a compound according to claim 1.
33. An N-oxide of a compound according to claim 2.
34. An N-oxide of a compound according to claim 3.
35. An N-oxide of a compound according to claim 4.
36. An N-oxide of a compound according to claim 5.
37. An N-oxide of a compound according to claim 6.
38. A pharmaceutical composition comprising a compound according to claim 1 and a pharmaceutically acceptable carrier.
39. A pharmaceutical composition comprising a compound according to claim 2 and a pharmaceutically acceptable carrier.
40. A pharmaceutical composition comprising a compound according to claim 3 and a pharmaceutically acceptable carrier.
41. A pharmaceutical composition comprising a compound according to claim 4 and a pharmaceutically acceptable carrier.
42. A pharmaceutical composition comprising a compound according to claim 5 and a pharmaceutically acceptable carrier.
43. A pharmaceutical composition comprising a compound according to claim 6 and a pharmaceutically acceptable carrier.
44. A method of inhibiting VEGF receptor signaling and HGF receptor signaling in an animal, the method comprising administering to the animal a receptor inhibiting amount of a compound according to claim 1, or an N-oxide thereof or a composition comprising said compound or an N-oxide thereof and a pharmaceutically acceptable carrier.
45. A method of inhibiting VEGF receptor signaling and HGF receptor signaling in an animal, the method comprising administering to the animal a receptor inhibiting amount of a compound according to claim 2, or an N-oxide thereof or a composition comprising said compound or an N-oxide thereof and a pharmaceutically acceptable carrier.
46. A method of inhibiting VEGF receptor signaling and HGF receptor signaling in an animal, the method comprising administering to the animal a receptor inhibiting amount of a compound according to claim 3, or an N-oxide thereof or a composition comprising said compound or an N-oxide thereof and a pharmaceutically acceptable carrier.
47. A method of inhibiting VEGF receptor signaling and HGF receptor signaling in an animal, the method comprising administering to the animal a receptor inhibiting amount of a compound according to claim 4, or an N-oxide thereof or a composition comprising said compound or an N-oxide thereof and a pharmaceutically acceptable carrier.
48. A method of inhibiting VEGF receptor signaling and HGF receptor signaling in an animal, the method comprising administering to the animal a receptor inhibiting amount of a compound according to claim 5, or an N-oxide thereof or a composition comprising said compound or an N-oxide thereof and a pharmaceutically acceptable carrier.
49. A method of inhibiting VEGF receptor signaling and HGF receptor signaling in an animal, the method comprising administering to the animal a receptor inhibiting amount of a compound according to claim 6, or an N-oxide thereof or a composition comprising said compound or an N-oxide thereof and a pharmaceutically acceptable carrier.
50. A method of treating an angiogenesis-mediated cell proliferative disease in a patient or inhibiting solid tumor growth in a patient, the method comprising administering to the patient in need thereof an effective therapeutical amount of a compound according to claim 1 or an N-oxide thereof or a composition comprising said compound or an N-oxide thereof and a pharmaceutically acceptable carrier.
51. A method of treating an angiogenesis-mediated cell proliferative disease in a patient or inhibiting solid tumor growth in a patient, the method comprising administering to the patient in need thereof an effective therapeutical amount of a compound according to claim 2 or an N-oxide thereof or a composition comprising said compound or an N-oxide thereof and a pharmaceutically acceptable carrier.
52. A method of treating an angiogenesis-mediated cell proliferative disease in a patient or inhibiting solid tumor growth in a patient, the method comprising administering to the patient in need thereof an effective therapeutical amount of a compound according to claim 3 or an N-oxide thereof or a composition comprising said compound or an N-oxide thereof and a pharmaceutically acceptable carrier.
53. A method of treating an angiogenesis-mediated cell proliferative disease in a patient or inhibiting solid tumor growth in a patient, the method comprising administering to the patient in need thereof an effective therapeutical amount of a compound according to claim 4 or an N-oxide thereof or a composition comprising said compound or an N-oxide thereof and a pharmaceutically acceptable carrier.
54. A method of treating an angiogenesis-mediated cell proliferative disease in a patient or inhibiting solid tumor growth in a patient, the method comprising administering to the patient in need thereof an effective therapeutical amount of a compound according to claim 5 or an N-oxide thereof or a composition comprising said compound or an N-oxide thereof and a pharmaceutically acceptable carrier.

55. A method of treating an angiogenesis-mediated cell proliferative disease in a patient or inhibiting solid tumor growth in a patient, the method comprising administering to the patient in need thereof an effective therapeutical amount of a compound according to claim 6 or an N-oxide thereof or a composition comprising said compound or an N-oxide thereof and a pharmaceutically acceptable carrier.

* * * * *

UNITED STATES PATENT AND TRADEMARK OFFICE
CERTIFICATE OF CORRECTION

PATENT NO. : 7,790,729 B2
APPLICATION NO. : 11/419353
DATED : September 7, 2010
INVENTOR(S) : Saavedra et al.

It is certified that error appears in the above-identified patent and that said Letters Patent is hereby corrected as shown below:

In Claim 1, Column 422, line 45 to line 50, please cancel the fifth chemical formula and insert the following chemical formula:

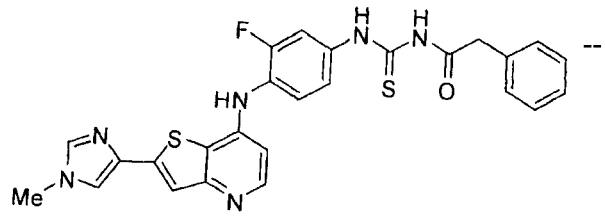

In Claim 1, Column 422, line 50 to line 55, please cancel the sixth chemical formula and insert the following chemical formula:

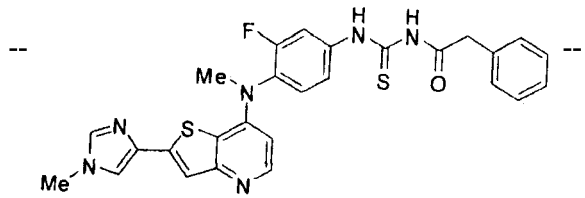

In Claim 1, Column 422, line 60 to line 65, please cancel the seventh chemical formula and insert the following chemical formula:

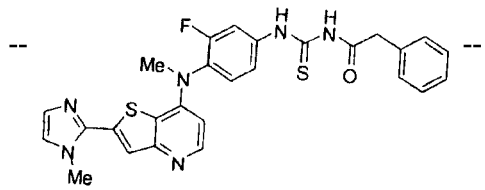

Signed and Sealed this

Seventh Day of December, 2010

David J. Kappos
*Director of the United States Patent and Trademark Office*

In Claim 1, Column 423, line 55 to line 65, please cancel the sixth chemical formula and insert the following chemical formula:

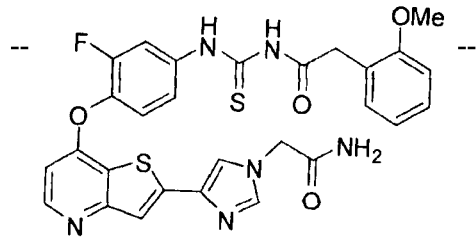

In Claim 1, Column 424, line 5 to line 15, please cancel the first chemical formula and insert the following chemical formula:

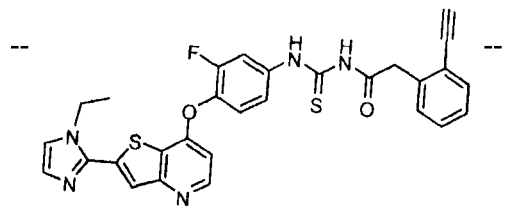

In Claim 1, Column 425, line 55 to line 65, please cancel the sixth chemical formula and insert the following chemical formula:

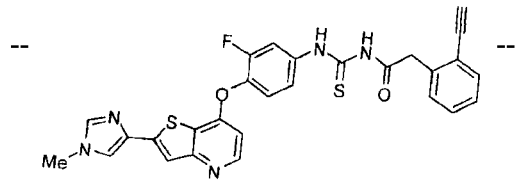

In Claim 1, Column 426, line 5 to line 15, please cancel the first chemical formula and insert the following chemical formula:

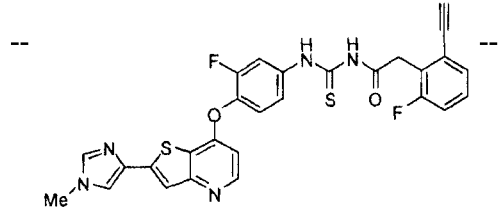

In Claim 1, Column 426, line 30 to line 45, please cancel the fourth and fifth chemical formulae and insert the following chemical formula:

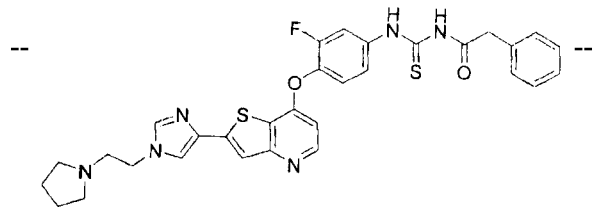

CERTIFICATE OF CORRECTION (continued)
U.S. Pat. No. 7,790,729 B2

In Claim 1, Column 426, line 50 to line 65, please cancel the sixth and seventh chemical formulae and insert the following chemical formula:

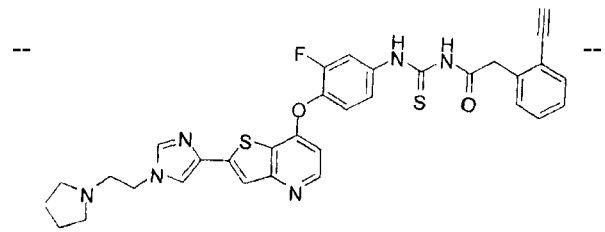

In Claim 1, Column 427, line 5 to line 20, please cancel the first and second chemical formulae and insert the following chemical formula:

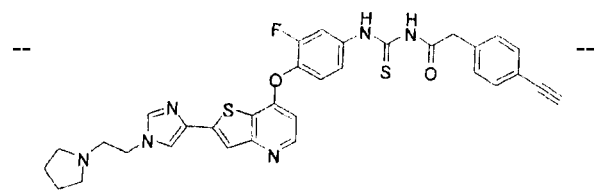

In Claim 1, Column 427, line 20 to line 40, please cancel the third and fourth chemical formulae and insert the following chemical formula:

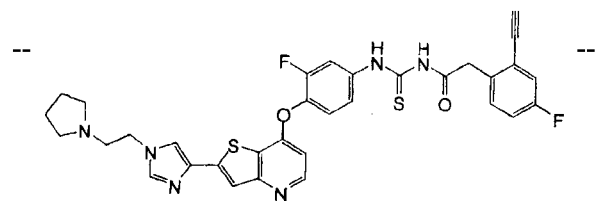

In Claim 3, Column 428, line 55 to line 65, please cancel the fifth and sixth chemical formulae and insert the following chemical formula:

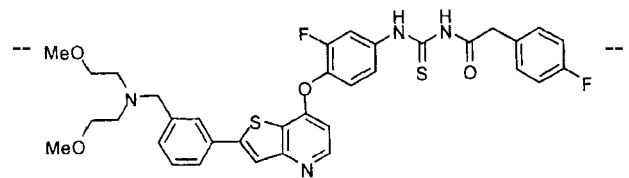

In Claim 3, Column 430, line 5 to line 10, please cancel the first chemical formula and insert the following chemical formula:

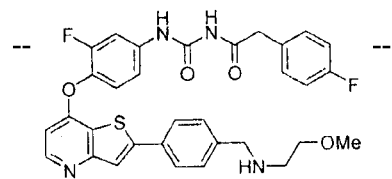

CERTIFICATE OF CORRECTION (continued)
U.S. Pat. No. 7,790,729 B2

In Claim 3, Column 430, line 15 to line 25, please cancel the second and third chemical formulae and insert the following chemical formula:

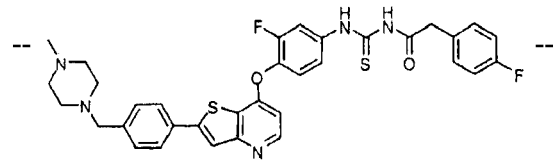

In Claim 3, Column 430, line 30 to line 45, please cancel the fourth and fifth chemical formulae and insert the following chemical formula:

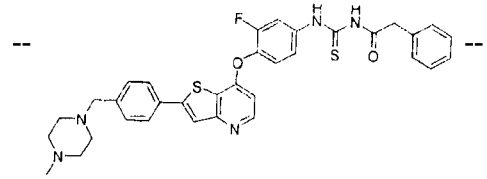

In Claim 3, Column 430, line 50 to line 65, please cancel the sixth and seventh chemical formulae and insert the following chemical formula:

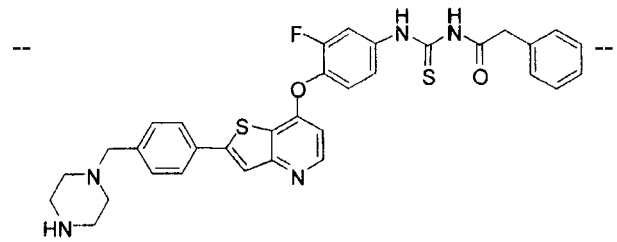

In Claim 3, Column 431, line 5 to line 20, please cancel the first and second chemical formulae and insert the following chemical formula:

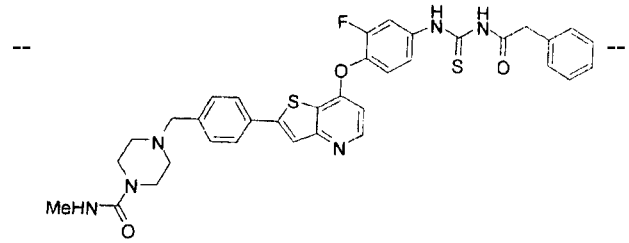

In Claim 3, Column 431, line 25 to line 45, please cancel the third and fourth chemical formulae and insert the following chemical formula:

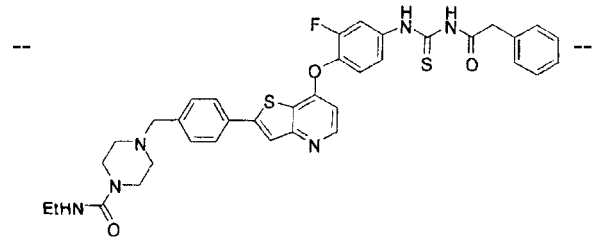

CERTIFICATE OF CORRECTION (continued)
U.S. Pat. No. 7,790,729 B2

In Claim 3, Column 431, line 50 to line 65, please cancel the fifth and sixth chemical formulae and insert the following chemical formula:

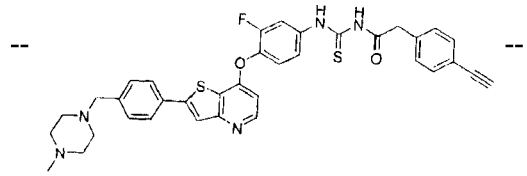

In Claim 3, Column 432, line 5 to line 20, please cancel the first and second chemical formulae and insert the following chemical formula:

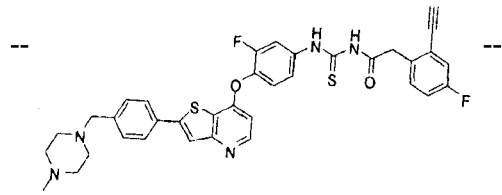

In Claim 3, Column 432, line 25 to line 35, please cancel the third and fourth chemical formulae and insert the following chemical formula:

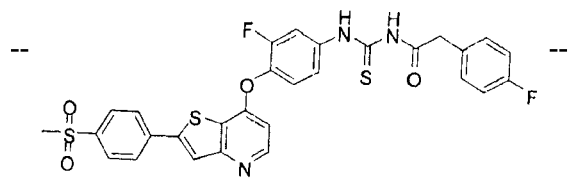

In Claim 3, Column 432, line 40 to line 50, please cancel the fifth and sixth chemical formulae and insert the following chemical formula:

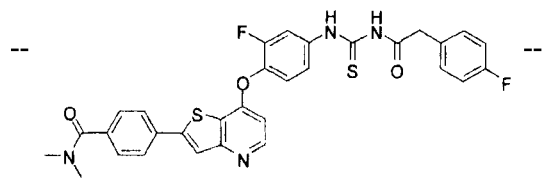

In Claim 4, Column 433, line 5 to line 10, please cancel the first chemical formula and insert the following chemical formula:

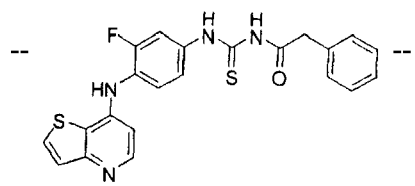

In Claim 4, Column 433, line 15 to line 20, please cancel the second chemical formula and insert the following chemical formula:

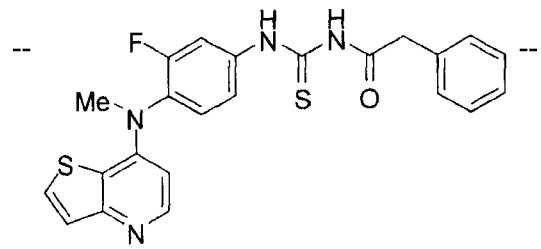

In Claim 4, Column 433, line 25 to line 30, please cancel the third chemical formula and insert the following chemical formula:

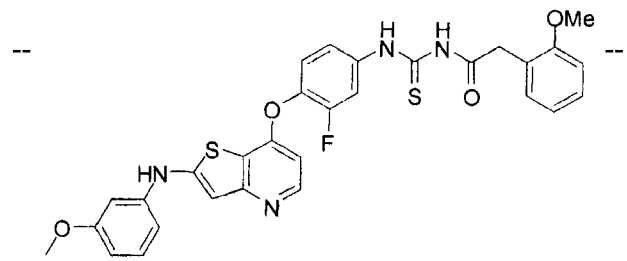

In Claim 6, Column 435, please cancel the fourth chemical formula and insert the following chemical formula:

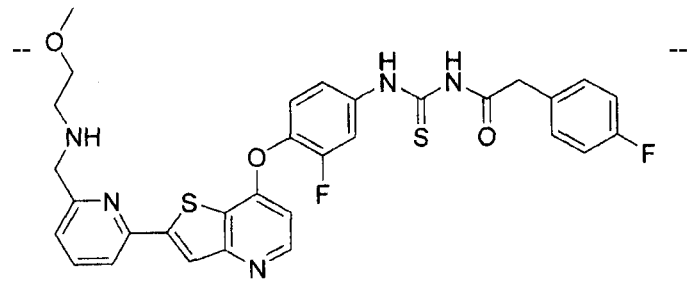

In Claim 6, Column 435, please cancel the fifth chemical formula and insert the following chemical formula:

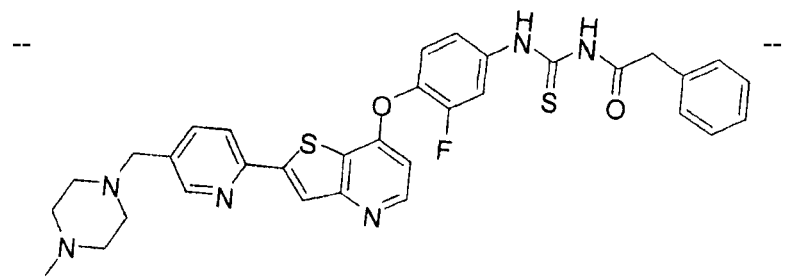

CERTIFICATE OF CORRECTION (continued)  Page 7 of 8
U.S. Pat. No. 7,790,729 B2

In Claim 6, Column 437, please cancel the first chemical formula and insert the following chemical formula:

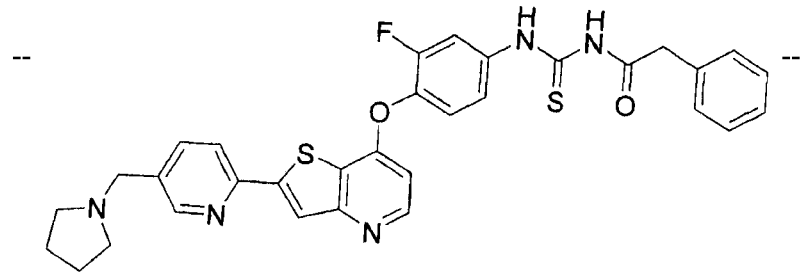

In Claim 6, Column 437, please cancel the second chemical formula and insert the following chemical formula:

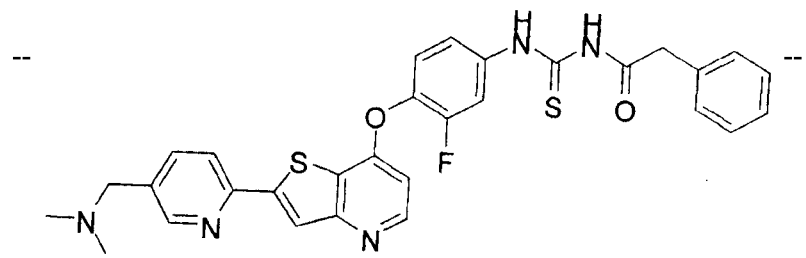

In Claim 9, Column 437, line 55 to line 65, please cancel the chemical formula and insert the following chemical formula:

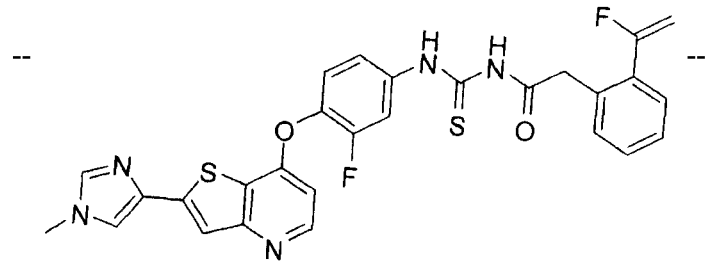

In Claim 17, Column 440, please cancel the chemical formula and insert the following chemical formula:

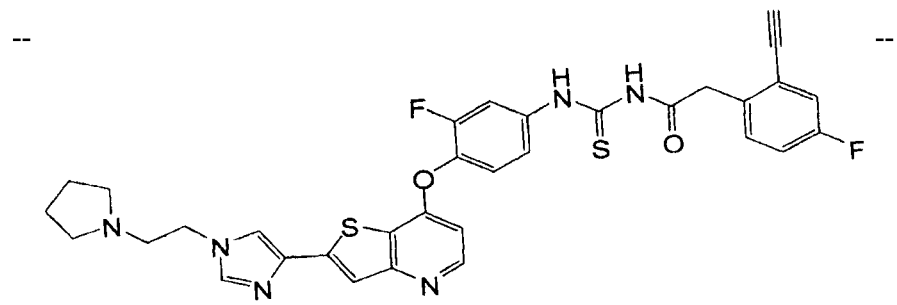

CERTIFICATE OF CORRECTION (continued)
U.S. Pat. No. 7,790,729 B2

In Claim 18, Column 441, line 5 to line 10, please cancel the chemical formula and insert the following chemical formula:

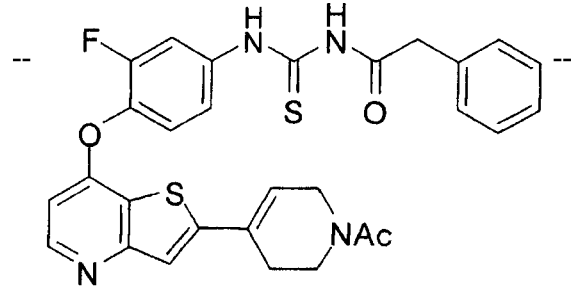

In Claim 22, Column 442, please cancel the chemical formula and insert the following chemical formula:

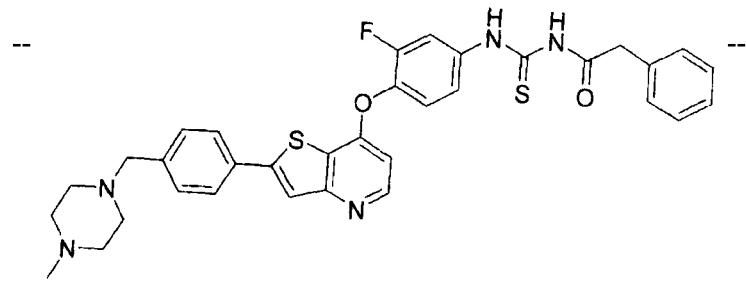

In Claim 24, Column 443, line 25 to line 30, please cancel the chemical formula and insert the following chemical formula:

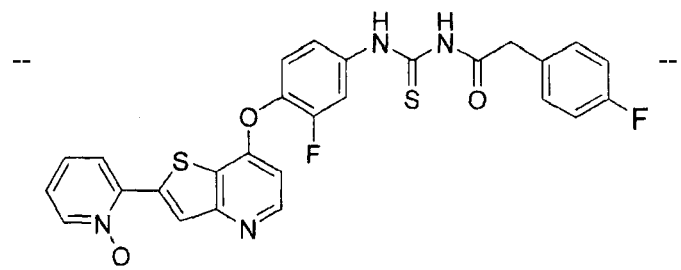

In Claim 31, Column 447, please cancel the chemical formula and insert the following chemical formula: